(12) United States Patent
Becknell et al.

(10) Patent No.: US 10,919,875 B2
(45) Date of Patent: Feb. 16, 2021

(54) SUBSTITUTED 4-BENZYL AND 4-BENZOYL PIPERIDINE DERIVATIVES

(71) Applicant: 89BIO LTD, Herzliya (IL)

(72) Inventors: Nadine C. Becknell, Coatesville, PA (US); Reddeppa Reddy Dandu, Downingtown, PA (US); Bruce D. Dorsey, Ambler, PA (US); Dimitar B. Gotchev, Hatboro, PA (US); Robert L. Hudkins, Chester Springs, PA (US); Linda Weinberg, King of Prussia, PA (US); Craig A. Zificsak, Downingtown, PA (US)

(73) Assignee: 89BIO LTD, Herzliya (IL)

( * ) Notice: Subject to any disclaimer, the term of this patent is extended or adjusted under 35 U.S.C. 154(b) by 244 days.

(21) Appl. No.: 15/735,811

(22) PCT Filed: Jun. 17, 2016

(86) PCT No.: PCT/US2016/037980
§ 371 (c)(1),
(2) Date: Dec. 12, 2017

(87) PCT Pub. No.: WO2016/205590
PCT Pub. Date: Dec. 22, 2016

(65) Prior Publication Data
US 2020/0031797 A1   Jan. 30, 2020

Related U.S. Application Data

(60) Provisional application No. 62/181,391, filed on Jun. 18, 2015.

(51) Int. Cl.
| C07D 471/04 | (2006.01) |
| C07D 413/14 | (2006.01) |
| C07D 401/10 | (2006.01) |
| C07D 405/10 | (2006.01) |
| C07D 405/14 | (2006.01) |

(52) U.S. Cl.
CPC ......... *C07D 401/10* (2013.01); *C07D 405/10* (2013.01); *C07D 405/14* (2013.01); *C07D 413/14* (2013.01); *C07D 471/04* (2013.01)

(58) Field of Classification Search
CPC .. C07D 401/10; C07D 405/10; C07D 405/14; C07D 413/14; C07D 471/04
See application file for complete search history.

(56) References Cited

U.S. PATENT DOCUMENTS

| 6,867,200 B1 | 3/2005 | Allen et al. |
| 9,902,696 B2 | 2/2018 | Becknell et al. |
| 10,221,135 B2 | 3/2019 | Becknell et al. |
| 2005/0182045 A1 | 8/2005 | Nagase et al. |
| 2006/0004039 A1 | 1/2006 | Breitenbucher et al. |
| 2013/0281399 A1 | 10/2013 | McLure et al. |
| 2015/0003506 A1 | 1/2015 | Kesling |
| 2015/0051190 A1 | 2/2015 | Takeda et al. |

FOREIGN PATENT DOCUMENTS

| EP | 1719761 A1 | 11/2006 |
| KR | 10-2013-0120795 A | 11/2013 |
| KR | 10-2014-0127991 A | 11/2014 |
| WO | 1995/016687 | 6/1995 |
| WO | 00/35886 A2 | 6/2000 |
| WO | 2002/014261 | 2/2002 |
| WO | 2004/026883 A1 | 4/2004 |
| WO | 2005/014543 A1 | 2/2005 |
| WO | 2005/037198 A2 | 4/2005 |
| WO | 2005/049622 A1 | 6/2005 |
| WO | 2007/075629 A2 | 7/2007 |
| WO | 2007/089634 A2 | 8/2007 |

(Continued)

OTHER PUBLICATIONS

Tu, et al., Synthesis and in Vitro and in Vivo Evaluation of 18-F-Labeled Positron Emission Tomography (PET) Ligands for Imaging the Vesicular Acetylcholine Transporter, J. Med. Chem., 52(5), 1358-1369 (2009) (Year: 2009).*

(Continued)

*Primary Examiner* — Erich A Leeser
(74) *Attorney, Agent, or Firm* — BakerHostetler

(57) ABSTRACT

Described herein are 1,4-substituted piperidine compounds according to Formula I that have demonstrated activity as fatty acid synthase inhibitors. Also described herein are pharmaceutical compositions containing the described 1,4-substituted piperidine compounds. Also described herein are methods of treating diseases mediated by fatty acid synthase, by administering one or more of the compounds or pharmaceutical formulations described herein. Also described herein are methods of synthesizing the described 1,4-substituted piperidine compounds and synthetic intermediates useful in those syntheses.

(I)

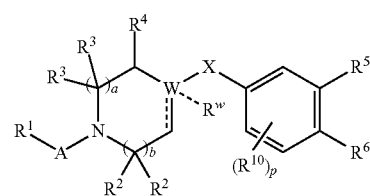

26 Claims, No Drawings

(56) References Cited

FOREIGN PATENT DOCUMENTS

| WO | 2007/146758 | | 12/2007 |
|---|---|---|---|
| WO | 2008/013818 | A2 | 1/2008 |
| WO | 2008/013838 | A2 | 1/2008 |
| WO | 2008/075070 | A1 | 6/2008 |
| WO | 2008/078091 | A1 | 7/2008 |
| WO | 2008/097991 | A1 | 8/2008 |
| WO | 2008/138834 | A1 | 11/2008 |
| WO | 2008/138889 | A2 | 11/2008 |
| WO | 2009/149066 | A1 | 12/2009 |
| WO | 2010/011653 | A1 | 1/2010 |
| WO | 2010/106436 | A2 | 9/2010 |
| WO | 2010/138758 | A1 | 12/2010 |
| WO | 2011/048018 | A1 | 4/2011 |
| WO | 2011/056635 | A1 | 5/2011 |
| WO | 2011/062253 | A1 | 5/2011 |
| WO | 2011/066211 | A1 | 6/2011 |
| WO | 2011/103202 | A2 | 8/2011 |
| WO | 2011/103516 | A2 | 8/2011 |
| WO | 2011/103546 | A1 | 8/2011 |
| WO | 2011/138427 | A2 | 11/2011 |
| WO | 2011/140190 | A1 | 11/2011 |
| WO | 2011/152485 | A1 | 12/2011 |
| WO | 2012/036233 | A1 | 3/2012 |
| WO | 2012/064642 | A1 | 5/2012 |
| WO | 2012/069917 | A1 | 5/2012 |
| WO | 2012/096928 | A2 | 7/2012 |
| WO | 2012/122391 | A1 | 9/2012 |
| WO | 2012/175520 | A1 | 12/2012 |
| WO | 2012/178125 | A1 | 12/2012 |
| WO | 2013/028445 | A1 | 2/2013 |
| WO | 2013/028447 | A1 | 2/2013 |
| WO | 2013/052716 | A1 | 4/2013 |
| WO | 2013/053051 | A1 | 4/2013 |
| WO | 2013/147711 | A1 | 10/2013 |
| WO | 2013/157022 | A1 | 10/2013 |
| WO | 2013/175281 | A1 | 11/2013 |
| WO | 2014/004863 | A2 | 1/2014 |
| WO | 2014/008197 | A1 | 1/2014 |
| WO | 2014/039769 | A1 | 3/2014 |
| WO | 2014/044356 | A1 | 3/2014 |
| WO | 2014/075754 | A1 | 5/2014 |
| WO | 2014/146747 | A1 | 9/2014 |
| WO | 2014/151784 | A1 | 9/2014 |
| WO | 2014/160203 | A2 | 10/2014 |
| WO | 2014/164749 | A1 | 10/2014 |
| WO | 2015/014446 | A1 | 2/2015 |
| WO | 2015/014543 | A1 | 2/2015 |
| WO | 2015/084606 | A1 | 6/2015 |
| WO | 2016/011019 | | 1/2016 |
| WO | 2016/041201 | | 3/2016 |
| WO | 2016/057731 | | 4/2016 |
| WO | 2016/205633 | A1 | 12/2016 |

OTHER PUBLICATIONS

Kim, et al., European Journal of Pharmacology, Inhibition of stearoyl-CoA desaturase1 activates AMPK and exhibits beneficial lipid ,etabolic effects in vitro, vol. 672, Sep. 29, 2011, pp. 38-44.
Wang, et al., ACS Chem. Neurosci., Pimozide, a Novel Fatty Acid Binding Protein 4 Inhibitor, Promotes Adipogensis of 3T3-L1 Cells by Activating PPARγ, vol. 16i, pp. 211-218.
Angeles et al. "Recent Advances in Targeting the Fatty Acid Biosynthetic Patlhway Using Fatty Acid Synthase Inhibitors" Expert Opinion on Drug Discovery, vol. 11., No. 12, pp. 1187-1199, 2016.
Berod et al "De novo fatty acid synthesis controls the fate between regulatory T and T helper 17 ceils" Nature Medicine, Mar. 2014, 20, 1327-1333.
Chung et al.; "A fluorescence-based thiol quantification assay for ultra-high-throughput screening for inhibitors of coenzyme A production," Assay Drug Dev Tech 2008; 6:361-374.
Curtin, M. et al., "Discovery and Evaluation of a Series of 3-Acylindole Imidazopyridine Platelet-Activating Factor Antagonists", Journal of Medicinal Chemistry, 1998, 41 (1), 74-95.

Database CAPLUS in STN, Acc. No. 2000:421114, Allen et al,, WO 2000035886 A2 (Jun. 22, 2000) (abstract).
Database CAPLUS in STN, Acc. No. 2005:823314, Nagase et al,, US 20050182045 A1 (Aug. 18, 2005) (abstract).
Everts, B. et al., "TLR-driven early glycolytic reprogramming via the kinases TBKI-IKKEpsilon: supports the anabolic demands of dendritic cell activation", Nature Immunology, 2014, 15, 323-332.
Hardwicke et al., "A Human Fatty Acid Synthase Inhibitor Binds B-Ketoacyl Reductase in The Keto-Substrate Site", Nature Chemical Biology, 2014, vol. 10, pp. 774-781.
Hu, Q. "Replacement of Imidazolyl by Pyridyl in Biphenylmethylenes Results in Selective CYP17 and Dual CYP17/CYP11B1 Inhibitors for the Treatment of Prostate Cancer" J. Med. Chem., 2010, 53, 5749-5758.
Hunt et al. "mRNA Stability and Overexpression of Fatty Acid Synthase in Human Breast Cancer Cell Lines" Anticancer Res. 2007, 27, 27-34.
Kuhajda "Fatty Acid Synthase and Cancer: New Application of an Old Pathway" Cancer Res., 2006, 66, 5977-5980.
Kuhajda, F. "Fatty-acid synthase and human cancer: new perspectives on its role in tumor biology", Nutrition, 2000, 16, 202-208.
Lin, J. et al., "Antisense Technologies Targeting Fatty Acid Synthetic Enzymes", Recent Patents on Anti-Cancer Drug Discovery, 2012, 7, 198-206.
Liu et al, The Discovery of Orally Bioavailable Tyrosine Threonine Kinase (TTK) Inhibitors: 3-(4-(heterocyclyl)phenyl)-1 H-indazole-5-carboxamides as Anticancer Agents, Journal of Medicinal Chemistry,vol. 58, No. 8, Apr. 23, 2015, p. 3366-3392.
Lupu, R. et al., "Pharmacological Inhibitors of Fatty Acid Synthase (FASN)-Catalyzed Endogenous Fatty Acid Biogenesis: A New Family of Anti-Cancer Agents", Current Pharmaceutical Biotechnology, 2006, 7, 483-494.
McFadden J. et al., "Application of a Flexible Synthesis of (5R) Thiolactomycin to Develop New Inhibitors of Type I Fatty Acid Synthase" J. Med. Chem., 2005, 48, 946-961.
Menendez et al. "Fatty acid synthase and the lipogenic phenotype in cancer pathogenesis" Nature Reviews Cancer, 2007, 7, 763-777.
Nasheri, N., "Modulation of fatty acid synthase enzyme activity and expression during hepatitis C virus replication", Chemistry and Biology, 2013, 570-582.
Notification of Transmittal of the International Search Report and The Written Opinion dated Aug. 19, 2016.
Oliveras et al., "Novel anti-fatty Acid Synthase Compounds with Anti-Cancer Activity in HER2+ Breast Cancer", Annals of the New York Academy of Sciences, 2010, 86-93.
Orita et al., "Selective Inhibition of Fatty Acid Synthase for Lung Cancer Treatment", Cancer Therapy: Preclinical, 13(23) pp. 7139-7145, Dec. 2007.
Pandey, "Anti-Cancer Drugs Targeting Fatty Acid Synthase" Bentham Science Publishers, 7, pp. 185-197, 2012.
Pollak, M., "Targeting Oxidative Phosphorylation: Why, When and How", Cancer Cell, 2013, 18, 263-264.
Puig, et al., "Novel Inhibitors of Fatty Acid Synthase with Anticancer Activity", Clinical Cancer Research, 15, pp. 7608-0615, Dec. 2009.
Purohit et al., "Practical, Catalytic, Asymmetric Synthesis of B-Lactones via A Sequential Ketene Dimerization/Hydrogenation Process: Inhibitors of the Thioesterase Domain of Fatty Acid Synthase" J. Organic Chemistry, 71, pp. 4549-4558, 2006.
Richardson et al., "Novel Antagonists of the Thioesterase Domain of Human Fatty Acid Synthase" Molecular Cancer Therapeutics, 6, pp. 2120-2126, 2007.
Rivkin et al. "3-Aryl-4-Hydroxyquinolin-2(1H) One Derivatives as Type I Fatty Acid Synthase Inhibitors", Bioorganic & Medicinal Chemistry Letters 16, pp. 4620-4623, 2006.
Schoemaker, H. E. et al, Biomimetic a-acylimmonium cyclisations of unactivated olefin, Tetrahedron, 1978, 34, 163-172.
Selvendiran et al., "HO-3867, a Synthetic Compound, Inhibits the Migration and Invasion of Ovarian Carcinoma Cells through Downregulation of Fatty Acid Synthase and Focal Adhesion Kinase", Molecular Cancer Research 8(9), Sep. 2010.

(56) References Cited

OTHER PUBLICATIONS

Sounni, N. et al., "Blocking Lipid Synthesis Overcomes Tumor Regrowth and Metastasis after Angiogenic Therapy Withdrawal", Cell Metabolism, 2014, 20, 1-15.

Tu, Z., et al., "Synthesis and in Vitro and in Vivo Evaluation of 18F-Labeled Positron Emission Tomography (PET) Ligands for Imaging the Vesicular Acetylcholine Transporter", Journal of Medicinal Chemistry, 2009, 52, 1358-1369.

Turrado et al., "New Synthetic Inhibitors of Fatty Acid Synthase with Anticancer Activity", Journal of Medicinal Chemistry, 2012, 55 (11), 5013-5023.

Vazquez et al., "Discovery of GSK837149A, An Inhibitor of Human Fatty Acid Synthase Targeting the B-Ketoacyl Reductase Reaction", The FEBS Journal, pp. 1556-1567, Jan. 2008.

Verma, S., et al., "Formylchromone derivatives as novel and selective PTP-1Binhibitors: a drug design aspect using molecular docking-based self-organizing molecular field analysis", Medicinal Chemistry Research, 2016, 25, 1433-1467.

Wang et al., "Novel Fatty Acid Synthase (FAS) Inhibitors: Design, Synthesis, Biological Evaluation, and Molecular Docking Studies", Bioorganic & Medicinal Chemistry 17, pp. 1898-1904, 2009.

Wu et al., "Antidiabetic and Antisteatotic Effects of the Selective Fatty Acid Synthase (FAS) Inhibitor Platensimycin in Mouse Models of Diabetes", PNAS, vol. 108, No. 13, Mar. 2011.

* cited by examiner

SUBSTITUTED 4-BENZYL AND 4-BENZOYL PIPERIDINE DERIVATIVES

CROSS-REFERENCE TO RELATED APPLICATIONS

This application is a National Stage Application filed under 35 U.S.C. 371 of International Application No. PCT/US2016/037980, filed Jun. 17, 2016, which claims the benefit of priority of U.S. Provisional Application No. 62/181,391, filed Jun. 18, 2015, the entirety of which is incorporated by reference herein.

CROSS REFERENCE TO RELATED APPLICATION

This application claims the benefit of U.S. Provisional Application No. 62/181,391, filed Jun. 18, 2015, the entirety of which is incorporated by reference herein.

FIELD OF THE INVENTION

The present invention relates to compounds according to Formula I, as well as to pharmaceutical compositions containing these compounds and to methods of treatment of cancer, and to methods of treatment of weight gain associated with antipsychotic drug therapy, the methods comprising administering a therapeutically effective dose of one or more of the compounds of Formula I, or a pharmaceutical composition comprising one or more of the compounds of Formula I, to a patient in need of such therapy.

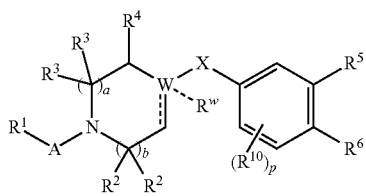

Background

Fatty acid synthase (FASN) is a multi-enzyme protein complex that catalyzes the synthesis of fatty acids involved in energy production and storage, cellular structure and formation of intermediates in the biosynthesis of hormones and other biologically significant molecules (*Nature Reviews Cancer*, 2007, 7, 763-777). FASN is composed of two identical 272 kDa multifunctional polypeptides. As its main function, it catalyzes the synthesis of palmitate from acetyl-CoA and malonyl-CoA, in the presence of nicotinamide adenine dinucleotide phosphate (NADPH). In normal human tissues (with the exception of liver and adipose tissue), fatty acids are preferentially acquired from the diet, and expression of FASN levels are low. In contrast, FASN expression and activity is highly elevated in several pathological states including cancer, inflammatory and metabolic diseases. In particular, evidence shows that increased endogenous fatty acid synthesis is critical for tumorigenesis.

Cancer is a disease of accelerated cell growth and proliferation and cancer cells adapt their metabolism to provide increased levels of lipids to support their anabolic requirements. Increased synthesis of fatty acids represents a fundamental metabolic adaptation of cancer cells and is facilitated by high levels of FASN expression. Increased expression of FASN is an early event in tumorigenesis and is found in numerous tumor types, often correlating with a poor prognosis (*Nature Reviews Cancer*, 2007, 7, 763-777). FASN gene amplification and protein overexpression was observed in human breast, ovarian, prostate, colon, lung, bladder, stomach and kidney cancers suggesting FASN as a potential drug target and marker of poor prognosis (*Nature Reviews Cancer*, 2007, 7, 763-777; *Anticancer Res.* 2007, 27, 27-34; *Cancer Res.*, 2006, 66, 5977-5980, *Nutrition*, 2000, 16, 202-208).

In addition to tumor cells, immune cells metabolically adapt, proliferate and differentiate into distinct functional classes in response to immunogenic stimuli. Studies have demonstrated that lipogenesis plays a critical role in immune responses and metabolic adaptation of activated immune cells. Inhibition of fatty acid synthesis during T-cell differentiation result in a switch from Th17 to Treg cells, suggesting a novel approach to treat autoimmune diseases, such as multiple sclerosis, and to modulate immune responses (Nature Medicine, 2014, 20, 1327-1333). Similarly, de novo fatty acid synthesis is critical for CD8+T cell expansion and dendritic cell activation (Nature Immunology, 2014, 15, 323-332). These results demonstrate that modulation of the fatty acid synthesis pathway might represent a strategy to control immune responses and to treat a wide range of autoimmune diseases.

FASN has been implicated as an important enzyme promoting a life cycle of multiple viruses and microorganisms. De novo lipid biosynthesis has been shown to be necessary for replication of the Flaviviridae family including Hepatitis C Virus, Dengue virus, yellow fever virus, West Nile virus and others (Chemistry and Biology, 2013, 570-582). Inhibition of FASN by small molecule inhibitors such as Cerulenin and Orlistat resulted in a strong inhibition of viral replication. Other viruses also depend on FASN activity including human cytomegalo virus (HCMV) influenza A, Epstein-Barr virus (EBV) and coxsackievirus B3 (CVB3). Numerous genome wide screens identified multiple host genes involved in lipid metabolism which are crucial for replication of viruses and increased expression FASN is often required for efficient viral replication (*Nature Biotechnology*, 2008, 26, 179-186). Taken together, these results provide a strong rationale for targeting FASN for the antiviral therapy.

Fatty acid accumulation is associated with variety of metabolic diseases and has been shown to contribute to their pathogenesis. The non-alcoholic hepatic steatosis (NASH), also called fatty liver disease, encompasses a spectrum of liver diseases (steatosis, steatosis with inflammation, cirrhosis) characterized by a fatty acid accumulation in hepatocytes. Currently, NASH is the most common liver disease in developed countries and is associated with obesity, insulin resistance and type 2 diabetes. Studies in animal models demonstrated that pharmacological inhibition of FASN improved hepatic function and decreased liver fat accumulation (PloS One, 2013, 9, 1-8).

FASN is highly expressed in tissues with high metabolic activity (liver, adipose tissue and brain), and is a critical enzyme for endogenous lipogenesis and modulation of key intermediates of lipid and carbohydrate cellular metabolism. A FASN inhibitor has been proposed for treatment of obesity, and inhibition of FASN in the hypothalamus may result in reduced food intake. The non-specific irreversible FASN inhibitors cerulenin and C-75 have been reported to decrease brain levels of orexigenic neuropeptides and decrease food intake. Therefore, FASN inhibition represents a therapeutic target in a wide spectrum of pathologies including cancer, antiviral, liver and cardiovascular diseases and treatment of obesity, diabetes and drug-induced body weight gain e.g. atypical antipsychotics.

Recent advances in the treatment and management of cancer have demonstrated that many anti-cancer therapies lead to profound changes in tumor metabolism. Inhibition of BRAF signaling by vemurafenib and inhibition of BCR-ABL by imatinib led to increase in oxidative phosphorylation (Pollak M, (2013) Targeting Oxidative Phosphorylation: Why, When and How. *Cancer Cell* 18, 263-63). Such a drug-induced reprogramming of cellular metabolism from glycolysis to oxidative phosphorylation might create a dependency on lipids which could be exploited therapeutically by use of FASN inhibitors. In yet another example, it was demonstrated that cessation of the anti-angiogenic therapy by sunitinib and sorafenib resulted in a rapid regrowth of tumors and increased metastasis which were mediated by a rapid metabolic switch of tumor and stromal cells to de novo lipogenesis. Pharmacological inhibition of FASN was sufficient to reverse tumor regrowth and metastatic dissemination further confirming the role of lipid metabolism in tumor adaptation to anti-cancer therapies (Sounni N E, Cimino J, Blacher S, Primac I, Truong A, Mazucchelli G, Paye A, calligaris D, Debois D, man B, de pauw E, Noel A (2014) Blocking Lipid Synthesis Overcomes Tumor Regrowth and Metastasis after Angiogenic Therapy Withdrawal. *Cell Metabolism* 20, 1-15) and providing a rationale for combinatorial treatments using FASN inhibitors.

SUMMARY

This application relates to compounds according to Formula I:

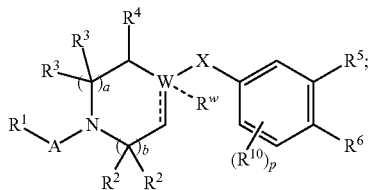

including all stereoisomeric forms, and mixtures thereof of the compounds.

The application further relates to salts of compounds according to Formula I, e.g., pharmaceutically acceptable salts, and to compositions, e.g., pharmaceutical compositions, that contain compounds according to Formula I, or salts thereof.

The compounds of Formula I and/or their pharmaceutically acceptable salts are useful for treating conditions, disorders and diseases that are directed or indirectly controlled, mediated, effected or influenced by FASN expression and activity.

Compounds of Formula I are receptor ligands and are therefore useful in the treatment of various conditions, disorders or diseases such as those related to cancer, metabolic disorders, and the central nervous system (CNS).

DETAILED DESCRIPTION

The following provides additional non-limiting details of the compounds of Formula I, as well as various species and more specific embodiments of the same, intermediates, and synthesis processes.

One aspect of this application is directed to compounds of Formula I:

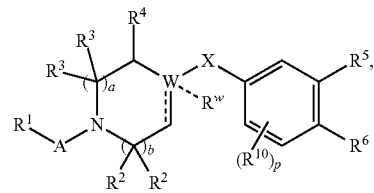

and salts thereof, e.g., pharmaceutically acceptable salts thereof, wherein:

A is —C(=O) or —SO$_2$—;

R$^1$ is selected from —H, —(C$_1$-C$_{10}$)hydrocarbyl, substituted —(C$_1$-C$_{10}$)hydrocarbyl, 3-7 membered heterocyclyl, substituted 3-7 membered heterocyclyl, —(C$_6$-C$_{10}$)aryl, substituted —(C$_6$-C$_{10}$)aryl, 5-6 membered heteroaryl, substituted 5-6 membered heteroaryl, —NR$^7$R$^8$, —N(OR$^8$)R$^7$, —SR$^7$, —N(SR$^8$)R$^7$, —C(=O)—(C$_1$-C$_6$) alkyl and —(C$_1$-C$_6$) heteroalkyl;

a and b are independently selected from 0 and 1;

each R$^2$ and each R$^3$ is independently selected from —H and —(C$_1$-C$_4$) alkyl;

R$^4$ is —H, —C$_1$-C$_6$ alkyl, —OH, =O, —O(C$_1$-C$_6$) alkyl, halogen or —CN;

wherein one of the R$^3$ groups can be structurally connected to one of the R$^2$ groups to form an alkylene bridge to produce a bicyclic ring; or one of the R$^3$ groups can be structurally connected to the R$^1$ group to form a 5 to 7 membered heterocyclyl ring fused to the 1-2 face of the piperidine ring; or one of the R$^3$ groups can be structurally connected to the R$^4$ group to form a 5-7 membered carbocyclic or heterocyclic ring fused to the 2-3 face of the piperidine ring;

R$^5$ is selected from —H, —C$_1$-C$_7$ hydrocarbyl, —C$_3$-C$_6$ heterocyclyl; halogen, —(C$_1$-C$_3$) haloalkyl, —OR$^{7a}$, —CN, —NR$^{7a}$R$^{8a}$, —O(CH$_2$)$_1$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O)NR$^{7a}$R$^{8a}$, —C(=O)OR$^{7a}$, 5-6 membered heteroaryl, substituted 5-6 membered heteroaryl, 8-10 membered bicyclic heteroaryl, and substituted 8-10 membered bicyclic heteroaryl; wherein n is an integer selected from 1, 2, 3, and 4;

W is an sp3 hybridized carbon atom bonded to a R$^w$ substituent, or is an sp2 hybridized carbon atom, and no R$^w$ substituent is present;

══ signifies that the designated bond is a carbon-carbon single bond or a carbon-carbon double bond;

------ signifies that the designated bond is a C—R$^w$ single bond when ══ is a carbon-carbon single bond, i.e., W is an sp$^3$ hybridized carbon atom, and a R$^w$ substituent is present, and that the ------ bond is not present bond when ══ is a carbon-carbon double bond, i.e., W is an sp$^2$ hybridized carbon atom, and there is no R$^w$ substituent;

R$^6$ is selected from 6 membered heteroaryl, substituted 6 membered heteroaryl, 9-10 membered bicyclic heteroaryl, and substituted 9-10 membered bicyclic heteroaryl;

R$^7$ is selected —H, —(C$_1$-C$_7$) hydrocarbyl, substituted —(C$_1$-C$_7$) hydrocarbyl, —C(=O)R$^8$, —(C$_1$-C$_6$) heteroalkyl, 6 membered aryl, 5-6 membered heteroaryl and 5-6 membered heterocyclyl;

R$^8$ is selected from —H, and —(C$_1$-C$_6$) alkyl, wherein R$^7$ can be structurally connected to R$^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^{8a}$ is selected from —H, and ($C_1$-$C_6$) alkyl, wherein $R^{7a}$ can be structurally connected to $R^{8a}$ to form a 5 to 7 membered heterocyclyl ring;

X is selected from $CH_2$, $CHR^9$, $C(R^9)_2$, C=C($R^{11})_2$, C(=O), C(=NO—($C_1$-$C_7$) hydrocarbyl), and C(=NO—C (=O)—($C_1$-$C_7$) hydrocarbyl);

each $R^9$ is independently selected from halogen, —($C_1$-$C_7$) hydrocarbyl, —O—$R^{11}$, —NH—$R^{11}$, —O—$(CH_2)_m$-(5-6 membered heterocyclyl), and —($C_1$-$C_6$) heteroalkyl; or the two $R^9$ groups can together form a spirofused heterocyclic ring or carbocyclic ring; wherein m is an integer selected from 1, 2, 3 and 4;

$R^w$ is selected from —H, halogen, —CN, —OH, —($C_1$-$C_7$) hydrocarbyl, and substituted —($C_1$-$C_7$) hydrocarbyl;

each $R^{10}$ is independently selected from halogen, —CN, —OH, —($C_1$-$C_7$) hydrocarbyl, and substituted —($C_1$-$C_7$) hydrocarbyl; p is an integer selected from 0, 1 and 2; and $R^{11}$ is selected from —H and —($C_1$-$C_7$) hydrocarbyl.

According to some embodiments, A is —C(=O)—.

According to some embodiments, $R^1$ is selected from —H, —($C_1$-$C_{10}$)hydrocarbyl, substituted —($C_1$-$C_{10}$)hydrocarbyl, 3-7 membered heterocyclyl, substituted 3-7 membered heterocyclyl, —($C_6$-$C_{10}$)aryl, substituted —($C_6$-$C_{10}$) aryl, 5-6 membered heteroaryl, substituted 5-6 membered heteroaryl, —$NR^7R^8$, —N(O$R^8$)$R^7$, —O$R^7$, —C(=O)—($C_1$-$C_6$) alkyl and ($C_1$-$C_6$) heteroalkyl.

According to some embodiments, a is 1 and b is 0. According to some embodiments, a is 0 and b is 1. According to some embodiments, a and b are both 1.

According to some embodiments, ═══ is a carbon-carbon single bond.

According to some embodiments, X is selected from —$CH_2$—, —CHF—, —$CF_2$—, —CH($CH_3$)—, —CH(ethyl)-, —CH(n-propyl)-, —CH(isopropyl)-, —C(($CH_3)_2$)—, —C($CH_3$)(O$CH_3$)—, C(Et)(O$CH_3$)—, —C($CH_3$)(OEt)-, —CH($NH_2$)—, —CH(cyclopropyl)-, spirocyclopropyl, —C(=$CH_2$)—, —C(=O)—, —C(=NO$CH_3$)—, —CH(NH-acetyl)-, —CH(NH-formyl)-, —CH(OH)—, —CH(O$CH_3$)—, —C$CH_3$(OH)—, —CH(O$(CH_2)_n$O$CH_3$)—, —CH(O$(CH_2)_n$-(5-6 membered heterocycle)), spiro-1,3-dioxolanyl, and spiro-dioxanyl. According to some embodiments, X is —$CH_2$—. According to some embodiments, X is —CHF— or —$CF_2$—.

According to some embodiments, $R^1$ is selected from —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —$NR^7R^8$, —N(O$R^8$)$R^7$, —SR', —N(S$R^8$)$R^7$ and —C(=O)—($C_1$-$C_6$) alkyl.

According to some embodiments, $R^1$ is selected from —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —$NR^7R^8$, —N(O$R^8$)$R^7$ and —C(=O)—($C_1$-$C_6$) alkyl.

According to some embodiments, $R^1$ is selected from —($C_1$-$C_6$) alkyl, substituted —($C_1$-$C_6$) alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —$NR^7R^8$, —$NR^7$—O$R^8$, —O$R^7$, —S$R^7$, —N(S$R^8$)$R^7$ and —C(=O)—($C_1$-$C_6$) alkyl.

According to some embodiments, $R^1$ is selected from —($C_1$-$C_6$) alkyl, substituted —($C_1$-$C_6$) alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —$NR^7R^8$, —$NR^7$—O$R^8$, —O$R^7$, and —C(=O)—($C_1$-$C_6$) alkyl. According to some embodiments, $R^1$ is selected from the moieties in Table 1 and Table 1a below.

TABLE 1

A selection of some suitable $R^1$ moieties.

—$CH_3$
—NHC$H_2$C$H_3$
—CH($CH_3$)$CH_3$
—$CH_2$—OH
—$CH_2$$CH_3$
—NHCH($CH_3$)$CH_3$
—$CH_2$—CN
—NHC$H_3$
—$(CH_2)_2$$CH_3$
—C(=O)$CH_3$
—CH($CH_3)_2$—OH
—$CF_3$
—(CH($CH_3$))$_3$
—$CH_2$—$SO_2$—$CH_3$
—$CF_2$—$CH_3$
—$CH_2$—O$CH_3$
—$NH_2$
—NH—OH
—NH—OC$H_2$C$H_3$
—N($CH_3$)—O$CH_3$
—$CH_2$CH($CH_3$)$CH_3$
—CH($CH_3$)—O$CH_3$
—NH—O$CH_3$
—N($CH_3)_2$

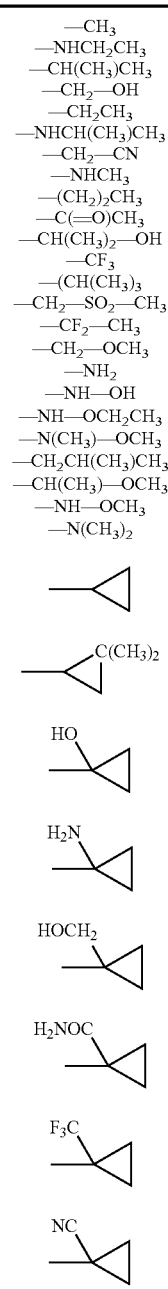

TABLE 1-continued
A selection of some suitable R¹ moieties.
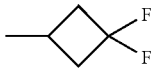
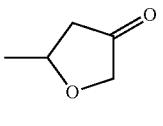
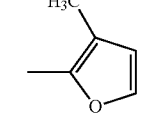
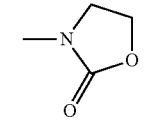
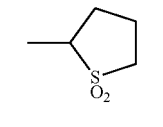
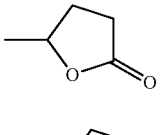
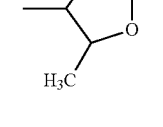
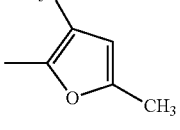
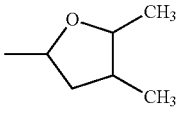
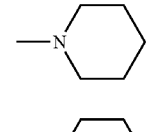
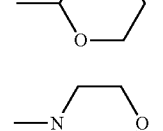
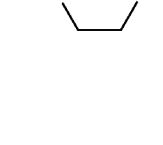
TABLE 1-continued
A selection of some suitable R¹ moieties.
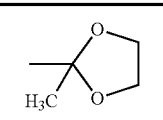
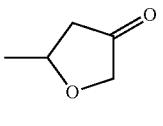
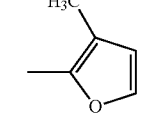
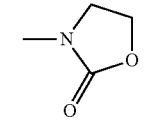
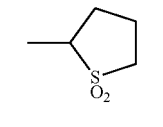
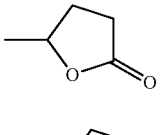
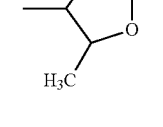
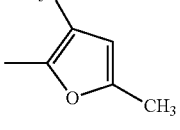
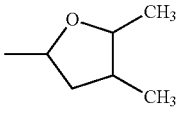
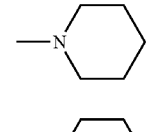
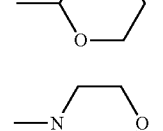
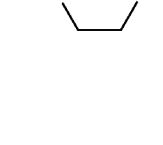

TABLE 1-continued
A selection of some suitable R¹ moieties.
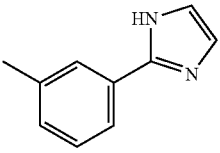
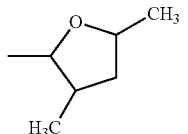
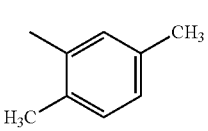
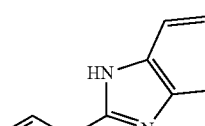
TABLE 1a
A Selection of Some Additional Suitable R¹ moieties.
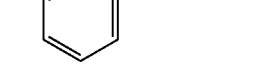
TABLE 1a-continued
A Selection of Some Additional Suitable R¹ moieties.
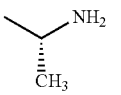
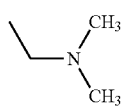
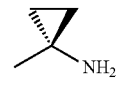
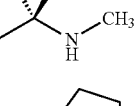
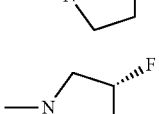
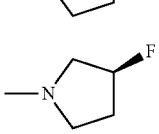
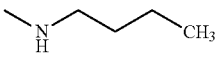
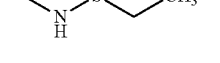
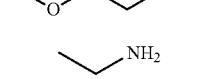
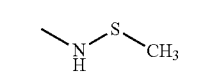
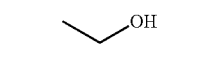
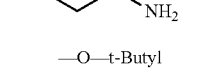

TABLE 1a-continued
A Selection of Some Additional Suitable R¹ moieties.
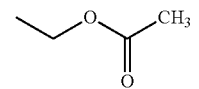
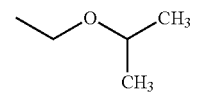
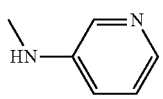
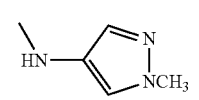
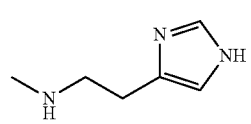
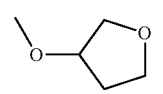
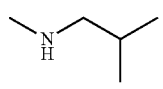
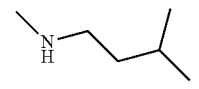
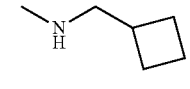
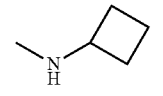
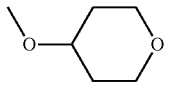
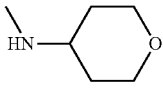
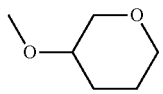
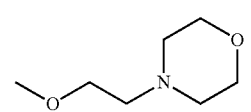
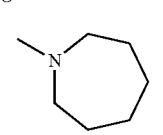
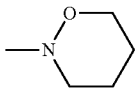
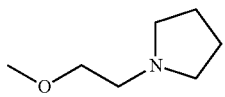
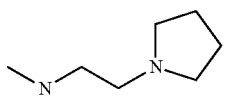
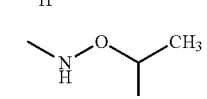
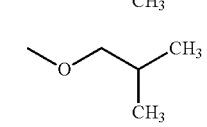
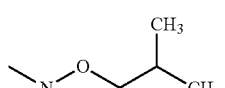
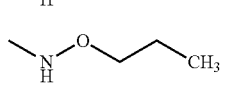
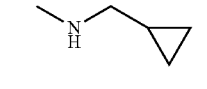
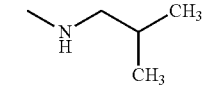
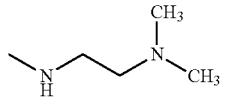
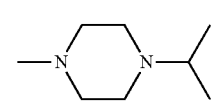
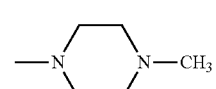
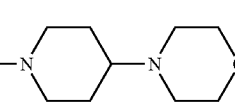
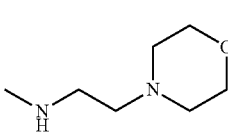

According to some embodiments, $R^2$ is —H.
According to some embodiments, $R^3$ is —H.
According to some embodiments, $R^4$ is selected from —H, —OH, =O, —O($C_1$-$C_6$) alkyl and halogen. According to some embodiments, $R^4$ is selected from —H, —OH, =O, —OCH$_3$ and —F. According to some embodiments, $R^4$ is H.

According to some embodiments, one of the $R^3$ groups is structurally connected to one of the $R^2$ groups to form a ($C_1$-$C_3$) alkylene bridge (e.g., a —CH$_2$—CH$_2$— bridge) to produce a bicyclic ring; for example:

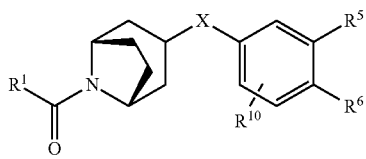

According to some embodiments, one of the $R^3$ groups is structurally connected to the $R^1$ group to form a 5-6 membered lactam ring fused to the 1-2 face of the piperidine ring; for example:

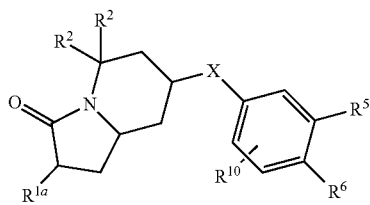

wherein the $R^{1a}$ moiety represents the residue of the $R^1$ substituent covalently bonded to one of the $R^2$ substituents (alpha to the A moiety carbonyl group). According to some embodiments, $R^{1a}$ is selected from —H, —($C_1$-$C_9$) hydrocarbyl, substituted —($C_1$-$C_9$) hydrocarbyl and —($C_1$-$C_5$) heteroalkyl;

According to some embodiments, one of the $R^3$ groups is structurally connected to the $R^4$ group to form a 5-6 membered carbocyclic or heterocyclic ring fused to the 2-3 face of the piperidine ring; for example:

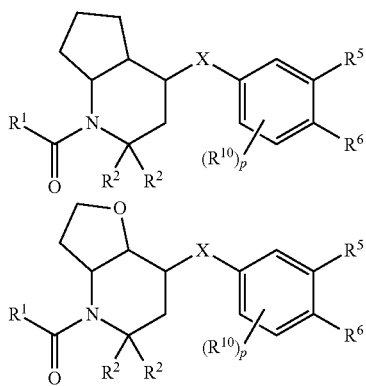

According to some embodiments, $R^5$ is selected from —H, —$C_1$-$C_6$ alkyl, and halogen. According to some embodiments, $R^5$ is —H.

According to some embodiments, $R^6$ is selected from 9-10 membered bicyclic heteroaryl, and substituted 9-10 membered bicyclic heteroaryl. According to some embodiments, $R^6$ is selected from:

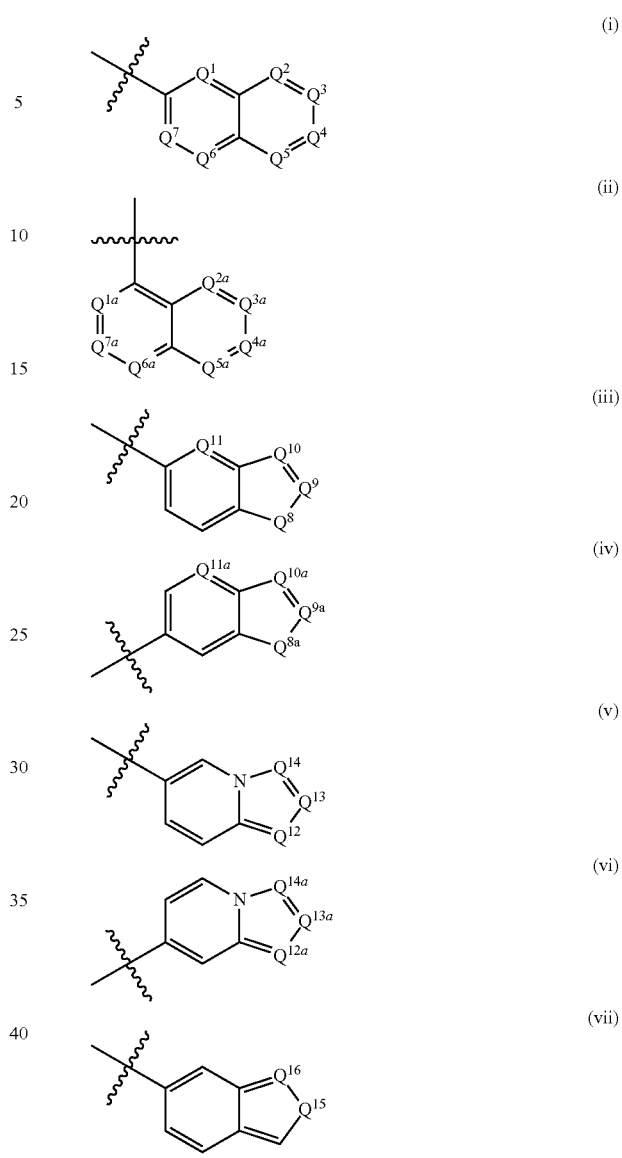

wherein, when $R^6$ is (i) $Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;

when $R^6$ is (ii), $Q^{1a}$, $Q^{2a}$, $Q^{3a}$, $Q^{4a}$, $Q^{5a}$, $Q^{6a}$ and $Q^{7a}$ are independently selected from N and C—$R^{12}$, provided that 1, 2 or 3 of $Q^{1a}$, $Q^{2a}$, $Q^{3a}$, $Q^{4a}$, $Q^{5a}$, $Q^{6a}$ and $Q^{7a}$ are N, and the remainder of $Q^{1a}$, $Q^{2a}$, $Q^{3a}$, $Q^{4a}$, $Q^{5a}$, $Q^{6a}$ and $Q^{7a}$ are C—$R^{12}$;

when $R^6$ is (iii), $Q^8$ is selected from O, S, and N—$R^{12n}$, $Q^9$, $Q^{10}$ and $Q^{11}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (iv), $Q^{8a}$ is selected from O, S, and N—$R^{12n}$, $Q^{9a}$, $Q^{10}$ and $Q^{11a}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (v), $Q^{12}$, $Q^{13}$ and $Q^{14}$ are independently selected from N and C—$R^{12}$; and when $R^6$ is (vi), $Q^{12n}$, $Q^{13a}$ and $Q^{14a}$ are independently selected from N and C—$R^{12}$;

when $R^6$ is (vii), $Q^{15}$ is selected from $N-R^{12n}$ and $C-R^{12}$ and $Q^{16}$ is selected from N and $C-R^{12}$; provided that one of $Q^{15}$ and $Q^{16}$ are not both $C-R^{12}$;

and wherein each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)$NH_2$, —C(=O)NH($C_1$-$C_6$) alkyl, —C(=O)N($C_1$-$C_6$ alkyl)$_2$, —($C_1$-$C_3$) haloalkyl, —O($C_1$-$C_3$) haloalkyl, and —O($CH_2$)$_r$—NH($C_1$-$C_6$ alkyl)$_2$; wherein r is an integer selected independently from 1, 2, 3, and 4; and each $R^{12n}$ is independently selected from —H, —($C_1$-$C_7$) hydrocarbyl and substituted —($C_1$-$C_7$) hydrocarbyl.

It will be understood that the non-bridgehead ring carbon ring atoms in (i), (ii), (iii), (iv), (v), (vi) and (vii) above (i.e., ring atoms which are not designated as Q) may optionally be substituted. According to some embodiments, none of these ring carbon ring atoms are substituted. According to some embodiments one or two of these ring carbon ring atoms is substituted. According to some embodiments one or two of these ring carbon ring atoms is substituted with a substituent selected from —OH, —($C_1$-$C_3$) alkyl, —O($C_1$-$C_3$)alkyl and halogen. According to some embodiments, one of these ring carbon ring atoms is substituted with a substituent selected from —OH, —$CH_3$, —$OCH_3$, —F and —Cl.

According to some embodiments, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$.

According to some embodiments, each $R^{12}$ is independently selected from —H, —Cl, —F, —$CH_3$, —$CH_2CH_3$, —$OCH_3$, —$OCH_2CH_3$, —$OCH(CH_3)_2$, —$CF_3$, —$OCF_3$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1-yl), —O($CH_2$)$_2$—$OCH_3$, —O($CH_2$)$_3$—$OCH_3$, —O($CH_2$)$_2$—N($CH_3$)$_2$, —O($CH_2$)$_3$—N($CH_3$)$_2$, —$NH_2$, $NHCH_3$, N($CH_3$)$_2$, N-methylpiperazin-1-yl, pyrrolidin-1-yl, morpholin-1-yl, and piperidin-1-yl.

According to some embodiments, each $R^{12}$ is independently selected from —H, —Cl, —F, —$CH_3$, —$CH_2CH_3$, —$OCH_3$, —$OCH_2CH_3$, —$OCH(CH_3)_2$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1-yl), —O($CH_2$)$_2$—$OCH_3$, —O($CH_2$)$_3$—$OCH_3$, —O($CH_2$)$_2$—N($CH_3$)$_2$, —O($CH_2$)$_3$—N($CH_3$)$_2$, —$NH_2$, $NHCH_3$, N($CH_3$)$_2$, N-methylpiperazin-1-yl, pyrrolidin-1-yl, morpholin-1-yl, and piperidin-1-yl.

According to some embodiments, each $R^{12n}$ is independently selected from —H, halogen, benzyl and —$C_1$-$C_6$ alkyl.

According to some embodiments, $R^6$ is selected from 9-10 membered bicyclic heteroaryl and substituted 9-10 membered bicyclic heteroaryl; provided that, when $R^6$ is a 9-membered bicyclic heteroaryl or a substituted 9-membered bicyclic heteroaryl, the point of attachment of $R^6$ is on a 6-membered ring portion of the 9-membered bicyclic heteroaryl or substituted 9-membered bicyclic heteroaryl.

According to some embodiments, $R^6$ may be selected from the bicyclic ring systems shown in Table 1b, wherein $R^{12n}$ is as defined herein, and the non-bridgehead carbon atoms in the bicyclic ring systems may optionally be substituted. According to some embodiments, 0, 1, 2 or 3 of the non-bridgehead carbon atoms in the ring systems shown in Table 1b may be substituted by $R^{12}$ substituents as $R^{12}$ is defined herein.

TABLE 1b

A selection of some suitable $R^6$ moieties.

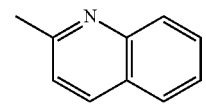

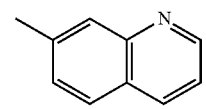

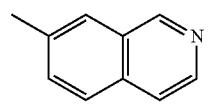

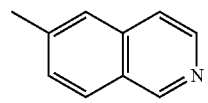

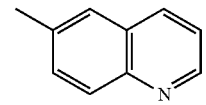

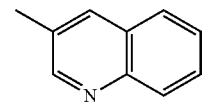

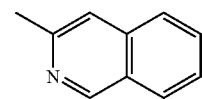

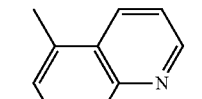

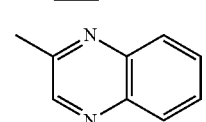

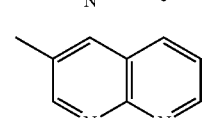

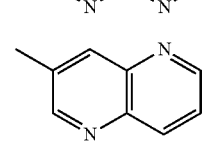

TABLE 1b-continued

A selection of some suitable $R^6$ moieties.

According to some embodiments, $R^7$ is selected from —H, —($C_1$-$C_7$) hydrocarbyl, substituted —($C_1$-$C_7$) hydrocarbyl, —C(=O)$R^8$, and —($C_1$-$C_6$) heteroalkyl.

According to some embodiments, $R^7$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$)

alkenyl, substituted —($C_2$-$C_6$)alkenyl, benzyl, substituted benzyl, —C(=O)$R^8$, and —($C_1$-$C_6$) heteroalkyl. According to some embodiments, $R^7$ is selected from —H, and —($C_1$-$C_6$) alkyl.

According to some embodiments, $R^{7a}$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^{7a}$ is selected from —H and —($C_1$-$C_6$) alkyl.

According to some embodiments, $R^8$ is selected from —H, and —($C_1$-$C_6$) alkyl. According to some embodiments, $R^8$ is selected from —H, —$CH_3$ and $CH_2CH_3$.

According to some embodiments, $R^{8a}$ is selected from —H, and —($C_1$-$C_6$) alkyl. According to some embodiments, $R^{8a}$ is selected from —H, —$CH_3$ and —$CH_2CH_3$.

According to some embodiments each $R^3$ is —H or —$CH_3$. According to other embodiments, each $R^3$ is —H.

According to some embodiments, one of the $R^3$ groups can be structurally connected to one of the $R^2$ groups to form a $C_2$-$C_3$ alkylene bridge to produce a bicyclic ring. According to some embodiments, one of the $R^3$ groups is structurally connected to one of the $R^2$ groups to form a —$CH_2$—$CH_2$— bridge to produce a bicyclic ring; for example:

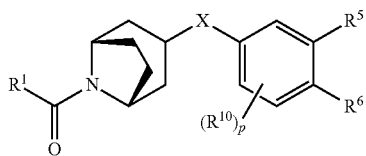

According to some embodiments, one of the $R^3$ groups, can be structurally connected to the $R^1$ group to form a 5 to 7 membered heterocyclyl ring fused to the 1-2 face of the piperidine ring. According to some embodiments, one of the $R^3$ groups is structurally connected to the $R^1$ group to form a 5 membered lactam ring fused to the 1-2 face of the piperidine ring; for example:

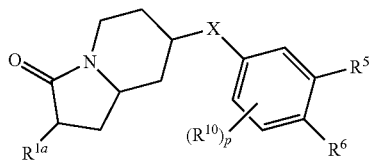

wherein the $R^{1a}$ moiety represents the residue of the $R^1$ substituent covalently bonded to one of the $R^2$ substituents (alpha to the A moiety carbonyl group).

According to some embodiments, one of the $R^3$ groups can be structurally connected to the $R^1$ group to form a 5-membered heterocyclyl ring fused to the 1-2 face of the piperidine ring.

According to some embodiments, one of the $R^3$ groups can be structurally connected to the $R^1$ group to form a bicyclic indolizin-3-one ring. According to some embodiments, one of the $R^3$ groups can be structurally connected to the $R^1$ group to form a 6-membered heterocyclyl ring fused to the 1-2 face of the piperidine ring. According to some embodiments, one of the $R^3$ groups can be structurally connected to the $R^1$ group to form a bicyclic quinolizin-4-one ring.

According to some embodiments, one of the $R^3$ groups can be structurally connected to the $R^4$ group to form a 5-7 membered carbocyclic or heterocyclic ring fused to the 2-3 face of the piperidine ring. According to some embodiments, one of the $R^3$ groups can be structurally connected to the $R^4$ group to form a 5-membered carbocyclic ring, a 6-membered carbocyclic ring or a 7-membered carbocyclic ring fused to the 2-3 face of the piperidine ring. According to some embodiments, one of the $R^3$ groups can be structurally connected to the $R^4$ group to form a 5-membered heterocyclic ring, a 6-membered heterocyclic ring or a 7-membered heterocyclic ring fused to the 2-3 face of the piperidine ring. According to some embodiments, one of the $R^3$ groups is structurally connected to the $R^4$ group to form a 5 membered carbocyclic or heterocyclic ring fused to the 2-3 face of the piperidine ring; for example:

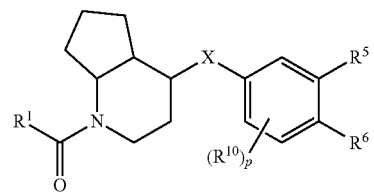

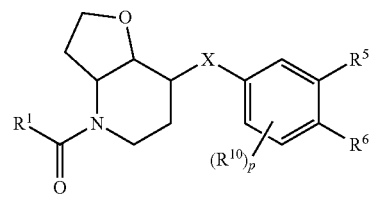

According to some embodiments, X is selected from —$CH_2$—, —$CHR^9$—, —$C(R^9)_2$—, —$C(=CR^{11})_2$—, —C(=O)—, —C(=NO—($C_1$-$C_7$) hydrocarbyl)-, and —C(=NO—C(=O)—($C_1$-$C_7$) hydrocarbyl)-.

According to some embodiments, $R^9$ is independently selected from ($C_1$-$C_6$) alkyl, —O($C_1$-$C_6$) alkyl, ($C_1$-$C_6$) heteroalkyl and halogen. According to some embodiments, $R^9$ is independently selected from —($C_1$-$C_6$) alkyl, —($C_1$-$C_6$) heteroalkyl and —F. According to some embodiments, both $R^9$ groups are —F. According to some embodiments, the two $R^9$ groups can together form a spirofused heterocyclic ring selected from 1,3-dioxolanyl and spiro-dioxanyl; or a $C_3$-$C_7$ carbocyclic ring selected from cyclopropyl, cyclobutyl, cyclopentyl and cyclohexyl.

According to some embodiments, $R^w$ is selected from —H, halogen —CN, and —OH. According to some embodiments, $R^w$ is selected from —H, —F—CN, and —OH. According to some embodiments, $R^w$ is —H. According to some embodiments, $R^w$ is —F. According to some embodiments, $R^w$ is —OH.

According to some embodiments, $R^{10}$ is halogen. According to some embodiments, $R^{10}$ is —F. According to some embodiments, p is 0 or 1.

According to some embodiments, $R^5$ is selected from —H, —$C_1$-$C_6$ alkyl, —$C_3$-$C_6$ cycloalkyl, and halogen. According to some embodiments, $R^5$ is —H.

According to some embodiments, R$^6$ is:

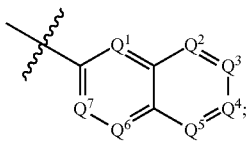

(i)

wherein 1 or 2 of Q$^1$, Q$^2$, Q$^3$, Q$^4$, Q$^5$, Q$^6$ and Q$^7$ are N, and the remainder of Q$^1$, Q$^2$, Q$^3$, Q$^4$, Q$^5$, Q$^6$ and Q$^7$ are C—R$^{12}$. According to some embodiments, when R$^6$ is (i), one of Q$^1$, Q$^2$, Q$^3$, Q$^4$, Q$^5$, Q$^6$ and Q$^7$ is N, and the remainder of Q$^1$, Q$^2$, Q$^3$, Q$^4$, Q$^5$, Q$^6$ and Q$^7$ are C—R$^{12}$. According to some embodiments, when R$^6$ is (i), Q$^2$ is N, and the remainder of Q$^1$, Q$^3$, Q$^4$, Q$^5$, Q$^5$ and Q$^7$ are C—R$^{12}$. According to some embodiments, when R$^6$ is (i), Q$^6$ is N, and Q$^1$, Q$^2$, Q$^3$, Q$^5$, Q$^5$ and Q$^7$ are C—R$^{12}$. According to some embodiments, when R$^6$ is (i), Q$^6$ is N, Q$^2$, Q$^3$, Q$^5$, Q$^5$ and Q$^7$ are CH, and Q$^1$ is C—R$^{12}$, wherein —R$^{12}$ is other than —H.

According to some embodiments, R$^6$ is selected from 9-10 membered bicyclic heteroaryl and substituted 9-10 membered bicyclic heteroaryl; provided that, when R$^6$ is a 9-membered bicyclic heteroaryl or a substituted 9-membered bicyclic heteroaryl, the point of attachment of R$^6$ is on a 6-membered ring portion of the 9-membered bicyclic heteroaryl or substituted 9-membered bicyclic heteroaryl.

According to some embodiments, R$^6$ is:

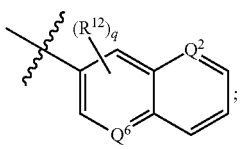

(i$^2$)

wherein one of Q$^2$ and Q$^6$ is N, and the other of Q$^2$ and Q$^6$ is C—R$^{12}$, and q is an integer selected from 0, 1, 2 and 3. According to some embodiments, Q$^2$ is N, and Q$^6$ is C—R$^{12}$. According to some embodiments, Q$^6$ is N, and Q$^2$ is C—R$^{12}$. According to some embodiments, q is selected from 0, 1 and 2. According to some embodiments, q is 0 or 1. It will be understood that a q value of 0 is the equivalent of designating all R$^{12}$ that are bonded to the i$^2$ bicyclic heteroaryl at other than Q$^2$ and Q$^6$ as being —H.

According to some embodiments of i$^2$, each R$^{12}$ is independently selected from —H, —Cl, —F, —CH$_3$, —CH$_2$CH$_3$, —OCH$_3$, —OCH$_2$CH$_3$, —OCH(CH$_3$)$_2$, —O(CH$_2$)$_2$(pyrrolidin-1-yl), —O(CH$_2$)$_3$(pyrrolidin-1-yl), —O(CH$_2$)$_2$(morpholin-1-yl), —O(CH$_2$)$_3$(morpholin-1-yl), —O(CH$_2$)$_2$(piperidin-1-yl), —O(CH$_2$)$_3$(piperidin-1-yl), —O(CH$_2$)$_2$(N-methylpiperazin-1-yl), —O(CH$_2$)$_3$(N-methylpiperazin-1-yl), —O(CH$_2$)$_2$—OCH$_3$, —O(CH$_2$)$_3$—OCH$_3$, —O(CH$_2$)$_2$—N(CH$_3$)$_2$, —O(CH$_2$)$_3$—N(CH$_3$)$_2$, —NH$_2$, NHCH$_3$, N(CH$_3$)$_2$, N-methylpiperazin-1-yl, pyrrolidin-1-yl, morpholin-1-yl, and piperidin-1-yl.

According to some embodiments of i$^{2''}$ is independently selected from —H, benzyl and —C$_1$-C$_6$ alkyl.

According to some embodiments, R$^6$ is:

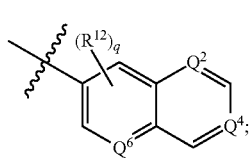

(i$^3$)

wherein one or two of Q$^2$, Q$^4$ and Q$^6$ is N, and the remainder of Q$^2$, Q$^4$ and Q$^6$ are C—R$^{12}$, and q is an integer selected from 0, 1, 2 and 3.

According to some embodiments of i$^3$, each R$^{12}$ is independently selected from —H, halogen, —(C$_1$-C$_6$) alkyl, —(C$_3$-C$_6$) cycloalkyl, 5-6 membered heterocyclyl, —OH, —O(C$_1$-C$_6$) alkyl, —O(CH$_2$)$_r$-(5-6 membered heterocyclyl), —O(CH$_2$)$_r$—O(C$_1$-C$_6$) alkyl, —NH$_2$, —CN, —NH (C$_1$-C$_6$) alkyl, —N(C$_1$-C$_6$ alkyl)$_2$, —NH(CH$_2$)$_r$—O(C$_1$-C$_6$) alkyl, —NH(CH$_2$)$_r$—N(C$_1$-C$_6$ alkyl)$_2$, —C(=O)NH$_2$, —C(=O)NH(C$_1$-C$_6$) alkyl, and —C(=O)N(C$_1$-C$_6$ alkyl)$_2$; wherein r is an integer selected from 1, 2, 3 and 4; or a salt thereof.

According to some embodiments of i$^3$, each R$^{12}$ is independently selected from —H, —Cl, —F, —CH$_3$, —CH$_2$CH$_3$, —OCH$_3$, —OCH$_2$CH$_3$, —OCH(CH$_3$)$_2$, —O(CH$_2$)$_2$(pyrrolidin-1-yl), —O(CH$_2$)$_3$(pyrrolidin-1-yl), —O(CH$_2$)$_2$(morpholin-1-yl), —O(CH$_2$)$_3$(morpholin-1-yl), —O(CH$_2$)$_2$(piperidin-1-yl), —O(CH$_2$)$_3$(piperidin-1-yl), —O(CH$_2$)$_2$(N-methylpiperazin-1-yl), —O(CH$_2$)$_3$(N-methylpiperazin-1-yl), —O(CH$_2$)$_2$—OCH$_3$, —O(CH$_2$)$_3$—OCH$_3$, —O(CH$_2$)$_2$—N(CH$_3$)$_2$, —O(CH$_2$)$_3$—N(CH$_3$)$_2$, —NH$_2$, NHCH$_3$, N(CH$_3$)$_2$, N-methylpiperazin-1-yl, pyrrolidin-1-yl, morpholin-1-yl, and piperidin-1-yl.

According to some embodiments of i$^3$, q is 0, 1 or 2. According to some embodiments, q is 0 or 1. It will be understood that a q value of 0 is the equivalent of designating all R$^{12}$ that are bonded to the bicyclic heteroaryl moiety at other than Q$^2$, Q$^4$ or Q$^6$ as being —H.

According to some embodiments of i$^3$, Q$^2$ is N, and Q$^4$ and Q$^6$ are C—R$^{12}$. According to some embodiments of i$^3$, Q$^6$ is N, and Q$^2$ and Q$^4$ are C—R$^{12}$. According to some embodiments, Q$^4$ is N, and Q$^2$ and Q$^6$ are C—R$^{12}$. According to some embodiments, Q$^2$ is C—R$^{12}$, and Q$^4$ and Q$^6$ are N. According to some embodiments of i$^3$, Q$^6$ is C—R$^{12}$, and Q$^2$ and Q$^4$ are N. According to some embodiments, Q$^4$ is C—R$^{12}$, and Q$^2$ and Q$^6$ are N.

Another aspect of this application is directed to compounds of Formula II:

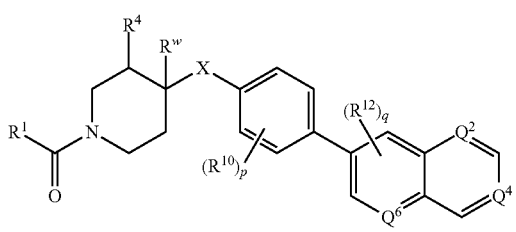

II and salts thereof, e.g., pharmaceutically acceptable salts thereof, wherein:

R$^1$ is selected from —(C$_1$-C$_{10}$) hydrocarbyl, substituted —(C$_1$-C$_{10}$) hydrocarbyl, 3-7 membered heterocyclyl, substituted 3-7 membered heterocyclyl, —NR$^7$R$^8$, —N(OR$^8$) R$^7$, —N(SR$^8$)R$^7$ and —SR$^7$;

$R^4$ is selected from —H, —$(C_1$-$C_6)$ alkyl, —OH, —O$(C_1$-$C_6)$ alkyl, =O, halogen, and —CN;

$R^7$ is selected from —H, —$(C_1$-$C_7)$ hydrocarbyl, substituted —$(C_1$-$C_7)$ hydrocarbyl, —C(=O)$R^8$, and —$(C_1$-$C_6)$ heteroalkyl;

$R^8$ is selected from —H, and —$(C_1$-$C_6)$ alkyl, wherein $R^7$ can be structurally connected to $R^8$ to form a 5 to 7 membered heterocyclyl ring;

X is selected from —$CH_2$—, —$CHR^9$— and —$C(R^9)_2$;

$R^9$ is independently selected from $(C_1$-$C_7)$ hydrocarbyl, $R^w$ is selected from H and halogen;

each $R^{19}$ is independently selected from halogen, —CN, —OH, —$(C_1$-$C_7)$ hydrocarbyl, and substituted —$(C_1$-$C_7)$ hydrocarbyl; p is an integer selected from 0, 1 and 2;

one or two of $Q^2$, $Q^4$ and $Q^6$ is N, and the remainder of $Q^2$, $Q^4$ and $Q^6$ are C—$R^{12}$;

each $R^{12}$ is independently selected from —H, halogen, —$(C_1$-$C_6)$ alkyl, —$(C_3$-$C_6)$ cycloalkyl, —$(C_1$-$C_3)$ haloalkyl, —O$(C_1$-$C_3)$ haloalkyl, 5-6 membered heterocyclyl, —OH, —O$(C_1$-$C_6)$ alkyl, —O$(CH_2)_r$-(5-6 membered heterocyclyl), —O$(CH_2)_r$—O$(C_1$-$C_6)$ alkyl, —$NH_2$, —CN, —NH$(C_1$-$C_6)$ alkyl, —N$(C_1$-$C_6$ alkyl$)_2$, —NH$(CH_2)_r$—O$(C_1$-$C_6)$ alkyl, —NH$(CH_2)_r$—N$(C_1$-$C_6$ alkyl$)_2$, —C(=O)$NH_2$, —C(=O)NH$(C_1$-$C_6)$ alkyl, and —C(=O)N$(C_1$-$C_6$ alkyl$)_2$; wherein q is an integer selected from 0, 1, 2 and 3; and r is an integer selected from 1, 2, 3 and 4; or a salt thereof.

According to some embodiments, each $R^{12}$ is independently selected from —H, halogen, —$(C_1$-$C_6)$ alkyl, —$(C_3$-$C_6)$ cycloalkyl, 5-6 membered heterocyclyl, —OH, —O$(C_1$-$C_6)$ alkyl, —O$(CH_2)_r$-(5-6 membered heterocyclyl), —O$(CH_2)_r$—O$(C_1$-$C_6)$ alkyl, —$NH_2$, —CN, —NH$(C_1$-$C_6)$ alkyl, —N$(C_1$-$C_6$ alkyl$)_2$, —NH$(CH_2)_r$—O$(C_1$-$C_6)$ alkyl, —NH$(CH_2)_r$—N$(C_1$-$C_6$ alkyl$)_2$, —C(=O)$NH_2$, —C(=O)NH$(C_1$-$C_6)$ alkyl, and —C(=O)N$(C_1$-$C_6$ alkyl$)_2$;

According to some embodiments, each $R^{12}$ is independently selected from —H, —F, —$CH_3$, —$CH_2CH_3$, —$OCH_3$, —$OCH_2CH_3$, —$OCH(CH_3)_2$, —O$(CH_2)_2$(pyrrolidin-1-yl), —O$(CH_2)_3$(pyrrolidin-1-yl), —O$(CH_2)_2$(morpholin-1-yl), —O$(CH_2)_3$(morpholin-1-yl), —O$(CH_2)_2$(piperidin-1-yl), —O$(CH_2)_3$(piperidin-1-yl), —O$(CH_2)_2$(N-methylpiperazin-1-yl), —O$(CH_2)_3$(N-methylpiperazin-1-yl), —O$(CH_2)_2$—$OCH_3$, —O$(CH_2)_3$—$OCH_3$, —O$(CH_2)_2$—N$(CH_3)_2$, —O$(CH_2)_3$—N$(CH_3)_2$, —$NH_2$, $NHCH_3$, N$(CH_3)_2$, N-methylpiperazin-1-yl, pyrrolidin-1-yl, morpholin-1-yl, and piperidin-1-yl.

According to some embodiments, q is 0, 1 or 2. According to some embodiments, q is 0 or 1. It will be understood that a q value of 0 is the equivalent of designating all $R^{12}$ that are bonded to the bicyclic heteroaryl moiety at other than $Q^2$, $Q^4$ or $Q^6$ as being —H.

According to some embodiments, $Q^2$ is N, and $Q^4$ and $Q^6$ are C—$R^{12}$. According to some embodiments, $Q^6$ is N, and $Q^2$ and $Q^4$ are C—$R^{12}$. According to some embodiments, $Q^4$ is N, and $Q^2$ and $Q^6$ are C—$R^{12}$. According to some embodiments, $Q^2$ is C—$R^{12}$, and $Q^4$ and $Q^6$ are N. According to some embodiments, $Q^6$ is C—$R^{12}$, and $Q^2$ and $Q^4$ are N. According to some embodiments, $Q^4$ is C—$R^{12}$, and $Q^2$ and $Q^6$ are N.

According to some embodiments, $R^4$ is selected from —H, —OH, =O, —O$(C_1$-$C_6)$ alkyl and halogen. According to some embodiments, $R^4$ is selected from —H, —OH, =O, —$OCH_3$ and —F. According to some embodiments, $R^4$ is —H.

According to some embodiments, $R^1$ is selected from —$(C_1$-$C_{10})$ hydrocarbyl, substituted —$(C_1$-$C_{10})$ hydrocarbyl, 3-7 membered heterocyclyl, substituted 3-7 membered heterocyclyl, —$NR^7R^8$, and —N(O$R^8$)$R^7$.

According to some embodiments, $R^1$ is selected from —$(C_1$-$C_7)$ hydrocarbyl, substituted —$(C_1$-$C_7)$ hydrocarbyl, 3-6 membered heterocyclyl, substituted 3-6 membered heterocyclyl, —$NR^7R^8$, —N(O$R^8$)$R^7$, —N(S$R^8$)$R^7$ and —$SR^7$.

According to some embodiments, $R^1$ is selected from —$(C_1$-$C_7)$ hydrocarbyl, substituted —$(C_1$-$C_7)$ hydrocarbyl, 3-6 membered heterocyclyl, substituted 3-6 membered heterocyclyl, —$NR^7R^8$ and —N(O$R^8$)$R^7$.

According to some embodiments, $R^1$ is selected from —$(C_1$-$C_6)$ alkyl, substituted —$(C_1$-$C_6)$ alkyl, —$(C_1$-$C_6)$ cycloalkyl, substituted —$(C_1$-$C_6)$ cycloalkyl, —C(=O)—$(C_1$-$C_6)$ alkyl, 5-6 membered heterocyclyl, substituted 5-6 membered heterocyclyl, $NH_2$, —NH$(C_1$-$C_6)$ alkyl, —N$((C_1$-$C_6)$ alkyl$)_2$, —NH—O$(C_1$-$C_6)$ alkyl, —S$(C_1$-$C_6)$ alkyl and —NH—S$(C_1$-$C_6)$alkyl.

According to some embodiments, $R^1$ is selected from —$(C_1$-$C_6)$ alkyl, substituted —$(C_1$-$C_6)$ alkyl, —$(C_1$-$C_6)$ cycloalkyl, substituted —$(C_1$-$C_6)$ cycloalkyl, —C(=O)—$(C_1$-$C_6)$ alkyl, 5-6 membered heterocyclyl, substituted 5-6 membered heterocyclyl, $NH_2$, —NH$(C_1$-$C_6)$ alkyl, —N$((C_1$-$C_6)$ alkyl$)_2$, and —NH—O$(C_1$-$C_6)$ alkyl.

According to other embodiments, $R^1$ is selected from —$CH_3$, —$CH_2CH_3$, —$(CH_2)_2CH_3$, —$(CH_2)_3CH_3$, —$(CH_2)_4CH_3$, —CH$(CH_3)_3$, —C$(CH_3)_3$, cyclopropyl, substituted cyclopropyl, cyclobutyl, substituted cyclobutyl, cyclopentyl, —NH—$OCH_3$, —NH—$OCH_2CH_3$, —N$(CH_3)$—$OCH_3$, —$NH_2$, —$NHCH_3$, —NH—$CH_2CH_3$, —NH$(CH_2)_2$—$CH_3$, —NH$(CH_2)_3$—$CH_3$, —NH$(CH_2)_4$—$CH_3$, —NH$(CH_2)_5$—$CH_3$, —N$(CH_3)_2$, —N(Et)$_2$, —NH—CH$(CH_3)_2$, —NH—$OCH_2CH_3$, tetrahydrofuranyl, substituted tetrahydrofuranyl, dioxolanyl, substituted dioxolanyl, tetrahydropyrrolyl, piperidinyl, morpholinyl, tetrahydropyranyl, tetrahydrothiophenyl, sulfolanyl, and tetrahydroisoxazolidinyl.

According to some embodiments, when $R^1$ is substituted cyclopropyl, the cyclopropyl ring is substituted with 1 or 2 substituents selected from —OH, —$CH_2$, —C(=O)$NH_2$, —$NH_2$, —$CH_3$, —CN, and —$CF_3$.

According to some embodiments, when $R^1$ is tetrahydrofuranyl, it is tetrahydrofuran-2-yl or tetrahydrofuran-3-yl. According to some embodiments, when $R^1$ is substituted tetrahydrofuranyl it is 2-methyltetrahydrofuran-2-yl, 5-methyltetra-hydrofuran-2-yl, 2,5-dimethyltetrahydrofuran-2-yl or tetrahydrofuran-4-one-2-yl, 4,4-difluorotetrahydrofuran-2-yl.

According to some embodiments, $R^w$ is —H or —F. According to some embodiments, $R^w$ is —H.

According to some embodiments, when $R^1$ is dioxolanyl, it is 1,3-dioxolan-2-yl. According to some embodiments, when $R^1$ is substituted dioxolanyl it is 2-methyl-1,3-dioxolan-2-yl.

According to some embodiments, when $R^1$ is tetrahydroisoxazolidine, it is tetrahydroisoxazolidin-2-yl. According to some embodiments, when $R^1$ is tetrahydropyrrolyl, it is tetrahydropyrrol-1-yl. According to some embodiments, when $R^1$ is morpholinyl, it is morpholin-1-yl. According to some embodiments, when $R^1$ is piperidinyl, it is piperidin-1-yl. According to some embodiments, when $R^1$ is tetrahydrothiophenyl, it is 2-tetrahydrothiophenyl or 2-tetrahydrothiophenyl. According to some embodiments, when $R^1$ is sulfolanyl, it is sulfolan-2-yl or sulfolan-3-yl.

According to some embodiments, $R^1$ is selected from the moieties depicted in Table 1 (infra) (except for the aryl and heteroaryl $R^1$ moieties in Table 1).

According to some embodiments, X is —$CH_2$—. According to some embodiments, X is CH$(C_1$-$C_6)$alkyl-.

According to some embodiments, R¹⁰ is halogen. According to some embodiments, R¹⁰ is —F. According to some embodiments, p is 0 or 1.

Another aspect of this application is directed to compounds of Formula III:

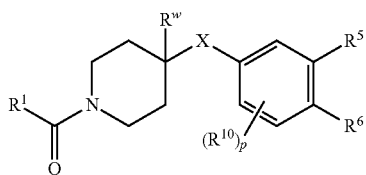

(III)

and salts thereof, e.g., pharmaceutically acceptable salts thereof, wherein:

R¹ is selected from —H, —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —NR⁷R⁸, —NR⁷—OR⁸, —OR⁷, —N(SR⁸)R⁷, —SR⁷, —C(=O)—($C_1$-$C_6$) alkyl and —($C_1$-$C_6$) heteroalkyl;

R⁵ is selected from —H, —($C_1$-$C_7$) hydrocarbyl, —$C_3$-$C_6$ heterocyclyl; halogen, —($C_1$-$C_3$) haloalkyl, —OR⁷ᵃ, —CN, —NR⁷ᵃR⁸ᵃ, —O(CH₂)ₙNR⁷ᵃR⁸ᵃ, —O(CH₂)ₙOR⁸ᵃ, —NR⁸ᵃ(CH₂)ₙNR⁷ᵃR⁸ᵃ, —NR⁸ᵃ(CH₂)ₙOR⁸ᵃ, —C(=O)NR⁷ᵃR⁸ᵃ, —C(=O)OR⁷ᵃ, 5-6 membered heteroaryl, substituted 5-6 membered heteroaryl, 8-10 membered bicyclic heteroaryl, and substituted 8-10 membered bicyclic heteroaryl; wherein n is an integer selected from 1, 2, 3, and 4;

Rʷ is selected from halogen, —CN, —OH, —($C_1$-$C_7$) hydrocarbyl, and substituted —($C_1$-$C_7$) hydrocarbyl;

R⁶ is selected from 6 membered heteroaryl, substituted 6 membered heteroaryl, 9-10 membered bicyclic heteroaryl, and substituted 9-10 membered bicyclic heteroaryl;

R⁷ is selected from —H, —($C_1$-$C_7$) hydrocarbyl, substituted —($C_1$-$C_7$) hydrocarbyl, —C(=O)R⁸, —($C_1$-$C_6$) heteroalkyl, 6 membered aryl, 5-6 membered heteroaryl and 5-6 membered heterocyclyl;

R⁸ is selected from —H, and —($C_1$-$C_6$) alkyl, wherein R⁷ can be structurally connected to R⁸ to form a 5 to 7 membered heterocyclyl ring;

R⁷ᵃ is selected from —H, —($C_1$-$C_7$) hydrocarbyl, substituted —($C_1$-$C_7$) hydrocarbyl, —C(=O)R⁸, and —($C_1$-$C_6$) heteroalkyl;

R⁸ᵃ is selected from —H, and —($C_1$-$C_6$) alkyl, wherein R⁷ᵃ can be structurally connected to R⁸ᵃ to form a 5 to 7 membered heterocyclyl ring;

X is selected from CH₂, CHR⁹, C(R⁹)₂, C=C(R¹¹)₂, C(=O), C(=NO—($C_1$-$C_7$) hydrocarbyl), and C(=NO—C(=O)—($C_1$-$C_7$) hydrocarbyl);

each R⁹ is independently selected from halogen, —($C_1$-$C_7$) hydrocarbyl, —OR¹¹, —NH—R¹¹, —O—(CH₂)ₘ-(5-6 membered heterocyclyl), and —($C_1$-$C_6$) heteroalkyl; or the two R⁹ groups can together form a spirofused heterocyclic ring or carbocyclic ring; wherein m is an integer selected from 1, 2, 3 and 4;

R¹⁰ is selected from halogen, —($C_1$-$C_6$) alkyl and —O($C_1$-$C_6$) alkyl;

p is an integer selected from 0, 1 and 2; and

R¹¹ is selected from —H and —($C_1$-$C_7$) hydrocarbyl.

According to some embodiments, X is selected from —CH₂—, —CHF—, —CF₂—, —CH(CH₃)—, —CH(ethyl)-, —CH(n-propyl)-, —CH(isopropyl)-, —C((CH₃)₂)—, —C(CH₃)(OCH₃)—, C(Et)(OCH₃)—, —C(CH₃)(OEt)-, —CH(NH₂)—, —CH(cyclopropyl)-, spirocyclopropyl, —C(=CH₂)—, —C(=O)—, —C(=NOCH₃)—, —CH(NH-acetyl)-, —CH(NH-formyl)-, —CH(OH)—, —CH(OCH₃)—, —CCH₃(OH)—, —CH(O(CH₂)ₙOCH₃)—, —CH(O(CH₂)ₙ-(5-6 membered heterocycle)), spiro-1,3-dioxolanyl, and spiro-dioxanyl. According to some embodiments, X is —CH₂—. According to some embodiments, X is —CHF— or —CF₂—.

According to some embodiments, R¹ is selected from —H, —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —NR⁷R⁸, —NR⁷—OR⁸, OR⁷, —C(=O)—($C_1$-$C_6$) alkyl and —($C_1$-$C_6$) heteroalkyl;

According to some embodiments, R¹ is selected from —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —NR⁷R⁸, —NR⁷—OR⁸, —OR⁷, and C(=O)—($C_1$-$C_6$) alkyl.

According to some embodiments, R¹ is selected from —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —NR⁷R⁸, —NR⁷—OR⁸, —N(SR⁸)R⁷, —SR⁷, —OR⁷, and —C(=O)—($C_1$-$C_6$) alkyl.

According to some embodiments, R¹ is selected from —($C_1$-$C_6$) alkyl, substituted —($C_1$-$C_6$) alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —NR⁷R⁸, —NR⁷—OR⁸, and —C(=O)—($C_1$-$C_6$) alkyl.

According to some embodiments, R¹ is selected from —($C_1$-$C_6$) alkyl, substituted —($C_1$-$C_6$) alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —NR⁷R⁸, —NR⁷—OR⁸, —N(SR⁸)R⁷, —SR⁷, —OR', and —C(=O)—($C_1$-$C_6$) alkyl.

According to some embodiments, R¹ is selected from the moieties in Table 1, infra.

According to some embodiments, R⁵ is selected from —H, —$C_1$-$C_6$ alkyl, and halogen. According to some embodiments, R⁵ is H.

According to some embodiments, R⁶ is selected from 9-10 membered bicyclic heteroaryl, and substituted 9-10 membered bicyclic heteroaryl. According to some embodiments, R⁶ is selected from:

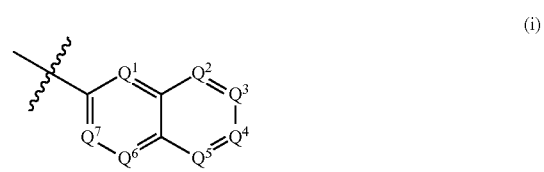

(i)

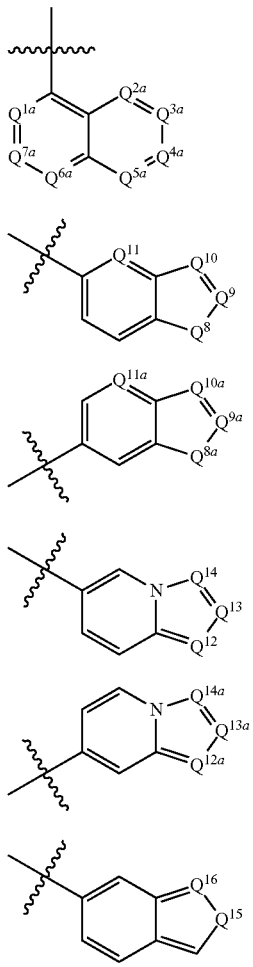

wherein, when $R^6$ is $Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;

when $R^6$ is (ii), $Q^{1a}$, $Q^{2a}$, $Q^{3a}$, $Q^{4a}$, $Q^{5a}$, $Q^{6a}$ and $Q^{7a}$ are independently selected from N and C—$R^{12}$, provided that 1, 2 or 3 of $Q^{1a}$, $Q^{2a}$, $Q^{3a}$, $Q^{4a}$, $Q^{5a}$, $Q^{6a}$ and $Q^{7a}$ are N, and the remainder of $Q^{1a}$, $Q^{2a}$, $Q^{3a}$, $Q^{4a}$, $Q^{5a}$, $Q^{6a}$ and $Q^{7a}$ are C—$R^{12}$;

when $R^6$ is (iii), $Q^8$ is selected from O, S, and N—$R^{12n}$, $Q^9$, $Q^{10}$ and $Q^{11}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (iv), $Q^{8a}$ is selected from O, S, and N—$R^{12n}$, $Q^{9a}$, $Q^{10a}$ and $Q^{11a}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (v), $Q^{12}$, $Q^{13}$ and $Q^{14}$ are independently selected from N and C—$R^{12}$; and when $R^6$ is (vi), $Q^{12n}$, $Q^{13a}$ and $Q^{14a}$ are independently selected from N and C—$R^{12}$;

when $R^6$ is (vii), $Q^{15}$ is selected from N—$R^{12n}$ and C—$R^{12}$ and $Q^{16}$ is selected from N and C—$R^{12}$; provided that one of $Q^{15}$ and $Q^{16}$ are not both C—$R^{12}$;

and wherein each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_p$-(5-6 membered heterocyclyl), —O($CH_2$)$_p$—O($C_1$-$C_6$) alkyl, —$NH_2$, —CN, —NH($C_1$-$C_6$) alkyl, —N($C_1$-$C_6$ alkyl)$_2$, —NH($CH_2$)$_p$—O($C_1$-$C_6$) alkyl, —NH($CH_2$)$_p$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$; wherein p is an integer selected independently from 1, 2, 3, and 4; and each $R^{12n}$ is independently selected from —H, —($C_1$-$C_7$) hydrocarbyl and substituted —($C_1$-$C_7$) hydrocarbyl.

According to some embodiments, $R^6$ is selected from the aromatic ring systems depicted in Table 1b (infra).

It will be understood that the non-bridgehead ring carbon ring atoms in (i), (ii), (iii), (iv), (v), (vi) and (vii) above (i.e., ring atoms which are not designated as Q) may optionally be substituted. According to some embodiments, none of these ring carbon ring atoms are substituted. According to some embodiments, one or two of these ring carbon ring atoms may be substituted. According to some embodiments, one or two of these ring carbon ring atoms may be substituted with a substituent selected from —OH, —($C_1$-$C_3$) alkyl, —O($C_1$-$C_3$)alkyl and halogen. According to some embodiments, one of these ring carbon ring atoms is substituted with a substituent selected from —OH, —$CH_3$, —$OCH_3$, —F and —Cl.

According to some embodiments, each $R^{12}$ is independently selected from —Cl, —F, —$CH_3$, —$CH_2CH_3$, —$OCH_3$, —$OCH_2CH_3$, —$OCH(CH_3)_2$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1-yl), —O($CH_2$)$_2$—$OCH_3$, —O($CH_2$)$_3$—$OCH_3$, —O($CH_2$)$_2$—N($CH_3$)$_2$, —O($CH_2$)$_3$—N($CH_3$)$_2$, —$NH_2$, $NHCH_3$, N($CH_3$)$_2$, N-methylpiperazin-1-yl, pyrrolidin-1-yl, morpholin-1-yl, and piperidin-1-yl.

According to some embodiments, each $R^{12n}$ is independently selected from —H, benzyl and —$C_1$-$C_6$ alkyl.

According to some embodiments, $R^6$ is selected from 9-10 membered bicyclic heteroaryl and substituted 9-10 membered bicyclic heteroaryl; provided that, when $R^6$ is a 9-membered bicyclic heteroaryl or a substituted 9-membered bicyclic heteroaryl, the point of attachment of $R^6$ is on a 6-membered ring portion of the 9-membered bicyclic heteroaryl or substituted 9-membered bicyclic heteroaryl.

According to some embodiments, $R^7$ is selected from —H, —($C_1$-$C_7$) hydrocarbyl, substituted —($C_1$-$C_7$) hydrocarbyl, —C(=O)$R^8$, and —($C_1$-$C_6$) heteroalkyl.

According to some embodiments, $R^7$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^7$ is selected from —H, and —($C_1$-$C_6$) alkyl.

According to some embodiments, $R^{7a}$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^{7a}$ is selected from —H and —($C_1$-$C_6$) alkyl.

According to some embodiments, $R^8$ is selected from —H, and —($C_1$-$C_6$) alkyl. According to some embodiments, $R^8$ is selected from —H, —$CH_3$ and $CH_2CH_3$.

According to some embodiments, $R^{8a}$ is selected from —H, and ($C_1$-$C_6$) alkyl. According to some embodiments, $R^{8a}$ is selected from —H, —$CH_3$ and $CH_2CH_3$.

According to some embodiments, X is selected from —$CH_2$—, —$CHR^9$—, —$C(R^9)_2$—, —$C(=CR^{11})_2$—, —$C(=O)$—, —$C(=NO)$—$(C_1$-$C_7)$ hydrocarbyl)-, and —$C(=NOC(=O))$—$(C_1$-$C_7)$ hydrocarbyl)-.

According to some embodiments, $R^9$ is independently selected from $(C_1$-$C_6)$ alkyl, $O(C_1$-$C_6)$ alkyl, $(C_1$-$C_6)$ heteroalkyl and halogen. According to some embodiments, $R^9$ is independently selected from $(C_1$-$C_6)$ alkyl, —$(C_1$-$C_6)$ heteroalkyl and —F. According to some embodiments, both $R^9$ groups are —F. According to some embodiments, the two $R^9$ groups can together form a spirofused heterocyclic ring selected from 1,3-dioxolanyl and spiro-dioxanyl; or a $C_3$-$C_7$ carbocyclic ring selected from cyclopropyl, cyclobutyl, cyclopentyl and cyclohexyl.

According to some embodiments, $R^w$ is selected from halogen —CN, and —OH. According to some embodiments, $R^w$ is selected from —F—CN, and —OH. According to some embodiments, $R^w$ is —F. According to some embodiments, $R^w$ is —OH.

According to some embodiments, $R^{10}$ is halogen. According to some embodiments, $R^{10}$ is —F.

According to some embodiments, $R^5$ is selected from —H, —$C_1$-$C_6$ alkyl, —$C_3$-$C_6$ cycloalkyl, and halogen. According to some embodiments, $R^5$ is —H.

According to some embodiments, $R^6$ is:

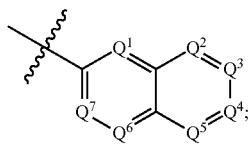

(i)

wherein 1 or 2 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$. According to some embodiments, when $R^6$ is (i), one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{12}$. According to some embodiments, when $R^6$ is (i), $Q^2$ is N, and the remainder of $Q^1$, $Q^2$, $Q^3$, $Q^4$, $Q^5$, $Q^6$ and $Q^7$ are C—$R^{12}$. According to some embodiments, when $R^6$ is (i), $Q^6$ is N, and $Q^1$, $Q^2$, $Q^3$, $Q^5$, $Q^5$ and $Q^7$ are C—$R^{12}$. According to some embodiments, when $R^6$ is (i), $Q^6$ is N, $Q^2$, $Q^3$, $Q^5$, $Q^5$ and $Q^7$ are CH, and $Q^1$ is C—$R^{12}$, wherein —$R^{12}$ is other than —H.

According to some embodiments, $R^6$ is:

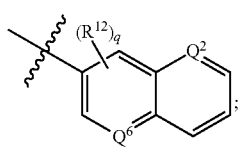

(i²)

wherein one of $Q^2$ and $Q^6$ is N, and the other of $Q^2$ and $Q^6$ is C—$R^{12}$. According to some embodiments of i², $Q^2$ is N, and $Q^6$ is C—$R^{12}$, and q is an integer selected from 0, 1, 2 and 3. According to some embodiments of i², $Q^6$ is N, and $Q^2$ is C—$R^{12}$.

According to some embodiments of i², each $R^{12}$ is independently selected from —H, —Cl, —F, —$CH_3$, —$CH_2CH_3$, —$OCH_3$, —$OCH_2CH_3$, —$OCH(CH_3)_2$, —$O(CH_2)_2$(pyrrolidin-1-yl), —$O(CH_2)_3$(pyrrolidin-1-yl), —$O(CH_2)_2$(morpholin-1-yl), —$O(CH_2)_3$(morpholin-1-yl), —$O(CH_2)_2$(piperidin-1-yl), —$O(CH_2)_3$(piperidin-1-yl), —$O(CH_2)_2$(N-methylpiperazin-1-yl), —$O(CH_2)_3$(N-methylpiperazin-1-yl), —$O(CH_2)_2$—$OCH_3$, —$O(CH_2)_3$—$OCH_3$, —$O(CH_2)_2$—$N(CH_3)_2$, —$O(CH_2)_3$—$N(CH_3)_2$, —$NH_2$, $NHCH_3$, $N(CH_3)_2$, N-methylpiperazin-1-yl, pyrrolidin-1-yl, morpholin-1-yl, and piperidin-1-yl.

According to some embodiments of i², q is 0, 1 or 2. According to some embodiments of i², q is 0 or 1. It will be understood that a q value of 0 is the equivalent of designating all $R^{12}$ that are bonded to the bicyclic heteroaryl moiety i² at other than $Q^2$ or $Q^6$ as being —H.

According to some embodiments, each $R^{12n}$ is independently selected from —H, benzyl and $C_1$-$C_6$ alkyl.

Another aspect of this application is directed to compounds of Formula IV:

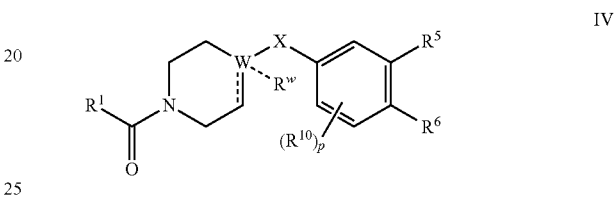

IV and salts thereof, e.g., pharmaceutically acceptable salts thereof, wherein:

$R^1$ is —$NR^7R^8$ or —$N(OR^8)$—$R^7$;

$R^5$ is selected from —H, —$C_1$-$C_7$ hydrocarbyl, —$C_3$-$C_6$ heterocyclyl; halogen, —$(C_1$-$C_3)$ haloalkyl, —$OR^{7a}$, —CN, —$NR^{7a}R^{8a}$, —$O(CH_2)_nNR^{7a}R^{8a}$, —$O(CH_2)_nOR^{8a}$, —$NR^{8a}(CH_2)_nNR^{7a}R^{8a}$, —$NR^{8a}(CH_2)_nOR^{8a}$, —$C(=O)NR^{7a}R^{8a}$, —$C(=O)OR^{7a}$, 5-6 membered heteroaryl, substituted 5-6 membered heteroaryl, 8-10 membered bicyclic heteroaryl, and substituted 8-10 membered bicyclic heteroaryl; wherein n is an integer selected from 1, 2, 3, and 4;

W is an sp³ hybridized carbon atom bonded to a $R^w$ substituent, or is an sp² hybridized carbon atom, and no $R^w$ substituent is present;

===== signifies that the designated bond is a carbon-carbon single bond or a carbon-carbon double bond;

------- signifies that the designated bond is a C—$R^w$ single bond when ===== is a carbon-carbon single bond, i.e., W is an sp³ hybridized carbon atom, and a $R^w$ substituent is present, and that the ------- bond is not present bond when ===== is a carbon-carbon double bond, i.e., W is an sp² hybridized carbon atom, and there is no $R^w$ substituent;

$R^w$ is selected from —H, halogen, —CN, —OH, —$(C_1$-$C_7)$ hydrocarbyl, and substituted —$(C_1$-$C_7)$ hydrocarbyl;

$R^6$ is selected from 6 membered heteroaryl, substituted 6 membered heteroaryl, 9-10 membered bicyclic heteroaryl, and substituted 9-10 membered bicyclic heteroaryl;

$R^7$ is selected from —H, —$(C_1$-$C_7)$ hydrocarbyl, substituted —$(C_1$-$C_7)$ hydrocarbyl, —$C(=O)R^8$, —$(C_1$-$C_6)$ heteroalkyl, 6 membered aryl, 5-6 membered heteroaryl and 5-6 membered heterocyclyl;

$R^8$ is selected from —H, and —$(C_1$-$C_6)$ alkyl, wherein $R^7$ can be structurally connected to $R^8$ to form a 5 to 7 membered heterocyclyl ring;

$R^{7a}$ is selected from —H, —$(C_1$-$C_7)$ hydrocarbyl, substituted —$(C_1$-$C_7)$ hydrocarbyl, —$C(=O)R^8$, and —$(C_1$-$C_6)$ heteroalkyl;

$R^{8a}$ is selected from —H, and —$(C_1$-$C_6)$ alkyl, wherein $R^{7a}$ can be structurally connected to $R^{8a}$ to form a 5 to 7 membered heterocyclyl ring;

X is selected from —CH$_2$—, —CHR$^9$—, —C(R$^9$)$_2$—, —C(=CR$^{11}$)$_2$—, —C(=O)—, —C(=NO—(C$_1$-C$_7$) hydrocarbyl)-, and —C(=NO—C(=O)—(C$_1$-C$_7$) hydrocarbyl)-;

each R$^9$ is independently selected from halogen, (C$_1$-C$_7$) hydrocarbyl, —OR$^{11}$, —NH—R$^{11}$, —O—(CH$_2$)$_m$-(5-6 membered heterocyclyl), and (C$_1$-C$_6$) heteroalkyl; or the two R$^9$ groups can together form a spirofused heterocyclic ring or carbocyclic ring; wherein m is an integer selected from 1, 2, 3 and 4;

R$^{10}$ is selected from halogen, (C$_1$-C$_6$) alkyl and —O(C$_1$-C$_6$) alkyl;

p is an integer selected from 0, 1 and 2; and

R$^{11}$ is selected from —H and —(C$_1$-C$_7$) hydrocarbyl.

According to some embodiments, ═══ is a carbon-carbon single bond.

According to some embodiments, X is selected from —CH$_2$—, —CHF—, —CF$_2$—, —CH(CH$_3$)—, —CH(ethyl)-, —CH(n-propyl)-, —CH(isopropyl)-, —C((CH$_3$)$_2$)—, —C(CH$_3$)(OCH$_3$)—, —C(Et)(OCH$_3$)—, —C(CH$_3$)(OEt)-, —CH(NH$_2$)—, —CH(cyclopropyl)-, spirocyclopropyl, —C(=CH$_2$)—, —C(=O)—, —C(=NOCH$_3$)—, —CH(NH-acetyl)-, —CH(NH-formyl)-, —CH(OH)—, —CH(OCH$_3$)—, —CCH$_3$(OH)—, —CH(O(CH$_2$)$_n$OCH$_3$)—, —CH(O(CH$_2$)$_n$-(5-6 membered heterocycle)), spiro-1,3-dioxolanyl, and spiro-dioxanyl. According to some embodiments, X is —CH$_2$—. According to some embodiments, X is —CHF— or —CF$_2$—.

According to some embodiments, R$^5$ is selected from —H, —C$_1$-C$_6$ alkyl, and halogen. According to some embodiments, R$^5$ is —H.

According to some embodiments, R$^6$ is selected from 9-10 membered bicyclic heteroaryl, and substituted 9-10 membered bicyclic heteroaryl. According to some embodiments, R$^6$ is selected from:

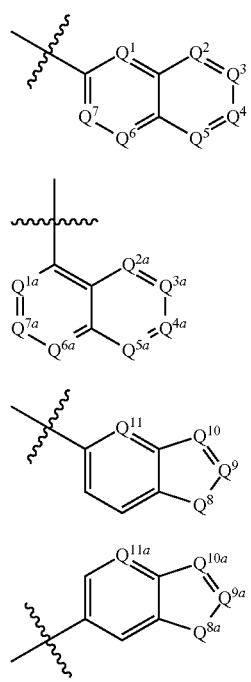

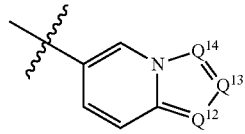

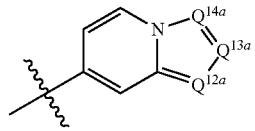

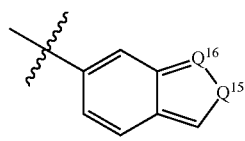

wherein, when R$^6$ is (i), Q$^1$, Q$^2$, Q$^3$, Q$^4$, Q$^5$, Q$^6$ and Q$^7$ are independently selected from N and C—R$^{12}$, provided that 1, 2 or 3 of Q$^1$, Q$^2$, Q$^3$, Q$^4$, Q$^5$, Q$^6$ and Q$^7$ are N, and the remainder of Q$^1$, Q$^2$, Q$^3$, Q$^4$, Q$^5$, Q$^6$ and Q$^7$ are C—R$^{12}$;

when R$^6$ is (ii), Q$^{1a}$, Q$^{2a}$, Q$^{3a}$, Q$^{4a}$, Q$^{5a}$, Q$^{6a}$ and Q$^{7a}$ are independently selected from N and C—R$^{12}$, provided that 1, 2 or 3 of Q$^{1a}$, Q$^{2a}$, Q$^{3a}$, Q$^{4a}$, Q$^{5a}$, Q$^{6a}$ and Q$^{7a}$ are N, and the remainder of Q$^{1a}$, Q$^{2a}$, Q$^{3a}$, Q$^{4a}$, Q$^{5a}$, Q$^{6a}$ and Q$^{7a}$ are C—R$^{12}$;

when R$^6$ is (iii), Q$^8$ is selected from O, S, and N—R$^{12n}$, Q$^9$, Q$^{10}$ and Q$^{11}$ are independently selected from N and C—R$^{12}$, provided that 1 or 2 of Q$^9$, Q$^{10}$ and Q$^{11}$ are N, and the remainder of Q$^9$, Q$^{10}$ and Q$^{11}$ are C—R$^{12}$;

when R$^6$ is (iv), Q$^{8a}$ is selected from O, S, and N—R$^{12n}$, Q$^{9a}$, Q$^{10a}$ and Q$^{11a}$ are independently selected from N and C—R$^{12}$, provided that 1 or 2 of Q$^9$, Q$^{10}$ and Q$^{11}$ are N, and the remainder of Q$^9$, Q$^{10}$ and Q$^{11}$ are C—R$^{12}$;

when R$^6$ is (v), Q$^{12}$, Q$^{13}$ and Q$^{14}$ are independently selected from N and C—R$^{12}$; and when R$^6$ is (vi), Q$^{12n}$, Q$^{13a}$ and Q$^{14a}$ are independently selected from N and C—R$^{12}$;

when R$^6$ is (vii), Q$^{15}$ is selected from N—R$^{12n}$ and C—R$^{12}$ and Q$^{16}$ is selected from N and C—R$^{12}$; provided that one of Q$^{15}$ and Q$^{16}$ are not both C—R$^{12}$;

and wherein each R$^{12}$ is independently selected from —H, halogen, —(C$_1$-C$_6$) alkyl, —(C$_3$-C$_6$) cycloalkyl, 5-6 membered heterocyclyl, —OH, —O(C$_1$-C$_6$) alkyl, —O(CH$_2$)$_p$-(5-6 membered heterocyclyl), —O(CH$_2$)$_p$—O(C$_1$-C$_6$) alkyl, —NH$_2$, —CN, —NH(C$_1$-C$_6$) alkyl, —N(C$_1$-C$_6$ alkyl)$_2$, —NH(CH$_2$)$_p$—O(C$_1$-C$_6$) alkyl, —NH(CH$_2$)$_p$—N(C$_1$-C$_6$ alkyl)$_2$, —C(=O)NH$_2$, —C(=O)NH(C$_1$-C$_6$) alkyl, —C(=O)N(C$_1$-C$_6$ alkyl)$_2$, —(C$_1$-C$_3$) haloalkyl, —O(C$_1$-C$_3$) haloalkyl, and —O(CH$_2$)$_r$—N(C$_1$-C$_6$ alkyl)$_2$; wherein p is an integer selected independently from 1, 2, 3, and 4; and each R$^{12n}$ is independently selected from —H, —(C$_1$-C$_7$) hydrocarbyl and substituted —(C$_1$-C$_7$) hydrocarbyl.

According to some embodiments, R$^6$ is selected from the aromatic ring systems depicted in Table 1b (infra).

It will be understood that the non-bridgehead ring carbon ring atoms in (i), (ii), (iii), (iv), (v), (vi) and (vii) above (i.e., ring atoms which are not designated as Q) may optionally be substituted. According to some embodiments, none of these ring carbon ring atoms are substituted. According to some embodiments, one or two of these ring carbon ring atoms may be substituted. According to some embodiments, one or two of these ring carbon ring atoms may be substituted with a substituent selected from —OH, —($C_1$-$C_3$) alkyl, —O($C_1$-$C_3$)alkyl and halogen. According to some embodiments, one of these ring carbon ring atoms is substituted with a substituent selected from —OH, —$CH_3$, —$OCH_3$, —F and —Cl.

According to some embodiments, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_p$-(5-6 membered heterocyclyl), —O($CH_2$)$_p$—O($C_1$-$C_6$) alkyl, —$NH_2$, —CN, —NH($C_1$-$C_6$) alkyl, —N($C_1$-$C_6$ alkyl)$_2$, —NH($CH_2$)$_p$—O($C_1$-$C_6$) alkyl, —NH($CH_2$)$_p$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$.

According to some embodiments, each $R^{12}$ is independently selected from —H, —Cl, —F, —$CH_3$, —$CH_2CH_3$, —$OCH_3$, —$OCH_2CH_3$, —$OCH(CH_3)_2$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1-yl), —O($CH_2$)$_2$—$OCH_3$, —O($CH_2$)$_3$—$OCH_3$, —O($CH_2$)$_2$—N($CH_3$)$_2$, —O($CH_2$)$_3$—N($CH_3$)$_2$, —$NH_2$, $NHCH_3$, N($CH_3$)$_2$, N-methylpiperazin-1-yl, pyrrolidin-1-yl, morpholin-1-yl and piperidin-1-yl.

According to some embodiments, each $R^{12n}$ is independently selected from —H, benzyl and $C_1$-$C_6$ alkyl.

According to some embodiments, $R^6$ is selected from 9-10 membered bicyclic heteroaryl and substituted 9-10 membered bicyclic heteroaryl; provided that, when $R^6$ is a 9-membered bicyclic heteroaryl or a substituted 9-membered bicyclic heteroaryl, the point of attachment of $R^6$ is on a 6-membered ring portion of the 9-membered bicyclic heteroaryl or substituted 9-membered bicyclic heteroaryl.

According to some embodiments, $R^7$ is selected from —H, —($C_1$-$C_7$) hydrocarbyl, substituted —($C_1$-$C_7$) hydrocarbyl, —C(=O)$R^8$, and —($C_1$-$C_6$) heteroalkyl.

According to some embodiments, $R^7$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^7$ is selected from —H, and —($C_1$-$C_6$) alkyl.

According to some embodiments, $R^{7a}$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^{7a}$ is selected from H and —($C_1$-$C_6$) alkyl.

According to some embodiments, $R^8$ is selected from —H, and —($C_1$-$C_6$) alkyl. According to some embodiments, $R^8$ is selected from —H, —$CH_3$ and —$CH_2CH_3$.

According to some embodiments, $R^{8a}$ is selected from —H, and —($C_1$-$C_6$) alkyl. According to some embodiments, $R^{8a}$ is selected from —H, —$CH_3$ and —$CH_2CH_3$.

According to some embodiments, X is selected from —$CH_2$—, —$CHR^9$—, —$C(R^9)_2$—, —C(=$CR^{11}$)$_2$—, —C(=O)—, —C(=NO—($C_1$-$C_7$) hydrocarbyl)-, and —C(=NO—C(=O)—($C_1$-$C_7$) hydrocarbyl)-.

According to some embodiments, $R^9$ is independently selected from —($C_1$-$C_6$) alkyl, —O($C_1$-$C_6$) alkyl, ($C_1$-$C_6$) heteroalkyl and halogen. According to some embodiments, $R^9$ is independently selected from —($C_1$-$C_6$) alkyl, —($C_1$-$C_6$) heteroalkyl and —F. According to some embodiments, both $R^9$ groups are —F. According to some embodiments, the two $R^9$ groups can together form a spirofused heterocyclic ring selected from 1,3-dioxolanyl and spiro-dioxanyl; or a $C_3$-$C_7$ carbocyclic ring selected from cyclopropyl, cyclobutyl, cyclopentyl and cyclohexyl.

According to some embodiments, $R^w$ is selected from —H, halogen —CN, and —OH. According to some embodiments, $R^w$ is selected from —H, —F—CN, and —OH. According to some embodiments, $R^w$ is —H. According to some embodiments, $R^w$ is —F. According to some embodiments, $R^w$ is —OH.

According to some embodiments, $R^{10}$ is halogen. According to some embodiments, $R^{10}$ is —F.

According to some embodiments, $R^5$ is selected from —H, —$C_1$-$C_6$ alkyl, —$C_3$-$C_6$ cycloalkyl, and halogen. According to some embodiments, $R^5$ is —H.

According to some embodiments, $R^6$ is:

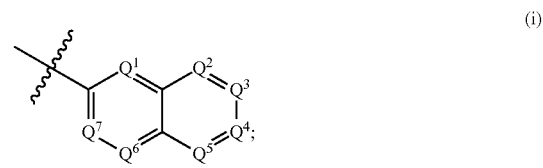

wherein 1 or 2 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$. According to some embodiments, when $R^6$ is (i), one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{12}$. According to some embodiments, when $R^6$ is (i), $Q^2$ is N, and the remainder of $Q^1$, $Q^3$, $Q^4$, $Q^5$, $Q^6$ and $Q^7$ are C—$R^{12}$. According to some embodiments, when $R^6$ is (i), $Q^6$ is N, and $Q^1$, $Q^2$, $Q^3$, $Q^5$, $Q^5$ and $Q^7$ are C—$R^{12}$. According to some embodiments, when $R^6$ is (i), $Q^6$ is N, $Q^2$, $Q^3$, $Q^5$, $Q^5$ and $Q^7$ are CH, and $Q^1$ is C—$R^{12}$, wherein —$R^{12}$ is other than —H.

According to some embodiments, $R^6$ is:

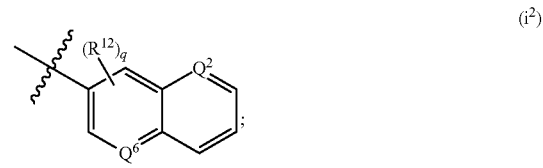

wherein one of $Q^2$ and $Q^6$ is N, and the other of $Q^2$ and $Q^6$ is C—$R^{12}$, and q is an integer selected from 0, 1, 2 and 3. According to some embodiments of $i^2$, $Q^2$ is N, and $Q^6$ is C—$R^{12}$. According to some embodiments of $i^2$, $Q^6$ is N, and $Q^2$ is C—$R^{12}$. According to some embodiments of $i^2$, q is 0, 1 or 2. According to some embodiments of $i^2$, q is 0 or 1. It will be understood that a q value of 0 is the equivalent of designating all $R^{12}$ that are bonded to the bicyclic heteroaryl moiety $i^2$ at other than $Q^2$ or $Q^6$ as being —H.

According to some embodiments of $i^2$, each $R^{12}$ is independently selected from —H, —Cl, —F, —$CH_3$, —$CH_2CH_3$, —$OCH_3$, —$OCH_2CH_3$, —$OCH(CH_3)_2$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1-yl), —O($CH_2$)$_2$—$OCH_3$, —O($CH_2$)$_3$—$OCH_3$, —O($CH_2$)$_2$—N($CH_3$)$_2$, —O($CH_2$)$_3$—N($CH_3$)$_2$, —$NH_2$, $NHCH_3$, N($CH_3$)$_2$, N-methylpiperazin-1-yl, pyrrolidin-1-yl, morpholin-1-yl, and piperidin-1-yl.

According to some embodiments of i², each $R^{12n}$ is independently selected from —H, benzyl and —$C_1$-$C_6$ alkyl.

Another aspect of this application is directed to compounds of Formula V:

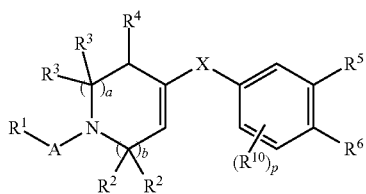

V and salts thereof, e.g., pharmaceutically acceptable salts thereof, wherein:

A is C(=O)— or —$SO_2$—;

$R^1$ is selected from —H, —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —$NR^7R^8$, —$N(OR^8)R^7$, —$N(SR^8)R^7$, C(=O)—($C_1$-$C_6$) alkyl and ($C_1$-$C_6$) heteroalkyl;

a and b are independently selected from 0 and 1;

each $R^2$ and each $R^3$ is independently selected from —H and —($C_1$-$C_4$) alkyl;

$R^4$ is selected from —H, —($C_1$-$C_6$) alkyl, =O, —OH, —O—($C_1$-$C_6$) alkyl, halogen, and —CN; wherein one of the $R^3$ groups can be structurally connected to one of the $R^2$ groups to form an alkylene bridge to produce a bicyclic ring; or one of the $R^3$ groups can be structurally connected to the $R^1$ group to form a 5 to 7 membered heterocyclyl ring fused to the 1-2 face of the piperidine ring; or one of the $R^3$ groups can be structurally connected to the $R^4$ group to form a 5-7 membered carbocyclic or heterocyclic ring fused to the 2-3 face of the piperidine ring;

$R^5$ is selected from —H, —$C_1$-$C_7$ hydrocarbyl, —$C_3$-$C_6$ heterocyclyl; halogen, —($C_1$-$C_3$) haloalkyl, —$OR^{7a}$, —CN, —$NR^{7a}R^{8a}$, —O(CH$_2$)$_n$$NR^{7a}R^{8a}$, —O(CH$_2$)$_n$$OR^{8a}$, —$NR^{8a}$(CH$_2$)$_n$$NR^{7a}R^{8a}$, —$NR^{8a}$(CH$_2$)$_n$$OR^{8a}$, —C(=O)$NR^{7a}R^{8a}$, —C(=O)$OR^{7a}$, 5-6 membered heteroaryl, substituted 5-6 membered heteroaryl, 8-10 membered bicyclic heteroaryl, and substituted 8-10 membered bicyclic heteroaryl; wherein n is an integer selected from 1, 2, 3, and 4;

$R^6$ is selected from 6 membered heteroaryl, substituted 6 membered heteroaryl, 9-10 membered bicyclic heteroaryl, and substituted 9-10 membered bicyclic heteroaryl;

$R^7$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^8$ is selected from —H and —($C_1$-$C_6$) alkyl, wherein $R^7$ can be structurally connected to $R^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^{8a}$ is selected from —H, and —($C_1$-$C_6$) alkyl, wherein $R^{7a}$ can be structurally connected to $R^{8a}$ to form a 5 to 7 membered heterocyclyl ring;

X is selected from —$CH_2$—, —$CHR^9$—, —$C(R^9)_2$—, —$C=C(R^{11})_2$—, —C(=O)—, —C(=NO—($C_1$-$C_7$) hydrocarbyl)-, and —C(=NO—C(=O)—($C_1$-$C_7$) hydrocarbyl)-;

each $R^9$ is independently selected from halogen, ($C_1$-$C_7$) hydrocarbyl, —$OR^{11}$, —NH—$R^{11}$, —O—(CH$_2$)$_m$-(5-6 membered heterocyclyl), and —($C_1$-$C_6$) heteroalkyl; or the two $R^9$ groups can together form a spirofused heterocyclic ring or carbocyclic ring; wherein m is an integer selected from 1, 2, 3 and 4;

$R^{10}$ is selected from halogen, —($C_1$-$C_6$) alkyl and —O($C_1$-$C_6$) alkyl;

p is an integer selected from 0, 1 and 2; and $R^{11}$ is selected from —H and —($C_1$-$C_7$) hydrocarbyl.

According to some embodiments, A is —C(=O)—.

According to some embodiments, a is 1 and b is 0. According to some embodiments, a is 0 and b is 1. According to some embodiments, a and b are both 1.

According to some embodiments, X is selected from —$CH_2$—, —CHF—, —$CF_2$—, —CH($CH_3$)—, —CH(ethyl)-, —CH(n-propyl)-, —CH(isopropyl)-, —C(($CH_3$)$_2$)—, —C($CH_3$)(OCH$_3$)—, C(Et)(OCH$_3$)—, —C($CH_3$)(OEt)-, —CH($NH_2$)—, —CH(cyclopropyl)-, spirocyclopropyl, —C(=$CH_2$)—, —C(=O)—, —C(=NOCH$_3$)—, —CH(NH-acetyl)-, —CH(NH-formyl)-, —CH(OH)—, —CH($OCH_3$)—, —$CCH_3$(OH)—, —CH(O(CH$_2$)$_m$$OCH_3$)—, —CH(O(CH$_2$)$_m$-(5-6 membered heterocycle)), Spiro-1,3-dioxolanyl, and spiro-dioxanyl. According to some embodiments, X is —$CH_2$—. According to some embodiments, X is —CHF— or —$CF_2$—.

According to some embodiments, $R^1$ is selected from —H, —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —$NR^7R^8$, —$N(OR^8)R^7$, —C(=O)—($C_1$-$C_6$) alkyl and —($C_1$-$C_6$) heteroalkyl;

According to some embodiments, $R^1$ is selected from —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —$NR^7R^8$, —$NR^7$—O—$R^8$, —$OR^7$, and —C(=O)—($C_1$-$C_6$) alkyl.

According to some embodiments, $R^1$ is selected from —($C_1$-$C_6$) alkyl, substituted —($C_1$-$C_6$) alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —$NR^7R^8$, —$NR^7$—$OR^8$, —$OR^7$, and —C(=O)—($C_1$-$C_6$) alkyl.

According to some embodiments, $R^1$ is selected from the moieties in Table 1, infra.

According to some embodiments, $R^2$ is —H.

According to some embodiments, $R^3$ is —H.

According to some embodiments, $R^4$ is selected from —H, —($C_1$-$C_6$) alkyl and halogen.

According to some embodiments, one of the $R^3$ groups is structurally connected to one of the $R^2$ groups to form a ($C_1$-$C_3$) alkylene bridge (e.g., a $CH_2$—$CH_2$— bridge) to produce a bicyclic ring; for example:

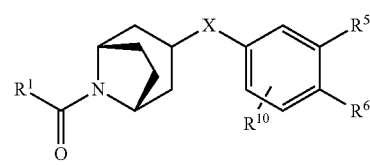

According to some embodiments, one of the $R^3$ groups is structurally connected to the $R^1$ group to form a 5-6 membered lactam ring fused to the 1-2 face of the piperidine ring; for example:

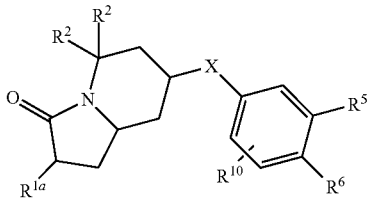

wherein the $R^{1a}$ moiety represents the residue of the $R^1$ substituent covalently bonded to one of the $R^2$ substituents (alpha to the A moiety carbonyl group). According to some embodiments, $R^{1a}$ is selected from —H, —($C_1$-$C_9$) hydrocarbyl, substituted —($C_1$-$C_9$) hydrocarbyl and ($C_1$-$C_5$) heteroalkyl;

According to some embodiments, one of the $R^3$ groups is structurally connected to the $R^4$ group to form a 5-6 membered carbocyclic or heterocyclic ring fused to the 2-3 face of the piperidine ring; for example:

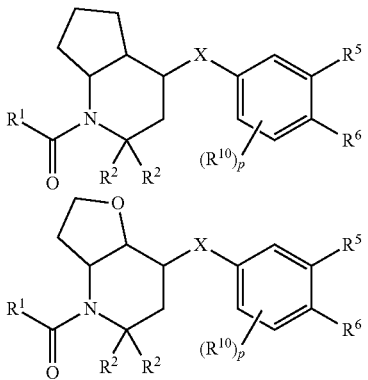

According to some embodiments, $R^5$ is selected from —H, —$C_1$-$C_6$ alkyl, and halogen. According to some embodiments, $R^5$ is —H.

According to some embodiments, $R^6$ is selected from 9-10 membered bicyclic heteroaryl, and substituted 9-10 membered bicyclic heteroaryl. According to some embodiments, $R^6$ is selected from

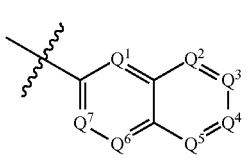

(i)

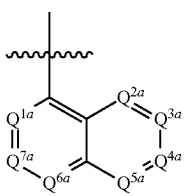

(ii)

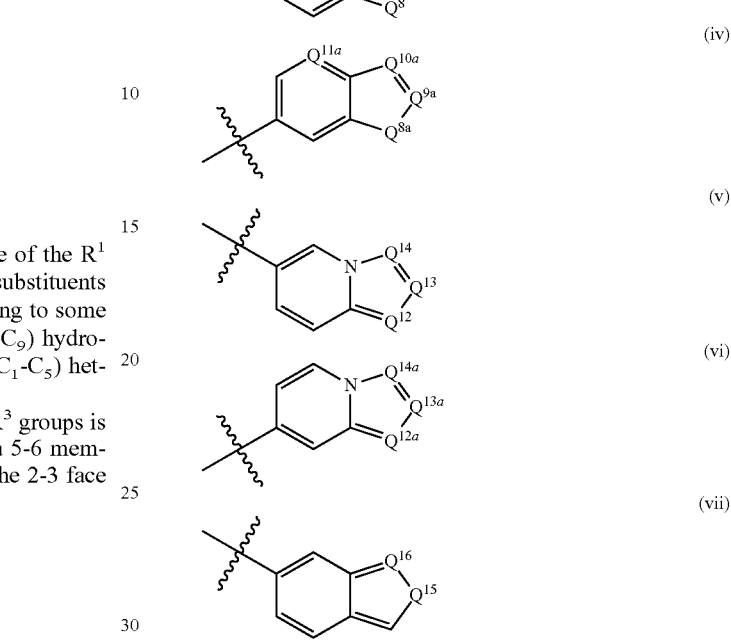

wherein, when $R^6$ is $Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;

when $R^6$ is (ii), $Q^{1a}$, $Q^{2a}$, $Q^{3a}$, $Q^{4a}$, $Q^5$, $Q^{6a}$ and $Q^{7a}$ are independently selected from N and C—$R^{12}$, provided that 1, 2 or 3 of $Q^{1a}$, $Q^{2a}$, $Q^{3a}$, $Q^{4a}$, $Q^{5a}$, $Q^{6a}$ and $Q^{7a}$ are N, and the remainder of $Q^{1a}$, $Q^{2a}$, $Q^{3a}$, $Q^{4a}$, $Q^{5a}$, $Q^{6a}$ and $Q^{7a}$ are C—$R^{12}$;

when $R^6$ is (iii), $Q^8$ is selected from O, S, and N—$R^{12n}$, $Q^9$, $Q^{10}$ and $Q^{11}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (iv), $Q^{8a}$ is selected from O, S, and N—$R^{12n}$, $Q^{9a}$, $Q^{10a}$ and $Q^{11a}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (v), $Q^{12}$, $Q^{13}$ and $Q^{14}$ are independently selected from N and C—$R^{12}$; and when $R^6$ is (vi), $Q^{12n}$, $Q^{13a}$ and $Q^{14a}$ are independently selected from N and C—$R^{12}$;

when $R^6$ is (vii), $Q^{15}$ is selected from N—$R^{12n}$ and C—$R^{12}$ and $Q^{16}$ is selected from N and C—$R^{12}$; provided that one of $Q^{15}$ and $Q^{16}$ are not both C—$R^{12}$;

and wherein each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_p$-(5-6 membered heterocyclyl), —O($CH_2$)$_p$—O($C_1$-$C_6$) alkyl, —$NH_2$, —CN, —NH($C_1$-$C_6$) alkyl, —N($C_1$-$C_6$ alkyl)$_2$, —NH($CH_2$)$_p$—O($C_1$-$C_6$) alkyl, —NH($CH_2$)$_p$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$, —($C_1$-$C_3$) haloalkyl, —O($C_1$-$C_3$) haloalkyl, and —O($CH_2$)—N($C_1$-$C_6$ alkyl)$_2$; wherein p is an integer selected independently from 1, 2, 3, and 4; and each $R^{12n}$ is independently selected from —H, —($C_1$-$C_7$) hydrocarbyl and substituted —($C_1$-$C_7$) hydrocarbyl.

According to some embodiments, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_p$-(5-6 membered heterocyclyl), —O($CH_2$)$_p$—O($C_1$-$C_6$) alkyl, —$NH_2$, —CN, —NH($C_1$-$C_6$) alkyl, —N($C_1$-$C_6$ alkyl)$_2$, —NH($CH_2$)$_p$—O($C_1$-$C_6$) alkyl, —NH($CH_2$)$_p$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$.

According to some embodiments, each $R^{12}$ is independently selected from —H, —Cl, —F, —$CH_3$, —$CH_2CH_3$, —$OCH_3$, —$OCH_2CH_3$, —$OCH(CH_3)_2$, —$O(CH_2)_2$(pyrrolidin-1-yl), —$O(CH_2)_3$(pyrrolidin-1-yl), —$O(CH_2)_2$(morpholin-1-yl), —$O(CH_2)_3$(morpholin-1-yl), —$O(CH_2)_2$(piperidin-1-yl), —$O(CH_2)_3$(piperidin-1-yl), —$O(CH_2)_2$(N-methylpiperazin-1-yl), —$O(CH_2)_3$(N-methylpiperazin-1-yl), —$O(CH_2)_2$—$OCH_3$, —$O(CH_2)_3$—$OCH_3$, —$O(CH_2)_2$—$N(CH_3)_2$, —$O(CH_2)_3$—$N(CH_3)_2$, —$NH_2$, $NHCH_3$, $N(CH_3)_2$, N-methylpiperazin-1-yl, pyrrolidin-1-yl, morpholin-1-yl, and piperidin-1-yl.

According to some embodiments, each $R^{12n}$ is independently selected from —H, benzyl and —$C_1$-$C_6$ alkyl.

According to some embodiments, $R^7$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^7$ is selected from —H, and —($C_1$-$C_6$) alkyl.

According to some embodiments, $R^{7a}$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^{7a}$ is selected from H and —($C_1$-$C_6$) alkyl.

According to some embodiments, $R^8$ is selected from —H, and —($C_1$-$C_6$) alkyl. According to some embodiments, $R^8$ is selected from —H, —$CH_3$ and $CH_2CH_3$.

According to some embodiments, $R^{8a}$ is selected from —H, and ($C_1$-$C_6$) alkyl. According to some embodiments, $R^{8a}$ is selected from —H, —$CH_3$ and —$CH_2CH_3$.

According to some embodiments each $R^3$ is —H or —$CH_3$. According to other embodiments, each $R^3$ is —H.

According to some embodiments, $R^4$ is selected from —H, ($C_1$-$C_6$)alkyl, —OH, —O($C_1$-$C_6$)alkyl, —CN and halogen According to other embodiments, $R^4$ is selected from —H, —$CH_3$, —OH, —$OCH_3$, —F, —Cl, and CN. According to some embodiments, $R^4$ is halogen or —H. According to some embodiments, $R^4$ is —F or —H. According to some embodiments, $R^4$ is —H.

According to some embodiments, one of the $R^3$ groups can be structurally connected to one of the $R^2$ groups to form a $C_2$-$C_3$ alkylene bridge to produce a bicyclic ring. According to some embodiments, one of the $R^3$ groups is structurally connected to one of the $R^2$ groups to form a $CH_2$—$CH_2$— bridge to produce a bicyclic ring; for example:

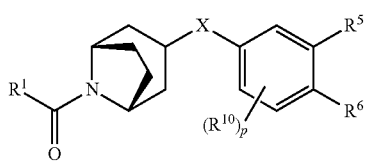

According to some embodiments, one of the $R^3$ groups can be structurally connected to the $R^1$ group to form a 5 to 7 membered heterocyclyl ring fused to the 1-2 face of the piperidine ring. According to some embodiments, one of the $R^3$ groups is structurally connected to the $R^1$ group to form a 5-membered lactam ring fused to the 1-2 face of the piperidine ring; for example:

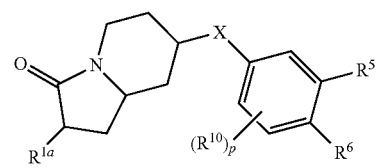

wherein the $R^{1a}$ moiety represents the residue of the $R^1$ substituent covalently bonded to one of the $R^2$ substituents (alpha to the A moiety carbonyl group).

According to some embodiments, one of the $R^3$ groups can be structurally connected to the $R^1$ group to form a 5-membered heterocyclyl ring fused to the 1-2 face of the piperidine ring.

According to some embodiments, one of the $R^3$ groups can be structurally connected to the $R^1$ group to form a bicyclic indolizin-3-one ring. According to some embodiments, one of the $R^3$ groups can be structurally connected to the $R^1$ group to form a 6 membered heterocyclyl ring fused to the 1-2 face of the piperidine ring. According to some embodiments, one of the $R^3$ groups can be structurally connected to the $R^1$ group to form a bicyclic quinolizin-4-one ring.

According to some embodiments, one of the $R^3$ groups can be structurally connected to the $R^4$ group to form a 5-7 membered carbocyclic or heterocyclic ring fused to the 2-3 face of the piperidine ring. According to some embodiments, one of the $R^3$ groups can be structurally connected to the $R^4$ group to form a 5-membered carbocyclic ring, a 6-membered carbocyclic ring or a 7-membered carbocyclic ring fused to the 2-3 face of the piperidine ring. According to some embodiments, one of the $R^3$ groups can be structurally connected to the $R^4$ group to form a 5-membered heterocyclic ring, a 6-membered heterocyclic ring or a 7-membered heterocyclic ring fused to the 2-3 face of the piperidine ring. According to some embodiments, one of the $R^3$ groups is structurally connected to the $R^4$ group to form a 5-membered carbocyclic or heterocyclic ring fused to the 2-3 face of the piperidine ring; for example:

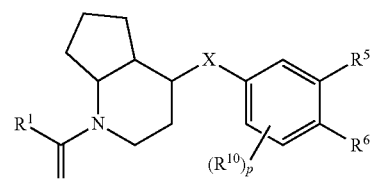

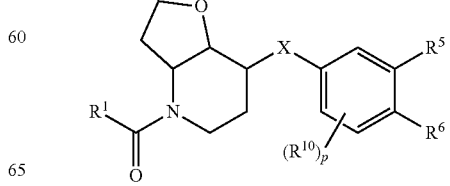

According to some embodiments, X is selected from —$CH_2$—, —$CHR^9$—, —$C(R^9)_2$—, —$C=C(R^{11})_2$—, —$C(=O)$—, —$C(=NO$—$(C_1$-$C_7)$ hydrocarbyl)-, and —$C(=NO$—$C(=O))$—$(C_1$-$C_7)$ hydrocarbyl)-;

According to some embodiments, $R^9$ is independently selected from —$(C_1$-$C_6)$ alkyl, —$O(C_1$-$C_6)$ alkyl, $(C_1$-$C_6)$ heteroalkyl and halogen. According to some embodiments, $R^9$ is independently selected from —$(C_1$-$C_6)$ alkyl, —$(C_1$-$C_6)$ heteroalkyl and —F. According to some embodiments, both $R^9$ groups are —F. According to some embodiments, the two $R^9$ groups can together form a spirofused heterocyclic ring selected from 1,3-dioxolanyl and spiro-dioxanyl; or a $C_3$-$C_7$ carbocyclic ring selected from cyclopropyl, cyclobutyl, cyclopentyl and cyclohexyl.

According to some embodiments, $R^{10}$ is halogen. According to some embodiments, $R^{10}$ is —F.

According to some embodiments, $R^5$ is selected from —H, —$C_1$-$C_6$ alkyl, —$C_3$-$C_6$ cycloalkyl and halogen. According to some embodiments, $R^5$ is —H.

According to some embodiments, $R^6$ is selected from the aromatic ring systems depicted in Table 1b (infra).

According to some embodiments, $R^6$ is:

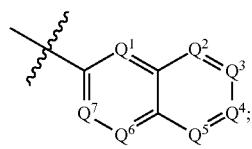

(i)

wherein 1 or 2 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$. According to some embodiments, when $R^6$ is (i), one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{12}$. According to some embodiments, when $R^6$ is (i), $Q^2$ is N, and the remainder of $Q^1$, $Q^3$, $Q^4$, $Q^5$, $Q^6$ and $Q^7$ are C—$R^{12}$. According to some embodiments, when $R^6$ is (i), $Q^6$ is N, and $Q^1$, $Q^2$, $Q^3$, $Q^5$, $Q^5$ and $Q^7$ are C—$R^{12}$. According to some embodiments, when $R^6$ is (i), $Q^6$ is N, $Q^2$, $Q^3$, $Q^5$, $Q^5$ and $Q^7$ are CH, and $Q^1$ is C—$R^{12}$, wherein —$R^{12}$ is other than —H.

According to some embodiments, $R^6$ is:

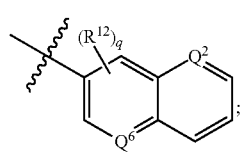

(i²)

wherein one of $Q^2$ and $Q^6$ is N, and the other of $Q^2$ and $Q^6$ is C—$R^{12}$ and q is an integer selected from 0, 1, 2 and 3. According to some embodiments of i², $Q^2$ is N, and $Q^6$ is C—$R^{12}$. According to some embodiments of i², $Q^6$ is N, and $Q^2$ is C—$R^{12}$. According to some embodiments, q is 0, 1 or 2. According to some embodiments of i², q is 0 or 1. It will be understood that a q value of 0 is the equivalent of designating all $R^{12}$ that are bonded to the bicyclic heteroaryl moiety i² at other than $Q^2$ or $Q^6$ as being —H.

According to some embodiments of i², each $R^{12}$ is independently selected from —H, —Cl, —F, —$CH_3$, —$CH_2CH_3$, —$OCH_3$, —$OCH_2CH_3$, —$OCH(CH_3)_2$, —$O(CH_2)_2$(pyrrolidin-1-yl), —$O(CH_2)_3$(pyrrolidin-1-yl), —$O(CH_2)_2$(morpholin-1-yl), —$O(CH_2)_3$(morpholin-1-yl), —$O(CH_2)_2$(piperidin-1-yl), —$O(CH_2)_3$(piperidin-1-yl), —$O(CH_2)_2$(N-methylpiperazin-1-yl), —$O(CH_2)_3$(N-methylpiperazin-1-yl), —$O(CH_2)_2$—$OCH_3$, —$O(CH_2)_3$—$OCH_3$, —$O(CH_2)_2$—$N(CH_3)_2$, —$O(CH_2)_3$—$N(CH_3)_2$, —$NH_2$, $NHCH_3$, $N(CH_3)_2$, N-methylpiperazin-1-yl, pyrrolidin-1-yl, morpholin-1-yl, and piperidin-1-yl.

According to some embodiments, each $R^{12n}$ is independently selected from —H, benzyl and —$C_1$-$C_6$ alkyl.

Compounds according to Formula I may include for example: 1-[4-(4-quinolin-3-yl-benzyl)-piperidin-1-yl]-propan-1-one; 2-methyl-1-[4-(4-quinolin-3-yl-benzyl)-piperidin-1-yl]-propan-1-one; cyclopropyl-[4-(4-quinolin-3-yl-benzyl)-piperidin-1-yl]-methanone; 4-(4-quinolin-3-yl-benzyl)-piperidin-1-yl]-(R)-tetrahydro-furan-2-yl-methanone; 4-(4-quinolin-3-yl-benzyl)-piperidin-1-yl]-(S)-tetrahydro-furan-2-yl-methanone; 1-{4-[fluoro-(4-quinolin-3-yl-phenyl)-methyl]-piperidin-1-yl}-propan-1-one; cyclopropyl-{4-[fluoro-(4-quinolin-3-yl-phenyl)-methyl]-piperidin-1-yl}-methanone; {4-[fluoro-(4-quinolin-3-yl-phenyl)-methyl]-piperidin-1-yl}-(R)-tetrahydrofuran-2-yl-methanone; 1-(4-{difluoro-[4-(4-methyl-quinolin-3-yl)-phenyl]-methyl}-piperidin-1-yl)-propan-1-one; cyclopropyl-(4-{difluoro-[4-(4-methyl-quinolin-3-yl)-phenyl]-methyl}-piperidin-1-yl)-methanone; (4-{difluoro-[4-(4-methyl-quinolin-3-yl)-phenyl]-methyl}-piperidin-1-yl)-(R)-tetrahydrofuran-2-yl-methanone; 1-{4-[4-(4-methyl-quinolin-3-yl)-benzyl]-piperidin-1-yl}-propan-1-one; cyclopropyl-{4-[4-(4-methyl-quinolin-3-yl)-benzyl]-piperidin-1-yl}-methanone; (3,3-difluoro-cyclobutyl)-{4-[4-(4-methyl-quinolin-3-yl)-benzyl]-piperidin-1-yl}-methanone; {4-[4-(4-methyl-quinolin-3-yl)-benzyl]-piperidin-1-yl}-(R)-tetrahydro-furan-2-yl-methanone; 1-{4-[difluoro-(4-quinolin-3-yl-phenyl)-methyl]-piperidin-1-yl}-propan-1-one; cyclopropyl-{4-[difluoro-(4-quinolin-3-yl-phenyl)-methyl]-piperidin-1-yl}-methanone; {4-[difluoro-(4-quinolin-3-yl-phenyl)-methyl]-piperidin-1-yl}-(R)-tetrahydrofuran-2-yl-methanone; 1-{4-[4-(4-chloro-quinolin-3-yl)-benzyl]-piperidin-1-yl}-propan-1-one; {4-[4-(4-chloro-quinolin-3-yl)-benzyl]-piperidin-1-yl}-cyclopropylmethanone; {4-[4-(4-chloro-quinolin-3-yl)-benzyl]-piperidin-1-yl}-(3,3-difluorocyclobutyl)-methanone; {4-[4-(4-chloro-quinolin-3-yl)-benzyl]-piperidin-1-yl}-(R)-tetrahydrofuran-2-yl-methanone; 1-{4-[4-(8-methyl-quinolin-7-yl)-benzyl]-piperidin-1-yl}-propan-1-one; cyclopropyl-{4-[4-(8-methyl-quinolin-7-yl)-benzyl]-piperidin-1-yl}-methanone; {4-[4-(8-methyl-quinolin-7-yl)-benzyl]-piperidin-1-yl}-(R)-tetrahydrofuran-2-yl-methanone; 1-[4-(4-isoquinolin-3-yl-benzyl)-piperidin-1-yl]-propan-1-one; cyclopropyl-[4-(4-isoquinolin-3-yl-benzyl)-piperidin-1-yl]-methanone; [4-(4-isoquinolin-3-yl-benzyl)-piperidin-1-yl]-(R)-tetrahydrofuran-2-yl-methanone; 1-{4-[4-(8-chloro-quinolin-7-yl)-benzyl]-piperidin-1-yl}-propan-1-one; {4-[4-(8-chloro-quinolin-7-yl)-benzyl]-piperidin-1-yl}-cyclopropylmethanone; {4-[4-(8-chloro-quinolin-7-yl)-benzyl]-piperidin-1-yl}-(R)-tetrahydrofuran-2-yl-methanone; 1-{4-[4-(8-methoxy-quinolin-7-yl)-benzyl]-piperidin-1-yl}-propan-1-one; cyclopropyl-{4-[4-(8-methoxy-quinolin-7-yl)-benzyl]-piperidin-1-yl}-methanone; {4-[4-(8-methoxy-quinolin-7-yl)-benzyl]-piperidin-1-yl}-(R)-tetrahydrofuran-2-yl-methanone; 1-{4-[4(1-methyl-isoquinolin-6-yl)-benzyl]-piperidin-1-yl}-propan-1-one; cyclopropyl-{4-[4-(1-methylisoquinolin-6-yl)-benzyl]-piperidin-1-yl}-methanone; {4-[4-(1-methyl-isoquinolin-6-yl)-benzyl]-piperidin-1-yl}-(R)-tetrahydro-furan-2-yl-methanone; 1-(4-(1-(4-(1,2,3,4- tetrahydroquinolin-7-yl)phenyl)ethyl)piperidin-1-yl) propan-1-one; 1-(4-(1-(4-(quinolin-3-yl)phenyl)ethyl) piperidin-1-yl)propan-1-one; 1-{4-[1-(4-quinolin-3-yl-phenyl)-cyclopropyl]-piperidin-1-yl}-propan-1-one; cyclopropyl-{4-[1-(4-quinolin-3-yl-phenyl)-vinyl]-piperidin-1-yl}-methanone; 1-{4-[1-(4-quinolin-7-yl-phenyl)-ethyl]-piperidin-1-yl}-propan-1-one; 1-{4-[amino-(4-quinolin-3-yl-phenyl)-methyl]-piperidin-1-yl}-propan-1-one; cyclopropyl-{4-[1-(4-quinolin-3-yl-phenyl)-cyclopropyl]-piperidin-1-yl}-methanone; cyclopropyl-{4-[1-(4-quinolin-7-yl-phenyl)-cyclopropyl]-piperidin-1-yl}-methanone; 1-{4-[[(E:Z)-methoxyimino]-(4-quinolin-3-yl-phenyl)-methyl]-piperidin-1-yl}-propan-1-one; 1-{4-[1-(4-quinolin-3-yl-phenyl)-propyl]-piperidin-1-yl}-propan-1-one; 1-{4-[cyclopropyl-(4-quinolin-3-yl-phenyl)-methyl]-piperidin-1-yl}-propan-1-one; [4-(4-quinolin-3-yl-benzoyl)-piperidin-1-yl]-(R)-tetrahydrofuran-2-yl-methanone; 1-{4-[[methoxyimino]-(4-quinolin-7-yl-phenyl)-methyl]-piperidin-1-yl}-propan-1-one; {4-[1-(4-quinolin-7-yl-phenyl)-ethyl]-piperidin-1-yl}-(R)-tetrahydrofuran-2-yl-methanone; {4-[1-(4-quinolin-3-yl-phenyl)-ethyl]-piperidin-1-yl}-(R)-tetrahydrofuran-2-yl-methanone; N-[(1-propionylpiperidin-4-yl)-(4-quinolin-3-yl-phenyl)-methyl]-acetamide; 1-{4-[1-(4-quinolin-3-yl-phenyl)-butyl]-piperidin-1-yl}-propan-1-one;

N-[(1-propionylpiperidin-4-yl)-(4-quinolin-3-yl-phenyl)-methyl]-formamide; 1-[4-methyl-4-(4-quinolin-3-yl-benzoyl)-piperidin-1-yl]-propan-1-one; 4-[1-(4-quinolin-3-yl-phenyl)-ethyl]-piperidine-1-carboxylic acid tert-butyl ester; cyclopropyl-{4-[1-(4-quinolin-3-yl-phenyl)-ethyl]-piperidin-1-yl}-methanone; 1-[4-methyl-4-(4-quinolin-3-yl-benzyl)-piperidin-1-yl]-propan-1-one; 4-[1-(4-quinolin-3-yl-phenyl)-ethyl]-piperidine-1-carbaldehyde; 1-{4-[2-methyl-1-(4-quinolin-3-yl-phenyl)-propyl]-piperidin-1-yl}-propan-1-one; 1-(4-{1-[4-(8-methylquinolin-7-yl)-phenyl]-ethyl}-piperidin-1-yl)-propan-1-one;

cyclopropyl-(4-{1-[4-(8-methylquinolin-7-yl)-phenyl]-ethyl}-piperidin-1-yl)-methanone;

1-(4-{1-[4-(8-methoxyquinolin-7-yl)-phenyl]-ethyl}-piperidin-1-yl)-propan-1-one; 1-(4-{1-[4-(4-methylquinolin-3-yl)-phenyl]-ethyl}-piperidin-1-yl)-propan-1-one; cyclopropyl-(4-{1-[4-(8-methoxyquinolin-7-yl)-phenyl]-ethyl}-piperidin-1-yl)-methanone; 1-{4-[1-(4-quinolin-3-yl-phenyl)-ethyl]-piperidin-1-yl}-propan-1-one; 1-{4-[1-(4-quinolin-3-yl-phenyl)-ethyl]-piperidin-1-yl}-propan-1-one; (4-{1-[4-(8-methoxyquinolin-7-yl)-phenyl]-ethyl}-piperidin-1-yl)-(R)-tetrahydrofuran-2-yl-methanone (including single isomers and diastereomeric mixtures); (4-{1-[4-(8-methylquinolin-7-yl)-phenyl]-ethyl}-piperidin-1-yl)-(R)-tetrahydrofuran-2-yl-methanone (including single isomers and diastereomeric mixtures); (4-{1-[4-(4-methylquinolin-3-yl)-phenyl]-ethyl}-piperidin-1-yl)-(R)-tetrahydrofuran-2-yl-methanone (including single isomers and diastereomeric mixtures); 1-(4-{1-[4-(8-chloroquinolin-7-yl)-phenyl]-ethyl}-piperidin-1-yl)-propan-1-one; (4-{1-[4-(8-chloroquinolin-7-yl)-phenyl]-ethyl}-piperidin-1-yl)-cyclopropyl-methanone; (4-{1-[4-(8-chloroquinolin-7-yl)-phenyl]-ethyl}-piperidin-1-yl)-(R)-tetrahydrofuran-2-yl-methanone (including single isomers and diastereomeric mixtures); 1-(4-{1-[4-(4-chloroquinolin-3-yl)-phenyl]-ethyl}-piperidin-1-yl)-propan-1-one; (4-{1-[4-(4-chloroquinolin-3-yl)-phenyl]-ethyl}-piperidin-1-yl)-cyclopropylmethanone; (4-{1-[4-(4-chloroquinolin-3-yl)-phenyl]-ethyl}-piperidin-1-yl)-(R)-tetrahydrofuran-2-yl-methanone (including single isomers and diastereomeric mixtures); (4-{1-[4-(1-methyl-isoquinolin-6-yl)-phenyl]-cyclopropyl}-piperidin-1-yl)-(R)-tetrahydrofuran-2-yl-methanone; (4-{1-[4-(8-methylquinolin-7-yl)-phenyl]-cyclopropyl}-piperidin-1-yl)-(R)-tetrahydrofuran-2-yl-methanone; (4-{(2-methoxy-ethoxy)-[4-(8-methylquinolin-7-yl)-phenyl]-methyl}-piperidin-1-yl)-(R)-tetrahydrofuran-2-yl-methanone; 1-(4-{(2-methoxy-ethoxy)-[4-(8-methylquinolin-7-yl)-phenyl]-methyl}-piperidin-1-yl)-propan-1-one; (4-{(2-methoxy-ethoxy)-[4-(1-methylisoquinolin-6-yl)-phenyl]-methyl}-piperidin-1-yl)-(R)-tetrahydrofuran-2-yl-methanone (including single isomers and diastereomeric mixtures); (4-{(2-methoxy-ethoxy)-[4-(4-methylquinolin-3-yl)-phenyl]-methyl}-piperidin-1-yl)-(R)-tetrahydrofuran-2-yl-methanone; {4-[[4-(8-methylquinolin-7-yl)-phenyl]-(3-morpholin-4-yl-propoxy)-methyl]-piperidin-1-yl}-(R)-tetrahydrofuran-2-yl-methanone; 1-{4-[[4-(8-methylquinolin-7-yl)-phenyl]-(3-morpholin-4-yl-propoxy)-methyl]-piperidin-1-yl}-propan-1-one; {4-[[4-(1-methylisoquinolin-6-yl)-phenyl]-(3-morpholin-4-yl-propoxy)-methyl]-piperidin-1-yl}-(R)-tetrahydrofuran-2-yl-methanone; {4-[[4-(4-methylquinolin-3-yl)-phenyl]-(3-morpholin-4-yl-propoxy)-methyl]-piperidin-1-yl}-(R)-tetrahydrofuran-2-yl-methanone; {4-[(2-pyrrolidin-1-yl-ethoxy)-(4-quinolin-3-yl-phenyl)-methyl]-piperidin-1-yl}-(R)-tetrahydrofuran-2-yl-methanone; {4-[[4-(8-methylquinolin-7-yl)-phenyl]-(2-pyrrolidin-1-yl-ethoxy)-methyl]-piperidin-1-yl}-(R)-tetrahydrofuran-2-yl-methanone; {4-[[4-(1-methylisoquinolin-6-yl)-phenyl]-(2-pyrrolidin-1-yl-ethoxy)-methyl]-piperidin-1-yl}-(R)-tetrahydrofuran-2-yl-methanone; 4-[4-(8-methoxyquinolin-7-yl)-benzyl]-1-((R)-tetrahydrofuran-2-carbonyl)-piperidine-4-carbonitrile; 4-[4-(8-methoxyquinolin-7-yl)-benzyl]-1-propionyl-piperidine-4-carbonitrile; {4-[4-(5-methylimidazo[1,2-a]pyridin-6-yl)-benzyl]-piperidin-1-yl}-(R)-tetrahydrofuran-2-yl-methanone; 1-{4-[4-(5-methylimidazo[1,2-a]pyridin-6-yl)-benzyl]-piperidin-1-yl}-propan-1-one; cyclopropyl-{4-[4-(5-methylimidazo[1,2-a]pyridin-6-yl)-benzyl]-piperidin-1-yl}-methanone; (1-hydroxycyclopropyl)-{4-[4-(5-methylimidazo[1,2-a]pyridin-6-yl)-benzyl]-piperidin-1-yl}-methanone;

(R)-(4-fluoro-4-(4-(5-methylimidazo[1,2-a]pyridin-6-yl)benzyl)piperidin-1-yl)(tetrahydrofuran-2-yl)methanone; 2,2,2-trifluoro-1-{4-[2-(4-quinolin-6-yl-phenyl)-1,3-dioxolan-2-yl]-piperidin-1-yl}-ethanone; cyclopropyl-{4-[2-(4-quinolin-6-yl-phenyl)-1,3-dioxolan-2-yl]-piperidin-1-yl}-methanone; 4-[2-(4-quinolin-6-yl-phenyl)-1,3-dioxolan-2-yl]-piperidine-1-sulfonic acid dimethylamide; 4-[2-(4-quinolin-6-yl-phenyl)-1,3-dioxolan-2-yl]-piperidine-1-carboxylic acid ethyl ester; 2-methyl-1-{4-[2-(4-quinolin-6-yl-phenyl)-1,3-dioxolan-2-yl]-piperidin-1-yl}-propan-1-one; 4-[2-(4-quinolin-6-yl-phenyl)-1,3-dioxolan-2-yl]-piperidine-1-carboxylic acid dimethylamide; 1-{4-[2-(4-quinolin-6-yl-phenyl)-1,3-dioxolan-2-yl]-piperidin-1-yl}-propan-1-one; 1-{4-[2-(4-quinolin-6-yl-phenyl)-1,3-dioxolan-2-yl]-piperidin-1-yl}-butan-1-one; 1-{4-[2-(4-quinolin-6-yl-phenyl)-1,3-dioxolan-2-yl]-piperidin-1-yl}-ethanone; 4-[2-(4-quinolin-6-yl-phenyl)-1,3-dioxolan-2-yl]-piperidine-1-carboxylic acid cyclopentylamide; 6-(4-{2-[1-(tetrahydropyran-4-yl)-piperidin-4-yl]-1,3-dioxolan-2-yl}-phenyl)-quinoline; 2-methyl-1-[4-(4-quinolin-6-yl-benzoyl)-piperidin-1-yl]-propan-1-one; 1-{4-[hydroxy-(4-quinolin-6-yl-phenyl)-methyl]-piperidin-1-yl}-2-methylpropan-1-one; 2-methyl-1-{4-[2-(4-quinolin-7-yl-phenyl)-1,3-di oxolan-2-yl]-piperidin-1-yl}-propan-1-one; cyclopropyl-{4-[2-(4-quinolin-7-yl-phenyl)-1,3-dioxolan-2-yl]-piperidin-1-yl}-methanone; 1-{4-[2-(4-quinolin-7-yl-phenyl)-1,3-dioxolan-2-yl]-piperidin-1-yl}-butan-1-one; 1-{4-[2-(4-quinolin-7-yl-phenyl)-1,3-dioxolan-2-yl]-piperidin-1-yl}-propan-1-one; 1-{4-[2-(4-isoquinolin-7-yl-phenyl)-1,3-dioxolan-2-yl]-piperidin-1-yl}-ethanone; 1-{4-[2-(4-isoquinolin-7-yl-phenyl)-1,3-dioxolan-2-yl]-piperidin-1-yl}-propan-1-one; 1-{4-[2-(4-isoquinolin-7-yl-phenyl)-1,3-dioxolan-2-yl]-piperidin-1-yl}-2-methyl-propan-1-one; 1-{4-[2-(4-isoquinolin-6-yl-phenyl)-1,3-dioxolan-2-yl]-piperidin-1-yl}-propan-1-one; 1-{4-[2-(4-isoquinolin-6-yl-phenyl)-1,3-dioxolan-2-yl]-piperidin-1-yl}-2-methyl-propan-1-one; 1-{4-[2-(4-isoquinolin-6-yl-phenyl)-1,3-dioxolan-2-yl]-piperidin-1-yl}-ethanone; 2-methyl-1-{4-[2-(4-quinolin-7-yl-phenyl)-1,3-dioxinan-2-yl]-piperidin-1-yl}-propan-1-one; cyclopropyl-{4-[2-(4-quinolin-7-yl-phenyl)-1,3-dioxinan-2-yl]-piperidin-1-yl}-methanone; 1-{4-[2-(4-quinolin-7-yl-phenyl)-1,3-dioxinan-2-yl]-piperidin-1-yl}-propan-1-one; 1-[4-(4-quinolin-7-yl-benzoyl)-piperidin-1-yl]-propan-1-one; 1-{4-[hydroxy-(4-quinolin-7-yl-phenyl)-methyl]-piperidin-1-yl}-propan-1-one; 1-{4-[1-hydroxy-1-(4-quinolin-7-yl-phenyl)-ethyl]-piperidin-1-yl}-propan-1-one; 1-[4-(2-fluoro-4-isoquinolin-6-yl-benzoyl)-piperidin-1-yl]-propan-1-one; 1-{4-[(2-fluoro-4-isoquinolin-6-yl-phenyl)-hydroxymethyl]-piperidin-1-yl}-propan-1-one; 1-[4-(4-isoquinolin-6-yl-benzoyl)-piperidin-1-yl]-propan-1-one; 1-{4-[hydroxy-(4-isoquinolin-6-yl-phenyl)-methyl]-piperidin-1-yl}-propan-1-one; 1-{4-[1-hydroxy-1-(4-isoquinolin-6-yl-phenyl)-ethyl]-piperidin-1-yl}-propan-1-one; 1-{4-[1-(2-fluoro-4-isoquinolin-6-yl-phenyl)-1-hydroxy-ethyl]-piperidin-1-yl}-propan-1-one; 1-[3-(4-isoquinolin-6-yl-benzoyl)-pyrrolidin-1-yl]-propan-1-one; 1-{3-[1-hydroxy-1-(4-isoquinolin-6-yl-phenyl)-ethyl]-pyrrolidin-1-yl}-propan-1-one; 1-{4-[2-(4'-dimethylamino-methyl-biphenyl-4-yl)-1,3-dioxolan-2-yl]piperidin-1-yl}-2-methyl-propan-1-one; 1-{4-[2-(4'-dimethylaminomethyl-biphenyl-4-yl)-1,3-dioxolan-2-yl]-piperidin-1-yl}-propan-1-one; cyclopropyl-{4-[2-(4'-dimethylaminomethyl-biphenyl-4-yl)-1,3-dioxolan-2-yl]-piperidin-1-yl}-methanone; 1-[4-(2,6-difluoro-4-isoquinolin-6-yl-benzoyl)-piperidin-1-yl]-propan-1-one; 1-{4-[2-(4-quinolin-3-yl-phenyl)-1,3-dioxolan-2-yl]-piperidin-1-yl}-propan-1-one; 2-methyl-1-{4-[2-(4-quinolin-3-yl-phenyl)-1,3-dioxolan-2-yl]-piperidin-1-yl}-propan-1-one;

cyclopropyl-{4-[2-(4-quinolin-3-yl-phenyl)-1,3-dioxolan-2-yl]-piperidin-1-yl}-methanone; 1-[4-(2-fluoro-4-quinolin-7-yl-benzoyl)-piperidin-1-yl]-propan-1-one; 1-[4-(2-fluoro-4-quinolin-3-yl-benzoyl)piperidin-1-yl]propan-1-one; 4-(2-fluoro-4-quinolin-3-yl-benzoyl)piperidine-1-carboxylic acid methyl ester; (4-hydroxy-4-(isoquinolin-3-yl)benzyl)piperidin-1-yl)(isoxazolidin-2-yl)methanone; [4-hydroxy-4-(4-isoquinolin-3-yl-benzyl)-piperidin-1-yl]-(R)-tetrahydrofuran-2-yl-methanone; 1-[4-hydroxy-4-(4-isoquinolin-6-yl-benzyl)-piperidin-1-yl]-2-methylpropan-1-one; 1-(4-hydroxy-4-(4-(quinolin-3-yl)benzyl)piperidin-1-yl)propan-1-one; 1-(4-hydroxy-4-(4-(quinolin-3-yl)benzyl)piperidin-1-yl)-2-methylpropan-1-one; 1-(4-hydroxy-4-(4-(quinolin-7-yl)benzyl)piperidin-1-yl)propan-1-one; 1-(4-hydroxy-4-(4-(quinolin-7-yl)benzyl)piperidin-1-yl)-2-methylpropan-1-one; 1-(4-(4-(benzofuran-5-yl)benzyl)-4-hydroxypiperidin-1-yl)propan-1-one; 1-(4-(4-(benzofuran-5-yl)benzyl)-4-hydroxypiperidin-1-yl)-2-methylpropan-1-one; 1-(4-(4-(1H-indol-5-yl)benzyl)-4-hydroxypiperidin-1-yl)propan-1-one; 1-(4-(4-(1H-indol-5-yl)benzyl)-4-hydroxypiperidin-1-yl)-2-methylpropan-1-one; 1-(4-(4-(benzofuran-2-yl)benzyl)-4-hydroxypiperidin-1-yl)propan-1-one; 1-(4-(4-(benzofuran-2-yl)benzyl)-4-hydroxypiperidin-1-yl)-2-methylpropan-1-one; 1-(4-hydroxy-4-(4-(isoquinolin-4-yl)benzyl)piperidin-1-yl)propan-1-one; 1-(4-hydroxy-4-(4-(isoquinolin-4-yl)benzyl)piperidin-1-yl)-2-methylpropan-1-one; 1-(4-hydroxy-4-(4-(isoquinolin-6-yl)benzyl)piperidin-1-yl)propan-1-one; 1-(4-fluoro-4-(4-(quinolin-3-yl)benzyl)piperidin-1-yl)propan-1-one; 1-(4-(4-(quinolin-3-yl)benzyl)-5,6-dihydropyridin-1(2H)-yl)propan-1-one; 1-(4-fluoro-4-(4-(quinolin-7-yl)benzyl)piperidin-1-yl)propan-1-one; 1-(4-(4-(quinolin-7-yl)benzyl)-5,6-dihydropyridin-1(2H)-yl)propan-1-one; 1-(4-fluoro-4-(4-(isoquinolin-6-yl)benzyl)piperidin-1-yl)propan-1-one; 1-(4-(4-(isoquinolin-6-yl)benzyl)-5,6-dihydropyridin-1(2H)-yl)propan-1-one; 1-(4-fluoro-4-(4-(isoquinolin-4-yl)benzyl)piperidin-1-yl)propan-1-one; 1-(4-(4-(isoquinolin-4-yl)benzyl)-5,6-dihydropyridin-1(2H)-yl)propan-1-one; 1-(4-(4-(benzofuran-5-yl)benzyl)-4-fluoropiperidin-1-yl)propan-1-one; 1-(4-(4-(benzofuran-5-yl)benzyl)-5,6-dihydropyridin-1(2H)-yl)propan-1-one; cyclopropyl(4-fluoro-4-(4-(quinolin-3-yl)benzyl)piperidin-1-yl)methanone; cyclopropyl(4-(4-(quinolin-3-yl)benzyl)-5,6-dihydropyridin-1(2H)-yl)methanone; cyclopropyl(4-fluoro-4-(4-(quinolin-7-yl)benzyl)piperidin-1-yl)methanone; cyclopropyl(4-(4-(quinolin-7-yl)benzyl)-5,6-dihydropyridin-1(2H)-yl)methanone; cyclopropyl(4-fluoro-4-(4-(isoquinolin-6-yl)benzyl)piperidin-1-yl)methanone; cyclopropyl(4-(4-(isoquinolin-6-yl)benzyl)-5,6-dihydropyridin-1(2H)-yl)methanone; cyclopropyl(4-fluoro-4-(4-(isoquinolin-4-yl)benzyl)piperidin-1-yl)methanone; cyclopropyl(4-(4-(isoquinolin-4-yl)benzyl)-5,6-dihydropyridin-1(2H)-yl)methanone; (4-(benzofuran-5-yl)benzyl)-4-fluoropiperidin-1-yl)(cyclopropyl)methanone; (4-(benzofuran-5-yl)benzyl)-5,6-dihydropyridin-1(2H)-yl)(cyclopropyl)methanone; (R)-(4-fluoro-4-(4-methylquinolin-3-yl)benzyl)piperidin-1-yl)(tetrahydrofuran-2-yl)methanone; (R)-(4-(4-(4-methylquinolin-3-yl)benzyl)-5,6-dihydropyridin-1(2H)-yl)(tetrahydro-furan-2-yl)methanone; cyclopropyl(4-fluoro-4-(4-(8-methylquinolin-7-yl)benzyl)-piperidin-1-yl)methanone; cyclopropyl(4-(4-(8-methylquinolin-7-yl)benzyl)-3,6-dihydro-pyridin-1(2H)-yl)methanone; 1-(4-fluoro-4-(4-(8-methylquinolin-7-yl)benzyl)piperidin-1-yl)propan-1-one; 1-(4-(4-(8-methylquinolin-7-yl)benzyl)-3,6-dihydropyridin-1(2H)-yl)-propan-1-one; (R)-(4-fluoro-4-(4-(quinolin-7-yl)benzyl)piperidin-1-yl)(tetrahydrofuran-2-yl)methanone; (R)-(4-(4-(quinolin-7-yl)benzyl)-5,6-dihydropyridin-1(2H)-yl)(tetrahydro-furan-2-yl)methanone; (R)-(4-fluoro-4-(4-(quinolin-3-yl)benzyl)piperidin-1-yl)(tetra-hydrofuran-2-yl)methanone; (R)-(4-(4-(quinolin-3-yl)benzyl)-5,6-dihydropyridin-1(2H)-yl)(tetrahydrofuran-2-yl)methanone; cyclopropyl(4-fluoro-4-(4-(4-methylquinolin-3-yl)-benzyl)piperidin-1-yl)methanone; cyclopropyl(4-(4-(4-methylquinolin-3-yl)benzyl)-5,6-dihydropyridin-1(2H)-yl)methanone; 1-(4-(4-(4-chloroquinolin-3-yl)benzyl)-4-fluoro-piperidin-1-yl)propan-1-one; 1-(4-(4-(4-chloroquinolin-3-yl)benzyl)-3,6-dihydropyridin-1(2H)-yl)propan-1-one; 1-(4-fluoro-4-(4-(4-methylquinolin-3-yl)benzyl)piperidin-1-yl)-propan-1-one; 1-(4-(4-(4-methylquinolin-3-yl)benzyl)-5,6-dihydropyridin-1(2H)-yl)-propan-1-one; (4-(4-(4-chloroquinolin-3-yl)benzyl)-4-fluoropiperidin-1-yl)(cyclopropyl)-methanone; (4-(4-(4-chloroquinolin-3-yl)benzyl)-3,6-dihydropyridin-1(2H)-yl)(cyclo-propyl)methanone; (R)-(4-fluoro-4-(4-(8-methylquinolin-7-yl)benzyl)piperidin-1-yl)(tetra-hydrofuran-2-yl)methanone; (R)-(4-(4-(8-methylquinolin-7-yl)benzyl)-3,6-dihydro-pyridin-1(2H)-yl)(tetrahydrofuran-2-yl)methanone; (R)-(4-(4-(4-chloroquinolin-3-yl)-benzyl)-4-fluoropiperidin-1-yl)(tetrahydrofuran-2-yl)methanone; (R)-(4-(4-(4-chloro-quinolin-3-yl)benzyl)-3,6-dihydropyridin-1(2H)-yl)(tetrahydrofuran-2-yl)methanone;
(R)-(4-(4-(quinolin-7-yl)benzyl)-5,6-dihydropyridin-1(2H)-yl)(tetrahydrofuran-2-yl)methanone; cyclopropyl(4-

(2-(4-(quinolin-3-yl)phenyl)propan-2-yl)piperidin-1-yl)methanone; 1-(4-(2-(4-(quinolin-3-yl)phenyl)propan-2-yl)piperidin-1-yl)propan-1-one;

1-{4-[1-ethoxy-1-(4-quinolin-3-yl-phenyl)-ethyl]-piperidin-1-yl}-propan-1-one; cyclopropyl-{4-[1-ethoxy-1-(4-quinolin-3-yl-phenyl)-ethyl]-piperidin-1-yl}-methanone; 1-{4-[1-methoxy-1-(4-quinolin-3-yl-phenyl)-ethyl]-piperidin-1-yl}-propan-1-one; cyclopropyl-{4-[1-methoxy-1-(4-quinolin-3-yl-phenyl)-ethyl]-piperidin-1-yl}-methanone; 1-{4-[1-methoxy-1-(4-quinolin-3-yl-phenyl)-propyl]-piperidin-1-yl}-propan-1-one; cyclopropyl-{4-[1-methoxy-1-(4-quinolin-3-yl-phenyl)-propyl]-piperidin-1-yl}-methanone; 1-{4-[1-methoxy-1-(4-quinolin-7-yl-phenyl)-ethyl]-piperidin-1-yl}-propan-1-one; cyclopropyl-{4-[1-methoxy-1-(4-quinolin-7-yl-phenyl)-ethyl]-piperidin-1-yl}-methanone; 1-{4-[1-ethoxy-1-(4-quinolin-7-yl-phenyl)-ethyl]-piperidin-1-yl}-propan-1-one; cyclopropyl-{4-[1-ethoxy-1-(4-quinolin-7-yl-phenyl)-ethyl]-piperidin-1-yl}-methanone; 1-{4-[1-methoxy-1-(4-quinolin-7-yl-phenyl)-propyl]-piperidin-1-yl}-propan-1-one; cyclopropyl-{4-[1-methoxy-1-(4-quinolin-7-yl-phenyl)-propyl]-piperidin-1-yl}-methanone; 1-[trans-3-hydroxy-4-(4-quinolin-3-yl-benzyl)-piperidin-1-yl]-propan-1-one; 1-[(trans)-3-methoxy-4-(4-quinolin-3-yl-benzyl))-piperidin-1-yl]-propan-1-one; 1-propionyl-4-(4-quinolin-3-yl-benzyl)-piperidin-3-one; 1-[cis-3-fluoro-4-(4-quinolin-3-yl-benzyl)-piperidin-1-yl]-propan-1-one; 1-{4-fluoro-4-[4-(8-methyl-quinolin-7-yl)-benzoyl]-piperidin-1-yl}-propan-1-one; 1-{4-fluoro-4-[4-(8-methyl-quinolin-7-yl)-benzoyl]-piperidin-1-yl}-propan-1-one;

[trans-3-hydroxy-4-(4-quinolin-3-yl-benzyl)-piperidin-1-yl]-(R)-tetrahydro-furan-2-yl-methanone; 1-(4-fluoro-4-{methoxy-[4-(8-methylquinolin-7-yl)-phenyl]-methyl}-piperidin-1-yl)-propan-1-one; 1-(4-fluoro-4-{(2-methoxyethoxy)-[4-(8-methyl-quinolin-7-yl)-phenyl]-methyl}-piperidin-1-yl)-propan-1-one; 1-{4-fluoro-4-[[4-(8-methylquinolin-7-yl)-phenyl]-(2-morpholin-4-yl-ethoxy)-methyl]-piperidin-1-yl}-propan-1-one; N-ethyl-4-fluoro-4-[[4-(8-methyl-7-quinolyl)phenyl]methyl]piperidine-1-carboxamide; N-ethyl-4-[[4-(8-methyl-7-quinolyl)phenyl]methyl]piperidine-1-carboxamide; N-ethyl-4-[[4-(8-methoxy-7-quinolyl)phenyl]methyl]piperidine-1-carboxamide; N-methoxy-4-[[4-(8-methyl-7-quinolyl)phenyl]methyl]piperidine-1-carboxamide; N-ethoxy-4-[[4-(8-methyl-7-quinolyl)phenyl]methyl]piperidine-1-carboxamide; N,N-dimethyl-4-[[4-(8-methyl-7-quinolyl)phenyl]methyl]piperidine-1-carboxamide; [4-[[4-(8-methyl-7-quinolyl)phenyl]methyl]-1-piperidyl]-pyrrolidin-1-yl-methanone; and pharmaceutically acceptable salts of such compounds.

Compounds according to Formula II may include for example: 1-[4-(4-quinolin-3-yl-benzyl)-piperidin-1-yl]-propan-1-one; 2-methyl-1-[4-(4-quinolin-3-yl-benzyl)-piperidin-1-yl]-propan-1-one; cyclopropyl-[4-(4-quinolin-3-yl-benzyl)-piperidin-1-yl]-methanone; 4-(4-quinolin-3-yl-benzyl)-piperidin-1-yl]-(R)-tetrahydrofuran-2-yl-methanone; 4-(4-quinolin-3-yl-benzyl)-piperidin-1-yl]-(S)-tetrahydrofuran-2-yl-methanone; 1-{4-[4-(4-methylquinolin-3-yl)-benzyl]-piperidin-1-yl}-propan-1-one; cyclopropyl-{4-[4-(4-methylquinolin-3-yl)-benzyl]-piperidin-1-yl}-methanone; (3,3-difluorocyclo-butyl)-{4-[4-(4-methylquinolin-3-yl)-benzyl]-piperidin-1-yl}-methanone; {4-[4-(4-methylquinolin-3-yl)-benzyl]-piperidin-1-yl}-(R)-tetrahydrofuran-2-yl-methanone; 1-{4-[4-(4-chloroquinolin-3-yl)-benzyl]-piperidin-1-yl}-propan-1-one; {4-[4-(4-chloroquinolin-3-yl)-benzyl]-piperidin-1-yl}-cyclopropylmethanone; {4-[4-(4-chloroquinolin-3-yl)-benzyl]-piperidin-1-yl}-(3,3-difluorocyclobutyl)-methanone; {4-[4-(4-chloroquinolin-3-yl)-benzyl]-piperidin-1-yl}-(R)-tetrahydrofuran-2-yl-methanone; 1-{4-[4-(8-methyl-quinolin-7-yl)-benzyl]-piperidin-1-yl}-propan-1-one; cyclopropyl-{4-[4-(8-methyl-quinolin-7-yl)-benzyl]-piperidin-1-yl}-methanone; {4-[4-(8-methylquinolin-7-yl)-benzyl]-piperidin-1-yl}-(R)-tetrahydrofuran-2-yl-methanone; 1-{4-[4-(8-chloroquinolin-7-yl)-benzyl]-piperidin-1-yl}-propan-1-one; {4-[4-(8-chloroquinolin-7-yl)-benzyl]-piperidin-1-yl}-cyclopropylmethanone; {4-[4-(8-chloroquinolin-7-yl)-benzyl]-piperidin-1-yl}-(R)-tetrahydrofuran-2-yl-methanone; 1-{4-[4-(8-methoxyquinolin-7-yl)-benzyl]-piperidin-1-yl}-propan-1-one; cyclopropyl-{4-[4-(8-methoxyquinolin-7-yl)-benzyl]-piperidin-1-yl}-methanone; {4-[4-(8-methoxyquinolin-7-yl)-benzyl]-piperidin-1-yl}-(R)-tetrahydrofuran-2-yl-methanone; 1-{4-[4-(1-methylisoquinolin-6-yl)-benzyl]-piperidin-1-yl}-propan-1-one; cyclopropyl-{4-[4-(1-methylisoquinolin-6-yl)-benzyl]-piperidin-1-yl}-methanone; {4-[4-(1-methylisoquinolin-6-yl)-benzyl]-piperidin-1-yl}-(R)-tetrahydrofuran-2-yl-methanone; 1-(4-(1-(4-(quinolin-3-yl)phenyl)ethyl)piperidin-1-yl)propan-1-one; 1-{4-[1-(4-quinolin-3-yl-phenyl)-cyclopropyl]-piperidin-1-yl}-propan-1-one; 1-{4-[1-(4-quinolin-7-yl-phenyl)-ethyl]-piperidin-1-yl}-propan-1-one; cyclopropyl-{4-[1-(4-quinolin-3-yl-phenyl)-cyclopropyl]-piperidin-1-yl}-methanone; cyclopropyl-{4-[1-(4-quinolin-7-yl-phenyl)-cyclopropyl]-piperidin-1-yl}-methanone; 1-{4-[1-(4-quinolin-3-yl-phenyl)-propyl]-piperidin-1-yl}-propan-1-one; 1-{4-[cyclopropyl-(4-quinolin-3-yl-phenyl)-methyl]-piperidin-1-yl}-propan-1-one; {4-[1-(4-quinolin-7-yl-phenyl)-ethyl]-piperidin-1-yl}-(R)-tetrahydrofuran-2-yl-methanone; {4-[1-(4-quinolin-3-yl-phenyl)-ethyl]-piperidin-1-yl}-(R)-tetrahydrofuran-2-yl-methanone; 1-{4-[1-(4-quinolin-3-yl-phenyl)-butyl]-piperidin-1-yl}-propan-1-one; cyclopropyl-{4-[1-(4-quinolin-3-yl-phenyl)-ethyl]-piperidin-1-yl}-methanone; 1-{4-[2-methyl-1-(4-quinolin-3-yl-phenyl)-propyl]-piperidin-1-yl}-propan-1-one; 1-(4-{1-[4-(8-methylquinolin-7-yl)-phenyl]-ethyl}-piperidin-1-yl)-propan-1-one; cyclopropyl-(4-{1-[4-(8-methylquinolin-7-yl)-phenyl]-ethyl}-piperidin-1-yl)-methanone; 1-(4-{1-[4-(8-methoxyquinolin-7-yl)-phenyl]-ethyl}-piperidin-1-yl)-propan-1-one; 1-(4-{1-[4-(4-methylquinolin-3-yl)-phenyl]-ethyl}-piperidin-1-yl)-propan-1-one; cyclopropyl-(4-{1-[4-(8-methoxyquinolin-7-yl)-phenyl]-ethyl}-piperidin-1-yl)-methanone; 1-{4-[1-(4-quinolin-3-yl-phenyl)-ethyl]-piperidin-1-yl}-propan-1-one; 1-{4-[1-(4-quinolin-3-yl-phenyl)-ethyl]-piperidin-1-yl}-propan-1-one; (4-{1-[4-(8-methoxy-quinolin-7-yl)-phenyl]-ethyl}-piperidin-1-yl)-(R)-tetrahydrofuran-2-yl-methanone; mixture of diastereomers; (4-{1-[4-(8-methylquinolin-7-yl)-phenyl]-ethyl}-piperidin-1-yl)-(R)-tetrahydrofuran-2-yl-methanone; mixture of diastereomers; (4-{1-[4-(4-methyl-quinolin-3-yl)-phenyl]-ethyl}-piperidin-1-yl)-(R)-tetrahydrofuran-2-yl-methanone; mixture of diastereomers; 1-(4-{1-[4-(8-chloroquinolin-7-yl)-phenyl]-ethyl}-piperidin-1-yl)-propan-1-one; (4-{1-[4-(8-chloroquinolin-7-yl)-phenyl]-ethyl}-piperidin-1-yl)-cyclopropylmethanone; (4-{1-[4-(8-chloroquinolin-7-yl)-phenyl]-ethyl}-piperidin-1-yl)-(R)-tetrahydrofuran-2-yl-methanone; mixture of diastereomers; 1-(4-{1-[4-(4-chloroquinolin-3-yl)-phenyl]-ethyl}-piperidin-1-yl)-propan-1-one; (4-{1-[4-(4-chloroquinolin-3-yl)-phenyl]-ethyl}-piperidin-1-yl)-cyclopropylmethanone; (4-{1-[4-(4-chloroquinolin-3-yl)-phenyl]-ethyl}-piperidin-1-yl)-(R)-tetrahydrofuran-2-yl-methanone; mixture of diastereomers; (4-{1-[4-(1-methylisoquinolin-6-yl)-phenyl]-cyclopropyl}-piperidin-1-yl)-(R)-tetra-hydrofuran-2- yl-methanone; (4-{1-[4-(8-methylquinolin-7-yl)-phenyl]-cyclopropyl}-piperidin-1-yl)-(R)-tetrahydrofuran-2-yl-methanone; 1-(4-fluoro-4-(4-(quinolin-3-yl)-benzyl)piperidin-1-yl)propan-1-one; 1-(4-fluoro-4-(4-(quinolin-7-yl)benzyl)piperidin-1-yl)propan-1-one; 1-(4-fluoro-4-(4-(isoquinolin-6-yl)benzyl)piperidin-1-yl)propan-1-one; cyclopropyl(4-fluoro-4-(4-(quinolin-3-yl)benzyl)piperidin-1-yl)methanone; cyclopropyl(4-fluoro-4-(4-(quinolin-7-yl)benzyl)piperidin-1-yl)methanone; cyclopropyl(4-fluoro-4-(4-(isoquinolin-6-yl)benzyl)piperidin-1-yl)methanone; (R)-(4-fluoro-4-(4-(4-methylquinolin-3-yl)benzyl)piperidin-1-yl)(tetrahydrofuran-2-yl)methanone; cyclopropyl(4-fluoro-4-(4-(8-methylquinolin-7-yl)benzyl)piperidin-1-yl)methanone; 1-(4-fluoro-4-(4-(8-methyl-quinolin-7-yl)benzyl)piperidin-1-yl)propan-1-one; (R)-(4-fluoro-4-(4-(quinolin-7-yl)-benzyl)piperidin-1-yl)(tetrahydrofuran-2-yl)methanone; (R)-(4-fluoro-4-(4-(quinolin-3-yl)benzyl)piperidin-1-yl)(tetrahydrofuran-2-yl)methanone; cyclopropyl(4-fluoro-4-(4-(4-methylquinolin-3-yl)benzyl)piperidin-1-yl)methanone; 1-(4-(4-(4-chloroquinolin-3-yl)-benzyl)-4-fluoropiperidin-1-yl)propan-1-one; 1-(4-fluoro-4-(4-(4-methylquinolin-3-yl)-benzyl)piperidin-1-yl)propan-1-one; (4-(4-(4-chloroquinolin-3-yl)benzyl)-4-fluoropiperidin-1-yl)(cyclopropyl)methanone; (R)-(4-fluoro-4-(4-(8-methylquinolin-7-yl)-benzyl)piperidin-1-yl)(tetrahydrofuran-2-yl)methanone; (R)-(4-(4-(4-chloroquinolin-3-yl)-benzyl)-4-fluoropiperidin-1-yl)(tetrahydrofuran-2-yl)methanone; (R)-(4-(4-(quinolin-7-yl)benzyl)-5,6-dihydropyridin-1(2H)-yl)(tetrahydrofuran-2-yl)methanone; cyclopropyl(4-(2-(4-(quinolin-3-yl)phenyl)propan-2-yl)piperidin-1-yl)methanone; 1-(4-(2-(4-(quinolin-3-yl)phenyl)propan-2-yl)piperidin-1-yl)propan-1-one; 1-[trans-3-hydroxy-4-(4-quinolin-3-ylbenzyl)-piperidin-1-yl]-propan-1-one; 1-[(trans)-3-methoxy-4-(4-quinolin-3-yl-benzyl)-piperidin-1-yl]-propan-1-one; 1-propionyl-4-(4-quinolin-3-yl-benzyl)-piperidin-3-one; 1-[cis-3-fluoro-4-(4-quinolin-3-yl-benzyl)-piperidin-1-yl]-propan-1-one; [trans-3-hydroxy-4-(4-quinolin-3-yl-benzyl)-piperidin-1-yl]-(R)-tetrahydrofuran-2-yl-methanone; N-ethyl-4-fluoro-[[4-(8-methyl-7-quinolyl)phenyl]methyl]piperidine-1-carboxamide; N-ethyl-4-[[4-(8-methyl-7-quinolyl)phenyl]methyl]piperidine-1-carboxamide; N-ethyl-[[4-(8-methoxy-7-quinolyl)phenyl]methyl]piperidine-1-carboxamide; N-methoxy-4-[[4-(8-methyl-7-quinolyl)phenyl]methyl]piperidine-1-carboxamide; N-ethoxy-4-[[4-(8-methyl-7-quinolyl)phenyl]methyl]piperidine-1-carboxamide; N,N-dimethyl-4-[[4-(8-methyl-7-quinolyl)phenyl]methyl]piperidine-1-carboxamide; [4-[[4-(8-methyl-7-quinolyl)phenyl]-methyl]-1-piperidyl]-pyrrolidin-1-yl-methanone; and pharmaceutically acceptable salts of such compounds.

Compounds according to Formula III may include for example: 1-[4-methyl-4-(4-quinolin-3-yl-benzoyl)-piperidin-1-yl]-propan-1-one; 1-[4-methyl-4-(4-quinolin-3-yl-benzyl)-piperidin-1-yl]-propan-1-one; 4-[4-(8-methoxyquinolin-7-yl)-benzyl]-1-((R)-tetrahydrofuran-2-carbonyl)-piperidine-4-carbonitrile; 4-[4-(8-methoxyquinolin-7-yl)-benzyl]-1-propionyl-piperidine-4-carbonitrile; (R)-(4-fluoro-4-(4-(5-methylimidazo[1,2-a]pyridin-6-yl)benzyl)piperidin-1-yl)(tetrahydrofuran-2-yl)methanone; (4-hydroxy-4-(4-(isoquinolin-3-yl)benzyl)piperidin-1-yl)(isoxazolidin-2-yl)methanone; [4-hydroxy-4-(4-isoquinolin-3-yl-benzyl)-piperidin-1-yl]-(R)-tetrahydrofuran-2-yl-methanone; 1-[4-hydroxy-4-(4-isoquinolin-6-yl-benzyl)-piperidin-1-yl]-2-methylpropan-1-one; 1-(4-hydroxy-4-(4-(quinolin-3-yl)benzyl)piperidin-1-yl)propan-1-one; 1-(4-hydroxy-4-(4-(quinolin-3-yl)benzyl)piperidin-1-yl)-2-methylpropan-1-one; 1-(4-hydroxy-4-(4-(quinolin-7-yl)benzyl)piperidin-1-yl)propan-1-one; 1-(4-hydroxy-4-(4-(quinolin-7-yl)benzyl)piperidin-1-yl)-2-methylpropan-1-one; 1-(4-(4-(benzofuran-5-yl)benzyl)-4-hydroxypiperidin-1-yl)propan-1-one; 1-(4-(4-(benzofuran-5-yl)benzyl)-4-hydroxypiperidin-1-yl)-2-methylpropan-1-one; 1-(4-(4-(1H-indol-5-yl)benzyl)-4-hydroxypiperidin-1-yl)propan-1-one; 1-(4-(4-(1H-indol-5-yl)benzyl)-4-hydroxypiperidin-1-yl)-2-methylpropan-1-one; 1-(4-(4-(benzofuran-2-yl)benzyl)-4-hydroxypiperidin-1-yl)propan-1-one; 1-(4-(4-(benzofuran-2-yl)benzyl)-4-hydroxy-piperidin-1-yl)-2-methylpropan-1-one; 1-(4-hydroxy-4-(4-(isoquinolin-4-yl)benzyl)-piperidin-1-yl)propan-1-one; 1-(4-hydroxy-4-(4-(isoquinolin-4-yl)benzyl)piperidin-1-yl)-2-methylpropan-1-one; 1-(4-hydroxy-4-(4-(isoquinolin-6-yl)benzyl)piperidin-1-yl)propan-1-one; 1-(4-fluoro-4-(4-(quinolin-3-yl)benzyl)piperidin-1-yl)propan-1-one; 1-(4-fluoro-4-(4-(quinolin-7-yl)benzyl)piperidin-1-yl)propan-1-one; 1-(4-fluoro-4-(4-(isoquinolin-6-yl)benzyl)piperidin-1-yl)propan-1-one; 1-(4-fluoro-4-(4-(isoquinolin-4-yl)benzyl)piperidin-1-yl)propan-1-one; 1-(4-(4-(benzofuran-5-yl)benzyl)-4-fluoropiperidin-1-yl)propan-1-one; cyclopropyl(4-fluoro-4-(4-(quinolin-3-yl)benzyl)-piperidin-1-yl)methanone; cyclopropyl(4-fluoro-4-(4-(quinolin-7-yl)benzyl)piperidin-1-yl)methanone; cyclopropyl(4-fluoro-4-(4-(isoquinolin-6-yl)benzyl)piperidin-1-yl)methanone; cyclopropyl(4-fluoro-4-(4-(isoquinolin-4-yl)benzyl)piperidin-1-yl)methanone; (4-(4-(benzofuran-5-yl)benzyl)-4-fluoropiperidin-1-yl)(cyclopropyl)methanone; (R)-(4-fluoro-4-(4-(4-methylquinolin-3-yl)benzyl)piperidin-1-yl)(tetrahydrofuran-2-yl)methanone; cyclopropyl(4-fluoro-4-(4-(8-methylquinolin-7-yl)benzyl)piperidin-1-yl)methanone; 1-(4-fluoro-4-(4-(8-methylquinolin-7-yl)benzyl)piperidin-1-yl)propan-1-one; (R)-(4-fluoro-4-(4-(quinolin-7-yl)benzyl)piperidin-1-yl)(tetrahydrofuran-2-yl)methanone; (R)-(4-fluoro-4-(4-(quinolin-3-yl)benzyl)piperidin-1-yl)(tetrahydrofuran-2-yl)methanone; cyclopropyl(4-fluoro-4-(4-(4-methylquinolin-3-yl)benzyl)piperidin-1-yl)methanone; 1-(4-(4-(4-chloroquinolin-3-yl)benzyl)-4-fluoropiperidin-1-yl)propan-1-one; 1-(4-fluoro-4-(4-(4-methylquinolin-3-yl)benzyl)piperidin-1-yl)propan-1-one; (4-(4-(4-chloroquinolin-3-yl)benzyl)-4-fluoropiperidin-1-yl)(cyclopropyl)methanone; (R)-(4-fluoro-4-(4-(8-methylquinolin-7-yl)benzyl)piperidin-1-yl)(tetrahydrofuran-2-yl)methanone; (R)-(4-(4-(4-chloroquinolin-3-yl)benzyl)-4-fluoropiperidin-1-yl)(tetrahydrofuran-2-yl)methanone; 1-{4-fluoro-4-[4-(8-methyl-quinolin-7-yl)-benzoyl]-piperidin-1-yl}-propan-1-one; 1-{4-fluoro-4-[4-(8-methyl-quinolin-7-yl)-benzoyl]-piperidin-1-yl}-propan-1-one; 1-(4-fluoro-4-{methoxy-[4-(8-methyl-quinolin-7-yl)-phenyl]-methyl}-piperidin-1-yl)-propan-1-one;

1-(4-fluoro-4-{(2-methoxy-ethoxy)-[4-(8-methyl-quinolin-7-yl)-phenyl]-methyl}-piperidin-1-yl)-propan-1-one; 1-{4-fluoro-4-[[4-(8-methyl-quinolin-7-yl)-phenyl]-(2-morpholin-4-yl-ethoxy)-methyl]-piperidin-1-yl}-propan-1-one; N-ethyl-4-fluoro-4-[[4-(8-methyl-7-quinolyl)phenyl]methyl]piperidine-1-carboxamide; and pharmaceutically acceptable salts of such compounds.

Compounds according to Formula IV may include for example: 4-[2-(4-quinolin-6-yl-phenyl)-1,3-dioxolan-2-yl]-piperidine-1-carboxylic acid dimethylamide; (4-hydroxy-4-(4-(isoquinolin-3-yl)benzyl)piperidin-1-yl)(isoxazolidin-2-yl)methanone; N-ethyl-4-[[4-(8-methyl-7-quinolyl)phenyl]methyl]piperidine-1-carboxamide; N-ethyl-4-[[4-(8-methoxy-7-quinolyl)phenyl]methyl]piperidine-1-carboxamide; N-methoxy-4-[[4-(8-methyl-7-quinolyl)phenyl]methyl]piperidine-1-carboxamide; N-ethoxy-4-[[4-

(8-methyl-7-quinolyl)phenyl]methyl]piperidine-1-carboxamide; N,N-dimethyl-4-[[4-(8-methyl-7-quinolyl)phenyl] methyl]piperidine-1-carboxamide; [4-[[4-(8-methyl-7-quinolyl)phenyl]-methyl]-1-piperidyl]-pyrrolidin-1-yl-methanone; and pharmaceutically acceptable salts of such compounds.

Compounds according to Formula V may include for example: 1-(4-(4-(quinolin-3-yl)benzyl)-5,6-dihydropyridin-1(2H)-yl)propan-1-one; 1-(4-(4-(quinolin-7-yl)benzyl)-5,6-dihydropyridin-1(2H)-yl)propan-1-one; 1-(4-(4-(isoquinolin-6-yl)benzyl)-5,6-dihydropyridin-1(2H)-yl)propan-1-one; 1-(4-(4-(isoquinolin-4-yl)benzyl)-5,6-dihydropyridin-1(2H)-yl)propan-1-one; 1-(4-(4-(benzofuran-5-yl)benzyl)-5,6-dihydropyridin-1(2H)-yl)propan-1-one; cyclopropyl(4-(4-(quinolin-3-yl)benzyl)-5,6-dihydropyridin-1(2H)-yl)methanone; cyclopropyl(4-(4-(quinolin-7-yl)benzyl)-5,6-dihydropyridin-1(2H)-yl)methanone; cyclopropyl(4-(4-(isoquinolin-6-yl)benzyl)-5,6-dihydropyridin-1(2H)-yl)methanone; cyclopropyl(4-(4-(isoquinolin-4-yl)benzyl)-5,6-dihydropyridin-1(2H)-yl)methanone; (4-(4-(benzofuran-5-yl)benzyl)-5,6-dihydropyridin-1(2H)-yl)(cyclopropyl) methanone; (R)-(4-(4-(4-methylquinolin-3-yl)benzyl)-5,6-dihydropyridin-1(2H)-yl)(tetrahydrofuran-2-yl)methanone; cyclopropyl(4-(4-(8-methylquinolin-7-yl)benzyl)-3,6-dihydropyridin-1(2H)-yl)methanone; 1-(4-(4-(8-methylquinolin-7-yl)benzyl)-3,6-dihydropyridin-1(2H)-yl)propan-1-one; (R)-(4-(4-(quinolin-7-yl)benzyl)-5,6-dihydropyridin-1(2H)-yl)(tetrahydrofuran-2-yl)methanone; (R)-(4-(4-(quinolin-3-yl)benzyl)-5,6-dihydropyridin-1(2H)-yl)(tetrahydrofuran-2-yl)methanone; cyclopropyl(4-(4-(4-methylquinolin-3-yl)benzyl)-5,6-dihydropyridin-1(2H)-yl)methanone; 1-(4-(4-(4-chloroquinolin-3-yl)benzyl)-3,6-dihydropyridin-1(2H)-yl)propan-1-one; 1-(4-(4-(4-Methylquinolin-3-yl)benzyl)-5,6-dihydropyridin-1(2H)-yl)propan-1-one; (4-(4-(4-chloroquinolin-3-yl)benzyl)-3,6-dihydropyridin-1(2H)-yl)(cyclopropyl)methanone; (R)-(4-(4-(8-methylquinolin-7-yl)benzyl)-3,6-dihydropyridin-1(2H)-yl)(tetrahydrofuran-2-yl)methanone; (R)-(4-(4-(4-chloroquinolin-3-yl)benzyl)-3,6-dihydropyridin-1(2H)-yl)(tetrahydrofuran-2-yl)methanone; and pharmaceutically acceptable salts of such compounds.

The following terms and expressions have meanings as discussed below.

As used herein, the term "about" refers to a range of values from ±10% of a specified value. For example, the phrase "about 50" would be understood to include ±10% of 50, or from 45 to 55. The phrase "from about 10 to 100" includes ±10% of 10 and ±10% of 100, or from 9 to 110.

As used herein, a range of integer values in the form "x-y" or "x to y", or "x through y", includes the integers x and y, and includes all of the integers between x and y. For example, the expressions "1-6", or "1 to 6" or "1 through 6" are intended to include the integers 1, 2, 3, 4, 5, and 6. Preferred embodiments include each individual integer in the range, as well as any subcombination of integers. For example, preferred integers for the expression "1-6" can include 1, 2, 3, 4, 5, 6, 1-2, 1-3, 1-4, 1-5, 2-3, 2-4, 2-5, 2-6, etc.

The term "acyl" means a radical of the general formula —C(═O)—R, wherein —R is hydrogen or hydrocarbyl. Examples include, acetyl (—C(═O)CH$_3$), propionyl (—C(═O)CH$_2$CH$_3$), benzoyl (—C(═O)C$_6$H$_5$), and phenylacetyl (—C(═O)CH$_2$C$_6$H$_5$).

The term "alkyl", by itself or as part of another substituent means, a straight, branched or cyclic chain hydrocarbon radical, including di- and multi-radicals, having the number of carbon atoms designated (i.e. C$_1$-C$_6$ designates an alkyl group having from one to six carbons), and includes straight, branched chain or cyclic groups. Examples of alkyl groups include: methyl, ethyl, propyl, isopropyl, butyl, isobutyl, tert-butyl, pentyl, neopentyl, hexyl, cyclohexyl and cyclopropylmethyl.

The term "alkylene," by itself or as part of another substituent means a divalent straight, branched or cyclic chain hydrocarbon radical having the stated number of carbon atoms. For example, —(C$_1$-C$_3$)-alkylene-CO$_2$H, would include, e.g., —CH$_2$CH$_2$CH$_2$—CO$_2$H, —CH$_2$CH (CH$_3$)—CO$_2$H, —C(CH$_3$)$_2$—CO$_2$H, -cyclopropyl-CO$_2$H, and —CH(CH$_3$)—CH$_2$—CO$_2$H.

The term "alkoxy," employed alone or in combination with other terms means an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers.

The term "alkenyl," employed alone or in combination with other terms, means a stable monounsaturated or di-unsaturated hydrocarbon radical straight chain, branched chain or cyclic hydrocarbon group having the stated number of carbon atoms. Examples include vinyl, propenyl(allyl), crotyl, isopentenyl, butadienyl, 1,3-pentadienyl, 1,4-pentadienyl, cyclopentenyl, cyclopentadienyl and the higher homologs and isomers. A divalent radical derived from an alkene is exemplified by CH═CH—CH$_2$—.

The term "amine" or "amino" refers to radicals of the general formula —NRR', wherein R and R' are independently selected from hydrogen and a hydrocarbyl radical, or wherein R and R' combined form a heterocyle. Examples of amino groups include: —NH$_2$, methylamino, diethylamino, anilino, benzylamino, piperidin-1-yl, piperazin-1-yl and indolin-1-yl.

The term "carbamyl" means the group —C(═O)NRR', wherein R and R' are independently selected from hydrogen and a hydrocarbyl radical, or wherein R and R' combined form a heterocyle. Examples of carbamyl groups include: —C(═O)NH$_2$ and —C(═O)N(CH$_3$)$_2$.

The term "cycloalkyl" refers to alkyl radicals that contain one or more rings, for example C$_3$ to C$_{10}$ cycloalkyl groups, e.g., cyclopropyl, cyclobutyl, cyclopentyl, cyclohexyl, cycloheptyl, norbornyl, and octahydro-1H-indenyl.

The term "heteroalkyl" by itself or in combination with another term, means a stable straight or branched chain radical consisting of the stated number of carbon atoms and one or two heteroatoms selected from O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, and —CH$_2$CH$_2$—S (═O)—CH$_3$. Up to two heteroatoms may be consecutive, such as, for example, —CH$_2$—NH—OCH$_3$ (wherein either or both of the two consecutive heteroatoms may also be oxidized S (SO or SO$_2$) or oxidized N (NO)).

The term "heteroalkenyl," by itself or in combination with another term, means a stable straight or branched chain mono- or di-unsaturated hydrocarbon radical consisting of the stated number of carbon atoms and one or two heteroatoms selected from O, N, and S, and wherein the nitrogen and sulfur atoms may optionally be oxidized and the nitrogen heteroatom may optionally be quaternized. Up to two heteroatoms may be placed consecutively. Examples include —CH═CH—O—CH$_3$, —CH═CH—CH$_2$—OH, —CH$_2$—CH═N—OCH$_3$, —CH═CH—N(CH$_3$)—CH$_3$, and —CH$_2$—CH═CH—CH$_2$—SH.

The term "hydroxyalkyl" refers to a subset of heteroalkyl groups that is an alkyl radical wherein one or more of the carbon atoms is substituted with hydroxy. Examples include —CH$_2$CH(OH)CH$_3$ and —CH$_2$CH$_2$OH.

The terms "halo" or "halogen" by themselves or as part of another substituent mean, a fluorine, chlorine, bromine, or iodine atom.

The term "haloalkyl" refers to a C$_1$-C$_6$ alkyl group in which one or more of the carbon atoms is substituted with one or more halogen atoms. Preferred haloalkyl groups are C$_1$-C$_4$ alkyl groups in which one or more of the carbon atoms is substituted with one or more halogen atoms. The alkyl group may be a straight, branched or cyclic alkyl group. The halogen atom is one or more of fluorine, chlorine, bromine and iodine. Examples of haloalkyl groups include, trifluoromethyl, 2,2,2-trifluoroethyl, 2,2,2-trichloroethyl and 2-chloroethyl.

The term "sulfamyl" means the group —SO$_2$NRR', wherein R and R' are independently selected from hydrogen or a hydrocarbyl radical, or wherein R and R' combined form a heterocycle. Examples of sulfamyl groups include: —SO$_2$NH$_2$, —SO$_2$N(CH$_3$)$_2$, —SO$_2$(pyrrol-1-yl) and —SO$_2$NH(C$_6$H$_5$).

The term "aromatic" refers to a carbocycle or heterocycle having one or more polyunsaturated rings having aromatic character (4n+2) delocalized π (pi) electrons).

The term "aryl," employed alone or in combination with other terms, means a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl.

The term "heterocycle" or "heterocyclyl" or "heterocyclic," by itself or as part of another substituent means, an unsubstituted or substituted, stable, mono- or multicyclic heterocyclic ring system which consists of carbon atoms and at least one heteroatom selected from N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

As used herein "stable structure" or "stable compound" refers to a compound that is sufficiently robust to survive isolation to a useful degree of purity from a reaction mixture. The compounds according to the present invention are stable compounds.

The term "heteroaryl" or "heteroaromatic" refers to a heterocycle having aromatic character.

Examples of non-aromatic heterocycles include monocyclic groups such as: Aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: Pyridyl, pyrazinyl, pyrimidinyl, particularly 2- and 4-pyrimidyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-traizolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: bicyclic heterocycles, such as, Indolyl, particularly 3-, 4-, 5-, 6- and 7-indolyl, indolinyl, quinolyl, tetrahydroquinolyl, isoquinolyl, particularly 1- and 5-isoquinolyl, tetrahydroisoquinolyl, cinnolinyl, quinoxalinyl, particularly 2- and 5-quinoxalinyl, quinazolinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl. Polycyclic heterocycles also include tricyclic and other polycyclic heterocycles such as dibenzofuran and benzofuro [2,3-b]pyridine.

The aforementioned listing of heterocyclyl and heteroaryl moieties is intended to be representative, not limiting.

The term "hydrocarbyl" refers to any moiety comprising only hydrogen and carbon atoms. For example, the term (C$_1$-C$_7$)hydrocarbyl would include hydrocarbon groups such as (C$_1$-C$_7$)alkyl groups and cycloalkyl, (C$_1$-C$_7$)alkenyl and cycloalkenyl groups, (C$_1$-C$_7$)alkynyl and cycloalkynyl groups, and aryl, e.g., benzyl and tolyl groups.

As used herein, the term "substituted" refers in general to any one or more hydrogen atoms on the indicated atom (preferably a carbon atom) being replaced with a selected group referred to herein as a "substituent", provided that the substituted atom's valency is not exceeded, and that the substitution results in a stable compound. A substituted group has from 1 to 5, preferably 1 to 3, and more preferably 1 independently selected substituents. Possible substituents include, but are not limited to halogens, —OH, —OR, —NR$_2$, —NHOH, —NO$_2$, —CN, —CF$_3$, —CF$_2$CF$_3$, —C$_1$-C$_7$ hydrocarbyl, —C$_1$-C$_6$ alkoxy, 3-7-membered heterocyclyl, 3-7-membered heteroaryl, ═O, ═S, —C(═O)R, —COOH, —CO$_2$R, —O—C(═O)R, —C(═O)NRR', —NRC(═O)R', —NRCO$_2$R', —OC(═O)NRR', —NRC (═O)NRR', —NRC(═S)NRR', and —SO$_2$NRR', wherein R and R' are each independently —H, —C$_1$-C$_7$ hydrocarbyl (e.g., —C$_1$-C$_6$ alkyl, —C$_2$-C$_6$ alkenyl C$_3$-C$_6$ cycloalkyl, benzyl, or phenyl) or (C$_1$-C$_7$)acyl.

Where a substituent is an alkyl or alkoxy group, the carbon chain may be branched, straight or cyclic, with straight being preferred.

Accordingly, the term "substituted hydrocarbyl" refers to: a hydrocarbyl group as defined above, having 1, 2, 3, 4 or 5 substituents, independently selected from the selection provided in the definition of the term "substituent" herein. Similarly, the expressions "substituted alkyl," "substituted cycloalkyl," "substituted alkenyl," "substituted alkynyl," "substituted aryl," "substituted benzyl," etc. refer to the specified (e.g., alkyl) group as defined herein, having 1, 2, 3, 4 or 5 substituents, independently selected from the selection provided in the definition of the term "substituent" herein.

As used herein, the term "subject" refers to a warm blooded animal such as a mammal, preferably a human, which is afflicted with, or has the potential to be afflicted with one or more diseases and conditions described herein.

As used herein, a "therapeutically effective amount" refers to an amount of a compound of the present invention that is effective to treat or prevent the symptoms of a particular disorder. Such disorders include, but are not limited to; those pathological and neurological disorders associated with the aberrant activity of the receptors described herein, wherein the treatment or prevention comprises inhibiting the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable salt" refers to salts of compounds of the present invention that may be derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, trifluoroacetic, tartaric, glutamic, salicylic, oxalic, methanesulfonic, benzenesulfonic, para-toluenesulfonic, succinic, and benzoic acid, and related inorganic and organic acids.

Base addition salts include those derived from inorganic bases such as ammonium and alkali and alkaline earth metal hydroxides, carbonates, and bicarbonates, as well as salts derived from basic organic amines such as aliphatic and aromatic amines, aliphatic diamines, and hydroxy alkamines. Such bases useful in preparing the salts of this invention thus include, for example, ammonium hydroxide, potassium carbonate, sodium bicarbonate, calcium hydroxide, methylamine, diethylamine, ethylenediamine, cyclohexylamine, diisopropylethyl amine (DIPEA), ethanolamine.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and THF. Mixtures of such solvates can also be prepared. The source of such solvate can be from the solvent of crystallization, inherent in the solvent of preparation or crystallization, or adventitious to such solvent. Such solvates are within the scope of the present invention.

It will be understood that compounds of the present invention may exist in various stereoisomeric forms. As such, the compounds of the present invention include both diastereomers and enantiomers. The compounds may be prepared as racemates and can conveniently be used as such. However, individual enantiomers can be isolated by resolution or chiral separation of a racemate, or may be synthesized by conventional techniques if so desired. Such racemates and individual enantiomers and mixtures thereof form part of the present invention.

It is known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. Stereochemistry of Organic Compounds; Wiley: New York, 1994, and Jacques, J, et al. Enantiomers, Racemates, and Resolutions; Wiley: New York, 1981.

It is further recognized that functional groups present on intermediates used for the synthesis of the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), methoxybenzyl, and dimethoxy (e.g., 2-4-dimethoxy) benzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

The compounds described herein are also intended to include such compounds wherein the molecular structures include isotopes of atoms in the chemical structure, e.g., carbon, hydrogen, nitrogen sulfur, and other atoms occurring on those structures. Isotopes include those atoms having the same atomic number but different mass numbers. For example, isotopes of hydrogen include deuterium; isotopes of carbon include $^{13}C$; isotopes of nitrogen include $^{15}N$; and isotopes of sulfur include $^{33}S$.

Accordingly, within the chemical structure of any compound that is taught in this application:

any hydrogen atom or group of hydrogen atoms, e.g., in a hydrocarbyl, heteroalkyl, aryl, heteroaryl, heterocyclyl or carbocyclyl group, could suitably be replaced by an isotope of hydrogen, i.e., deuterium;

any carbon atom or group of carbon atoms, e.g., in a hydrocarbyl, heteroalkyl, aryl, heteroaryl, heterocyclyl or carbocyclyl group, could suitably be replaced by an isotope of carbon, e.g., $^{13}C$;

any nitrogen atom or group of nitrogen atoms, e.g., in a heteroalkyl, heteroaryl, or heterocyclyl group, could suitably be replaced by an isotope of nitrogen, e.g., $^{15}N$; and any sulfur atom or group of sulfur atoms, e.g., in a heteroalkyl, heteroaryl, or heterocyclyl group, could suitably be replaced by an isotope of sulfur, e.g., $^{33}S$.

As used herein, a compound that is termed "isotopically-enriched" means that the abundance, e.g., of deuterium, $^{13}C$, or $^{15}N$ or $^{33}S$ at any relevant site of the compound is substantially more than the abundance of deuterium, $^{13}C$, or $^{15}N$ or $^{33}S$ naturally occurring at that site in an amount of the compound. A relevant site in a compound as used above is a site which would be designated as "H" or "C" or "N" or "S" in a chemical structure representation of the compound when not enriched. Relevant sites in the chemical structure of compounds taught herein for isotopic replacement an atom or atoms can include any site that is synthetically accessible for such isotopic replacement. The expression, "naturally occurring," as used above refers to the abundance of the particular atom which would be present at a relevant site in a compound if the compound was prepared without any affirmative synthesis step to enrich the abundance of a different isotope.

Thus, for example in a "deuterium-enriched" compound, the abundance of deuterium at any relevant site in the chemical structure can range from an amount that is substantially more than the natural abundance of deuterium (about 0.0115%) up to 100%, for example, from about 1% to about 100%, or from about 10% to about 100%, or from about 50% to about 100%, or from about 90% to about 100%.

Similarly, for a "$^{13}$C-enriched" compound, the abundance of $^{13}$C at any relevant site in the chemical structure of the compound can range from an amount that is substantially more than the natural abundance of $^{13}$C (about 1.109%) all the way up to 100%, for example, from about 5% to about 100%, or from about 10% to about 100%, or from about 50% to about 100%, or from about 90% to about 100%. Similarly for a "$^{15}$N-enriched" compound, the abundance of $^{15}$N at any relevant site in the chemical structure of the compound can range from an amount that is substantially more than the natural abundance of $^{15}$N (about 0.364%) all the way up to 100%, for example, from about 1% to about 100%, or from about 10% to about 100%, or from about 50% to about 100%, or from about 90% to about 100%.

Isotopically-enriched compounds can generally be prepared by conventional techniques known to those skilled in the art. Such isotopically-enriched compounds can also be prepared by adapting conventional processes as described in the scientific literature for synthesis of compounds disclosed herein, and using an appropriate isotopically-substituted reagent (or reagents) in place of the corresponding non isotopically-substituted reagent(s) employed in the conventional synthesis of the non isotopically-enriched compounds. Examples of ways to obtain a deuterium-enriched compound include exchanging hydrogen with deuterium or synthesizing the compound with deuterium-enriched starting materials.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described herein.

All other terms that are used herein in the description of the present invention will be understood to have meanings such as would be understood and accepted in the art.

For therapeutic purposes, the compounds that are described herein may be administered to a subject by any means that results in the contact of the active agent with the agent's site of action in the body of the subject. The compounds may be administered by any conventional means available for use in conjunction with pharmaceuticals, either as individual therapeutic agents, or in combination with other therapeutic agents. The compounds are preferably administered in therapeutically effective amounts for the treatment of the diseases and disorders described herein to a subject in need thereof.

A therapeutically effective amount of a compound as described herein may be readily determined by an attending diagnostician, as one skilled in the art, by the use of conventional techniques. The effective dose will vary depending upon a number of factors, including the type of disease or disorder treated, the extent of progression of the disease or disorder, the overall health status of the subject to be treated, the relative biological efficacy of the compound selected, the formulation of the active agent, and the route of administration used in treatment. Typically, the compounds are initially administered at lower dosage levels, with a gradual increase until the desired therapeutic effect is obtained.

Typical dose ranges may be from about 0.01 mg/kg to about 100 mg/kg of body weight per day, or from about 0.01 mg/kg to 10 mg/kg of body weight per day. Daily doses for adult humans may include about 25, 50, 100 and 200 mg, and an equivalent dose in a human child. The compounds may be administered in one or more unit dose forms. The unit dose may range from about 1 to about 500 mg administered one to four times a day, e.g., from about 10 mg to about 300 mg, administered two times a day. In an alternate method of describing an effective dose, an oral unit dose is one that is necessary to achieve a therapeutic blood serum level, e.g., a blood serum level of about 0.05 to 20 micrograms/mL in a subject, or about 1 to 20 micrograms/mL. The compounds described herein may be administered as the pure chemicals; however it is preferable to administer the active ingredient as a pharmaceutical composition.

Generally, compounds described herein may be administered to a patient alone or in combination with a pharmaceutically acceptable carrier. Accordingly, the compounds of the invention, for example, compounds of Formulae I-V(a), are preferably combined with a pharmaceutical carrier selected on the basis of the chosen route of administration and standard pharmaceutical practice—as described, for example, in Remington's Pharmaceutical Sciences (Mack Publishing Co., Easton, Pa., 1980), the disclosures of which are hereby incorporated herein by reference, in their entireties. The carrier(s) must be acceptable in the sense of being compatible with the other ingredients of the composition and not deleterious to the subject. The relative proportions of active ingredient and carrier may be determined, for example, by the solubility and chemical nature of the compounds, the chosen route of administration and standard pharmaceutical practice.

The compounds described herein may be formulated into pharmaceutical compositions by admixture with one or more pharmaceutically acceptable excipients. The excipients may be selected on the basis of the chosen route of administration and standard pharmaceutical practice, as described, for example, in Remington: The Science and Practice of Pharmacy, 20th ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations.

According to some embodiments of the invention, a pharmaceutical composition herein may contain both an amount of a FASN inhibitor having a chemical structure as described herein, and an amount of an antipsychotic agent. Suitable antipsychotic agents for such a dual API pharmaceutical composition include, for example, clozapine, risperidone, aripiprazole, olanzapine, quetiapine and ziprasidone. Such a dual API pharmaceutical composition may contain, for example, per dosage unit, from about 5 to about 1000 mg, or more, of a FASN inhibitor having a chemical structure as described herein, and from about 5 to about 1000 mg of an antipsychoric agent. In such embodiment, it is not necessary that each single dosage unit include an effective amount so long as the total amount of drug administered to a patient is an effective amount of each. Therefore, for example, a patient may require two or more single dosage units to receive effective amounts of both agents. The dosage may be adjusted appropriately to achieve desired drug levels, locally or systemically of both drugs.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders.

For oral administration, e.g., tablets, pills, powders, capsules, and troches, formulations can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; and flavoring agents such as peppermint or cherry flavoring. Capsules may contain any of the excipients as listed above, and may additionally contain a semi-solid or liquid carrier, such as a polyethylene glycol. Solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include, for example, mixtures of alcohols and water, and buffered media. Nonaqueous solvents include, for example, alcohols and glycols, such as ethanol, and polyethylene glycols; oils, such as vegetable oils; fatty acids and fatty acid esters. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; and antibacterial agents, such as chlorobutanol, or phenol; buffers. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol or drops. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

Pharmaceutical kits may comprise a therapeutically effective amount of a therapeutic compound as described herein, in one or more sterile containers are also within the ambit of the present invention. Sterilization of the container may be carried out using conventional sterilization methodology well known to those skilled in the art. The sterile containers of materials may comprise separate containers, or one or more multi-part containers. The compound as described herein may be separate, or may be combined into a single dosage form as described above. Such kits may further include, if desired, one or more of various conventional pharmaceutical kit components, e.g., one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in such a kit.

The compounds of the present invention may be used in methods for treating a condition or disorder associated with increased FASN expression and/or activity.

Such disorders include, for example:
obesity,
eating disorders
drug induced body weight gain; e.g. atypical antipsychotic-induced weight gain
cardiovascular diseases,
gastrointestinal disorders,
dermatological disorders,
metabolic diseases (e.g., non-alcoholic hepatic steatosis) and Type 2 diabetes (NASH is a serious liver disease for which the pathogenesis and prognosis have not been clearly determined. It is generally believed that abnormal fatty acid metabolism may be involved in the pathogenesis of NASH, with triacylglycerols and their fatty acid precursors likely possibly accumulating in the hepatocyte.)
viral disorders wherein FASN inhibition correlates inhibition of viral replication, and
cancers and/or cancer metastasis (e.g., human breast, ovarian, prostate, colon, lung, bladder, stomach and kidney cancers).

The methods of treatment provided herein comprise administering to a subject in need of such treatment a therapeutically effective amount of a compound of the invention, preferably a compound of Formulae I-V. Accordingly, the invention includes a method of treatment of a subject suffering from a disorder mediated by fatty acid synthase, comprising administering to the subject a therapeutically effective amount of a compound according to Formulae I, II, III, IV or V; or a therapeutically effective amount of a pharmaceutical composition comprising a compound according to Formulae I, II, III, IV or V. The invention also includes a method of treating a subject who is suffering from obesity, weight gain, or weight gain, or weight gain associated with drug therapy, e.g., drug therapy with an antipsychotic agent, e.g., clozapine, risperidone, aripiprazole, olanzapine, quetiapine and ziprasidone. The method comprises administering to the subject a therapeutically effective amount of a compound according to Formulae I, II, III, IV, or V; or a therapeutically effective amount of a pharmaceutical composition comprising a compound according to Formulae I-V.

The compounds of the present invention can be synthesized using the methods as described generally herein and by methods that are described in the working examples that are provided herein, or variations thereon. The compounds of the invention may also be prepared by using other known synthetic methods, or variations thereon. Unless otherwise stated, starting compounds in the synthetic methods described herein are commercially available, or may be readily synthesized by known methods. The reactions are generally performed in solvents that are appropriate to the reagents and reaction conditions. The materials employed in the reactions are understood to be suitable for the transformations being effected, and the materials and methods employed in product isolation understood to be suitable for the product compounds. Also, in the description of the synthetic methods herein, it is to be understood that all proposed reaction conditions, including choice of solvent, reaction atmosphere, reaction temperature, duration of experiment and workup procedures are chosen to be conditions appropriate for that reaction as would be understood by one skilled in the art of organic synthesis. It is understood that the examples and embodiments described herein are provided for illustrative purposes only and that various modifications or changes in light thereof will be clearly understood to be included within the scope of this application and the scope of the appended claims. Specific chemical transformations are listed in the schemes and working examples provided herein, and the skilled person will readily appreciate that a variety of different reagents may be used in place of those listed. Common replacements for such reagents can be found in, for example, in texts such as "Encyclopedia of Reagents for Organic Synthesis" Leo A. Paquette, John Wiley & Son Ltd (1995) or "Comprehensive 5 Organic Transformations: A Guide to Functional Group Preparations" Richard C. Larock. Wiley-VCH and "Strategic Applications of Named Reactions in Organic Synthesis" Kurti and Czako, Elsevier, 2005, and references therein.

Compounds according to Formula I (or II-V) may be prepared by organic syntheses utilizing known organic reactions as outlined in the following schemes, or as described in the chemical synthesis steps using standard functional group transformations. Scheme 1 outlines the general routes that were used to synthesize numerous examples of the invention. In Scheme 1, starting with an Intermediate of structure 1 (for example, the known 1-[4-(4-bromobenzyl)-piperidin-1-yl]-2,2,2-trifluoroethanone, 4-(4-bromobenzyl)-piperidine-1-carboxylic acid tert-butyl ester, or 1-[4-(4-bromobenzoyl)-piperidin-1-yl]-2,2,2-trifluoroethanone) (also referred to herein as Intermediate 6),

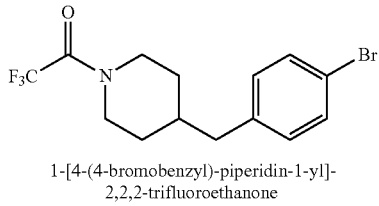

1-[4-(4-bromobenzyl)-piperidin-1-yl]-
2,2,2-trifluoroethanone

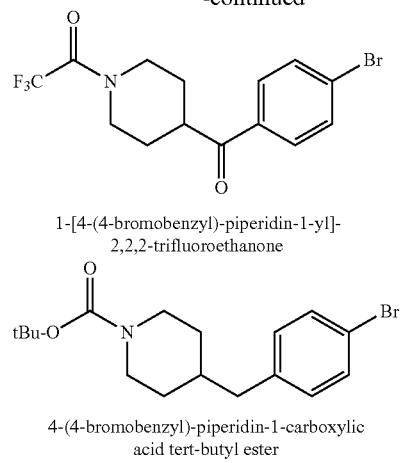

1-[4-(4-bromobenzyl)-piperidin-1-yl]-
2,2,2-trifluoroethanone 4-(4-bromobenzyl)-piperidin-1-carboxylic
acid tert-butyl ester a transition metal (e.g., palladium) catalyzed coupling reaction with an appropriate $R^6$ boronic acid or $R^6$ organostannane reagent can be used to produce an intermediate of structure 3. Alternatively, the coupling partners may be reversed, i.e., Intermediate 2, e.g., 4-[4-(4,4,5,5-tetramethyl-[1,3,2]dioxaborolan-2-yl)-benzyl]-piperidine-1-carboxylic acid tert-butyl ester:

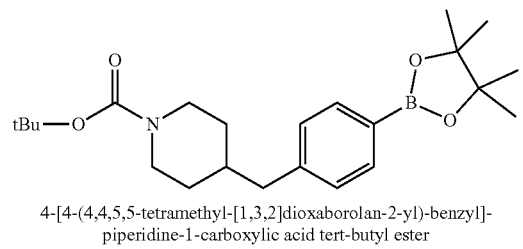 [SMILES: CC(C)(C)OC(=O)N1CCC(Cc2ccc(B3OC(C)(C)C(C)(C)O3)cc2)CC1]

4-[4-(4,4,5,5-tetramethyl-[1,3,2]dioxaborolan-2-yl)-benzyl]-
piperidine-1-carboxylic acid tert-butyl ester may be prepared and coupled with a bromo- or iodo-substituted heteroaryl, or heteroaryl triflate to produce intermediates of structure 3.

The intermediate 3 can then be deprotected to remove the protecting group (PG) (for example, under acidic conditions if the PG is a Boc or trifluoroacetyl group) to give an amine Intermediate 4. The amine Intermediate 4 may then be reacted with reagents such as carboxylic acids, carbonyl chlorides, carboxylic acid anhydrides, isocyanates, or sulfonyl halides to produce compounds according to Formula I (or II-V), e.g., to produce amide, urea, and carbamate examples as described above. Examples 1-5, 12-15, 19-37, 93-96 and 228-234 were synthesized by the general route described in Scheme 1.

Scheme 1. General synthesis methods

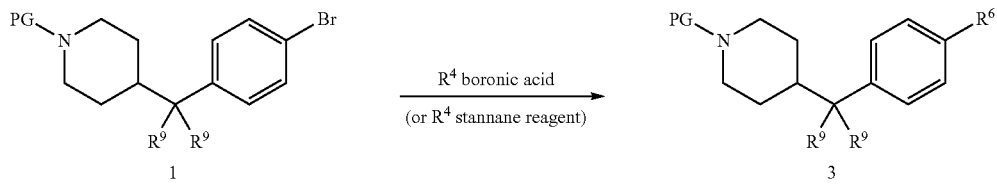

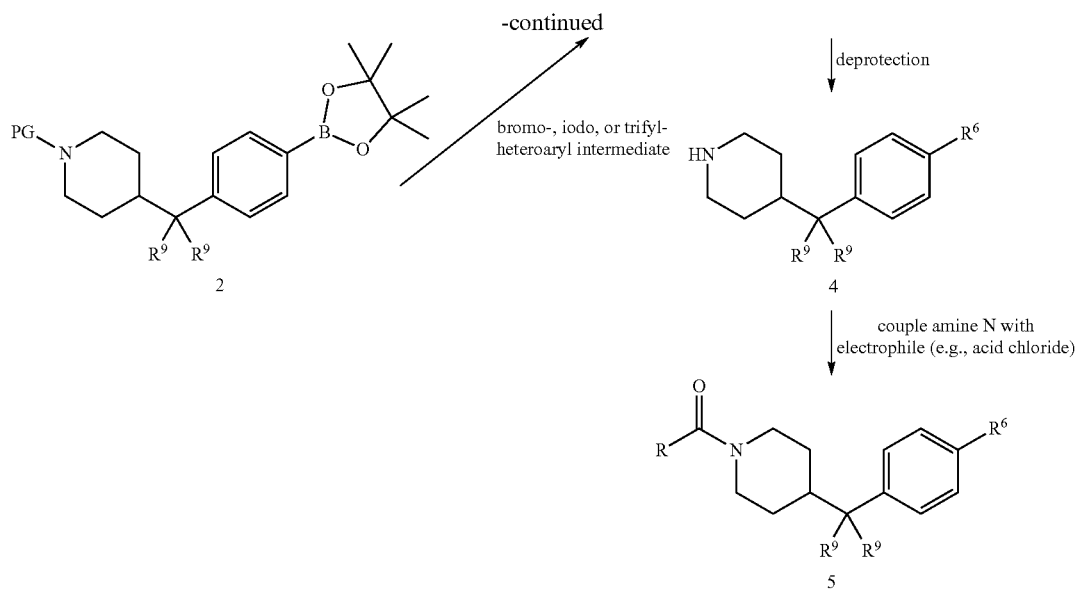

Scheme 2 outlines a route to the examples wherein both R$^9$ groups are —F, e.g., 1-(4-{difluoro-[4-(4-methyl-quinolin-3-yl)-phenyl]-methyl}-piperidin-1-yl)-propan-1-one (Example 9). The known 1-[4-(4-bromobenzoyl)-piperidin-1-yl]-2,2,2-trifluoroethanone (Intermediate 6) was treated with the reagent bis(2-methoxyethyl) aminosulfur trifluoride (deoxofluor) in methylene chloride to produce 1-{4-[(4-bromophenyl)-difluoromethyl]-piperidin-1-yl}-2,2,2-trifluoroethanone (Intermediate 7). Intermediate 7 is essentially an example of compounds having a structure according to intermediate 1 in Scheme 1 above. Accordingly, intermediates such as Intermediate 7 may be reacted in a transition metal (e.g., palladium) catalyzed coupling reaction with an appropriate R$^6$ boronic acid or R$^6$ organostannane reagent can be used to produce an intermediate of structure 3. As shown in Scheme 2, Intermediate 7 may converted to the corresponding borolane, for example by Palladium catalyzed coupling with 4,4,5,5,4',4',5',5'-octamethyl-[2,2']bi[[1,3,2]dioxaborolanyl], to produce 1-(4-{difluoro-[4-(4,4,5,5-tetramethyl-1,3,2-dioxaborolan-2-yl)-phenyl]-methyl}-piperidin-1-yl)-2,2,2-trifluoroethanone (Intermediate 8). Intermediate 8 is essentially an example of compounds having a structure according to Intermediate 2 in Scheme 1 above. Accordingly, synthetic intermediates such as Intermediate 8 may be reacted under Suzuki coupling conditions with an bromo-, iodo- or trifyl heteroaryl intermediate, for example 3-bromo-4-methylquinolne to produce a coupled product such as intermediate amine 9. (The trifluoroacetyl protecting group is typically removed during the Suzuki reaction, however the reaction time and conditions may alternatively be adjusted so as to isolate the Suzuki product with the trifluoroacetyl protected piperidine nitrogen.) The piperidine Intermediate 9 can then be functionalized at the piperidine nitrogen, e.g., by reacting with an acyl halide, e.g., propionyl chloride, to produce a final product; in this instance, the compound prepared in Example 9.

Scheme 2. Synthesis of compounds such as Example 9

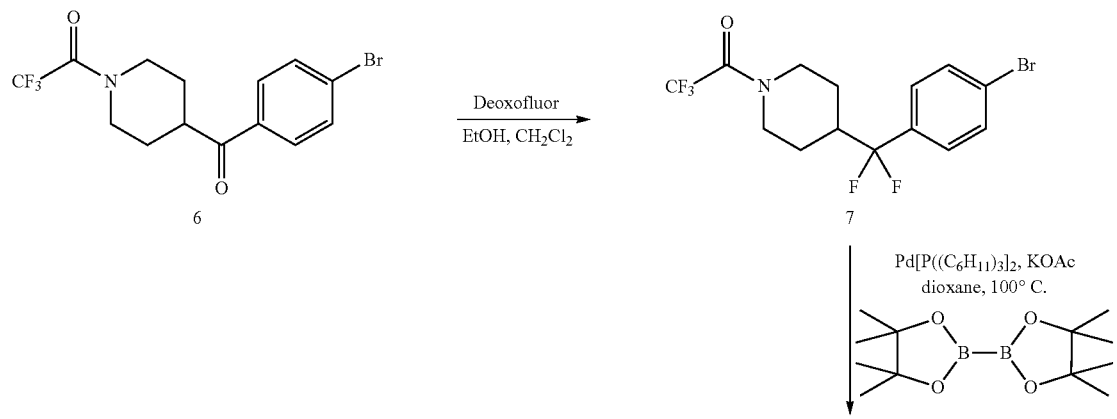

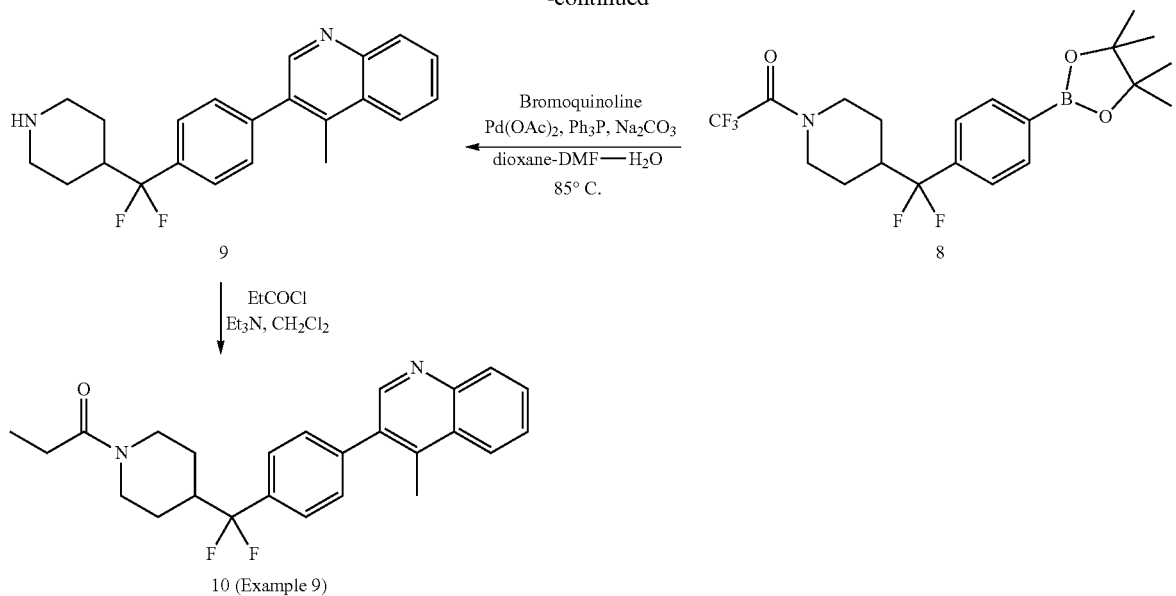

By analogy to this procedure, Examples 6-11 and Examples 16-18 were synthesized. In a similar synthesis, mono-fluoro examples 6-8 were prepared starting with 4-[(4-bromophenyl)-hydroxy-methyl]-piperidine-1-carboxylic acid tert-butyl ester.

Scheme 3 outlines methods that may be used to synthesize $R^w$=OH Examples 145-160. The known 4-(4-bromobenzyl)-4-hydroxypiperidine-1-carboxylic acid tert-butyl ester 11 may be synthesized by Grignard reaction with 4-bromobenzyl bromide and 1-boc-4-piperidone. Intermediate 11 may be deprotected (Boc removal) by treatment with acid to produce the deprotected piperidine Intermediate 12. Acylation of piperidine Intermediate 12 may be used to install an $R^1$ moiety (Intermediate 13). $R^6$ moieties may subsequently be installed as described above via Suzuki reaction: either A) replacing the —Br of intermediate 12 with a borolane moiety and reacting with a Bromo-, iodo or trifl heteroaryl Intermediate; or B) reacting Intermediate 12 with a heteroaryl borolane reagent with Pd catalysis. Alternatively, the order of incorporating the $R^1$ and $R^6$ moieties may be reversed as outlined in Scheme 3 Method B.

The $R^w$=F, and tetrahydropiperidine Examples 161-202 were also synthesized according to Scheme 3, Method A; starting from tert-butyl 4-(4-bromobenzyl)-4-hydroxy piperidine-1-carboxylate.

Scheme 3a: General synthesis of 4-(4-substituted-benzyl)-4-hydroxypiperidine amides-Method A

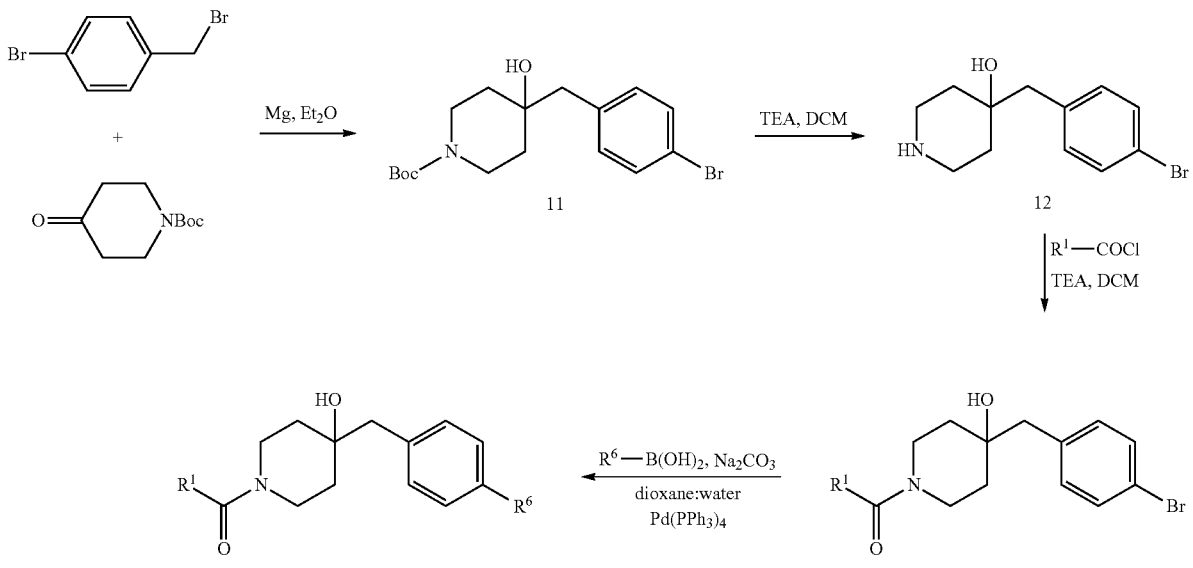

Scheme 3b: General synthesis of 4-(4-substituted-benzyl)-4-hydroxypiperidine amides-Method B

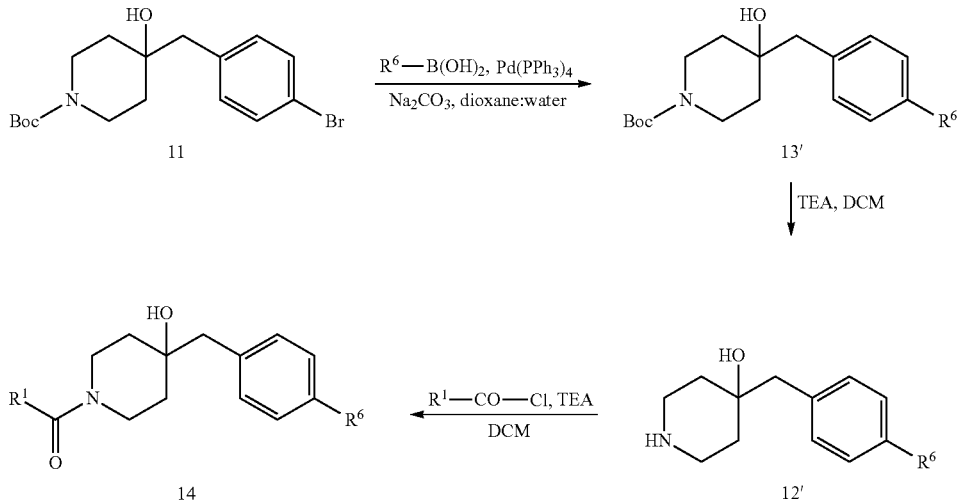

Scheme 4 outlines the route used to synthesize ketal Examples 98-123 starting from the known 1-[4-(4-bromobenzoyl)-1-piperidyl]ethanone. As also illustrated in the synthesis of Scheme 2, the trifluoroacetyl protecting group can be readily removed during the Suzuki coupling step by increasing the reaction time.

Scheme 4. Route to ketal examples

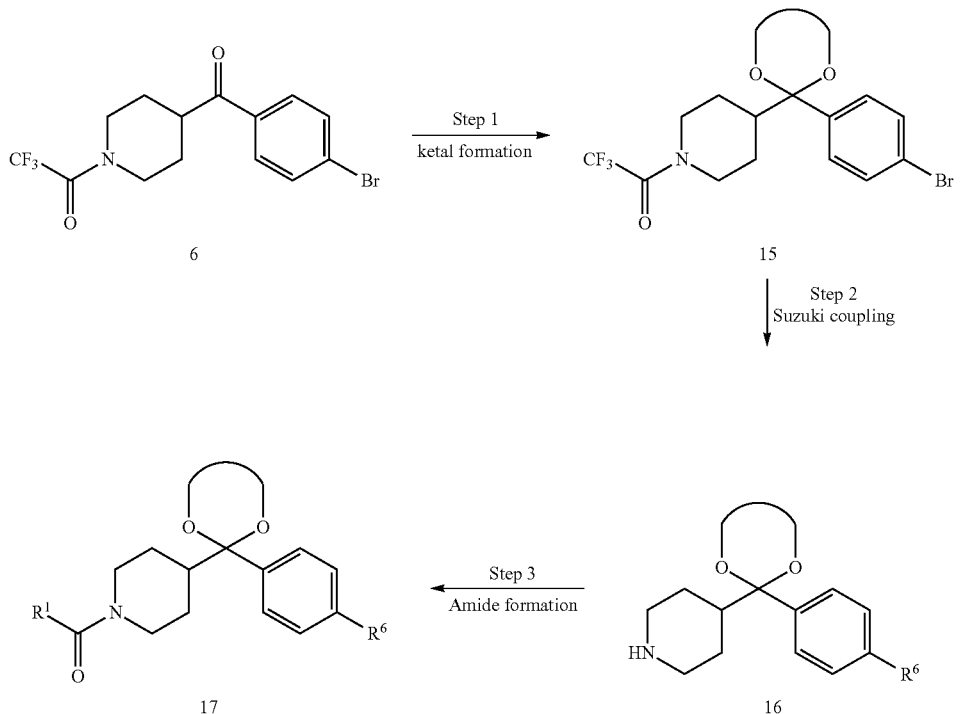

Scheme 5 outlines the route used to synthesize $R^9$ di-substituted examples 206-217. In step 1, alkyl Grignard addition to 1-[4-(4-bromobenzoyl)-1-piperidyl]ethanone provided the corresponding tertiary alcohol (Intermediate 18), follow by alkylation of the alcohol in Step 2 to give an ether intermediate (Intermediate 19). Step 3 Suzuki coupling and Step 4 amide coupling procedures were conducted as described previously to provide a final compound having a structure according to Intermediate 20.

Scheme 5. Route to $R^9$ disubstituted examples

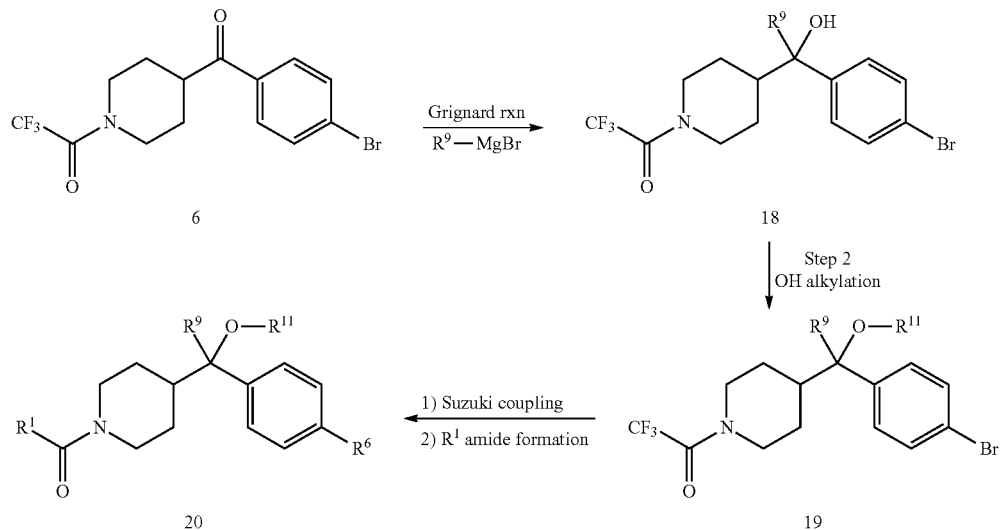

Scheme 6 outlines routes to Examples 222, 223, 225-228. The synthesis starts with Intermediate 21 (1-[4-(4-bromobenzoyl)-4-fluoro-piperidin-1-yl]-2,2,2-trifluoroethanone), which was prepared from Intermediate 6 and a fluorinating agent, e.g., 1-chloromethyl-4-fluoro-1,4-diazoniabicyclo[2.2.2]octane bis(tetrafluoroborate) (Selectfluor) under electrophilic fluorination conditions. Step 2 of the synthesis is a Suzuki coupling as described previously to form Intermediate 22. Step 3 is an $R^1$ amide formation as described previously to produce Intermediate 23. In Step 4, the ketone carbonyl group is reduced to the corresponding —OH to produce compounds having the structure of Intermediate 24. This ketone reduction provided $R^9$—OH examples such as Example 223. Alkylation of the —OH moiety using a base and the appropriate $R^{11}$ electrophile provided compounds according to Intermediate 25, such as Examples 225-227.

Scheme 6. Route to $R^9$ disubstituted examples

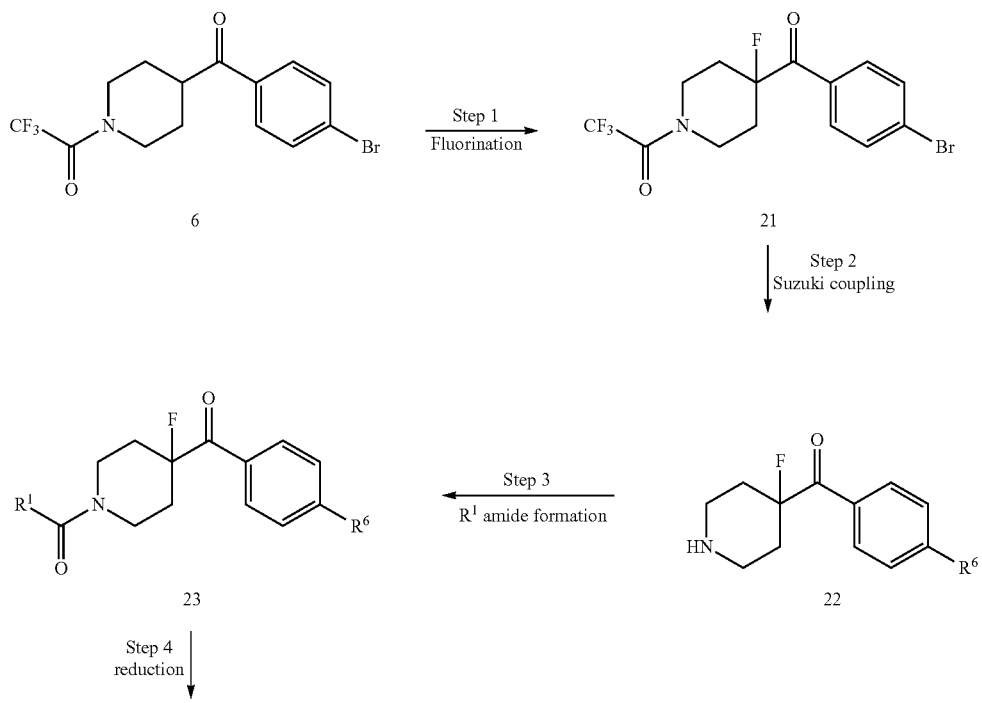

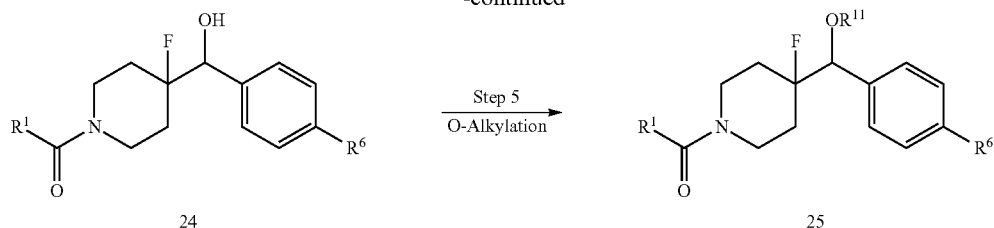

R⁹ mono alkyl examples were synthesized by alkyl Grignard addition to an appropriated 4-(4-bromobenzoyl)-piperidine, followed by deoxygenation using triethylsilane and TFA in DCM. Alternative R⁹ alkyl examples, such as Examples 51, 52, 63-77 may be synthesized as outlined in Scheme 7. In Scheme 7, an Intermediate 6' (having the R¹ mediate Intermediate 29 to install the R⁶ group serves to provide compounds having the Intermediate 30 structure.

Spiro-cyclopropyl Examples 40, 44, 45, 78-79 were prepared by cyclopropanation of the vinyl intermediate The R1 amide and R6 group may be installed as described previously.

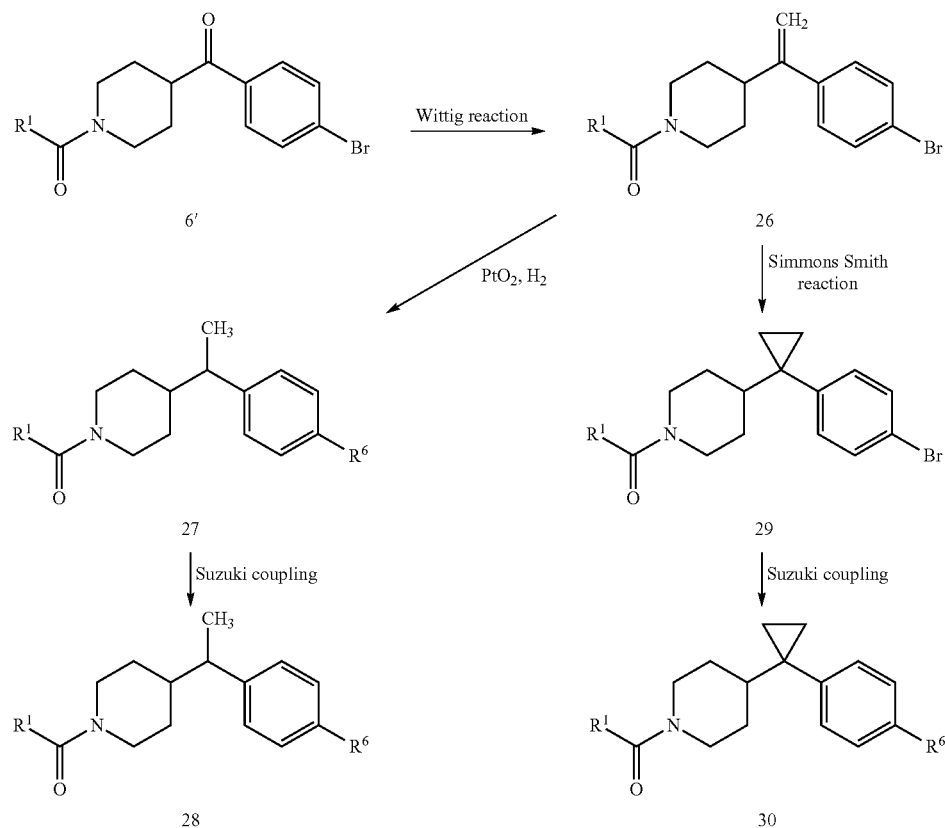

amide already installed) was reacted under Wittig reaction conditions using methyltriphenylphosphonium bromide to produce the corresponding vinyl intermediate 26. Hydrogenation of the Intermediate 26 provides Intermediate 27, wherein R⁹=methyl. Suzuki coupling of intermediate Intermediate 27 to install the R⁶ group serves to provide compounds having the Intermediate 28 structure. Intermediate 26 may also be a substrate for cyclopropanation using a Simmons-Smith reaction generated from diiodomethane and diethyl zinc to produce spiro-cycloprobyl intermediates having the Intermediate 29 structure. Suzuki coupling of inter- FASN Enzyme activity may be determined by detecting coenzyme A (CoA), a product of FASN-catalyzed synthesis of palmitate from acetyl-CoA and malonyl-CoA with NADPH as a cofactor. The assay is fluorescence-based and measures the interaction of free CoA with 7-diethylamino-3-(4'-malemimidylphenyl)-4-methylcoumarin (CPM; Life Technologies, CA) as described in Chung et al (2008). The coumarin derivative CPM contains a thiol-reactive maleimide that becomes fluorescent upon interaction with the sulfhydryl group of CoA.

For the example compounds described herein, the reaction was performed in 384-well low volume non-binding platews (Corning, N.Y.) using recombinant human baculovirus-expressed GST-tagged FASN. The 20-4 assay mixture contained 50 mM HEPES (pH 7.5), 5 nM FASN, 150 µM NADPH (Sigma, St. Louis, Mo.), 10 µM acetyl-CoA (Sigma), 25 µM malonyl-CoA (Sigma) and test compound [diluted in dimethyl sulfoxide (DMSO); 0.5% DMSO final in assay after 100 nL addition]. See, Chung et al.; "A fluorescence-based thiol quantification assay for ultra-high-throughput screening for inhibitors of coenzyme A production," Assay Drug Dev Tech 2008; 6:361-374.

The reaction was initiated by adding malonyl-CoA, followed by incubation for 90 minutes at 250° C. A stock solution of the CPM reagent was prepared in DMSO at 66 µM and stored at −200° C. To detect CoA produced in the FASN reaction, the CPM stock was diluted to 50 µM in 70% ethanol and added at 4 µL/well to the assay plate. The reaction mixture was then incubated for 30 minutes. Fluorescence was measured using the EnVision™ 2102 multi-label plate reader (PerkinElmer, Waltham, Mass.) utilizing a general dual mirror, a 390 nM excitation filter and a 530 nM emission filter. Data analysis was performed using ActivityBase (IDBS, Guilford, UK). $IC_{50}$ values were calculated by plotting the percent inhibition versus log 10 of the concentration of the compound, and fitting to the nonlinear regression sigmoidal dose-response (variable slope) equation in XLFit (IDBS). The $IC_{50}$ data for the Examples described herein is provided in Table 2 below.

TABLE 2

$IC_{50}$ data for Compounds of Formulae I, II, III and IV

| Ex # | Activity |
|---|---|
| 1 | A |
| 2 | A |
| 3 | A |
| 4 | A |
| 5 | A |
| 6 | A |
| 7 | A |
| 8 | A |
| 9 | B |
| 10 | B |
| 11 | A |
| 12 | A |
| 13 | A |
| 14 | C |
| 15 | A |
| 16 | B |
| 17 | B |
| 18 | A |
| 19 | A |
| 20 | A |
| 21 | C |
| 22 | A |
| 23 | A |
| 24 | A |
| 25 | A |
| 26 | C |
| 27 | C |
| 28 | A |
| 29 | A |
| 30 | A |
| 31 | A |
| 32 | A |
| 33 | A |
| 34 | A |
| 35 | A |
| 36 | A |
| 37 | A |
| 38 | C |
| 39 | A |
| 40 | A |
| 41 | A |
| 42 | A |
| 43 | C |
| 44 | B |
| 45 | B |
| 46 | A |
| 47 | A |
| 48 | B |
| 49 | A |
| 50 | A |
| 51 | A |
| 52 | A |
| 53 | C |
| 54 | A |
| 55 | C |
| 56 | B |
| 57 | C |
| 58 | A |
| 59 | B |
| 60 | C |
| 61 | B |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | C |
| 79 | C |
| 80 | A |
| 81 | A |
| 82 | A |
| 83 | A |
| 84 | A |
| 85 | A |
| 86 | B |
| 87 | A |
| 88 | B |
| 89 | A |
| 90 | B |
| 91 | A |
| 92 | A |
| 93 | A |
| 94 | B |
| 95 | B |
| 96 | A |
| 97 | A |
| 98 | C |
| 99 | C |
| 100 | C |
| 101 | C |
| 102 | C |
| 103 | C |
| 104 | C |
| 105 | C |
| 106 | C |
| 107 | C |
| 108 | C |
| 109 | C |
| 110 | C |
| 111 | C |
| 112 | C |
| 113 | C |
| 114 | B |
| 115 | C |
| 116 | C |
| 117 | C |

TABLE 2-continued

IC$_{50}$ data for Compounds of Formulae I, II, III and IV

| Ex # | Activity |
|---|---|
| 118 | N |
| 119 | N |
| 120 | N |
| 121 | C |
| 122 | C |
| 123 | C |
| 124 | C |
| 125 | A |
| 126 | B |
| 127 | A |
| 128 | A |
| 129 | C |
| 130 | A |
| 131 | B |
| 132 | A |
| 133 | C |
| 134 | C |
| 135 | C |
| 136 | C |
| 137 | C |
| 138 | B |
| 139 | A |
| 140 | B |
| 141 | B |
| 142 | B |
| 143 | A |
| 144 | C |
| 145 | C |
| 146 | B |
| 147 | C |
| 148 | C |
| 149 | C |
| 150 | B |
| 151 | C |
| 152 | C |
| 153 | C |
| 154 | C |
| 155 | C |
| 156 | C |
| 157 | C |
| 158 | C |
| 159 | C |
| 160 | B |
| 161 | A |
| 162 | A |
| 163 | A |
| 164 | B |
| 165 | A |
| 166 | B |
| 167 | A |
| 168 | C |
| 169 | B |
| 170 | A |
| 171 | A |
| 172 | B |
| 173 | B |
| 174 | B |
| 175 | A |
| 176 | B |
| 177 | A |
| 178 | B |
| 179 | B |
| 180 | C |
| 181 | A |
| 182 | A |
| 183 | A |
| 184 | B |
| 185 | A |
| 186 | A |
| 187 | A |
| 188 | A |
| 189 | A |
| 190 | A |
| 191 | A |
| 192 | B |
| 193 | A |

TABLE 2-continued

IC$_{50}$ data for Compounds of Formulae I, II, III and IV

| Ex # | Activity |
|---|---|
| 194 | B |
| 195 | A |
| 196 | A |
| 197 | A |
| 198 | B |
| 199 | A |
| 200 | A |
| 201 | A |
| 202 | A |
| 203 | A |
| 204 | B |
| 205 | B |
| 206 | B |
| 207 | B |
| 208 | B |
| 209 | A |
| 210 | C |
| 211 | C |
| 212 | A |
| 213 | B |
| 214 | B |
| 215 | B |
| 216 | C |
| 217 | C |
| 218 | B |
| 219 | B |
| 220 | B |
| 221 | A |
| 222 | C |
| 223 | A |
| 224 | A |
| 225 | A |
| 226 | A |
| 227 | A |
| 228 | A |
| 229 | A |
| 230 | A |
| 231 | A |
| 232 | A |
| 233 | A |
| 234 | A |

A = 1 to 99 nM;
B = 100 to 999 nM;
C = 1000-10,000 nM

EXAMPLES

Example 1

1-[4-(4-Quinolin-3-yl-benzyl)-piperidin-1-yl]-propan-1-one, HCl

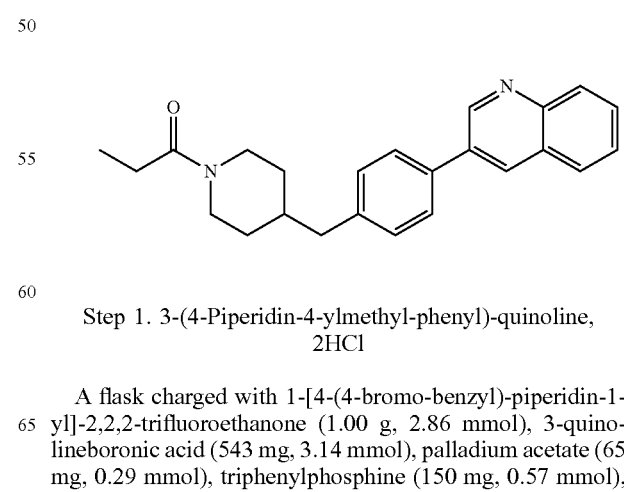

Step 1. 3-(4-Piperidin-4-ylmethyl-phenyl)-quinoline, 2HCl

A flask charged with 1-[4-(4-bromo-benzyl)-piperidin-1-yl]-2,2,2-trifluoroethanone (1.00 g, 2.86 mmol), 3-quinolineboronic acid (543 mg, 3.14 mmol), palladium acetate (65 mg, 0.29 mmol), triphenylphosphine (150 mg, 0.57 mmol), 1.0 M NaCO₃ (20 mL), 1,4-dioxane (10 mL), and DMF (10 mL). The mixture was flushed with N₂ for 15 min and then heated at 90° C. for 22 h. After cooling to room temperature, the reaction mixture was concentrated. The reaction was mixture was diluted with EtOAc (100 mL), washed with 1M Na₂CO₃ solution (30 mL), H₂O, brine, dried (Na₂SO₄), and concentrated. The crude product was purified by chromatography on silica gel [0-20% MeOH/DCM then (iPr₂NH:MeOH:DCM=1:4:5)] to give the product as colorless oil. The product was dissolved in dichloromethane (DCM) (~10 mL) and mixed with 2 eq. of 0.5 M HCl in MeOH and concentrated. The residue was dissolved in a small amount of DCM, concentrated and dried to give the HCl salt as an off-white solid 763 mg (71%).

Step 2. A 10 mL vial charged with 3-(4-piperidin-4-ylmethyl-phenyl)-quinoline 2HCl (101 mg, 0.269 mmol) and DCM (5 mL); Et₃N (0.30 μL, 2.2 mmol) was added followed by propanoyl chloride (26 μL, 0.30 mmol). After 35 min, the reaction was quenched with sat. NaHCO₃ solution (2 mL). The reaction was diluted with DCM (50 mL), washed with sat. NaHCO₃ (10 mL), brine, dried (Na₂SO₄), and concentrated. The residue was purified by chromatography on silica gel (0-10% MeOH/DCM) and the isolated product was dissolved in DCM (~5 mL) and mixed with 1.2 eq. of 0.5 M HCl in MeOH and concentrated. The residue was dissolved in a small amount of DCM and concentrated, and dried to give an off-white solid 81 mg (76%). LCMS m/z=359 (M+1); ¹H NMR (DMSO-d₆) δ: 9.56-9.61 (1H, m), 9.27-9.33 (1H, m), 8.29-8.36 (2H, m), 8.02-8.08 (1H, m), 7.91-7.96 (2H, m), 7.40-7.44 (2H, m), 7.25-7.31 (1H, m), 7.15-7.20 (1H, m), 4.31-4.43 (1H, m), 3.76-3.89 (1H, m), 2.85-3.00 (1H, m), 2.60-2.65 (2H, m), 2.39-2.49 (1H, m), 2.26-2.30 (2H, m), 1.51-1.68 (3H, m), 1.02-1.17 (2H, m), 0.96-0.99 (3H, m).

The following compounds were synthesized using the procedure for Example 1.

Example 2

2-Methyl-1-[4-(4-quinolin-3-yl-benzyl)-piperidin-1-yl]-propan-1-one, HCl

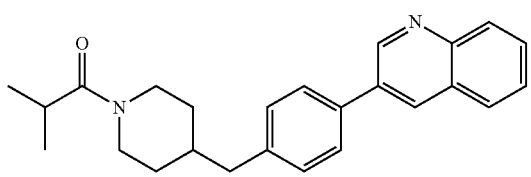 [SMILES: CCC(=O)N1CCC(Cc2ccc(-c3cnc4ccccc4c3)cc2)CC1]

The title compound was synthesized using the procedure for Example 1, except for reaction with isobutyryl chloride in Step 2- to produce the product as an off-white solid. LCMS m/z=373 (M+1); ¹H NMR (DMSO-d₆) δ: 9.53-9.57 (1H, m), 9.19-9.25 (1H, m), 8.26-8.33 (2H, m), 7.98-8.05 (1H, m), 7.90-7.94 (2H, m), 7.84-7.90 (1H, m), 7.40-7.44 (2H, m), 4.35-4.44 (1H, m), 3.89-3.99 (1H, m), 2.91-3.02 (1H, m), 2.81-2.89 (1H, m), 2.60-2.65 (2H, m), 2.39-2.49 (1H, m), 1.77-1.91 (1H, m), 1.57-1.71 (2H, m), 1.02-1.19 (2H, m), 0.94-1.02 (7H, m).

Example 3

Cyclopropyl-[4-(4-quinolin-3-yl-benzyl)-piperidin-1-yl]-methanone, HCl

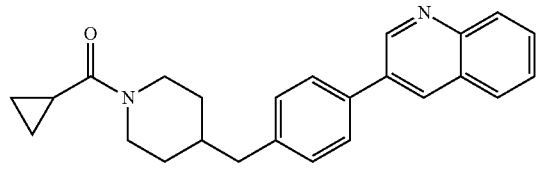 [SMILES: O=C(C1CC1)N1CCC(Cc2ccc(-c3cnc4ccccc4c3)cc2)CC1]

The title compound was synthesized using the procedure for Example 1, except for reaction with cyclopropanecarbonyl chloride in Step 2—to produce the product as an off-white solid. LCMS m/z=371 (M+1); ¹H NMR (DMSO-d₆) δ: 9.50-9.53 (1H, m), 9.14-9.18 (1H, m), 8.22-8.30 (3H, m), 7.96-8.02 (1H, m), 7.89-7.94 (2H, m), 7.81-7.88 (1H, m), 7.40-7.44 (2H, m), 4.31-4.40 (1H, m), 4.19-4.29 (1H, m), 2.98-3.09 (1H, m), 2.61-2.66 (2H, m), 1.91-1.99 (1H, m), 1.79-1.91 (1H, m), 1.58-1.72 (2H, m), 0.96-1.20 (3H, m), 0.65-0.73 (4H, m).

Example 4

4-(4-Quinolin-3-yl-benzyl)-piperidin-1-yl]-(R)-tetrahydrofuran-2-yl-methanone, TFA Salt

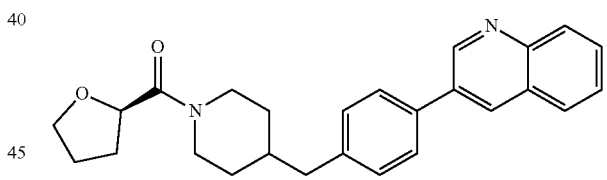

A vial charged with 3-(4-piperidin-4-ylmethyl-phenyl)-quinoline; 2HCl (151 mg, 0.40 mmol), (R)-tetrahydro-furan-2-carboxylic acid (40 μL, 0.42 mmol), HATU (306 mg, 0.81 mmol), iPr₂NEt (701 μL, 4.02 mmol), and CH₃CN was stirred at room temp for 1 h. The reaction was diluted with DCM (50 mL), washed with H₂O, brine, and then dried (Na₂SO₄), and concentrated. The residue was purified by prep-HPLC to give an off-white solid 80 mg (40%) as the TFA salt. LCMS m/z=401 (M+1); ¹H NMR (DMSO-d₆) δ: 9.35-9.38 (1H, m), 8.82-8.86 (1H, m), 8.09-8.16 (2H, m), 7.82-7.89 (3H, m), 7.70-7.76 (1H, m), 7.36-7.42 (2H, m), 4.59-4.67 (1H, m), 4.29-4.37 (1H, m), 3.94-4.03 (1H, m), 3.69-3.79 (2H, m), 2.88-3.01 (1H, m), 2.59-2.64 (2H, m), 2.52-2.57 (1H, m), 1.91-2.05 (2H, m), 1.74-1.91 (3H, m), 1.59-1.69 (2H, m), 0.98-1.21 (2H, m).

The following compound was synthesized using the procedure for Example 4.

Example 5

4-(4-Quinolin-3-yl-benzyl)-piperidin-1-yl]-(S)-tetrahydrofuran-2-yl-methanone, TFA Salt

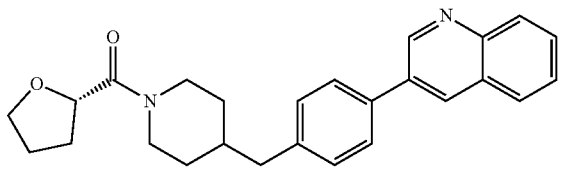 [SMILES: O=C([C@@H]1CCCO1)N1CCC(Cc2ccc(-c3cnc4ccccc4c3)cc2)CC1]

The title compound was synthesized using the procedure for Example 4, and reacting with (S)-tetrahydrofuran-2-carboxylic acid to produce the product as an off-white solid. LCMS m/z=401 (M+1); $^1$H NMR (DMSO-$d_6$) δ: 9.36-9.39 (1H, m), 8.85-8.88 (1H, m), 8.09-8.16 (3H, m), 7.84-7.89 (3H, m), 7.71-7.77 (1H, m), 7.37-7.42 (2H, m), 4.60-4.66 (1H, m), 4.29-4.37 (1H, m), 3.94-4.04 (1H, m), 3.69-3.80 (2H, m), 2.88-3.01 (1H, m), 2.59-2.64 (2H, m), 1.91-2.06 (2H, m), 1.74-1.90 (4H, m), 1.58-1.68 (2H, m), 0.98-1.21 (2H, m).

Example 6

1-{4-[Fluoro-(4-quinolin-3-yl-phenyl)-methyl]-piperidin-1-yl}-propan-1-one, HCl

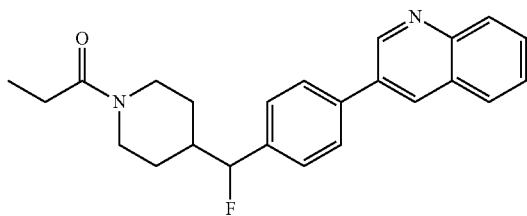 [SMILES: CCC(=O)N1CCC(C(F)c2ccc(-c3cnc4ccccc4c3)cc2)CC1]

Step 1. 4-[(4-Bromophenyl)-hydroxymethyl]-piperidine-1-carboxylic acid t-butyl ester To a stirred solution of 4-formyl-piperidine-1-carboxylic acid tert-butyl ester (1.00 g, 4.69 mmol) in THF at 0° C. was added 0.5 M of 4-bromophenyl MgBr in THF (23.4 mL, 11.7 mmol) slowly. After 2.5 h at room temp, the reaction was quenched with sat. NH$_4$Cl solution (50 mL), and extracted with EtOAc (3×50 mL). The combined organic layer was washed with brine, dried (Na$_2$SO$_4$), and concentrated. The residue was purified by chromatography on silica gel (0-20% EtOAc/DCM) to give a white semi-solid 943 mg (54%).

Step 2. 4-[Hydroxy-(4-quinolin-3-yl-phenyl)-methyl]-piperidine-1-carboxylic acid tert-butyl ester A flask charged with 4-[(4-bromophenyl)-hydroxymethyl]-piperidine-1-carboxylic acid tert-butyl ester (0.804 g, 2.17 mmol), 3-quinolineboronic acid (413 mg, 2.39 mmol), palladium acetate (49 mg, 0.22 mmol), triphenylphosphine (114 mg, 0.44 mmol), 1.0 M of sodium carbonate in water (15 mL), 1,4-dioxane (7.5 mL), and N,N-dimethylformamide (DMF)(15 mL) was flushed with N$_2$ for 15 min and then heated at 85° C. for 5 h. After cooling to room temp, the reaction mixture was concentrated. The concentrated reaction mixture was diluted with EtOAc (100 mL), washed with 1M Na$_2$CO$_3$ solution (30 mL), H$_2$O, brine, dried (Na$_2$SO$_4$), and concentrated. The crude product was purified by chromatography on silica gel (0-50% EtOAc/DCM) to give a white solid 523 mg (57%).

Step 3. 4-[Fluoro-(4-quinolin-3-yl-phenyl)-methyl]-piperidine-1-carboxylic acid t-butyl ester To a stirred solution of 4-[hydroxy-(4-quinolin-3-yl-phenyl)-methyl]-piperidine-1-carboxylic acid t-butyl ester (398 mg, 0.95 mmol) in DCM was added deoxofluor (877 µL, 4.75 mmol) slowly. After 5 h at room temp, the reaction was quenched with sat. NH$_4$Cl solution carefully, and extracted with EtOAc (3×30 mL). The combined organic layers were washed with brine, dried (Na$_2$SO$_4$), and concentrated. The crude product was purified by chromatography on silica gel [0-70% EtOAc/Hexanes) to give a colorless gum 350 mg (88%).

Step 4. 3-[4-(Fluoropiperidin-4-yl-methyl)-phenyl]-quinoline, 2HCl

To a solution of 4-[fluoro-(4-quinolin-3-yl-phenyl)-methyl]-piperidine-1-carboxylic acid t-butyl ester (0.352 mg, 0.84 mmol) in DCM (10 mL) was added 4.0 M HCl in 1,4-dioxane (2.09 mL, 8.37 mmol) slowly. After stirring 22 h at room temp, the reaction was concentrated. The residue was dissolved in a small amount of DCM and concentrated (repeated this procedure several times) and dried to give 390 mg crude product as an off-white solid. This material was used for next step without purification.

Step 5

A vial was charged with 3-[4-(fluoropiperidin-4-yl-methyl)-phenyl]-quinoline; 2HCl (102 mg, 0.26 mmol) and Et$_3$N (0.29 mL, 2.1 mmol) in DCM. Propanoyl chloride (25 µL, 0.285 mmol) was added dropwise. After 20 min, the reaction was quenched with sat. NaHCO$_3$ solution (4 mL), diluted with DCM (50 mL), washed with sat. NaHCO$_3$ solution (10 mL), washed with brine, dried (Na$_2$SO$_4$), and concentrated. The crude product was purified by chromatography on silica gel (0-10% MeOH/DCM) and the isolated product dissolved in DCM (~5 mL) and mixed with 1.2 eq. of 0.5 M HCl in MeOH and concentrated. The residue was dissolved in a small amount of DCM and concentrated (repeated this procedure several times), dried to give an off-white solid 80 mg (70%). LCMS m/z=377 (M+1); $^1$HNMR (DMSO-$d_6$) δ: 9.55 (m, 1H), 9.22 (s, 1H), 8.29 (m, 2H), 8.03 (m, 3H), 7.87 (m, 1H), 7.57 (m, 2H), 5.55-5.36 (m, 1H), 4.44 (m, 1H), 3.89 (m, 1H), 2.96 (m, 1H), 2.48 (m, 1H), 2.36-2.08 (m, 3H), 1.83 (m, 1H), 1.43-1.04 (m, 3H), 1.02-0.91 (m, 3H).

The following compound was synthesized using the procedure for Example 6.

Example 7

Cyclopropyl-{4-[fluoro-(4-quinolin-3-yl-phenyl)-methyl]-piperidin-1-yl}-methanone, HCl

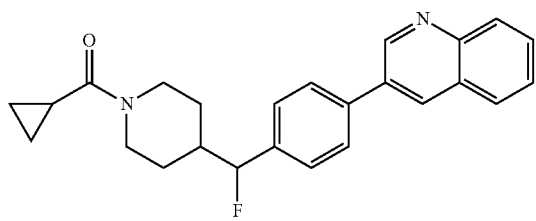 [SMILES: O=C(C1CC1)N1CCC(C(F)c2ccc(-c3cnc4ccccc4c3)cc2)CC1]

The title compound was synthesized using the procedure for Example 6, except for reaction with cyclopropanecarbonyl chloride in Step 5 to produce the product as an off-white solid. LCMS m/z=389 (M+1); $^1$HNMR (DMSO-$d_6$) δ: 9.56 (m, 1H), 9.24 (s, 1H), 8.29 (m, 2H), 8.03 (m, 3H), 7.88 (m, 1H), 7.58 (m, 2H), 5.56-5.38 (m, 1H), 4.53-4.17 (m, 2H), 3.18-2.93 (m, 1H), 2.64-2.42 (m, 1H), 2.28-2.10 (m, 1H), 2.03-1.75 (m, 1H), 1.46-1.01 (m, 3H), 0.84-0.59 (m, 5H).

Example 8

{4-[Fluoro-(4-quinolin-3-yl-phenyl)-methyl]-piperidin-1-yl}-(R)-tetrahydro-furan-2-yl-methanone, HCl

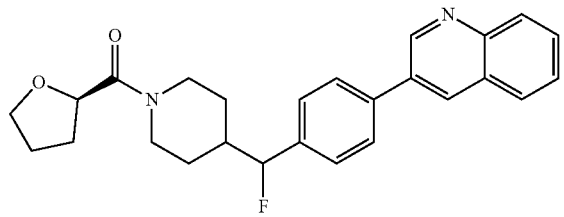 [SMILES: O=C([C@H]1CCCO1)N1CCC(C(F)c2ccc(-c3cnc4ccccc4c3)cc2)CC1]

A vial charged with 3-[4-(fluoro-piperidin-4-yl-methyl)-phenyl]-quinoline 2HCl (187 mg, 0.475 mmol), (R)-tetrahydrofuran-2-carboxylic acid (48 μL, 0.50 mmol), HATU (362 mg, 0.95 mmol), iPr$_2$NEt (828 μL, 4.75 mmol), and CH$_3$CN was stirred at room temp for 2 h. The reaction was diluted with DCM (50 mL), washed with H$_2$O, brine, dried (Na$_2$SO$_4$), and concentrated. The residue was purified by chromatography on silica gel (0-10% MeOH/DCM) and the isolated product was dissolved in small amount of DCM and mixed with 1.2 eq. of 0.5M HCl in MeOH and concentrated. The residue was dissolved in a small amount of DCM and concentrated (repeated this procedure several times), and dried to give a light-brown solid 200 mg (90%). LCMS m/z=419 (M+1); $^1$HNMR (DMSO-$d_6$) δ: 9.58 (s, 1H), 9.27 (s, 1H), 8.31 (m, 2H), 8.03 (m, 3H), 7.89 (m, 1H), 7.58 (m, 1H), 5.57-5.35 (m, 1H), 4.63 (m, 1H), 4.38 (m, 1H), 4.13-3.95 (m, 1H), 3.82-3.67 (m, 2H), 3.06-2.85 (m, 1H), 2.48 (m, 1H), 2.26-1.71 (m, 5H), 1.43-1.06 (m, 5H).

Example 9

1-(4-{Difluoro-[4-(4-methylquinolin-3-yl)-phenyl]-methyl}-piperidin-1-yl)-propan-1-one, HCl

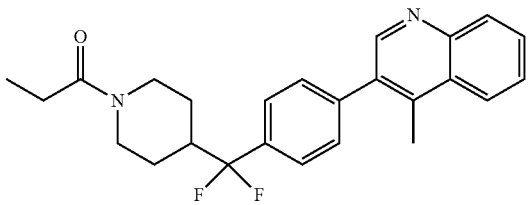 [SMILES: CCC(=O)N1CCC(C(F)(F)c2ccc(-c3cnc4ccccc4c3C)cc2)CC1]

Step 1. 1-{4-[(4-Bromophenyl)-difluoromethyl]-piperidin-1-yl}-2,2,2-trifluoroethanone A 30 mL Teflon bottle was charged with 1-[4-(4-bromobenzoyl)-piperidin-1-yl]-2,2,2-trifluoroethanone (1.5 g, 4.12 mmol) and deoxofluor (7.59 mL, 41.2 mmol) in DCM. To this was carefully and slowly added EtOH (722 μL, 12.4 mmol). After stirring at room temp for 6 days, the reaction was carefully dropwise added into a sat. NaHCO$_3$ solution (~150 mL) and then extracted with DCM (3×80 mL). The combined organic layers were dried (Na$_2$SO$_4$) and concentrated. The residue was purified by chromatography on silica gel (10% EtOAc/Hexanes) to give colorless oil 1.25 g (78%). $^1$H NMR (DMSO-$d_6$) δ: 7.92-7.98 (2H, m), 7.74-7.80 (2H, m), 4.25-4.34 (1H, m), 3.86-3.95 (1H, m), 3.76-3.85 (1H, m), 3.38-3.49 (1H, m), 3.06-3.16 (1H, m), 1.88-1.99 (2H, m), 1.42-1.61 (2H, m).

Step 2. 1-(4-{Difluoro-[4-(4,4,5,5-tetramethyl-1,3,2-dioxaborolan-2-yl)-phenyl]-methyl}-piperidin-1-yl)-2,2,2-trifluoroethanone A flask charged with 1-{4-[(4-bromo-phenyl)-difluoromethyl]-piperidin-1-yl}-2,2,2-trifluoroethanone (452 mg, 1.20 mmol), 4,4,5,5,4',4',5',5'-octamethyl-[2,2']bi[[1,3,2]dioxaborolanyl] (456 mg, 1.79 mmol), bis(tricyclohexylphosphine)palladium (0) (84 mg, 0.12 mmol), potassium acetate (176 mg, 1.79 mmol), and dioxane (10 mL) was heated at 100° C. over 3 days. The reaction was then cooled to rt and concentrated. The residue was added DCM (10 mL) and filtered through a pad of Celite (diatomaceous earth), washed with DCM, and the filtrate was concentrated to give the desired crude product which was used for next step without purification.

Step 3. 3-[4-(Difluoropiperidin-4-yl-methyl)-phenyl]-4-methyl-quinoline

A flask charged with 1-(4-{difluoro-[4-(4,4,5,5-tetramethyl-1,3,2-dioxaborolan-2-yl)-phenyl]-methyl}-piperidin-1-yl)-2,2,2-trifluoro-ethanone (518 mg, 1.20 mmol), 3-bromo-4-methylquinoline (266 mg, 1.20 mmol), palladium acetate (27 mg, 0.12 mmol), triphenylphosphine (63 mg, 0.24 mmol), 1.0 M of Na$_2$CO$_3$ in water (6 mL, 6 mmol), dioxane (6 mL), and DMF (6 mL) was flushed with N$_2$ for 15 min. After heating at 85° C. for 15 h, the reaction was diluted with EtOAc (80 mL), washed with 1.0 M of Na$_2$CO$_3$ in water (30 mL). The aqueous layer was extracted with EtOAc (30 mL) and the combined organic layers were washed with H$_2$O, brine, dried (Na$_2$SO$_4$), and concentrated.

83

The residue was purified by chromatography on silica gel [0-10% MeOH/DCM then solvent (iPr$_2$NH:MeOH:DCM=1:4:20)] to give a brown oil 204 mg (48%, 2 steps from Step b). The product was dissolved in DCM and mixed with 2 eq. of 0.5 M HCl in MeOH and concentrated. The residue was dissolved in a small amount of DCM and concentrated (repeated this procedure several times), and dried to give a white solid (HCl salt). LCMS m/z=353 (M+1); $^1$H NMR (DMSO-d$_6$) δ: 9.04-9.09 (1H, m), 8.41-8.48 (1H, m), 8.28-8.36 (1H, m), 8.01-8.09 (1H, m), 7.88-7.95 (1H, m), 7.66-7.75 (5H, m), 3.27-3.37 (2H, m), 2.81-2.96 (2H, m), 2.78 (3H, s), 2.61-2.71 (1H, m), 1.78-1.87 (2H, m), 1.61-1.75 (2H, m).

Step 4

A vial was charged with 3-[4-(difluoropiperidin-4-yl-methyl)-phenyl]-4-methyl-quinoline; 2HCl (60 mg, 0.14 mmol) and Et$_3$N (190 μL, 1.40 mmol) in DCM. Propanoyl chloride (16 μL, 0.19 mmol) was added dropwise. After 25 min, the reaction was quenched with sat. NaHCO$_3$ solution (3 mL) diluted with DCM (50 mL), washed with H$_2$O, brine, dried (Na$_2$SO$_4$), and concentrated. The crude product was purified by pre-HPLC and the isolated fractions were combined, neutralized with sat. NaHCO$_3$ solution (25 mL), and extracted with DCM (3×25 mL). The combined organic layers were dried (Na$_2$SO$_4$), and concentrated. The product was dissolved in DCM (~5 mL) and mixed with 1.2 eq. of 0.5 M HCl in MeOH and concentrated. The residue was dissolved in a small amount of DCM and concentrated (repeated this procedure several times), and dried to give an off-white solid 51 mg (81%). LCMS m/z=409 (M+1); $^1$HNMR (DMSO-d$_6$) δ: 9.13 (s, 1H), 8.47 (m, 1H), 8.33 (m, 1H), 8.08 (m, 1H), 7.94 (m, 1H), 7.70 (m, 4H), 4.50 (m, 1H), 3.94 (m, 1H), 2.99 (m, 0.5H), 2.79 (s, 3H), 2.63-2.46 (m, 2H), 2.31 (m, 2H), 1.71 (m, 2H), 1.42-1.09 (m, 2.5H), 0.97 (t, J=7 Hz, 3H).

The following compounds were synthesized using the procedure for Example 9.

Example 10

Cyclopropyl-(4-{difluoro-[4-(4-methyl-quinolin-3-yl)-phenyl]-methyl}-piperidin-1-yl)-methanone, HCl

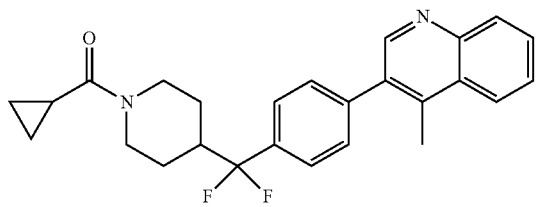 [SMILES: Cc1c(-c2ccc(C(F)(F)C3CCN(C(=O)C4CC4)CC3)cc2)cnc2ccccc12]

The title compound was synthesized using the procedure for Example 9, except for reaction with cyclopropanecarbonyl chloride in Step 4 to produce the product as an off-white solid (HCl salt). LCMS m/z=421 (M+1); $^1$HNMR (DMSO-d$_6$) δ: 9.11 (s, 1H), 8.46 (m, 1H), 8.30 (m, 1H), 8.06 (m, 1H), 7.92 (m, 1H), 7.70 (m, 4H), 4.41 (m, 2H), 3.09 (m, 1H), 2.78 (s, 3H), 2.58 (m, 2H), 1.97 (m, 1H), 1.74 (m, 2H), 1.30 (m, 2H), 0.69 (m, 4H).

84

Example 11

(4-{Difluoro-[4-(4-methylquinolin-3-yl)-phenyl]-methyl}-piperidin-1-yl)-(R)-tetrahydrofuran-2-yl-methanone, HCl

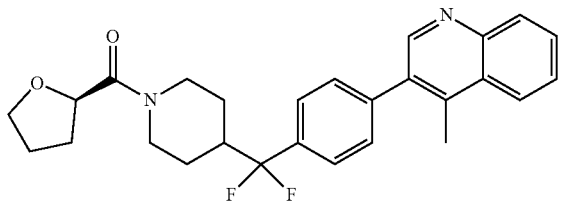 [SMILES: Cc1c(-c2ccc(C(F)(F)C3CCN(C(=O)[C@H]4CCCO4)CC3)cc2)cnc2ccccc12]

The title compound was synthesized using the procedure for Example 9, except for reaction with (S)-tetrahydrofuran-2-carbonyl chloride in Step 4 to produce the product as an off-white solid (HCl salt). LCMS m/z=451 (M+1); $^1$HNMR (DMSO-d$_6$) δ: 9.12 (s, 1H), 8.47 (m, 1H), 8.32 (m, 1H), 8.07 (m, 1H), 7.93 (m, 1H), 7.70 (m, 4H), 4.65 (m, 1H), 4.44 (m, 1H), 4.09 (m, 1H), 3.73 (m, 2H), 2.99 (m, 1H), 2.79 (s, 3H), 2.57 (m, 2H), 2.09-1.64 (m, 6H), 1.45-1.10 (m, 2H).

Example 12

1-{4-[4-(4-Methylquinolin-3-yl)-benzyl]-piperidin-1-yl}-propan-1-one, HCl

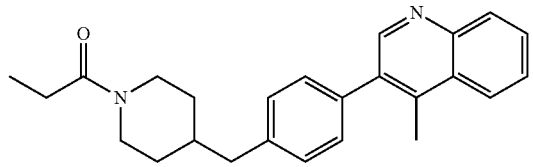 [SMILES: CCC(=O)N1CCC(Cc2ccc(-c3cnc4ccccc4c3C)cc2)CC1]

The title compound was synthesized using the procedure for Example 9, except for starting with 1-{4-[(4-Bromophenyl)-difluoromethyl]-piperidin-1-yl}-2,2,2-trifluoro-ethanone in Step 1, and reaction with propionyl chloride in Step 4, to produce the product as a white solid. LCMS m/z=373 (M+1); $^1$H NMR (DMSO-d$_6$) δ: 9.10-9.15 (1 H, m), 8.44-8.51 (1H, m), 8.31-8.38 (1H, m), 8.04-8.13 (1H, m), 7.91-7.99 (1H, m), 7.46-7.53 (2H, m), 7.37-7.43 (2H, m), 4.34-4.44 (1H, m), 3.81-3.90 (1H, m), 2.89-3.01 (1H, m), 2.81 (3H, s), 2.60-2.67 (2H, m), 2.42-2.49 (1H, m), 2.25-2.35 (2H, m), 1.78-1.92 (1H, m), 1.58-1.72 (2H, m), 1.01-1.21 (2H, m), 0.98 (3H, t, J=7.4 Hz).

Example 13

Cyclopropyl-{4-[4-(4-methylquinolin-3-yl)-benzyl]-piperidin-1-yl}-methanone, HCl

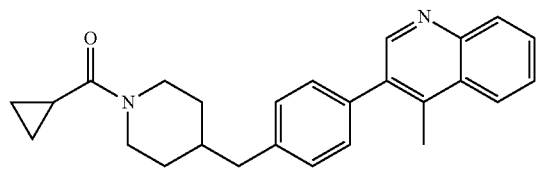

The title compound was synthesized using the procedure for Example 9, except for starting with 1-{4-[(4-bromophenyl)-difluoromethyl]-piperidin-1-yl}-2,2,2-trifluoroethanone in Step 1, and reaction with cyclopropanecarbonyl chloride in Step 4 to produce the product as an off-white solid. LCMS m/z=385 (M+1); $^1$H NMR (DMSO-d$_6$) δ: 9.10-9.15 (1H, m), 8.43-8.49 (1H, m), 8.30-8.35 (1H, m), 8.04-8.11 (1H, m), 7.90-7.98 (1H, m), 7.47-7.53 (2H, m), 7.38-7.44 (2H, m), 4.32-4.42 (1H, m), 4.20-4.31 (1H, m), 2.98-3.12 (1H, m), 2.81 (3H, s), 2.62-2.69 (2H, m), 2.52-2.60 (1H, m), 1.81-2.01 (2H, m), 1.59-1.77 (2H, m), 0.99-1.22 (2H, m), 0.62-0.76 (4H, m).

Example 14

(3,3-Difluorocyclobutyl)-{4-[4-(4-methylquinolin-3-yl)-benzyl]-piperidin-1-yl}-methanone, HCl

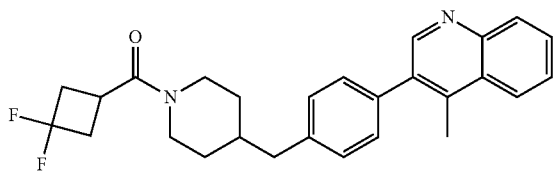 [SMILES: Cc1c(-c2ccc(CC3CCN(C(=O)C4CC(F)(F)C4)CC3)cc2)cnc2ccccc12]

The title compound was synthesized using the procedure for Example 9, except for starting with 1-{4-[(4-bromophenyl)-difluoro-methyl]-piperidin-1-yl}-2,2,2-trifluoro-ethanone in Step 1, and reaction with 3,3-difluorocyclobutane-1-carbonyl chloride in Step 4 to produce the product as an off-white solid. LCMS m/z=435 (M+1); $^1$H NMR (DMSO-d$_6$) δ: 9.09-9.13 (1H, m), 8.43-8.50 (1H, m), 8.29-8.36 (1H, m), 8.04-8.11 (1H, m), 7.90-7.98 (1H, m), 7.46-7.52 (2H, m), 7.37-7.42 (2H, m), 4.32-4.41 (1H, m), 3.72-3.80 (1H, m), 3.17-3.29 (1H, m), 2.89-3.00 (1H, m), 2.80 (3H, s), 2.68-2.79 (4H, m), 2.52-2.66 (3H, m), 1.78-1.92 (1H, m), 1.60-1.69 (2H, m), 1.01-1.20 (2H, m).

Example 15

{4-[4-(4-Methylquinolin-3-yl)-benzyl]-piperidin-1-yl}-(R)-tetrahydrofuran-2-yl-methanone, HCl

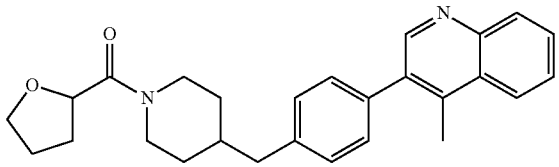 [SMILES: Cc1c(-c2ccc(CC3CCN(C(=O)C4CCCO4)CC3)cc2)cnc2ccccc12]

The title compound was synthesized using the procedure for Example 9, except for starting with 1-{4-[(4-bromophenyl)-difluoro-methyl]-piperidin-1-yl}-2,2,2-trifluoroethanone in Step 1, and reaction with (R)-tetrahydrofuran-2-carbonyl chloride in Step 4 to produce the product as an off-white solid. LCMS m/z=415 (M+1); $^1$H NMR (DMSO-d$_6$) δ: 9.10-9.15 (1H, m), 8.44-8.50 (1H, m), 8.29-8.35 (1H, m), 8.04-8.11 (1H, m), 7.91-7.98 (1H, m), 7.46-7.52 (2H, m), 7.37-7.43 (2H, m), 4.60-4.68 (1H, m), 4.30-4.39 (1H, m), 3.95-4.05 (1H, m), 3.68-3.82 (2H, m), 2.89-3.04 (1H, m), 2.81 (3H, s), 2.61-2.68 (2H, m), 2.52-2.59 (1H, m), 1.74-2.07 (5H, m), 1.59-1.71 (2H, m), 0.99-1.22 (2H, m).

Example 16

1-{4-[Difluoro-(4-quinolin-3-yl-phenyl)-methyl]-piperidin-1-yl}-propan-1-one, HCl

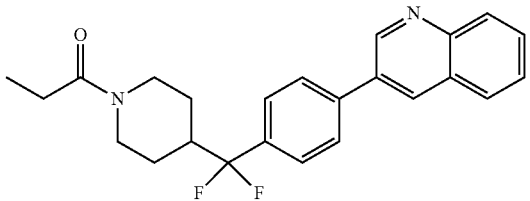 [SMILES: CCC(=O)N1CCC(C(F)(F)c2ccc(-c3cnc4ccccc4c3)cc2)CC1]

The title compound was synthesized using the procedure for Example 9, except for reacting with 3-bromo-4-methylquinoline in Step 3, and reaction with propionyl chloride in Step 4, to produce the product as an off-white solid. LCMS m/z=395 (M+1); $^1$H NMR (DMSO-d$_6$) δ: 9.50-9.55 (1H, m), 9.12-9.19 (1H, m), 8.21-8.30 (2H, m), 8.07-8.14 (2H, m), 7.96-8.02 (1H, m), 7.80-7.88 (1H, m), 7.65-7.73 (2H, m), 4.44-4.53 (1H, m), 3.87-3.97 (1H, m), 2.92-3.04 (1H, m), 2.53-2.65 (1H, m), 2.42-2.49 (1H, m), 2.25-2.35 (2H, m), 1.62-1.76 (2H, m), 1.11-1.39 (2H, m), 0.96 (3H, t, J=7.4 Hz).

Example 17

Cyclopropyl-{4-[difluoro-(4-quinolin-3-yl-phenyl)-methyl]-piperidin-1-yl}-methanone, HCl

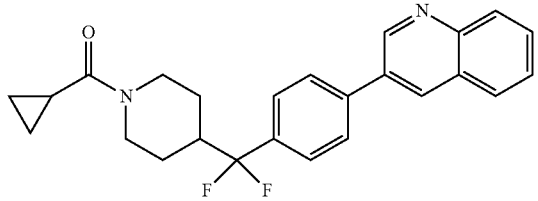 [SMILES: O=C(C1CC1)N1CCC(C(F)(F)c2ccc(-c3cnc4ccccc4c3)cc2)CC1]

The title compound was synthesized using the procedure for Example 9, except for reacting with 3-bromo-4-methylquinoline in Step 3, and reaction with cyclopropanecarbonyl chloride in Step 4, to produce the product as an off-white solid. LCMS m/z=407 (M+1); $^1$H NMR (DMSO-d$_6$) δ: 9.51-9.56 (1H, m), 9.15-9.20 (1H, m), 8.23-8.31 (2H, m), 8.08-8.14 (2H, m), 7.96-8.03 (1H, m), 7.81-7.89 (1H, m), 7.67-7.73 (2H, m), 4.41-4.51 (1H, m), 4.29-4.39 (1H, m), 3.00-3.15 (1H, m), 2.52-2.66 (2H, m), 1.90-2.00 (1H, m), 1.62-1.81 (2H, m), 1.14-1.36 (2H, m), 0.63-0.74 (4H, m).

Example 18

{4-[Difluoro-(4-quinolin-3-yl-phenyl)-methyl]-piperidin-1-yl}-(R)-tetrahydrofuran-2-yl-methanone, HCl

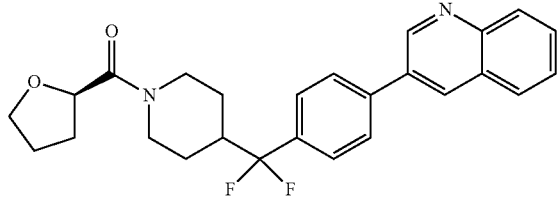 [SMILES: O=C([C@H]1CCCO1)N1CCC(C(F)(F)c2ccc(-c3cnc4ccccc4c3)cc2)CC1]

The title compound was synthesized using the procedure for Example 9, except for reacting with 3-bromo-4-methyl-quinoline in Step 3, and reaction with (R)-tetrahydrofuran-2-carbonyl chloride in Step 4, to produce the product as an off-white solid. LCMS m/z=437 (M+1); $^1$H NMR (DMSO-$d_6$) δ: 9.50-9.55 (1H, m), 9.13-9.20 (1H, m), 8.22-8.30 (2H, m), 8.07-8.14 (2H, m), 7.95-8.03 (1H, m), 7.81-7.88 (1H, m), 7.66-7.73 (2H, m), 4.60-4.66 (1H, m), 4.39-4.48 (1H, m), 4.04-4.14 (1H, m), 3.67-3.78 (2H, m), 2.93-3.07 (1H, m), 2.52-2.65 (2H, m), 1.89-2.07 (2H, m), 1.76-1.88 (2H, m), 1.65-1.76 (2H, m), 1.29-1.41 (1H, m), 1.14-1.27 (1H, m).

Example 19

1-{4-[4-(4-Chloroquinolin-3-yl)-benzyl]-piperidin-1-yl}-propan-1-one, HCl

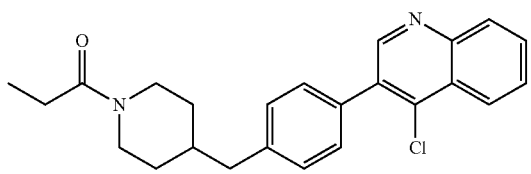 [SMILES: CCC(=O)N1CCC(Cc2ccc(-c3cnc4ccccc4c3Cl)cc2)CC1]

The title compound was synthesized using the procedure for Example 9, except for reacting with 3-bromo-4-chloro-quinoline in Step 3, and reaction with propionyl chloride in Step 4, to produce the product as an off-white solid. LCMS m/z=393 (M+1); $^1$H NMR (DMSO-$d_6$) δ: 8.92 (1H, s), 8.31-8.38 (1H, m), 8.14-8.20 (1H, m), 7.89-7.97 (1H, m), 7.81-7.88 (1H, m), 7.52-7.59 (2H, m), 7.34-7.41 (2H, m), 4.34-4.43 (1H, m), 3.79-3.90 (1H, m), 2.88-3.01 (1H, m), 2.58-2.65 (2H, m), 2.43-2.49 (1H, m), 2.30 (2H, m, J=1.0 Hz), 1.76-1.91 (1H, m), 1.59-1.71 (2H, m), 1.01-1.20 (2H, m), 0.98 (3H, t, J=7.5 Hz).

Example 20

{4-[4-(4-Chloroquinolin-3-yl)-benzyl]-piperidin-1-yl}-cyclopropylmethanone, HCl

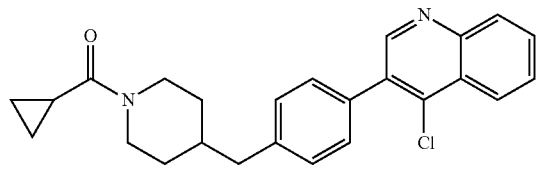 [SMILES: O=C(C1CC1)N1CCC(Cc2ccc(-c3cnc4ccccc4c3Cl)cc2)CC1]

The title compound was synthesized using the procedure for Example 9, except for reacting with 3-bromo-4-chloro-quinoline in Step 3, and reaction with cyclopropanecarbonyl chloride in Step 4, to produce the product as an off-white solid. LCMS m/z=405 (M+1); $^1$H NMR (DMSO-$d_6$) δ: 8.92 (1H, s), 8.31-8.37 (1H, m), 8.14-8.19 (1H, m), 7.89-7.96 (1H, m), 7.81-7.89 (1H, m), 7.53-7.59 (2H, m), 7.35-7.42 (2H, m), 4.33-4.39 (1H, m), 4.18-4.30 (1H, m), 2.96-3.12 (1H, m), 2.61-2.66 (2H, m), 2.51-2.59 (1H, m), 1.80-2.00 (2H, m), 1.57-1.77 (2H, m), 0.97-1.27 (2H, m), 0.63-0.78 (4H, m).

Example 21

{4-[4-(4-Chloroquinolin-3-yl)-benzyl]-piperidin-1-yl}-(3,3-difluorocyclobutyl)-methanone, HCl

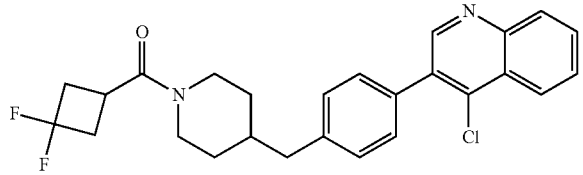 [SMILES: O=C(C1CC(F)(F)C1)N1CCC(Cc2ccc(-c3cnc4ccccc4c3Cl)cc2)CC1]

The title compound was synthesized using the procedure for Example 9, except for reacting with 3-bromo-4-chloro-quinoline in Step 3, and reaction with 3,3-difluorocyclobutane-1-carbonyl chloride in Step 4, to produce the product as an off-white solid. LCMS m/z=455 (M+1); $^1$H NMR (DMSO-$d_6$) δ: 8.94 (1H, s), 8.32-8.38 (1H, m), 8.15-8.21 (1H, m), 7.90-7.98 (1H, m), 7.82-7.89 (1H, m), 7.53-7.60 (2H, m), 7.35-7.41 (2H, m), 4.32-4.41 (1H, m), 3.71-3.80 (1H, m), 3.17-3.29 (1H, m), 2.88-3.00 (1H, m), 2.68-2.86 (4H, m), 2.53-2.66 (3H, m), 1.78-1.93 (1H, m), 1.60-1.70 (2H, m), 1.00-1.19 (2H, m).

Example 22

{4-[4-(4-Chloroquinolin-3-yl)-benzyl]-piperidin-1-yl}-(R)-tetrahydrofuran-2-yl-methanone, HCl

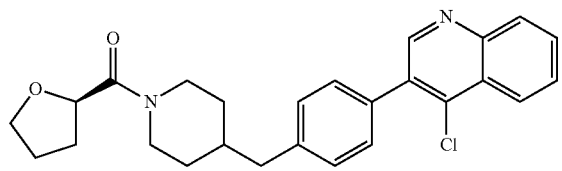 [SMILES: O=C([C@H]1CCCO1)N1CCC(Cc2ccc(-c3cnc4ccccc4c3Cl)cc2)CC1]

The title compound was synthesized using the procedure for Example 9, except for reacting with 3-bromo-4-chloroquinoline in Step 3, and reaction with (R)-tetrahydrofuran-2-carbonyl chloride in Step 4, to produce the product as an off-white solid. LCMS m/z=435 (M+1); $^1$H NMR (DMSO-d$_6$) δ: 8.93 (1H, s), 8.32-8.38 (1H, m), 8.14-8.20 (1H, m), 7.90-7.96 (1H, m), 7.82-7.88 (1H, m), 7.55 (2H, s), 7.35-7.41 (2H, m), 4.62-4.65 (1H, m), 4.29-4.39 (1H, m), 3.94-4.05 (1H, m), 3.68-3.82 (2H, m), 2.89-3.04 (1H, m), 2.60-2.66 (2H, m), 2.52-2.59 (1H, m), 1.92-2.06 (2H, m), 1.75-1.91 (3H, m), 1.61-1.70 (2H, m), 1.12-1.25 (1H, m), 0.99-1.12 (1H, m).

Example 23

1-{4-[4-(8-Methylquinolin-7-yl)-benzyl]-piperidin-1-yl}-propan-1-one, HCl

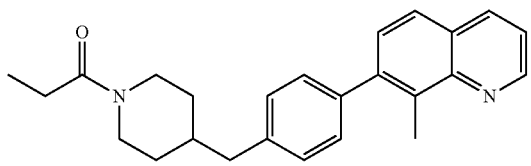 [SMILES: CCC(=O)N1CCC(Cc2ccc(-c3ccc4cccnc4c3C)cc2)CC1]

The title compound was synthesized using the procedure for Example 9, except for reacting with 7-bromo-8-methylquinoline in Step 3, and reaction with propionyl chloride in Step 4, to produce the product as a light brown solid. LCMS m/z=373 (M+1); $^1$H NMR (DMSO-d$_6$) δ: 9.10-9.18 (1H, m), 8.79-8.90 (1H, m), 8.05-8.14 (1H, m), 7.82-7.92 (1H, m), 7.65-7.73 (1H, m), 7.31-7.44 (4H, m), 4.33-4.43 (1H, m), 3.78-3.89 (1H, m), 2.86-3.00 (1H, m), 2.72 (3H, s), 2.58-2.64 (2H, m), 2.40-2.48 (1H, m), 2.25-2.35 (2H, m), 1.74-1.91 (1H, m), 1.57-1.70 (2H, m), 1.01-1.30 (1H, m), 0.93-1.01 (3H, m), 0.84-0.92 (1H, m).

Example 24

Cyclopropyl-{4-[4-(8-methylquinolin-7-yl)-benzyl]-piperidin-1-yl}-methanone, HCl

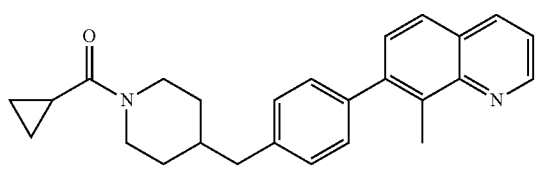 [SMILES: Cc1c(-c2ccc(CC3CCN(C(=O)C4CC4)CC3)cc2)ccc2cccnc12]

The title compound was synthesized using the procedure for Example 9, except for reacting with 7-bromo-8-methylquinoline in Step 3, and reaction with cyclopropanecarbonyl chloride in Step 4, to produce the product as an off-white solid. LCMS m/z=385 (M+1); $^1$H NMR (DMSO-d$_6$) δ: 9.09-9.16 (1H, m), 8.74-8.86 (1H, m), 8.02-8.12 (1H, m), 7.79-7.89 (1H, m), 7.64-7.72 (1H, m), 7.31-7.44 (4H, m), 4.18-4.43 (2H, m), 2.98-3.13 (1H, m), 2.71 (3H, s), 2.59-2.66 (2H, m), 2.52-2.58 (1H, m), 1.80-2.00 (2H, m), 1.56-1.76 (2H, m), 1.11-1.26 (1H, m), 1.03-1.11 (1H, m), 0.75-0.80 (1H, m), 0.63-0.74 (4H, m).

Example 25

{4-[4-(8-Methylquinolin-7-yl)-benzyl]-piperidin-1-yl}-(R)-tetrahydrofuran-2-yl-methanone, HCl

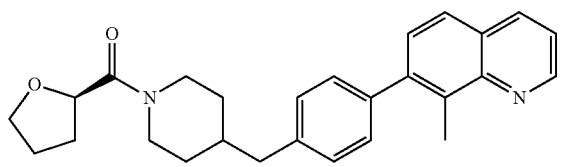 [SMILES: Cc1c(-c2ccc(CC3CCN(C(=O)[C@H]4CCCO4)CC3)cc2)ccc2cccnc12]

The title compound was synthesized using the procedure for Example 9, except for reacting with 7-bromo-8-methylquinoline in Step 3, and reaction with (R)-tetrahydrofuran-2-carbonyl chloride in Step 4, to produce the product as a light-brown solid. LCMS m/z=415 (M+1); $^1$H NMR (DMSO-d$_6$) δ: 9.08-9.17 (1H, m), 8.74-8.86 (1H, m), 8.02-8.11 (1H, m), 7.80-7.90 (1H, m), 7.64-7.72 (1H, m), 7.31-7.44 (4H, m), 4.60-4.68 (1H, m), 4.29-4.40 (1H, m), 3.93-4.05 (1H, m), 3.69-3.83 (2H, m), 2.89-3.05 (1H, m), 2.71 (3H, s), 2.58-2.65 (2H, m), 2.52-2.57 (1H, m), 1.920-2.06 (2H, m), 1.74-1.92 (3H, m), 1.60-1.71 (2H, m), 0.98-1.26 (2H, m).

Example 26

1-[4-(4-Isoquinolin-3-yl-benzyl)-piperidin-1-yl]-propan-1-one, HCl

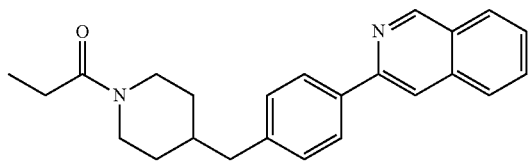 [SMILES: CCC(=O)N1CCC(Cc2ccc(-c3cc4ccccc4cn3)cc2)CC1]

The title compound was synthesized using the procedure for Example 9, except for reacting with 3-bromoisoquinoline in Step 3, and reaction with propionyl chloride in Step 4, to produce the product as a light yellow solid. LCMS m/z=359 (M+1); $^1$H NMR (DMSO-d$_6$) δ: 9.60-9.67 (1H, m), 8.58-8.64 (1H, m), 8.31-8.38 (1H, m), 8.08-8.18 (3H, m), 7.93-8.04 (1H, m), 7.78-7.86 (1H, m), 7.37-7.44 (2H, m), 4.33-4.43 (1H, m), 3.79-3.88 (1H, m), 2.88-2.99 (1H, m), 2.58-2.66 (2H, m), 2.42-2.49 (1H, m), 2.23-2.34 (2H, m), 1.77-1.90 (1H, m), 1.56-1.70 (2H, m), 1.00-1.20 (2H, m), 0.97 (3H, s).

Example 27

Cyclopropyl-[4-(4-isoquinolin-3-yl-benzyl)-piperidin-1-yl]-methanone, HCl

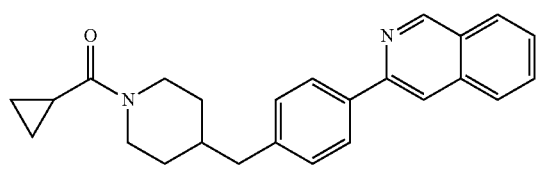 [SMILES: O=C(C1CC1)N1CCC(Cc2ccc(-c3cc4ccccc4cn3)cc2)CC1]

The title compound was synthesized using the procedure for Example 9, except for reacting with 3-bromoisoquinoline in Step 3, and reaction with cyclopropanecarbonyl chloride in Step 4, to produce the product as an off-white solid. LCMS m/z=371 (M+1); $^1$H NMR (DMSO-d$_6$) δ: 9.61-9.68 (1H, m), 8.59-8.65 (1H, m), 8.31-8.40 (1H, m), 8.08-8.20 (3H, m), 7.95-8.04 (1H, m), 7.78-7.86 (1H, m), 7.38-7.44 (2H, m), 4.17-4.42 (2H, m), 2.95-3.11 (1H, m), 2.60-2.67 (2H, m), 2.52-2.58 (1H, m), 1.79-2.00 (2H, m), 1.55-1.75 (2H, m), 0.97-1.23 (2H, m), 0.75-0.84 (1H, m), 0.61-0.74 (4H, m).

Example 28

[4-(4-Isoquinolin-3-yl-benzyl)-piperidin-1-yl]-(R)-tetrahydrofuran-2-yl-methanone, HCl

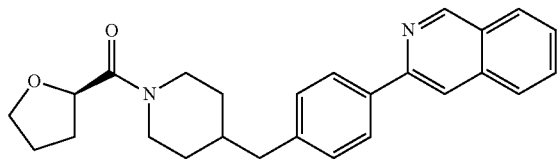 [SMILES: O=C([C@H]1CCCO1)N1CCC(Cc2ccc(-c3cc4ccccc4cn3)cc2)CC1]

The title compound was synthesized using the procedure for Example 9, except for reacting with 3-bromoisoquinoline in Step 3, and reaction with (R)-tetrahydrofuran-2-carbonyl chloride in Step 4, to produce the product as an off-white solid. LCMS m/z=401 (M+1); $^1$H NMR (DMSO-d$_6$) δ: 9.64-9.71 (1H, m), 8.62-8.68 (1H, m), 8.34-8.42 (1H, m), 8.08-8.21 (3H, m), 7.97-8.05 (1H, m), 7.80-7.88 (1H, m), 7.38-7.46 (2H, m), 4.59-4.67 (1H, m), 4.28-4.38 (1H, m), 3.94-4.04 (1H, m), 3.67-3.82 (2H, m), 2.88-3.02 (1H, m), 2.59-2.66 (2H, m), 2.52-2.58 (1H, m), 1.91-2.06 (2H, m), 1.74-1.90 (3H, m), 1.58-1.70 (2H, m), 0.96-1.22 (2H, m).

Example 29

1-{4-[4-(8-Chloroquinolin-7-yl)-benzyl]-piperidin-1-yl}-propan-1-one, HCl

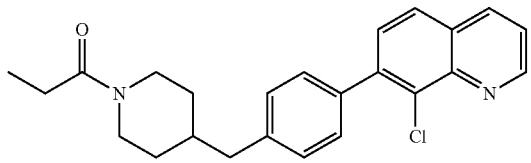 [SMILES: CCC(=O)N1CCC(Cc2ccc(-c3ccc4cccnc4c3Cl)cc2)CC1]

The title compound was synthesized using the procedure for Example 9, except for reacting with 7-bromo-8-chloroquinoline in Step 3, and reaction with propionyl chloride in Step 4, to produce the product as an off-white solid. LCMS m/z=393 (M+1); $^1$H NMR (DMSO-d$_6$) δ: 9.05-9.10 (1H, m), 8.50-8.56 (1H, m), 8.03-8.08 (1H, m), 7.62-7.73 (2H, m), 7.47-7.52 (2H, m), 7.30-7.37 (2H, m), 4.38-4.40 (1H, m), 3.80-3.90 (1H, m), 2.89-3.00 (1H, m), 2.58-2.64 (2H, m), 2.44-2.49 (1H, m), 2.25-2.35 (2H, m), 1.77-1.89 (1H, m), 1.59-1.71 (2H, m), 1.01-1.20 (2H, m), 0.95-1.01 (3H, m).

Example 30

{4-[4-(8-Chloroquinolin-7-yl)-benzyl]-piperidin-1-yl}-cyclopropylmethanone, HCl

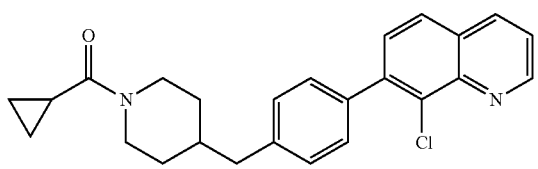

The title compound was synthesized using the procedure for Example 9, except for reacting with 7-bromo-8-chloroquinoline in Step 3, and reaction with cyclopropanecarbonyl chloride in Step 4, to produce the product as a light-brown solid. LCMS m/z=405 (M+1); $^1$H NMR (DMSO-d$_6$) δ: 9.06-9.10 (1H, m), 8.51-8.55 (1H, m), 8.03-8.08 (1H, m), 7.63-7.72 (2H, m), 7.47-7.52 (2H, m), 7.32-7.37 (2H, m), 4.31-4.41 (1H, m), 4.20-4.30 (1H, m), 2.98-3.11 (1H, m), 2.59-2.65 (2H, m), 2.52-2.59 (1H, m), 1.79-2.00 (2H, m), 1.58-1.76 (2H, m), 0.97-1.22 (2H, m), 0.63-0.76 (4H, m).

Example 31

{4-[4-(8-Chloroquinolin-7-yl)-benzyl]-piperidin-1-yl}-(R)-tetrahydrofuran-2-yl-methanone, HCl

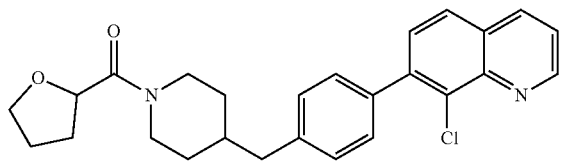 [SMILES: O=C(C1CCCO1)N1CCC(Cc2ccc(-c3ccc4cccnc4c3Cl)cc2)CC1]

The title compound was synthesized using the procedure for Example 9, except for reacting with 7-bromo-8-chloroquinoline in Step 3, and reaction with (R)-tetrahydrofuran-2-carbonyl chloride in Step 4, to produce the product as an off-white solid. LCMS m/z=435 (M+1); $^1$H NMR (DMSO-d$_6$) δ: 9.05-9.10 (1H, m), 8.50-8.56 (1H, m), 8.02-8.09 (1H, m), 7.62-7.73 (2H, m), 7.46-7.53 (2H, m), 7.31-7.38 (2H, m), 4.60-4.67 (1H, m), 4.34-4.36 (1H, m), 3.94-4.05 (1H, m), 3.69-3.81 (2H, m), 2.88-3.04 (1H, m), 2.59-2.64 (2H, m), 2.52-2.59 (1H, m), 1.92-2.07 (2H, m), 1.74-1.91 (3H, m), 1.60-1.71 (2H, m), 0.99-1.22 (2H, m).

Example 32

1-{4-[4-(8-Methoxy quinolin-7-yl)-benzyl]-piperidin-1-yl}-propan-1-one, HCl

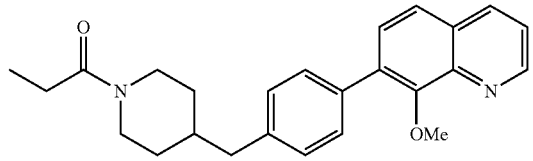 [SMILES: CCC(=O)N1CCC(Cc2ccc(-c3ccc4cccnc4c3OC)cc2)CC1]

The title compound was synthesized using the procedure for Example 9, except for reacting with 7-bromo-8-methoxyquinoline in Step 3, and reaction with propionyl chloride in Step 4, to produce the product as a tan solid. LCMS m/z=389 (M+1); $^1$H NMR (DMSO-d$_6$) δ: 9.10-9.18 (1H, m), 8.86-8.97 (1H, m), 8.01-8.08 (1H, m), 7.81-7.96 (2H, m), 7.62-7.69 (2H, m), 7.33-7.40 (2H, m), 4.33-4.44 (1H, m), 3.79-3.90 (1H, m), 3.72-3.77 (3H, m), 3.64-3.71 (1H, m), 2.88-3.01 (1H, m), 2.58-2.66 (2H, m), 2.41-2.48 (1H, m), 2.24-2.35 (2H, m), 1.75-1.92 (1H, m), 1.56-1.71 (2H, m), 1.01-1.21 (2H, m), 0.94-1.01 (3H, m).

Example 33

Cyclopropyl-{4-[4-(8-methoxyquinolin-7-yl)-benzyl]-piperidin-1-yl}-methanone, HCl

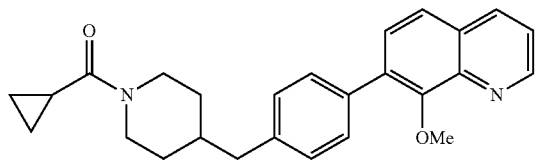 [SMILES: COc1c(-c2ccc(CC3CCN(C(=O)C4CC4)CC3)cc2)ccc2cccnc12]

The title compound was synthesized using the procedure for Example 9, except for reacting with 7-bromo-8-methoxyquinoline in Step 3, and reaction with cyclopropanecarbonyl chloride in Step 4, to produce the product as a light-yellow solid. LCMS m/z=401 (M+1); $^1$H NMR (DMSO-d$_6$) δ: 9.10-9.18 (1H, m), 8.88-8.98 (1H, m), 8.02-8.10 (1H, m), 7.82-7.97 (2H, m), 7.62-7.70 (2H, m), 7.34-7.41 (2H, m), 4.31-4.43 (1H, m), 4.18-4.30 (1H, m), 3.75 (3H, s), 2.96-3.13 (1H, m), 2.60-2.67 (2H, m), 2.52-2.59 (1H, m), 1.79-2.01 (2H, m), 1.57-1.75 (2H, m), 0.97-1.22 (2H, m), 0.63-0.75 (4H, m).

Example 34

{4-[4-(8-Methoxy quinolin-7-yl)-benzyl]-piperidin-1-yl}-(R)-tetrahydrofuran-2-yl-methanone, HCl

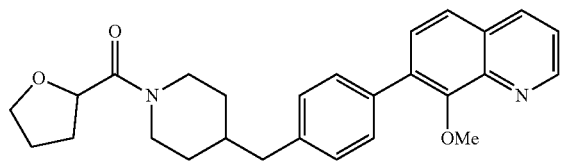 [SMILES: COc1c(-c2ccc(CC3CCN(C(=O)C4CCCO4)CC3)cc2)ccc2cccnc12]

The title compound was synthesized using the procedure for Example 9, except for reacting with 7-bromo-8-methoxyquinoline in Step 3, and reaction with (R)-tetrahydrofuran-2-carbonyl chloride in Step 4, to produce the product as a light-yellow solid. LCMS m/z=431 (M+1); $^1$H NMR (DMSO-d$_6$) δ: 9.11-9.19 (1H, m), 8.89-9.01 (1H, m), 8.03-8.11 (1H, m), 7.84-7.98 (2H, m), 7.62-7.70 (2H, m), 7.34-7.41 (2H, m), 4.59-4.67 (1H, m), 4.28-4.39 (1H, m), 3.94-4.05 (1H, m), 3.75-3.82 (1H, m), 3.73 (3H, s), 3.62-3.72 (2H, m), 2.88-3.04 (1H, m), 2.59-2.66 (2H, m), 2.52-2.58 (1H, m), 1.93-2.08 (2H, m), 1.72-1.92 (3H, m), 1.58-1.70 (2H, m), 0.97-1.22 (2H, m).

Example 35

1-{4-[4-(1-methylisoquinolin-6-yl)-benzyl]-piperidin-1-yl}-propan-1-one, HCl

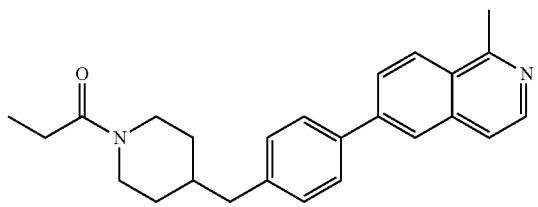 [SMILES: CCC(=O)N1CCC(Cc2ccc(-c3ccc4c(C)nccc4c3)cc2)CC1]

Step 1. 4-(4-Bromobenzyl)-piperidine-1-carboxylic acid tert-butyl ester

A flask charged with 1-[4-(4-bromobenzyl)-piperidin-1-yl]-2,2,2-trifluoroethanone (5.00 g, 14.3 mmol), sodium carbonate (7.57 g, 71.4 mmol), and 100 mL of MeOH—H$_2$O (1:1) was stirred at 50° C. for 2 h. The reaction was concentrated and the residue was stirred with di-tert-butyl-dicarbonate (3.12 g, 14.3 mmol) in 100 mL of THF-H$_2$O (1:1) at room temp for 2 h. The organic solvent was removed and the aqueous layer was extracted with DCM (3×80 mL), the combined organic layers were washed with H$_2$O, and with brine, dried (Na$_2$SO$_4$), and concentrated to isolate the desired intermediate. This intermediate was used for next step without purification.

Step 2. 4-[4-(4,4,5,5-Tetramethyl-1,3,2-dioxaborolan-2-yl)-benzyl]-piperidine-1-carboxylic acid tert-butyl ester A flask charged with 4-(4-bromobenzyl)-piperidine-1-carboxylic acid t-butyl ester (5.06 g, 14.3 mmol), 4,4,5,5,4',4',5',5'-octamethyl-[2,2']bi[[1,3,2]dioxaborolanyl] (5.44 g, 21.4 mmol), bis(tricyclohexylphosphine)palladium (0) (1.0 g, 1.5 mmol), potassium acetate (2.10 g, 21.4 mmol), and 1,4-dioxane (100 mL) was stirred at 100° C. over 3 days. After cooling to room temp, the reaction was filtered through a pad of Celite, eluted with DCM, and the combined filtrate was collected and concentrated. The residue was purified by chromatography on silica gel (DCM) to give a brown oil 4.58 g (80%, 3 steps).

Step 3. 4-[4-(1-methylisoquinolin-6-yl)-benzyl]-piperidine-1-carboxylic acid t-butyl ester A flask charged with 4-[4-(4,4,5,5-tetramethyl-1,3,2-dioxaborolan-2-yl)-benzyl]-piperidine-1-carboxylic acid tert-butyl ester (1.09 g, 2.72 mmol), 6-bromo-1-methyl-isoquinoline (603 mg, 2.72 mmol), palladium acetate (62 mg. 0.27 mmol), triphenylphosphine (140 mg, 0.54 mmol), 1.0 M of Na$_2$CO$_4$ in water (10 mL, 10 mmol), 1,4-dioxane (10 mL), and DMF (10 mL) was flushed with N$_2$ for 15 min. The reaction was stirred at 85° C. for 5 h and then cooled to room temp. EtOAc (100 mL) was added to the reaction mixture, and the resulting mixture was washed with sat. NaHCO$_3$ solution (30 mL) and the aqueous layer was extracted once with EtOAc (50 mL). The combined organic layers were washed with H$_2$O (30 mL), and with brine, dried (Na$_2$SO$_4$), and concentrated. The residue was purified by chromatography on silica gel (0-70% EtOAc/Hexanes) to give 560 mg (50%) of the desired product.

Step 4. 1-Methyl-6-(4-piperidin-4-ylmethyl-phenyl)-isoquinoline, 2HCl

4-[4-(1-Methylisoquinolin-6-yl)-benzyl]-piperidine-1-carboxylic acid t-butyl ester (560 mg, 1.34 mmol) was stirred with HCl in 1,4-dioxane (4.0 M, 3.36 mL, 13.4 mmol) in DCM at room temp over night (18 h). The resulting precipitate was collected by filtration, washed with DCM, and dried to give 421 mg (80%) of the desired product.

Step 5. 1-{4-[4-(1-methylisoquinolin-6-yl)-benzyl]-piperidin-1-yl}-propan-1-one, HCl To a vial charged with 1-methyl-6-(4-piperidin-4-ylmethyl-phenyl)-isoquinoline; 2HCl (103 mg, 0.264 mmol) and N,N-diisopropylethylamine (DIPEA)(230 µL, 1.32 mmol) in THF (8 mL) was added propanoyl chloride (25 µL, 0.29 mmol) dropwise. After 25 min, the reaction was quenched with a small amount of MeOH and then concentrated. The residue was purified by pre-HPLC, and the isolated fractions were combined, free-based with sat. NaHCO$_3$ solution (25 mL), and then extracted with DCM (3×25 mL). The combined organic layers were dried (Na$_2$SO$_4$) and concentrated. The residue was dissolved in DCM (~5 mL) and mixed with 1.2 eq. of 0.5M HCl in MeOH and concentrated. The residue was dissolved in a small amount of DCM and concentrated (repeated this procedure several times), and dried to give an off-white solid; 89.5 mg (83%). LCMS m/z=373 (M+1); $^1$H NMR (DMSO-d$_6$) δ: 8.60-8.66 (2H, m), 8.47-8.51 (1H, m), 8.34-8.39 (1H, m), 8.29-8.33 (1H, m), 7.88-7.93 (2H, m), 7.39-7.44 (2H, m), 4.33-4.43 (1H, m), 3.79-3.88 (1H, m), 3.23 (3H, s), 2.88-3.00 (1H, m), 2.60-2.65 (2H, m), 2.60-2.65 (2H, m), 2.42-2.49 (1H, m), 2.29 (2H, q, J=7.5 Hz), 1.76-1.90 (1H, m), 1.56-1.69 (2H, m), 0.97 (3H, t, J=7.4 Hz).

The following compounds were synthesized using the procedure for Example 35.

Example 36

Cyclopropyl-{4-[4-(1-methyl-isoquinolin-6-yl)-benzyl]-piperidin-1-yl}-methanone, HCl

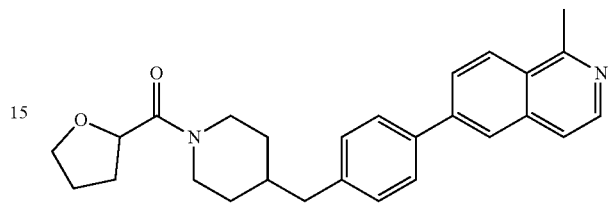

The title compound was synthesized using the procedure for Example 35, except for reaction with cyclopropanecarbonyl chloride in Step 5, to produce the product as an off-white solid. LCMS m/z=385 (M+1); $^1$H NMR (DMSO-d$_6$) δ: 8.60-8.65 (2H, m), 8.47-8.50 (1H, m), 8.34-8.38 (1H, m), 8.29-8.32 (1H, m), 7.88-7.93 (2H, m), 7.40-7.45 (2H, m), 4.30-4.41 (1H, m), 4.18-4.30 (1H, m), 3.22 (3H, s), 2.97-3.10 (1H, m), 2.64 (2H, d, J=7.3 Hz), 1.90-1.99 (1H, m), 1.80-1.90 (1H, m), 1.55-1.74 (2H, m), 1.11-1.26 (1H, m), 0.97-1.11 (2H, m), 0.67 (4H, d, J=7.8 Hz).

Example 37

{4-[4-(1-methylisoquinolin-6-yl)-benzyl]-piperidin-1-yl}-(R)-tetrahydro-furan-2-yl-methanone, TFA Salt

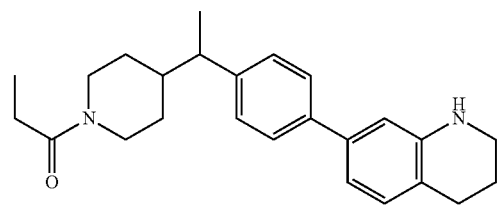

The title compound was synthesized using the procedure for Example 35, except for reaction with (R)-tetrahydro-furan-2-carbonyl chloride in Step 5, to produce the product as a white solid. LCMS m/z=415 (M+1); $^1$H NMR (DMSO-d$_6$) δ: 8.59-8.67 (2H, m), 8.50-8.54 (1H, m), 8.34-8.39 (1H, m), 8.29-8.33 (1H, m), 7.88-7.94 (2H, m), 7.39-7.45 (2H, m), 4.60-4.66 (1H, m), 4.29-4.38 (1H, m), 3.94-4.03 (1H, m), 3.68-3.80 (2H, m), 3.18 (3H, s), 2.88-3.02 (1H, m), 2.60-2.66 (2H, m), 2.52-2.57 (1H, m), 1.91-2.07 (2H, m), 1.75-1.91 (3H, m), 1.57-1.69 (2H, m), 0.96-1.24 (2H, m).

Example 38

1-(4-(1-(4-(1,2,3,4-tetrahydroquinolin-7-yl)phenyl)ethyl)piperidin-1-yl)propan-1-one

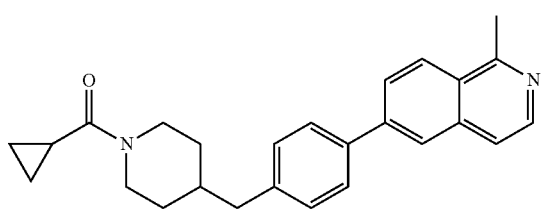 [SMILES: Cc1nccc2cc(-c3ccc(CC4CCN(C(=O)C5CC5)CC4)cc3)ccc12]

Step 1. 1-{4-[1-Hydroxy-1-(4-quinolin-7-yl-phenyl)-ethyl]-piperidin-1-yl}-propan-1-one To a stirred solution of 1-[4-(4-quinolin-7-yl-benzoyl)-piperidin-1-yl]-propan-1-one (0.120 g, 0.322 mmol) in THF (2.00 mL) at 0° C. was added methyl MgBr (0.0499 g, 0.419 mmol) dropwise under argon. After the addition, the cooling bath was removed and the mixture was warmed to room temperature. After 30 min, the reaction mixture was quenched with saturated aqueous NH$_4$Cl and the aqueous layer was extracted twice with EtOAc. The combined organics were washed with brine, dried, filtered, and concentrated to produce the desired product, 0.150 g as a crude product. LCMS m/z=389 (M+1).

Step 2.1-(4-{1-[4-(1,2,3,4-Tetrahydroquinolin-7-yl)-phenyl]-ethyl}-piperidin-1-yl)-propan-1-one To an stirred solution of 1-{4-[1-hydroxy-1-(4-quinolin-7-yl-phenyl)-ethyl]-piperidin-1-yl}-propan-1-one (0.135 g, 0.347 mmol) and triethylsilane (0.278 mL, 1.74 mmol) in DCM (3.00 mL, 46.8 mmol) at 5° C. was added TFA (0.268 mL, 3.47 mmol) dropwise under argon. The cooling bath was removed, and the reaction warmed to rt. The reaction mixture was concentrated and the crude residue was purified by Gilson.

The mixture was dissolved in EtOAc, MeOH and DIEA and placed in a Parr shaker along with Pd/C (10%) and hydrogenated at 47 psi for 15 h. The reaction mixture was filtered through a pad of celite/silica gel and the filtrate was concentrated to obtain a crude product. The crude product was purified by Gilson and then treated with 4M HCl in dioxane to produce the desired product, 0.063 g (38%) as an off-white solid. mp: 169-171° C. (EtOAc, MeOH, ether and 2-Me-butane); LCMS m/z=377 (M+1); $^1$H NMR (DMSO-$d_6$) δ: 7.48 (d, 2H, J=8 Hz), 7.25 (d, 2H, J=8 Hz), 7.11 (s, 2H), 7.04 (s, 1H), 4.26-4.49 (m, 1H), 3.82-3.93 (m, 1H), 3.30 (t, 2H, J=6 Hz), 2.71-2.99 (m, 3H), 2.17-2.49 (m, 4H), 1.77-1.97 (m, 3H), 1.57-1.71 (m, 1H), 1.27-1.39 (m, 1H), 1.21 (d, 3H, J=7 Hz), 0.76-1.01 (m, 4H).

Example 39

1-(4-(1-(4-(quinolin-3-yl)phenyl)ethyl)piperidin-1-yl)propan-1-one

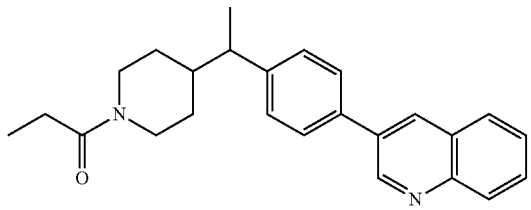 [SMILES: CCC(=O)N1CCC(C(C)c2ccc(-c3cnc4ccccc4c3)cc2)CC1]

Step 1. (4-Bromophenyl)-piperidin-4-yl-methanone

To a well stirred solution of 1-[4-(4-bromobenzoyl)-piperidin-1-yl]-2,2,2-trifluoroethanone (10.0 g, 27.5 mmol) in a mixture of methanol (50 mL) and water (3.00 mL) was added $K_2CO_3$ (7.59 g, 54.92 mmol). The reaction mixture was heated at 70° C. for 2 h, then concentrated in vacuo, and partitioned between EtOAc and water. The aqueous layer was extracted twice (EtOAc) and the combined organics was washed with brine, dried, filtered, and concentrated to give 7.4 g (100%) of the desired product. LCMS m/z=268 (M$^+$).

Step 2. 1-[4-(4-Bromobenzoyl)-piperidin-1-yl]-propan-1-one

To a solution of (4-bromophenyl)-piperidin-4-yl-methanone (2.50 g, 9.32 mmol) and DIPEA (8.10 mL, 46.62 mmol) in DCM (20 mL) was added propanoyl chloride (1.22 mL, 13.98 mmol) dropwise at RT. The reaction mixture was stirred at rt and monitored by HPLC and LCMS. After 2 h, the reaction mixture was concentrated and partitioned between EtOAc and saturated aqueous $NaHCO_3$. The aqueous layer was extracted twice with EtOAc and the combined organics was washed with brine, dried, filtered, and concentrated to give a crude product. The crude product was purified by silica gel column chromatography to produce the purified product, 2.97 g (98.2%). LCMS m/z=324 (M$^+$).

Step 3. 1-{4-[1-(4-Bromophenyl)-vinyl]-piperidin-1-yl}-propan-1-one

To a cold (0° C.) stirred suspension of methyltriphenylphosphonium bromide (6.5 g, 18.3 mmol) in THF (40.0 mL) was added n-butyllithium (1.11 mL, 17.4 mmol; 1.6 M solution in hexanes) dropwise under an argon atmosphere. The reaction mixture was slowly warmed to rt over 1 h, and then allowed to settle over 1 h. The top clear ylide solution was transferred to 1-[4-(4-bromobenzoyl)-piperidin-1-yl]-propan-1-one (2.97 g, 9.16 mmol) in THF at −25° C. The reaction mixture was slowly warmed to rt (1.5 h) and monitored by HPLC and LCMS. When the reaction was complete, it was quenched with saturated aqueous $NH_4Cl$ and water, and then extracted twice with EtOAc. The combined extract was washed with brine, dried, filtered, and concentrated to give a crude product. The crude product was purified by silica gel column chromatography (80 g ISCO column, using 5 to 75% EtOAc in hexanes) to produce the purified product, 2.71 g (91.8%). LCMS m/z=324 (M+1).

Step 4. 1-{4-[1-(4-Bromophenyl)-ethyl]-piperidin-1-yl}-propan-1-one

To a stirred solution of 1-{4-[1-(4-bromophenyl)-vinyl]-piperidin-1-yl}-propan-1-one (2.75 g, 8.53 mmol) in EtOAc (3 mL) was added platinum dioxide (345 mg, 1.52 mmol). The reaction mixture was connected to a hydrogen balloon and monitored by HPLC and LCMS. After completion, the reaction mixture was filtered through a pad of celite/silica gel and the filtrate was concentrated to isolate the desired product, 2.8 g (100%). LCMS m/z=326 (M+1).

Step 5. 1-{4-[1-(4-Quinolin-3-yl-phenyl)-ethyl]-piperidin-1-yl}-propan-1-one To a 100 mL round bottom flask was added 1,4-dioxane (2.00 mL, 25.6 mmol), triphenylphosphine (0.0307 g, 0.117 mmol) and palladium acetate (0.00658 g, 0.0293 mmol). The reaction mixture was stirred for 15 min at rt under an argon atmosphere. 1-{4-[1-(4-Bromophenyl)-ethyl]-piperidin-1-yl}-propan-1-one (0.19 g, 0.58 mmol), 3-quinolineboronic acid (0.142 g, 0.820 mmol), DMF (2.00 mL) and aqueous 1M $Na_2CO_3$ (5 mL) were added and the mixture was flushed with argon five times. The reaction mixture was then heated at 80° C. for 7 h and then concentrated in vacuo. The residue was suspended in a mixture of aqueous 1M $Na_2CO_3$ and EtOAc and then filtered through a pad of celite/silica gel. The filtrate was separated, the aqueous layer was extracted twice with EtOAc and the combined organic extract was washed with brine, filtered, and concentrated to give a crude product. The product was purified by Gilson and then was stirred with 4 M HCl in dioxane (2 mL) for 15 min. and concentrated. The HCl salt was treated twice with fresh EtOAc, concentrated, and then crystallized from a mixture of EtOAc, MeOH, ether, and 2-Me-butane to produce the purified product, 130 mg, (60%). mp 178-180° C. (EtOAc, MeOH, ether, and 2-Me-butane); LCMS m/z=373 (M+1); $^1$H NMR (DMSO-$d_6$) δ: 9.43 (s, 1H), 8.98 (s, 1H), 8.14-8.22 (m, 2H), 7.83-7.96 (M, 3H), 7.78 (t, 1H, J=8 Hz), 7.40 (d, 2H, J=9 Hz), 4.27-4.51 (m, 1H), 2.77-3.02 (m, 1H), 2.53-2.64 (m, 1H), 2.17-2.46 (m, 3H), 1.86 (t, 1H, J=11 Hz), 1.62-1.77 (m, 1H), 1.30-1.41 (m, 1H), 1.26 (d, 3H, J=7 Hz), 0.79-1.18 (m, 4H).

The following compounds were prepared using the procedure as described in Example 39.

Example 40

1-{4-[1-(4-quinolin-3-yl-phenyl)-cyclopropyl]-piperidin-1-yl}-propan-1-one

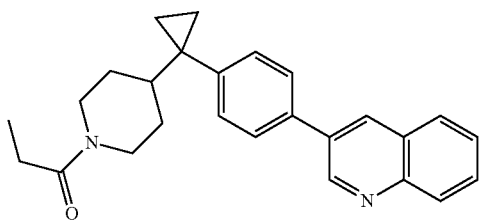 [SMILES: CCC(=O)N1CCC(C2(c3ccc(-c4cnc5ccccc5c4)cc3)CC2)CC1]

Step 1. 1-{4-[1-(4-Bromophenyl)-cyclopropyl]-piperidin-1-yl}-propan-1-one

To a 0° C. stirred solution of 1-{4-[1-(4-bromophenyl)-vinyl]-piperidin-1-yl}-propan-1-one (0.155 g, 0.481 mmol) and CH$_2$I$_2$ (0.3487 mL, 4.329 mmol) in toluene (2.00 mL) was added diethyl zinc (0.3565 g, 2.886 mmol, 1M solution in hexane) dropwise under argon. The reaction mixture was brought to rt and monitored by HPLC and LCMS. The reaction mixture was quenched with aqueous 1M HCl, extracted twice with EtOAc and the combined organics was washed with brine, dried, filtered, and evaporated to give a crude product. The product was purified by Gilson to produce 1-{4-[1-(4-bromo-phenyl)-cyclopropyl]-piperidin-1-yl}-propan-1-one, 100 mg (62%). LCMS m/z=336 (M+).

Step 2

The Step 1 product was coupled with 3-quinolineboronic acid according to the procedure set out in example 39, step 5 to produce the title compound, 1-{4-[1-(4-quinolin-3-yl-phenyl)-cyclopropyl]-piperidin-1-yl}-propan-1-one. mp: 153-155° C. (EtOAc, MeOH, ether, and 2-methyl butane); LCMS m/z=385 (M+1); $^1$H NMR (DMSO-d$_6$) δ: 9.33 (d, 1H, J=2 Hz), 8.82 (s, 1H), 8.11 (d, 2H, J=9 Hz), 7.79-7.89 (m, 3H), 7.72 (t, 1H, J=8 Hz), 7.41 (d, 2H, J=8 Hz), 4.44 (d, 1H, J=13 Hz), 3.84 (d, 1H, J=13 Hz), 2.87 (t, 1H, J=13 Hz), 2.36 (t, 1H, J=13 Hz), 2.13-2.27 (m, 2H), 1.71-1.84 (m, 2H), 1.12-1.24 (m, 1H), 0.89-1.07 (m, 2H), 0.88 (t, 3H, J=13 Hz), 0.67-0.83 (m, 4H).

Example 41

Cyclopropyl-{4-[1-(4-quinolin-3-yl-phenyl)-vinyl]-piperidin-1-yl}-methanone

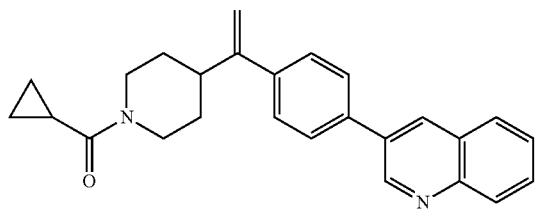 [SMILES: C=C(c1ccc(-c2cnc3ccccc3c2)cc1)C1CCN(C(=O)C2CC2)CC1]

Analysis: mp: 100-102° C. (DCM); LCMS m/z=383 (M+1); $^1$H NMR (DMSO-d$_6$) δ: 9.28 (d, 1H, J=2 Hz), 8.67 (d, 1H, J=2 Hz), 8.06 (d, 2H, J=8 Hz), 7.90 (d, 2H, J=8 Hz), 7.74-7.82 (m, 1H), 7.62-7.69 (m, 1H), 7.60 (d, 2H, J=8 Hz), 5.34 (s, 1H), 5.10 (s, 1H), 4.25-4.56 (m, 2H), 3.08-3.26 (m, 1H), 2.82-2.95 (m, 1H), 2.57-2.74 (m, 1H), 1.92-2.03 (m, 1H), 1.70-1.92 (m, 2H), 1.10-1.43 (m, 2H), 0.61-0.79 (m, 4H).

Example 42

1-{4-[1-(4-Quinolin-7-yl-phenyl)-ethyl]-piperidin-1-yl}-propan-1-one

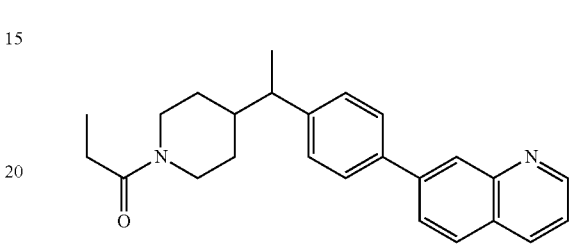

Analysis: LCMS m/z=373 (M+1); $^1$H NMR (DMSO-d$_6$) δ: 8.92 (dd, 1H, J1=2 Hz, J2=4 Hz), 8.39 (d, 1H, J=8 Hz), 8.25 (s, 1H), 8.06 (d, 1H, J=8 Hz), 7.95 (dd, 1H, J1=2 Hz, J2=8 Hz), 7.79 (d, 2H, J=8 Hz), 7.49-7.57 (m, 1H), 7.34 (d, 2H, J=8 Hz), 4.26-4.51 (m, 1H), 3.70-3.94 (m, 1H), 2.76-3.01 (m, 1H), 2.52-2.62 (m, 1H), 2.17-2.51 (m, 3H), 1.79-1.93 (m, 1H), 1.61-1.76 (m, 1H), 1.31-1.43 (m, 1H), 0.74-1.20 (m, 6H).

Example 43

1-{4-[amino-(4-quinolin-3-yl-phenyl)-methyl]-piperidin-1-yl}-propan-1-one

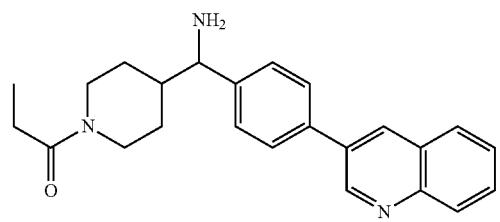 [SMILES: CCC(=O)N1CCC(C(N)c2ccc(-c3cnc4ccccc4c3)cc2)CC1]

Step 1. 1-{4-[Amino-(4-bromophenyl)-methyl]-piperidin-1-yl}-propan-1-one

To a well stirred solution of 1-[4-(4-bromobenzoyl)-piperidin-1-yl]-propan-1-one (0.20 g, 0.62 mmol) and NH$_4$OAc (0.476 g, 6.17 mmol in methanol (5.00 mL, 123 mmol) was added NaBH$_3$CN (0.16 g, 2.5 mmol) at rt then refluxed for 2 days. After completion, the reaction mixture was evaporated in vacuo and partitioned between DCM and saturated aqueous NaHCO$_3$. The aqueous layer was extracted twice with DCM and the combined organics was washed with brine, dried, filtered, and evaporated to give a crude product. The crude product was purified by Gilson to produce 1-{4-[amino-(4-bromophenyl)-methyl]-piperidin-1-yl}-propan-1-one, 120 mg (60%). LCMS m/z=310 (M-4).

Step 2. 1-{4-[Amino-(4-quinolin-3-yl-phenyl)-methyl]-piperidin-1-yl}-propan-1-one The Step 1 product was coupled with 3-quinolineboronic acid according to the procedure set out in example 39, step 5 to produce the title compound. LCMS m/z=373 (MW); $^1$H NMR (DMSO-$d_6$) δ: 9.33 (d, 1H, J=2 Hz), 8.78 (d, 1H, J=2 Hz), 8.17 (d, 2H, J=8 Hz), 8.05-8.13 (m, 3H), 7.78-7.85 (m, 1H), 7.68 (t, 1H, J=8 Hz), 4.42 (d, 1H, J=13 Hz), 3.92 (d, 1H, J=13 Hz), 3.73-3.85 (m, 1H), 3.21 (t, 1H, J=13 Hz), 2.78 (t, 1H, J=12 Hz), 2.33 (q, 2H, J=7 Hz), 1.78-1.92 (m, 2H), 1.46-1.61 (m, 1H), 1.31-1.46 (m, 1H), 1.09-1.31 (m, 1H), 0.99 (t, 3H, J=7 Hz).

Example 44

Cyclopropyl-{4-[1-(4-quinolin-3-yl-phenyl)-cyclopropyl]-piperidin-1-yl}-methanone

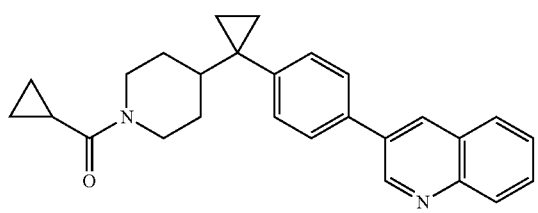 [SMILES: O=C(C1CC1)N1CCC(C2(c3ccc(-c4cnc5ccccc5c4)cc3)CC2)CC1]

Analysis: LCMS m/z=397 (M+1); $^1$H NMR (DMSO-$d_6$) δ: 9.24 (d, 1H, J=2 Hz), 8.62 (d, 1H, J=2 hz), 8.00-8.08 (m, 2H), 7.73-7.83 (m, 3H), 7.60-7.68 (m, 1H), 7.40 (d, 2H, J=8 Hz), 4.17-4.50 (m, 2H), 2.86-3.04 (m, 1H), 2.34-2.48 (m, 1H), 1.69-1.93 (m, 3H), 1.13-1.28 (m, 1H), 0.84-1.12 (m, 2H), 0.67-0.83 (m, 4H), 0.50-0.67 (m, 4H).

Example 45

Cyclopropyl-{4-[1-(4-quinolin-7-yl-phenyl)-cyclopropyl]-piperidin-1-yl}-methanone

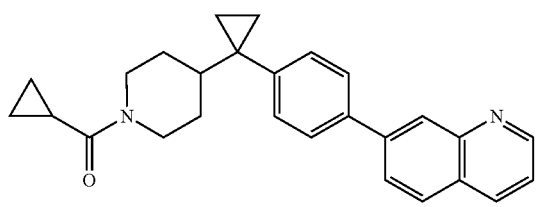 [SMILES: O=C(C1CC1)N1CCC(C2(c3ccc(-c4ccc5cccnc5c4)cc3)CC2)CC1]

Analysis: LCMS m/z=397 (M+1); $^1$H NMR (DMSO-$d_6$) δ: 8.93 (dd, J1=2 Hz, J2=4 Hz), 8.39 (d, 1H, J=8 Hz), 8.25 (s, 1H), 8.06 (d, 1H, J=8 Hz), 7.91-7.98 (m, 1H), 7.78 (d, 2H, J=8 Hz), 7.49-7.56 (m, 1H), 7.38 (d, 2H, J=8 Hz), 4.18-4.49 (m, 2H), 2.86-3.03 (m, 1H), 2.34-2.47 (m, 1H), 1.68-1.93 (m, 3H), 0.83-1.28 (m, 3H), 0.67-0.83 (m, 4H), 0.50-0.66 (m, 4H).

Example 46

1-{4-[[(E:Z)-Methoxyimino]-(4-quinolin-3-yl-phenyl)-methyl]-piperidin-1-yl}-propan-1-one

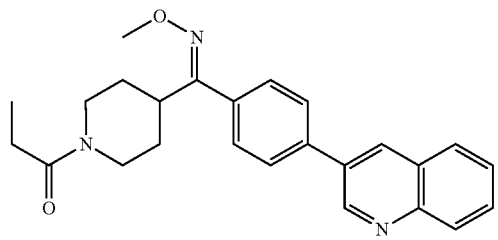 [SMILES: CCC(=O)N1CCC(/C(=N\OC)c2ccc(-c3cnc4ccccc4c3)cc2)CC1]

Step 1. 1-(4-{(4-Bromophenyl)-[E:Z]-methoxyimino]-methyl}-piperidin-1-yl)-propan-1-one To a 25 mL R. B. flask was charged with 1-[4-(4-bromobenzoyl)-piperidin-1-yl]-propan-1-one (0.120 g, 0.370 mmol), ethanol (3.00 mL, 51.4 mmol), and methoxylamine hydrochloride (0.108 g, 1.30 mmol). The reaction mixture was heated at 70° C. for 5 h. The reaction mixture was evaporated and purified by Gilson to produce 1-(4-{(4-bromo-phenyl)-[(E:Z)-methoxyimino]-methyl}-piperidin-1-yl)-propan-1-one, 150 mg (95%). LCMS m/z=353 (M+).

Step 2

The Step 1 product was coupled with 3-quinolineboronic acid according to the procedure set out in example 39, step 5 to produce the title compound. LCMS m/z=402 (M+1); $^1$H NMR (DMSO-$d_6$) δ: 9.25-9.31 (m, 1H), 8.69 (d, 1H, J=2H), 8.07 (d, 2H, J=9 Hz), 7.89-7.97 (m, 2H), 7.74-7.83 (m, 1H), 7.66 (t, 1H, J=8 Hz), 7.57 (d, 1H, J=8 Hz), 7.45 (d, 2H, J=8 Hz), 4.32-4.56 (m, 1H), 3.81-3.96 (m, 2H), 3.70 (s, 2H), 2.97-3.12 (m, 1H), 2.80-2.92 (m, 1H), 2.53-2.65 (m, 1H), 2.29 (q, 2H, J=7 Hz), 1.52-1.89 (m, 3H), 1.20-1.50 (m, 1H), 0.96 (t, 3H, J=7 Hz).

Example 47

1-{4-[1-(4-Quinolin-3-yl-phenyl)-propyl]-piperidin-1-yl}-propan-1-one

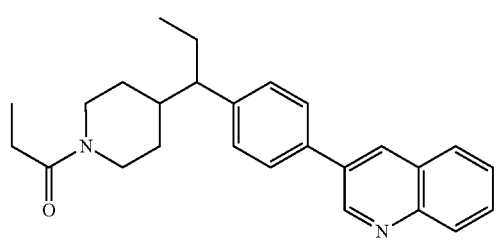 [SMILES: CCC(=O)N1CCC(C(CC)c2ccc(-c3cnc4ccccc4c3)cc2)CC1]

Step 1. 1-{4-[1-(4-Bromophenyl)-1-hydroxypropyl]-piperidin-1-yl}-propan-1-one

To a 0° C. stirred solution of 1-[4-(4-bromo-benzoyl)-piperidin-1-yl]-propan-1-one (0.200 g, 0.617 mmol) in tetrahydrofuran (THF)(2 mL) was added EtMgBr (0.247 g, 1.85 mmol) dropwise under argon. The reaction mixture was stirred at rt for 2 h, quenched with saturated aqueous NH₄Cl and the aqueous layer was extracted twice with EtOAc. The combined organics was washed with brine, dried, filtered, and evaporated to give a crude product. The product was purified by Gilson to produce 1-{4-[1-(4-bromophenyl)-1-hydroxypropyl]-piperidin-1-yl}-propan-1-one, 137 mg (63%). LCMS m/z=354 (M+).

Step 2. 1-{4-[1-(4-Bromophenyl)-propyl]-piperidin-1-yl}-propan-1-one

To an ice-cold (5° C.) stirred solution of 1-{4-[1-(4-bromophenyl)-1-hydroxy-propyl]-piperidin-1-yl}-propan-1-one (0.137 g, 0.387 mmol) and triethylsilane (0.62 mL, 3.9 mmol) in DCM (1 mL) was added trifluoroacetic acid (0.45 mL, 5.8 mmol) dropwise under Argon. After the addition, the reaction mixture was stirred at rt for 15 h, concentrated, and then purified by Gilson to produce 1-{4-[1-(4-bromo-phenyl)-propyl]-piperidin-1-yl}-propan-1-one, 120 mg (92%). LCMS m/z=338 (M+1).

Step 3

The Step 2 product above was coupled with 3-quinoline-boronic acid according to the procedure set out in example 39, step 5 to produce the title compound. LCMS m/z=387 (M+1); ¹H NMR (DMSO-d₆) δ: 9.26 (d, 1H, J=2 Hz), 8.64 (d, 1H, J=2 Hz), 8.05 (d, 2H, J=8 Hz), 7.83 (d, 2H, J=8 Hz), 7.73-7.80 (m, 1H), 7.60-7.68 (m, 1H), 7.32 (d, 2H, J=8 Hz), 4.26-4.50 (m, 1H), 3.70-3.93 (m, 1H), 2.76-3.02 (m, 1H), 2.17-2.41 (m, 3H), 1.53-1.95 (m, 4H), 1.29-1.41 (m, 1H), 0.76-1.14 (m, 6H), 0.69 (t, 3H, J=7 Hz).

Example 48

1-{4-[Cyclopropyl-(4-quinolin-3-yl-phenyl)-methyl]-piperidin-1-yl}-propan-1-one

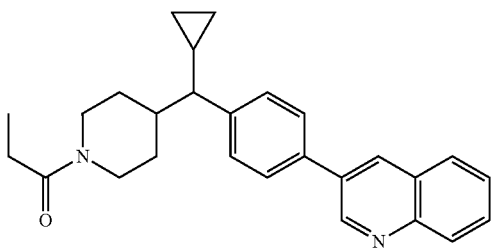 [SMILES: CCC(=O)N1CCC(C(c2ccc(-c3cnc4ccccc4c3)cc2)C2CC2)CC1]

Analysis: LCMS m/z=399 (M+1); ¹H NMR (DMSO-d₆) δ: 9.37 (d, 1H, J=2 Hz), 8.83 (d, 1H, J=2 Hz), 8.11 (t, 2H, J=7 Hz), 7.91 (d, 2H, J=8 Hz), 7.81-7.88 (m, 1H), 7.68-7.76 (m, 1H), 7.28 (d, 2H, J=8 Hz), 5.48 (t, 1H, J=7 Hz), 4.45 (d, 1H, J=13 Hz), 3.87 (d, 1H, J=13 Hz), 2.96 (t, 1H, J=12 Hz), 2.27 (q, 2H, J=7 Hz), 1.80-1.91 (m, 2H), 1.70 (t, 2H, J=12 Hz), 1.05-1.32 (m, 2H), 0.85-0.99 (m, 6H).

Example 49

[4-(4-Quinolin-3-yl-benzoyl)-piperidin-1-yl]-(R)-tetrahydrofuran-2-yl-methanone

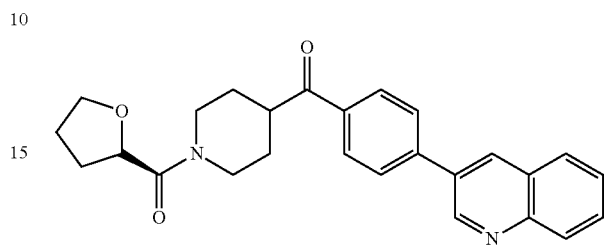

Analysis: LCMS m/z=415 (M+1); ¹H NMR (DMSO-d₆) δ: 9.35 (d, 1H, J=2 Hz), 8.83 (d, 1H, J=2 Hz), 8.18 (d, 2H, J=8 Hz), 8.05-8.14 (m, 3H), 7.80-7.87 (m, 1H), 7.65-7.74 (m, 1H), 4.63-4.71 (m, 1H), 4.30-4.44 (m, 1H), 3.14-3.33 (m, 1H), 2.75-2.92 (m, 1H), 1.92-2.13 (m, 2H), 1.72-1.92 (m, 4H), 1.30-1.66 (m, 2H).

Example 50

1-{4-[[Methoxyimino]-(4-quinolin-7-yl-phenyl)-methyl]-piperidin-1-yl}-propan-1-one

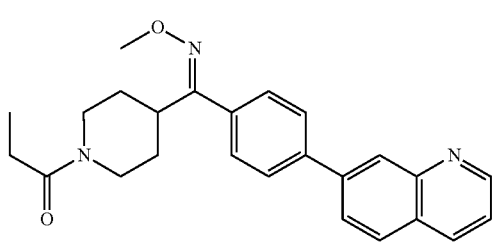 [SMILES: CCC(=O)N1CCC(/C(=N\OC)c2ccc(-c3ccc4cccnc4c3)cc2)CC1]

To a 50 mL R. B. flask was charged with 1-[4-(4-quinolin-7-yl-benzoyl)-piperidin-1-yl]-propan-1-one (0.09 g, 0.2 mmol), methoxylamine HCl (0.13 g, 1.6 mmol) and EtOH (4 mL). The reaction mixture was heated at 75° C. for 15 h then concentrated to obtain a crude product. The product was purified by Gilson and then lyophilized to produce 1-{4-[[(E:Z(2:1)-methoxyimino]-(4-quinolin-7-yl-phenyl)-methyl]-piperidin-1-yl}-propan-1-one, 85 mg (90%). LCMS m/z=402 (M+1); ¹H NMR (DMSO-d₆) δ: 9.08 (dd, 1H, J1=1 Hz, J2=4 Hz), 8.65 (d, 1H, J=8 Hz), 8.35 (s, 1H), 8.21 (d, 1H, J=9 Hz), 8.06-8.13 (m, 1H), 7.86-7.96 (m, 2H), 7.69-7.76 (m, 1H), 7.58 (d, 1H, J=8 Hz), 7.45 (d, 1H, J=8 Hz), 4.31-4.56 (m, 1H), 3.81-3.97 (m, 2H), 3.73 (s, 2H), 3.33-3.47 (m, 1H), 2.96-3.12 (m, 1H), 2.79-2.92 (m, 1H), 2.53-2.65 (m, 1H), 2.29 (q, 2H, J=8 Hz), 1.51-1.87 (m, 3H), 1.19-1.53 (m, 1H), 0.96 (t, 3H, J=8 Hz).

Example 51

{4-[1-(4-Quinolin-7-yl-phenyl)-ethyl]-piperidin-1-yl}-(R)-tetrahydrofuran-2-yl-methanone

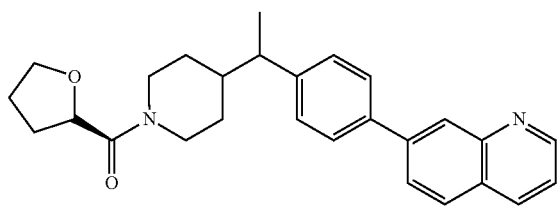

Analysis: LCMS m/z=415 (M+1); $^1$H NMR (DMSO-d$_6$) δ: 9.06 (d, 1H, J=2 Hz), 8.64 (d, 1H, J=8 Hz), 8.30 (s, 1H), 8.19 (d, 1H, J=8 Hz), 8.07 (d, 1H, J=9 Hz), 7.81 (d, 2H, J=8 Hz), 7.66-7.75 (m, 1H), 7.37 (d, 2H, J=8 Hz), 5.75 (s, 1H), 4.51-4.67 (m, 1H), 4.21-4.45 (m, 1H), 3.85-4.12 (m, 1H), 3.63-3.79 (m, 2H), 2.77-3.05 (m, 1H), 2.53-2.62 (m, 1H), 1.59-2.05 (m, 6H), 1.30-1.42 (m, 1H), 1.25 (d, 3H, J=17 Hz), 0.79-1.20 (m, 3H).

Example 52

{4-[1-(4-Quinolin-3-yl-phenyl)-ethyl]-piperidin-1-yl}-(R)-tetrahydrofuran-2-yl-methanone

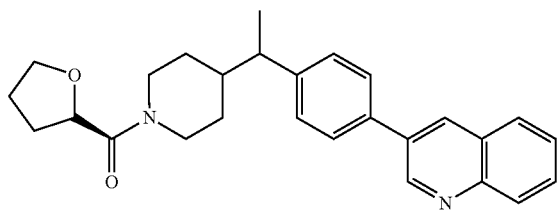

Analysis: LCMS m/z=415 (M+1); $^1$H NMR (DMSO-d$_6$) δ: 9.38 (d, 1H, J=2 Hz), 8.87 (s, 1H), 8.07-8.17 (m, 2H), 7.81-7.91 (m, 3H), 7.69-7.78 (m, 1H), 7.39 (d, 2H, J=8 Hz), 4.52-4.67 (m, 1H), 4.21-4.46 (m, 1H), 3.86-4.11 (m, 1H), 3.62-3.80 (m, 2H), 2.76-3.04 (m, 1H), 2.53-2.65 (m, 1H), 2.35-2.46 (m, 1H), 1.63-2.06 (m, 6H), 1.31-1.42 (m, 1H), 1.26 (d, 3H, J=7 Hz), 0.80-1.21 (m, 2H).

Example 53

N-[(1-Propionylpiperidin-4-yl)-(4-quinolin-3-yl-phenyl)-methyl]-acetamide

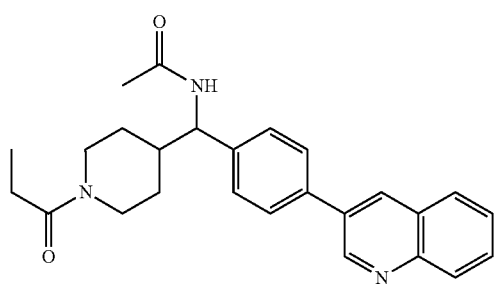 [SMILES: CCC(=O)N1CCC(C(NC(C)=O)c2ccc(-c3cnc4ccccc4c3)cc2)CC1]

Step 1. N-[(4-Bromophenyl)-(1-propionyl-piperidin-4-yl)-methyl]-acetamide

To a stirred solution of 1-{4-[amino-(4-bromophenyl)-methyl]-piperidin-1-yl}-propan-1-one (0.1 g, 0.3 mmol) and DIPEA (0.4 mL, 2 mmol) in DCM (2 mL) was added acetyl chloride (0.04 mL, 0.6 mmol) dropwise at rt. After 1 h, the reaction mixture was evaporated and purified by Gilson to produce N-[(4-bromophenyl)-(1-propionyl-piperidin-4-yl)-methyl]-acetamide, 114 mg (100%). LCMS m/z=369 (M+1).

Step 2

The Step 1 product was coupled with 3-quinolineboronic acid according to the procedure set out in example 39, step 5 to produce the title compound. LCMS m/z=416 (M+1); $^1$H NMR (DMSO-d$_6$) δ: 9.37 (s, 1H), 8.87 (s, 1H), 8.32-8.42 (m, 1H), 8.12 (t, 2H, J=9 Hz), 7.83-7.93 (m, 3H), 7.74 (t, 1H, J=8 Hz), 7.48 (d, 2H, J=8 Hz), 4.64-4.79 (m, 1H), 4.26-4.51 (m, 1H), 3.73-3.97 (m, 1H), 2.78-2.99 (m, 1H), 2.35-2.49 (m, 1H), 2.19-2.35 (m, 2H), 1.66-1.95 (m, 5H), 1.22-1.40 (m, 1H), 0.87-1.22 (m, 5H).

Example 54

1-{4-[1-(4-Quinolin-3-yl-phenyl)-butyl]-piperidin-1-yl}-propan-1-one

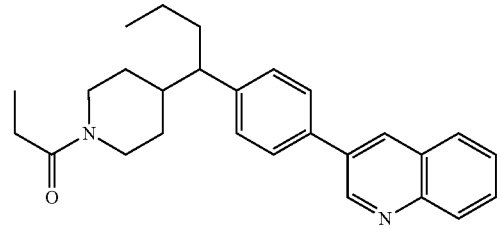 [SMILES: CCCC(c1ccc(-c2cnc3ccccc3c2)cc1)C1CCN(C(=O)CC)CC1]

Analysis: LCMS m/z=401 (M+1); $^1$H NMR (DMSO-d$_6$) δ: 9.33 (s, 1H), 8.78 (s, 1H), 8.09 (t, 2H, J=7 Hz), 7.79-7.88 (m, 2H), 7.70 (t, 1H, J=8 Hz), 7.34 (d, 2H, J=9 Hz), 4.26-4.49 (m, 1H), 3.70-3.93 (m, 1H), 2.76-3.02 (m, 1H), 2.17-2.41 (m, 3H), 1.83-1.97 (m, 1H), 1.54-1.83 (m, 3H), 1.27-1.41 (m, 1H), 0.87-1.14 (m, 6H), 0.82 (t, 3H, J=7 Hz).

Example 55

N-[(1-Propionylpiperidin-4-yl-(4-quinolin-3-yl-phenyl)-methyl]-formamide

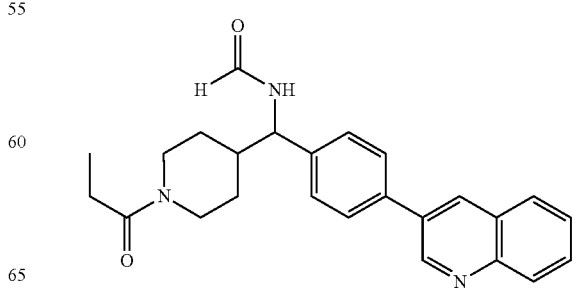

Step 1. N-[(4-Bromophenyl)-(1-propionyl-piperidin-4-yl)-methyl]-formamide

To a 25 mL R. B. flask was charged with 1-{4-[amino-(4-bromophenyl)-methyl]-piperidin-1-yl}-propan-1-one (0.164 g, 0.504 mmol), toluene (6 mL), and formic acid (3 mL). The reaction mixture was stirred and refluxed using a Dean-stark apparatus under an argon atmosphere. The crude product was purified by Gilson to produce N-[(4-bromophenyl)-(1-propionyl-piperidin-4-yl)-methyl]-formamide, 130 mg (73%). LCMS m/z=353 (MW).

Step 2. The Step 1 product was coupled with 3-quinolineboronic acid according to the procedure set out in example 39, step 5 to produce the title compound. LCMS m/z=402 (M+1); $^1$H NMR (DMSO-$d_6$) δ: 9.34 (d, 1H, J=2 Hz), 8.81 (s, 1H), 8.68 (d, 1H, J=8 Hz), 8.04-8.15 (m, 3H), 7.80-7.94 (m, 3H), 7.71 (t, 1H, J=8 Hz 7.44-7.55 (m, 2H), 4.74-4.87 (m, 1H), 4.28-4.50 (m, 1H), 3.74-3.98 (m, 1H), 2.81-2.98 (m, 1H), 2.35-2.48 (m, 1H), 2.19-2.34 (m, 2H), 1.83-1.99 (m, 1H), 1.64-1.83 (m, 1H), 1.26-1.44 (m, 1H), 0.88-1.24 (m, 5H).

Example 56

1-[4-Methyl-4-(4-quinolin-3-yl-benzoyl)-piperidin-1-yl]-propan-1-one

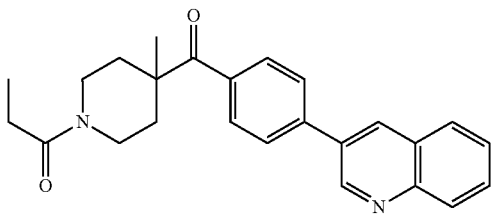 [SMILES: CCC(=O)N1CCC(C)(C(=O)c2ccc(-c3cnc4ccccc4c3)cc2)CC1]

Step 1. 1-[4-(4-Bromobenzoyl)-4-methyl-piperidin-1-yl]-propan-1-one

To a well stirred solution of 1-[4-(4-bromobenzoyl)-piperidin-1-yl]-propan-1-one (0.3 g, 0.9 mmol) in THF (2 mL) was added lithium hexamethyldisilazide (0.17 g, 1.0 mmol, 1M solution in THF, 1 mL) under argon at rt. After 15 min at rt, MeI (0.29 mL, 4.6 mmol) was added dropwise. After 2 h the reaction was quenched with saturated aqueous NH$_4$Cl and then extracted twice with EtOAc. The combined organics was washed with brine, dried, filtered, and evaporated to give a crude product. The product was purified by Gilson to produce 1-[4-(4-Bromo-benzoyl)-4-methyl-piperidin-1-yl]-propan-1-one, 0.21 g (70%). LCMS m/z=338 (M+).

Step 2

The Step 1 product was coupled with 3-quinolineboronic acid according to the procedure set out in example 39, step 5 to produce the title compound. LCMS m/z=387 (M+1); $^1$H NMR (DMSO-$d_6$) δ: 9.38 (d, 1H, J=2 Hz), 8.90 (s, 1H), 8.09-8.19 (m, 2H), 8.02 (d, 2H, J=8 Hz), 7.84-7.95 (m, 2H), 7.74 (t, 1H, J=8 Hz), 3.63-3.75 (m, 1H), 3.50-3.61 (m, 1H), 3.09-3.30 (m, 2H), 2.29 (q, 2H, J=7 Hz), 2.02-2.21 (m, 2H), 1.50-1.67 (m, 2H), 1.46 (s, 3H), 0.96 (t, 3H, J=7 Hz).

Example 57

4-[1-(4-quinolin-3-yl-phenyl)-ethyl]-piperidine-1-carboxylic acid t-butyl ester

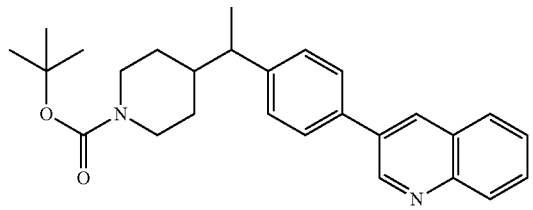 [SMILES: CC(c1ccc(-c2cnc3ccccc3c2)cc1)C1CCN(C(=O)OC(C)(C)C)CC1]

Step 1. 4-(4-Bromobenzoyl)-piperidine-1-carboxylic acid tert-butyl ester

To a 250 mL R. B. flask was charged with (4-bromophenyl)-piperidin-4-yl-methanone (5 g, 20 mmol), THF (30 mL), water (30 mL), Na$_2$CO$_3$ (10 g, 90 mmol), and di-t-butyldicarbonate (4.35 g, 20.0 mmol). The reaction mixture was stirred at rt for 2 h and partitioned between EtOAc and water. The aqueous layer was extracted twice with EtOAc and the combined organics was washed with brine, dried, filtered, and evaporated to produce 4-(4-bromobenzoyl)-piperidine-1-carboxylic acid t-butyl ester, 7.1 g (100%).

Step 2. 4-[1-(4-Bromophenyl)-vinyl]-piperidine-1-carboxylic acid tert-butyl ester To a 0° C. stirred suspension of methyltriphenylphosphonium bromide (11.7 g, 32.8 mmol) in THF (60.0 mL) was added n-butyllithium (2.04 g, 31.8 mmol) dropwise under argon. The reaction mixture was brought to rt for 1 h and then allowed the suspension to settle. The top clear ylide solution was transferred to the starting ketone in THF at −25° C. and the reaction mixture brought to rt over 1.5 h then quenched with saturated aqueous NH$_4$Cl and water, then extracted twice with EtOAc. The combined organics was washed with brine, dried, filtered, and evaporated to give a crude product. The product was triturated with a mixture of EtOAc, ether, and hexane to remove triphenyl phosphine oxide by-product. The filtrate was evaporated in vacuo and purified by silica gel column chromatography (120 g ISCO column, using 0 to 10% EtOAc in hexane) to produce 4-[1-(4-bromo-phenyl)-vinyl]-piperidine-1-carboxylic acid tert-butyl ester, 6.24 g (88%). LCMS m/z=310 (M-56).

Step 3. 4-[1-(4-Bromophenyl)-ethyl]-piperidine-1-carboxylic acid tert-butyl ester To a 250 mL R. B. flask was charged with 4-[1-(4-bromophenyl)-vinyl]-piperidine-1-carboxylic acid tert-butyl ester (6.24 g, 17.0 mmol), ethyl acetate (35 mL, 360 mmol), and platinum dioxide (0.4 mg, 0.002 mmol). The mixture was stirred and connected to a hydrogen balloon at rt. After 15 h, the reaction mixture was filtered through a pad of celite/silica gel and washed with EtOAc, and evaporated to produce 4-[1-(4-bromo-phenyl)-ethyl]-piperidine-1-carboxylic acid tert-butyl ester, 6.39 g (95%). LCMS m/z=314 (MW-54).

Step 4

The Step 3 product above was coupled with 3-quinolineboronic acid according to the procedure set out in example 39, step 5 to produce the title compound. LCMS m/z=417 (M+1). $^1$H NMR (CDCl$_3$) δ: 9.18 (d, 1H, J=2 Hz), 8.29 (d, 1H, J=2H), 8.13 (d, 1H, J=8 Hz), 7.87 (d, 1H, J=8 Hz), 7.71 (t, 1H, J=8 Hz), 7.65 (d, 2H, J=8 Hz), 7.57 (t, 1H, J=8 Hz), 7.29 (d, 2H, J=8 Hz), 4.25-3.95 (m, 2H), 2.76-2.49 (m, 3H), 1.92-1.82 (m, 1H), 1.65-1.52 (m, 1H), 1.48-1.37 (m, 1H), 1.31 (d, 3H, J=7 Hz), 1.25-1.00 (m, 2H).

Example 58

Cyclopropyl-{4-[1-(4-quinolin-3-yl-phenyl)-ethyl]-piperidin-1-yl}-methanone

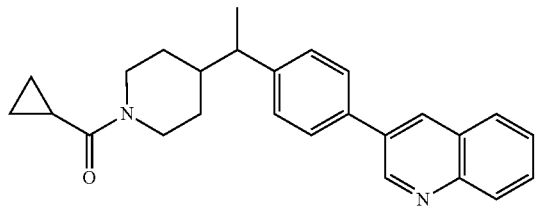 [SMILES: CC(c1ccc(-c2cnc3ccccc3c2)cc1)C1CCN(C(=O)C2CC2)CC1]

Step 1. 3-[4-(1-Piperidin-4-yl-ethyl)-phenyl]-quinoline

To a stirred solution of 4-[1-(4-quinolin-3-yl-phenyl)-ethyl]-piperidine-1-carboxylic acid tert-butyl ester (1.06 g, 2.54 mmol) in DCM (7 mL, 100 mmol) was added 4M HCl in dioxane (0.186 g) at rt. The reaction mixture was stirred at rt for 15 h and evaporated in vacuo. Fresh EtOAc was added and evaporated then crystallized from a mixture EtOAc, MeOH, DCM, ether, and 2-Me-butane to produce 3-[4-(1-Piperidin-4-yl-ethyl)-phenyl]-quinoline, 99 mg (120%). LCMS m/z=317 (M+1).

Step 2

To a well stirred solution of 3-[4-(1-piperidin-4-yl-ethyl)-phenyl]-quinoline (0.25 g, 0.79 mmol) and DIPEA (0.96 mL, 5.5 mmol) in DCM (4 mL) was added cyclopropanecarbonyl chloride (1.9 mL, 2.0 mmol) at rt. The reaction mixture was stirred for 1.5 h and evaporated to obtain a crude product. The product was purified by Gilson and then lyophilized to produce cyclopropyl-{4-[1-(4-quinolin-3-yl-phenyl)-ethyl]-piperidin-1-yl}-methanone, 0.2 g (60%). LCMS m/z=385 (M+1); $^1$H NMR (DMSO-d$_6$) δ: 9.35 (d, 1H, J=2 Hz), 8.82 (s, 1H), 8.11 (t, 2H, J=8 Hz), 7.81-7.90 (m, 3H), 7.72 (t, 1H, J=8 Hz), 7.39 (d, 2H, J=8 Hz), 4.11-4.51 (m, 2H), 2.83-3.13 (m, 1H), 2.53-2.65 (m, 1H), 1.65-2.01 (m, 3H), 1.30-1.47 (m, 1H), 1.27 (d, 3H, J=7 Hz), 1.21 (d, 1H, J=7 Hz), 0.79-1.17 (m, 2H), 0.53-0.74 (m, 4H).

Example 59

1-[4-Methyl-4-(4-quinolin-3-yl-benzyl)-piperidin-1-yl]-propan-1-one

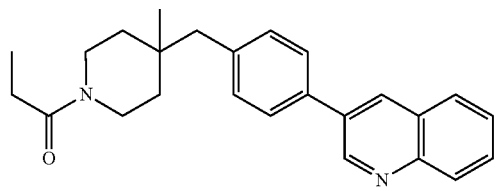 [SMILES: CCC(=O)N1CCC(C)(Cc2ccc(-c3cnc4ccccc4c3)cc2)CC1]

Step 1. 4-(4-Bromobenzoyl)-4-methyl-piperidine-1-carboxylic acid tert-butyl ester To a well stirred solution of 4-(4-bromobenzoyl)-piperidine-1-carboxylic acid t-butyl ester (1 g, 3 mmol) in THF (10 mL) was added lithium hexamethyldisilazide (3 mL, 3.0 mmol, 1M in THF,) dropwise at rt. After 15 min methyl iodide (0.68 mL, 11 mmol) was added dropwise and the reaction mixture was further stirred for 2.5 h, quenched with saturated aqueous NH$_4$Cl then extracted twice with EtOAc. The combined organics was washed with brine, dried, filtered, and evaporated to produce 4-(4-bromobenzoyl)-4-methylpiperidine-1-carboxylic acid tert-butyl ester 0.9 g (90%). LCMS m/z=328 (MW-54); 282 (M-100).

Step 2. 4-(4-Bromobenzyl)-4-methylpiperidine

To a 100 mL R. B. flask was charged with 4-(4-bromobenzoyl)-4-methyl-piperidine-1-carboxylic acid t-butyl ester (0.3 g, 0.8 mmol), hydrazine (10 mL, 300 mmol), KOH (1 g, 20 mmol), and 1,2-ethanediol (4 mL, 70 mmol). The reaction was stirred and heated at 155° C. for 5 h, was cooled to rt, evaporated in vacuo, and then partitioned between water and DCM. The aqueous layer was extracted twice with DCM and the combined organics was washed brine, dried (Na$_2$SO$_4$), filtered, and concentrated to obtain a crude product. The crude product was purified by Gilson to produce 4-(4-bromo-benzyl)-4-methyl-piperidine, 90 mg (40%). LCMS m/z=268 (M+).

Step 3. 1-[4-(4-Bromobenzyl)-4-methyl-piperidin-1-yl]-propan-1-one

To a stirred solution of 4-(4-bromobenzyl)-4-methylpiperidine (0.09 g, 0.3 mmol) and DIPEA (0.2 mL, 1 mmol) in DCM (2 mL) was added propanoyl chloride (0.038 mL, 0.44 mmol) dropwise at rt. After completion, the reaction mixture was concentrated and purified by Gilson to produce 1-{4-(4-bromobenzyl)-4-methyl-piperidin-1-yl}-propan-1-one, 90 mg (80%). LCMS m/z=324 (M+).

Step 4

The Step 3 product above was coupled with 3-quinolineboronic acid according to the procedure set out in example 39, step 5 to produce the title compound. LCMS m/z=373 (M+1); $^1$H NMR (DMSO-d$_6$) δ: 9.36 (d, 1H, J=2 Hz), 8.84 (d, 1H, J=2 Hz), 8.11 (t, 2H, J=9 Hz), 7.80-7.90 (m, 3H), 7.69-7.72 (m, 1H), 7.35 (d, 2H, J=8 Hz), 3.82-3.93 (m, 1H), 3.55-3.67 (m, 1H), 3.21-3.34 (m, 1H), 3.06-3.19 (m, 1H), 2.66 (s, 2H), 2.29 (q, 2H, J=7 Hz), 1.19-1.52 (m, 4H), 0.97 (t, 3H, J=7 Hz), 0.94 (s, 3H).

Example 60

4-[1-(4-Quinolin-3-yl-phenyl)-ethyl]-piperidine-1-carbaldehyde

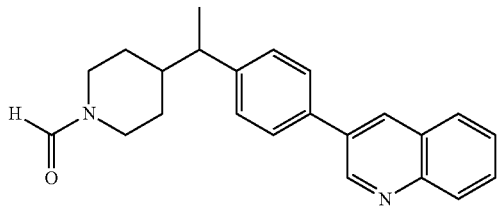 [SMILES: CC(c1ccc(-c2cnc3ccccc3c2)cc1)C1CCN(C=O)CC1]

To a 50 mL R. B. flask was charged with 3-[4-(1-piperidin-4-yl-ethyl)-phenyl]-quinoline (0.1 g, 0.3 mmol), toluene (8 mL), and formic acid (2 mL). The reaction mixture was stirred at reflux using a Dear-Stark apparatus under an argon atmosphere for 2 days. After completion, the reaction mixture was concentrated and partitioned between EtOAc and saturated aqueous NaHCO₃. The aqueous layer was extracted twice with EtOAc and the combined organic was washed with brine, dried, filtered, and concentrated to give a crude product. The product was purified by Gilson and then lyophilized to give 52 mg (50%) as an off-white solid. LCMS m/z=345 (M+1); $^1$H NMR (DMSO-$d_6$) δ: 9.39 (t, 1H, J=2 Hz), 8.89 (t, 1H, J=2 Hz), 8.08-8.18 (m, 2H), 7.82-7.97 (m, 4H), 7.75 (t, 1H, J=7 Hz), 7.40 (d, 2H, J=8 Hz), 4.05-4.27 (m, 1H), 3.53-3.76 (m, 1H), 2.84-3.06 (m, 1H), 2.39-2.69 (m, 2H), 1.82-1.96 (m, 1H), 1.68-1.81 (m, 1H), 1.34-1.47 (m, 1H), 1.26 (d, 3H, J=7 Hz), 0.78-1.51 (m, 2H).

Example 61

1-{4-[2-Methyl-1-(4-quinolin-3-yl-phenyl)-propyl]-piperidin-1-yl}-propan-1-one

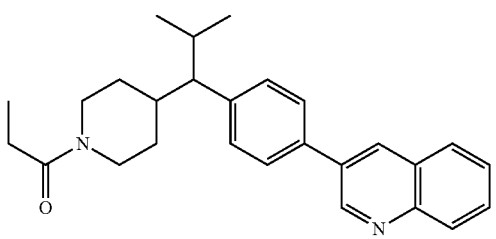 [SMILES: CCC(=O)N1CCC(C(c2ccc(-c3cnc4ccccc4c3)cc2)C(C)C)CC1]

Analysis: LCMS m/z=401 (M+1); $^1$H NMR (DMSO-$d_6$) δ: 9.34 (s, 1H), 8.78 (s, 1H), 8.05-8.13 (m, 2H), 7.77-7.90 (m, 3H), 7.70 (t, 1H, J=8 Hz), 7.30 (d, 2H, J=8 Hz), 7.12 (d, 1H, J=8 Hz), 4.30-4.48 (m, 1H), 3.71-3.91 (m, 1H), 2.83-3.10 (m, 1H), 2.38-2.58 (m, 1H), 2.30-2.37 (m, 1H), 2.13-2.30 (m, 3H), 2.00-2.13 (m, 1H, 1.87 (s, 1H), 1.70-1.84 (m, 1H), 1.55-1.66 (m, 1H), 1.44-1.54 (m, 1H), 1.40 (s, 1H), 0.56-1.16 (m, 10H).

The following compounds were synthesized using the procedures as described in examples 57 and 58.

Example 62

1-(4-{1-[4-(8-methylquinolin-7-yl)-phenyl]-ethyl}-piperidin-1-yl)-propan-1-one

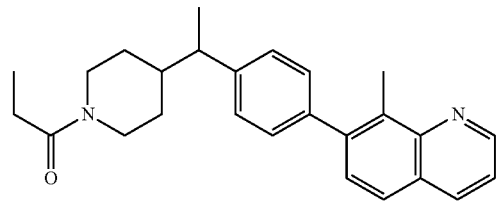 [SMILES: CCC(=O)N1CCC(C(C)c2ccc(-c3ccc4cccnc4c3C)cc2)CC1]

LCMS m/z=387 (M+1); $^1$H NMR (DMSO-$d_6$) δ: 9.01 (dd, 1H, J1=1.5 Hz, J2=4 Hz), 8.50 (d, 1H, J=8 Hz), 7.92 (d, 1H, J=8 Hz), 7.60-7.69 (m, 1H), 7.55 (m, 1H), 7.38 (d, 2H, J=8 Hz), 7.32 (d, 2H, J=8 Hz), 4.29-4.52 (m, 1H), 3.73-3.95 (m, 1H), 2.78-3.02 (m, 1H), 2.67 (s, 3H), 2.52-2.62 (m, 1H), 2.33-2.52 (m, 1H), 2.20-2.34 (m, 1H), 1.81-1.93 (m, 1H), 1.62-1.77 (m, 1H), 1.32-1.43 (m, 1H), 1.26 (d, 3H, J=7 Hz), 0.78-1.18 (m, 5 Hz).

Example 63

Cyclopropyl-(4-{1-[4-(8-methylquinolin-7-yl)-phenyl]-ethyl}-piperidin-1-yl)-methanone

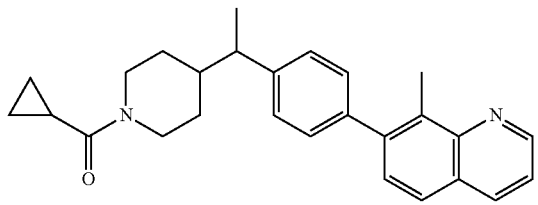 [SMILES: Cc1c(-c2ccc(C(C)C3CCN(C(=O)C4CC4)CC3)cc2)ccc2cccnc12]

LCMS m/z=399 (M+1); $^1$H NMR (DMSO-$d_6$) δ: 9.06 (d, 1H, J=2 Hz), 8.64 (s, 1H), 8.00 (d, 1H, J=8 Hz), 7.69-7.79 (m, 1H), 7.62 (d, 1H, J=8 Hz), 7.39 (d, 2H, J=8 Hz), 7.34 (d, 2H, J=8 Hz), 4.12 (m, 3H), 2.85-3.13 (m, 1H), 2.69 (s, 3H), 2.54-2.64 (m, 1H), 2.35-2.54 (m, 1H), 1.80-2.02 (m, 2H), 1.65-1.80 (m, 1H), 1.32-1.47 (m, 1H), 1.27 (d, 3H, J=8 Hz), 0.80-1.22 (m, 2H), 0.56-0.76 (m, 4H).

Example 64

1-(4-{1-[4-(8-Methoxyquinolin-7-yl)-phenyl]-ethyl}-piperidin-1-yl)-propan-1-one

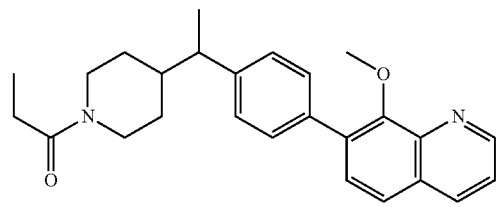 [SMILES: CCC(=O)N1CCC(C(C)c2ccc(-c3ccc4cccnc4c3OC)cc2)CC1]

LCMS m/z=403 (M+1); $^1$H NMR (DMSO-$d_6$) δ: 9.10 (d, 1H, J=2 Hz), 8.10 (d, 1H, J=7 Hz), 7.98 (d, 1H, J=8 Hz), 7.77-7.89 (m, 2H), 7.64 (d, 2H, J=8 Hz), 7.36 (d, 2H, J=8 Hz), 4.27-4.54 (m, 1H), 3.72-3.95 (m, 1H), 3.79 (s, 3H), 2.78-3.03 (m, 1H), 2.53-2.64 (m, 1H), 2.33-2.52 (m, 1H), 2.16-2.33 (m, 2H), 1.79-1.94 (m, 1H), 1.62-1.78 (m, 1H), 1.31-1.44 (m, 1H), 1.26 (d, 3H, J=7 Hz), 0.77-1.20 (m, 5H).

Example 65

1-(4-{1-[4-(4-Methylquinolin-3-yl)-phenyl]-ethyl}-piperidin-1-yl)-propan-1-one

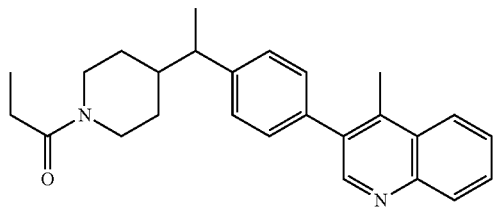 [SMILES: CCC(=O)N1CCC(C(C)c2ccc(-c3cnc4ccccc4c3C)cc2)CC1]

LCMS m/z=387 (M+1); $^1$H NMR (DMSO-d$_6$) δ: 9.03 (d, 1H, J=5 Hz), 8.37 (d, 1H, J=8 Hz), 8.17 (d, 1H, J=8 Hz), 7.97 (t, 1H, J=7 Hz), 7.86 (t, 1H, J=7 Hz), 7.47 (d, 2H, J=8 Hz), 7.39 (d, 2H, J=8 Hz), 4.28-4.53 (m, 1H), 3.73-3.96 (m, 1H), 2.79-3.02 (m, 1H), 2.75 (s, 3H), 2.54-2.65 (m, 1H), 2.34-2.52 (m, 1H), 2.20-2.34 (m, 1H), 1.80-1.94 (m, 1H), 1.63-1.79 (m, 1H), 1.32-1.43 (m, 1H, 1.27 (d, 3H, J=7 Hz), 0.80-1.18 (m, 5 Hz).

Example 66

Cyclopropyl-(4-{1-[4-(8-methoxyquinolin-7-yl)-phenyl]-ethyl}-piperidin-1-yl)-methanone

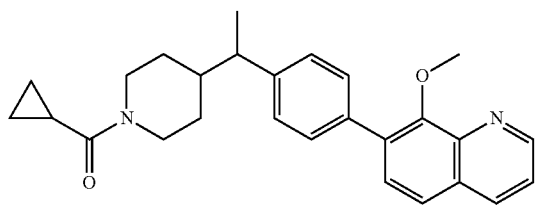 [SMILES: COc1c(-c2ccc(C(C)C3CCN(C(=O)C4CC4)CC3)cc2)ccc2cccnc12]

LCMS m/z=415 (M+1); $^1$H NMR (DMSO-d$_6$) δ: 9.04 (dd, 1H, J1=1.4 Hz, J2=4 Hz), 8.67 (d, 1H, J=8 Hz), 7.92 (d, 1H, J=8 Hz), 7.70-7.79 (m, 2H), 7.61 (d, 2H, J=8 Hz), 7.35 (d, 2H, J=8 Hz), 4.26-4.51 (m, 1H), 3.83 (s, 3H), 2.84-3.13 (m, 1H), 2.54-2.64 (m, 1H), 2.34-2.51 (m, 1H), 1.80-2.01 (m, 2H), 1.65-1.80 (m, 1H), 1.31-1.48 (m, 1H), 1.27 (d, 3H, J=7 Hz), 0.82-1.21 (m, 2H), 0.56-0.74 (m, 4H).

Example 67

1-{4-[1-(4-Quinolin-3-yl-phenyl)-ethyl]-piperidin-1-yl}-propan-1-one

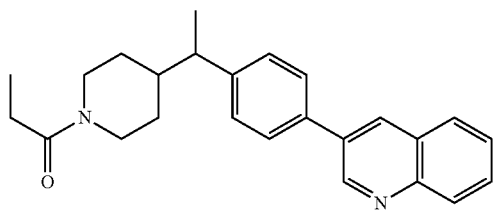 [SMILES: CCC(=O)N1CCC(C(C)c2ccc(-c3cnc4ccccc4c3)cc2)CC1]

The racemic product of Example 38 (2.6 g) was separated using the Supercritical Fluid chromatography (SFC) (ASH 4.6×250 mm column, 15% MeOH and 0.2% diethyl amine-isocratic). The 2 enantiomers were partitioned between EtOAc and aqueous 0.5 M NaHCO$_3$ and the aqueous phase was extracted twice with EtOAc. The combined organics was washed with brine, dried, filtered, and evaporated to produce the free base (Peak A-950 mg and Peak B-890 mg). To HCl salts were synthesized by adding 2.54 mL of 2M HCl in ether to a DCM solution of base. After evaporation the salts was crystallized from EtOAc, DCM, MeOH, ether, and 2-Me-butane. Isomer-A-HCl salt, off-white solid, mp: 215-219° C.; LCMS m/z=373 (M+1); $^1$H NMR (DMSO-d$_6$) δ: 9.41 (s, 1H) 8.94 (br. s., 1H) 8.11-8.21 (m, 2H) 7.83-7.95 (m, 3H) 7.72-7.81 (m, 1H) 7.40 (d, J=8.03 Hz, 2H) 4.27-4.51 (m, 1H) 3.73-3.96 (m, 4H) 2.77-3.01 (m, 1H) 2.54-2.64 (m, 1H) 2.31-2.48 (m, 2H) 2.19-2.31 (m, 2H) 1.87 (br. s., 1H) 1.70 (dd, J=7.53, 3.76 Hz, 1H) 1.36 (br. s., 1H) 1.26 (d, J=7.03 Hz, 3H) 0.79-1.17 (m, 5H).

Example 68

1-{4-[1-(4-Quinolin-3-yl-phenyl)-ethyl]-piperidin-1-yl}-propan-1-one

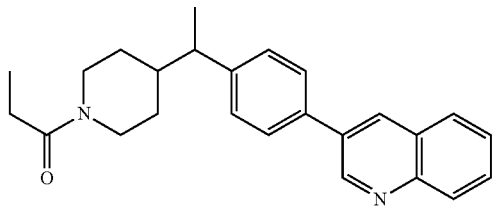 [SMILES: CCC(=O)N1CCC(C(C)c2ccc(-c3cnc4ccccc4c3)cc2)CC1]

See the procedure of Example 67 above. Isomer-B—HCl salt, off-white solid, mp: 219-221° C.; LCMS m/z=373 (M+1); $^1$H NMR (DMSO-d$_6$) δ: 9.35 (s, 1H) 8.82 (br. s., 1H) 8.07-8.16 (m, 2H) 7.85 (d, J=8.03 Hz, 3H) 7.68-7.76 (m, 1H) 7.39 (d, J=8.28 Hz, 2H) 4.28-4.51 (m, 1H) 3.72-3.95 (m, 2H) 2.78-3.01 (m, 1H) 2.54-2.63 (m, 1H) 2.17-2.48 (m, 4H) 1.87 (br. s., 1H) 1.70 (d, J=8.28 Hz, 1H) 1.35 (br. s., 1H) 1.26 (d, J=7.03 Hz, 3H) 0.78-1.18 (m, 5H).

Example 69

(4-{1-[4-(8-Methoxyquinolin-7-yl)-phenyl]-ethyl}-piperidin-1-yl)-(R)-tetrahydrofuran-2-yl-methanone; Mixture of diastereomers

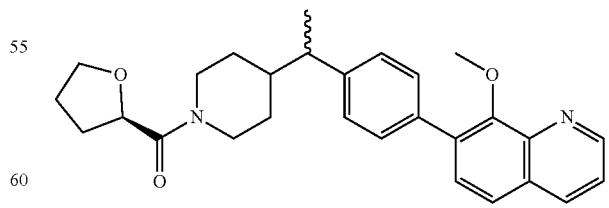

Analysis: LCMS m/z=445 (M+1); $^1$H NMR (DMSO-d$_6$) δ: 9.05 (d, 1H, J=3 Hz), 8.69 (d, 1H, J=6 Hz), 7.93 (d, 1H, J=8 Hz), 7.71-7.81 (m, 2H), 7.61 (d, 2H, J=8 Hz), 7.34 (d, 2H, J=8 Hz), 4.54-4.67 (m, 1H), 4.23-4.46 (m, 1H), 3.88-4.11 (m, 1H), 3.82 (s, 3H), 3.65-3.79 (m, 2H), 2.78-3.05 (m, 1H), 2.53-2.61 (m, 1H), 1.63-2.05 (m, 1H), 1.31-1.42 (m, 1H), 1.26 (d, 3H, J=7 Hz), 0.82-1.21 (m, 3H).

Example 70

(4-{1-[4-(8-Methylquinolin-7-yl)-phenyl]-ethyl}-piperidin-1-yl)-(R)-tetrahydrofuran-2-yl-methanone; Mixture of diastereomers

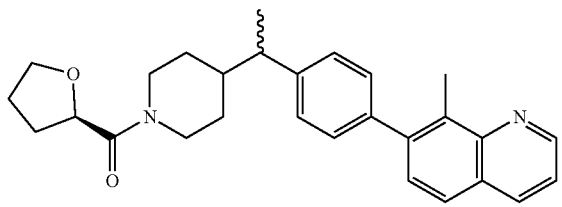 [SMILES: Cc1c(-c2ccc(C(C)C3CCN(C(=O)[C@H]4CCCO4)CC3)cc2)ccc2cccnc12]

Analysis: LCMS m/z=429 (M+1); $^1$H NMR (DMSO-d$_6$) δ: 9.04 (dd, J=4.39, 1.63 Hz, 1H) 8.56 (d, J=7.53 Hz, 1H) 7.95 (d, J=8.53 Hz, 1H) 7.68 (dd, J=8.16, 4.39 Hz, 1H) 7.58 (d, J=8.53 Hz, 1H) 7.30-7.43 (m, 4H) 4.55-4.70 (m, 1H) 4.24-4.47 (m, 1H) 3.88-4.12 (m, 1H) 3.64-3.82 (m, 2H) 2.79-3.06 (m, 1H) 2.68 (s, 3H) 2.53-2.63 (m, 1H) 2.36-2.49 (m, 1H) 1.63-2.07 (m, 6H) 1.38 (d, J=12.30 Hz, 1H) 1.27 (d, J=6.78 Hz, 3H) 0.81-1.22 (m, 2H).

Example 71

(4-{1-[4-(4-Methylquinolin-3-yl)-phenyl]-ethyl}-piperidin-1-yl)-(R)-tetrahydrofuran-2-yl-methanone; Mixture of diastereomers

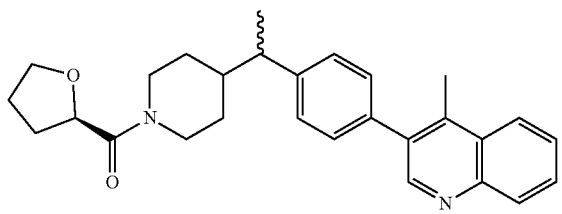 [SMILES: Cc1c(-c2ccc(C(C)C3CCN(C(=O)[C@H]4CCCO4)CC3)cc2)cnc2ccccc12]

Analysis: LCMS m/z=429 (M+1); $^1$H NMR (DMSO-d$_6$) δ: 8.99 (s, 1H) 8.35 (d, J=8.28 Hz, 1H) 8.15 (d, J=8.28 Hz, 1H) 7.94 (t, J=7.53 Hz, 1H) 7.79-7.87 (m, 1H) 7.43-7.49 (m, 2H) 7.34-7.42 (m, 2H) 4.62 (dq, J=17.85, 6.01 Hz, 1H) 4.24-4.47 (m, 1H) 3.88-4.12 (m, 1H) 3.65-3.80 (m, 2H) 2.80-3.05 (m, 1H) 2.73 (s, 3H) 2.60 (br. s., 1H) 2.43 (br. s., 2H) 1.65-2.06 (m, 7H) 1.38 (d, J=12.30 Hz, 1H) 1.28 (d, J=7.03 Hz, 3H) 0.83-1.21 (m, 3H).

Example 72

1-(4-{1-[4-(8-chloroquinolin-7-yl)-phenyl]-ethyl}-piperidin-1-yl)-propan-1-one

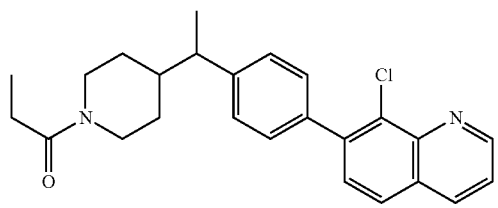 [SMILES: CCC(=O)N1CCC(C(C)c2ccc(-c3ccc4cccnc4c3Cl)cc2)CC1]

Analysis: LCMS m/z=407 (M+1); $^1$H NMR (DMSO-d$_6$) δ: 9.07 (dd, J=4.14, 1.63 Hz, 1H) 8.51 (dd, J=8.28, 1.76 Hz, 1H) 8.04 (d, J=8.53 Hz, 1H) 7.62-7.72 (m, 2H) 7.50 (d, J=8.03 Hz, 2H) 7.34 (d, J=8.03 Hz, 2H) 3.74-3.96 (m, 2H) 2.79-3.02 (m, 1H) 2.53-2.64 (m, 1H) 2.21-2.49 (m, 4H) 1.88 (d, J=12.80 Hz, 1H) 1.63-1.78 (m, 1H) 1.38 (d, J=12.30 Hz, 1H) 1.27 (d, J=7.03 Hz, 3H) 1.08-1.19 (m, 1H) 0.84-0.88 (m, 1H) 0.81-1.08 (m, 5H).

Example 73

(4-{1-[4-(8-Chloroquinolin-7-yl)-phenyl]-ethyl}-piperidin-1-yl)-cyclopropylmethanone

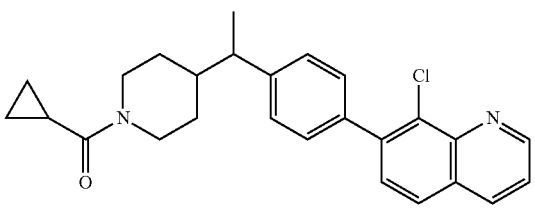 [SMILES: CC(c1ccc(-c2ccc3cccnc3c2Cl)cc1)C1CCN(C(=O)C2CC2)CC1]

Analysis: LCMS m/z=419 (M+1); $^1$H NMR (DMSO-d$_6$) δ: 9.07 (dd, J=4.27, 1.76 Hz, 1H) 8.51 (dd, J=8.28, 1.76 Hz, 1H) 8.04 (d, J=8.53 Hz, 1H) 7.62-7.71 (m, 2H) 7.51 (d, J=8.03 Hz, 2H) 7.35 (d, J=8.28 Hz, 2H) 4.11-4.51 (m, 3H) 2.86-3.13 (m, 1H) 2.54-2.65 (m, 1H) 2.43 (br. s., 1H) 1.92 (br. s., 2H) 1.66-1.80 (m, 1H) 1.32-1.49 (m, 1H) 1.28 (d, J=7.03 Hz, 3H) 0.83-1.20 (m, 2H) 0.68 (br. s., 4H).

Example 74

(4-{1-[4-(8-Chloroquinolin-7-yl)-phenyl]-ethyl}-piperidin-1-yl)-(R)-tetrahydrofuran-2-yl-methanone; Mixture of diastereomers

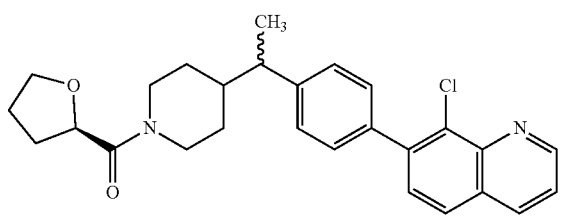 [SMILES: CC(c1ccc(-c2ccc3cccnc3c2Cl)cc1)C1CCN(C(=O)[C@H]2CCCO2)CC1]

Analysis: LCMS m/z=449 (M+1); $^1$H NMR (DMSO-d$_6$) δ: 9.07 (dd, J=4.14, 1.63 Hz, 1H) 8.51 (dd, J=8.28, 1.76 Hz, 1H) 8.04 (d, J=8.53 Hz, 1H) 7.62-7.72 (m, 2H) 7.50 (d, J=8.28 Hz, 2H) 7.34 (d, J=8.03 Hz, 2H) 4.59 (d, J=5.77 Hz, 4H) 4.25-4.46 (m, 4H) 3.89-4.11 (m, 3H) 3.73 (d, J=5.77 Hz, 2H) 2.79-3.05 (m, 1H) 2.54-2.63 (m, 1H) 2.43 (br. s., 1H) 1.64-2.07 (m, 6H) 1.38 (d, J=13.30 Hz, 1H) 1.27 (d, J=7.03 Hz, 3H) 1.03 (d, J=11.54 Hz, 2H).

Example 75

1-(4-{1-[4-(4-Chloroquinolin-3-yl)-phenyl]-ethyl}-piperidin-1-yl)-propan-1-one

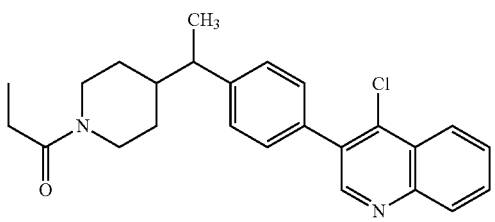 [SMILES: CCC(=O)N1CCC(C(C)c2ccc(-c3cnc4ccccc4c3Cl)cc2)CC1]

Analysis: LCMS m/z=407 (M+1); ¹H NMR (DMSO-d$_6$) δ: 8.93 (s, 1H) 8.34 (dd, J=8.41, 0.88 Hz, 1H) 8.16 (d, J=7.78 Hz, 1H) 7.92 (ddd, J=8.34, 6.96, 1.51 Hz, 1H) 7.80-7.88 (m, 1H) 7.57 (d, J=8.03 Hz, 2H) 7.38 (d, J=8.03 Hz, 2H) 4.29-4.53 (m, 1H) 3.73-3.96 (m, 1H) 2.78-3.02 (m, 1H) 2.53-2.65 (m, 1H) 2.34-2.51 (m, 2H) 2.19-2.34 (m, 2H) 1.88 (d, J=13.05 Hz, 1H) 1.64-1.78 (m, 1H) 1.38 (d, J=12.55 Hz, 1H) 1.27 (d, J=7.03 Hz, 3H) 0.82-1.20 (m, 5H).

Example 76

(4-{1-[4-(4-Chloroquinolin-3-yl)-phenyl]-ethyl}-piperidin-1-yl)-cyclopropylmethanone

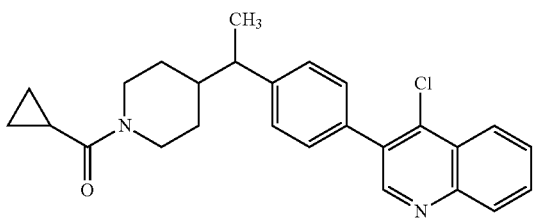 [SMILES: CC(c1ccc(-c2cnc3ccccc3c2Cl)cc1)C1CCN(C(=O)C2CC2)CC1]

Analysis: LCMS m/z=419 ((M+1); ¹H NMR (DMSO-d$_6$) δ: 8.92 (s, 1H) 8.34 (dd, J=8.41, 0.88 Hz, 1H) 8.12-8.19 (m, 1H) 7.92 (ddd, J=8.34, 6.96, 1.51 Hz, 1H) 7.79-7.87 (m, 1H) 7.57 (d, J=8.28 Hz, 2H) 7.39 (d, J=8.03 Hz, 2H) 4.13-4.50 (m, 2H) 2.86-3.13 (m, 1H) 2.55-2.66 (m, 1H) 2.37-2.49 (m, 1H) 1.92 (br. s., 2H) 1.67-1.81 (m, 1H) 1.40 (br. s., 1H) 1.28 (d, J=7.03 Hz, 3H) 0.83-1.22 (m, 2H) 0.68 (br. s., 4H).

Example 77

(4-{1-[4-(4-Chloroquinolin-3-yl)-phenyl]-ethyl}-piperidin-1-yl)-(R)-tetrahydrofuran-2-yl-methanone; Mixture of diastereomers

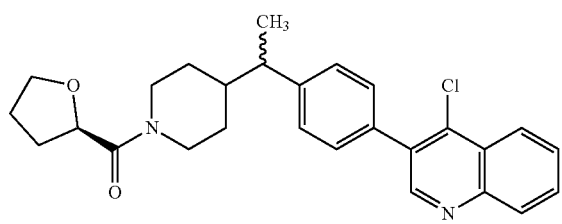 [SMILES: CC(c1ccc(-c2cnc3ccccc3c2Cl)cc1)C1CCN(C(=O)[C@H]2CCCO2)CC1]

Analysis: LCMS m/z=449 (M+1); ¹H NMR (DMSO-d$_6$) δ: 8.91 (s, 1H) 8.34 (dd, J=8.28, 1.00 Hz, 1H) 8.15 (d, J=7.78 Hz, 1H) 7.91 (ddd, J=8.34, 6.96, 1.51 Hz, 1H) 7.80-7.87 (m, 1H) 7.57 (d, J=8.03 Hz, 2H) 7.38 (d, J=8.03 Hz, 2H) 4.55-4.68 (m, 1H) 4.26-4.47 (m, 4H) 3.88-4.10 (m, 5H) 3.65-3.81 (m, 3H) 2.79-3.05 (m, 1H) 2.54-2.65 (m, 1H) 2.36-2.47 (m, 1H) 1.65-2.06 (m, 6H) 1.38 (d, J=13.55 Hz, 1H) 1.27 (d, J=7.03 Hz, 3H) 0.85-1.20 (m, 2H).

Example 78

(4-{1-[4-(1-Methylisoquinolin-6-yl)-phenyl]-cyclopropyl]-piperidin-1-yl)-(R)-tetrahydrofuran-2-yl-methanone

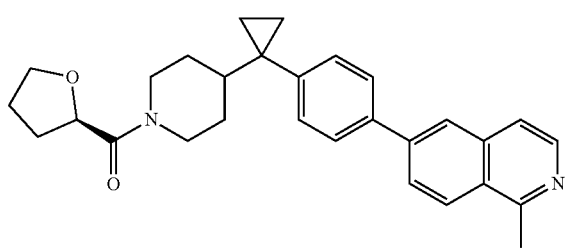 [SMILES: Cc1nccc2cc(-c3ccc(C4(C5CCN(C(=O)[C@H]6CCCO6)CC5)CC4)cc3)ccc12]

Step 1. (R)-Tetrahydrofuran-2-yl-(4-{1-[4-(4,4,5,5-tetramethyl-1,3,2-dioxaborolan-2-yl)-phenyl]-cyclopropyl}-piperidin-1-yl)-methanone To a 100 mL R. B. flask was charged with {4-[1-(4-bromo-phenyl)-cyclopropyl]-piperidin-1-yl}-(R)-tetrahydrofuran-2-yl-methanone (0.2 g, 0.5 mmol), 4,4,5,5,4',4',5',5'-octamethyl-[2,2']bi[[1,3,2]dioxaborolanyl] (0.20 g, 0.79 mmol), 1,4-dioxane (4 mL), potassium acetate (0.078 g, 0.79 mmol), and bis(tricyclohexylphosphine)palladium (0) (0.035 g, 0.053 mmol). The reaction mixture was stirred and heated at 100° C. for 15 h, cooled to rt, filtered through a pad of celite/silica gel, and washed with DCM. The filtrate was evaporated and the material used directly in the next step without purification. LCMS m/z=426 (M+1).

Step 2. Analysis: LCMS m/z=441 (M+1); ¹H NMR (DMSO-d$_6$) δ: 8.60 (d, J=9.03 Hz, 1H) 8.53-8.57 (m, 1H) 8.50 (d, J=6.52 Hz, 1H) 8.31 (d, J=8.53 Hz, 1H) 8.23 (d, J=6.02 Hz, 1H) 7.87 (d, J=8.03 Hz, 2H) 7.44 (d, J=8.28 Hz, 2H) 4.53 (t, J=6.65 Hz, 1H) 4.38 (d, J=12.80 Hz, 1H) 3.94-4.07 (m, 2H) 3.59-3.71 (m, 7H) 3.15 (s, 3H) 2.82-2.96 (m, 1H) 2.36-2.48 (m, 3H) 1.84-1.97 (m, 2H) 1.69-1.83 (m, 4H) 1.12-1.29 (m, 1H) 0.85-1.11 (m, 2H) 0.67-0.83 (m, 4H).

Example 79

(4-{1-[4-(8-Methylquinolin-7-yl)-phenyl]-cyclopropyl}-piperidin-1-yl)-(R)-tetrahydrofuran-2-yl-methanone

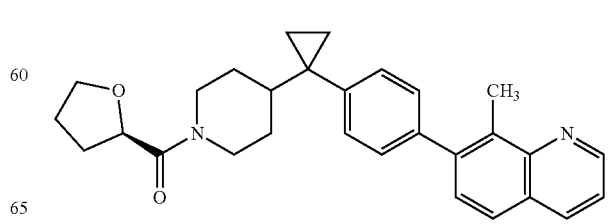

Analysis: LCMS m/z=441 (M+1); $^1$H NMR (DMSO-d$_6$) δ: 9.02 (dd, J=4.39, 1.63 Hz, 1H) 8.51 (d, J=8.03 Hz, 1H) 7.92 (d, J=8.53 Hz, 1H) 7.65 (dd, J=8.28, 4.27 Hz, 1H) 7.52-7.60 (m, 1H) 7.37 (s, 4H) 4.57 (t, J=6.65 Hz, 2H) 4.34-4.44 (m, 2H) 3.95-4.08 (m, 1H) 3.60-3.75 (m, 2H) 2.80-2.98 (m, 1H) 2.66 (s, 3H) 2.36-2.49 (m, 1H) 1.88 (s, 2H) 1.68-1.83 (m, 4H) 0.87-1.29 (m, 3H) 0.67-0.83 (m, 4H).

Example 80

(4-{(2-Methoxy ethoxy)-[4-(8-methyl-quinolin-7-yl)-phenyl]-methyl}-piperidin-1-yl)-(R)-tetrahydro-furan-2-yl-methanone

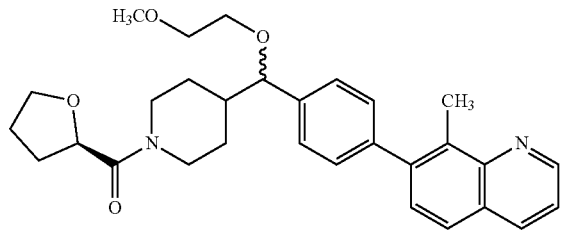 [SMILES: COCCOC(c1ccc(-c2ccc3cccnc3c2C)cc1)C1CCN(C(=O)[C@H]2CCCO2)CC1]

Step 1. 4-[(4-Bromophenyl)-hydroxy-methyl]-piperidine-1-carboxylic acid tert-butyl ester To a stirred solution of 4-(4-bromobenzoyl)-piperidine-1-carboxylic acid t-butyl ester (3 g, 8 mmol) in THF (12 mL) and methanol (12 mL) at 0° C. was added sodium borohydride (1 g, 30 mmol) portionwise. After stirring at rt 2 h mixture was evaporated and quenched with water. The resulting white solid was filtered, washed with water, and dried to produce 2.9 g (100%); $^1$H NMR (CDCl$_3$) δ: 7.44-7.51 (m, 1H) 7.13-7.23 (m, 1H) 4.37 (dd, J=7.28, 3.01 Hz, 1H) 3.92-4.27 (m, 1H) 2.46-2.77 (m, 1H) 1.81-2.00 (m, 1H) 1.63-1.77 (m, 1H) 1.56 (s, 1H) 1.44 (s, 5H) 1.04-1.34 (m, 2H).

Step 2. 4-[(4-Bromophenyl)-(2-methoxy-ethoxy)-methyl]-piperidine-1-carboxylic acid t-butyl ester To a 0° C. stirred solution of 4-[(4-bromophenyl)-hydroxymethyl]-piperidine-1-carboxylic acid tert-butyl ester (1 g, 3 mmol) in DMF (8 mL) was added sodium hydride (60%; 0.6 g, 20 mmol) portionwise and further stirred at rt for 15 min. 1-Chloro-2-methoxy-ethane (2 g, 20 mmol) was added then heated at 75° C. overnight. The reaction mixture was evaporated and partitioned between saturated aqueous NaHCO$_3$ and EtOAc. The aqueous layer was extracted twice with EtOAc and the combined organic layer was washed with brine, dried, filtered, and evaporated to give a crude product. The product was purified by silica gel column chromatography (40 g ISCO column, using 0 to 60% EtOAc in hexanes) to produce 4-[(4-bromophenyl)-(2-methoxy-ethoxy)-methyl]-piperidine-1-carboxylic acid tert-butyl ester, 0.83 g (70%). LCMS m/z=328 (M-100); $^1$H NMR (CDCl$_3$) δ: 7.42-7.51 (m, 1H) 7.13 (d, J=8.28 Hz, 1H) 3.95-4.23 (m, 1H) 3.90 (d, J=7.78 Hz, 1H) 3.39-3.56 (m, 2H) 3.34 (s, 2H) 2.44-2.74 (m, 1H) 1.96-2.08 (m, 1H) 1.64-1.79 (m, 1H) 1.58 (s, 1H) 1.44 (s, 5H) 1.00-1.29 (m, 2H).

Step 3. 4-{(2-Methoxyethoxy)-[4-(4,4,5,5-tetramethyl-1,3,2-dioxaborolan-2-yl)-phenyl]-methyl}-piperidine-1-carboxylic acid tert-butyl ester A 100 mL R. B. flask was charged with 4-[(4-bromophenyl)-(2-methoxyethoxy)-methyl]-piperidine-1-carboxylic acid tert-butyl ester (0.82 g, 1.9 mmol), 4,4,5,5,4',4',5',5'-octamethyl-[2,2']bi[[1,3,2]dioxaborolanyl] (0.73 g, 2.9 mmol), 1,4-dioxane (4 mL), potassium acetate (0.28 g, 2.9 mmol), and bis(tricyclohexylphosphine)palladium (0) (0.13 g, 0.19 mmol). The reaction mixture was heated at 100° C. for 15 h then cooled to rt and filtered through a pad of celite/silica gel. The filtrate was evaporated to produce 4-{(2-methoxyethoxy)-[4-(4,4,5,5-tetramethyl-1,3,2-dioxaborolan-2-yl)-phenyl]-methyl}-piperidine-1-carboxylic acid t-butyl ester, which was used for the next reaction without further purification. LCMS m/z=476 (M+1).

Step 4. 4-{(2-Methoxyethoxy)-[4-(8-methylquinolin-7-yl)-phenyl]-methyl}-piperidine-1-carboxylic acid tert-butyl ester A 100 mL R. B. flask was charged with 1,4-dioxane (4.00 mL), triphenylphosphine (0.0552 g, 0.210 mmol), and palladium acetate (0.0118 g, 0.0526 mmol) and stirred at rt for 15 min under argon. 4-{(2-Methoxyethoxy)-[4-(4,4,5,5-tetramethyl-1,3,2-dioxaborolan-2-yl)-phenyl]-methyl}-piperidine-1-carboxylic acid t-butyl ester (0.5 g, 1 mmol), 7-bromo-8-methylquinoline (0.257 g, 1.16 mmol), DMF (4.00 mL) and aqueous 1M Na$_2$CO$_3$ (4 mL) were added and flushed with argon five times. The reaction mixture was heated at 80° C. for 15 h and evaporated. The crude residue was suspended in a mixture of aqueous 1M Na$_2$CO$_3$ and EtOAc and then filtered through a pad of celite/silica gel. The filtrate was separated and the aqueous layer was extracted twice with EtOAc. The combined organic layer was washed with brine, dried (Na$_2$SO$_4$), filtered, and evaporated to give a crude product. The product was purified by silica gel column chromatography (40 g ISCO column, 0 to 5% MeOH in DCM) to produce 0.51 g (100%). LCMS m/z=491 (M+1); $^1$H NMR (CDCl$_3$) δ: 9.00 (dd, J=4.14, 1.88 Hz, 1H) 8.17 (dd, J=8.03, 1.76 Hz, 1H) 7.71 (d, J=8.28 Hz, 1H) 7.31-7.52 (m, 6H) 3.93-4.28 (m, 3H) 3.55 (s, 3H) 3.38 (s, 4H) 2.76 (s, 5H) 2.06-2.17 (m, 1H) 1.94 (s, 2H) 1.77-1.89 (m, 1H) 1.61 (s, 3H) 1.45 (s, 10H) 1.24 (s, 19H).

Step 5. 7-{4-[(2-Methoxyethoxy)-piperidin-4-yl-methyl]-phenyl}-8-methylquinoline To a well stirred solution of 4-{(2-methoxy-ethoxy)-[4-(8-methyl-quinolin-7-yl)-phenyl]-methyl}-piperidine-1-carboxylic acid tert-butyl ester (0.51 g, 1.0 mmol) in DCM (8 mL) was added TFA (1.50 mL, 19.5 mmol) dropwise at rt. The reaction mixture was stirred at rt for 2.5 h. After completion, the reaction was evaporated and was added twice EtOAc and evaporated to produce 7-{4-[(2-methoxy-ethoxy)-piperidin-4-yl-methyl]-phenyl}-8-methylquinoline Step 6. (4-{(2-Methoxyethoxy)-[4-(8-methylquinolin-7-yl)-phenyl]-methyl}-piperidin-1-yl)-(R)-tetrahydrofuran-2-yl-methanone To an ice-cold (5° C.) stirred solution of (R)-tetrahydrofuran-2-carboxylic acid (0.16 g, 1.3 mmol) and triethylamine (0.87 mL, 6.3 mmol) in DCM (5 mL) was added HATU (0.48 g, 1.2 mmol). After stirring for 15 min, 7-{4-[(2-methoxyethoxy)-piperidin-4-yl-methyl]-phenyl}-8-methylquinoline (0.35 g, 0.90 mmol) was added and further stirred for 2 h. The reaction was evaporated, partitioned between EtOAc and saturated aqueous $NaHCO_3$ and the aqueous layer was extracted twice with EtOAc. The combined organic layer was washed with brine, dried, filtered, and concentrated to give a crude product. The product was purified by Gilson and then lyophilized to produce (4-{(2-methoxyethoxy)-[4-(8-methylquinolin-7-yl)-phenyl]-methyl}-piperidin-1-yl)-(R)-tetrahydrofuran-2-yl-methanone. TFA salt, 85 mg (19%). LCMS m/z=489 (M+1); $^1$H NMR (DMSO-$d_6$) δ: 9.05 (dd, J=4.52, 1.76 Hz, 1H) 8.57 (d, J=8.03 Hz, 1H) 7.97 (d, J=8.28 Hz, 1H) 7.69 (dd, J=8.28, 4.27 Hz, 1H) 7.60 (d, J=8.53 Hz, 1H) 7.37-7.49 (m, 4H) 4.56-4.69 (m, 2H) 4.26-4.44 (m, 1H) 4.13-4.21 (m, 1H) 3.91-4.09 (m, 1H) 3.65-3.82 (m, 2H) 3.31-3.54 (m, 4H) 3.25 (s, 3H) 2.81-3.04 (m, 1H) 2.68 (s, 3H) 2.39-2.58 (m, 9H) 1.70-2.08 (m, 7H) 0.99-1.37 (m, 3H).

Example 81

1-(4-{(2-Methoxyethoxy)-[4-(8-methyl-quinolin-7-yl)-phenyl]-methyl}-piperidin-1-yl)-propan-1-one

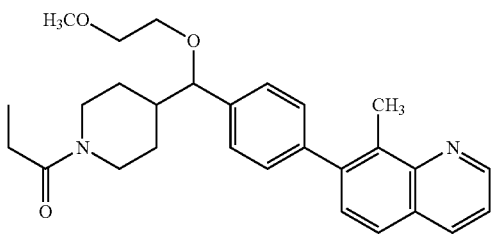 [SMILES: CCC(=O)N1CCC(C(OCCOC)c2ccc(-c3ccc4cccnc4c3C)cc2)CC1]

To a stirred solution of 7-{4-[(2-methoxyethoxy)-piperidin-4-yl-methyl]-phenyl}-8-methyl-quinoline (0.35 g, 0.90 mmol) and DIPEA (1.1 mL, 6.3 mmol) in DCM (5 mL) was added propanoyl chloride (0.093 mL, 1.1 mmol) at rt. After 2 h, the reaction was evaporated and partitioned between saturated aqueous $NaHCO_3$ and EtOAc. The aqueous layer was extracted twice with EtOAc and the combined organic layer was washed with brine, dried, filtered and evaporated to obtain a crude product. The product was purified by Gilson and then lyophilized to produce 1-(4-{(2-methoxyethoxy)-[4-(8-methyl-quinolin-7-yl)-phenyl]-methyl}-piperidin-1-yl)-propan-1-one. TFA salt, 118 mg (29%). LCMS m/z=447 (M+1); $^1$H NMR (DMSO-$d_6$) δ: 9.05 (dd, J=4.27, 1.76 Hz, 1H) 8.57 (d, J=8.03 Hz, 1H) 7.97 (d, J=8.53 Hz, 1H) 7.69 (dd, J=8.16, 4.39 Hz, 1H) 7.59 (d, J=8.53 Hz, 1H) 7.37-7.50 (m, 4H) 4.31-4.49 (m, 1H) 4.17 (d, J=7.28 Hz, 1H) 3.75-3.96 (m, 1H) 3.32-3.55 (m, 4H) 3.25 (s, 3H) 2.81-3.01 (m, 1H) 2.68 (s, 3H) 2.50 (dt, J=3.70, 1.79 Hz, 8H) 2.21-2.35 (m, 2H) 1.78-2.00 (m, 2H) 1.01-1.36 (m, 3H) 0.91-1.01 (m, 3H). The following compounds were synthesized according to the procedure of examples 80 and 81.

Example 82

(4-{(2-Methoxyethoxy)-[4-(1-methylisoquinolin-6-yl)-phenyl]-methyl}-piperidin-1-yl)-(R)-tetrahydrofuran-2-yl-methanone; Mixture of diastereomers

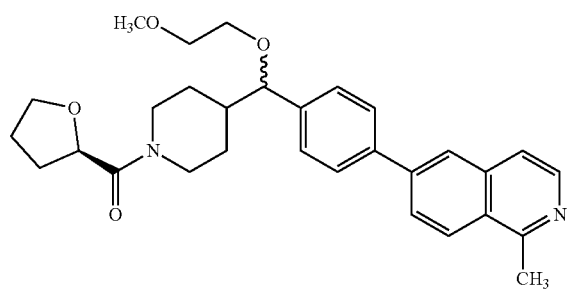 [SMILES: COCCOC(c1ccc(-c2ccc3c(C)nccc3c2)cc1)C1CCN(C(=O)[C@H]2CCCO2)CC1]

Analysis: LCMS m/z=489 (M+1); $^1$H NMR (DMSO-$d_6$) δ: 8.59-8.68 (m, 2H) 8.52 (d, J=6.52 Hz, 1H) 8.37 (dd, J=8.91, 1.63 Hz, 1H) 8.28 (d, J=6.52 Hz, 1H) 7.97 (d, J=8.28 Hz, 2H) 7.50 (d, J=8.28 Hz, 2H) 4.54-4.68 (m, 1H) 4.25-4.44 (m, 3H) 4.16-4.25 (m, 2H) 3.90-4.09 (m, 3H) 3.65-3.81 (m, 3H) 3.32-3.53 (m, 4H) 3.25 (s, 3H) 3.18 (s, 3H) 2.80-3.03 (m, 1H) 2.50 (dt, J=3.70, 1.79 Hz, 16H) 1.70-2.06 (m, 6H) 0.97-1.37 (m, 3H).

Example 83

(4-{(2-Methoxyethoxy)-[4-(4-methyl-quinolin-3-yl)-phenyl]-methyl}-piperidin-1-yl)-(R)-tetrahydrofuran-2-yl-methanone

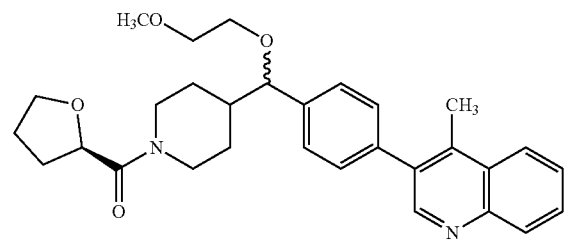 [SMILES: COCCOC(c1ccc(-c2cnc3ccccc3c2C)cc1)C1CCN(C(=O)[C@H]2CCCO2)CC1]

Analysis: LCMS m/z=489 (M+1); $^1$H NMR (DMSO-$d_6$) δ: 8.94 (s, 1H) 8.32 (d, J=8.78 Hz, 1H) 8.13 (d, J=8.28 Hz, 1H) 7.91 (t, J=7.53 Hz, 1H) 7.76-7.84 (m, 1H) 7.49-7.56 (m, 2H) 7.42-7.48 (m, 2H) 4.56-4.69 (m, 1H) 4.26-4.43 (m, 2H) 4.15-4.24 (m, 1H) 3.92-4.10 (m, 3H) 3.33-3.53 (m, 7H) 3.26 (s, 3H) 2.79-3.04 (m, 2H) 2.71 (s, 3H) 2.50 (dt, J=3.70, 1.79 Hz, 33H) 1.71-2.08 (m, 6H) 1.00-1.37 (m, 3H).

Example 84

{4-[[4-(8-Methylquinolin-7-yl)-phenyl]-(3-morpholin-4-yl-propoxy)-methyl]-piperidin-1-yl}-(R)-tetrahydrofuran-2-yl-methanone

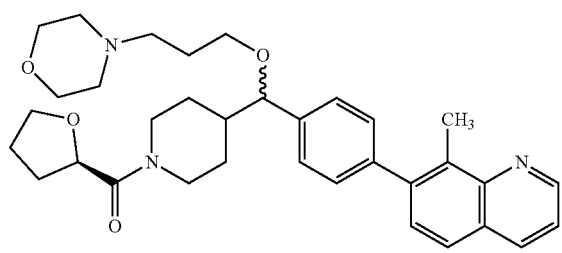 [SMILES: Cc1c(-c2ccc(C(OCCCN3CCOCC3)C3CCN(C(=O)[C@H]4CCCO4)CC3)cc2)ccc2cccnc12]

Analysis: LCMS m/z=558 (M+1); $^1$H NMR (DMSO-d$_6$) δ: 9.63-9.82 (m, 1H) 9.01 (dd, J=4.02, 1.76 Hz, 1H) 8.45 (dd, J=8.28, 1.76 Hz, 1H) 7.91 (d, J=8.53 Hz, 1H) 7.58-7.65 (m, 1H) 7.53 (d, J=8.28 Hz, 1H) 7.44-7.50 (m, 2H) 7.37-7.43 (m, 2H) 4.56-4.68 (m, 4H) 4.27-4.46 (m, 2H) 4.10-4.19 (m, 1H) 3.91-4.09 (m, 3H) 3.68-3.81 (m, 2H) 3.64 (t, J=12.30 Hz, 2H) 3.40-3.51 (m, 2H) 3.27-3.40 (m, 2H) 3.01-3.27 (m, 4H) 2.81-3.00 (m, 1H) 2.68 (s, 3H) 2.50 (dt, J=3.58, 1.85 Hz, 11H) 1.71-2.08 (m, 9H) 0.99-1.36 (m, 3H).

Example 85

1-{4-[[4-(8-Methylquinolin-7-yl)-phenyl]-(3-morpholin-4-yl-propoxy)-methyl]-piperidin-1-yl}-propan-1-one

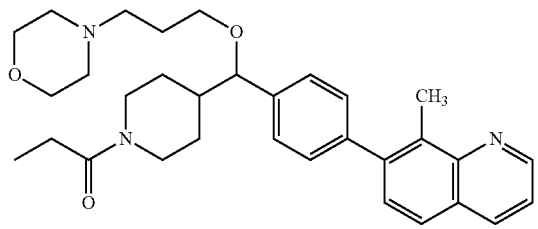 [SMILES: CCC(=O)N1CCC(C(OCCCN2CCOCC2)c2ccc(-c3ccc4cccnc4c3C)cc2)CC1]

Analysis: LCMS m/z=516 (M+1); $^1$H NMR (DMSO-d$_6$) δ: 9.67-9.89 (m, 1H) 9.02 (dd, J=4.27, 1.76 Hz, 1H) 8.47 (dd, J=8.16, 1.63 Hz, 1H) 7.93 (d, J=8.53 Hz, 1H) 7.63 (dd, J=8.03, 4.27 Hz, 1H) 7.54 (d, J=8.53 Hz, 1H) 7.44-7.50 (m, 2H) 7.38-7.43 (m, 2H) 4.32-4.52 (m, 2H) 4.14 (t, J=7.91 Hz, 1H) 3.97 (br. s, 2H) 3.76-3.93 (m, 1H) 3.64 (t, J=12.30 Hz, 2H) 3.39-3.52 (m, 2H) 3.27-3.39 (m, 2H) 3.00-3.27 (m, 5H) 2.80-3.00 (m, 1H) 2.68 (s, 3H) 2.50 (dt, J=3.70, 1.79 Hz, 9H) 2.19-2.35 (m, 3H) 1.77-2.03 (m, 5H) 1.03-1.33 (m, 3H) 0.91-1.02 (m, 4H).

Example 86

{4-[[4-(1-Methylisoquinolin-6-yl)-phenyl]-(3-morpholin-4-yl-propoxy)-methyl]-piperidin-1-yl}-(R)-tetrahydrofuran-2-yl-methanone

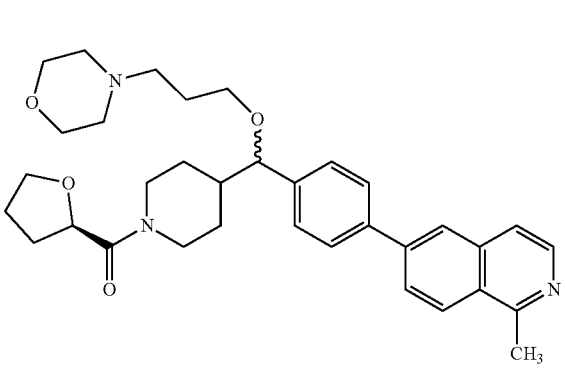 [SMILES: Cc1nccc2cc(-c3ccc(C(OCCCN4CCOCC4)C4CCN(C(=O)[C@H]5CCCO5)CC4)cc3)ccc12]

Analysis: LCMS m/z=558 (M+1); $^1$H NMR (DMSO-d$_6$) δ: 9.88 (br. s., 1H) 8.60-8.66 (m, 1H) 8.58 (s, 1H) 8.52 (d, J=6.53 Hz, 1H) 8.30-8.37 (m, 1H) 8.26 (d, J=6.52 Hz, 1H) 7.98 (d, J=8.28 Hz, 2H) 7.50 (d, J=8.03 Hz, 2H) 4.54-4.67 (m, 2H) 4.26-4.45 (m, 3H) 4.14-4.21 (m, 2H) 3.89-4.10 (m, 7H) 3.55-3.81 (m, 6H) 3.38-3.52 (m, 3H) 3.32 (t, J=5.52 Hz, 2H) 3.01-3.26 (m, 8H) 2.80-2.99 (m, 1H) 2.50 (dt, J=3.51, 1.76 Hz, 14H) 1.71-2.08 (m, 9H) 0.95-1.33 (m, 3H).

Example 87

{4-[[4-(4-Methylquinolin-3-yl)-phenyl]-(3-morpholin-4-yl-propoxy)-methyl]-piperidin-1-yl}-(R)-tetrahydrofuran-2-yl-methanone

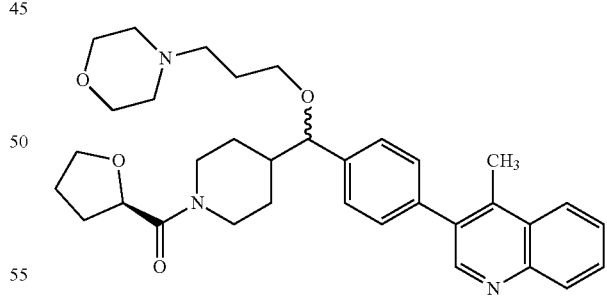

LCMS m/z=558 (M+1); $^1$H NMR (DMSO-d$_6$) δ ppm 9.77 (br. s., 1H) 8.90 (s, 1H) 8.30 (d, J=8.28 Hz, 1H) 8.12 (d, J=8.28 Hz, 1H) 7.90 (t, J=7.65 Hz, 1H) 7.76-7.83 (m, 1H) 7.51-7.58 (m, 2H) 7.43-7.49 (m, 2H) 4.57-4.69 (m, 1H) 4.28-4.46 (m, 1H) 4.12-4.22 (m, 1H) 3.91-4.10 (m, 3H) 3.69-3.81 (m, 2H) 3.58-3.69 (m, 2H) 3.40-3.52 (m, 2H) 3.27-3.40 (m, 2H) 3.00-3.27 (m, 4H) 2.82-3.00 (m, 1H) 2.70 (s, 3H) 2.50 (dt, J=3.70, 1.79 Hz, 9H) 1.71-2.08 (m, 8H) 0.99-1.35 (m, 3H).

Example 88

{4-[(2-Pyrrolidin-1-yl-ethoxy)-(4-quinolin-3-yl-phenyl)-methyl]-piperidin-1-yl}-(R)-tetrahydrofuran-2-yl-methanone

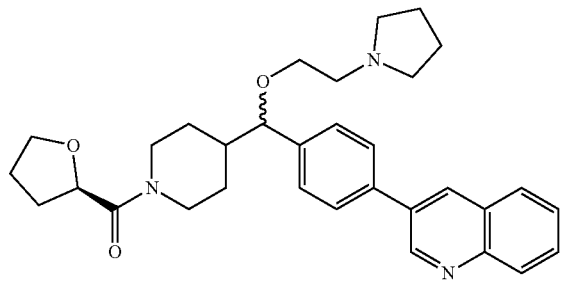 [SMILES: O=C([C@H]1CCCO1)N1CCC(C(OCCN2CCCC2)c2ccc(-c3cnc4ccccc4c3)cc2)CC1]

Analysis: LCMS m/z=514 (M+1); $^1$H NMR (DMSO-d$_6$) δ: 9.57 (br. s., 1H) 9.32 (d, J=2.26 Hz, 1H) 8.75 (s, 1H) 8.09 (dd, J=7.91, 3.39 Hz, 2H) 7.95 (d, J=8.03 Hz, 2H) 7.82 (td, J=7.78, 1.25 Hz, 1H) 7.65-7.74 (m, 1H) 7.51 (d, J=8.03 Hz, 2H) 4.55-4.68 (m, 1H) 4.27-4.46 (m, 1H) 4.17-4.26 (m, 1H) 3.90-4.12 (m, 1H) 3.65-3.80 (m, 2H) 3.26-3.63 (m, 6H) 2.80-3.16 (m, 3H) 2.38-2.59 (m, 10H) 1.70-2.09 (m, 10H) 0.97-1.36 (m, 3H).

Example 89

{4-[[4-(8-Methylquinolin-7-yl)-phenyl]-(2-pyrrolidin-1-yl-ethoxy)-methyl]-piperidin-1-yl}-(R)-tetrahydrofuran-2-yl-methanone

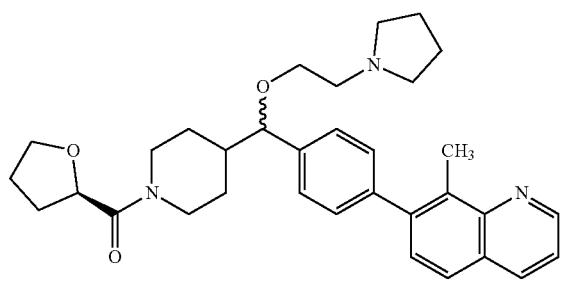 [SMILES: Cc1c(-c2ccc(C(OCCN3CCCC3)C3CCN(C(=O)[C@H]4CCCO4)CC3)cc2)ccc2cccnc12]

Analysis: LCMS m/z=528 (M+1); $^1$H NMR (DMSO-d$_6$) δ: 9.52 (br. s., 1H) 9.00 (dd, J=4.14, 1.88 Hz, 1H) 8.44 (dd, J=8.28, 1.51 Hz, 1H) 7.91 (d, J=8.53 Hz, 1H) 7.61 (dd, J=8.16, 4.14 Hz, 1H) 7.40-7.56 (m, 5H) 4.57-4.69 (m, 3H) 4.27-4.47 (m, 2H) 4.17-4.26 (m, 1H) 3.91-4.12 (m, 1H) 3.66-3.81 (m, 2H) 3.28-3.62 (m, 6H) 2.81-3.16 (m, 3H) 2.68 (s, 3H) 1.72-2.10 (m, 11H) 0.98-1.36 (m, 4H).

Example 90

{4-[[4-(1-Methylisoquinolin-6-yl)-phenyl]-(2-pyrrolidin-1-yl-ethoxy)-methyl]-piperidin-1-yl}-(R)-tetrahydrofuran-2-yl-methanone

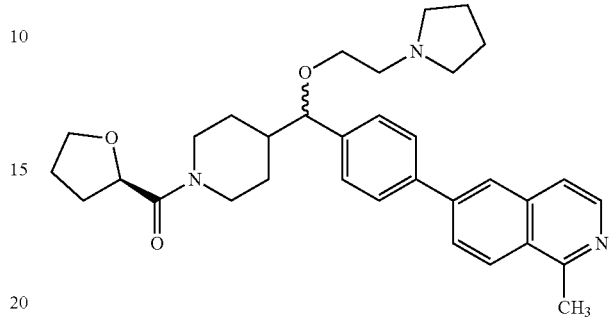

LCMS m/z=528 (M+1); $^1$H NMR (DMSO-d$_6$) δ: 9.71 (br. s., 1H) 8.57-8.67 (m, 2H) 8.53 (d, J=6.53 Hz, 1H) 8.35 (dd, J=8.91, 1.38 Hz, 1H) 8.27 (d, J=6.53 Hz, 1H) 8.00 (d, J=8.28 Hz, 2H) 7.54 (d, J=8.28 Hz, 2H) 4.54-4.68 (m, 2H) 4.20-4.46 (m, 3H) 3.90-4.12 (m, 1H) 3.65-3.80 (m, 2H) 3.26-3.63 (m, 6H) 3.17 (s, 3H) 2.80-3.14 (m, 3H) 2.50 (dt, J=3.51, 1.76 Hz, 11H) 1.70-2.09 (m, 11H) 0.96-1.34 (m, 3H).

Example 91

4-[4-(8-Methoxyquinolin-7-yl)-benzyl]-1-((R)-tetrahydrofuran-2-carbonyl)-piperidine-4-carbonitrile

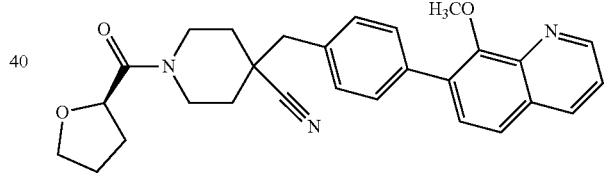

Step 1. tert-Butyl 4-[(4-bromophenyl)methyl]-4-cyano-piperidine-1-carboxylate 1.6 M n-butyllithium in THF (3.42 mL, 5.47 mmol) was added at −78° C. to a solution of N,N-diisopropylamine (0.77 mL, 5.47 mmol) in THF (15 mL). After 10 min a solution of t-butyl 4-cyanopiperidine-1-carboxylate (1.00 g, 5.00 mmol) in THF (6 mL) was added at −78° C. After 1 h a solution of 4-bromobenzyl bromide (1.43 g, 5.71 mmol) in THF (3 mL) was added drop-wise (5 min) and the solution was warmed to rt over 15 hours. H$_2$O (30 mL) was added and the mixture was extracted with Et2O (2×30 mL). The organic extract was dried (Na$_2$SO$_4$) and solvent evaporated under reduced pressure. The crude product was purified by silica gel (0-40% EtOAc/hexanes) to give tert-butyl 4-[(4-bromophenyl)methyl]-4-cyano-piperidine-1-carboxylate as an yellow oil (1.3 g, 70%); LCMS m/z=280 (M-Boc); $^1$H NMR (CDCl$_3$): δ: 7.47 (d, J=8.53 Hz, 2H), 7.15 (d, J=8.53 Hz, 2H), 4.08-4.23 (m, 2H), 2.92-3.06 (m, 2H), 2.81 (s, 2H), 1.78-1.86 (m, 2H), 1.45 (s, 11H).

Step 2. tert-Butyl 4-cyano-4-[[4-(4,4,5,5-tetramethyl-1,3,2-dioxaborolan-2-yl)phenyl]methyl]piperidine-1-carboxylate A flask charged with tert-butyl 4-[(4-bromophenyl)methyl]-4-cyano-piperidine-1-carboxylate (1.3 g, 3.4 mmol), 4,4,5,5,4',4',5',5'-octamethyl [2,2]bi[[1,3,2]dioxaborolanyl] (1.30 g, 5.14 mmol), bis(tricyclohexylphosphine)palladium (0) (0.24 g, 0.36 mmol), potassium acetate (0.504 g, 5.14 mmol), and 1,4-dioxane (30 mL) and was heated at 85° C. for 16 h. The reaction was cooled to rt, filtered through a pad of Celite, washed with DCM (2×50 mL) and the filtrate was concentrated. Purification by silica gel (0-40% EtOAc/hexanes) gave tert-butyl 4-cyano-4-[[4-(4,4,5,5-tetramethyl-1,3,2-dioxaborolan-2-yl)phenyl]methyl]piperidine-1-carboxylate as a white foam (1.2 g, 78%); LCMS m/z=327 (M-Boc); $^1$H NMR (CDCl$_3$) δ: 7.78 (d, J=8.28 Hz, 2H), 7.28 (d, J=8.03 Hz, 2H), 4.02-4.23 (m, 2H), 2.91-3.07 (m, 2H), 2.88 (s, 2H), 1.77-1.87 (m, 2H), 1.47-1.53 (m, 2H), 1.45 (s, 9H), 1.34 (s, 12H).

Step 3. t-Butyl 4-cyano-4-[[4-(8-methoxy-7-quinolyl)phenyl]methyl]piperidine-1-carboxylate Palladium acetate (31.6 mg, 0.141 mmol) and triphenylphosphine (148 mg, 0.563 mmol) in 1,4-dioxane (7 mL) were stirred for 15 min under an atmosphere of nitrogen. tert-butyl 4-cyano-4-[[4-(4,4,5,5-tetramethyl-1,3,2-dioxaborolan-2-yl)phenyl]methyl]piperidine-1-carboxylate (1.2 g, 2.8 mmol), 7-bromo-8-methoxyquinoline (1.01 g, 4.22 mmol), DMF (10 mL) and 1 M of sodium carbonate in H$_2$O (11.2 mL, 11.2 mmol) were added, purged under an atmosphere of nitrogen and then the contents of the flask were heated at 80° C. for 2 h. The reaction mixture was then cooled to room temperature, diluted with EtOAc (100 mL), was washed with 1N Na$_2$CO$_3$ (50 mL), brine (50 mL) then dried (Na$_2$SO$_4$). The organics were evaporated in vacuo. The crude product was purified by silica gel (10-50% EtOAc/hexanes) to give the desired tert-butyl 4-cyano-4-[[4-(8-methoxy-7-quinolyl)phenyl]methyl]piperidine-1-carboxylate as an yellow foam (1.4 g, 92%); LCMS m/z=458 (M+1); $^1$H NMR (CDCl$_3$) δ: 8.99 (dd, J=4.14, 1.63 Hz, 1H), 8.18 (dd, J=8.41, 1.63 Hz, 1H), 7.67-7.73 (m, 2H), 7.62-7.66 (m, 1H), 7.53-7.60 (m, 1H), 7.36-7.46 (m, 3H), 4.12 (d, J=7.28 Hz, 2H), 3.89 (s, 3H), 3.03 (br. s., 2H), 2.93-2.97 (m, 2H), 1.93 (s, 2H), 1.54-1.60 (m, 2H), 1.46 (s, 9H).

Step 4. 4-[[4-(8-Methoxy-7-quinolyl)phenyl]methyl]piperidine-4-carbonitrile

To a stirred solution of t-butyl 4-cyano-4-[[4-(8-methoxy-7-quinolyl)phenyl]methyl]piperidine-1-carboxylate (600 mg, 1 mmol) in DCM (15 mL) was added HCl (4.0 M solution in 1,4-dioxane, 3.28 mL, 13.1 mmol) drop-wise. The reaction was stirred at 35° C. for 4 h and then concentrated under reduced pressure. The crude contents were re-dissolved in DCM (2×30 mL) and concentrated under reduced pressure to give the desired product as an yellow foam. The crude product was triturated with Et$_2$O (2×10 mL) to give 4-[[4-(8-methoxy-7-quinolyl)phenyl]methyl]piperidine-4-carbonitrile as an yellow solid (460 mg, 80%); LCMS m/z=358 (M+1); $^1$H NMR (CD$_3$OD): δ: 9.12-9.21 (m, 2H), 8.13-8.19 (m, 1H), 8.07-8.13 (m, 1H), 8.02 (s, 1H), 7.84 (d, J=8.28 Hz, 2H), 7.63 (d, J=8.53 Hz, 2H), 3.74 (s, 3H), 3.56 (br. s., 2H), 3.18 (s, 4H), 2.23 (br. s., 2H), 1.99-2.12 (m, 2H).

Step 5. 4-[4-(8-Methoxyquinolin-7-yl)-benzyl]-1-((R)-tetrahydrofuran-2-carbonyl)-piperidine-4-carbonitrile A solution of (R)-tetrahydrofuran-2-carboxylic acid (0.034 mL, 0.36 mmol), HATU (142 mg, 0.373 mmol) and DIPEA (0.25 mL, 1.4 mmol) in acetonitrile (1 mL) was stirred at room temperature for 10 min. 4-[[4-(8-Methoxy-7-quinolyl)phenyl]methyl]piperidine-4-carbonitrile (140 mg, 0.36 mmol) was added and the mixture was stirred at room temperature for 1 hour. The reaction was quenched by the addition of MeOH (1 mL). The solvent was evaporated in vacuo. The crude product was purified by HPLC (reverse phase, 13-55% ACN/H2O). The combined aqueous fractions were diluted with sat. Na2CO3 (25 mL) extracted with DCM (3×30 mL) to give 4-[4-(8-methoxy-quinolin-7-yl)-benzyl]-1-((R)-tetrahydro-furan-2-carbonyl)-piperidine-4-carbonitrile as an yellow foam (100 mg, 50%, mp=102-5° C.); LCMS m/z=456 (M+1); $^1$H NMR (CD$_3$OD): δ: (dd, J=4.27, 1.76 Hz, 1H), 8.18 (dd, J=8.41, 1.63 Hz, 1H), 7.70 (d, J=8.28 Hz, 2H), 7.61-7.67 (m, 1H), 7.55-7.59 (m, 1H), 7.37-7.46 (m, 3H), 4.63-4.74 (m, 1H), 4.56-4.63 (m, 1H), 4.15-4.24 (m, 1H), 3.89 (s, 5H), 3.26-3.47 (m, 1H), 2.95 (s, 3H), 2.27-2.42 (m, 1H), 1.87-2.08 (m, 5H), 1.57-1.74 (m, 2H).

The following compounds were synthesized using the procedure for Example 91.

Example 92

4-[4-(8-methoxyquinolin-7-yl)-benzyl]-1-propionylpiperidine-4-carbonitrile

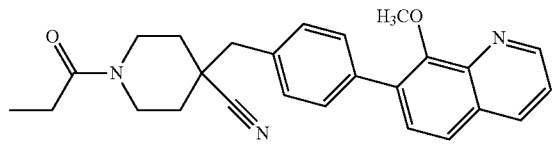 [SMILES: CCC(=O)N1CCC(C#N)(Cc2ccc(-c3ccc4cccnc4c3OC)cc2)CC1]

The title compound was synthesized using the procedure for Example 91, except for reaction with propionyl chloride in Step 5. LCMS m/z=414 (M+1); 1H NMR (CDCl$_3$): δ: 8.99 (dd, J=4.14, 1.63 Hz, 1H), 8.13-8.23 (m, 1H), 7.70 (d, J=8.03 Hz, 2H), 7.62-7.67 (m, 1H), 7.54-7.60 (m, 1H), 7.45 (s, 1H), 7.39 (d, J=8.28 Hz, 2H), 4.66-4.80 (m, 1H), 3.89 (s, 4H), 3.30-3.41 (m, 1H), 2.95 (d, J=5.27 Hz, 3H), 2.32-2.42 (m, 2H), 1.96-2.04 (m, 2H), 1.55 (br. s., 2H), 1.16 (t, J=7.40 Hz, 3H).

Example 93

{4-[4-(5-Methyl-imidazo[1,2-a]pyridin-6-yl)-benzyl]-piperidin-1-yl}-(R)-tetrahydrofuran-2-yl-methanone

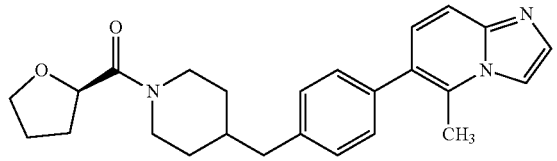 [SMILES: Cc1c(-c2ccc(CC3CCN(C(=O)[C@H]4CCCO4)CC3)cc2)ccc2nccn12]

The title compound was synthesized using the procedure for Example 91, except for coupling with 6-bromo-5-methylimidazo[1,2-a]pyridine in Step 3. LCMS m/z=404 (M+1); $^1$H NMR (CDCl$_3$): δ: 7.74 (d, J=1.25 Hz, 1H), 7.52-7.62 (m, 2H), 7.28 (s, 2H), 7.16-7.24 (m, 3H), 4.62 (d, J=4.52 Hz, 2H), 3.58-4.13 (m, 4H), 2.88-3.08 (m, 1H), 2.62 (d, J=7.03 Hz, 2H), 2.55 (s, 3H), 2.26 (br. s., 1H), 1.71-2.12 (m, 7H).

Example 94

1-{4-[4-(5-Methylimidazo[1,2-a]pyridin-6-yl)-benzyl]-piperidin-1-yl}-propan-1-one

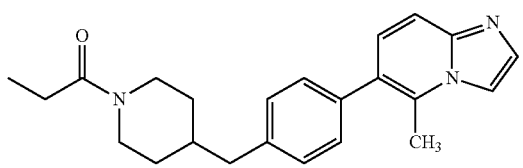 [SMILES: CCC(=O)N1CCC(Cc2ccc(-c3ccc4nccn4c3C)cc2)CC1]

The title compound was synthesized using the procedure for Example 91, except for coupling with 6-bromo-5-methylimidazo[1,2-a]pyridine in Step 3, and reaction with propionyl chloride in Step 5. LCMS m/z=362 (M+1); $^1$H NMR (CDCl$_3$): δ: 7.74 (d, J=1.26 Hz, 1H), 7.59 (d, J=9.29 Hz, 1H), 7.54 (d, J=1.25 Hz, 1H), 7.28 (d, J=6.27 Hz, 2H), 7.17-7.25 (m, 3H), 4.60-4.71 (m, 1H), 3.82-3.91 (m, 1H), 2.93-3.03 (m, 1H), 2.62 (dd, J=6.90, 1.88 Hz, 2H), 2.55 (s, 4H), 2.31-2.39 (m, 2H), 1.71-1.88 (m, 3H), 1.22-1.27 (m, 1H), 1.14-1.18 (m, 3H).

Example 95

Cyclopropyl-{4-[4-(5-methylimidazo[1,2-a]pyridin-6-yl)-benzyl]-piperidin-1-yl}-methanone

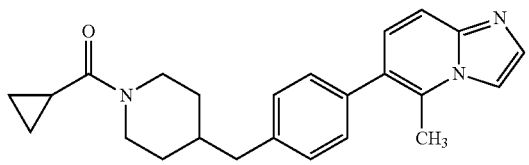 [SMILES: Cc1c(-c2ccc(CC3CCN(C(=O)C4CC4)CC3)cc2)ccc2nccn12]

The title compound was synthesized using the procedure for Example 91, except that the coupling in Step 3 was with 6-bromo-5-methylimidazo[1,2-a]pyridine, and the reaction in Step 5 was with cyclopropanecarbonyl chloride. LCMS m/z=374 (M+1); $^1$H NMR (CDCl$_3$): δ: 7.74 (d, J=1.25 Hz, 1H), 7.52-7.62 (m, 2H), 7.28 (s, 2H), 7.16-7.24 (m, 3H), 4.62 (d, J=4.52 Hz, 2H), 3.58-4.13 (m, 4H), 2.88-3.08 (m, 1H), 2.62 (d, J=7.03 Hz, 2H), 2.55 (s, 3H), 2.26 (br. s., 1H), 1.71-2.12 (m, 7H).

Example 96

(1-Hydroxy cyclopropyl)-{4-[4-(5-methylimidazo[1,2-a]pyridin-6-yl)-benzyl]-piperidin-1-yl}-methanone

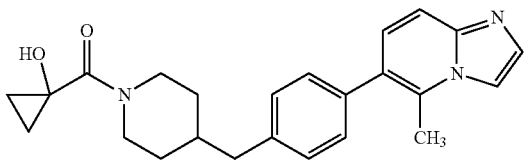 [SMILES: Cc1c(-c2ccc(CC3CCN(C(=O)C4(O)CC4)CC3)cc2)ccc2nccn12]

The title compound was synthesized using the procedure for Example 91, except for coupling with 6-bromo-5-methylimidazo[1,2-a]pyridine in Step 3, and reaction with in Step 5. LCMS m/z=390 (M+1); $^1$H NMR (CDCL$_3$): δ: 7.74 (d, J=1.25 Hz, 1H), 7.52-7.62 (m, 2H), 7.28 (s, 2H), 7.16-7.24 (m, 3H), 4.62 (d, J=4.52 Hz, 2H), 3.58-4.13 (m, 4H), 2.88-3.08 (m, 1H), 2.62 (d, J=7.03 Hz, 2H), 2.55 (s, 3H), 2.26 (br. s., 1H), 1.71-2.12 (m, 7H).

Example 97

(R)-(4-fluoro-4-(4-(5-methylimidazo[1,2-a]pyridin-6-yl)benzyl)piperidin-1-yl)(tetrahydrofuran-2-yl)methanone

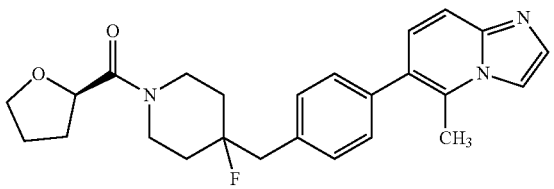 [SMILES: Cc1c(-c2ccc(CC3(F)CCN(C(=O)[C@H]4CCCO4)CC3)cc2)ccc2nccn12]

Step 1. tert-Butyl 4-[(4-2,2,2-trifluoro-1-{4-fluoro-4-[4-(4,4,5,5-tetramethyl-[1,3,2]dioxaborolan-2-yl)-benzoyl)]-piperidin-1-yl}]-ethanone A flask charged with 1-[4-(4-bromobenzoyl)-4-fluoropiperidin-1-yl]-2,2,2-trifluoroethanone (1.7 g, 4.4 mmol), 4,4,5,5,4',4',5',5'-octamethyl-[2,2']bi[[1,3,2]dioxaborolanyl] (1.69 g, 6.67 mmol), bis(tricyclohexylphosphine)palladium (0) (0.31 g, 0.47 mmol), potassium acetate (0.655 g, 6.67 mmol), and 1,4-dioxane (40 mL) and was heated at 85° C. for 16 h. The reaction was cooled to rt and filtered through a pad of Celite, washed with DCM (2×50 mL), and the filtrate was concentrated. The crude product was purified by silica gel (0-20% EtOAc/hexanes) to give tert-butyl 4-[(4-2,2,2-trifluoro-1-{4-fluoro-4-[4-(4,4,5,5-tetramethyl-[1,3,2]dioxaborolan-2-yl)-benzoyl]-piperidin-1-yl}-ethanone as a white solid (1.4 g, 70%); LCMS m/z=430 (M+1); $^1$H NMR (CDCl$_3$): δ: 7.98-8.04 (m, 2H), 7.89 (d, J=8.28 Hz, 2H), 4.44-4.55 (m, 1H), 3.97-4.06 (m, 1H), 3.55-3.68 (m, 1H), 3.25-3.35 (m, 1H), 2.12-2.36 (m, 4H), 1.36 (s, 12H).

Step 2. (4-Fluoropiperidin-4-yl)-[4-(5-methylimidazo[1,2-a]pyridin-6-yl)-phenyl]-methanone, TFA Salt Palladium acetate (36.6 mg, 0.163 mmol) and triphenylphosphine (171 mg, 0.65 mmol) in 1,4-dioxane (8 mL)

were stirred for 15 min under an atmosphere of nitrogen. tert-Butyl 4-[(4-2,2,2-trifluoro-1-{4-fluoro-4-[4-(4,4,5,5-tetramethyl-[1,3,2]dioxaborolan-2-yl)-benzoyl]-piperidin-1-yl}-ethanone (1.4 g, 3.3 mmol), 6-bromo-5-methyl-imidazo[1,2-a]pyridine (830 mg, 3.9 mmol), DMF (10 mL) and 1M of sodium carbonate in H$_2$O (13.0 mL) were added, purged under an atmosphere of nitrogen and then the reaction mixture was heated at 80° C. for 16h. The organics were evaporated in vacuo. The crude residue was dissolved in EtOAc (100 mL), washed with 1N Na$_2$CO$_3$ (50 mL), brine (50 mL) then dried (Na$_2$SO$_4$). The crude product was purified by HPLC (reverse phase, 5-30% ACN/H$_2$O). The combined fraction were lyophilized to give (4-fluoro-piperidin-4-yl)-[4-(5-methyl-imidazo[1,2-a]pyridin-6-yl)-phenyl]-methanone; 2,2,2-trifluoroacetic acid as a brown foam (1 g, 60%). LCMS 338 (M+1).

Step 3. {3-Fluoro-3-[4-(5-methylimidazo[1,2-a]pyridin-6-yl)-benzoyl]-pentyl}-methyl-carbamic acid tert-butyl ester A mixture of (4-fluoro-4-piperidyl)-[4-(5-methylimidazo[1,2-a]pyridin-6-yl)phenyl]methanone; TFA (1 g, 2 mmol), di-tert-butyldicarbonate (0.483 g, 2.22 mmol) and DIPEA (0.772 mL, 4.43 mmol) in DCM (1.42 mL) were stirred at rt for 3 h. The solvent was removed under reduced pressure. The crude product was purified by silica gel (0-100% EtOAc/hexanes, then 0-10% MeOH/DCM). The combined fractions were evaporated under reduced pressure to give {3-fluoro-3-[4-(5-methyl-imidazo[1,2-a]-pyridin-6-yl)-benzoyl]-pentyl}-methyl-carbamic acid tert-butyl ester as an off-white solid (700 mg, 70%); LCMS m/z=438 (M+1); $^1$H NMR (CDCl$_3$): δ: 8.17 (d, J=7.53 Hz, 2H), 7.76 (d, J=1.25 Hz, 1H), 7.63 (d, J=9.29 Hz, 1H), 7.57 (s, 1H), 7.44-7.50 (m, 2H), 7.19 (d, J=9.03 Hz, 1H), 4.04-4.19 (m, 2H), 3.17-3.31 (m, 2H), 2.57 (s, 3H), 2.05-2.29 (m, 4H), 1.49 (s, 9H).

Step 4. (3-Fluoro-3-{hydroxy-[4-(5-methylimidazo[1,2-a]pyridin-6-yl)-phenyl]-methyl}-pentyl)-methylcarbamic acid tert-butyl ester {3-Fluoro-3-[4-(5-methylimidazo[1,2-a]pyridin-6-yl)-benzoyl]-pentyl}-methyl-carbamic acid tert-butyl ester (700 mg, 2 mmol) was dissolved in ethanol (1.60 mL) and THF (11.0 mL), then treated with sodium borohydride (94.4 mg, 2.50 mmol). After stirring for 1h, the mixture was quenched with acetone (1.45 mL). After stirring for 20 min, the mixture was diluted with sat. NH$_4$Cl (20 mL) and stirred for 1h. The mixture was then diluted with EtOAc (50 mL) and sat. NaHCO$_3$ (20 mL, to basic pH), the layers were separated and the aqueous phase extracted with EtOAc (2×25 mL). The combined organic extracts were washed with brine (25 mL), dried (Na$_2$SO$_4$) and filtered. The organics were evaporated in vacuo. The crude product was purified by silica gel (0-100% EtOAc/hexanes; then 0-10% MeOH/DCM). The combined fractions were evaporated under reduced pressure to give the (3-fluoro-3-{hydroxy-[4-(5-methyl-imidazo[1,2-a]-pyridin-6-yl)-phenyl]-methyl}-pentyl)-methyl-carbamic acid tert-butyl ester as a white foam (500 mg, 70%); LCMS m/z=440 (M+1).

Step 5. (3-{Chloro-[4-(5-methylimidazo[1,2-a]pyridin-6-yl)-phenyl]-methyl}-3-fluoro-pentyl)-methyl-carbamic acid tert-butyl ester Thionyl chloride (0.636 mL, 8.71 mmol) was added to a solution of (3-fluoro-3-{hydroxy-[4-(5-methyl-imidazo[1,2-a]pyridin-6-yl)-phenyl]-methyl}-pentyl)-methyl-carbamic acid t-butyl ester (500 mg, 1 mmol) in DCM (20 mL) and stirred at room temperature overnight. The mixture was concentrated in vacuo and the residue was partitioned between aq. sat. NaHCO$_3$ (30 mL) and EtOAc: DCM (1:2, 50 mL). The layers were separated, the aqueous layer was back-extracted with DCM (30 mL). The combined organics were washed with sat. aq. NaHCO$_3$:brine (1:1, 30 mL), dried (Na$_2$SO$_4$), filtered and concentrated in vacuo. The crude product was purified by silica gel (0-10% MeOH/DCM). The combined fractions were evaporated under reduced pressure to give (3-{chloro-[4-(5-methylimidazo[1,2-a]pyridin-6-yl)-phenyl]-methyl}-3-fluoropentyl)-methyl-carbamic acid tert-butyl ester as a white foam (300 mg, 50%); LCMS m/z=458 (M+1).

Step 6. {3-Fluoro-3-[4-(5-methylimidazo[1,2-a]pyridin-6-yl)-benzyl]-pentyl}-methyl-carbamic acid tert-butyl ester A mixture of (3-{chloro-[4-(5-methylimidazo[1,2-a]pyridin-6-yl)-phenyl]-methyl}-3-fluoropentyl)-methylcarbamic acid tert-butyl ester (300 mg, 0.6 mmol), tris(trimethylsilyl)silane (0.605 mL, 1.96 mmol) and 2,2'-azo-bis-isobutyronitrile (12 mg, 0.076 mmol) in toluene (7 mL) were heated to 100° C. for 3 h then cooled to room temperature. The mixture was concentrated in vacuo. The crude product was purified on silica gel (10-85% EtOAc/hexane; then 0-10% MeOH/DCM). The combined fractions still had an impurity, so the crude product was purified by HPLC (reverse phase, 25-82% ACN/H$_2$O). The combined aqueous fractions were diluted with sat. Na$_2$CO$_3$ (25 ml) extracted with DCM (3×30 ml) to give {3-fluoro-3-[4-(5-methyl-imidazo[1,2-a]pyridin-6-yl)-benzyl]-pentyl}-methyl-carbamic acid tert-butyl ester (free base) as a colorless oil (11 mg, 4%); LCMS m/z=424 (M+1).

Step 7. {4-Fluoro-4-[4-(5-methylimidazo[1,2-a]pyridin-6-yl)-benzyl]-piperidin-1-yl}-(R)-tetrahydrofuran-2-yl-methanone To a stirred solution of {3-fluoro-3-[4-(5-methylimidazo[1,2-a]pyridin-6-yl)-benzyl]-pentyl}-methylcarbamic acid tert-butyl ester (11 mg, 0.026 mmol) in DCM (0.3 mL) was added 4.0 M of HCl in 1,4-dioxane (0.06 mL, 0.3 mmol) solution dropwise. The reaction was stirred at 35° C. (4 h) and was concentrated under reduced pressure. The crude contents were re-dissolved in DCM (2×30 mL) and concentrated under reduced pressure to give the desired product as yellow foam. The crude product was triturated with Et$_2$O (2×10 mL) to give 6-[4-[(4-fluoro-4-piperidyl)methyl]phenyl]-5-methylimidazo-[1,2-a]pyridine HCl as yellow foam (10 mg; 100%); LCMS m/z=324 (M+1). Used without further purification in the next step.

Step 8. (R)-(4-fluoro-4-(4-(5-methylimidazo[1,2-a]pyridin-6-yl)benzyl)piperidin-1-yl)(tetrahydrofuran-2-yl)methanone A solution of (R)-tetrahydrofuran-2-carboxylic acid (0.002 mL, 0.03 mmol), HATU (10 mg, 0.027 mmol) and DIPEA (0.02 mL, 0.1 mmol) in acetonitrile (0.1 mL) was stirred at room temperature for 10 min. 6-[4-[(4-fluoro-4-piperidyl)methyl]phenyl]-5-methylimidazo[1,2-a]pyridine HCl (9.3 mg, 0.026 mmol) was added and the mixture was stirred at room temperature for 1 hour. The reaction was quenched by addition of MeOH (1 mL). The solvent was evaporated in vacuo. The crude product was purified by HPLC (reverse phase, 6-50% ACN/H₂O). The combined aqueous fractions were diluted with sat. Na₂CO₃ (25 mL) extracted with DCM (3×30 mL) to give the desired product (free base) as an off-white foam. It was lyophilized to give {4-fluoro-4-[4-(5-methyl-imidazo[1,2-a]pyridin-6-yl)-benzyl]-piperidin-1-yl}-(R)-tetrahydrofuran-2-yl-methanone white powder (8 mg, 70%); LCMS m/z=422 (M+1); ¹H NMR (CDCl₃): δ: 7.75 (d, J=1.25 Hz, 1H), 7.63 (d, J=9.29 Hz, 1H), 7.55 (s, 1H), 7.29 (s, 4H), 7.21-7.25 (m, 1H), 4.57-4.65 (m, 1H), 4.42-4.54 (m, 1H), 3.26-4.02 (m, 5H), 2.95-3.03 (m, 2H), 2.56 (s, 3H), 2.23-2.37 (m, 1H), 1.79-2.10 (m, 6H).

Example 98

2,2,2-Trifluoro-1-{4-[2-(4-quinolin-6-yl-phenyl)-1,3-dioxolan-2-yl]-piperidin-1-yl}-ethanone

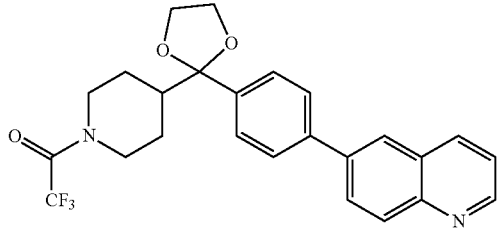 [SMILES: O=C(N1CCC(C2(c3ccc(-c4ccc5ncccc5c4)cc3)OCCO2)CC1)C(F)(F)F]

Palladium acetate (0.0275 g, 0.122 mmol) and triphenylphosphine (0.128 g, 0.490 mmol) in dioxane (10 mL) was stirred 15 min under an atmosphere of nitrogen. Then, 1-{4-[2-(4-bromophenyl)-1,3-dioxolan-2-yl]-piperidin-1-yl}-2,2,2-trifluoroethanone (1.00 g, 2.45 mmol), quinoline-6-boronic acid (0.636 g, 3.67 mmol), DMF (10 mL) and 1 M of sodium carbonate in (4.90 mL) was added and heated at 80° C. for 4 h. The mixture was concentrated, dissolved in EtOAc and washed with 1N Na₂CO₃, water and brine, then dried over MgSO₄. The product was purified by ISCO (silica get, 40 g, 40-90% EtOAc/hexanes) to give a white solid (530 mg; 47%). LCMS m/z=457 (M+1); ¹H NMR (CDCl₃) δ: 8.92 (m, 1H), 8.17-8.23 (m, 2H), 7.97-8.01 (m, 2H), 7.78 (d, 2H, J=8 Hz), 7.52 (d, 2H, J=8 Hz), 7.43 (dd, 1H, J=4, 8 Hz), 4.56-4.60 (m, 1H), 4.01-4.05 (m, 3H), 3.80-3.83 (m, 2H), 3.03 (d, t, 1H, J=2, 12 Hz), 2.66 (t, 1H, J=12 Hz), 2.09-2.7 (m, 1H), 1.82 (bd, 2H, J=14 Hz), 1.42-1.54 (m, 2H).

Example 99

Cyclopropyl-{4-[2-(4-quinolin-6-yl-phenyl)-1,3-dioxolan-2-yl]-piperidin-1-yl}-methanone

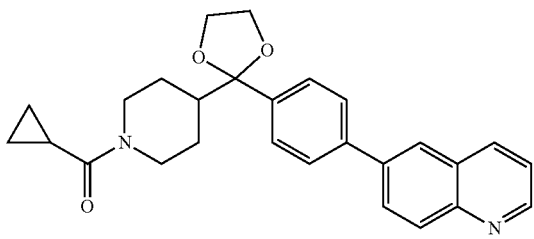 [SMILES: O=C(C1CC1)N1CCC(C2(c3ccc(-c4ccc5ncccc5c4)cc3)OCCO2)CC1]

Step 1. 6-[4-(2-Piperidin-4-yl-1,3-dioxolan-2-yl)-phenyl]-quinoline 2,2,2-Trifluoro-1-{4-[2-(4-quinolin-6-yl-phenyl)-1,3-dioxolan-2-yl]-piperidin-1-yl}-ethanone (0.17 g, 0.37 mmol), methanol (1 mL), water (0.29 mL), and K₂CO₃ (0.1379 g, 0.9980 mmol) was stirred at rt for 18 h. The mixture was diluted with EtOAc and washed with water, and brine then dried over MgSO4. 6-[4-(2-Piperidin-4-yl-1,3-dioxolan-2-yl)-phenyl]-quinoline was triturated with ether and hexanes, collected and dried over MgSO₄. LCMS m/z=361 (M+1); ¹H NMR (CDCl₃) δ: 8.91 (m, 1H), 8.16-8.22 (m, 1H), 7.97-8.00 (m, 2H), 7.68 (d, 2, J=8 Hz), 7.53 (d, 2H, J=8 Hz), 7.44 (m, 1H), 4.00-4.04 (m, 2H), 3.79-3.82 (m, 2H), 3.09 (bd, 2H, J=12 Hz), 2.54 (dt, 2H, H=2, 12 Hz), 1.95 (tt, 1H, J=2, 10 Hz), 1.72 (s, 1H), 1.28-1.38 (m, 2H).

Step 2. Cyclopropyl-{4-[2-(4-quinolin-6-yl-phenyl)-1,3-dioxolan-2-yl]-piperidin-1-yl}-methanone 6-[4-(2-Piperidin-4-yl-1,3-dioxolan-2-yl)-phenyl]-quinoline (0.040 g, 0.11 mmol) and DIPEA (1 mL) in THF (2 mL) was added cyclopropanecarbonyl chloride (0.0189 mL, 0.208 mmol). After 2 h stirring at rt the mixture was concentrated, dissolved in EtOAc, and washed with 1N Na₂CO₃, and brine, then dried (MgSO₄). The product was recrystallized from ether and hexanes to give a white solid (30 mg, 63%). LCMS m/z=429 (M+1); ¹H NMR (CDCl₃) δ: 8.93 (s, 1H), 8.17-8.23 (m, 2H), 7.97-8.01 (m, 2H), 7.70 (d, 2H, J=8 Hz), 7.53 (d, 2H, J=8 Hz), 7.42-7.45 (m, 1H), 4.66 (bd, 1H, J=12 Hz), 4.25 (bd, 1H, J=12 Hz), 4.0-4.04 (m, 2H), 3.80-3.83 (m, 2H), 3.00 (t, 1H, J=12 Hz), 2.47 (t, 1H, J=12 Hz), 2.05-2.13 (tt, 1H, J=4, 12 Hz), 1.68-1.74 (m, 3H), 1.37-1.54 (m, 2H), 0.94-097 (m, 2H), 0.69-0.72 (m, 2H).

Example 100

4-[2-(4-Quinolin-6-yl-phenyl)-1,3-dioxolan-2-yl]-piperidine-1-sulfonic acid dimethylamide, HCl

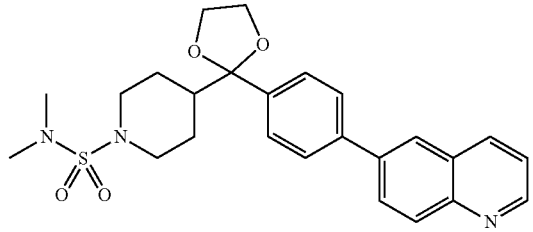 [SMILES: CN(C)S(=O)(=O)N1CCC(C2(c3ccc(-c4ccc5ncccc5c4)cc3)OCCO2)CC1]

6-[4-(2-Piperidin-4-yl-1,3-dioxolan-2-yl)-phenyl]-quinoline (0.075 g, 0.21 mmol) and DIEA (0.181 mL, 1.04 mmol) in THF (4 mL) was added N,N-dimethylsufamyl chloride (0.0394 mL, 0.390 mmol). After 2 h stirring at rt the mixture was concentrated, dissolved in EtOAc, and washed with 1N Na₂CO₃, and brine, then dried (MgSO₄). The HCl salt was synthesized by adding 1N HCl/ether to an ether solution of base, give a white solid. LCMS m/z=468 (M+1); ¹H NMR (DMSO) δ: 9.12 (m, 1H), 8.82 (d, 1H, J=8.4 Hz), 8.50 (m, 1H), 8.32-8.34 (m, 1H), 8.25-8.27 (m, 1H), 7.85-7.89 (d, m, 3H), 7.52 (d, 2H, J=8 Hz), 3.98-4.02 (m, 2H), 3.70-3.73 (m, 2H), 3.55-3.58 (m, 2H), 2.73-2.77 (m, 3H), 2.69 (s, 6H), 1.64-1.67 (m, 2H), 1.25-1.35 (m, 2H).

The following examples were synthesized by the methods for examples 98-100.

Example 101

4-[2-(4-Quinolin-6-yl-phenyl)-1,3-dioxolan-2-yl]-piperidine-1-carboxylic acid ethyl ester

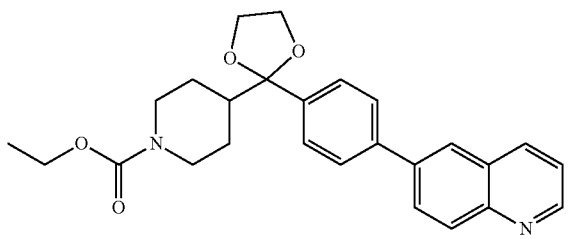 [SMILES: CCOC(=O)N1CCC(C2(c3ccc(-c4ccc5ncccc5c4)cc3)OCCO2)CC1]

The title compound was synthesized using the procedure for Example 98, except for coupling with 6-bromoquinoline in Step 2, and reaction with ethylchloroformate in Step 8. LCMS m/z=433 (M+1); $^1$H NMR (CDCl$_3$) δ: 8.68 (d, 1H, J=8.6 Hz), 7.50-7.55 (m, 3H), 7.43-7.46 (m, 3H), 6.79 (d, 1H, J=8.6 Hz), 6.34-6.37 (m, 1H), 6.18-6.22 (m, 1H), 4.35-4.45 (m, 1H), 4.08 (q, 2H, J=7.6 Hz), 3.97-4.02 (m, 2H), 3.76-3.80 (m, 2H), 2.73 (d, 1H, J=6 Hz), 2.64 (m, 2H), 1.92-2.0 (m, 1H), 1.67 (m, 2H), 1.40 (t, 3H, J=7.6 Hz), 1.32-1.38 (m, 2H).

Example 102

2-Methyl-1-{4-[2-(4-quinolin-6-yl-phenyl)-1,3-dioxolan-2-yl]-piperidin-1-yl}-propan-1-one

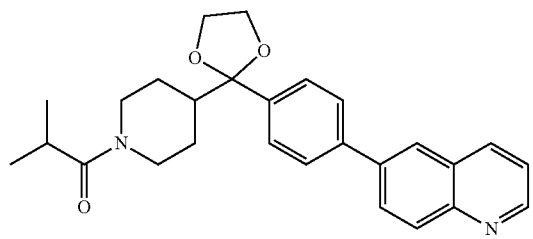

The title compound was synthesized using the procedure for Example 98, except for coupling with 6-bromoquinoline in Step 2, and reaction with isobutyryl chloride in Step 8. LCMS m/z=431 (M+1): $^1$HNMR (DMSO) δ: 9.20 (d, 1H, J=4 Hz), 8.97 (d, 1H, J=8 Hz), 8.58 (s, 1H), 8.33-8.41 (m, 2H), 7.95-7.98 (m, 1H), 7.88 (d, 2H, J=8.6 Hz), 7.53 (d, 2H, J=8.6 Hz), 4.44 (b, 1H), 3.94-3.99 (m, 3H), 3.71 (m, 2H), 2.78-2.94 (m, 2H), 2.34-2.45 (m, 1H), 2.09 (t, 1H, J=6 Hz), 1.63 (bt, 2H, J=12 Hz), 1.19-1.27 (m, 2H), 0.95 (d, 6H, J=7 Hz).

Example 103

4-[2-(4-Quinolin-6-yl-phenyl)-1,3-dioxolan-2-yl]-piperidine-1-carboxylic acid dimethylamide

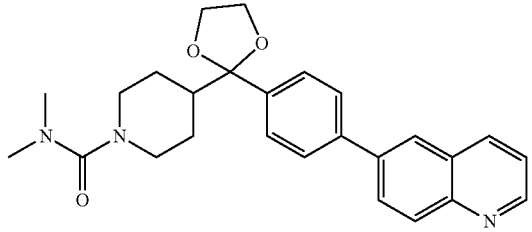 [SMILES: CN(C)C(=O)N1CCC(C2(c3ccc(-c4ccc5ncccc5c4)cc3)OCCO2)CC1]

The title compound was synthesized using the procedure for Example 98, except for coupling with 6-bromo-quinoline in Step 2, and reaction with dimethylcarbamic chloride in Step 8. LCMS m/z=432 (M+1); $^1$H NMR (DMSO) δ: 9.30 (d, 1H, J=6 Hz), 9.19 (d, 1H, J=8 Hz), 8.70 (s, 1H), 8.85 (b, 2H), 8.10-8.13 (m, 1H), 7.90 (d, 2H, J=8 Hz), 7.55 (d, 2H, J=8 Hz), 4.0 (b, 2H), 3.70 (b, 2H), 3.52 (bd, 2H, J=13 Hz), 2.68 (s, 6H), 2.53-2.60 (m, 2H), 1.95-2.0 (m, 1H), 1.56 (d, 2H, J=12 Hz), 1.22-1.30 (m, 2H).

Example 104

1-{4-[2-(4-Quinolin-6-yl-phenyl)-1,3-dioxolan-2-yl]-piperidin-1-yl}-propan-1-one

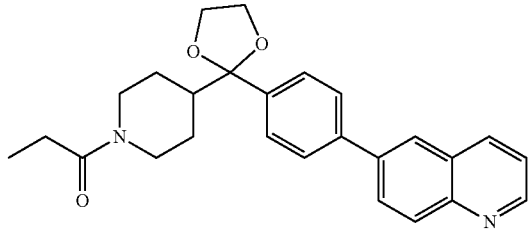 [SMILES: CCC(=O)N1CCC(C2(c3ccc(-c4ccc5ncccc5c4)cc3)OCCO2)CC1]

The title compound was synthesized using the procedure for Example 98, except for coupling with 6-bromo-quinoline in Step 2, and reaction with propionyl chloride in Step 8. LCMS m/z=417 (M+1); $^1$H NMR (CDCl$_3$) δ: 9.31 (d, 1H, J=6 Hz), 8.89 (d, 1H, J=8 Hz), 8.68 (d, 1H, J=9 Hz), 8.33 (dd, 1H, J=2, 8.5 Hz), 8.27 (d, 1H, J=2 Hz), 7.94 (dd, 1H, J=4, 8 Hz), 7.69 (d, 2H, J=8 Hz), 7.59 (d, 2H, J=8 Hz), 4.01-4.05 (m, 2H), 3.78-3.82 (m, 2H), 2.98 (bs, 4H), 2.36 (q, 2H, J=8 Hz), 2.03-2.10 (m, 3H), 1.76 (bd, 3H, J=12 Hz), 1.33-1.41 (m, 2H), 1.14 (t, 3H, J=8 Hz).

Example 105

1-{4-[2-(4-Quinolin-6-yl-phenyl)-1,3-dioxolan-2-yl]-piperidin-1-yl}-butan-1-one

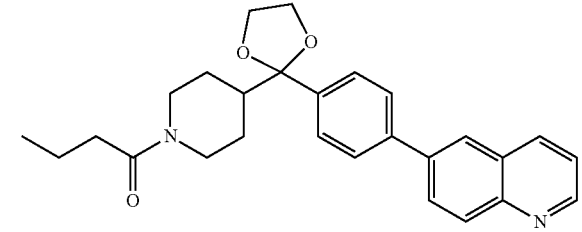 [SMILES: CCCC(=O)N1CCC(C2(c3ccc(-c4ccc5ncccc5c4)cc3)OCCO2)CC1]

The title compound was synthesized using the procedure for Example 98, except for coupling with 6-bromo-quinoline in Step 2, and reaction with butyryl chloride in Step 8.

LCMS m/z=431 (M+1); $^1$H NMR (CDCl$_3$) δ: 9.02 (m, 2H), 8.90 (d, 1H, J=8 Hz), 8.32 (d, 1H, J=8.5 Hz), 8.27 (s, 1H), 7.94 (b, 1H), 7.70 (d, 2H, J=8 Hz), 7.59 (d, 2H, J=8 Hz), 4.01-4.05 (m, 2H), 3.78-3.82 (m, 2H), 2.30 (t, 2H, J=7.8 Hz), 2.03-2.09 (m, 1H), 1.70-1.80 (m, 3H), 1.60-1.66 (m, 4H), 1.29-1.39 (m, 3H), 0.95 (t, 3H, J=7.4 Hz).

Example 106

1-{4-[2-(4-Quinolin-6-yl-phenyl)-1,3-dioxolan-2-yl]-piperidin-1-yl}-ethanone

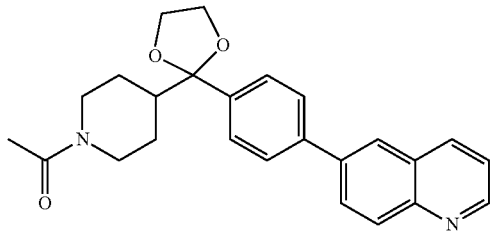 [SMILES: CC(=O)N1CCC(C2(c3ccc(-c4ccc5ncccc5c4)cc3)OCCO2)CC1]

The title compound was synthesized using the procedure for Example 98, except for coupling with 6-bromo-quinoline in Step 2, and reaction with acetyl chloride in Step 8. LCMS m/z=403 (M+1); $^1$H NMR (CDCl$_3$) δ: 9.01 (m, 2H), 8.88 (d, 1H, J=8.5 Hz), 8.33 (d, 1H, J=8 Hz), 8.26 (b, 1H), 7.93 (m, 1H), 7.71 (d, 2H, J=8 Hz), 7.60 (d, 2H, J=8 Hz), 4.03 (m, 2H), 3.80 (m, 2H), 2.9 (b, 1H), 2.6 (b, 1H), 2.09 (s, 3H), 2.03-2.09 (m, 1H), 1.74 (m, 3H), 1.30-1.40 (m, 3H), Example 107

4-[2-(4-Quinolin-6-yl-phenyl)-1,3-dioxolan-2-yl]-piperidine-1-carboxylic acid cyclopentylamide

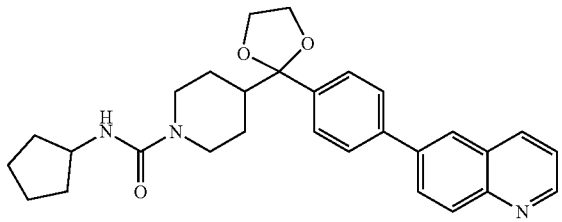 [SMILES: O=C(NC1CCCC1)N1CCC(C2(c3ccc(-c4ccc5ncccc5c4)cc3)OCCO2)CC1]

6-[4-(2-Piperidin-4-yl-1,3-dioxolan-2-yl)-phenyl]-quinoline (0.0750 g, 0.208 mmol) and DIEA (0.0725 mL, 0.416 mmol) in DCE (4 mL) was added isocyanatocyclopentane (0.0225 mL, 0.218 mmol). After 4 h stirring at rt the mixture was concentrated, dissolved in EtOAc, and washed with 1N Na$_2$CO$_3$, and brine, then dried over MgSO$_4$. The product was recrystallized from ether and hexanes to give a white solid. LCMS m/z=472 (M+1); $^1$H NMR (CDCl$_3$) δ: 8.92 (m, 1H), 8.18-8.22 (m, 2H), 7.97-8.01 (m, 3H), 7.69 (d, 2H, J=8.4 Hz), 7.52 (d, 2H, j=8.4 Hz), 7.42-7.45 (m, 1H), 4.27 (d, 1H, J=7 Hz), 4.00-4.09 (m, 3H), 3.94 (bd, 2H, J=12 Hz), 3.79-3.82 (m, 2H), 2.66 (tt, 2H, J=2, 13 Hz), 1.95-2.01 (m, 3H), 1.71 (bd, 2H, J=13 Hz), 1.54-1.59 (m, 3H), 1.28-1.43 (m, 4H).

Example 108

6-(4-{2-[1-(Tetrahydropyran-4-yl)-piperidin-4-yl]-1,3-dioxolan-2-yl}-phenyl)-quinoline

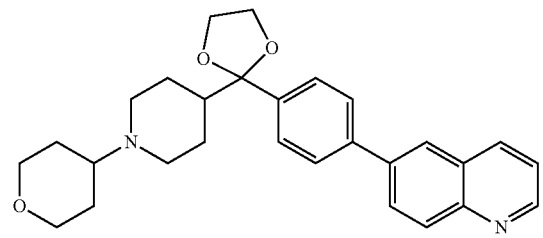 [SMILES: c1cnc2ccc(-c3ccc(C4(C5CCN(C6CCOCC6)CC5)OCCO4)cc3)cc2c1]

6-[4-(2-Piperidin-4-yl-1,3-dioxolan-2-yl)-phenyl]-quinoline (0.050 g, 0.14 mmol) and tetrahydro-4H-pyran-4-one (0.0386 mL, 0.416 mmol) in DMF (1 mL, 10 mmol) MeOH (2 mL) and acetic acid (0.25 mL, 4.4 mmol) was added sodium cyanoborohydride (0.0697 g, 1.11 mmol). After heating at 75° C. for 6 h, the solution was concentrated, dissolved in EtOAc, and washed with 1N Na$_2$CO$_3$, and brine, then dried over MgSO$_4$. The product was purified by ISCO (silica get, 12 g column, 95/5 DCM/MeOH) to give a white solid. LCMS m/z=445 (M+1); 361 (M-THP); $^1$H NMR (DMSO) δ: 9.57 (s, 1H), 9.07 (s, 1H, 8.72 (m, 1H), 8.45 (s, 1H), 8.25 (b, 2H), 7.90 (d, 2H, J=8 Hz), 7.79 (b, 1H), 7.53 (d, 2H, J=8 Hz), 4.02 (m, 2H), 3.94 (m, 4H), 3.76 (m, 2H), 3.44-3.47 (m, 2H), 3.25-3.33 (m, 3H), 2.98 (m, 2H), 1.91 (m, 2H), 1.80 (m, 2H), 1.62-1.68 (m, 3H).

Example 109

2-Methyl-1-[4-(4-quinolin-6-yl-benzoyl)-piperidin-1-yl]-propan-1-one

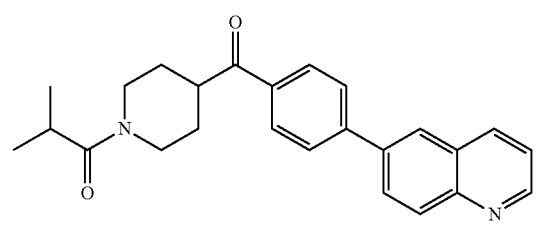 [SMILES: CC(C)C(=O)N1CCC(C(=O)c2ccc(-c3ccc4ncccc4c3)cc2)CC1]

2-Methyl-1-{4-[2-(4-quinolin-6-yl-phenyl)-1,3-dioxolan-2-yl]-piperidin-1-yl}-propan-1-one (250 mg, 0.58 mmol) was stirred in 6 M HCl (10 mL) for 4 h, then made basic with solid Na$_2$CO$_3$ on an ice-bath and extracted with EtOAc and dried (MgSO4) to give a white solid (185 mg, 82%). LCMS m/z=387 (M+1): $^1$H NMR (CDCl$_3$): 8.95 (m, 1H), 8.21-8.26 (m, 1H), 8.06-8.09 (m, 3H), 7.99 (dd, 1H, J=3, 8.6 Hz), 7.83 (d, 2H, J=7.6 Hz), 7.46 (dd, 1H, J=4, 8 Hz), 4.63 (d, 1H, J=12 Hz), 4.05 (d, 1H, J=12 Hz), 3.53-3.60 m, 1H), 3.25 (t, 1H, J=12 Hz), 2.80-2.90 (m, 2H), 1.85-2.0 (m, 3H), 1.14 (d, 6H, J=7.6 Hz).

Example 110

1-{4-[Hydroxy-(4-quinolin-6-yl-phenyl)-methyl]-piperidin-1-yl}-2-methyl-propan-1-one

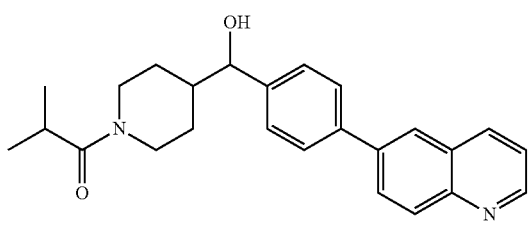 [SMILES: CC(C)C(=O)N1CCC(C(O)c2ccc(-c3ccc4ncccc4c3)cc2)CC1]

Sodium borohydride (0.0979 g, 2.59 mmol) was added to 2-methyl-1-[4-(4-quinolin-6-yl-benzoyl)-piperidin-1-yl]-propan-1-one (0.200 g, 0.517 mmol) in ethanol (5 mL) and stirred at rt for 2 h. The solution was concentrated, dissolved in EtOAc and washed with water and brine. The resulting solid was recrystallized from ether-hexanes to give a white solid. LCMS m/z=389 (M+1); $^1$H NMR (CDCl$_3$) δ: 8.92 (s, 1H), 8.17-8.22 (m, 2H), 7.96-8.00 (m, 2H), 7.71 (s, 2H, J=8 Hz), 7.43-7.45 (m, 3H), 4.66 (m, 1H), 4.84 (m, 1H), 3.94 (m, 1H), 2.92-3.00 (m, 1H), 2.74-2.83 (m, 1H), 2.42-2.54 (m, 1H), 2.0-2.13 (m, 2H), 1.90 (m, 1H), 1.2-1.3 (m, 3H), 1.11 (d, 6H, J=7 Hz).

Example 111

2-Methyl-1-{4-[2-(4-quinolin-7-yl-phenyl)-1,3-dioxolan-2-yl]-piperidin-1-yl}-propan-1-one

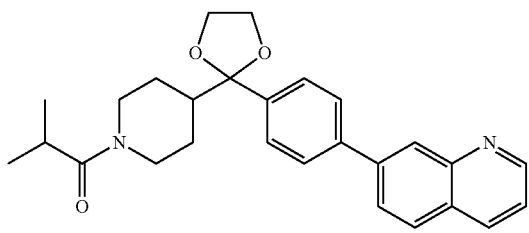 [SMILES: CC(C)C(=O)N1CCC(C2(c3ccc(-c4ccc5cccnc5c4)cc3)OCCO2)CC1]

Step 1. 7-[4-(2-Piperidin-4-yl-1,3-dioxolan-2-yl)-phenyl]-quinoline

Palladium acetate (0.0137 g, 0.0612 mmol) and triphenylphosphine (0.0642 g, 0.245 mmol) in dioxane (10 mL) were stirred 15 min under an atmosphere of nitrogen. 1-{4-[2-(4-Bromophenyl)-1,3-dioxolan-2-yl]-piperidin-1-yl}-2,2,2-trifluoroethanone (0.50 g, 1.2 mmol), quinoline-7-boronic acid (0.233 g, 1.35 mmol), DMF (5 mL) and 1 M of sodium carbonate i(4.90 mL) were added and heated at 80° C. for 17 h. The mixture was concentrated, was dissolved in EtOAc, washed with 1N Na$_2$CO$_3$, water and brine, then dried (MgSO4). The product was purified by ISCO (silica get, 40 g column, 60-90% EtOAc/hexanes, then 80/20 DCM/MeOH/1% iPrNH$_2$) to give the target compound as an oil. LCMS m/z=361 (M+1); $^1$H NMR (CDCl$_3$) δ: 8.94 (m, 1H), 8.33 (s, 1H), 8.18 (d, 1H, J=8 Hz), 7.89 (d, 1H, J=8.8 Hz), 8.81-8.84 (dd, 1H, J=2, 8.6 Hz), 7.73 (d, 2H, J=8 Hz), 7.53 (d, 2H, J=8.5 Hz), 7.39-7.43 (dd, 1H, J=4, 8 Hz), 4.00-4.03 (m, 2H), 3.79-3.83 (m, 2H), 3.07-3.10 (bd, 2H, J=12 Hz), 2.53 (dt, 2H, J=2, 12 Hz), 1.93-2.01 (tt, 1H, J=3, 12 Hz), 1.72 (bd, 2H, J=12 Hz), 1.24-1.37 (m, 3H), Step 2. 2-Methyl-1-{4-[2-(4-quinolin-7-yl-phenyl)-1,3-dioxolan-2-yl]-piperidin-1-yl}-propan-1-one 6-[4-(2-Piperidin-4-yl-1,3-dioxolan-2-yl)-phenyl]quinoline (0.0400 g, 0.111 mmol) and DIPEA (0.0966 mL, 0.555 mmol) in DCM (2 mL) was added isobutyryl chloride (0.0293 mL, 0.277 mmol). After 2h stirring at rt the mixture was concentrated, dissolved in EtOAc, and washed with 1N Na$_2$CO$_3$, and brine, then dried (MgSO4). The product was chromatographed on ISCO (4 g silica gel column, 0-5% MeOH/DCM to give an oil. The HCl salt was synthesized by adding 0.5 mL of 2N HCl-ether to a DCM solution of the base. The resulting solid was recrystallized from CHCl$_3$-ether to give a white solid. LCMS m/z=431 (M+1); $^1$H NMR (CDCl$_3$) δ: 9.00 (b, 2H), 8.87 (b, 1H), 8.16-8.21 (m, 2H), 7.89 (b, 1H), 7.78 (d, 2H, J=8 Hz), 7.58 (d, 2H, J=8 Hz), 4.71 (b, 1H), 4.02 (m, 3H), 3.80 (m, 2H), 2.93 (b, 1H), 2.78 (q, 1H, J=7 Hz), 2.43 (b, 1H), 2.06 (m, 1H), 1.72-1.77 (m, 3H), 1.34-1.40 (m, 3H), 1.10 (d, 6H).

The following examples were synthesized using the previous method starting with an appropriate acid chloride and quinoline or isoquinoline boronic acid.

Example 112

Cyclopropyl-{4-[2-(4-quinolin-7-yl-phenyl)-1,3-dioxolan-2-yl]-piperidin-1-yl}-methanone

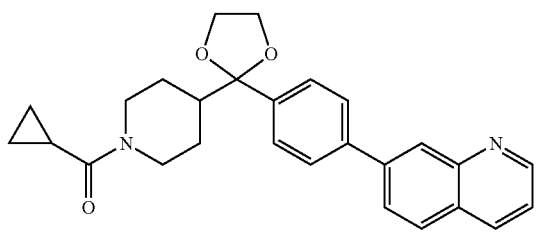 [SMILES: O=C(C1CC1)N1CCC(C2(c3ccc(-c4ccc5cccnc5c4)cc3)OCCO2)CC1]

The title compound was synthesized using the procedure for Example 111, reacting with cyclopropanecarbonyl chloride in Step 2. LCMS m/z=429 (M+1); $^1$H NMR (CDCl$_3$ HCl salt) δ: 9.06 (b, 2H), 8.86 (d, 1H, J=8 Hz), 8.18 (d, 2H, J=3 Hz), 7.88 (b, 1H), 7.76 (d, 2H, J=8 Hz), 7.59 (d, 2H, J=8 Hz), 4.65 (b, 1H), 4.27 (b, 1H), 4.03 (m, 2H), 3.80 (m, 2H), 2.99 (b, 1H), 2.50 (b, 1H), 2.09 (tt, 1H, J=3, 12 Hz), 1.64-1.77 (m, 3H), 1.39 (m, 2H), 0.94 (m, 2H), 0.72 (dd, 2H, J=3, 7.6 Hz).

Example 113

1-{4-[2-(4-Quinolin-7-yl-phenyl)-1,3-dioxolan-2-yl]-piperidin-1-yl}-butan-1-one

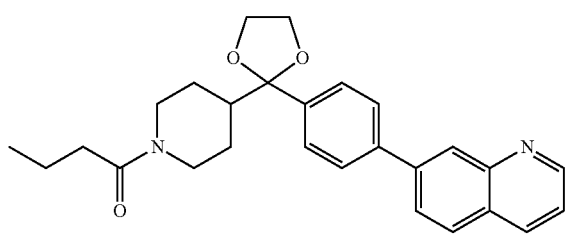 [SMILES: CCCC(=O)N1CCC(C2(c3ccc(-c4ccc5cccnc5c4)cc3)OCCO2)CC1]

The title compound was synthesized using the procedure for Example 111, reacting with butyryl chloride in Step 2. LCMS m/z=431 (M+1); $^1$H NMR (CDCl$_3$; HCl salt) δ: 9.07 (s, 2H), 8.86 (s, 1H), 8.18 (b, 2H), 7.89 (b, 1H), 7.78 (d, 2H, J=7 Hz), 7.57 (d, 2H, J=7 Hz), 4.02 (m, 2H), 3.80 (m, 2H), 2.73 (b, 1H), 2.36 (m, 2H), 2.05-2.09 (m, 1H), 1.7-1.8 (m, 4H), 1.35-1.40 (m, 3H), 1.25 (m, 2H), 0.96 (t, 3H, J=7 Hz).

Example 114

1-{4-[2-(4-Quinolin-7-yl-phenyl)-1,3-dioxolan-2-yl]-piperidin-1-yl}-propan-1-one

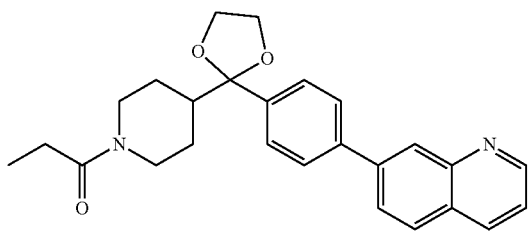 [SMILES: CCC(=O)N1CCC(C2(c3ccc(-c4ccc5cccnc5c4)cc3)OCCO2)CC1]

The title compound was synthesized using the procedure for Example 111, reacting with propanoyl chloride in Step 2. LCMS m/z=417 (M+1); $^1$H NMR (CDCl$_3$ HCl salt) δ: 9.06 (b, 2H), 8.86 (m, 1H), 8.16-8.21 (m, 2H), 7.89 (b, 1H), 7.76 (d, 2H, J=8 Hz), 7.57 (d, 2H, J=8 Hz), 4.46 (b, 1H), 4.02 (m, 2H), 3.79 (m, 2H), 2.71 (b, 1H), 2.35 (q, 2H, J=7.6 Hz), 2.03-2.09 (m, 1H), 1.6 (b, 4H), 1.30-1.40 (m, 2H), 1.14 (t, 3H, J=7.6 Hz).

Example 115

1-{4-[2-(4-Isoquinolin-7-yl-phenyl)-1,3-dioxolan-2-yl]-piperidin-1-yl}-ethanone

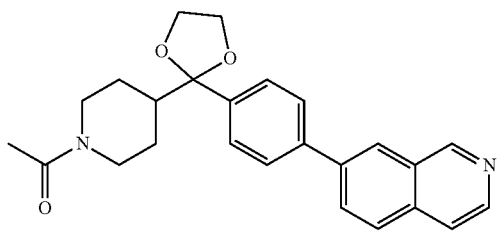 [SMILES: CC(=O)N1CCC(C2(c3ccc(-c4ccc5ccncc5c4)cc3)OCCO2)CC1]

The title compound was synthesized using the procedure for Example 111, reacting with isoquinoline-7-boronic acid in step 1 and with acetyl chloride in Step 2. LCMS m/z=403 (M+1); $^1$H NMR (CDCl$_3$ HCl salt) δ: 9.60 (s, 1H), 8.52 (d, 1H, J=7 Hz), 8.47 (s, 1H), 8.39 (m, 1H), 8.21-8.25 (m, 3H), 7.70 (d, 2H, J=8 Hz), 7.62 (d, 2H, J=8 Hz), 4.04 (m, 2H), 3.80 (m, 2H), 2.9 (b, 1H), 2.6 (b, 1H), 2.09 (s, 3H), 2.04-2.1 (m, 2H), 1.75 (m, 2H), 1.32-1.40 (m, 3H).

Example 116

1-{4-[2-(4-Isoquinolin-7-yl-phenyl)-1,3-dioxolan-2-yl]-piperidin-1-yl}-propan-1-one

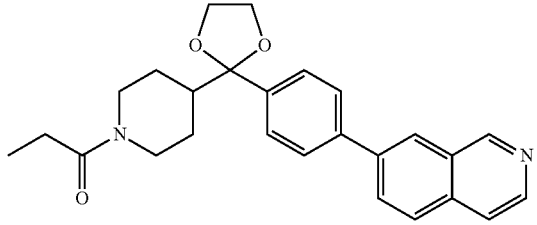 [SMILES: CCC(=O)N1CCC(C2(c3ccc(-c4ccc5ccncc5c4)cc3)OCCO2)CC1]

The title compound was synthesized using the procedure for Example 111, reacting with isoquinoline-7-boronic acid in step 1 and with propionyl chloride in Step 2. LCMS m/z=431 (M+1); 1H NMR (CDCl$_3$ HCl salt) δ: 9.60 (s, 1H), 8.52 (d, 1H, J=6 Hz), 8.47 (s, 1H), 8.39 (d, 1H, J=8.5 Hz), 8.21-8.25 (m, 2H), 7.71 (d, 2H, J=8 Hz), 7.61 (d, 2H, J=8 Hz), 4.03 (m, 2H), 3.80 (m, 2H), 2.70 (b, 1H), 2.33 (q, 2H, J=7 Hz), 2.07 (tt, 1H, J=2, 12 Hz), 1.74 (d, 2H, J=12 Hz), 1.38 (dq, 1H, J=4, 12 Hz), 1.29 (t, 3H, J=8 Hz).

Example 117

1-{4-[2-(4-Isoquinolin-7-yl-phenyl)-1,3-dioxolan-2-yl]-piperidin-1-yl}-2-methyl-propan-1-one

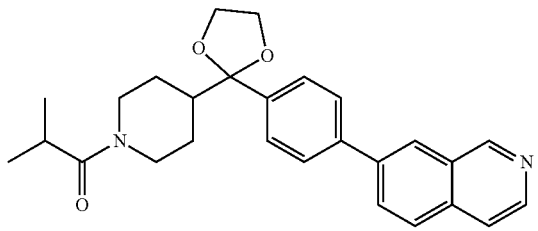 [SMILES: CC(C)C(=O)N1CCC(C2(c3ccc(-c4ccc5ccncc5c4)cc3)OCCO2)CC1]

The title compound was synthesized using the procedure for Example 111, reacting with isoquinoline-7-boronic acid in step 1 and with isobutyryl chloride in Step 2. LCMS m/z=417 (M+1); $^1$H NMR (CDCl$_3$ HCl salt) δ: 9.59 (s, 1H), 8.53 (d, 1H, J=7 Hz), 8.46 (s, 1H), 8.39 (d, 1H, J=8 Hz), 8.21-8.24 (m, 2H), 7.71 (d, 2H, J=8 Hz), 7.61 (d, 2H, J=8 Hz), 4.70 (d, 1H, J=12 Hz), 4.03 (m, 2H), 3.98 (d, 1H, J=14 Hz), 3.80 (m, 2H), 2.93 (t, 1H, J=12 Hz), 2.77 (q, 1H, J=7 Hz), 2.41 (t, 1H, J=12 Hz), 2.07 (tt, 1H, J=2, 12 Hz), 1.70-1.79 (m, 3H), 1.38 (m, 2H), 1.10 (d, 6H, J=6 Hz).

Example 118

1-{4-[2-(4-Isoquinolin-6-yl-phenyl)-1,3-dioxolan-2-yl]-piperidin-1-yl}-propan-1-one

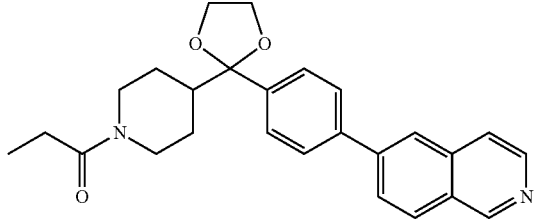 [SMILES: CCC(=O)N1CCC(C2(c3ccc(-c4ccc5cnccc5c4)cc3)OCCO2)CC1]

The title compound was synthesized using the procedure for Example 111, reacting with isoquinoline-6-boronic acid in step 1 and with propionyl chloride in Step 2. LCMS m/z=417 (M+1); $^1$H NMR (CDCl$_3$) δ: 9.53 (s, 1H), 8.52 (d, 1H, J=4 Hz), 8.42 (d, 1H, J=7 Hz), 8.28 (s, 1H), 8.22 (m, 2H), 7.73 (d, 2H, J=8 Hz), 7.61 (d, 2H, J=8 Hz), 4.28 (b, 1H), 4.04 (m, 2H), 3.80 (m, 2H), 2.71 (b, 1H), 2.34 (q, 2H, J=7.6 Hz), 2.07 (m, 1H), 1.74 (m, 3H, J=12 Hz), 1.36 (m, 3H, J=3, 12 Hz), 1.13 (t, 3H, J=7.6 Hz).

Example 119

1-{4-[2-(4-Isoquinolin-6-yl-phenyl)-1,3-dioxolan-2-yl]-piperidin-1-yl}-2-methyl-propan-1-one

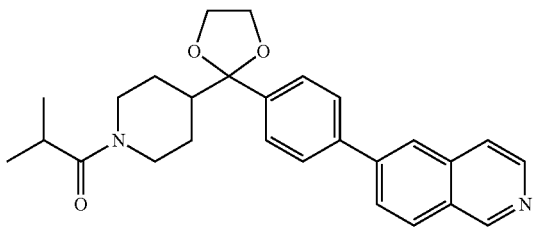 [SMILES: CC(C)C(=O)N1CCC(C2(c3ccc(-c4ccc5cnccc5c4)cc3)OCCO2)CC1]

The title compound was synthesized using the procedure for Example 111, reacting with isoquinoline-6-boronic acid in step 1 and with isobutyryl chloride in Step 2. LCMS m/z=431 (M+1); $^1$H NMR (CDCl$_3$) δ: 9.51 (s, 1H), 8.52 (m, 1H), 8.39 (m, 1H), 8.27 (s, 1H), 8.22 (m, 1H). 7.74 (d, 2H, J=8 Hz), 7.61 (d, 2H, J=8 Hz), 4.70 (m, 1H), 4.04 (m, 2H), 3.95 (m, 1H), 3.80 (m, 2H), 2.94 (m, 1H), 2.76 (q, 1H, J=7 Hz), 2.44 (m, 1H), 2.04-2.10 (m, 1H), 1.69-1.77 (m, 3H), 1.35 (m, 3H), 1.10 (d, 6H, J=7 Hz).

Example 120

1-{4-[2-(4-Isoquinolin-6-yl-phenyl)-1,3-dioxolan-2-yl]-piperidin-1-yl}-ethanone

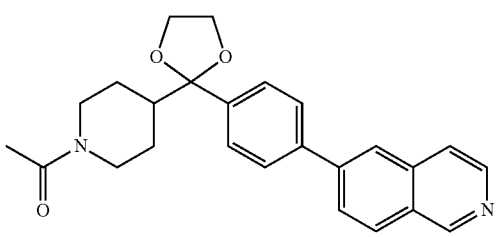 [SMILES: CC(=O)N1CCC(C2(c3ccc(-c4ccc5cnccc5c4)cc3)OCCO2)CC1]

The title compound was synthesized using the procedure for Example 111, reacting with isoquinoline-6-boronic acid in step 1 and with acetyl chloride in Step 2. LCMS m/z=403 (M+1); $^1$H NMR (CDCl$_3$) δ: 9.52 (s, 1H), 8.52 (d, 1H, J=5 Hz), 8.40 (d, 1H, J=5 Hz), 8.28 (s, 1H), 8.22 (d, 2H, J=6 Hz), 7.74 (d, 2H, J=8 Hz), 7.61 (d, 2H, J=8 Hz), 4.5 (b, 1H), 4.04 (m, 3H), 3.80 (m, 2H), 2.75 (b, 1H), 2.11 (s, 3H), 2.05-2.10 (m, 1H), 1.75 (d, 3H, J=12 Hz), 1.32-1.40 (m, 3H).

The following examples were synthesized using the previous method starting with 7-[4-(2-piperidin-4-yl-1,3-dioxinan-2-yl)-phenyl]-quinoline (synthesized from 1-{4-[2-(4-bromo-phenyl)-1,3-dioxinan-2-yl]-piperidin-1-yl}-2,2,2-trifluoroethanone and quinoline-7-boronic acid) and the appropriate acid chloride.

Example 121

2-Methyl-1-{4-[2-(4-quinolin-7-yl-phenyl)-1,3-dioxinan-2-yl]-piperidin-1-yl}-propan-1-one

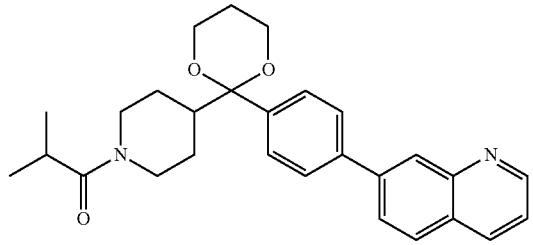 [SMILES: CC(C)C(=O)N1CCC(C2(c3ccc(-c4ccc5cccnc5c4)cc3)OCCCO2)CC1]

Analysis: LCMS m/z=445 (M+1); $^1$H NMR (CDCl$_3$ HCl salt) δ: 9.08 (s, 1H), 9.03 (d, 1H, J=6 Hz), 8.84 (d, 1H, J=8 Hz), 8.20 (s, 2H), 7.87 (dd, 1H, J=5, 8 Hz), 7.82 (d, 2H, J=8.5 Hz), 7.51 (d, 2H, J=8.5 Hz), 4.66 (d, 1H, J=12 Hz), 3.95 (s, 1H), 3.90 (dd, 1H, J=4, 12 Hz), 3.80 (t, 2H, J=12 Hz), 2.89 (t, 1H, J=13 Hz), 2.76 (q, 1H, J=7 Hz), 2.37 (t, 1H, J=12 Hz), 2.07-2.17 (m, 1H), 1.79-1.85 (m, 2H), 1.72-1.75 (m, 1H), 1.23-1.32 (m, 4H), 1.08 (b, 6H).

Example 122

Cyclopropyl-{4-[2-(4-quinolin-7-yl-phenyl)-1,3-dioxinan-2-yl]-piperidin-1-yl}-methanone

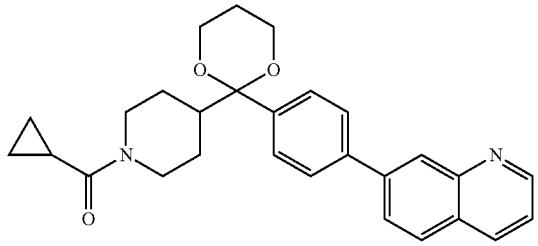 [SMILES: O=C(C1CC1)N1CCC(C2(c3ccc(-c4ccc5cccnc5c4)cc3)OCCCO2)CC1]

Analysis: LCMS m/z=443 (M+1); $^1$H NMR (CDCl$_3$ HCl salt) δ: 9.08 (s, 1H), 9.04 (s, 1H), 8.85 (d, 1H, J=7.5 Hz), 8.20 (s, 2H), 7.86 (b, 1H), 7.82 (d, 2H, J=8 Hz), 7.52 (d, 2H, J=8 Hz), 4.61 (b, 1H), 4.22 (b, 1H), 3.89-3.93 (m, 2H), 3.80 (t, 2H, J=12 Hz), 2.96 (b, 1H), 2.44 (b, 1H), 2.04-2.17 (m, 1H), 1.83-1.89 (m, 2H), 1.67-1.73 (m, 2H), 1.20-1.30 (m, 4H), 0.85 (b, 2H), 0.68 (dd, 2H, J=2, 7 Hz).

Example 123

1-{4-[2-(4-Quinolin-7-yl-phenyl)-1,3-dioxinan-2-yl]-piperidin-1-yl}-propan-1-one

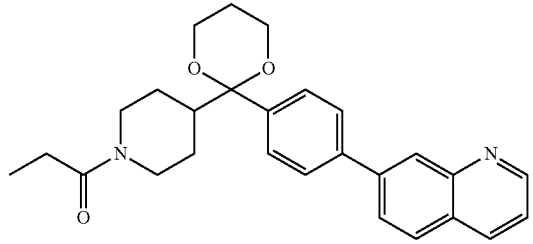 [SMILES: CCC(=O)N1CCC(C2(c3ccc(-c4ccc5cccnc5c4)cc3)OCCCO2)CC1]

Analysis: LCMS m/z=431 (M+1): $^1$H NMR (CDCl$_3$ HCL salt) δ: 9.09 (s, 1H), 9.05 (s, 1H), 8.86 (d, 1H, J=7.5 Hz), 8.21 (s, 2H), 7.89 (b, 1H), 7.82 (d, 2H, J=8.5 Hz), 7.50 (d, 2H, J=8 Hz), 4.60 (b, 1H), 3.88-3.92 (m, 2H), 3.79 (t, 2H, 11 Hz), 2.6 (b, 1H), 2.30 (q, 2H, J=7.5 Hz), 2.07-2.16 (m, 1H), 1.4 (m, 1H), 1.77-1.84 (m, 3H), 1.20-1.29 (m, 4H), 1.10 (t, 3H, J=7.5 Hz).

Example 124

1-[4-(4-Quinolin-7-yl-benzoyl)-piperidin-1-yl]-propan-1-one

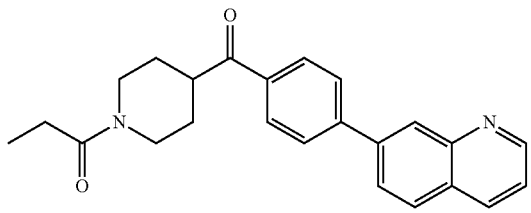 [SMILES: CCC(=O)N1CCC(C(=O)c2ccc(-c3ccc4cccnc4c3)cc2)CC1]

1-{4-[2-(4-Quinolin-7-yl-phenyl)-1,3-dioxinan-2-yl]-piperidin-1-yl}-propan-1-one (0.45 g, 1.0 mmol) was stirred in 6 M HCL (5 mL) for 4 h. The solution was made basic with solid Na$_2$CO$_3$, extracted with EtOAc, and washed with water and brine, then dried over MgSO$_4$. The product was recrystallized from ether-hexanes to give a white solid (300 mg, 77%). LCMS m/z=373 (M+1); $^1$H NMR (CDCl$_3$) δ: 8.97 (s, 1H), 8.38 (s, 1H), 8.20 (d, 1H, J=7.3 Hz), 8.08 (d, 2H, J=8 Hz), 7.92 (d, 1H, J=8 Hz), 7.87 (d, 2H, J=8 Hz), 7.84 (dd, 1H, J=2, 8 Hz), 7.46 (dd, 1H, J=4, 8 Hz), 4.61 (d, 1H, J=12 Hz), 3.96 (d, 1H, J=12 Hz), 3.52-3.59 (m, 1H), 3.23 (dt, 1H, J=2, 12 Hz), 2.87 (dt, 1H, J=2, 12 Hz), 2.38 (q, 2H, J=7 Hz), 1.93-2.00 (m, 2H), 1.82-1.89 (m, 1H), 1.74 (m, 1H), 1.14 (t, 3H, J=7 Hz).

Example 125

1-{4-[Hydroxy-(4-quinolin-7-yl-phenyl)-methyl]-piperidin-1-yl}-propan-1-one

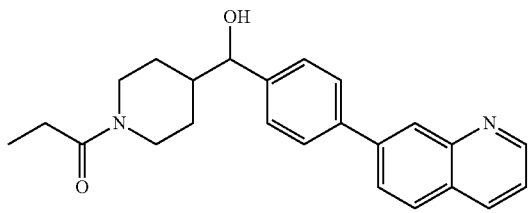 [SMILES: CCC(=O)N1CCC(C(O)c2ccc(-c3ccc4cccnc4c3)cc2)CC1]

NaBH$_4$ (0.010 g, 0.27 mmol) was added to 1-[4-(4-quinolin-7-yl-benzoyl)-piperidin-1-yl]-propan-1-one (0.030 g, 0.080 mmol) in ethanol (3 mL, 50 mmol). After 4 h stirring at rt, the mixture was concentrated, acidified with HOAc, made basic with 1N Na$_2$CO$_3$, washed with water and brine, then dried over MgSO$_4$. The product was purified by ISCO (4 g silica gel column; 0-5% MeOH/DCM) to give an oil. The HCl salt was prepared by addition of 0.5 mL of 2N HCl-ether to a DCM solution of base and the salt recrystallized from DCM-ether to give a light yellow solid (20 mg, 66%). LCMS m/z=375 (M+1); $^1$H NMR (DMSO) δ: 9.27 (d, 1H, J=4.5 Hz), 9.07 (d, 1H, J=8 Hz), 8.56 (s, 1H), 8.39 (m, 1H), 8.27 (d, 1H, J=8.5 Hz), 7.98 (m, 1H), 7.85 (d, 2H, J=8 Hz), 7.52 (d, 2H, J=8 Hz), 4.37-4.46 (m, 3H), 3.85 (t, 1H, J=14 Hz), 2.87 (q, 1H, J=8 Hz), 2.36-2.45 (m, 1H), 2.25-2.29 (m, 2H), 1.79 (m, 2H), 1.35 (m, 1H), 1.15-1.25 (m, 1H), 0.96 (t, 3H, J=7 Hz).

Example 126

1-{4-[1-Hydroxy-1-(4-quinolin-7-yl-phenyl)-ethyl]-piperidin-1-yl}-propan-1-one

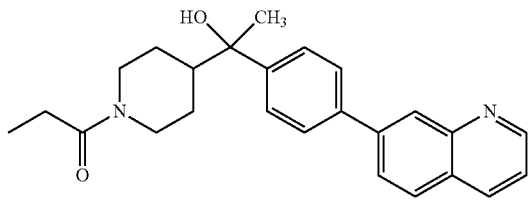 [SMILES: CCC(=O)N1CCC(C(C)(O)c2ccc(-c3ccc4cccnc4c3)cc2)CC1]

Methylmagnesium iodide (0.04247 mL, 0.3222 mmol) was added dropwise to 1-[4-(4-quinolin-7-yl-benzoyl)-piperidin-1-yl]-propan-1-one (0.0800 g, 0.215 mmol) in THF (2 mL). After 4 h, the mixture was concentrated and partitioned between sat NH$_4$Cl and EtOAc. The EtOAc was washed with water and brine then dried MgSO$_4$. The product was recrystallized from ether-hexanes to give a white solid (60 mg, 72%). LCMS m/z=389 (M+1), 371 (M−H2O); $^1$H NMR (CDCl$_3$) δ: 8.89 (dd, 1H, J=2.4 Hz), 8.33 (s, 1H), 8.17 (d, 1H), J=8 Hz), 8.89 (d, 1H, J=8.5 Hz), 7.83 (dd, 1H, J=2, 8 Hz), 7.74 (d, 2H, J=7 Hz), 7.54 (d, 2H, J=2, 8 Hz), 7.41 (dd, 1H, J=4, 8 Hz), 4.71 (m, 1H), 3.87 (m, 1H), 2.90 (q, 1H, J=14 Hz), 2.40-2.48 (m, 1H), 2.30 (q, 2H, J=7.6 Hz), 1.86 (m, 1H), 1.76 (m, 2H), 1.62 (s, 3H), 1.23-1.32 (m, 3H), 1.11 (t, 3H, J=7.5 Hz).

Example 127

1-[4-(2-Fluoro-4-isoquinolin-6-yl-benzoyl)-piperidin-1-yl]-propan-1-one

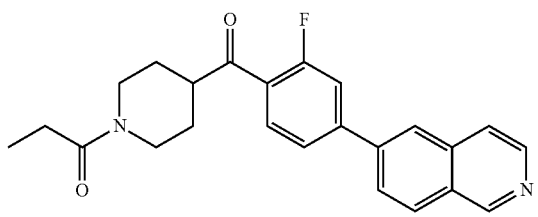 [SMILES: CCC(=O)N1CCC(C(=O)c2ccc(-c3ccc4cnccc4c3)cc2F)CC1]

Step 1. (2-Fluoro-4-isoquinolin-6-yl-phenyl)-piperidin-4-yl-methanone

Palladium Acetate (0.0137 g, 0.0612 mmol) and triphenylphosphine (0.0642 g, 0.245 mmol) were stirred 15 min under an atmosphere of nitrogen. Then 1-[4-(4-bromo-2-fluorobenzoyl)-piperidin-1-yl]-2,2,2-trifluoro-ethanone (0.47 g, 1.2 mmol), isoquinoline-6-boronic acid (0.233 g, 1.35 mmol), DMF (5 mL) and 1 M of sodium carbonate (4.90 mL) was added and heated at 80° C. for 17 h. The mixture was concentrated, dissolved in EtOAc and washed with 1N Na$_2$CO$_3$, water and brine then dried over MgSO$_4$. The product was purified by ISCO (12 g silica gel column, 0-25% MeOH/DCM/1% iPrNH$_2$) to give the product as an oil (275 mg, 67%). LCMS m/z=335 (M+1);

Step 2. 1-[4-(2-Fluoro-4-isoquinolin-6-yl-benzoyl)-piperidin-1-yl]-propan-1-one (2-Fluoro-4-isoquinolin-6-yl-phenyl)-piperidin-4-yl-methanone (0.25 g, 0.75 mmol) and DIPEA (0.193 g, 1.50 mmol) in THF (4 mL, 60 mmol) was added propanoyl chloride (0.130 mL, 1.50 mmol). After 4 h stirring at rt, the mixture was concentrated, dissolved in EtOAc and washed with 1N Na$_2$CO$_3$, water and brine. The product was purified on an ISCO (12 g silica gel column, 0-5% MeOH/DCM) to give an oil (250 mg, 95%). LCMS m/z=391 (M+1); $^1$H NMR (CDCl$_3$): 9.32 (s, 1H), 8.60 (d, 1H, J=6 Hz), 8.09 (d, 1H, j=8.2 Hz), 8.04 (s, 1H), 7.94 (t, 1H, J=8.2 Hz), 7.85 (dd, 1H, J=2, 8 Hz), 7.73 (d, 1H, J=6 Hz), 7.62 (dd, 1H, J=2, 8 Hz), 7.51 (d, 1H, J=2, 8 Hz), 4.57 (d, 1H, J=12 Hz), 3.92 (d, 1H, J=12 Hz), 3.40-3.48 (m, 1H), 3.19 (m, 1H), 3.82-3.86 (m, 1H), 2.38 (q, 2H, J=7 Hz), 2.02 (d, 1H, J=12 Hz), 1.71-1.80 (m, 1H), 1.62 (m, 2H), 1.76 (t, 3H, J=7 Hz).

Example 128

1-{4-[(2-Fluoro-4-isoquinolin-6-yl-phenyl)-hydroxy-methyl]-piperidin-1-yl}-propan-1-one

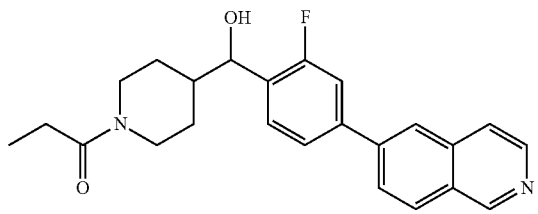 [SMILES: CCC(=O)N1CCC(C(O)c2ccc(-c3ccc4cnccc4c3)cc2F)CC1]

NaBH$_4$ (0.0097 g, 0.26 mmol) was added to 1-[4-(2-fluoro-4-isoquinolin-6-yl-benzoyl)-piperidin-1-yl]-propan-1-one (0.050 g, 0.13 mmol) in ethanol (4 mL, 70 mmol). After 4 h stirring at rt, the mixture was concentrated, partitioned between EtOAc and NH$_4$Cl, water and brine, then dried over MgSO$_4$. The product was purified by ISCO (4 g silica gel column, 0-5% MeOH/DCM) to give an oil. The HCl salt was prepared by adding 0.2 mL 1N HCl-ether to a DCM solution of base and was recrystallized from DCM-ether to give a white solid (12 mg, 23%). LCMS m/z=393 (M+1); $^1$H NMR (DMSO) δ: 9.88 (s, 1H), 8.69 (m, 2H), 8.60 (d, 1H, J=8 Hz), 8.45 (d, 1H, J=6 Hz), 8.42 (d, 1H, J=8.5 Hz), 7.79-7.85 (m, 2H), 7.67 (t, 1H, J=8 Hz), 4.70 (d, 1H, J=7 Hz), 4.41 (m, 1H), 3.85 (t, 1H, J=12 Hz), 2.90 (t, 1H, J=12 Hz), 2.38-2.45 (m, 2H), 2.28 (q, 2H, J=7 Hz), 1.74-1.84 (m, 2H), 1.36-1.44 (m, 2H), 1.05-1.26 (m, 2H), 0.96 (t, 3H, J=7 Hz).

Example 129

1-[4-(4-Isoquinolin-6-yl-benzoyl)-piperidin-1-yl]-propan-1-one

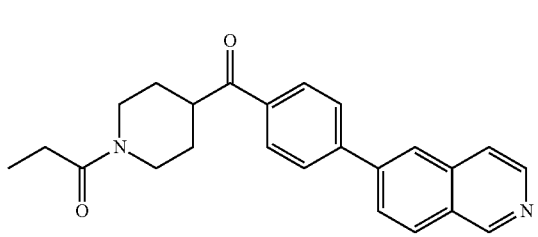 [SMILES: CCC(=O)N1CCC(C(=O)c2ccc(-c3ccc4cnccc4c3)cc2)CC1]

1-{4-[2-(4-Isoquinolin-6-yl-phenyl)-1,3-dioxinan-2-yl]-piperidin-1-yl}-propan-1-one (1.40 g) in 2 M of HCl (15 mL) was stirred at rt for 4 h, made basic with solid Na$_2$CO$_3$ and extracted with EtOAc. The product was purified by ISCO silica gel chromatography (0-5% MeOH/DCM) to give an oil (750 mg, 58%). LCMS m/z=373 (M+1); $^1$H NMR (CDCl$_3$) δ: 9.31 (s, 1H), 8.58 (d, 1H, J=6 Hz), 8.05-8.10 (m, 3H), 7.87 (dd, 1H, J=2, 9 Hz), 7.82 (d, 2H, J=8 Hz), 7.72 (d, 1H, J=6 Hz), 6.61 (b, 1H), 3.96 (bd, 1H, J=12 Hz), 3.53-3.59 (m, 1H), 2.84-2.90 (m, 1H), 3.19-3.26 (m, 1H), 2.84-2.90 (m, 1H), 2.38 (q, 2H, J=7 Hz), 1.81-2.0 (m, 3H), 1.67-1.74 (m, 1H), 1.17 (t, 3H, J=7 Hz).

Example 130

1-{4-[Hydroxy-(4-isoquinolin-6-yl-phenyl)-methyl]-piperidin-1-yl}-propan-1-one

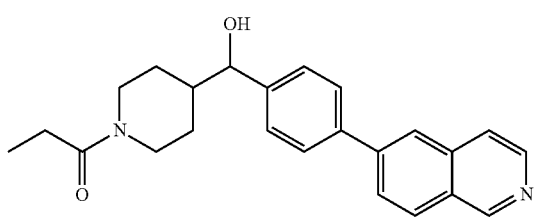 [SMILES: CCC(=O)N1CCC(C(O)c2ccc(-c3ccc4cnccc4c3)cc2)CC1]

Sodium borohydride (0.0122 g, 0.322 mmol) was added to 1-[4-(4-isoquinolin-6-yl-benzoyl)-piperidin-1-yl]-propan-1-one (0.100 g, 0.268 mmol) in THF (1 mL) and methanol (1 mL). After 4 h stirring at 5° C., the mixture was concentrated, added brine and extracted with EtOAc. The product was purified by ISCO (12 g silica gel column, 0-5% MeOH/DCM) to give a white solid (35 mg, 34%). LCMS m/z=375 (M+1): $^1$H NMR (CDCl$_3$) δ: 9.15 (s, 1H), 8.42 (s, 1H), 7.95-7.99 (m, 2H), 7.81 (d, 1H, J=8 Hz), 7.63-7.66 (m, 3H), 7.42 (d, 2H, J=8 Hz), 7.57-7.69 (m, 1H), 4.47-4.50 (m, 1H), 3.77-3.93 (m, 1H), 1.87-2.99 (m, 1H), 2.40-2.51 (m, 1H), 2.28 (q, 2H, J=7 Hz), 2.01-2.09 (m, 1H), 1.88 (b, 1H), 1.23-1.40 (m, 3H), 1.09 (t, 3H, J=7 Hz).

Example 131

1-{4-[1-Hydroxy-1-(4-isoquinolin-6-yl-phenyl)-ethyl]-piperidin-1-yl}-propan-1-one

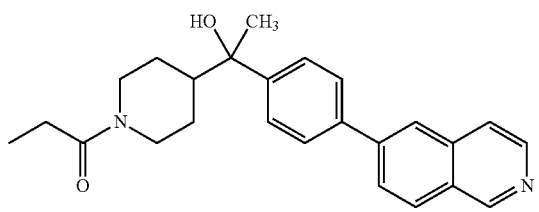 [SMILES: CCC(=O)N1CCC(C(C)(O)c2ccc(-c3ccc4cnccc4c3)cc2)CC1]

Methylmagnesium bromide (0.115 g, 0.966 mmol) was added to 1-{4-(4-isoquinolin-6-yl-benzoyl)-piperidin-1-yl}-propan-1-one (0.300 g, 0.805 mmol) in THF (4 mL). After 2 h stirring at rt, the mixture was concentrated, partitioned between EtOAc and NH$_4$Cl (sat) washed with brine and dried over MgSO$_4$. The product was triturated with ether-hexanes to give a white solid (175 mg, 56%). LCMS m/z=389 (M+1); $^1$H NMR (DMSO-base) δ: 9.33 (s, 1H), 8.51 (d, 1H, J=5 Hz), 8.26 (s, 1H), 8.20 (d, 1H, J=8 Hz), 8.03 (d, 1H, J=8 Hz), 7.86 (d, 1h, J=6 Hz), 7.80 (d, 2H, J=7 Hz), 7.55 (d, 2H, J=7 Hz), 4.95 (s, 1H; D2O exch), 4.37-4.89 (dd, 1H, J=12 Hz), 3.78-3.90 (dd, 1H, J=12 Hz), 2.76-2.91 (m, 1H), 2.31-2.41 (m, 1H), 2.24 (m, 2H), 1.68-1.81 (m, 2H), 1.47 (s, 3H), 1.33 (d, 1H, J=12 Hz), 1.09-1.19 (m, 2H), 0.94 (t, 3H, J=6 Hz).

Example 132

1-{4-[1-(2-Fluoro-4-isoquinolin-6-yl-phenyl)-1-hydroxy-ethyl]-piperidin-1-yl}-propan-1-one

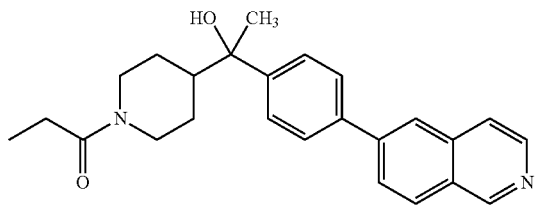 [SMILES: CCC(=O)N1CCC(C(C)(O)c2ccc(-c3ccc4cnccc4c3)cc2)CC1]

Methylmagnesium bromide (0.12 g, 1 mmol) was added to 1-[4-(2-fluoro-4-isoquinolin-6-yl-benzoyl)-piperidin-1-yl]-propan-1-one (0.050 g, 0.13 mmol) in THF (2 mL). After 4 h stirring at rt, the mixture was concentrated, partitioned between EtOAc and NH$_4$Cl, water and brine and dried over MgSO$_4$. The product was triturated with ether-hexanes to give a white solid (40 mg, 79%). LCMS m/z=407 (M+1); $^1$H NMR (DMSO) δ: 9.34 (s, 1H), 8.53 (d, 1H, J=5 Hz), 8.33 (s, 1H), 8.20 (d, 1H, J=8.6 Hz), 8.06 (d, 1H, J=8.6 Hz), 7.87 (d, 1H, J=8.6 Hz), 7.63-7.73 (m, 3H), 5.17 (s, 1H, exch D$_2$O), 4.35-4.49 (dd, 1h, J=12 Hz), 3.77, 3.91 (dd, 1H, J=12 Hz), 2.80, 2.93 (tt, 1H, J=12 Hz), 2.44 (m, 1H), 2.22-2.29 (m, 2H), 1.99 (m, 1H), 1.78 (m, 1H), 1.55 (s, 3H), 1.09-1.26 (m, 3H), 0.94 (m, 3H).

Example 133

1-[3-(4-Isoquinolin-6-yl-benzoyl)-pyrrolidin-1-yl]-propan-1-one

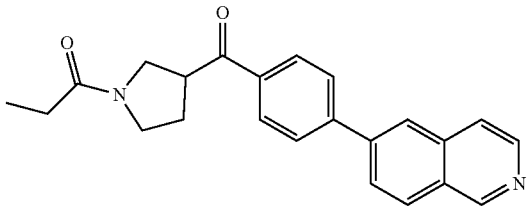 [SMILES: CCC(=O)N1CCC(C(=O)c2ccc(-c3ccc4cnccc4c3)cc2)C1]

Step 1. (4-Isoquinolin-6-yl-phenyl)-pyrrolidin-3-yl-methanone

Palladium acetate (0.0206 g, 0.0920 mmol) and triphenylphosphine (0.0965 g, 0.368 mmol) were stirred 15 min under an atmosphere of nitrogen. 1-[3-(4-Bromobenzoyl)pyrrolidin-1-yl]-2,2,2-trifluoroethanone (0.644 g, 1.84 mmol), isoquinoline-6-boronic acid (0.350 g, 2.02 mmol), DMF (8 mL) and 1 M of sodium carbonate (7.36 mL) was added and heated at 80° C. for 17 h. The mixture was concentrated, dissolved in EtOAc and washed with 1N Na$_2$CO$_3$, water and brine, then dried over MgSO$_4$. The product was purified by ISCO (silica gel 24 g column, 10-20% MeOH/DCM/1% iPrNH$_2$) to give the piperidine compound as an oil. LCMS m/z=303 (M+1). This material was used directly in the next step.

Step 2. 1-[3-(4-Isoquinolin-6-yl-benzoyl)-pyrrolidin-1-yl]-propan-1-one (4-Isoquinolin-6-yl-phenyl)-pyrrolidin-3-yl-methanone (0.080 g, 0.26 mmol) and DIPEA (0.184 mL, 1.06 mmol) in THF (4 mL, 50 mmol) was added propanoyl chloride (0.0460 mL, 0.529 mmol). After stirring 2 h at rt the mixture was concentrated, dissolved in EtOAc, washed with 1N Na$_2$CO$_3$, water and brine, then dried over MgSO$_4$. The product was chromatographed on ISCO (12 g silica gel column MeOH/DCM 0-5%) to give an oil (80 mg, 84%). LCMS m/z=359 (M+1); $^1$H NMR (CDCl$_3$) δ: 9.31 (s, 1H), 4.58-4.60 (m, 1H), 8.05-8.12 (m, 4H), 7.82-7.90 (m, 3H), 7.72 (d, 1H, J=6 Hz), 4.10-4.16 (m, 0.6H), 4.00-4.07 (m, 0.4H), 3.88-3.96 (m, 1H), 3.54-3.78 (m, 3H), 2.43-2.51 (m, 0.6H), 2.22-2.40 (m, 2.8H), 2.1-2.20 (m, 0.6H), 1.14-1.20 (m, 3H).

Example 134

1-{3-[1-Hydroxy-1-(4-isoquinolin-6-yl-phenyl)-ethyl]-pyrrolidin-1-yl}-propan-1-one

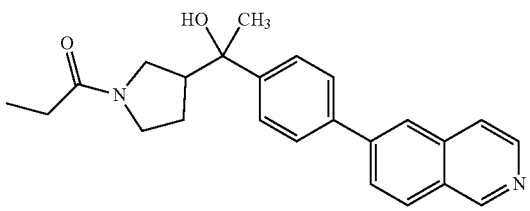 [SMILES: CCC(=O)N1CCC(C(C)(O)c2ccc(-c3ccc4cnccc4c3)cc2)C1]

Methyl magnesium bromide (0.50 mL, 4.32 mmol) was added to 1-[3-(4-isoquinolin-6-yl-benzoyl)pyrrolidin-1-yl]propan-1-one (0.080 g, 0.22 mmol) in THF (4 mL) and stirred at rt for 4 h. Mixture was concentrated, saturated NH₄Cl added and extracted with EtOAc. The solid was recrystallized from EtOAc-ether-hexanes to give a white solid. LCMS m/z=375 (M+1); ¹H NMR (DMSO); δ 9.33 (s, 1H), 8.52 (d, 1H, J=5 Hz), 8.26 (s, 1H), 8.20 (d, 1H, J=8.6 Hz), 8.02-8.05 (m, 1H), 7.88 9d, 1H, J=5 Hz), 7.80-7.83 (m, 2H), 7.61-7.65 (m, 2H), 5.18-5.23 (4 singlets, 1H, D₂O exch), 3.49-3.60 (m, 1H), 3.35-3.46 (m, 1H), 3.16-3.26 (m, 1H), 2.92-3.05 (m, 1H), 2.55-2.77 (m, 1H), 2.21-2.30 (m, 1H), 2.10-2.19 (m, 1H), 1.58-1.91 (m, 1H), 1.50 (s, 3H), 1.27-1.44 (m, 1H), 0.86-1.00 (m, 3H). OH assignments 5.23 (1); 5.21 (3) 5.19 (1); 5.18 (3).

The following examples were synthesized using the method for Example 111 with the required acid chloride and boronic acid.

Example 135

1-{4-[2-(4'-Dimethylaminomethyl-biphenyl-4-yl)-1,3-dioxolan-2-yl]piperidin-1-yl}-2-methyl-propan-1-one

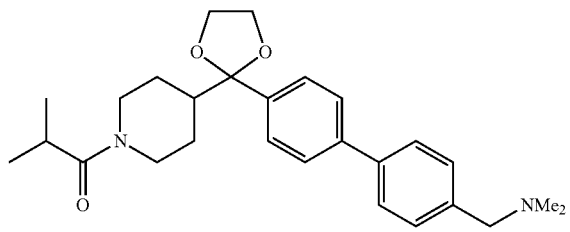 [SMILES: CC(C)C(=O)N1CCC(C2(c3ccc(-c4ccc(CN(C)C)cc4)cc3)OCCO2)CC1]

The title compound was synthesized using the procedure for Example 111, reacting with (4-((dimethylamino)methyl)phenyl)boronic acid in step 1 and with isobutyryl chloride in Step 2. LCMS m/z=437 (M+1); ¹H NMR (DMSO HCl salt) δ: 10.23 (s, 1H, D₂O exch), 7.77 (d, 2H, J=8 Hz), 7.70 (d, 2H, J=8 Hz), 7.61 (d, 2H, J=8 Hz), 7.44 (d, 2H, J=8 Hz), 4.41 (d, 1H, J=12 Hz), 4.30 (d, 2H, J=5 Hz), 3.93-3.99 (m, 3H), 3.70 (m, 2H), 2.89 (t, 1H, J=12 Hz), 2.82 (q, 1H, J=7.5 Hz), 2.73 (s, 3H), 2.72 (s, 3H), 2.36 (t, 1H, J=12 Hz), 2.03-2.09 (m, 1H), 1.56-1.63 (m, 2H), 1.06-1.19 (m, 2H), 0.94 (d, 6H, J=7.5 Hz).

Example 136

1-{4-[2-(4'-Dimethylaminomethyl-biphenyl-4-yl)-1,3-dioxolan-2-yl]-piperidin-1-yl}-propan-1-one

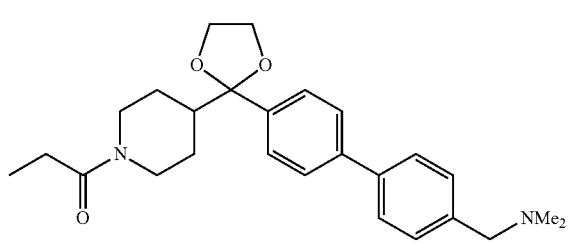 [SMILES: CCC(=O)N1CCC(C2(c3ccc(-c4ccc(CN(C)C)cc4)cc3)OCCO2)CC1]

The title compound was synthesized using the procedure for Example 111, reacting with (4-((dimethylamino)methyl)phenyl)boronic acid in step 1 and with propionyl chloride in Step 2. LCMS m/z=423 (M+1); ¹H NMR (DMSO HCl salt) δ: 10.49 (s, 1H, D2O exch), 7.76 (d, 2H, J=8 Hz), 7.70 (d, 2H, J=8 Hz), 7.63 (d, 2H, J=8 Hz), 7.44 (d, 2H, J=8 Hz), 4.41 (d, 1H, J=12 Hz), 4.31 (d, 2H, J=4.2 Hz), 3.97 (m, 2H), 3.82 (d, 1 h, J=12 Hz), 3.68 (m, 2H), 2.87 (t, 1H, J=12 Hz), 2.71 (s, 3H), 2.72 (s, 3H), 2.37 (t, 1H, J=12 Hz), 2.24 (q, 2H, J=7 Hz), 2.02-2.08 (m, 1H), 1.60 (t, 2H, J=12 Hz), 1.06-1.20 (m, 2H), 0.93 (t, 3H, J=7 Hz).

Example 137

Cyclopropyl-{4-[2-(4'-dimethylaminomethyl-biphenyl-4-yl)-1,3-dioxolan-2-yl]-piperidin-1-yl}-methanone

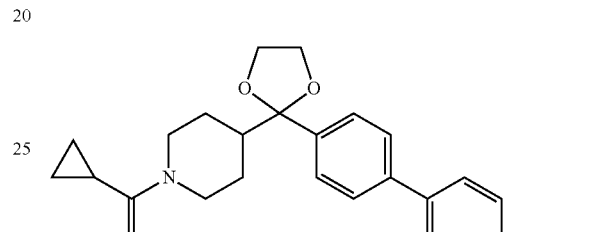

The title compound was synthesized using the procedure for Example 111, reacting with (4-((dimethylamino)methyl)phenyl)boronic acid in step 1 and with cyclopropanecarbonyl chloride in Step 2. LCMS m/z=435 (m +1); ¹H NMR (DMSO HCl salt) δ: 10.37 (s, 1H), 7.77 (d, 2H, J=8 Hz), 7.70 (d, 2H, J=8 Hz), 7.62 (d, 2H, J=8 Hz), 7.44 (d, 2H, J=8 Hz), 4.37 (d, 1H, J=12 Hz), 4.03 (d, 2H, J=5 Hz), 4.24 (d, 1H, J=12 Hz), 3.98 (m, 2H), 3.69 (m, 2H), 2.93-2.98 (m, 1H), 2.73 (s, 3H), 2.72 (s, 3H), 2.45 (m, 1H), 2.04-2.12 (m, 1H), 1.87-1.92 (m, 1H), 1.57-1.64 (m, 2H), 1.07-1.25 (m, 2H), 0.65 (m, 4H).

Example 138

1-[4-(2,6-Difluoro-4-isoquinolin-6-yl-benzoyl)-piperidin-1-yl]-propan-1-one

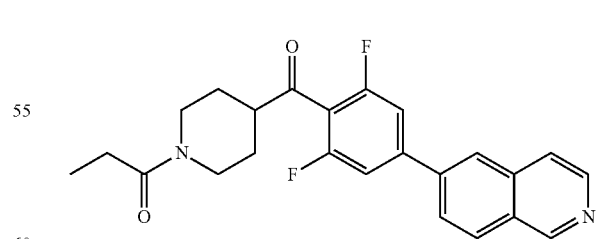

Step 1. (2,6-Difluoro-4-isoquinolin-6-yl-phenyl)-piperidin-4-yl-methanone

Palladium acetate (0.0112 g, 0.0500 mmol) and triphenylphosphine (0.0524 g, 0.200 mmol) were stirred 15 min under an atmosphere of nitrogen. 1-[4-(4-Bromo-2,6-difluorobenzoyl)piperidin-1-yl]-2,2,2-trifluoroethanone (0.400 g, 1.00 mmol), isoquinoline-6-boronic acid (0.190 g, 1.10 mmol), DMF (4 mL, 50 mmol) and 1 M Na₂CO₃ (4.00 mL) was added and was heated at 80° C. for 17 h. The mixture was concentrated, was dissolved in EtOAc and washed with 1N Na₂CO₃, water and brine, then dried (MgSO₄). The product was purified by ISCO (silica gel, 12 g column, 0-25% MeOH/DCM/1% iPrNH₂) to give the piperidine as an oil (280 mg. 79%). LCMS m/z=353 (M+1).

Step 2. 1-[4-(2,6-Difluoro-4-isoquinolin-6-yl-benzoyl)-piperidin-1-yl]-propan-1-one To (2,6-difluoro-4-isoquinolin-6-yl-phenyl)-piperidin-4-yl-methanone (0.200 g, 0.568 mmol) and DIPEA (0.40 mL, 2.3 mmol) in THF (8 mL, 100 mmol) was added propanoyl chloride (0.1 mL, 1.1 mmol). After 4 h stirring at rt, the mixture was concentrated, diluted with EtOAc and washed with 1N Na₂CO₃, water and brine, then dried (MgSO4). The product was purified by ISCO silica gel (0-5% MOH/DCM 1% DIEA). The HCl salt was prepared by adding 0.25 mL 1N HCl-ether to a DCM solution of the base, and recrystallized from DCM ether to give a white solid (200 mg, 88%). LCMS m/z=409 (M+1); ¹H NMR (DMSO) δ: 9.70 (s, 1H); 8.67 (d, 1H, J=6.5 Hz), 8.44 (d, 1H, J=8 Hz), 8.25 (d, 1H, J=6 Hz), 8.12 (s, 1H), 7.80 (d, 1H, J=8 Hz), 7.61 (m, 1H), 7.45 (d, 1H, J=8 Hz), 4.18 (m, 1H), 3.68 (d, 1H, J=12 Hz), 2.76 (m, 1H), 2.5 (m, 1H), 2.32-2.37 (m, 1H), 2.17-2.22 (q, 2H, J=7 Hz), 1.52 (d, 2H, J=12 Hz), 1.23-1.29 (m, 1H), 1.07-1.14 (m, 1H), 0.89 (t, 3H, J=7 Hz).

The following examples were synthesized using the method for Example 111 with an appropriate acid chloride and quinoline-3-boronic acid.

Example 139

1-{4-[2-(4-Quinolin-3-yl-phenyl)-1,3-dioxolan-2-yl]-piperidin-1-yl}-propan-1-one

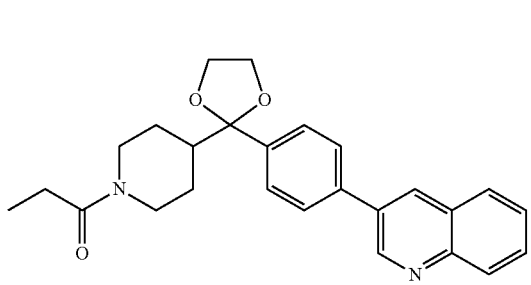 [SMILES: CCC(=O)N1CCC(C2(c3ccc(-c4cnc5ccccc5c4)cc3)OCCO2)CC1]

The title compound was synthesized using the procedure for Example 111, reacting with quinolin-3-ylboronic acid in step 1 and with propionyl chloride in Step 2. LCMS m'z=417 (M+1); ¹H NMR (DMSO) δ: 9.43 (s, 1H), 8.99 (s, 1H), 8.16-8.19 (m, 2H), 7.90-7.95 (m, 3H), 7.76-7.80 (m, 1H), 7.53 (d, 2H, J=8 Hz), 4.42 (d, 1H, J=12 Hz), 3.99 (m, 2H), 3.84 (d, 1H, J=12 Hz), 3.70 (m, 2H), 2.88 (t, 1H, J=12 Hz), 2.35-2.42 (m, 1H), 2.23-2.28 (q, 2H, J=7 Hz), 2.06-2.12 (m, 1H), 1.62 (m, 2H), 1.14-1.25 (m, 2H), 0.94 (t, 3H, J=7 Hz).

Example 140

2-Methyl-1-{4-[2-(4-quinolin-3-yl-phenyl)-1,3-dioxolan-2-yl]-piperidin-1-yl}-propan-1-one

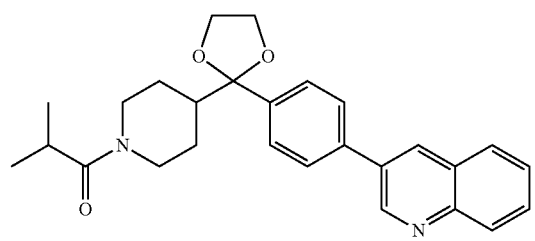 [SMILES: CC(C)C(=O)N1CCC(C2(c3ccc(-c4cnc5ccccc5c4)cc3)OCCO2)CC1]

The title compound was synthesized using the procedure for Example 111, reacting with quinolin-3-ylboronic acid in step 1 and with isobutyryl chloride in Step 2. LCMS m/z=431 (M+1); ¹H NMTR (DMSO) δ: 9.42 (s, 1H), 8.96 (s, 1H), 8.15-8.18 (m, 2H), 8.89-8.95 (m, 3H), 7.77 9t, 1H, J=7 Hz), 7.54 (d, 2H, J=7 Hz), 4.43 (d, 1H, J=12 Hz), 3.94-4.01 (m, 3H), 3.71 (m, 2H), 2.91 (t, 1H, J=12 Hz), 2.81 (q, 1H, J=7 Hz), 2.32-2.41 (m, 1H), 2.07-2.13 (m, 1H), 1.63 (t, 2H, J=12 Hz), 1.09-1.22 (m, 2H), 0.95 (d, 6H, J=7 Hz).

Example 141

Cyclopropyl-{4-[2-(4-quinolin-3-yl-phenyl)-1,3-dioxolan-2-yl]-piperidin-1-yl}-methanone

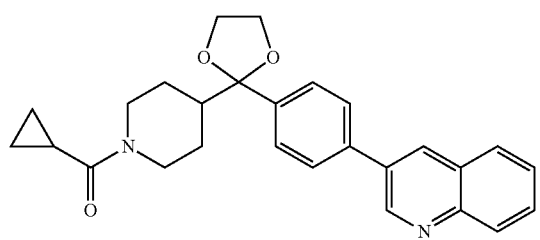 [SMILES: O=C(C1CC1)N1CCC(C2(c3ccc(-c4cnc5ccccc5c4)cc3)OCCO2)CC1]

The title compound was synthesized using the procedure for Example 111, reacting with quinolin-3-ylboronic acid in step 1 and with cyclopropanecarbonyl chloride in Step 2. LCMS m/z=429 (M+1); ¹H NMR (DMSO; HCl salt) δ: 9.38 (s, 1H), 8.90 (s, 1H), 8.14 (m, 2H), 7.92 (d, 2H, J=8 Hz), 7.88 (t, 1H, J=7.5 Hz), 7.74 (t, 1H, J=7.5 Hz), 7.52 (d, 2H, J=8 Hz), 4.38 (b, 1H), 4.26 (b, 1H), 3.98 (m, 2H), 3.71 (m, 2H), 2.94-2.98 (m, 1H), 2.44 (m, 1H), 2.09-2.15 (m, 1H), 1.85-1.94 (m, 1H), 1.58-1.67 (m, 2H), 1.07-1.25 (m, 2H), 0.64-0.66 (m, 4H).

Example 142

1-[4-(2-Fluoro-4-quinolin-7-yl-benzoyl)-piperidin-1-yl]-propan-1-one

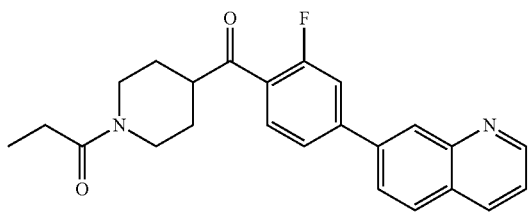 [SMILES: CCC(=O)N1CCC(C(=O)c2ccc(-c3ccc4cccnc4c3)cc2F)CC1]

Step 1. (2-Fluoro-4-quinolin-7-yl-phenyl)-piperidin-4-yl-methanone

Palladium acetate (0.0220 g, 0.0981 mmol) and triphenylphosphine (0.103 g, 0.392 mmol) in dioxane (5 mL) was stirred 15 min under an atmosphere of nitrogen. 1-[4-(4-Bromo-2-fluorobenzoyl)piperidin-1-yl]-2,2,2-trifluoro-ethanone (0.7500 g, 1.962 mmol), quinoline-7-boronic acid (0.373 g, 2.16 mmol), DMF (8 mL) and 1 M sodium carbonate (7.85 mL) was added and heated at 80° C. for 17 h. The mixture was concentrated, was dissolved in EtOAc, washed with 1M Na$_2$CO$_3$, water and brine then dried (MgSO$_4$). The product was purified by ISCO (12 g silica gel column, 0-25% MeOH/DCM/1% iPrNH$_2$) to give the piperidine compound. This material was used in the next step. LCMS m/z=335 (M+1); $^1$H NMR (CDCl$_3$) δ: 8.97 (m, 1H), 8.35 (m, 1H), 7.91-7.95 (m, 2H), 7.79-7.82 (m, 1H), 7.62-7.65 (m, 1H), 7.50-7.53 (m, 1H), 7.44-7.48 (m, 1H), 3.31-3.36 (m, 2H), 3.17-3.24 (m, 2H), 2.76-2.85 (m, 3H), 1.97-2.01 (m, 2H), 1.85-1.88 (m, 1H),

Step 2. 1-[4-(2-Fluoro-4-quinolin-7-yl-benzoyl)-piperidin-1-yl]-propan-1-one (2-Fluoro-4-quinolin-7-yl-phenyl)piperidin-4-yl-methanone (0.200 g, 0.598 mmol) and DIPEA (0.42 mL, 2.4 mmol) in THF (9 mL) was added propanoyl chloride (0.10 mL, 1.2 mmol). After 4 h stirring at rt, the mixture was concentrated, diluted with EtOAc and washed with 1M Na$_2$CO$_3$, water and brine then dried (MgSO$_4$). The product was purified by ISCO (12 g silica gel column 80-95% EtOAc/hexanes). LCMS m/z=391 (M+1); $^1$H NMR (DMSO) δ: 8.97 (m, 1H), 8.43 (m, 2H), 8.12 (d, 1H, J=8.5 Hz), 8.05 (dd, 1H, J=2, 8 Hz), 7.87-7.95 (m, 3H), 7.58 (dd, 1H, J=4, 8 Hz), 4.36 (d, 1H, J=12 Hz), 3.87 (d, 1H, J=12 Hz), 3.46 (tt, 1H, J=3, 12 Hz), 3.15 (t, 1H, J=12 Hz), 2.75 (t, 1H, J=12 Hz), 2.32 (dq, 2H, J=2, 7 Hz), 1.89 (b, 2H), 1.47-1.55 (m, 1H), 1.32-1.41 9m, 1H), 0.98 (t, 3H, J=7 Hz).

The following examples were synthesized using the procedure for Example 142.

Example 143

1-[4-(2-Fluoro-4-quinolin-3-yl-benzoyl)piperidin-1-yl]propan-1-one

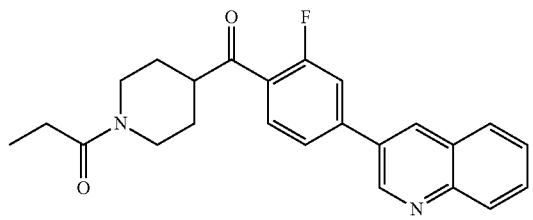 [SMILES: CCC(=O)N1CCC(C(=O)c2ccc(-c3cnc4ccccc4c3)cc2F)CC1]

The title compound was synthesized using the procedure for Example 111, reacting with quinolin-3-ylboronic acid in step 1 and with propionyl chloride in Step 2. LCMS m/z=391 (M+1); $^1$H NMR (DMSO HCl salt) δ: 9.46 (d, 1H, J=2 Hz), 9.05 (s, 1H), 8.16 (d, 2H, J=), 7.90-8.04 (m, 4H), 7.77 (t, 1H, J=8 Hz), 4.35 (d, 1H, J=12 Hz), 3.87 (d, 1H, J=12 Hz), 3.44-3.50 (m, 1H), 3.15 (t, 1H, J=12 Hz), 2.75 (t, 1H, J=12 Hz), 2.33 (q, 2H, J=8 Hz), 1.89 (b, 2H), 1.47-1.55 (m, 1H), 1.32-1.41 (m, 1H), 0.98 (t, 3H, J=8 Hz).

Example 144

4-(2-Fluoro-4-quinolin-3-yl-benzoyl)piperidine-1-carboxylic acid methyl ester

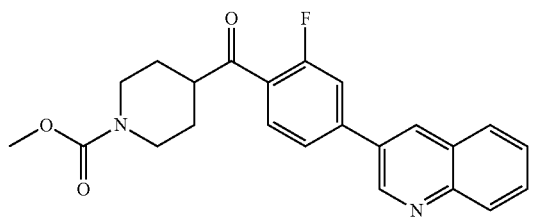 [SMILES: COC(=O)N1CCC(C(=O)c2ccc(-c3cnc4ccccc4c3)cc2F)CC1]

The title compound was synthesized using the procedure for Example 111, reacting with quinolin-3-ylboronic acid in step 1 and with methylchloroformate in Step 2. LCMS m/z=393 (M+1); $^1$H NMR (DMSO HCl salt) δ: 9.50 (m, 1H), 9.13 (s, 1H), 8.20 (t, 2H, J=7 Hz), 7.94-8.05 (m, 4H), 7.80 (t, 1H, J=8 Hz), 3.98 (bd, 2H, J=11 Hz), 3.60 (s, 3H), 3.39-3.45 (m, 1H), 2.98 (b, 2H), 1.89 (bd, 2H, J=11 Hz), 1.39-1.50 (m, 2H).

Example 145

(4-hydroxy-4-(4-(isoquinolin-3-yl)benzyl)piperidin-1-yl)(isoxazolidin-2-yl)methanone

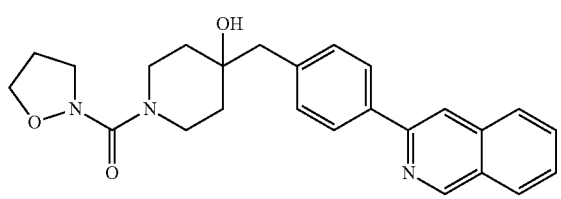 [SMILES: O=C(N1CCC(O)(Cc2ccc(-c3cc4ccccc4cn3)cc2)CC1)N1CCCO1]

Step 1. 4-Hydroxy-4-[4-(4,4,5,5-tetramethyl-1,3,2-dioxaborolan-2-yl)-benzyl]-piperidine-1-carboxylic acid tert-butyl ester A Schlenk flask was added 4-(4-bromobenzyl)-4-hydroxy-piperidine-1-carboxylic acid tert-butyl ester (5.00 g, 13.5 mmol), 4,4,5,5,4',4',5',5'-octamethyl-[2,2]'bi[[1,3,2]dioxaborolanyl] (5.14 g, 20.2 mmol), 1,4-dioxane (40 mL), potassium acetate (1.99 g, 20.2 mmol), and bis(tricyclohexylphosphine)palladium (0) (0.901 g, 1.35 mmol) and heated at 100° C. for 16 h. The mixture was cooled to rt, filtered through celite, washed with EtOAc and concentrated. The product was chromatographed on ISCO (80 g silica gel column, 30-70% EtOAc/hexanes) and the product was triturated with ether-hexanes to give a white power. LCMS m/z=440 (M+23); $^1$H NMR (CDCl$_3$) δ: 7.56 (d, 2H, J=8 Hz), 7.21 (d, 2H, J=8 Hz), 4.39 (s, 1H, D$_2$O exch), 3.61 (b, 2H), 3.00 (b, 2H), 2.70 (s, 2H), 1.35 (s, 9H), 1.33 (m, 4H), 1.28 (s, 12H).

Step 2. 4-Hydroxy-4-(4-isoquinolin-3-yl-benzyl)-piperidin-1-yl]-isoxazolidin-2-yl-methanone 4-(4-Isoquinolin-3-yl-benzyl)-piperidin-4-ol .2 TFA. 4-Hydroxy-4-[4-(4,4,5,5-tetramethyl-1,3,2-dioxaborolan-2-yl)-benzyl]-piperidine-1-carboxylic acid tert-butyl ester in DCM (4 mL) was added TFA (4 mL) and stirred at rt for 4 h, concentrated, and collected. LCMS m/z=319 (M+1).

Step 3. 4-Hydroxy-4-(4-isoquinolin-3-yl-benzyl)-piperidin-1-yl]-isoxazolidin-2-yl-methanone 4-(4-Isoquinolin-3-yl-benzyl)-piperidin-4-ol .2 TFA (0.200 g, 0.366 mmol) and DIPEA (0.255 mL, 1.46 mmol) in DCM (2 mL) was added triphosgene (0.0597 g, 0.201 mmol) on an ice bath. The mixture was warmed to rt and stirred 4 h, then was concentrated. The residue was dissolved in DCM and was concentrated. This material in DCM (4 mL) was added DIPEA (0.127 mL, 0.732 mmol) and isoxazolidine HCL (0.0501 g, 0.457 mmol) was added and stirred at rt for 2 h. The reaction was concentrated, dissolved in EtOAc and washed with 1N Na$_2$CO$_3$ and brine then dried (MgSO$_4$). The product was chromatographed on Isco (12 g silica gel column, EtOAc/hexanes 50-80%). The free base was recrystallized from ether-hexanes to give a white solid (100 mg, 65%). LCMS m/z=418 (M+1); $^1$H NMR (DMSO) δ: 9.39 (s, 1H), 8.38 (s, 1H), 8.13 (m, 3H), 8.02 (d, 1H, J=8 Hz), 7.78 (t, 1H, J=7.2 Hz), 7.65 (t, 1H, J=7 Hz), 7.37 (d, 2H, J=8 Hz), 4.49 (s, 1H, D$_2$O), 3.73-3.79 (m, 4H), 3.37 (t, 2H, J=7 Hz), 3.11-3.17 (m, 2H), 2.76 (s, 2H), 2.08 (q, 2H, J=7.2 Hz), 1.40-1.51 (m, 4H).

Example 146

[4-Hydroxy-4-(4-isoquinolin-3-yl-benzyl)-piperidin-1-yl]-(R)-tetrahydro-furan-2-yl-methanone

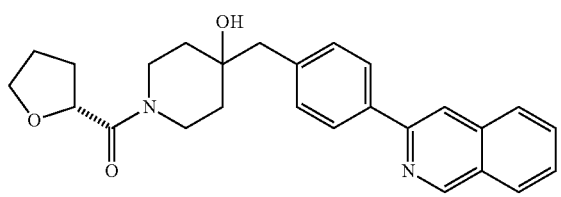

HATU (0.4871 g, 1.281 mmol) and DIPEA (0.67 mL, 3.84 mmol) in DMF (7 mL) was stirred 15 min, then was added (R)-tetrahydrofuran-2-carboxylic acid (0.123 mL, 1.28 mmol). After 15 min 4-(4-isoquinolin-3-yl-benzyl)-piperidin-4-ol .2 TFA (0.35 g, 0.64 mmol) was added and stirred 18 h at rt and concentrated. The mixture was dissolved in EtOAc, washed with 1N Na$_2$CO$_3$ and brine then dried over MgSO$_4$. The product was purified by ISCO (4 g silica gel column, 50-90% EtOAc/hexanes) to give a white solid (ether-hexanes, 150 mg, 58%). LCMS m/z=417 (M+1); $^1$H NMR (DMSO) δ: 9.39 (s, 1H), 8.38 (s, 1H), 8.11 (m, 3H), 8.00 (d, 1H, J=7 Hz), 7.78 (t, 1H, J=7.5 Hz), 7.66 (t, 1H, J=7.5 Hz), 7.35 (d, 2H, J=8 Hz), 4.16 (t, 1H, J=7 Hz), 4.52 (s, 1H, D$_2$O exch), 4.05 (b, 1H), 3.67-3.75 (m, 3H), 3.31 (m, 1H), 2.92 (m, 1H), 2.76 (s, 2H), 1.96 (m, 2H), 1.78 (m, 2H), 1.42 (m, 4H).

Example 147

1-[4-Hydroxy-4-(4-isoquinolin-6-yl-benzyl)-piperidin-1-yl]-2-methyl-propan-1-one

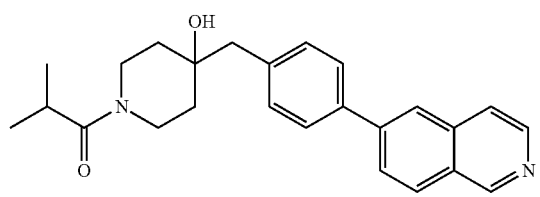 [SMILES: CC(C)C(=O)N1CCC(O)(Cc2ccc(-c3ccc4cnccc4c3)cc2)CC1]

Step 1. tert-butyl 4-(4-bromobenzyl)-4-hydroxypiperidine-1-carboxylate

To a suspension of magnesium turnings (1.21 g, 50 mmol) in diethyl ether (100 mL) was added 1-bromo-4-(bromomethyl)benzene (6.9 g, 27.2 mmol) at 0° C. and stirred at rt for 1 h. The reaction mixture was cooled to 0° C. and tert-butyl 4-oxopiperidine-1-carboxylate (5.0 g, 25.0 mmol) in diethyl ether was added slowly followed by stirring at rt for 2h. The reaction was quenched with NH$_4$Cl solution and extracted with ethyl acetate then washed with water. The organic layer was washed with brine, dried over Na$_2$SO$_4$, filtered and concentrated. The crude residue was purified by column chromatography on silica gel with 15-20% EtOAc/hexane to give tert-butyl 4-(4-bromobenzyl)-4-hydroxypiperidine-1-carboxylate (2.9 g, 32%) as a white solid. $^1$H NMR (400 MHz, DCCl$_3$) δ 7.44 (d, J=7.9 Hz, 2H), 7.07 (d, J=7.9 Hz, 2H), 3.85 (s, 2H), 3.08 (t, J=11.9 Hz, 2H), 2.71 (s, 2H), 1.63-1.45 (m, 4H), 1.27 (s, 9H).

Step 2. 4-(4-bromobenzyl)piperidin-4-ol

To a solution of tert-butyl 4-(4-bromobenzyl)-4-hydroxypiperidine-1-carboxylate (4.0 g, 10.8 mmol) in DCM (30 mL) at 0° C. was added trifluoroacetic acid (12 mL) and stirred at rt for 2h. Volatiles were removed at reduced pressure. Reaction mixture was diluted with ethyl acetate and washed with K$_2$CO$_3$ solution and brine. The organic layer was dried over Na$_2$SO$_4$, filtered and concentrated to give 4-(4-bromobenzyl)piperidin-4-ol (2.1 g, 72%) as a white solid. LCMS (ESI): 270 (M+H); $^1$H NMR (DMSO-d6) δ: 7.51-7.40 (m, 2H), 7.31-7.11 (m, 2H), 3.07-2.88 (m, 4H), 2.75-2.64 (m, 2H), 2.56-2.50 (m, 1H), 1.66-1.45 (m, 4H).

Step 3. 1-(4-(4-bromobenzyl)-4-hydroxypiperidin-1-yl)-2-methylpropan-1-one

To a solution of 4-(4-bromobenzyl)piperidin-4-ol (1 equiv) in DCM at 0° C. was added Et₃N (3.0 equiv) followed by isobutyryl chloride (1.5 equiv) and stirred for 6 h. Reaction mixture was diluted with DCM and washed with water, brine, dried over Na₂SO₄, filtered and concentrated. Residue was purified by column chromatography on silica gel. 1-(4-(4-bromobenzyl)-4-hydroxypiperidin-1-yl)-2-methylpropan-1-one was isolated in 48% yield. LCMS (ESI): 342 (M+H); ¹H NMR (400 MHz, Chloroform-d) δ 7.49-7.41 (m, 2H), 7.11-7.03 (m, 2H), 4.40 (d, J=13.2 Hz, 1H), 3.71 (d, J=13.6 Hz, 1H), 3.39-3.37 (m, 1H), 2.98-2.96 (m, 1H), 2.87-2.70 (m, 3H), 1.64-1.45 (m, 4H), 1.24 (d, J=11.1 Hz, 1H), 1.12 (t, J=6.5 Hz, 6H).

Step 4. 1-(4-hydroxy-4-(4-(isoquinolin-6-yl)benzyl)piperidin-1-yl)-2-methylpropan-1-one A solution of 1-(4-(4-bromobenzyl)-4-hydroxypiperidin-1-yl)-2-methylpropan-1-one (1 equiv), isoquinoline-6-boronic acid (1.1 equiv) and Na₂CO₃ (2.5 equiv) in 1,4-dioxane and water (2:1) was degassed by argon for 1 h followed by addition of tetrakis(triphenylphosphine)palladium(0) (0.05 equiv). The reaction mixture was heated at 100° C. after degassing again with argon, for 15 h. The reaction mixture was filtered through a bed of Celite. The filtrate was diluted with ethyl acetate, washed with water, brine, dried over Na₂SO₄, filtered and concentrated. Residue was purified by column chromatography on silica gel to afford 1-(4-hydroxy-4-(4-(isoquinolin-6-yl)benzyl)-piperidin-1-yl)-2-methylpropan-1-one (26%) as an off-white solid. mp 175° C.; LCMS (ESI): 389 (M+H); ¹H NMR (DMSO-d6) δ: 9.33 (s, 1H), 8.52 (d, J=5.7 Hz, 1H), 8.28-8.16 (m, 2H), 8.02 (dd, J=8.6, 1.7 Hz, 1H), 7.87 (d, J=5.7 Hz, 1H), 7.77 (d, J=8.1 Hz, 2H), 7.39 (d, J=7.8 Hz, 2H), 4.52 (s, 1H), 4.09 (d, J=12.9 Hz, 1H), 3.69 (d, J=13.3 Hz, 1H), 2.96-2.75 (m, 4H), 1.51-1.16 (m, 5H), 0.96 (d, J=6.7 Hz, 6H).

The following compounds were prepared in an analogous manner to Example 147, using the specified acid chloride in Step 3 and the specified boronic acid in Step 4.

Example 148

1-(4-hydroxy-4-(4-(quinolin-3-yl)benzyl)piperidin-1-yl)propan-1-one

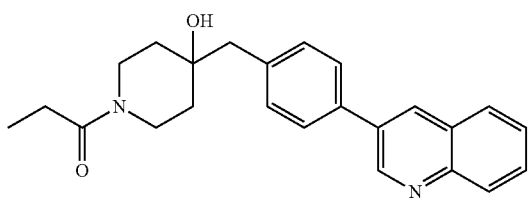 [SMILES: CCC(=O)N1CCC(O)(Cc2ccc(-c3cnc4ccccc4c3)cc2)CC1]

The title compound was synthesized using the procedure for Example 147, reacting with propionyl chloride in step 3, and with quinolin-3-ylboronic acid in Step 4, and isolating the product as a white solid. mp 89° C.; LCMS (ESI): 375 (M+H); ¹H NMR (400 MHz, DMSO-d6) δ: 9.25 (d, J=2.4 Hz, 1H), 8.63 (d, J=2.3 Hz, 1H), 8.09-8.01 (m, 2H), 7.83-7.72 (m, 3H), 7.68-7.64 (m, 1H), 7.43-7.36 (m, 2H), 4.52 (s, 1H), 4.1-4.08 (m, 1H), 3.64-3.54 (m, 1H), 3.34-3.20 (m, 1H), 2.9-2.87 (m, 1H), 2.77 (s, 2H), 2.28 (q, J=7.4 Hz, 2H), 1.55-1.32 (m, 4H), 0.96 (t, J=7.4 Hz, 3H).

Example 149

1-(4-hydroxy-4-(4-(quinolin-3-yl)benzyl)piperidin-1-yl)-2-methylpropan-1-one

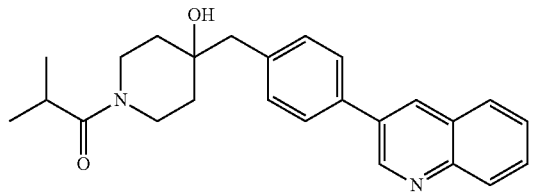 [SMILES: CC(C)C(=O)N1CCC(O)(Cc2ccc(-c3cnc4ccccc4c3)cc2)CC1]

The title compound was synthesized using the procedure for Example 147, reacting with isobutyryl chloride in step 3, and with quinolin-3-ylboronic acid in Step 4, and isolating the product as a white solid. mp 168° C.; LCMS (ESI): 389 (M+H); ¹H NMR (DMSO-d6) δ: 9.25 (d, J=2.3 Hz, 1H), 8.63 (d, J=2.4 Hz, 1H), 8.08-8.01 (m, 2H), 7.83-7.72 (m, 3H), 7.69-7.60 (m, 1H), 7.40 (d, J=7.9 Hz, 2H), 4.52 (s, 1H), 4.10 (dd, J=12.6, 4.7 Hz, 1H), 3.69 (d, J=13.4 Hz, 1H), 2.96-2.75 (m, 4H), 1.54-1.31 (m, 2H), 1.23 (d, J=2.6 Hz, 2H), 0.96 (dd, J=6.8, 2.3 Hz, 6H).

Example 150

1-(4-hydroxy-4-(4-(quinolin-7-yl)benzyl)piperidin-1-yl)propan-1-one

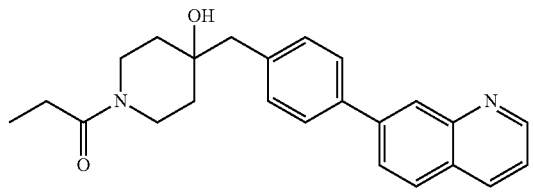 [SMILES: CCC(=O)N1CCC(O)(Cc2ccc(-c3ccc4cccnc4c3)cc2)CC1]

The title compound was synthesized using the procedure for Example 147, reacting with propionyl chloride in step 3, and with quinolin-7-ylboronic acid in Step 4, and isolating the product as an off-white solid. mp 171° C.; LCMS (ESI): 375 (M+H); ¹H NMR (Chloroform-d) δ: 8.94 (d, J=4.3 Hz, 1H), 8.35-8.29 (m, 1H), 8.23-8.15 (m, 1H), 7.90 (d, J=8.5 Hz, 1H), 7.82 (d, J=8.5 Hz, 1H), 7.77-7.69 (m, 2H), 7.41 (dd, J=8.2, 4.2 Hz, 1H), 7.38-7.29 (m, 2H), 4.47-4.38 (m, 1H), 3.71-3.61 (m, 1H), 3.45-3.42 (m, 1H), 3.0-2.98 (m, 1H), 2.84 (s, 2H), 2.36 (q, J=7.5 Hz, 2H), 1.72-1.55 (m, 5H), 1.15 (t, J=7.4 Hz, 3H).

Example 151

1-(4-hydroxy-4-(4-(quinolin-7-yl)benzyl)piperidin-1-yl)-2-methylpropan-1-one

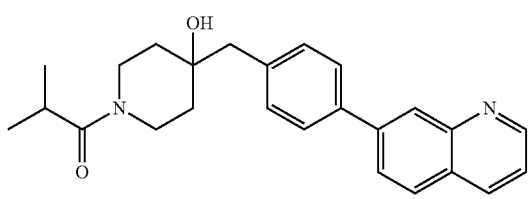 [SMILES: CC(C)C(=O)N1CCC(O)(Cc2ccc(-c3ccc4cccnc4c3)cc2)CC1]

The title compound was synthesized using the procedure for Example 147, reacting with isobutyryl chloride in step 3, and with quinolin-7-ylboronic acid in Step 4, and isolating the product as an off-white solid. mp 153° C.; LCMS (ESI): 389 (M+H); $^1$H NMR (Chloroform-d) δ: 8.95 (dd, J=4.2, 1.8 Hz, 1H), 8.35-8.15 (m, 1H), 8.23-8.15 (m, 1H), 7.90 (d, J=8.5 Hz, 1H), 7.82 (dd, J=8.5, 1.8 Hz, 1H), 7.73 (d, J=7.9 Hz, 2H), 7.45-7.30 (m, 3H), 4.44 (d, J=13.3 Hz, 1H), 3.79-3.70 (m, 1H), 3.45-3.42 (m, 1H), 3.0-2.98 (m, 1H), 2.87-2.74 (m, 3H), 1.72-1.56 (m, 4H), 1.42 (s, 1H), 1.13 (dd, J=9.4, 6.6 Hz, 6H).

Example 152

1-(4-(4-(benzofuran-5-yl)benzyl)-4-hydroxypiperidin-1-yl)propan-1-one

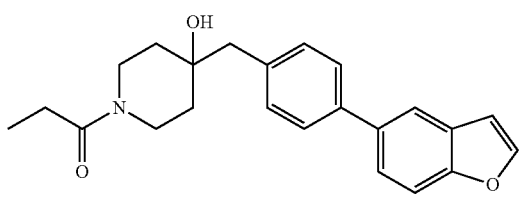 [SMILES: CCC(=O)N1CCC(O)(Cc2ccc(-c3ccc4occc4c3)cc2)CC1]

The title compound was synthesized using the procedure for Example 147, reacting with propionyl chloride in step 3, and with benzofuran-5-ylboronic acid in Step 4, and isolating the product as a light green solid. mp 76° C.; LCMS (ESI): 364 (M+H); $^1$H NMR (methanol-d4) δ: 7.84-7.74 (m, 2H), 7.69-7.45 (m, 4H), 7.37-7.17 (m, 2H), 6.88 (d, J=2.2 Hz, 1H), 4.33-4.22 (m, 1H), 3.78-3.68 (m, 1H), 3.42-3.41 (m, 1H), 3.07-2.95 (m, 1H), 2.81 (s, 2H), 2.40 (q, J=7.5 Hz, 2H), 1.62-1.60 (m, 4H), 1.35-1.20 (m, 1H), 1.10 (t, J=7.5 Hz, 3H).

Example 153

1-(4-(4-(benzofuran-5-yl)benzyl)-4-hydroxypiperidin-1-yl)-2-methylpropan-1-one

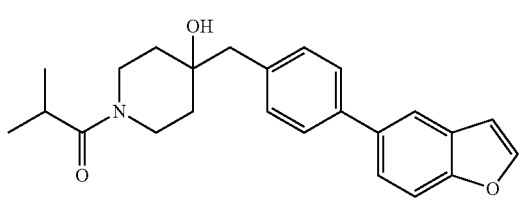 [SMILES: CC(C)C(=O)N1CCC(O)(Cc2ccc(-c3ccc4occc4c3)cc2)CC1]

The title compound was synthesized using the procedure for Example 147, reacting with isobutyryl chloride in step 3, and with benzofuran-5-ylboronic acid in Step 4, and isolating the product as a light yellow solid. mp 129° C.; LCMS (ESI): 378 (M+H); $^1$H NMR (methanol-d4) δ: 7.87-7.74 (m, 2H), 7.60-7.47 (m, 4H), 7.31 (d, J=7.8 Hz, 2H), 6.88 (d, J=2.3 Hz, 1H), 4.28 (dd, J=10.8, 6.3 Hz, 1H), 3.89-3.78 (m, 1H), 3.45-3.43 (m, 1H), 3.08-2.87 (m, 2H), 2.82 (s, 2H), 1.70-1.51 (m, 5H), 1.20-0.99 (m, 6H).

Example 154

1-(4-(4-(1H-indol-5-yl)benzyl)-4-hydroxypiperidin-1-yl)propan-1-one

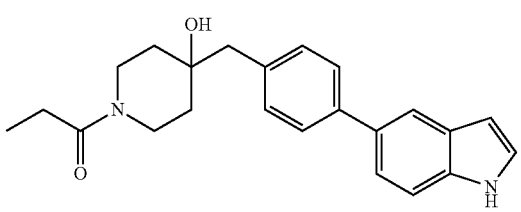 [SMILES: CCC(=O)N1CCC(O)(Cc2ccc(-c3ccc4[nH]ccc4c3)cc2)CC1]

The title compound was synthesized using the procedure for Example 147, reacting with propionyl chloride in step 3, and with indole-5-ylboronic acid in Step 4, and isolating the product as an off-white solid. mp 100° C.; LCMS (ESI): 363 (M+H); $^1$H NMR (DCCl$_3$) δ: 8.29-8.24 (m, 1H), 7.85 (d, J=1.7 Hz, 1H), 7.65-7.57 (m, 2H), 7.50-7.40 (m, 2H), 7.28-7.17 (m, 2H), 4.45-4.41 (m, 1H), 3.69-3.60 (m, 1H), 3.45-3.42 (m, 1H), 3.04-2.92 (m, 1H), 2.80 (s, 2H), 2.36 (q, J=7.5 Hz, 2H), 1.63 (d, J=15.2 Hz, 4H), 1.32-1.04 (m, 4H).

Example 155

1-(4-(4-(1H-indol-5-yl)benzyl)-4-hydroxypiperidin-1-yl)-2-methylpropan-1-one

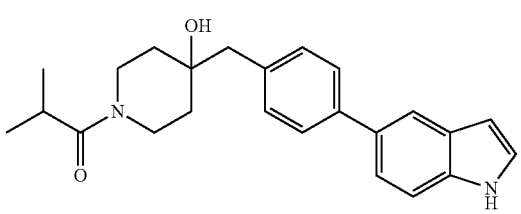 [SMILES: CC(C)C(=O)N1CCC(O)(Cc2ccc(-c3ccc4[nH]ccc4c3)cc2)CC1]

The title compound was synthesized using the procedure for Example 147, reacting with isobutyryl chloride in step 3, and with indole-5-ylboronic acid in Step 4, and isolating the product as an off-white solid. mp 176° C.; LCMS (ESI): 377 (M+H); $^1$H NMR (DCCl$_3$) δ: 8.25 (s, 1H), 7.85 (dt, J=1.8, 0.9 Hz, 1H), 7.66-7.58 (m, 2H), 7.50-7.40 (m, 2H), 7.29-7.21 (m, 3H), 6.65-6.63 (m, 1H), 4.43 (d, J=13.2 Hz, 1H), 3.73 (d, J=13.6 Hz, 1H), 3.53-3.35 (m, 1H), 3.04-2.92 (m, 1H), 2.82 (d, J=5.4 Hz, 4H), 1.82-1.80 (m, 2H), 1.37-1.09 (m, 6H).

Example 156

1-(4-(4-(benzofuran-2-yl)benzyl)-4-hydroxypiperidin-1-yl)propan-1-one

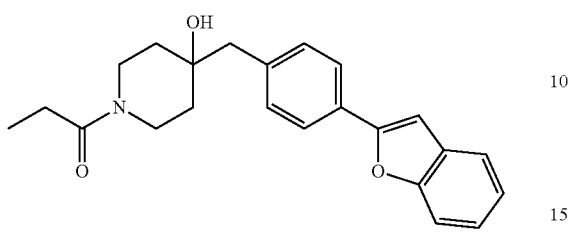

The title compound was synthesized using the procedure for Example 147, reacting with propionyl chloride in step 3, and with benzofuran-2-ylboronic acid in Step 4, and isolating the product as a grey solid. mp 174° C.; LCMS (ESI): 364 (M+H); $^1$H NMR (methanol-d4) δ: 7.82 (d, J=8.1 Hz, 2H), 7.64-7.55 (m, 1H), 7.54-7.46 (m, 1H), 7.37-7.17 (m, 4H), 7.14 (d, J=1.0 Hz, 1H), 4.32-4.22 (m, 1H), 3.78-3.68 (m, 1H), 3.54-3.29 (m, 1H), 3.05-3.02 (m, 1H), 2.81 (s, 2H), 2.39 (q, J=7.5 Hz, 2H), 1.70-1.52 (m, 4H), 1.22-1.05 (m, 3H).

Example 157

1-(4-(4-(benzofuran-2-yl)benzyl)-4-hydroxypiperidin-1-yl)-2-methylpropan-1-one

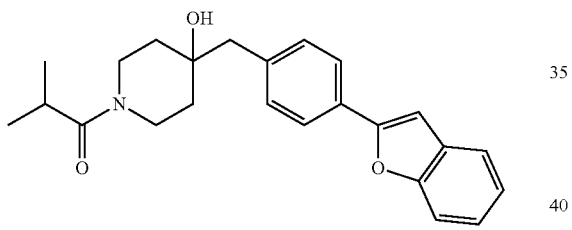

The title compound was synthesized using the procedure for Example 147, reacting with isobutyryl chloride in step 3, and with benzofuran-2-ylboronic acid in Step 4, and isolating the product as an off-white solid. mp 203° C.; LCMS (ESI): 378 (M+H); $^1$H NMR (400 MHz, methanol-d4) δ 7.82 (d, J=8.1 Hz, 2H), 7.62-7.47 (m, 2H), 7.37-7.17 (m, 4H), 7.13 (s, 1H), 4.33-4.22 (m, 1H), 3.87-3.76 (m, 1H), 3.44-3.41 (m, 1H), 3.09-2.86 (m, 2H), 2.81 (s, 2H), 1.68-1.49 (m, 4H), 1.07 (dd, J=6.7, 5.1 Hz, 6H).

Example 158

1-(4-hydroxy-4-(4-(isoquinolin-4-yl)benzyl)piperidin-1-yl)propan-1-one

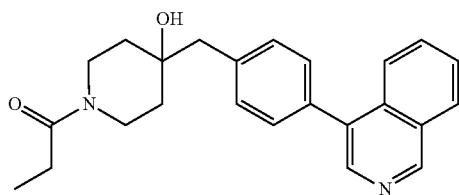 [SMILES: CCC(=O)N1CCC(O)(Cc2ccc(-c3cncc4ccccc34)cc2)CC1]

The title compound was synthesized using the procedure for Example 147, reacting with propionyl chloride in step 3, and with isoquinoline-4-boronic acid in Step 4, and isolating the product as a light yellow solid. mp 78° C.; LCMS (ESI): 375 (M+H); $^1$H NMR (methanol-d4) δ 9.24 (s, 1H), 8.35 (d, J=0.8 Hz, 1H), 8.24-8.15 (m, 1H), 7.95 (dt, J=8.0, 1.2 Hz, 1H), 7.83-7.67 (m, 2H), 7.50-7.40 (m, 4H), 4.32 (dd, J=10.7, 6.6 Hz, 1H), 3.77 (d, J=13.5 Hz, 1H), 3.45-3.42 (m, 1H), 3.05-3.02 (m, 1H), 2.89 (s, 2H), 2.42 (q, J=7.5 Hz, 2H), 1.76-1.58 (m, 4H), 1.15-1.12 (m, 3H).

Example 159

1-(4-hydroxy-4-(4-(isoquinolin-4-yl)benzyl)piperidin-1-yl)-2-methylpropan-1-one

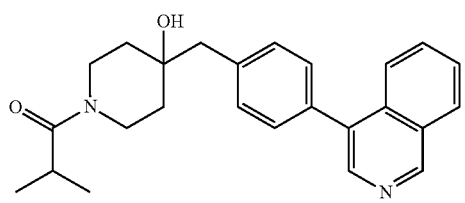 [SMILES: CC(C)C(=O)N1CCC(O)(Cc2ccc(-c3cncc4ccccc34)cc2)CC1]

The title compound was synthesized using the procedure for Example 147, reacting with isobutyryl chloride in step 3, and with isoquinoline-4-boronic acid in Step 4, and isolating the product as a light yellow solid. mp 196° C.; LCMS (ESI): 389 (M+H); $^1$H NMR (Chloroform-d) δ 9.25 (d, J=0.9 Hz, 1H), 8.43 (s, 1H), 8.08-8.01 (m, 1H), 7.92 (dd, J=8.4, 1.4 Hz, 1H), 7.68-7.66 (m, 2H), 7.52-7.44 (m, 2H), 7.40-7.30 (m, 2H), 4.46 (d, J=13.2 Hz, 1H), 3.80-3.72 (m, 1H), 3.51-3.39 (m, 1H), 3.05-3.01 (m, 1H), 2.91-2.76 (m, 3H), 1.39-1.09 (m, 10H).

Example 160

1-(4-hydroxy-4-(4-(isoquinolin-6-yl)benzyl)piperidin-1-yl)propan-1-one

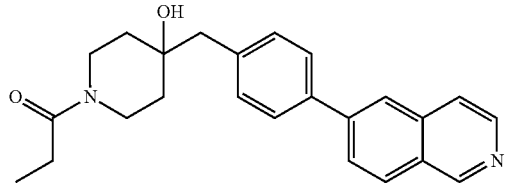 [SMILES: CCC(=O)N1CCC(O)(Cc2ccc(-c3ccc4cnccc4c3)cc2)CC1]

The title compound was synthesized using the procedure for Example 147, reacting with propionyl chloride in step 3, and with isoquinoline-6-boronic acid in Step 4, and isolating the product as an off-white solid. mp 94° C.; LCMS (ESI): 375 (M+H); $^1$H NMR (DMSO-d6) δ: 9.33 (s, 1H), 8.52 (d, J=5.7 Hz, 1H), 8.27-8.16 (m, 2H), 8.02 (dd, J=8.6, 1.8 Hz, 1H), 7.87 (d, J=5.7 Hz, 1H), 7.80-7.73 (m, 2H), 7.38 (d, J=8.1 Hz, 2H), 4.52 (s, 1H), 4.1-4.08 (m, 1H), 3.64-3.54 (m, 1H), 3.28-3.25 (m, 1H), 2.9-2.87 (m, 1H), 2.76 (s, 2H), 2.28 (q, J=7.5 Hz, 2H), 1.54-1.29 (m, 2H), 1.23 (d, J=3.0 Hz, 2H), 0.96 (t, J=7.4 Hz, 3H).

Example 161

1-(4-fluoro-4-(4-(quinolin-3-yl)benzyl)piperidin-1-yl)propan-1-one

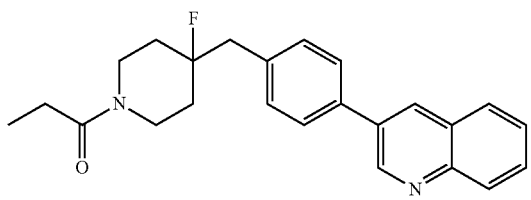 [SMILES: CCC(=O)N1CCC(F)(Cc2ccc(-c3cnc4ccccc4c3)cc2)CC1]

Step 1. 4-(4-Bromobenzyl)-4-fluoropiperidine-1-carboxylic acid tert-butyl ester and 4-(4-bromobenzyl)-3,6-dihydro-2H-pyridine-1-carboxylic acid tert-butyl ester To a DCM solution of tert-butyl 4-(4-bromobenzyl)-4-hydroxypiperidine-1-carboxylate (1.4 g, 3.71 mmol) at -70° C. was added diethylaminosulfur trifluoride (DAST) (1.21 g, 7.5 mmol) and stirred at same temperature for 1 h. The reaction mixture was warmed to −10° C. and stirred for 2h. Reaction mixture was diluted with DCM and washed successively with water and saturated potassium carbonate solution. The organic layer was washed with brine, dried over $Na_2SO_4$ and concentrated to dryness. Purification by column chromatography using silica gel (20% EtOAc/hexane) afforded (1:1) mixture of 4-(4-bromo-benzyl)-4-fluoro-piperidine-1-carboxylic acid tert-butyl ester and 4-(4-bromo-benzyl)-3,6-dihydro-2H-pyridine-1-carboxylic acid tert-butyl ester.

Step 2. 4-(4-Bromobenzyl)-4-fluoropiperidine and 4-(4-bromobenzyl)-1,2,3,6-tetrahydro-pyridine To a DCM solution of 4-(4-Bromo-benzyl)-4-fluoro-piperidine-1-carboxylic acid tert-butyl ester and 4-(4-Bromo-benzyl)-3,6-dihydro-2H-pyridine-1-carboxylic acid tert-butyl ester (0.5 g) was added TFA (0.5 mL) at 0° C. and the resulting mixture was stirred at rt for 3h. Volatiles were removed at reduced pressure. The resulting residue was triturated with diethyl ether to give 4-(4-bromobenzyl)-4-fluoropiperidine and 4-(4-bromo-benzyl)-1,2,3,6-tetrahydro-pyridine (0.5 g) as a mixture of the trifluoroacetic acid salts.

Step 3. 1-[4-(4-Bromobenzyl)-4-fluoropiperidin-1-yl]-propan-1-one and 1-[4-(4-Bromo-benzyl)-3,6-dihydro-2H-pyridin-1-yl]-propan-1-one To a solution of 4-(4-bromo-benzyl)-4-fluoro-piperidine and 4-(4-bromo-benzyl)-1,2,3,6-tetrahydro-pyridine (1 equiv) in DCM was added $Et_3N$ (3 equiv) followed by drop-wise addition of propanoyl chloride (1 equiv) at 0° C., and the reaction mixture was then stirred overnight at rt. The reaction mixture was diluted with DCM and washed with water, brine, dried over $Na_2SO_4$ and concentrated to dryness. The crude product thus obtained was purified by column chromatography using silica gel (20% EtOac/hexane) to afford a mixture of 1-[4-(4-bromo-benzyl)-4-fluoro-piperidin-1-yl]-propan-1-one and 1-[4-(4-bromo-benzyl)-3,6-dihydro-2H-pyridin-1-yl]-propan-1-one.

Step 4. 1-(4-fluoro-4-(4-(quinolin-3-yl)benzyl)piperidin-1-yl)propan-1-one, TFA Salt A solution of 1-[4-(4-bromobenzyl)-4-fluoro-piperidin-1-yl]-propan-1-one and 1-[4-(4-bromobenzyl)-3,6-dihydro-2H-pyridin-1-yl]-propan-1-one (1 equiv), quinolin-3-yl boronic acid (1 equiv) and $Na_2CO_3$ (2.5 equiv) in 1,4-dioxane and water (2:1) was degassed by argon for 1 h followed by addition of tetrakis(triphenylphosphine)-palladium(0) (0.05 equiv) and the resulting reaction mixture was heated at 100° C. after degassing again with argon, for 15h. The reaction mixture was then filtered through a bed of Celite. The filtrate was concentrated and purified by preparative HPLC to afford 1-(4-fluoro-4-(4-(quinolin-3-yl)benzyl)piperidin-1-yl)propan-1-one trifluoroacetic acid salt. LCMS (ESI): 377 (M+H); $^1$H NMR (DMSO-d6) δ: 9.37 (d, J=2.2 Hz, 1H), 8.85 (d, J=2.5 Hz, 1H), 8.12 (dd, J=10.5, 8.5 Hz, 2H), 7.86 (t, J=7.9 Hz, 3H), 7.73 (t, J=7.5 Hz, 1H), 7.42 (d, J=8.0 Hz, 2H), 4.22 (d, J=13.6 Hz, 1H), 3.74 (d, J=13.6 Hz, 1H), 4.00-3.18 (m, 1H), 3.07 (s, 1H), 3.01 (s, 1H), 2.9-2.85 (m, 1H), 2.32 (q, J=7.4 Hz, 2H), 1.79-1.47 (m, 4H), 0.97 (t, J=7.4 Hz, 3H).

Example 162

1-(4-(4-(quinolin-3-yl)benzyl)-5,6-dihydropyridin-1(2H)-yl)propan-1-one TFA Salt

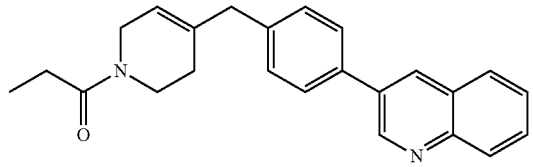 [SMILES: CCC(=O)N1CC=C(Cc2ccc(-c3cnc4ccccc4c3)cc2)CC1]

Following the steps described in Example 161, 1-(4-(4-(quinolin-3-yl)benzyl)-5,6-dihydropyridin-1(2H)-yl)propan-1-one was also isolated following Step 4 by preparative HPLC as the trifluoroacetic acid salt. LCMS (ESI): 357 (M+H); $^1$H NMR (Chloroform-d) δ 9.19 (s, 1H), 8.31 (s, 1H), 8.15 (d, J=8.5 Hz, 1H), 7.89 (d, J=8.1 Hz, 1H), 7.77-7.63 (m, 2H), 7.63-7.50 (m, 2H), 7.34 (d, J=7.7 Hz, 2H), 6.63 (d, J=8.3 Hz, 1H), 4.91-4.83 (m, 1H), 3.49-3.30 (m, 1H), 2.83-2.54 (m, 2H), 2.5-2.35 (m, 2H), 1.27 (d, J=12.5 Hz, 3H), 1.2-1.16 (m, 4H).

The following compounds were prepared in an analogous manner to Examples 161 and 162, using the specified acid chloride reagent in Step 3 and the specified boronic acid reagent in Step 4.

Example 163

1-(4-fluoro-4-(4-(quinolin-7-yl)benzyl)piperidin-1-yl)propan-1-one, TFA Salt

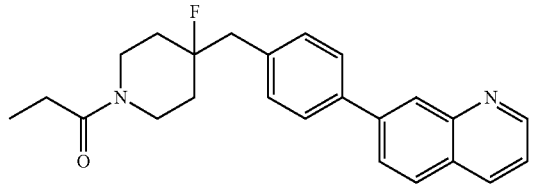 [SMILES: CCC(=O)N1CCC(F)(Cc2ccc(-c3ccc4cccnc4c3)cc2)CC1]

The title compound was synthesized using the procedure for Example 161, reacting with propionyl chloride in step 3, and with quinoline-7-boronic acid in Step 4. LCMS (ESI): 377 (M+H); ¹H NMR (Chloroform-d) δ: 8.95 (dd, J=4.5, 2.1 Hz, 1H), 8.33 (s, 1H), 8.19 (d, J=8.3 Hz, 1H), 7.94-7.79 (m, 2H), 7.71 (d, J=7.9 Hz, 2H), 7.41 (dd, J=8.3, 4.1 Hz, 1H), 7.33 (d, J=7.7 Hz, 2H), 4.51 (dd, J=13.0, 5.1 Hz, 1H), 3.76-3.66 (m, 1H), 3.34 (t, J=12.4 Hz, 1H), 3.08-2.85 (m, 3H), 2.35 (q, J=7.5 Hz, 2H), 1.92-1.81 (m, 3H), 1.6-1.57 (m, 1H), 1.14 (t, J=7.5 Hz, 3H).

Example 164

1-(4-(4-(quinolin-7-yl)benzyl)-5,6-dihydropyridin-1(2H)-yl)propan-1-one, TFA Salt

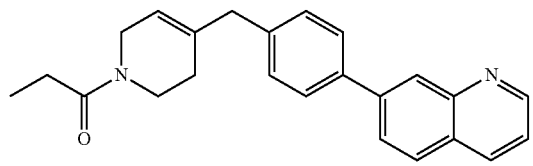 [SMILES: CCC(=O)N1CC=C(Cc2ccc(-c3ccc4cccnc4c3)cc2)CC1]

The title compound was synthesized using the procedure for Example 161/162, reacting with propionyl chloride in step 3, and with quinoline-7-boronic acid in Step 4. LCMS (ESI): 357 (M+H); ¹H NMR (Chloroform-d) δ: 8.95 (dd, J=4.2, 2.1 Hz, 1H), 8.33 (s, 1H), 8.19 (d, J=7.9 Hz, 1H), 7.93-7.79 (m, 2H), 7.74-7.62 (m, 2H), 7.41 (dd, J=8.3, 4.2 Hz, 1H), 7.34-7.18 (m, 2H), 5.55 (s, 1H), 4.10 (d, J=4.1 Hz, 1H), 3.96 (s, 1H), 3.69 (t, J=5.7 Hz, 1H), 3.51 (t, J=6.0 Hz, 1H), 3.39 (s, 2H), 2.39-2.31 (m, 2H), 2.08 (d, J=6.3 Hz, 2H), 1.15 (t, J=7.9 Hz, 3H).

Example 165

1-(4-fluoro-4-(4-(isoquinolin-6-yl)benzyl)piperidin-1-yl)propan-1-one, TFA Salt

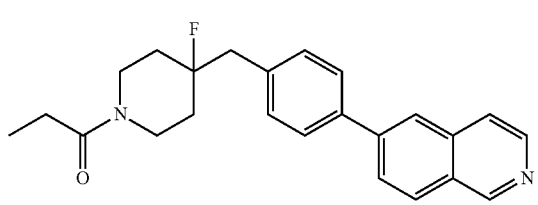 [SMILES: CCC(=O)N1CCC(F)(Cc2ccc(-c3ccc4cnccc4c3)cc2)CC1]

The title compound was synthesized using the procedure for Example 161, reacting with propionyl chloride in step 3, and with isoquinoline-6-boronic acid in Step 4. LCMS (ESI): 377 (M+H); ¹H NMR (Chloroform-d) δ: 9.32 (s, 1H), 8.54 (d, J=5.9 Hz, 1H), 8.10 (d, J=8.5 Hz, 1H), 8.04 (s, 1H), 7.92 (dd, J=8.6, 1.9 Hz, 1H), 7.77 (d, J=6.0 Hz, 1H), 7.71-7.42 (m, 2H), 7.35 (d, J=7.7 Hz, 2H), 4.51 (dd, J=13.0, 4.8 Hz, 1H), 3.76-3.67 (m, 1H), 3.43-3.28 (m, 1H), 3.05-2.84 (m, 2H), 2.43-2.25 (m, 2H), 1.92-1.79 (m, 3H), 1.74-1.50 (m, 2H), 1.14 (t, J=7.5 Hz, 3H).

Example 166

1-(4-(4-(isoquinolin-6-yl)benzyl)-5,6-dihydropyridin-1(2H)-yl)propan-1-one, TFA Salt

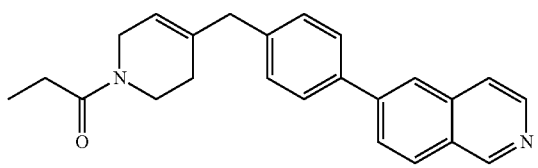 [SMILES: CCC(=O)N1CC=C(Cc2ccc(-c3ccc4cnccc4c3)cc2)CC1]

The title compound was synthesized using the procedure for Example 161/162, reacting with propionyl chloride in step 3, and with isoquinoline-6-boronic acid in Step 4. LCMS (ESI): 357 (M+H); ¹H NMR (CDCl₃) δ: 9.28 (s, 1H), 8.54 (d, J=5.8 Hz, 1H), 8.09-7.97 (m, 2H), 7.87 (d, J=8.6 Hz, 1H), 7.68 (dd, J=20.6, 6.8 Hz, 3H), 7.30 (d, J=7.8 Hz, 2H), 5.54 (s, 1H), 4.10 (s, 1H), 3.96 (s, 1H), 3.68 (t, J=5.9 Hz, 1H), 3.51 (t, J=5.8 Hz, 1H), 2.44 (s, 2H), 2.41-2.27 (m, 2H), 2.09 (d, J=5.3 Hz, 2H), 1.15 (t, J=7.5 Hz, 3H).

Example 167

1-(4-fluoro-4-(4-(isoquinolin-4-yl)benzyl)piperidin-1-yl)propan-1-one, TFA Salt

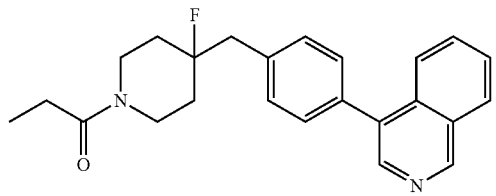 [SMILES: CCC(=O)N1CCC(F)(Cc2ccc(-c3cncc4ccccc34)cc2)CC1]

The title compound was synthesized using the procedure for Example 161, reacting with propionyl chloride in step 3, and with isoquinoline-4-boronic acid in Step 4. LCMS (ESI): 377 (M+H); ¹H NMR (400 MHz, Chloroform-d) δ 9.27 (s, 1H), 8.49 (s, 1H), 8.06 (d, J=7.9 Hz, 1H), 7.94 (d, J=8.3 Hz, 1H), 7.69-7.65 (m, 2H), 7.50-7.43 (m, 2H), 7.36 (d, J=7.7 Hz, 1H), 7.26 (s, 1H), 4.54 (dd, J=14.4, 4.8 Hz, 1H), 3.78-3.69 (m, 1H), 3.37 (t, J=13.2 Hz, 1H), 3.11-2.87 (m, 3H), 2.39-2.34 (m, 2H), 1.87 (s, 1H), 1.69-1.65 (m, 3H), 1.31-1.11 (m, 3H).

Example 168

1-(4-(4-(isoquinolin-4-yl)benzyl)-5,6-dihydropyridin-1(2H)-yl)propan-1-one, TFA Salt

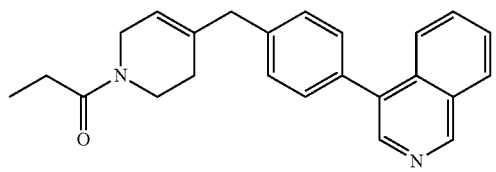 [SMILES: CCC(=O)N1CC=C(Cc2ccc(-c3cncc4ccccc34)cc2)CC1]

The title compound was synthesized using the procedure for Example 161/162, reacting with propionyl chloride in step 3, and with isoquinoline-4-boronic acid in Step 4. LCMS (ESI): 357 (M+H); $^1$H NMR (Chloroform-d) δ: 9.26 (s, 1H), 8.48 (s, 1H), 8.06 (d, J=7.9 Hz, 1H), 7.94 (d, J=8.4 Hz, 1H), 7.67 (dt, J=19.8, 7.3 Hz, 2H), 7.45 (d, J=7.8 Hz, 2H), 7.32 (d, J=7.7 Hz, 2H), 5.57 (s, 1H), 4.12 (s, 1H), 3.98 (s, 1H), 3.71 (t, J=5.9 Hz, 1H), 3.54 (t, J=5.8 Hz, 1H), 3.43 (s, 2H), 2.39-2.34 (m, 2H), 2.12 (d, J=6.4 Hz, 2H), 1.31-1.12 (m, 3H).

Example 169

1-(4-(4-(benzofuran-5-yl)benzyl)-4-fluoropiperidin-1-yl)propan-1-one, TFA Salt

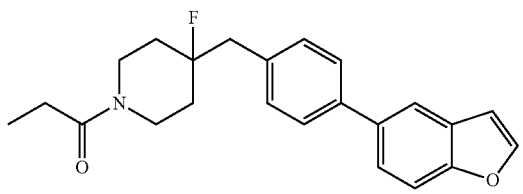 [SMILES: CCC(=O)N1CCC(F)(Cc2ccc(-c3ccc4occc4c3)cc2)CC1]

The title compound was synthesized using the procedure for Example 161, reacting with propionyl chloride in step 3, and with benzofuran-5-boronic acid in Step 4. LCMS (ESI): 366 (M+H); $^1$H NMR (400 MHz, Chloroform-d) δ: 7.78 (s, 1H), 7.66 (d, J=2.1 Hz, 1H), 7.55 (t, J=9.0 Hz, 3H), 7.30-7.23 (m, 2H), 7.17 (s, 1H), 6.82 (d, J=2.1 Hz, 1H), 4.55-4.46 (m, 1H), 3.75-3.65 (m, 1H), 3.33 (t, J=13.5 Hz, 1H), 3.02-2.84 (m, 2H), 2.38-2.34 (m, 2H), 1.91-1.80 (m, 3H), 1.59-1.56 (m, 2H), 1.14 (dd, J=8.4, 6.6 Hz, 3H).

Example 170

1-(4-(4-(benzofuran-5-yl)benzyl)-5,6-dihydropyridin-1(2H)-yl)propan-1-one, TFA Salt

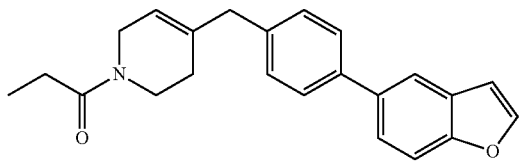 [SMILES: CCC(=O)N1CC=C(Cc2ccc(-c3ccc4occc4c3)cc2)CC1]

The title compound was synthesized using the procedure for Example 161/162, reacting with propionyl chloride in step 3, and with benzofuran-5-boronic acid in Step 4. LCMS (ESI): 346 (M+H); $^1$H NMR (400 MHz, Chloroform-d) δ 7.78 (s, 1H), 7.65 (d, J=2.1 Hz, 1H), 7.59-7.47 (m, 4H), 7.23 (d, J=7.6 Hz, 2H), 6.81 (s, 1H), 5.56 (s, 1H), 4.09 (s, 1H), 3.95 (d, J=3.7 Hz, 1H), 3.68 (t, J=5.7 Hz, 1H), 3.50 (t, J=5.7 Hz, 1H), 3.37 (s, 2H), 2.35-2.32 (m, 2H), 2.08 (s, 1H), 1.15 (t, J=7.4 Hz, 2H), 0.87 (q, J=11.2, 8.8 Hz, 2H).

Example 171

Cyclopropyl(4-fluoro-4-(4-(quinolin-3-yl)benzyl)piperidin-1-yl)methanone, TFA Salt

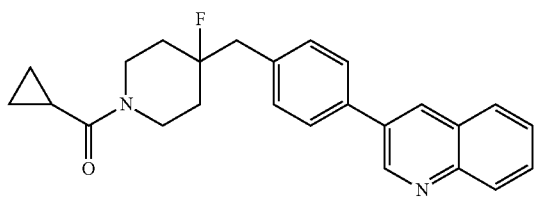 [SMILES: O=C(C1CC1)N1CCC(F)(Cc2ccc(-c3cnc4ccccc4c3)cc2)CC1]

The title compound was synthesized using the procedure for Example 161, reacting with cyclopropanecarbonyl chloride in step 3, and with quinoline-3-boronic acid in Step 4. LCMS (ESI): 389 (M+H); $^1$H NMR (DMSO-d6) δ: 9.35 (d, J=2.3 Hz, 1H), 8.82 (s, 1H), 8.11 (t, J=8.7 Hz, 2H), 7.91-7.78 (m, 3H), 7.72 (t, J=7.5 Hz, 1H), 7.43 (d, J=7.9 Hz, 2H), 4.61 (s, 1H), 4.45 (s, 1H), 4.12 (d, J=12.6 Hz, 1H), 3.08 (s, 1H), 3.03 (s, 1H), 2.84 (t, J=12.6 Hz, 1H), 2.0-1.97 (m, 1H), 1.79-1.65 (m, 4H), 0.74-0.65 (m, 4H).

Example 172

Cyclopropyl(4-(4-(quinolin-3-yl)benzyl)-5,6-dihydropyridin-1(2H)-yl)methanone, TFA Salt

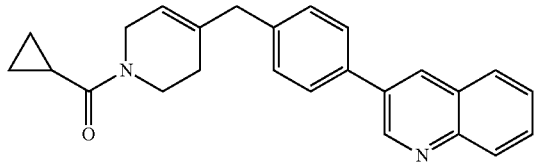 [SMILES: O=C(C1CC1)N1CC=C(Cc2ccc(-c3cnc4ccccc4c3)cc2)CC1]

The title compound was synthesized using the procedure for Example 161/162, reacting with cyclopropanecarbonyl chloride in step 3, and with quinoline-3-boronic acid in Step 4. LCMS (ESI): 369 (M+H); $^1$H NMR (400 MHz, Chloroform-d) δ: 9.19 (d, J=2.4 Hz, 1H), 8.31 (d, J=6.7 Hz, 1H), 8.14 (d, J=8.4 Hz, 1H), 7.89 (d, J=8.1 Hz, 1H), 7.77-7.63 (m, 4H), 7.58 (t, J=7.5 Hz, 1H), 7.35 (dd, J=16.0, 7.7 Hz, 1H), 5.57-5.51 (m, 1H), 3.8-3.72 (m, 3H), 3.41 (s, 2H), 2.14 (s, 1H), 2.09 (s, 1H), 1.27 (d, J=12.2 Hz, 2H), 0.74-0.65 (m, 4H).

Example 173

Cyclopropyl(4-fluoro-4-(4-(quinolin-7-yl)benzyl)piperidin-1-yl)methanone, TFA Salt

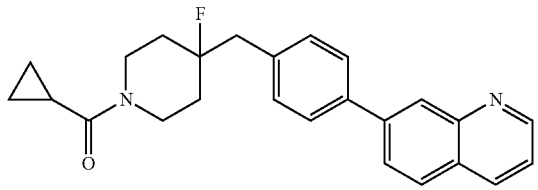 [SMILES: O=C(C1CC1)N1CCC(F)(Cc2ccc(-c3ccc4cccnc4c3)cc2)CC1]

The title compound was synthesized using the procedure for Example 161, reacting with cyclopropanecarbonyl chloride in step 3, and with quinoline-7-boronic acid in Step 4. LCMS (ESI): 389 (M+H); ¹H NMR (Chloroform-d) δ: 8.95 (dd, J=4.3, 2.1 Hz, 1H), 8.34 (s, 1H), 8.20 (d, J=8.2 Hz, 1H), 7.94-7.73 (m, 2H), 7.72 (d, J=7.8 Hz, 2H), 7.56-7.31 (m, 3H), 4.47 (s, 1H), 4.07 (d, J=13.5 Hz, 1H), 3.44 (t, J=13.1 Hz, 1H), 3.00-2.97 (m, 2H), 1.88 (q, J=12.0, 11.1 Hz, 2H), 1.80-1.58 (m, 3H), 1.25 (s, 1H), 0.97 (q, J=3.7 Hz, 2H), 0.75 (dd, J=7.9, 3.3 Hz, 2H).

Example 174

Cyclopropyl(4-(4-(quinolin-7-yl)benzyl)-5,6-dihydropyridin-1(2H)-yl)methanone, TFA Salt

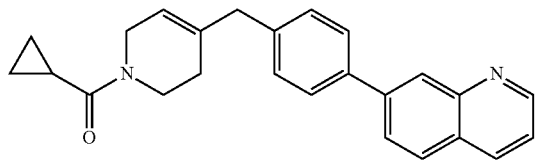 [SMILES: O=C(C1CC1)N1CC=C(Cc2ccc(-c3ccc4cccnc4c3)cc2)CC1]

The title compound was synthesized using the procedure for Example 161/162, reacting with cyclopropanecarbonyl chloride in step 3, and with quinoline-7-boronic acid in Step 4. LCMS (ESI): 369 (M+H); ¹H NMR (Chloroform-d) δ: 8.95 (d, J=4.2 Hz, 1H), 8.34 (s, 1H), 8.20 (d, J=8.3 Hz, 1H), 7.94-7.80 (m, 2H), 7.71 (d, J=7.8 Hz, 2H), 7.51-7.25 (m, 3H), 5.30 (s, 1H), 4.20 (s, 1H), 4.11 (s, 1H), 3.8-3.75 (m, 2H), 3.41 (s, 2H), 2.15 (s, 1H), 2.10 (s, 1H), 1.25 (s, 1H), 0.99-0.94 (m, 2H), 0.79-0.71 (m, 2H).

Example 175

Cyclopropyl(4-fluoro-4-(4-(isoquinolin-6-yl)benzyl)piperidin-1-yl)methanone, TFA Salt

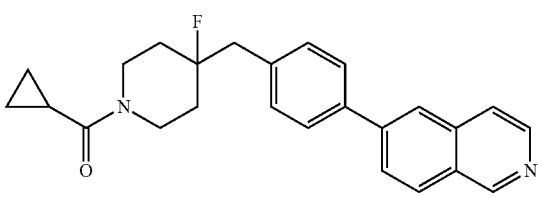 [SMILES: O=C(C1CC1)N1CCC(F)(Cc2ccc(-c3ccc4cnccc4c3)cc2)CC1]

The title compound was synthesized using the procedure for Example 161, reacting with cyclopropanecarbonyl chloride in step 3, and with isoquinoline-6-boronic acid in Step 4. LCMS (ESI): 389 (M+H); ¹H NMR (400 MHz, Chloroform-d) δ: 9.29 (s, 1H), 8.55 (d, J=5.7 Hz, 1H), 8.10-7.98 (m, 2H), 7.91-7.84 (m, 1H), 7.69 (dd, J=16.6, 6.4 Hz, 3H), 7.35 (d, J=7.9 Hz, 2H), 4.48 (d, J=13.4 Hz, 1H), 4.07 (d, J=12.5 Hz, 1H), 3.44 (t, J=13.4 Hz, 1H), 3.03 (s, 1H), 2.96 (d, J=12.5 Hz, 2H), 1.95-1.54 (m, 5H), 0.99-0.94 (m, 2H), 0.75 (dd, J=7.8, 3.3 Hz, 2H).

Example 176

Cyclopropyl(4-(4-(isoquinolin-6-yl)benzyl)-5,6-dihydropyridin-1(2H)-yl)methanone, TFA Salt

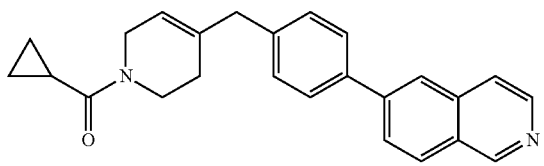 [SMILES: O=C(C1CC1)N1CC=C(Cc2ccc(-c3ccc4cnccc4c3)cc2)CC1]

The title compound was synthesized using the procedure for Example 161/162, reacting with cyclopropanecarbonyl chloride in step 3, and with isoquinoline-6-boronic acid in Step 4. LCMS (ESI): 369 (M+H); ¹H NMR (400 MHz, Chloroform-d) δ: 9.28 (s, 1H), 8.54 (d, J=5.7 Hz, 1H), 8.09-7.98 (m, 2H), 7.91-7.84 (m, 1H), 7.75-7.62 (m, 3H), 7.38-7.23 (m, 2H), 5.50 (d, J=19.4 Hz, 1H), 4.21 (d, J=4.3 Hz, 1H), 4.10 (s, 1H), 3.72-3.69 (m, 2H), 3.41 (s, 2H), 2.14 (s, 1H), 2.11-2.05 (m, 1H), 1.52-1.44 (m, 1H), 1.00 (s, 2H), 0.75 (d, J=8.5 Hz, 2H).

Example 177

Cyclopropyl(4-fluoro-4-(4-(isoquinolin-4-yl)benzyl)piperidin-1-yl)methanone, TFA Salt

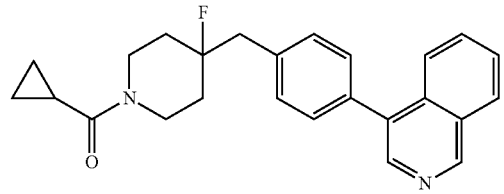 [SMILES: O=C(C1CC1)N1CCC(F)(Cc2ccc(-c3cncc4ccccc34)cc2)CC1]

The title compound was synthesized using the procedure for Example 161, reacting with cyclopropanecarbonyl chloride in step 3, and with isoquinoline-4-boronic acid in Step 4. LCMS (ESI): 389 (M+H); ¹H NMR (400 MHz, Chloroform-d) δ: 9.26 (s, 1H), 8.49 (d, J=1.7 Hz, 1H), 8.05 (d, J=7.9 Hz, 1H), 7.94 (d, J=8.3 Hz, 1H), 7.73-7.60 (m, 2H), 7.51-7.43 (m, 2H), 7.36 (d, J=7.6 Hz, 1H), 7.26 (s, 1H), 4.56-4.46 (m, 1H), 4.10 (dd, J=13.2, 5.1 Hz, 1H), 3.53-3.41 (m, 1H), 3.06 (s, 1H), 3.03-2.91 (m, 2H), 1.82-1.57 (m, 4H), 1.27 (d, J=12.0 Hz, 1H), 0.98 (q, J=3.7 Hz, 2H), 0.76-0.74 (m, 2H).

Example 178

Cyclopropyl(4-(4-(isoquinolin-4-yl)benzyl)-5,6-dihydropyridin-1(2H)-yl)methanone, TFA Salt

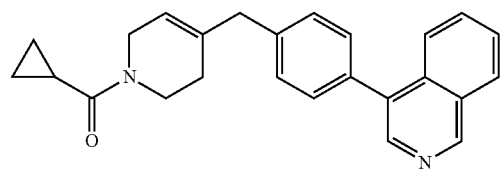 [SMILES: O=C(C1CC1)N1CC=C(Cc2ccc(-c3cncc4ccccc34)cc2)CC1]

The title compound was synthesized using the procedure for Example 161/162, reacting with cyclopropanecarbonyl chloride in step 3, and with isoquinoline-4-boronic acid in Step 4. LCMS (ESI): 369 (M+H); $^1$H NMR (400 MHz, CDCl$_3$) δ: 9.26 (s, 1H), 8.48 (d, J=1.5 Hz, 1H), 8.05 (d, J=7.9 Hz, 1H), 7.94 (d, J=8.3 Hz, 1H), 7.7-7.65 (m, 2H), 7.57-7.42 (m, 2H), 7.41-7.29 (m, 2H), 5.57 (s, 1H), 4.22 (s, 1H), 4.12 (s, 1H), 3.74 (dt, J=18.3, 5.8 Hz, 2H), 3.44 (s, 1H), 2.65-2.55 (m, 1H), 2.54-2.26 (m, 1H), 2.18 (s, 1H), 1.27 (d, J=12.0 Hz, 1H), 0.90-0.84 (m, 2H), 0.79-0.72 (m, 2H).

Example 179

(4-(4-(benzofuran-5-yl)benzyl)-4-fluoropiperidin-1-yl)(cyclopropyl)methanone, TFA Salt

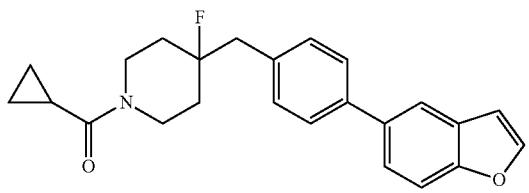 [SMILES: O=C(C1CC1)N1CCC(F)(Cc2ccc(-c3ccc4occc4c3)cc2)CC1]

The title compound was synthesized using the procedure for Example 161, reacting with cyclopropanecarbonyl chloride in step 3, and with benzofuran-6-boronic acid in Step 4. LCMS (ESI): 378 (M+H); $^1$H NMR (400 MHz, Chloroform-d) δ 7.78 (s, 1H), 7.66 (d, J=2.3 Hz, 1H), 7.60-7.43 (m, 5H), 7.29 (s, 1H), 6.82 (d, J=2.4 Hz, 1H), 4.47 (d, J=13.3 Hz, 1H), 4.06 (d, J=13.4 Hz, 1H), 3.43 (t, J=13.8 Hz, 1H), 3.0-2.95 (m, 2H), 1.87 (q, J=13.4, 12.9 Hz, 2H), 1.80-1.66 (m, 2H), 0.97 (q, J=3.7 Hz, 2H), 0.87 (dt, J=12.7, 7.7 Hz, 2H), 0.74 (dt, J=6.9, 3.5 Hz, 2H).

Example 180

(4-(4-(benzofuran-5-yl)benzyl)-5,6-dihydropyridin-1(2H)-yl)(cyclopropyl)methanone, TFA Salt

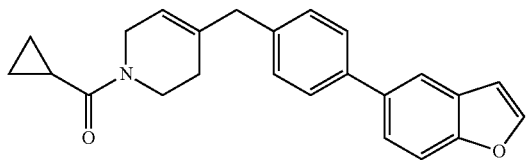 [SMILES: O=C(C1CC1)N1CC=C(Cc2ccc(-c3ccc4occc4c3)cc2)CC1]

The title compound was synthesized using the procedure for Example 161/162, reacting with cyclopropanecarbonyl chloride in step 3, and with benzofuran-6-boronic acid in Step 4. LCMS (ESI): 358 (M+H); $^1$H NMR (400 MHz, Chloroform-d) δ 7.78 (s, 1H), 7.72-7.41 (m, 5H), 7.24 (s, 1H), 7.13 (s, 1H), 6.82 (d, J=2.3 Hz, 1H), 5.46 (s, 1H), 4.19 (s, 1H), 4.10 (s, 1H), 3.78-3.72 (m, 2H), 3.38 (s, 1H), 2.11 (d, J=21.6 Hz, 2H), 1.73 (d, J=8.7 Hz, 2H), 1.26 (s, 2H), 0.87 (q, J=11.8, 9.1 Hz, 1H), 0.79-0.71 (m, 2H).

Example 181

(R)-(4-fluoro-4-(4-(4-methylquinolin-3-yl)benzyl)piperidin-1-yl)(tetrahydrofuran-2-yl)methanone

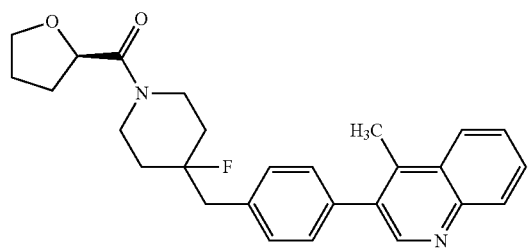 [SMILES: Cc1c(-c2ccc(CC3(F)CCN(C(=O)[C@H]4CCCO4)CC3)cc2)cnc2ccccc12]

Step 1. tert-butyl 4-hydroxy-4-(4-(4-methylquinolin-3-yl)benzyl)piperidine-1-carboxylate i) To a degassed solution of t-butyl 4-(4-bromobenzyl)-4-hydroxypiperidine-1-carboxylate (5.0 g, 13.5 mmol) in dioxane was added bispinacolatodiborane (5.1 g, 20.2 mmol), KOAc (1.98 g, 20.2 mmol) and bis(tricyclohexylphosphine)palladium(0) (0.9 g, 1.35 mmol) and heated at 100° C. for 15 h. The reaction was filtered through a bed of Celite and the filtrate was diluted with EtOAc and washed with water. The combined organic phases was concentrated to get the crude product which was triturated with pentane to give t-butyl 4-hydroxy-4-(4-(4,4,5,5-tetramethyl-1,3,2-dioxaborolan-2-yl)benzyl)piperidine-1-carboxylate (3.0 g, 53%) as white solid. LCMS (ESI): 318 (M+H-Boc)+.

ii) To a degassed solution of tert-butyl 4-hydroxy-4-(4-(4,4,5,5-tetramethyl-1,3,2-dioxaborolan-2-yl)benzyl)piperidine-1-carboxylate (1.4 g, 3.3 mmol), 3-bromo-4-methylquinoline (0.5 g, 2.25 mmol) and Na$_2$CO$_3$ (0.71 g, 6.7 mmol) in dioxane (10 mL) and water (2 mL) was added tetrakis(triphenylphosphine)palladium (0.26 g, 0.1 mmol) and the reaction mixture was heated at 100° C. for 16 h when TLC confirmed completion of reaction. The reaction was filtered through a bed of Celite and the filtrate was diluted with ethyl acetate and washed with water. The combined organic phases was concentrated to get the crude product which was purified by column chromatography using silica gel and 2-3% MeOH in DCM as eluent to give tert-butyl 4-hydroxy-4-(4-(4-methylquinolin-3-yl)benzyl)piperidine-1-carboxylate (0.4 g, 41%) as yellow oil. LCMS (ESI): 433 (M+H); 1H NMR (400 MHz, DMSO-d6) δ 8.73 (s, 1H), 8.23-8.16 (m, 1H), 8.04 (d, J=8.3 Hz, 1H), 7.78 (t, J=7.6 Hz, 1H), 7.73-7.64 (m, 1H), 7.36-7.32 (m, 4H), 3.68 (d, J=13.0 Hz, 2H), 3.05 (s, 2H), 2.77 (s, 2H), 2.63 (s, 3H), 1.36-1.43 (m, 13H).

Step 2. 4-(4-(4-methylquinolin-3-yl)benzyl)piperidin-4-ol

To a solution of tert-butyl 4-hydroxy-4-(4-(4-methylquinolin-3-yl)benzyl)piperidine-1-carboxylate (0.4 g, 0.9 mmol) in DCM (5 mL) was added trifluoroacetic acid (1 mL) at 0° C. and the reaction mixture was then stirred for 2 h at rt. Volatiles were removed at reduced pressure. Residue was triturated with diethyl ether to give 4-(4-(4-methylquinolin-3-yl)benzyl)piperidin-4-ol (0.29 g, 97%) as off-white solid. LCMS (ESI): 333 (M+H)

Step 3. General Protocols for Acylation Reaction

Method 1: To a solution of the product from Step 2 above (1 equiv) in DCM (10 mL) was added at 0° C., Et₃N (3 equiv) and acid chloride (1.5 equiv) and the reaction mixture was stirred for 3 h at rt. On completion of reaction, the reaction mixture was diluted with DCM and washed with water. The organic layer was washed with brine, dried over Na₂SO₄, filtered and concentrated. The crude product was purified by column chromatography using silica gel and 2-3% MeOH/DCM as eluent.

Method 2: (R)-tetrahydrofuran-2-carboxylic acid (1.5 equiv) was added to a solution of HATU (1.5 equiv), and DIPEA (3 equiv) in DMF and stirred for 20 minutes. The product from Step 2 above (1 equiv) was added to the reaction mixture and stirred at rt for 15h. On completion of reaction, the reaction mixture was diluted with EtOAc and washed with water. The organic extract was concentrated and the crude product was purified by column chromatography using silica gel and 2-5% MeOH/DCM as eluent.

Step 4. (R)-(4-fluoro-4-(4-(4-methylquinolin-3-yl)benzyl)piperidin-1-yl)(tetrahydrofuran-2-yl)methanone General protocol for DAST reaction: DAST (2 equiv) was added to a solution of the product from Step 3 above (1 equiv) in DCM at −78° C. and stirred for 1 h followed by stirring at −10° C. for 2h. On completion of the reaction, the reaction mixture was quenched with water and extracted with DCM. The organic extract was concentrated and the crude product was purified by preparative HPLC to afford the fluorinated product after free basing the isolated trifluoroacetic acid salt.

(R)-(4-fluoro-4-(4-(4-methylquinolin-3-yl)benzyl)piperidin-1-yl)(tetrahydrofuran-2-yl)methanone. LCMS (ESI): LCMS (ESI): 433 (M+H); ¹H NMR (400 MHz, DMSO-d6) δ 8.74 (s, 1H), 8.20 (dd, J=8.4, 1.5 Hz, 1H), 8.05 (dd, J=8.3, 1.3 Hz, 1H), 7.8-7.76 (m, 1H), 7.7-7.65 (m, 1H), 7.45-7.37 (m, 4H), 4.66 (dd, J=7.7, 5.6 Hz, 1H), 4.18 (d, J=11.9 Hz, 1H), 3.90 (d, J=13.9 Hz, 1H), 3.81-3.67 (m, 2H), 3.30-3.15 (m, 1H), 3.07 (s, 1H), 3.02 (s, 1H), 2.84 (q, J=11.8 Hz, 1H), 2.62 (s, 3H), 2.0-1.98 (m, 2H), 1.89-1.63 (m, 6H).

Example 182

(R)-(4-(4-(4-methylquinolin-3-yl)benzyl)-5,6-dihydropyridin-1(2H)-yl)(tetrahydrofuran-2-yl)methanone, HCl

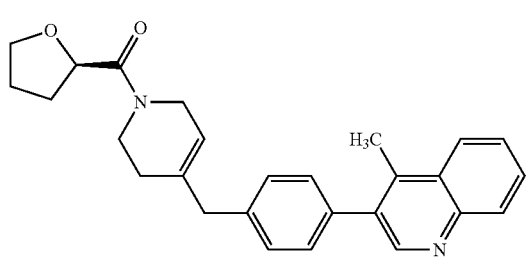 [SMILES: Cc1c(-c2ccc(CC3=CCN(C(=O)[C@H]4CCCO4)CC3)cc2)cnc2ccccc12]

Following the steps described in Example 181, (R)-(4-(4-(4-methylquinolin-3-yl)benzyl)-5,6-dihydropyridin-1(2H)-yl)(tetrahydrofuran-2-yl)methanone was also isolated following Step 4 by preparative HPLC after free basing the trifluoroacetic acid salt and subsequent hydrochloride salt formation.

Analysis: LCMS (ESI): 413 (M+H); ¹H NMR (400 MHz, DMSO-d6) δ: 8.74 (s, 1H), 8.20 (d, J=8.3 Hz, 1H), 8.04 (d, J=8.4 Hz, 1H), 7.83-7.74 (m, 1H), 7.73-7.64 (m, 1H), 7.45-7.31 (m, 4H), 5.56-5.50 (m, 1H), 4.70-4.60 (m, 1H), 4.15-3.66 (m, 4H), 3.59-3.51 (m, 2H), 3.43-3.37 (m, 2H), 2.62 (s, 3H), 2.10-1.89 (m, 4H), 1.91-1.73 (m, 2H).

The following compounds were prepared in an analogous manner to Examples 181 and 182, using the specified boronic acid or pinacol ester in Step 1 (with non-commercial boronic esters generated when appropriate) and the specified acid chloride in Step 3.

Example 183

Cyclopropyl(4-fluoro-4-(4-(8-methylquinolin-7-yl)benzyl)piperidin-1-yl)methanone, HCl

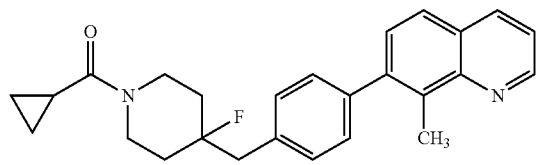 [SMILES: Cc1c(-c2ccc(CC3(F)CCN(C(=O)C4CC4)CC3)cc2)ccc2cccnc12]

Analysis: LCMS (ESI): 403 (M+H); ¹H NMR (400 MHz, DMSO-d6) δ 9.16-9.04 (m, 1H), 8.78-8.64 (m, 1H), 8.09-7.97 (m, 1H), 7.83-7.73 (m, 1H), 7.71-7.58 (m, 1H), 7.52-7.29 (m, 4H), 4.28-4.10 (m, 2H), 3.37-3.25 (m, 2H), 3.13-2.98 (m, 2H), 2.92-2.80 (m, 1H), 2.69 (s, 3H), 2.05-1.92 (m, 1H), 1.86-1.62 (m, 4H), 0.79-0.62 (m, 4H)

Example 184

Cyclopropyl(4-(4-(8-methylquinolin-7-yl)benzyl)-3,6-dihydropyridin-1(2H)-yl)methanone, HCl

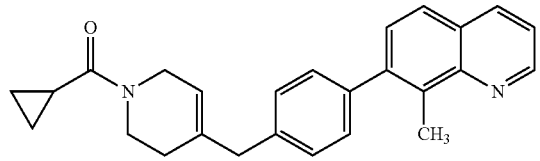 [SMILES: Cc1c(-c2ccc(CC3=CCN(C(=O)C4CC4)CC3)cc2)ccc2cccnc12]

Analysis: LCMS (ESI): 383 (M+H); ¹H NMR (400 MHz, DMSO-d6) δ 9.07-9.01 (m, 1H), 8.77-8.71 (m, 1H), 8.08-7.99 (m, 1H), 7.84-7.76 (m, 1H), 7.66-7.61 (m, 1H), 7.43-7.30 (m, 4H), 5.58-5.48 (m, 1H), 4.23-4.15 (m, 1H), 3.95-3.90 (m, 1H), 3.73-3.69 (m, 1H), 3.54-3.49 (m, 1H), 3.42-3.35 (m, 2H), 2.71-2.66 (m, 1H), 2.65 (s, 3H), 2.15-2.02 (m, 1H), 1.99-1.92 (m, 1H), 0.76-0.63 (m, 4H)

Example 185

1-(4-fluoro-4-(4-(8-methylquinolin-7-yl)benzyl)piperidin-1-yl)propan-1-one, HCl

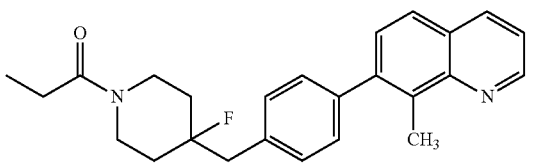 [SMILES: CCC(=O)N1CCC(F)(Cc2ccc(-c3ccc4cccnc4c3C)cc2)CC1]

Analysis: LCMS (ESI): 391 (M+H); $^1$H NMR (400 MHz, DMSO-d6) δ 9.11 (dd, J=4.5, 1.5 Hz, 1H) 8.67-8.86 (m, 1H) 8.06 (d, J=8.5 Hz, 1H) 7.81 (dd, J=7.7, 4.6 Hz, 1H) 7.66 (d, J=8.3 Hz, 1H) 7.32-7.49 (m, 4H) 4.16-4.31 (m, 1H) 3.70-3.84 (m, 1H) 3.14-3.28 (m, 1H) 2.98-3.11 (m, 2H) 2.76-2.89 (m, 1H) 2.70 (s, 3H) 2.33 (q, J=7.3 Hz, 2H) 1.48-1.85 (m, 4H) 0.98 (t, J=7.4 Hz, 3H); 19F NMR (377 MHz, DMSO-d6) δ−158.46 (s, 1F)

Example 185 may also be Prepared by the Following Alternative Steps

Step 1. 1-(4-{Chloro-[4-(8-methyl-quinolin-7-yl)-phenyl]-methyl}-4-fluoro-piperidin-1-yl)-propan-1-one Thionyl chloride (1.60 mL, 21.9 mmol) was added to a solution of 1-(4-Fluoro-4-{hydroxy-[4-(8-methyl-quinolin-7-yl)-phenyl]-methyl}-piperidin-1-yl)-propan-1-one (1.10 g, 2.71 mmol, Example 189) in DCM (55 mL) and stirred at room temperature overnight. The mixture was partitioned between aq. satd. sodium bicarbonate (50 mL) and ethyl acetate (100 mL). The layers were separated, the aq. was back extracted with ethyl acetate (20 mL) and the combined organics were washed with satd. aq. sodium bicarbonate (50 mL) and brine (50 mL), dried over sodium sulfate and filtered. The filtrate was concentrated in vacuo to afford 1-(4-{Chloro-[4-(8-methyl-quinolin-7-yl)-phenyl]-methyl}-4-fluoro-piperidin-1-yl)-propan-1-one (0.552 g, 48%).

Step 2. 1-(4-fluoro-4-(4-(8-methylquinolin-7-yl)benzyl)piperidin-1-yl)propan-1-one, HCl 1-(4-{Chloro-[4-(8-methyl-quinolin-7-yl)-phenyl]-methyl}-4-fluoro-piperidin-1-yl)-propan-1-one was dissolved in toluene (27.0 mL) and combined with 2,2'-azo-bis-isobutyronitrile (22.2 mg, 0.135 mmol) and tris(trimethylsilyl)silane (2.50 mL, 8.12 mmol). The mixture was then heated to 85° C. for 1 h, then at 100° C. for 5 h. A second aliquot of 2,2'-azo-bis-isobutyronitrile (20 mg) was added to further drive the reaction. After 2 additional hours, ca. 95% conversion was achieved. The mixture was concentrated then redissolved in DCM and methanol, then washed with 50% satd. sodium chloride, then brine. The organic layer was dried over sodium sulfate, filtered and concentrated in vacuo onto silica gel/Celite (4 g:4 g). Purification on silica gel (80 g, 20-90% ethyl acetate:hexane) afforded the free base after concentration in vacuo. This residue was dissolved in ethyl acetate (20 mL) then treated with 2M HCl in ether (3 mL) with stirring, generating a white solid. Concentration in vacuo afforded 1-{4-Fluoro-4-[4-(8-methyl-quinolin-7-yl)-benzyl]-piperidin-1-yl}-propan-1-one hydrochloride (0.451 g, 39%).

Example 186

1-(4-(4-(8-methylquinolin-7-yl)benzyl)-3,6-dihydropyridin-1(2H)-yl)propan-1-one, HCl

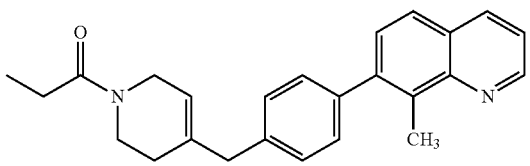 [SMILES: CCC(=O)N1CC=C(Cc2ccc(-c3ccc4cccnc4c3C)cc2)CC1]

Analysis: LCMS (ESI): 371 (M+H); $^1$H NMR (400 MHz, DMSO-d6) δ 9.16-9.06 (m, 1H), 8.88 (d, J=8.4 Hz, 1H), 8.09 (d, J=8.4 Hz, 1H), 7.89 (dd, J=8.4, 4.9 Hz, 1H), 7.69 (d, J=8.4 Hz, 1H), 7.42-7.29 (m, 4H), 5.58-5.46 (m, 1H), 3.99-3.87 (m, 2H), 3.51-3.44 (m, 2H), 3.41-3.33 (m, 2H), 2.67 (s, 3H), 2.34-2.25 (m, 2H), 2.09-2.00 (m, 1H), 1.99-1.92 (m, 1H), 0.95 (t, J=7.3 Hz, 3H).

Example 187

(R)-(4-fluoro-4-(4-(quinolin-7-yl)benzyl)piperidin-1-yl)(tetrahydrofuran-2-yl)methanone

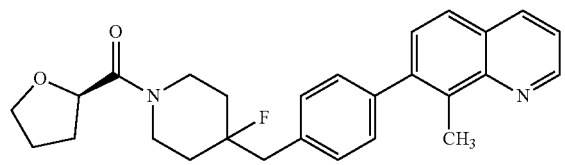 [SMILES: Cc1c(-c2ccc(CC3(F)CCN(C(=O)[C@H]4CCCO4)CC3)cc2)ccc2cccnc12]

Analysis: LCMS (ESI): 419 (M+H); $^1$H NMR (400 MHz, DMSO-d6) δ 8.93 (dd, J=4.2, 1.7 Hz, 1H), 8.43-8.36 (m, 1H), 8.27 (d, J=1.8 Hz, 1H), 8.07 (d, J=8.6 Hz, 1H), 7.96 (dd, J=8.5, 1.9 Hz, 1H), 7.85-7.78 (m, 2H), 7.54 (dd, J=8.3, 4.2 Hz, 1H), 7.39 (dd, J=7.6, 1.5 Hz, 2H), 4.69-4.61 (m, 1H), 4.18 (s, 1H), 3.88 (d, J=13.9 Hz, 1H), 3.81-3.67 (m, 2H), 3.25-3.16 (m, 1H), 3.06 (s, 1H), 3.00 (s, 1H), 2.83 (q, J=11.8 Hz, 1H), 2.10-1.88 (m, 2H), 1.88-1.62 (m, 6H).

Example 188

(R)-(4-(4-(quinolin-7-yl)benzyl)-5,6-dihydropyridin-1(2H)-yl)(tetrahydrofuran-2-yl)methanone, HCl

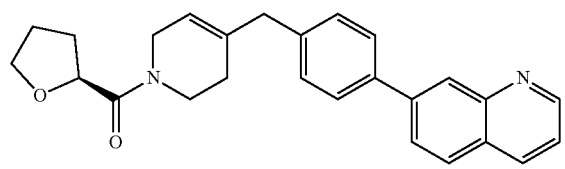 [SMILES: O=C([C@@H]1CCCO1)N1CC=C(Cc2ccc(-c3ccc4cccnc4c3)cc2)CC1]

Analysis: LCMS (ESI): 399 (M+H); $^1$H NMR (400 MHz, DMSO-d6) δ 9.11 (d, J=4.5 Hz, 1H), 8.89 (d, J=8.4 Hz, 1H), 8.36-8.26 (m, 2H), 8.17 (d, J=8.6 Hz, 1H), 7.84 (dd, J=20.4, 8.0 Hz, 3H), 7.38 (d, J=7.8 Hz, 2H), 5.51 (s, 1H), 4.61 (q, J=6.7 Hz, 1H), 3.90 (d, J=17.0 Hz, 1H), 3.72-3.64 (m, 2H), 3.61-3.35 (m, 5H), 2.0-1.96 (m, 4H), 1.80-1.72 (m, 2H).

Example 189

(R)-(4-fluoro-4-(4-(quinolin-3-yl)benzyl)piperidin-1-yl)(tetrahydrofuran-2-yl)methanone

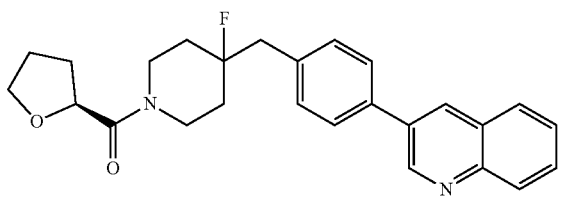 [SMILES: O=C([C@@H]1CCCO1)N1CCC(F)(Cc2ccc(-c3cnc4ccccc4c3)cc2)CC1]

Analysis: LCMS (ESI): 419 (M+H); $^1$H NMR (400 MHz, DMSO-d6) δ 9.26 (d, J=2.4 Hz, 1H), 8.64 (d, J=2.4 Hz, 1H), 8.05 (dd, J=8.3, 1.4 Hz, 2H), 7.88-7.73 (m, 3H), 7.65 (t, J=7.7 Hz, 1H), 7.41 (d, J=7.5 Hz, 2H), 4.65 (t, J=6.6 Hz, 1H), 4.18 (t, J=11.6 Hz, 1H), 3.88 (d, J=13.7 Hz, 1H), 3.73 (h, J=7.1 Hz, 2H), 3.25-3.21 (m, 1H), 3.06 (s, 1H), 3.01 (s, 1H), 2.83 (q, J=11.7 Hz, 1H), 2.01-1.98 (m, 2H), 1.90-1.61 (m, 6H).

Example 190

(R)-(4-(4-(quinolin-3-yl)benzyl)-5,6-dihydropyridin-1(2H)-yl)(tetrahydrofuran-2-yl)methanone

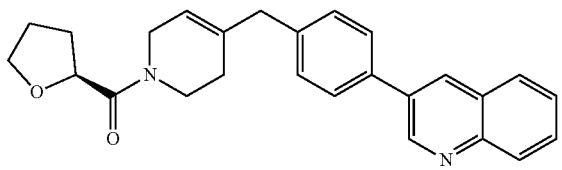 [SMILES: O=C([C@@H]1CCCO1)N1CC=C(Cc2ccc(-c3cnc4ccccc4c3)cc2)CC1]

Analysis: LCMS (ESI): 399 (M+H); $^1$H NMR (400 MHz, methanol-d4) δ9.13 (d, J=2.3 Hz, 1H), 8.62-8.52 (m, 1H), 8.09-7.98 (m, 2H), 7.85-7.71 (m, 3H), 7.7-7.64 (m, 1H), 7.47-7.34 (m, 2H), 5.59-5.46 (m, 1H), 4.73-4.69 (m, 1H), 4.18-3.77 (m, 4H), 3.74-3.52 (m, 2H), 3.43 (s, 2H), 2.26-1.85 (m, 6H).

Example 191

Cyclopropyl(4-fluoro-4-(4-(4-methylquinolin-3-yl)benzyl)piperidin-1-yl)methanone

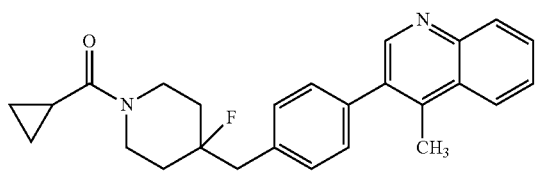 [SMILES: Cc1c(-c2ccc(CC3(F)CCN(C(=O)C4CC4)CC3)cc2)cnc2ccccc12]

Analysis: LCMS (ESI): 403 (M+H); $^1$H NMR (400 MHz, DMSO-d6) δ 8.75 (s, 1H), 8.24-8.16 (m, 1H), 8.05 (d, J=8.4 Hz, 1H), 7.81-7.76 (m, 1H), 7.7-7.68 (m, 1H), 7.41 (q, J=7.9 Hz, 4H), 4.22-4.09 (m, 2H), 3.29 (d, J=10.3 Hz, 1H), 3.09 (s, 1H), 3.03 (s, 1H), 2.85 (s, 1H), 2.63 (s, 3H), 2.00-1.98 (m, 1H), 1.78 (s, 1H), 1.73 (s, 3H), 0.74-0.65 (m, 4H).

Example 192

Cyclopropyl(4-(4-(4-methylquinolin-3-yl)benzyl)-5,6-dihydropyridin-1(2H)-yl)methanone

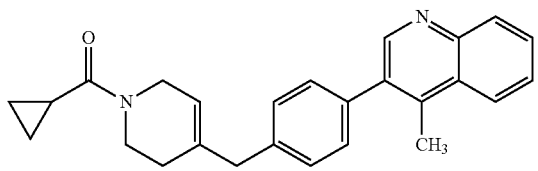

Analysis: LCMS (ESI): 383 (M+H); $^1$H NMR (400 MHz, DMSO-d6) δ 8.75 (s, 1H), 8.22-8.15 (m. 1H), 8.05 (dd, J=8.4, 1.4 Hz, 1H), 7.90-7.79 (m, 1H), 7.7-7.68 (m, 1H), 7.49-7.32 (m, 4H), 5.55 (s, 1H), 4.21 (s, 1H), 3.94 (d, J=4.2 Hz, 1H), 3.78-3.70 (m, 1H), 3.55 (t, J=5.5 Hz, 1H), 3.42 (s, 2H), 2.63 (s, 3H), 1.99 (s, 2H), 1.24 (d, J=4.0 Hz, 1H), 0.71 (d, J=9.6 Hz, 4H).

Example 193

1-(4-(4-(4-chloroquinolin-3-yl)benzyl)-4-fluoropiperidin-1-yl)propan-1-one

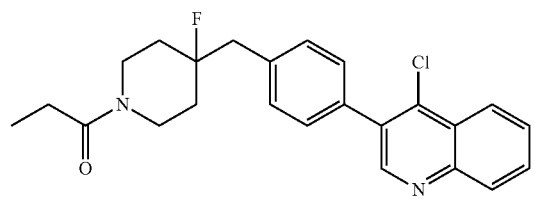 [SMILES: CCC(=O)N1CCC(F)(Cc2ccc(-c3cnc4ccccc4c3Cl)cc2)CC1]

Analysis: LCMS (ESI): 411 (M+H); $^1$H NMR (400 MHz, DMSO-d6) δ 8.94-8.92 (m, 1H), 8.33 (d, J=7.5 Hz, 1H), 8.15 (d, J=7.9 Hz, 1H), 7.96-7.88 (m, 1H), 7.87-7.79 (m, 1H), 7.58 (d, J=8.1 Hz, 2H), 7.41 (d, J=7.9 Hz, 2H), 4.30-4.15 (m, 1H), 3.82-3.69 (m, 1H), 3.25-3.13 (m, 1H), 3.11-2.99 (m, 2H), 2.87-2.75 (m, 1H), 2.33 (q, J=7.5 Hz, 2H), 1.82-1.51 (m, 4H), 0.98 (t, J=7.4 Hz, 3H).

Example 194

1-(4-(4-(4-Chloroquinolin-3-yl)benzyl)-3,6-dihydropyridin-1(2H)-yl)propan-1-one

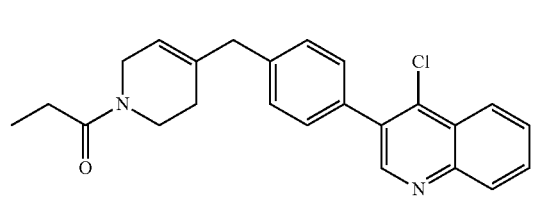 [SMILES: CCC(=O)N1CC=C(Cc2ccc(-c3cnc4ccccc4c3Cl)cc2)CC1]

Analysis: LCMS (ESI): 391 (M+H); $^1$H NMR (400 MHz, DMSO-d6) δ 8.89 (s, 1H), 8.33 (d, J=7.7 Hz, 1H), 8.15 (d, J=7.7 Hz, 1H), 7.97-7.87 (m, 1H), 7.86-7.80 (m, 1H), 7.60-7.54 (m, 2H), 7.40-7.34 (m, 2H), 5.59-5.50 (m, 1H), 4.00-3.91 (m, 2H), 3.58-3.45 (m, 2H), 3.45-3.38 (m, 2H), 2.37-2.25 (m, 2H), 2.12-1.94 (m, 2H), 0.97 (t, J=7.7 Hz, 3H).

Example 195

1-(4-Fluoro-4-(4-(4-methylquinolin-3-yl)benzyl)piperidin-1-yl)propan-1-one

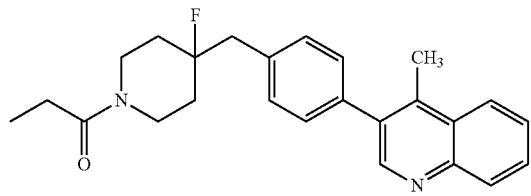 [SMILES: CCC(=O)N1CCC(F)(Cc2ccc(-c3cnc4ccccc4c3C)cc2)CC1]

Analysis: LCMS (ESI): 391 (M+H); $^1$H NMR (400 MHz, DMSO-d6) δ 8.74 (s, 1H), 8.20 (d, J=8.5 Hz, 1H), 8.05 (d, J=8.3 Hz, 1H), 7.83-7.74 (m, 1H), 7.69 (t, J=7.6 Hz, 1H), 7.47-7.35 (m, 4H), 4.23 (d, J=13.0 Hz, 1H), 3.75 (d, J=13.7 Hz, 1H), 3.26-3.14 (m, 1H), 3.07 (s, 1H), 3.01 (s, 1H), 2.81 (t, J=12.1 Hz, 1H), 2.63 (s, 3H), 2.33 (q, J=7.4 Hz, 2H), 1.77-1.65 (m, 4H), 0.98 (t, J=7.4 Hz, 3H).

Example 196

1-(4-(4-(4-Methylquinolin-3-yl)benzyl)-5,6-dihydropyridin-1(2H)-yl)propan-1-one

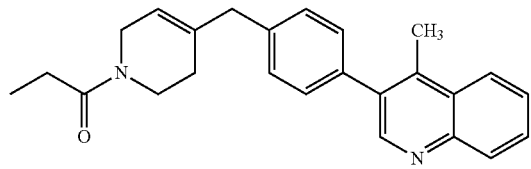

LCMS (ESI): 371 (M+H); $^1$H NMR (400 MHz, DMSO-d6) δ 8.74 (s, 1H), 8.20 (d, J=8.3 Hz, 1H), 8.04 (d, J=8.3 Hz, 1H), 7.83-7.73 (m, 1H), 7.73-7.64 (m, 1H), 7.42 (d, J=7.7 Hz, 2H), 7.34 (d, J=7.8 Hz, 2H), 5.55 (s, 1H), 3.99-3.91 (m, 1H), 3.53-3.51 (m, 2H), 3.41 (d, J=4.8 Hz, 2H), 2.62 (s, 3H), 2.49 (s, 1H), 2.35-2.31 (m, 2H), 2.06 (d, J=5.9 Hz, 1H), 1.98 (d, J=5.6 Hz, 1H), 0.97 (t, J=7.4 Hz, 3H).

Example 197

(4-(4-(4-Chloroquinolin-3-yl)benzyl)-4-fluoropiperidin-1-yl)(cyclopropyl)-methanone

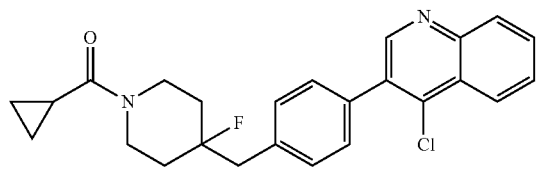 [SMILES: O=C(C1CC1)N1CCC(F)(Cc2ccc(-c3cnc4ccccc4c3Cl)cc2)CC1]

Analysis: LCMS (ESI): 423 (M+H); $^1$H NMR (400 MHz, DMSO-d6) δ 8.90 (s, 1H), 8.33 (d, J=7.5 Hz, 1H), 8.15 (d, J=8.1 Hz, 1H), 7.96-7.87 (m, 1H), 7.87-7.80 (m, 1H), 7.58 (d, J=8.1 Hz, 2H), 7.42 (d, J=7.9 Hz, 2H), 4.29-4.05 (m, 2H), 3.13-3.00 (m, 2H), 2.92-2.80 (m, 1H), 2.63-2.51 (m, 2H), 2.09-1.94 (m, 1H), 1.87-1.52 (m, 4H), 0.78-0.63 (m, 3H).

Example 198

(4-(4-(4-Chloroquinolin-3-yl)benzyl)-3,6-dihydropyridin-1(2H)-yl)(cyclopropyl)methanone

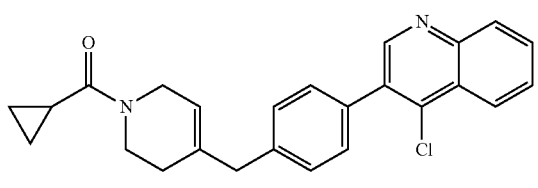 [SMILES: O=C(C1CC1)N1CC=C(Cc2ccc(-c3cnc4ccccc4c3Cl)cc2)CC1]

Analysis: LCMS (ESI): 403 (M+H); $^1$H NMR (400 MHz, DMSO-d6) δ 8.90 (s, 1H), 8.33 (dd, J=8.3, 0.8 Hz, 1H), 8.15 (d, J=7.9 Hz, 1H), 7.96-7.88 (m, 1H), 7.88-7.79 (m, 1H), 7.57 (d, J=7.9 Hz, 2H), 7.38 (d, J=8.3 Hz, 2H), 5.56 (br. s. 1H), 4.21 (br. s., 1H), 3.95 (br. s., 1H), 3.79-3.70 (m, 1H), 3.59-3.52 (m, 1H), 3.46-3.40 (m, 2H), 2.19-1.87 (m, 3H), 0.79-0.63 (m, 4H).

Example 199

(R)-(4-fluoro-4-(4-(8-methylquinolin-7-yl)benzyl)piperidin-1-yl)(tetrahydrofuran-2-yl)methanone, HCl

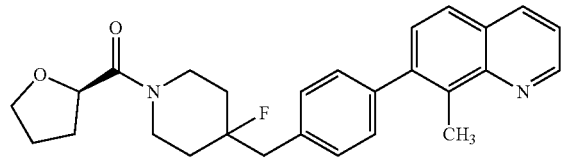 [SMILES: Cc1c(-c2ccc(CC3(F)CCN(C(=O)[C@H]4CCCO4)CC3)cc2)ccc2cccnc12]

Analysis: LCMS (ESI): 433 (M+H); $^1$H NMR (400 MHz, DMSO-d6) δ 9.08-9.01 (m, 1H), 8.76 (d, J=7.7 Hz, 1H), 8.04 (d, J=8.5 Hz, 1H), 7.88-7.76 (m, 1H), 7.65 (d, J=8.1 Hz, 1H), 7.43-7.33 (m, 4H), 4.64 (t, J=6.5 Hz, 1H), 4.22-4.10 (m, 1H), 3.78-3.70 (m, 3H), 3.25-3.12 (m, 1H), 3.06-2.95 (m, 2H), 2.88-2.74 (m, 1H), 2.65 (s, 3H), 2.09-1.87 (m, 3H), 1.87-1.66 (m, 5H).

Example 200

(R)-(4-(4-(8-methylquinolin-7-yl)benzyl)-3,6-dihydropyridin-1(2H)-yl)(tetrahydrofuran-2-yl)methanone, HCl

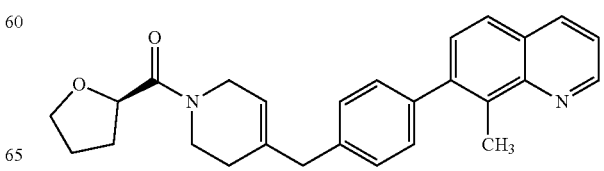

Analysis: LCMS (ESI): 413 (M+H); ¹H NMR (400 MHz, DMSO-d6) δ 9.07-9.02 (m, 1H), 8.77 (d, J=8.1 Hz, 1H), 8.04 (d, J=8.5 Hz, 1H), 7.82 (dd, J=8.5, 4.8 Hz, 1H), 7.65 (d, J=8.5 Hz, 1H), 7.40-7.30 (m, 4H), 5.51 (br. s. 1H), 4.67-4.58 (m, 1H), 3.70-3.66 (m, 1H), 3.52-3.41 (m, 2H), 3.39-3.35 (m, 2H), 2.65 (s, 4H), 2.07-1.72 (m, 8H).

Example 201

(R)-(4-(4-(4-chloroquinolin-3-yl)benzyl)-4-fluoropiperidin-1-yl)(tetrahydrofuran-2-yl)methanone

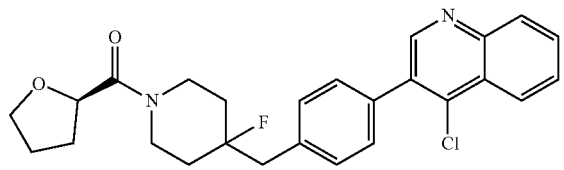 [SMILES: O=C([C@H]1CCCO1)N1CCC(F)(Cc2ccc(-c3cnc4ccccc4c3Cl)cc2)CC1]

Analysis: LCMS (ESI): 453 (M+H); ¹H NMR (400 MHz, DMSO-d6) δ 8.90 (s, 1H), 8.36-8.29 (m, 1H), 8.15 (d, J=7.9 Hz, 1H), 7.96-7.88 (m, 1H), 7.86-7.80 (m, 1H), 7.58 (d, J=8.1 Hz, 2H), 7.41 (d, J=7.5 Hz, 2H), 4.70-4.62 (m, 1H), 4.26-4.14 (m, 1H), 3.96-3.86 (m, 1H), 3.81-3.67 (m, 2H), 3.29-3.15 (m, 1H), 3.11-3.00 (m, 2H), 2.91-2.77 (m, 1H), 2.11-1.92 (m, 2H), 1.88-1.52 (m, 6H).

Example 202

(R)-(4-(4-(4-chloroquinolin-3-yl)benzyl)-3,6-dihydropyridin-1(2H)-yl)(tetrahydrofuran-2-yl)methanone

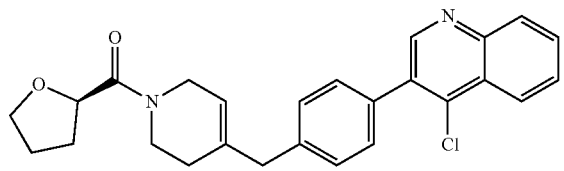 [SMILES: O=C([C@H]1CCCO1)N1CC=C(Cc2ccc(-c3cnc4ccccc4c3Cl)cc2)CC1]

Analysis: LCMS (ESI): 433 (M+H); ¹H NMR (400 MHz, DMSO-d6) δ 8.89 (s, 1H), 8.33 (dd, J=8.4, 0.9 Hz, 1H), 8.15 (d, J=8.3 Hz, 1H), 7.95-7.87 (m, 1H), 7.87-7.79 (m, 1H), 7.57 (d, J=8.3 Hz, 2H), 7.37 (d, J=8.1 Hz, 2H), 5.55 (br. s., 1H), 4.71-4.59 (m, 1H), 4.14-3.85 (m, 3H), 3.81-3.68 (m, 2H), 3.61-3.55 (m, 1H), 3.44-3.38 (m, 2H), 2.13-1.92 (m, 4H), 1.89-1.76 (m, 2H).

Example 203

(R)-(4-(4-(quinolin-7-yl)benzyl)-5,6-dihydropyridin-1(2H)-yl)(tetrahydrofuran-2-yl)methanone, HCl

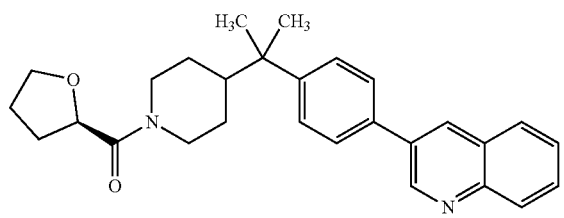 [SMILES: CC(C)(c1ccc(-c2cnc3ccccc3c2)cc1)C1CCN(C(=O)[C@H]2CCCO2)CC1]

Step 1. 4-(2-(4-bromophenyl)propan-2-yl)-1-methylpyridin-1-ium iodide

To a solution of 4-(4-bromobenzyl)pyridine (Prepared according to Hu, Qingzhong et al, *J. Med. Chem.* 2010, 53, 5749-5758) (9.0 g, 36.43 mmol) in DCM at 0° C. was added TBAI (0.672 g, 1.82 mmol) and 5N aqueous NaOH solution. Iodomethane (25.87 g, 182 mmol) was added under vigorous stirring at 0° C. followed by overnight stirring at rt. The organic layer was separated and aqueous layer was extracted with DCM. The combined organic layer was washed with brine, dried over Na₂SO₄, filtered and concentrated. Residue was triturated with diethyl ether and dried to give 4-(2-(4-bromophenyl)propan-2-yl)-1-methylpyridin-1-ium iodide (14 g crude) that was used for next step without further purification. ¹H NMR (400 MHz, Chloroform-d) δ 9.24 (d, J=6.1 Hz, 2H), 7.78 (d, J=6.1 Hz, 2H), 7.44 (d, J=8.0 Hz, 2H), 7.06 (d, J=8.0 Hz, 2H), 4.61 (s, 3H), 1.72 (s, 6H).

Step 2. 4-(2-(4-bromophenyl)propan-2-yl)-1-methyl-1,2,3,6-tetrahydropyridine

To a solution of 4-(2-(4-bromophenyl)propan-2-yl)-1-methylpyridin-1-ium iodide (2.0 g, 6.89 mmol) in methanol (30 mL) and DCM (15 mL) was added NaBH₄ (1.04 g, 27.5 mmol) in portions at 0° C. Reaction mixture was stirred at rt for 3 h. Solvent was evaporated under reduced pressure. Residue was dissolved in water and extracted with ethyl acetate. The organic layer was washed with brine, dried over Na₂SO₄, filtered and concentrated to give 4-(2-(4-bromophenyl)propan-2-yl)-1-methyl-1,2,3,6-tetrahydropyridine (1.2 g, 59%). LCMS (ESI): 295 (M+H); ¹H NMR (400 MHz, Chloroform-d) δ 7.46-7.33 (m, 2H), 7.27 (d, J=3.3 Hz, 1H), 7.19-7.15 (m, 2H), 3.02 (q, J=3.0 Hz, 2H), 2.44-2.30 (m, 5H), 1.95-1.84 (m, 2H), 1.37 (s, 6H).

Step 3. 3-(4-(2-(1-methyl-1,2,3,6-tetrahydropyridin-4-yl)propan-2-yl)phenyl)quinoline To a solution of 4-(2-(4-bromophenyl)propan-2-yl)-1-methyl-1,2,3,6-tetrahydropyridine (3.45 g, 11.70 mmol) in 1,4-dioxane (30 mL) and water (6 mL) was added quinoline-3-boronic acid (2.43 g, 14.0 mmol) and Na₂CO₃ (3.72 g, 35.1 mmol) and resulting solution was degassed with argon for 30 min. Pd(PPh₃)₄ (0.67 g, 0.58 mmol) was added to the reaction mixture followed by heating at 100° C. for 15 h. Reaction mixture was filtered through Celite. Filtrate was washed with water, brine, dried over Na₂SO₄, filtered and concentrated. The crude residue was purified by column chromatography upon silica gel (10-50% ethyl acetate in hexane) to give 3-(4-(2-(1-methyl-1,2,3,6-tetrahydropyridin-4-yl)propan-2-yl)phenyl)quinoline (2.1 g, 53%) brown solid. LCMS (ESI): 343 (M+H); ¹H NMR (400 MHz, Chloroform-d) δ 9.19 (s, 1H), 8.29 (s, 1H), 8.13 (d, J=8.4 Hz, 1H), 7.88 (d, J=8.1 Hz, 1H), 7.68-7.64 (m, 4H), 7.44 (d, J=7. 8 Hz, 2H), 5.72 (s, 1H), 3.11-3.05 (m, 2H), 2.48-2.41 (m, 2H), 2.36 (s, 3H), 2.02-1.95 (m, 2H), 1.46-1.18 (m, 6H).

Step 4. 3-(4-(2-(1-methylpiperidin-4-yl)propan-2-yl)phenyl)-1,2,3,4-tetrahydroquinoline A solution of 3-(4-(2-(1-methyl-1,2,3,6-tetrahydropyridin-4-yl)propan-2-yl)phenyl)quinoline (1.5 g, 4.31 mmol) in methanol was charged to a Parr apparatus followed by 20% Pd(OH)₂/C (0.3 g, 20% w/w) and stirred under H₂ (100 psi) for 16h at rt. Reaction mixture was filtered through Celite. Filtrate was concentrated and residue was purified by column chromatography upon silica gel (1-10% methanol in DCM) to give 3-(4-(2-(1-methylpiperidin-4-yl)propan-2-yl) phenyl)-1,2,3,4-tetrahydroquinoline (0.79 g, 52%) as a white solid. LCMS (ESI): 349 (M+H); $^1$H NMR (400 MHz, Chloroform-d) δ 7.35-7.07 (m, 4H), 7.06-6.96 (m, 2H), 6.68-6.61 (m, 1H), 6.59-6.51 (m, 1H), 3.39-3.24 (m, 1H), 3.23-2.91 (m, 8H), 2.44 (s, 3H), 1.56-1.44 (m, 5H), 1.35-1.22 (m, 6H).

Step 5. 3-(4-(2-(1-methylpiperidin-4-yl)propan-2-yl) phenyl)quinoline

To a solution of 3-(4-(2-(1-methylpiperidin-4-yl)propan-2-yl)phenyl)-1,2,3,4-tetrahydroquinoline (0.4 g, 1.15 mmol) in DCM (20 mL) was added DDQ (0.65 g, 2.87 mmol) and stirred at rt for 24h. Reaction mixture was diluted with ethyl acetate and washed with 2N NaOH till yellow color appears in solution. The organic layer was washed with brine, dried over Na$_2$SO$_4$, filtered and concentrated. Residue was purified by column chromatography upon silica gel (1-10% methanol in DCM) to give 3-(4-(2-(1-methylpiperidin-4-yl) propan-2-yl)phenyl)quinoline (0.17 g, 43%) as a white solid. LCMS (ESI): 345 (M+H); $^1$H NMR (400 MHz, Chloroform-d) δ 9.19 (s, 1H), 8.30 (s, 1H), 8.14 (d, J=8.5 Hz, 1H), 7.88 (d, J=8.3 Hz, 1H), 7.72-7.55 (m, 4H), 7.63-7.44 (m, 2H), 3.55-3.47 (m, 2H), 2.72 (s, 3H), 2.55-2.47 (m, 2H), 1.84-1.56 (m, 5H), 1.33 (m, 6H).

Step 6. 3-(4-(2-(piperidin-4-yl)propan-2-yl)phenyl) quinoline

To a solution of 3-(4-(2-(1-methylpiperidin-4-yl)propan-2-yl)phenyl)quinoline (0.38 g, 1.1 mmol) at 0° C. in DCM was added Et$_3$N (0.22 g, 2.2 mmol) followed by 1-chloroethyl chloroformate (0.23 g, 1.66 mmol) and stirred at rt for 3h. Volatiles were removed under reduced pressure. Residue was diluted with 2 mL methanol and heated under reflux for 1 h. methanol was removed under reduced pressure. Residue was diluted with water and extracted with DCM. The organic layer was washed with brine, dried over Na$_2$SO$_4$, filtered and concentrated. Residue was purified by column chromatography upon silica gel (1-10% methanol in DCM) to give 3-(4-(2-(piperidin-4-yl)propan-2-yl)phenyl)quinoline (0.16 g, 44%) as a white solid. LCMS (ESI): 331 (M+H); $^1$H NMR (400 MHz, Chloroform-d) δ 9.55 (s, 1H), 9.21 (s, 1H), 8.37 (s, 1H), 8.21 (d, J=8.7 Hz, 1H), 7.91 (d, J=8.3 Hz, 1H), 7.80-7.57 (m, 4H), 7.46 (d, J=7.9 Hz, 2H), 3.53-3.45 (m, 2H), 2.77 (s, 2H), 1.78-1.62 (m, 5H) 1.46-1.18 (m, 6H).

Step 7. (R)-(4-(4-(quinolin-7-yl)benzyl)-5,6-dihydropyridin-1(2H)-yl)(tetrahydrofuran-2-yl)methanone HCl 3-(4-(2-(piperidin-4-yl)propan-2-yl)phenyl)quinoline was treated with (R)-tetrahydrofuran-2-carboxylic acid as described in Example 146, Step c to afford (R)-(4-(4-(quinolin-7-yl)benzyl)-5,6-dihydropyridin-1(2H)-yl)(tetrahydrofuran-2-yl)methanone HCl (46% yield) following purification on silica gel and formation of the hydrochloride salt. LCMS (ESI): 429 (M+H); $^1$H NMR (400 MHz, DMSO-d6) δ 9.38 (d, J=2.2 Hz, 1H), 8.95 (s, 1H), 8.23-8.07 (m, 2H), 7.96-7.83 (m, 3H), 7.77 (t, J=7.6 Hz, 1H), 7.54 (d, J=8.2 Hz, 2H), 4.63-4.51 (m, 1H), 4.35 (d, J=12.8 Hz, 1H), 3.97 (d, J=13.5 Hz, 1H), 3.52-3.41 (m, 1H), 3.42-3.35 (m, 2H), 2.90-2.81 (m, 2H), 2.39 (t, J=12.5 Hz, 1H), 1.96-1.92 (m, 2H), 1.81-1.72 (m, 3H), 1.49 (d, J=12.4 Hz, 2H), 1.27 (s, 6H).

The following compounds were prepared in an analogous manner to Example 203, using cyclopropanecarbonyl chloride or propanoyl chloride in Step 7.

Example 204

Cyclopropyl(4-(2-(4-(quinolin-3-yl)phenyl)propan-2-yl)piperidin-1-yl)methanone, HCl

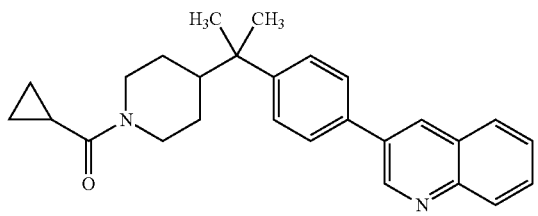 [SMILES: CC(C)(c1ccc(-c2cnc3ccccc3c2)cc1)C1CCN(C(=O)C2CC2)CC1]

Analysis: LCMS (ESI): 399 (M+H); $^1$H NMR (400 MHz, DMSO-d6) δ 9.44 (d, J=2.2 Hz, 1H), 8.99 (s, 1H), 8.17 (dd, J=14.6, 8.3 Hz, 2H), 7.96-7.85 (m, 3H), 7.78 (t, J=7.6 Hz, 1H), 7.56 (d, J=8.2 Hz, 2H), 4.41 (d, J=13.3 Hz, 1H), 4.26 (s, 1H), 2.99-2.88 (m, 1H), 2.38 (d, J=13.3 Hz, 1H), 1.97-1.76 (m, 2H), 1.55-1.49 (m, 2H), 1.30 (s, 6H), 1.10 (d, J=13.1 Hz, 1H), 0.98 (s, 1H), 0.71-0.61 (m, 4H).

Example 205

1-(4-(2-(4-(quinolin-3-yl)phenyl)propan-2-yl)piperidin-1-yl)propan-1-one, HCl

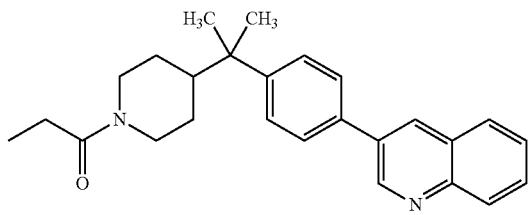 [SMILES: CCC(=O)N1CCC(C(C)(C)c2ccc(-c3cnc4ccccc4c3)cc2)CC1]

Analysis: LCMS (ESI): 387 (M+H); $^1$H NMR (400 MHz, Chloroform-d) δ 9.20 (d, J=2.3 Hz, 1H), 8.31 (d, J=2.3 Hz, 1H), 8.14 (d, J=8.5 Hz, 1H), 7.89 (d, J=8.2 Hz, 1H), 7.77-7.64 (m, 3H), 7.63-7.54 (m, 1H), 7.47 (d, J=8.2 Hz, 2H), 4.70 (d, J=13.3 Hz, 2H), 3.85 (d, J=13.5 Hz, 1H), 2.90 (t, J=13.3 Hz, 2H), 2.47-2.26 (m, 4H), 1.74 (t, J=12.1 Hz, 2H), 1.31-1.08 (m, 6H), 0.91-0.81 (m, 3H).

Example 206

1-{4-[1-Ethoxy-1-(4-quinolin-3-yl-phenyl)-ethyl]-piperidin-1-yl}-propan-1-one

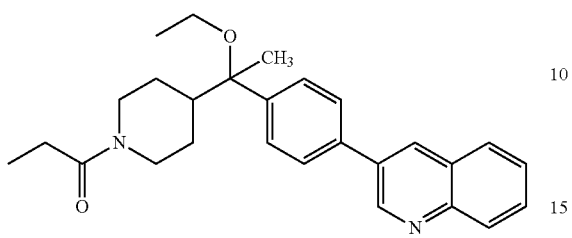

Step 1. Palladium acetate (0.008 g, 0.04 mmol), triphenylphosphine (0.020 g, 0.076 mmol) and 1,4-dioxane (3.9 mL) were combined in a flask. 4-[1-(4-bromophenyl)-1-ethoxy-ethyl]-piperidine-1-carboxylic acid tert-butyl ester (0.352 g, 0.854 mmol), 3-quinolineboronic acid (0.179 g, 1.03 mmol) and DMF (5.7 mL) were combined and added to the first mixture, 1 M of aqueous sodium carbonate solution (2.6 mL, 2.6 mmol) was added and the reaction was purged with nitrogen. The reaction was heated at 80° C. for 26 h under nitrogen, concentrated and the residue dissolved in ethyl acetate, washed with 1M sodium carbonate, water, and brine. The organic phase was dried over magnesium sulfate, filtered, concentrated and purified by normal phase chromatography eluting with ethyl acetate/heptane to yield 244 mg (62%). LC-MS: m/z=461.26 (M+H); $^1$H NMR (DMSO-d6) δ: 9.27 (d, 1H, J=2.4 Hz), 8.66 (d, 1H, J=2.2 Hz), 8.05 (m, 2H), 7.88 (d, 2H, J=8.4 Hz), 7.78 (m, 1H), 7.65 (m, 1H), 7.47 (d, 2H, J=8.4 Hz), 3.93 (m, 2H), 3.36 (m, 2H), 3.06 (m, 1H), 2.55 (m, 2H), 1.72 (m, 2H), 1.53 (s, 3H), 1.35 (s, 9H), 1.08 (m, 5H).

Step 2. 3-[4-(1-Ethoxy-1-piperidin-4-yl-ethyl)-phenyl]-quinoline; HCl

4-[1-Ethoxy-1-(4-quinolin-3-yl-phenyl)-ethyl]-piperidine-1-carboxylic acid tert-butyl ester (0.214 g, 0.465 mmol) and 4 M HCl in 1,4-dioxane (5.0 mL, 20 mmol) were combined in a flask and stirred at rt for 30 min. The reaction was concentrated, diluted with DCM and concentrated again. Residual solid was triturated with ether then dried by high vacuum at 40° C. overnight to yield 148 mg (80%) of a light yellow solid, 3-[4-(1-ethoxy-1-piperidin-4-yl-ethyl)-phenyl]-quinoline; hydrochloride. LC-MS: m/z=361.18 (M+H); $^1$H NMR (DMSO-d6) δ: 9.41 (s, 1H), 8.92 (br s, 1H), 8.76 (m, 1H), 8.26 (m, 1H), 8.16 (d, 2H, J=8.6 Hz), 7.95 (d, 2H, J=8.3 Hz), 7.89 (m, 1H), 7.76 (m, 1H), 7.50 (d, 2H, J=8.3 Hz), 3.39 (m, 1H), 3.23 (m, 2H), 3.09 (m, 1H), 2.74 (m, 2H), 1.83 (m, 2H), 1.57 (m, 4H), 1.15 (m, 3H).

Step 3. 1-{4-[1-Ethoxy-1-(4-quinolin-3-yl-phenyl)-ethyl]-piperidin-1-yl}-propan-1-one 3-[4-(1-Ethoxy-1-piperidin-4-yl-ethyl)-phenyl]-quinoline; HCl (0.0404 g, 0.102 mmol) was combined with anhydrous THF (2.0 mL). DIPEA (0.053 mL, 0.30 mmol), then propanoyl chloride (18 uL, 0.20 mmol) were added and the reaction was stirred at room temperature for 50 minutes. Reaction was concentrated. The residue was dissolved in ethyl acetate, then washed with 1 M aq. sodium carbonate solution, then water, then brine. Organic phase was dried with magnesium sulfate, filtered and concentrated. The residue was purified by normal phase chromatography eluting with hexane/ethyl acetate to yield 32.8 mg (77%) of a white solid, 1-{4-[1-Ethoxy-1-(4-quinolin-3-yl-phenyl)-ethyl]-piperidin-1-yl}-propan-1-one. HPLC 5.25 min. rt=2.643 min.; LC-MS: m/z=417.27 (M+H); 1H NMR (400 MHz, DMSO-d6) δ 9.27 (d, 1H, J=2.3 Hz), 8.66 (d, 1H, J=2.3 Hz), 8.05 (m, 2H), 7.88 (d, 2H, J=8.4 Hz), 7.78 (m, 1H), 7.65 (m, 1H), 7.47 (d, 2H, J=8.4 Hz), 4.44 (m, 1H), 3.85 (m, 1H), 3.37 (m, 1H), 3.06 (m, 1H), 2.82 (m, 1H), 2.29 (m, 3H), 1.75 (m, 2H), 1.53 (s, 3H), 1.37 (m, 1H), 1.24 (m, 1H), 1.13 (m, 3H), 0.95 (m, 4H)

Example 207

Cyclopropyl-{4-[1-ethoxy-1-(4-quinolin-3-yl-phenyl)-ethyl]-piperidin-1-yl}-methanone

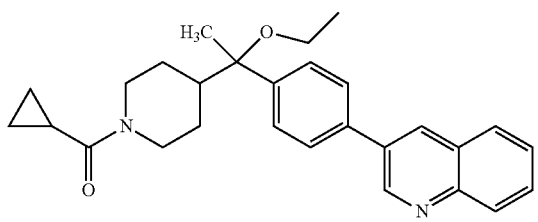 [SMILES: CCOC(C)(c1ccc(-c2cnc3ccccc3c2)cc1)C1CCN(C(=O)C2CC2)CC1]

This example was prepared in a manner similar to the procedure used to prepare Example 206 using cyclopropanecarbonyl chloride was used in place of propanoyl chloride to yield a white solid, in 54% yield. LC-MS: m/z=429.27 (M+H); $^1$H NMR (DMSO-d6) δ: 9.28 (d, 1H, J=2.3 Hz), 8.67 (d, 1H, J=2.2 Hz), 8.05 (m, 2H), 7.89 (d, 2H, J=8.4 Hz), 7.78 (m, 1H), 7.65 (m, 1H), 7.48 (d, 2H, J=8.4 Hz), 4.33 (m, 2H), 3.37 (m, 1H), 3.08 (m, 1H), 2.90 (m, 1H), 2.36 (m, 1H), 1.89 (m, 1H), 1.79 (m, 2H), 1.54 (s, 3H), 1.40 (m, 1H), 1.14 (m, 4H), 1.01 (m, 1H), 0.65 (m, 4H)

Example 208

1-{4-[1-Methoxy-1-(4-quinolin-3-yl-phenyl)-ethyl]-piperidin-1-yl}-propan-1-one

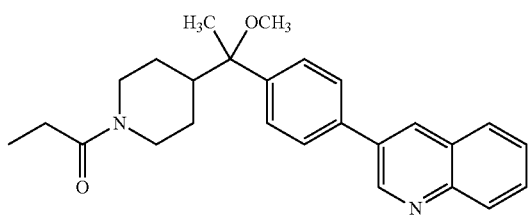 [SMILES: CCC(=O)N1CCC(C(C)(OC)c2ccc(-c3cnc4ccccc4c3)cc2)CC1]

Step 1. of 4-[1-Methoxy-1-(4-quinolin-3-yl-phenyl)-ethyl]-piperidine-1-carboxylic acid tert-butyl ester Palladium acetate (0.015 g, 0.067 mmol), triphenylphosphine (0.038 g, 0.14 mmol) and 1,4-dioxane (4.0 mL) were combined in a flask. 4-[1-(4-bromo-phenyl)-1-methoxy-ethyl]-piperidine-1-carboxylic acid tert-butyl ester (0.356 g, 0.894 mmol), 3-Quinolineboronic acid (0.198 g, 1.14 mmol) and DMF (6.0 mL) were combined a separate flask. The second mixture was added to the first mixture. 1 M of aqueous sodium carbonate solution (2.7 mL, 2.7 mmol) was added then the reaction was purged with nitrogen and heated at 80° C. for 27 h under nitrogen. The reaction was concentrated and the residue was dissolved in ethyl acetate, washed with 1M sodium carbonate, then water, then brine. The organic phase was dried with magnesium sulfate, filtered, concentrated and purified by normal phase chromatography eluting with ethyl acetate/heptane to yield 284 mg (71%) of 4-[1-Methoxy-1-(4-quinolin-3-yl-phenyl)-ethyl]-piperidine-1-carboxylic acid tert-butyl ester. $^1$H NMR (DMSO-d6) δ: 9.27 (d, 1H, J=2.3 Hz), 8.66 (d, 1H, J=2.3 Hz), 8.05 (m, 2H), 7.89 (d, 2H, J=8.4 Hz), 7.78 (m, 1H), 7.66 (m, 1H), 7.46 (d, 2H, J=8.4 Hz), 4.00-3.90 (m, 2H), 3.04 (s, 3H), 2.55 (m, 1H), 1.70 (m, 2H), 1.52 (s, 3H), 1.35 (s, 9H), 1.05 (m, 2H), 0.85 (m, 2H).

Step 2. 4-[1-Methoxy-1-(4-quinolin-3-yl-phenyl)-ethyl]-piperidine-1-carboxylic acid tert-butyl ester (0.284 g, 0.636 mmol) and 4 M of hydrogen chloride in 1,4-dioxane (6.9 mL, 28 mmol) were combined in a flask and stirred at room temperature for 30 min. The reaction was concentrated, then diluted with DCM and concentrated again. Residual solid was triturated with ether then dried by high vacuum at 40° C. overnight to yield 198 mg (81%). LC-MS: m/z=347.25 (M+H); $^1$H NMR (DMSO-d6) δ: 9.48 (br s, 1H), 9.00 (m, 2H), 8.45 (m, 1H), 8.24 (m, 2H), 7.98 (m, 3H), 7.81 (m, 1H), 7.51 (d, 2H, J=8.3 Hz), 3.22 (m, 2H), 3.07 (s, 3H), 2.73 (m, 2H), 1.84 (m, 2H), 1.51 (m, 6H).

Step 3. 3-[4-(1-Methoxy-1-piperidin-4-yl-ethyl)-phenyl]-quinoline; HCl (0.038 g, 0.099 mmol) was combined with anhydrous THF (2.0 mL). DIPEA (55 uL, 0.32 mmol). Then propanoyl chloride (18 uL, 0.21 mmol) was added and the reaction was stirred at room temperature for 70 min. The reaction was concentrated, the residue dissolved in EtOAc, then washed with 1 M aqueous Na$_2$CO$_3$ solution, water, and brine. Organic phase was dried with magnesium sulfate, filtered and concentrated. The residue was purified by normal phase chromatography eluting with hexane/EtOAc to yield 40 mg (54%) of a white solid. LC-MS: m/z=403.26 (M+H); $^1$H NMR (400 MHz, DMSO-d6) δ: 9.28 (d, 1H, J=2.3 Hz), 8.66 (d, 1H, J=2.3 Hz), 8.05 (d, 2H, J=9.4 Hz), 7.89 (d, 2H, J=8.3 Hz), 7.78 (m, 1H), 7.66 (m, 1H), 7.46 (d, 2H, J=8.3 Hz), 4.42 (m, 1H), 3.83 (m, 1H), 3.04 (s, 3H), 2.82 (m, 1H), 2.27 (m, 3H), 1.77 (m, 2H), 1.53 (s, 3H), 1.35 (m, 1H), 1.01 (m, 5H).

Example 209

Cyclopropyl-{4-[1-methoxy-1-(4-quinolin-3-yl-phenyl)-ethyl]-piperidin-1-yl}-methanone

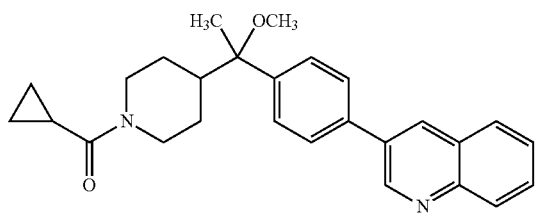 [SMILES: COC(C)(c1ccc(-c2cnc3ccccc3c2)cc1)C1CCN(C(=O)C2CC2)CC1]

This compound was prepared in a manner similar to the procedure used for Example 208 using cyclopropanecarbonyl chloride yield a white solid in 17% yield. LC-MS: m/z=415.26 (M+H); $^1$H NMR (400 MHz, DMSO-d6) δ: 9.28 (d, 1H, J=2.4 Hz), 8.67 (d, 1H, J=2.3 Hz), 8.05 (d, 2H, J=9.5 Hz), 7.90 (d, 2H, J=8.4 Hz), 7.78 (m, 1H), 7.66 (m, 1H), 7.47 (d, 2H, J=8.4 Hz), 4.32 (m, 2H), 3.05 (s, 3H), 2.89 (m, 1H), 2.37 (m, 1H), 1.84 (m, 3H), 1.54 (s, 3H), 1.39 (m, 1H), 1.16 (m, 2H), 0.65 (m, 4H).

Example 210

1-{4-[1-Methoxy-1-(4-quinolin-3-yl-phenyl)-propyl]-piperidin-1-yl}-propan-1-one

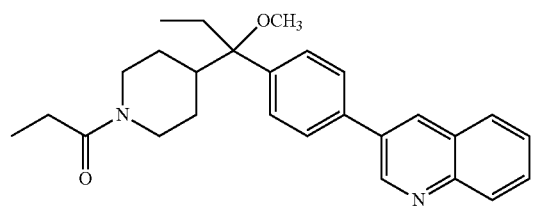 [SMILES: CCC(=O)N1CCC(C(CC)(OC)c2ccc(-c3cnc4ccccc4c3)cc2)CC1]

Step 1. Palladium acetate (0.012 g, 0.054 mmol), triphenylphosphine (0.025 g, 0.095 mmol) and 1,4-dioxane (3.3 mL) were combined in a flask. 4-[1-(4-Bromo-phenyl)-1-methoxy-propyl]-piperidine-1-carboxylic acid tert-butyl ester (0.304 g, 0.737 mmol), 3-quinolineboronic acid (0.161 g, 0.932 mmol), DMF (4.8 mL) and 1 M of aqueous sodium carbonate solution (2.2 mL, 2.2 mmol) were added. The reaction was purged with nitrogen and heated at 80° C. for 27 h under nitrogen. The reaction was concentrated and the residue was dissolved in ethyl acetate, washed with 1M sodium carbonate, water, and brine. The organic phase was dried with MgSO$_4$, filtered, concentrated and purified by normal phase chromatography eluting with ethyl acetate/heptane to yield 206 mg (61%). LC-MS: m/z=461.27 (M+1); $^1$H NMR (400 MHz, DMSO-d6) δ 9.27 (d, 1H, J=2.3 Hz), 8.66 (d, 1H, J=2.2 Hz), 8.05 (m, 2H), 7.86 (d, 2H, J=8.4 Hz), 7.77 (m, 1H), 7.65 (m, 1H), 7.45 (d, 2H, J=8.5 Hz), 3.90 (m, 2H), 3.14 (s, 3H), 2.62 (m, 2H), 2.20 (m, 1H), 1.97 (m, 2H), 1.83 (m, 1H), 1.68 (m, 1H), 1.27 (s, 9H), 0.84 (m, 3H), 0.64 (m, 2H).

Step 2. 4-[1-Methoxy-1-(4-quinolin-3-yl-phenyl)-propyl]-piperidine-1-carboxylic acid tert-butyl ester (0.206 g, 0.447 mmol) and 4 M of hydrogen chloride in 1,4-dioxane (4.8 mL, 19 mmol) were combined in a flask and stirred at room temperature for 45 min. The reaction was concentrated, then diluted with DCM and concentrated again. Residual solid was triturated with ether then dried by high vacuum at 40° C. overnight to yield 178 mg (99%) the hydrochloride. LC-MS: m/z=361.24 (M+H); $^1$H NMR (400 MHz, DMSO-d6) δ 9.38 (s, 1H), 8.84 (br s, 1H), 8.64 (m, 1H), 8.14 (m, 2H), 7.95 (d, 2H, J=8.4 Hz), 7.86 (m, 2H), 7.73 (m, 1H), 7.49 (d, 2H, J=8.4 Hz), 3.20 (m, 2H), 3.14 (s, 3H), 2.85 (m, 2H), 2.20 (m, 1H), 2.03 (m, 3H), 1.84 (m, 1H), 1.01 (m, 2H), 0.85 (m, 3H).

Step 3. 3-[4-(1-Methoxy-1-piperidin-4-yl-propyl)-phenyl]-quinoline; HCl (0.038 g, 0.096 mmol) in anhydrous THF (1.9 mL) was added DIPEA (53 uL, 0.30 mmol) and propanoyl chloride (18 uL, 0.20 mmol) and the reaction was stirred at room temperature for 1.5 h. Reaction was concentrated, the residue dissolved in ethyl acetate, then washed with 1 M aq. sodium carbonate solution, water, and brine. Organic phase was dried with MgSO$_4$, filtered and concentrated. The residue was purified by normal phase chromatography eluting with hexane/EtOAc to yield 24.9 mg (62%) of an off-white solid, LC-MS: m/z=417.27 (M+H); $^1$H NMR (400 MHz, DMSO-d6) δ: 9.27 (d, 1H, J=2.4 Hz), 8.66 (d, 1H, J=2.2 Hz), 8.04 (m, 2H), 7.86 (d, 2H, J=8.5 Hz), 7.77 (m, 1H), 7.65 (m, 1H), 7.44 (d, 2H, J=8.4 Hz), 4.41 (m, 1H), 3.81 (m, 1H), 3.14 (s, 3H), 2.91 (m, 1H), 2.41 (m, 1H), 2.19 (m, 3H), 2.01 (m, 2H), 1.89 (m, 1H). 1.72 (m, 1H). 1.24 (m, 1H). 0.85 (m, 6H). 0.63 (m, 1H).

Example 211

Cyclopropyl-{4-[1-methoxy-1-(4-quinolin-3-yl-phenyl)-propyl]-piperidin-1-yl}-methanone

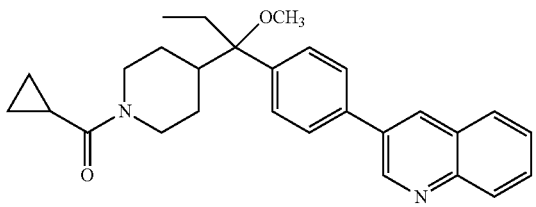 [SMILES: CCC(OC)(c1ccc(-c2cnc3ccccc3c2)cc1)C1CCN(C(=O)C2CC2)CC1]

This compound was prepared using the procedure for Example 210 to give an off-white solid, 62% yield. LC-MS: m/z=429.26 (M+H); $^1$H NMR (400 MHz, DMSO-d6) δ: 9.27 (d, 1H, J=2.3 Hz), 8.66 (d, 1H, J=2.1 Hz), 8.05 (m, 2H), 7.86 (d, 2H, J=8.4 Hz), 7.77 (m, 1H), 7.65 (m, 1H), 7.45 (d, 2H, J=8.4 Hz), 4.38 (m, 1H), 4.23 (m, 1H), 3.15 (s, 3H), 2.99 (m, 1H), 2.44 (m, 1H), 2.21 (m, 1H), 1.90 (m, 5H), 0.85 (m, 3H). 0.57 (m, 6H).

Example 212. 1-{4-[1-Methoxy-1-(4-quinolin-7-yl-phenyl)-ethyl]-piperidin-1-yl}-propan-1-one

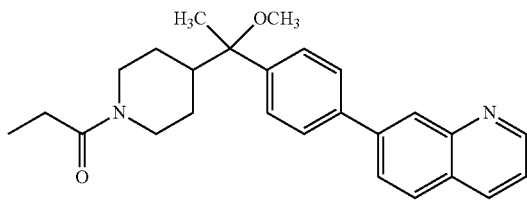 [SMILES: CCC(=O)N1CCC(C(C)(OC)c2ccc(-c3ccc4cccnc4c3)cc2)CC1]

Step 1. Palladium acetate (17 mg, 0.076 mmol), and triphenylphosphine (33 mg, 0.12 mmol) in 1,4-dioxane (2.8 mL) was added 4-[1-(4-bromo-phenyl)-1-methoxy-ethyl]-piperidine-1-carboxylic acid tert-butyl ester (0.245 g, 0.615 mmol), quinoline-7-boronic acid (0.149 g, 0.861 mmol) DMF (4.2 mL) and 1 M of aqueous sodium carbonate solution (1.9 mL, 1.9 mmol). The reaction was purged with nitrogen and heated at 80° C. for 17 h under nitrogen. The reaction was concentrated and the residue was dissolved in EtOAc, washed with 1M Na$_2$CO$_4$, water, and brine. The organic phase was dried over MgSO$_4$, filtered, concentrated and purified by normal phase chromatography eluting with ethyl acetate/heptane to yield 105 mg (38%). LC-MS: m/z=447.25 (M+H); $^1$H NMR (400 MHz, DMSO-d6) δ: 8.94 (m, 1H), 8.40 (m, 1H), 8.29 (s, 1H), 8.08 (d, 1H, J=8.5 Hz), 7.98 (m, 1H), 7.87 (d, 2H, J=8.4 Hz), 7.54 (m, 1H), 7.44 (d, 2H, J=8.4 Hz), 3.95 (m, 2H), 3.04 (s, 3H), 1.70 (m, 2H), 1.52 (m, 3H), 1.35 (s, 9H), 1.05 (m, 2H), 0.85 (m, 3H)

Step 2. 4-[1-Methoxy-1-(4-quinolin-7-yl-phenyl)-ethyl]-piperidine-1-carboxylic acid tert-butyl ester (0.105 g, 0.235 mmol) and 4 M of HCl in 1,4-dioxane (2.5 mL, 10 mmol) were combined in a flask and stirred at room temperature for 30 min. The reaction was concentrated, then diluted with DCM and concentrated again. Residual solid was triturated with ether then dried by high vacuum at 40° C. overnight to yield 89 mg (99%) of the hydrochloride salt. LC-MS: m/z=347.23 (M+H); $^1$H NMR (400 MHz, DMSO-d6) δ: 9.08 (d, 1H, J=3.1 Hz), 8.66 (m, 2H), 8.41 (s, 1H), 8.16 (m, 3H), 7.91 (d, 2H, J=8.5 Hz), 7.74 (m, 1H), 7.48 (d, 2H, J=8.4 Hz), 3.23 (m, 2H), 3.08 (s, 3H), 2.75 (m, 2H), 1.85 (m, 2H), 1.56 (m, 4H), 1.39 (m, 2H).

Step 3. 7-[4-(1-Methoxy-1-piperidin-4-yl-ethyl)-phenyl]-quinoline; HCl (0.040 g, 0.10 mmol) in anhydrous THF (2.0 mL) was added DIPEA (55 uL, 0.32 mmol) and propanoyl chloride (18 uL, 0.21 mmol). The reaction was stirred at room temperature for 80 min and was concentrated. The residue was dissolved in ethyl acetate, and then washed with 1 M aq. sodium carbonate solution, water, and brine. The organic phase was dried over magnesium sulfate, filtered and concentrated. The residue was purified by normal phase chromatography eluting with hexane/ethyl acetate to yield 21 mg (49%) of a white solid, m/z=403.26 (M+H); $^1$H NMR (400 MHz, DMSO-d6) δ: 8.94 (m, 1H), 8.40 (d, 1H, J=8.3 Hz), 8.29 (d, 1H, J=1.8 Hz), 8.08 (d, 1H, J=8.6 Hz), 7.98 (m, 1H), 7.87 (d, 2H, J=8.4 Hz), 7.53 (m, 1H), 7.44 (d, 2H, J=8.4 Hz), 4.42 (m, 1H), 3.84 (m, 1H), 3.04 (s, 3H), 2.82 (m, 1H), 2.25 (m, 3H), 1.77 (m, 2H), 1.52 (s, 3H), 1.34 (m, 1H), 1.00 (m, 5H).

Example 213

Cyclopropyl-{4-[1-methoxy-1-(4-quinolin-7-yl-phenyl)-ethyl]-piperidin-1-yl}-methanone

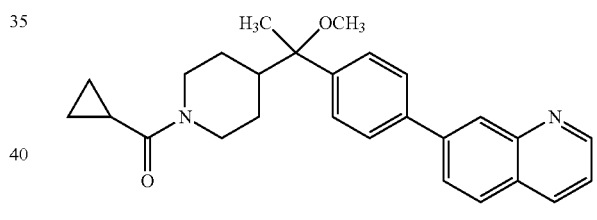

The title compound was prepared in a similar manner to Example 207 in 50% yield. LC-MS: m/z=415.24 (M+H); 1H NMR (400 MHz, DMSO-d6) δ 8.94 (m, 1H), 8.40 (m, 1H), 8.29 (m, 1H), 8.08 (m, 1H), 7.99 (m, 1H), 7.88 (d, 2H, J=8.4 Hz), 7.54 (m, 1H), 7.45 (d, 2H, J=8.4 Hz), 4.32 (m, 2H), 3.05 (s, 3H), 2.90 (m, 1H), 2.37 (m, 1H), 1.90 (m, 1H), 1.80 (m, 2H), 1.53 (s, 3H), 1.38 (m, 1H), 1.04 (m, 2H), 0.65 (m, 4H).

Example 214

1-{4-[1-Ethoxy-1-(4-quinolin-7-yl-phenyl)-ethyl]-piperidin-1-yl}-propan-1-one

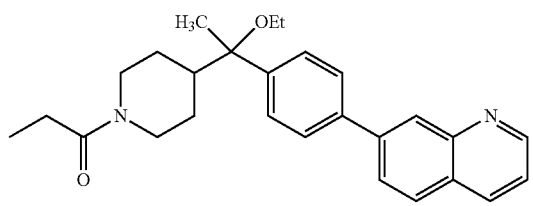 [SMILES: CCOC(C)(c1ccc(-c2ccc3cccnc3c2)cc1)C1CCN(C(=O)CC)CC1]

Step 1. Palladium acetate (12 mg, 0.053 mmol), and triphenylphosphine (30 mg, 0.1 mmol) in 1,4-dioxane (3.9 mL) was added 4-[1-(4-bromophenyl)-1-ethoxy-ethyl]-piperidine-1-carboxylic acid tert-butyl ester (0.347 g, 0.841 mmol), quinoline-7-boronic acid (0.211 g, 1.22 mmol), DMF (5.7 mL) and 1 M of aqueous sodium carbonate solution (2.6 mL, 2.6 mmol). The reaction was purged with nitrogen and heated at 80° C. for 26 h under nitrogen. The reaction was concentrated and the residue was dissolved in ethyl acetate, washed with 1M sodium carbonate, water, and brine. The organic phase was dried over magnesium sulfate, filtered, concentrated and purified by normal phase chromatography eluting with ethyl acetate/heptane to yield 221 mg (57%) LC-MS: m/z=461.27 (M+H); $^1$H NMR (400 MHz, DMSO-d6) δ: 8.93 (m, 1H), 8.39 (d, 1H, J=8.1 Hz), 8.29 (s, 1H), 8.07 (d, 1H, J=8.5 Hz), 7.98 (m, 1H), 7.86 (d, 2H, J=8.3 Hz), 7.54 (m, 1H), 7.45 (d, 2H, J=8.3 Hz), 3.96 (m, 2H), 3.07 (m, 1H), 1.69 (m, 2H), 1.53 (s, 3H), 1.35 (s, 9H), 1.24 (m, 1H), 1.13 (m, 3H), 1.04 (m, 2H), 0.85 (m, 3H).

Step 2. 4-[1-Ethoxy-1-(4-quinolin-7-yl-phenyl)-ethyl]-piperidine-1-carboxylic acid tert-butyl ester (0.221 g, 0.480 mmol) and 4 M of hydrogen chloride in 1,4-dioxane (5.2 mL, 21 mmol) were combined in a flask and stirred at room temperature for 40 minutes. The reaction was concentrated, diluted with DCM and concentrated again. Residual solid was triturated with ether then dried by high vacuum at 40° C. overnight to yield 185 mg (97%) of the hydrochloride salt. LC-MS: m/z=361.22 (M+H); $^1$H NMR (400 MHz, DMSO-d6) δ: 9.18 (m, 1H), 8.87 (m, 2H), 8.53 (s, 1H), 8.32 (m, 2H), 8.20 (m, 1H), 7.89 (m, 3H), 7.51 (d, 2H, J=8.4 Hz), 3.23 (m, 3H), 3.09 (m, 1H), 2.74 (m, 2H), 1.84 (m, 2H), 1.57 (m, 4H), 1.42 (m, 2H), 1.15 (m, 3H).

Step 3. 7-[4-(1-Ethoxy-1-piperidin-4-yl-ethyl)-phenyl]-quinoline; hydrochloride (0.043 g, 0.11 mmol) in anhydrous THF (2.1 mL) was added DIPEA (57 uL, 0.33 mmol) and then propanoyl chloride (19 uL, 0.22 mmol). The reaction was stirred at room temperature for 1 h and was concentrated. The residue was dissolved in ethyl acetate, washed with 1 M aq. sodium carbonate solution, water, and brine. The organic phase was dried with MgSO$_4$, filtered and concentrated. The residue was purified by normal phase chromatography eluting with hexane/ethyl acetate to yield 21.7 mg (48%). LC-MS: m/z=417.26 (M+H); $^1$H NMR (400 MHz, DMSO-d6) δ 8.93 (m, 1H), 8.39 (d, 1H, J=7.3 Hz), 8.29 (s, 1H), 8.08 (d, 1H, J=8.6 Hz), 7.98 (m, 1H), 7.87 (d, 2H, J=8.3 Hz), 7.54 (m, 1H), 7.45 (d, 2H, J=8.3 Hz), 4.44 (m, 1H), 3.83 (m, 1H), 3.07 (m, 1H), 2.82 (m, 1H), 2.25 (m, 3H), 1.75 (m, 2H), 1.53 (s, 3H), 1.35 (m, 1H), 1.13 (m, 4H), 0.94 (m, 5H).

Example 215

Cyclopropyl-{4-[1-ethoxy-1-(4-quinolin-7-yl-phenyl)-ethyl]-piperidin-1-yl}-methanone

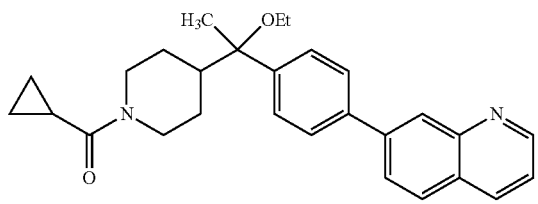 [SMILES: CCOC(C)(c1ccc(-c2ccc3cccnc3c2)cc1)C1CCN(C(=O)C2CC2)CC1]

This compound was prepared in a manner similar to the procedure used to prepare Example 207 in 49% yield. LC-MS: m/z=429.26 (M+H); $^1$H NMR (400 MHz, DMSO-d6) δ: 8.94 (m, 1H), 8.39 (m, 1H), 8.29 (s, 1H), 8.08 (d, 1H, J=8.5 Hz), 7.98 (m, 1H), 7.87 (d, 2H, J=8.4 Hz), 7.54 (m, 1H), 7.46 (d, 2H, J=8.4 Hz), 4.33 (m, 2H), 3.36 (m, 1H), 3.07 (m, 1H), 2.90 (m, 1H), 2.36 (m, 1H), 1.90 (m, 1H), 1.78 (m, 2H), 1.54 (s, 3H), 1.39 (m, 2H), 1.14 (m, 3H), 1.02 (m, 1H), 0.65 (m, 4H).

Example 216

1-{4-[1-Methoxy-1-(4-quinolin-7-yl-phenyl)-propyl]-piperidin-1-yl}-propan-1-one

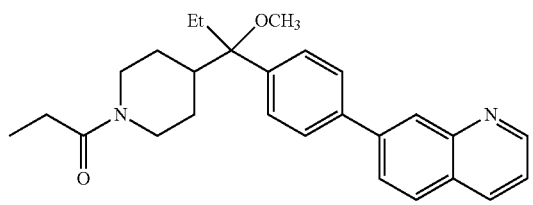 [SMILES: CCC(=O)N1CCC(C(CC)(OC)c2ccc(-c3ccc4cccnc4c3)cc2)CC1]

Step 1. Palladium acetate (16 mg, 0.071 mmol) and triphenylphosphine (26 mg, 0.099 mmol) in 1,4-dioxane (3.9 mL) was added 4-[1-(4-bromo-phenyl)-1-methoxy-propyl]-piperidine-1-carboxylic acid tert-butyl ester (0.353 g, 0.856 mmol), quinoline-7-boronic acid (0.209 g, 1.21 mmol), DMF (5.7 mL), and 1 M of sodium carbonate (2.6 mL, 2.6 mmol). The reaction was purged with nitrogen and heated at 80° C. for 5 h. The reaction was concentrated and the residue was dissolved in ethyl acetate, washed with 1M sodium carbonate, then water, then brine. The organic phase was dried with magnesium sulfate, filtered, concentrated and purified by normal phase chromatography eluting with ethyl acetate/heptane to yield 234 mg (59%). LC-MS: m/z=405.23 (M+H); $^1$H NMR (400 MHz, DMSO-d6) δ: 8.93 (m, 1H), 8.39 (d, 1H, J=8.4 Hz), 8.29 (s, 1H), 8.07 (d, 1H, J=8.6 Hz), 7.98 (m, 1H), 7.84 (d, 2H, J=8.5 Hz), 7.53 (m, 1H), 7.42 (d, 2H, J=8.4 Hz), 3.90 (m, 2H), 3.13 (s, 3H), 2.64 (m, 2H), 2.20 (m, 1H), 1.96 (m, 2H), 1.83 (m, 1H), 1.67 (m, 1H), 1.27 (s, 9H), 0.84 (m, 3H), 0.65 (m, 2H).

Step 2. 4-[1-Methoxy-1-(4-quinolin-7-yl-phenyl)-propyl]-piperidine-1-carboxylic acid tert-butyl ester (0.234 g, 0.508 mmol) and 4 M of HCl in 1,4-dioxane (5.5 mL, 22 mmol) was stirred at room temperature for 40 minutes. The reaction was concentrated, then diluted with DCM and concentrated again. Residual solid was triturated with ether then dried by high vacuum at 40° C. overnight to yield 195 mg (97%) of the hydrochloride salt. LC-MS: m/z=361.22 (M+H); $^1$H NMR (400 MHz, DMSO-d6) δ: 9.17 (d, 1H, J=3.8 Hz), 8.83 (m, 2H), 8.53 (s, 1H), 8.32 (d, 1H, J=8.6 Hz), 8.18 (d, 1H, J=8.5 Hz), 7.89 (m, 4H), 7.51 (d, 2H, J=8.4 Hz), 3.20 (m, 2H), 3.15 (s, 3H), 2.84 (m, 2H), 2.21 (m, 1H), 2.03 (m, 3H), 1.83 (m, 1H), 1.01 (m, 2H), 0.85 (m, 3H).

Step 3. 7-[4-(1-Methoxy-1-piperidin-4-yl-propyl)-phenyl]-quinoline; HCl (0.036 g, 0.091 mmol) in anhydrous THF (1.7 mL) was added DIPEA (48 uL, 0.27 mmol). then propanoyl chloride (16 uL, 0.18 mmol) and the reaction was stirred at room temperature for 15 h. Reaction was concentrated, the residue dissolved in EtOAc, and washed with 1 M aq. sodium carbonate solution, water, and brine. The organic phase was dried with MgSO$_4$, filtered and concentrated. The residue was purified by normal phase chromatography eluting with hexane/ethyl acetate to yield 21 mg (56%). LC-MS: m/z=417.25 (M+H); $^1$H NMR (400 MHz, DMSO-d6) δ: 8.94 (m, 1H), 8.93 (m, 1H), 8.39 (m, 1H), 8.28 (m, 1H), 8.07 (d, 1H, J=8.5 Hz), 7.98 (m, 1H), 7.84 (d, 2H, J=8.5 Hz), 7.54 (m, 1H), 7.42 (d, 2H, J=8.4 Hz), 4.41 (m, 1H), 3.81 (m, 1H), 3.14 (s, 3H), 2.91 (m, 1H), 2.41 (m, 1H), 2.18 (m, 3H), 2.00 (m, 2H), 1.88 (m, 1H), 1.71 (m, 1H), 0.85 (m, 6H), 0.67 (m, 2H).

Example 217

Cyclopropyl-{4-[1-methoxy-1-(4-quinolin-7-yl-phenyl)-propyl]-piperidin-1-yl}-methanone

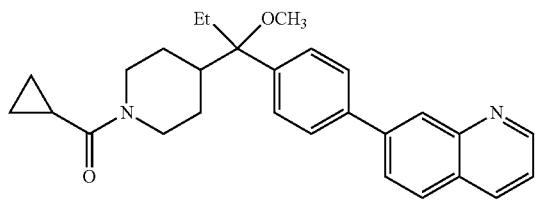 [SMILES: CCC(OC)(c1ccc(-c2ccc3cccnc3c2)cc1)C1CCN(C(=O)C2CC2)CC1]

This title compound was prepared in a manner similar to the procedure used to prepare Example 207 in 54% yield. LC-MS: m/z=429.26 (M+H); 1H NMR (400 MHz, DMSO-d6) δ 8.93 (m, 1H), 8.93 (m, 1H), 8.39 (m, 1H), 8.29 (m, 1H), 8.07 (d, 1H, J=8.6 Hz), 8.00 (m, 1H), 7.85 (d, 2H, J=8.5 Hz), 7.53 (m, 1H), 7.43 (d, 2H, J=8.4 Hz), 4.30 (m, 2H), 3.15 (s, 3H), 2.99 (m, 1H), 2.21 (m, 1H), 2.01 (m, 3H), 1.79 (m, 3H), 0.85 (m, 4H), 0.64 (m, 5H).

Example 218

1-[trans-3-Hydroxy-4-(4-quinolin-3-yl-benzyl)-piperidin-1-yl]-propan-1-one

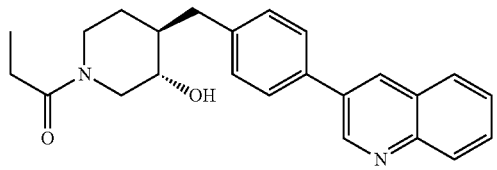 [SMILES: CCC(=O)N1CC[C@@H](Cc2ccc(-c3cnc4ccccc4c3)cc2)[C@H](O)C1]

Step 1. tert-Butyl 4-[(4-bromophenyl)methyl]-3,6-dihydro-2H-pyridine-1-carboxylate. 4-(4-bromo-benzyl)-4-hydroxy-piperidine-1-carboxylic acid tert-butyl ester (2.50 g, 6.75 mmol) and pyridine (3.30 mL, 40.8 mmol) were combined in DCM (30.0 mL, 468 mmol) and cooled to −10° C. for 10 min. Thionyl chloride (1.00 mL, 13.7 mmol) was then added and the mixture was stirred in a resealable vial at −10° C. for 1 h, then was diluted with ethyl acetate:hexane (7:3, 100 mL) and 1M HCl (50 mL). The mixture was separated, the organic was washed with 1M HCl (2×20 mL) and brine (20 mL). The organics were dried over sodium sulfate, filtered through silica gel (4 mL) and concentrated in vacuo. 1H-NMR shows the product to be a 3:1 mixture of regioisomers. The residue was dissolved in a DCM, applied to a silica gel loading cartridge (25 g) and purified on silica gel (80 g, 0-15% ethyl acetate:hexane, UV detection) to afford 4-(4-Bromo-benzylidene)-piperidine-1-carboxylic acid tert-butyl ester (0.36 g, 15%) as the first eluting, most UV active component, followed by a mixed fraction (0.5 g) then tert-butyl 4-[(4-bromophenyl)methyl]-3,6-dihydro-2H-pyridine-1-carboxylate (1.02 g, 42.9%). $^1$H NMR (400 MHz, chloroform-d) δ 7.40 (d, J=8.3 Hz, 2H) 7.03 (d, J=8.5 Hz, 2H) 5.39 (br. s, 1H) 3.88 (br. s., 2H) 3.44 (t, J=5.6 Hz, 2H) 3.25 (s, 2H) 1.96 (br. s., 2H) 1.45 (s, 9H)

Step 2. trans-4-(4-Bromo-benzyl)-3-hydroxy-piperidine-1-carboxylic acid tert-butyl ester trans-4-(4-Bromo-benzyl)-3-hydroxy-piperidine-1-carboxylic acid tert-butyl ester. tert-butyl 4-[(4-bromophenyl)methyl]-3,6-dihydro-2H-pyridine-1-carboxylate (0.901 g, 2.56 mmol) in THF (18.0 mL) was treated at room temperature with 1.00 M of borane in THF (9.0 mL, 9.0 mmol). After 45 min, the mixture was placed in an ice bath and 5.00 M of sodium hydroxide in water (50.0 mL, 250 mmol) (exothermic) followed by 30% hydrogen peroxide (9.0 g, 79 mmol). After 1 h, the mixture was diluted with satd. aq. sodium thiosulfate (50 mL) (exothermic) and DCM (50 mL). Ethyl acetate was added to aid in phase separation and the layers were separated, the aq. extracted with EtOAc and the combined organics washed with 1:1 brine:saturated aq. sodium thiosulfate, then dried over sodium sulfate, filtered and concentrated in vacuo to afford trans-4-(4-Bromo-benzyl)-3-hydroxy-piperidine-1-carboxylic acid tert-butyl ester (95% yield). $^1$H NMR (400 MHz, DCCl$_3$) δ 7.41 (2H, d, J=8.3 Hz), 7.05 (2H, d, J=8.3 Hz), 4.13-4.24 (1H, m), 3.85-4.04 (1H, m), 3.28-3.43 (1H, m), 3.14 (1H, dd, J=13.7, 3.4 Hz), 2.52-2.66 (2H, m), 2.34 (1H, dd, J=13.6, 9.3 Hz), 1.58-1.69 (2H, m), 1.44 (9H, s), 1.04-1.20 (1H, m)

Step 3. 1-[trans-3-Hydroxy-4-(4-quinolin-3-yl-benzyl)-piperidin-1-yl]-propan-1-one. trans-3-Hydroxy-4-(4-quinolin-3-yl-benzyl)-piperidine-1-carboxylic acid tert-butyl ester (50.0 mg, 0.119 mmol) and 4.0 M of HCl in 1,4-dioxane (0.150 mL, 0.600 mmol) in THF (1.00 mL) were combined at room temperature and after 1 h, DCM (1.00 mL) was added to aid solubility. The reaction proceeded slowly and was heterogeneous. After stirring over 3 d, LCMS indicated complete consumption of starting material. The mixture was diluted with water (0.50 mL) and 5.00 M of sodium hydroxide in water (0.200 mL, 1.00 mmol). After stirring for 5 min, Propanoyl chloride (15.0 uL, 0.172 mmol) was added to the biphasic mixture, which was stirred vigorously for 1 h. The mixture was separated, the aq. was extracted with DCM (2 mL) and the combined organics were diluted with ethyl acetate (10 mL), washed with brine (1 mL), dried over sodium sulfate, filtered and concentrated in vacuo. The residue was dissolved in DCM, applied to a silica gel loading cartridge (5 g) and purified on silica gel (4 g, 20-100% ethyl acetate:hexane) to afford 1-[trans-3-Hydroxy-4-(4-quinolin-3-yl-benzyl)-piperidin-1-yl]-propan-1-one (36.0 mg, 80.5%) as a white foam after reconcentration from methanol then acetone. LCMS (ESI): 375 (M+H); $^1$H NMR (400 MHz, DCCl$_3$) δ 9.15 (d, J=2.3 Hz, 1H) 8.23 (d, J=2.3 Hz, 1H) 8.12 (d, J=8.5 Hz, 1H) 7.83 (dd, J=8.5, 1.0 Hz, 1H) 7.58-7.72 (m, 3H) 7.49-7.58 (m, 1H) 7.31 (d, J=8.3 Hz, 2H) 3.84-4.50 (m, 2H) 3.41 (td, J=9.2, 4.8 Hz, 1H) 3.20 (dd, J=13.7, 4.1 Hz, 1H) 2.67-2.85 (m, 2H) 2.53 (dd, J=13.6, 8.5 Hz, 1H) 2.32 (q, J=7.4 Hz, 2H) 1.68-1.85 (m, 3H) 1.18-1.26 (m, 1H) 1.14 (t, J=7.4 Hz, 3H)

Example 219

1-[(trans)-3-Methoxy-4-(4-quinolin-3-yl-benzyl)-piperidin-1-yl]-propan-1-one, HCl

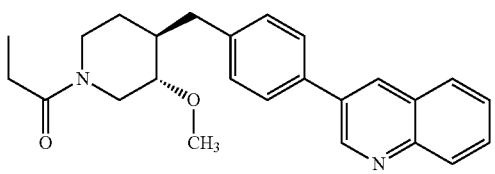 [SMILES: CCC(=O)N1CC[C@@H](Cc2ccc(-c3cnc4ccccc4c3)cc2)[C@H](OC)C1]

Sodium hydride, 60% disp. in mineral oil (31 mg, 0.78 mmol) was added to 1-[trans-3-Hydroxy-4-(4-quinolin-3-yl-benzyl)-piperidin-1-yl]-propan-1-one (71 mg, 0.19 mmol) in THF (3.00 mL). After 5 min, methyl iodide (14.0 uL, 0.225 mmol) was added and the mixture was stirred at room temperature for 48h. The mixture was concentrated in vacuo. The residue was dissolved in DCM, applied to a silica gel loading cartridge (5 g) and purified on silica gel (4 g, 10-100% ethyl acetate:hexane) to afford 1-[(trans)-3-methoxy-4-(4-quinolin-3-yl-benzyl)-piperidin-1-yl]-propan-1-one HCl (28 mg, 35%) after treatment of product containing fractions with HCl in dioxane and concentration. LCMS (ESI): 389 (M+H); $^1$H NMR (400 MHz, DMSO-d6) δ 9.24 (d, J=2.3 Hz, 1H) 8.62 (d, J=2.0 Hz, 1H) 8.00-8.14 (m, 2H) 7.73-7.83 (m, 3H) 7.60-7.69 (m, 1H) 7.35 (d, J=8.3 Hz, 2H) 4.14-4.42 (m, 1H) 3.76-3.97 (m, 1H) 3.39 (s, 3H) 3.10 (dd, J=13.6, 4.3 Hz, 1H) 2.69-2.96 (m, 3H) 2.50-2.56 (m, 1H) 2.30 (q, J=7.4 Hz, 2H) 1.77-1.92 (m, 1H) 1.55-1.70 (m, 1H) 1.08-1.22 (m, 1H) 1.00 (t, J=7.4 Hz, 3H);

Example 220

1-Propionyl-4-(4-quinolin-3-yl-benzyl)-piperidin-3-one

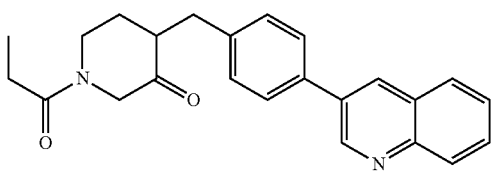 [SMILES: CCC(=O)N1CCC(Cc2ccc(-c3cnc4ccccc4c3)cc2)C(=O)C1]

Dess-Martin periodinane (0.130 g, 0.307 mmol) was added to a solution of 1-[trans-3-Hydroxy-4-(4-quinolin-3-yl-benzyl)-piperidin-1-yl]-propan-1-one (92 mg, 0.24 mmol) in DCM (2.0 mL). After 1 h, the mixture was applied to a silica gel loading cartridge (5 g) then purified on silica gel (12 g, 5-100% ethyl acetate:hexane) to afford 1-Propionyl-4-(4-quinolin-3-yl-benzyl)-piperidin-3-one (74 mg, 81%). LCMS (ESI): 373 (M+H); $^1$H NMR (400 MHz, DMSO-d6) δ 9.19 (d, J=2.3 Hz, 1H) 8.52 (d, J=2.0 Hz, 1H) 7.98-8.07 (m, 2H) 7.70-7.82 (m, 3H) 7.57-7.64 (m, 1H) 7.37 (d, J=8.5 Hz, 2H) 4.00-4.21 (m, 2H) 3.77-3.89 (m, 1H) 3.40-3.54 (m, 1H) 3.20 (dd, J=14.1, 5.3 Hz, 1H) 2.82-2.91 (m, 1H) 2.63 (dd, J=14.1, 8.0 Hz, 1H) 2.32 (q, J=7.3 Hz, 2H) 1.97-2.08 (m, 1H) 1.57-1.73 (m, 1H) 1.01 (t, J=7.4 Hz, 3H).

Example 221

1-[cis-3-Fluoro-4-(4-quinolin-3-yl-benzyl)-piperidin-1-yl]-propan-1-one, TFA Salt

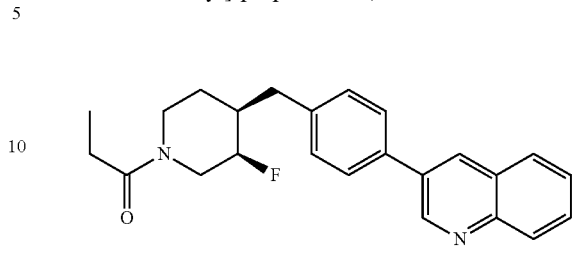

1-[trans-3-Hydroxy-4-(4-quinolin-3-yl-benzyl)-piperidin-1-yl]-propan-1-one (131 mg, 0.350 mmol) and 1,8-diazabicyclo[5.4.0]undec-7-ene (101 uL, 0.675 mmol) were combined in DCM (3.00 mL), cooled in a −78° C. bath then treated with XtalFluor-E (119 mg, 0.520 mmol). The mixture was allowed to slowly warm to room temperature. After stirring overnight, a small amount of elimination and fluoride product was observed by LCMS and the bulk of the material was starting material. Deoxofluor (0.25 mL, 1.4 mmol) was added and stirring was continued at room temperature for 24 h. The mixture was applied to a silica gel loading cartridge (5 g) then purified on silica gel (12 g, 5-70% EtOAc:hexane) to afford semi-purified fluoride and 1-[4-(4-Quinolin-3-yl-benzyl)-3,6-dihydro-2H-pyridin-1-yl]-propan-1-one, which was not recovered. The fluoride product was further purified by HPLC (10-55% acetonitrile:water, both containing 0.1% TFA) to afford 1-[cis-3-Fluoro-4-(4-quinolin-3-yl-benzyl)-piperidin-1-yl]-propan-1-one TFA salt (15.0 mg, 9%) after lyophilization of product containing fractions. LCMS (ESI): 377 (M+H); $^1$H NMR (400 MHz, DMSO-d6) δ 9.36 (d, J=2.3 Hz, 1H) 8.83 (s, 1H) 8.07-8.18 (m, 2H) 7.82-7.92 (m, 3H) 7.68-7.77 (m, 1H) 7.41 (d, J=7.8 Hz, 2H) 3.64-4.45 (m, 3H) 2.76-3.33 (m, 3H) 2.59 (br. s., 1H) 2.30 (d, J=7.5 Hz, 2H) 1.99-2.14 (m, 1H) 1.54-1.69 (m, 1H) 1.04-1.31 (m, 1H) 0.97 (t, J=7.3 Hz, 3H).

Example 222

1-{4-Fluoro-4-[4-(8-methylquinolin-7-yl)-benzoyl]-piperidin-1-yl}-propan-1-one

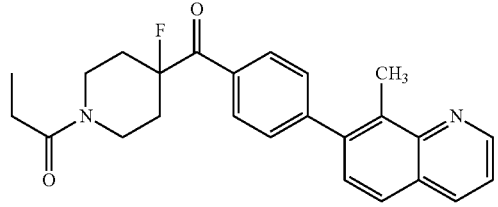 [SMILES: CCC(=O)N1CCC(F)(C(=O)c2ccc(-c3ccc4cccnc4c3C)cc2)CC1]

Step 1. 1-[4-(4-Bromobenzoyl)-4-fluoro-piperidin-1-yl]-2,2,2-trifluoroethanone

1-[4-(4-Bromobenzoyl)-piperidin-1-yl]-2,2,2-trifluoroethanone (7.22 g, 19.8 mmol) in DMF (202 mL) was cooled in an ice bath then treated with sodium tert-pentoxide 45% in toluene (7.00 mL, 26.2 mmol). After 30 min, tert-butyldimethylsilyl chloride (3.88 g, 25.7 mmol) was added to the yellow solution and stirring was continued for 1 h. The solution had turned to a cream color; LCMS and TLC (20% EtOAc:hexane) indicated complete conversion to the silylenol ether. Selectfluor (7.65 g, 21.6 mmol) was then added to the cool mixture in one portion as a solid, generating a white mixture. The mixture was stirred overnight then was poured into water (500 mL). The mixture was extracted with ethyl acetate:hexane (4:1, 3×100 mL) then the organic extract was washed with brine (2×50 mL). The organic layer was dried over $Na_2SO_4$ and filtered through silica gel (10 mL), rinsing the filter pad with additional ethyl acetate hexane (4:1, 50 mL). The filtrate was concentrated in vacuo to afford crude product as a cream solid. Purification was accomplished by adsorption onto silica gel (25 g, from EtOAc solution and drying) followed by chromatography (220 g silica gel, 0-10% EtOAc:hexane) to afford 1-[4-(4-bromobenzoyl)-4-fluoro-piperidin-1-yl]-2,2,2-trifluoroethanone (6.68 g, 88%).

Step 2. (4-Fluoropiperidin-4-yl)-[4-(8-methylquinolin-7-yl)-phenyl]-methanone 1,4-Dioxane (20.0 mL) was added to a mixture of 7-bromo-8-methyl-quinoline (0.689 g, 3.10 mmol), 4,4,5,5,4',4',5',5'-octamethyl-[2,2]'bi[[1,3,2]dioxaborolanyl] (1.06 g, 4.19 mmol), potassium acetate (0.913 g, 9.31 mmol) and [1,1'-bis(diphenylphosphino)ferrocene]-dichloropalladium (II), complex with DCM (1:1) (0.304 g, 0.372 mmol) under nitrogen. The mixture was stirred and vacuum degassed, then heated at 85° C. for 2.5 h, at which point LCMS showed complete conversion of 7-bromo-8-methyl-quinoline to 8-methyl-7-(4,4,5,5-tetramethyl-[1,3,2]-dioxaborolan-2-yl)-quinoline intermediate (m/z=270). The reaction mixture was removed from the heat and allowed to cool, then sodium carbonate (0.925 g, 8.73 mmol) in water (20.0 mL) was added, followed by a solution of 1-[4-(4-Bromo-benzoyl)-4-fluoro-piperidin-1-yl]-2,2,2-trifluoro-ethanone (0.677 g, 1.77 mmol) in 1,4-dioxane (20.0 mL). The mixture was again vacuum degassed then heated at 85° C. After 90 min, the mixture was treated with methanol (1.0 mL) and 5.00 M of sodium hydroxide in water (1.0 mL, 5.0 mmol) to fully hydrolyze the trifluoroacetamide from the Suzuki-coupled product. After 1 h, the mixture was partitioned between ethyl acetate (100 mL) and water (50 mL). The layers were separated, the organic phase was then extracted with aq. 1M HCl (3×50 mL). The acidic extract was washed with ethyl acetate (20 mL, discarded) then basified with 5M NaOH to pH 9-10. The basic solution was extracted with DCM (3×30 mL) and the DCM extract was dried over sodium sulfate, filtered and concentrated in vacuo. The residue was dissolved in DCM, applied to a silica gel loading cartridge (5 g) and purified on silica gel (24 g, 0-80% ethyl acetate: hexane, then 0-10% methanol: DCM) to afford (4-Fluoro-piperidin-4-yl)-[4-(8-methyl-quinolin-7-yl)-phenyl]-methanone (0.254 g, 41%) contaminated with (4-Fluoro-piperidin-4-yl)-phenyl-methanone (ca 4:1 ratio, 87% mass purity).

Step 3. 1-{4-Fluoro-4-[4-(8-methylquinolin-7-yl)-benzoyl]-piperidin-1-yl}-propan-1-one Semi-purified (4-Fluoropiperidin-4-yl)-[4-(8-methyl-quinolin-7-yl)-phenyl]-methanone (225 mg, 0.646 mmol) was dissolved in THF (4.00 mL) then treated with 5.00 M of NaOH in water (0.350 mL, 1.75 mmol) and propanoyl chloride (101 uL, 1.16 mmol). After 4h, the mixture was diluted with water (20 ml) and acetone (5 mL, to dissolve insoluble material) then after 30 additional minutes was diluted with EtOAc (50 mL). The layers were separated, the organic phase was washed with brine, filtered and concentrated in vacuo. The residue was dissolved in DCM, applied to a silica gel loading cartridge (5 g) and purified on silica gel (12 g, 0-50% EtOAc:hexane) to afford 1-{4-Fluoro-4-[4-(8-methylquinolin-7-yl)-benzoyl]-piperidin-1-yl}-propan-1-one (0.174 g, 67%) as a white solid. LCMS (ESI): 405 (M+H); $^{19}$F NMR (377 MHz, DMSO-d6) δ −162.82 (s, 1F); $^1$H NMR (400 MHz, DMSO-d6) δ 9.01 (dd, J=4.3, 1.8 Hz, 1H) 8.41 (dd, J=8.3, 1.8 Hz, 1H) 8.14 (dd, J=8.3, 1.3 Hz, 2H) 7.93 (d, J=8.3 Hz, 1H) 7.64 (d, J=8.5 Hz, 2H) 7.58-7.62 (m, 1H) 7.51 (d, J=8.5 Hz, 1H) 4.33-4.46 (m, 1H) 3.84-3.95 (m, 1H) 3.34-3.47 (m, 1H) 2.91-3.06 (m, 1H) 2.68 (s, 3H) 2.35-2.45 (m, 2H) 1.82-2.24 (m, 4H) 1.02 (t, J=7.4 Hz, 3H).

Example 223

1-{4-Fluoro-4-[4-(8-methylquinolin-7-yl)-benzoyl]-piperidin-1-yl}-propan-1-one

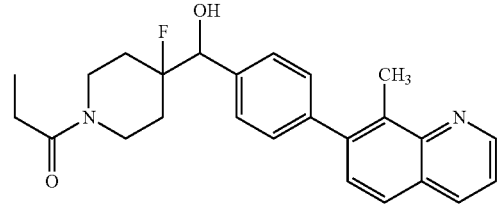 [SMILES: CCC(=O)N1CCC(F)(C(O)c2ccc(-c3ccc4cccnc4c3C)cc2)CC1]

1-{4-Fluoro-4-[4-(8-methyl-quinolin-7-yl)-benzoyl]-piperidin-1-yl}-propan-1-one (0.151 g, 0.373 mmol, Example 188) was dissolved in ethanol (3.00 mL) and THF (3.00 mL) then sodium borohydride (0.050 g, 1.3 mmol) was added. After stirring for 45 min, the mixture was quenched with acetone (2 mL); after stirring 20 min, the mixture was diluted with water (20 mL) and extracted with DCM (3×10 mL). The combined organic extracts were washed with brine (10 mL), dried over $Na_2SO_4$, filtered and concentrated in vacuo to afford 1-{4-Fluoro-4-[4-(8-methyl-quinolin-7-yl)-benzoyl]-piperidin-1-yl}-propan-1-one as a white solid. LCMS (ESI): 407 (M+H); $^1$H NMR (400 MHz, DMSO-d6) δ 8.98 (dd, J=4.3, 1.8 Hz, 1H) 8.38 (dd, J=8.3, 2.0 Hz, 1H) 7.88 (d, J=8.5 Hz, 1H) 7.56 (dd, J=8.3, 4.3 Hz, 1H) 7.45-7.53 (m, 3H) 7.38-7.45 (m, 2H) 5.84 (t, J=5.3 Hz, 1H) 4.63 (dd, J=16.2, 4.9 Hz, 1H) 4.29-4.40 (m, 1H) 3.75-3.85 (m, 1H) 3.04-3.21 (m, 1H) 2.61-2.79 (m, 4H) 2.32 (q, J=7.3 Hz, 2H) 1.56-1.91 (m, 4H) 0.98 (t, J=7.4 Hz, 3H)

Example 224

[trans-3-Hydroxy-4-(4-quinolin-3-yl-benzyl)-piperidin-1-yl]-(R)-tetrahydrofuran-2-yl-methanone

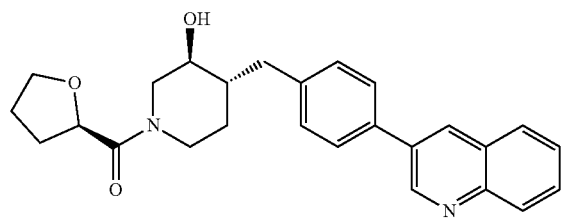 [SMILES: O=C([C@H]1CCCO1)N1CC[C@@H](Cc2ccc(-c3cnc4ccccc4c3)cc2)[C@H](O)C1]

Step 1. 1-Benzyl-4-(4-bromobenzyl)-pyridinium bromide 4-(4-Bromo-benzyl)-pyridine (2.429 g, 9.790 mmol) was dissolved in DCM (29.0 mL) then benzyl bromide (1.25 mL, 10.5 mmol) was added to the solution. After stirring overnight, the mixture was slowly added to ether (145 mL), triturated for 30 min and the resultant solids were collected by filtration to afford 1-benzyl-4-(4-bromobenzyl)-pyridinium bromide (3.65 g, 89.0%) as a white solid.

Step 2. 1-Benzyl-4-(4-bromobenzyl)-1,2,3,6-tetrahydropyridine

1-Benzyl-4-(4-bromobenzyl)-pyridinium bromide (1.78 g, 4.25 mmol) was dissolved in methanol (10.0 mL) and DCM (30.0 mL), then treated portionwise with sodium borohydride (0.964 g, 25.5 mmol). After 1 h, the mixture was quenched with acetone, satd. ammonium chloride then satd. sodium bicarbonate. Ethyl acetate (50 mL) was added, the phases were separated and the aq. phase was further extracted with ethyl acetate (2×50 mL). The combined organic extracts were dried over sodium sulfate, filtered through silica gel (4 mL) then concentrated in vacuo to furnish 1-Benzyl-4-(4-bromo-benzyl)-1,2,3,6-tetrahydropyridine (1.44 g, 99%) as an oil. $^1$H NMR (400 MHz, DMSO-d6) δ 7.47 (d, J=8.5 Hz, 2H) 7.29 (s, 5H) 7.13 (d, J=8.3 Hz, 2H) 5.34-5.43 (m, 1H) 3.45-3.53 (m, 2H) 3.19-3.25 (m, 2H) 2.81-2.91 (m, 2H) 2.44 (t, J=5.8 Hz, 2H) 1.86-1.96 (m, 2H); LCMS (ESI): 342/344 (M+H, 79Br)/(M+H, 81Br).

Step 3. trans-1-Benzyl-4-(4-bromobenzyl)-piperidin-3-ol

1-Benzyl-4-(4-bromo-benzyl)-1,2,3,6-tetrahydro-pyridine (1.29 g, 3.77 mmol) in THF (18 mL) was treated with 1.00 M of borane in THF (17.0 mL, 17.0 mmol) at room temperature. After 45 min, water (8.0 mL, 440 mmol) was cautiously added (gas evolution, exotherm) and then 5.00 M of sodium hydroxide in water (6.00 mL, 30.0 mmol) and 30% Hydrogen Peroxide (6.00 mL, 52.9 mmol) were added. After stirring overnight at room temperature, the mixture was diluted with ethyl acetate (100 mL) and 1M HCl (50 mL). The mixture was then basified with 5M NaOH, separated and the aq. was extracted with ethylacetate (100 mL). The combined organics were washed with satd. aq. sodium thiosulfate (2×50 mL) and brine (50 mL), dried over sodium sulfate, filtered through silica gel (2 mL) and the filtrate was concentrated in vacuo to afford the crude trans-1-Benzyl-4-(4-bromo-benzyl)-piperidin-3-ol.

Step 4. trans-1-Benzyl-4-(4-quinolin-3-yl-benzyl)-piperidin-3-ol trans-1-Benzyl-4-(4-bromobenzyl)-piperidin-3-ol (1.36 g, 3.77 mmol), 3-quinolineboronic acid (1.01 g, 5.85 mmol), tetrakis(triphenylphosphine)palladium(0) (0.218 g, 0.189 mmol) and sodium carbonate (1.20 g, 11.3 mmol) were combined in water (22 mL):1,4-dioxane (66 mL), vacuum degassed, backfilled with nitrogen then heated at 90° C. for 4h. The mixture was cooled, diluted with 1M HCl (50 mL) and ethyl acetate (100 mL). The layers were separated, the organic was further extracted with 1M HCl (2×50 mL). The combined aqueous extract was washed with 1:1 ethyl acetate:hexane (50 mL), then treated with 5M NaOH (30 mL) then extracted with DCM (3×50 mL). The combined DCM extract was washed with brine (50 mL), dried over sodium sulfate, filtered and concentrated in vacuo onto silica gel (12 g). The crude product was purified on silica gel (80 g, 0-5% methanol: DCM) to afford trans-1-Benzyl-4-(4-quinolin-3-yl-benzyl)-piperidin-3-ol (1.04 g, 67%). $^1$H NMR (400 MHz, Chloroform-D) δ 9.18 (1H, d, J=2.3 Hz), 8.29 (1H, d, J=2.0 Hz), 8.13 (1H, d, J=8.5 Hz), 7.88 (1H, d, J=8.0 Hz), 7.68-7.77 (1H, m), 7.64 (2H, d, J=8.0 Hz), 7.53-7.61 (1H, m), 7.22-7.40 (18H, m), 3.42-3.62 (4H, m), 3.12-3.23 (1H, m), 2.93-3.04 (1H, m), 2.66-2.78 (1H, m), 2.48-2.59 (1H, m), 1.95-2.04 (2H, m), 1.58-1.83 (4H, m), 1.28-1.41 (2H, m).

Step 5. 3-{4-[trans-1-Benzyl-3-(tert-butyl-dimethyl-silanyloxy)-piperidin-4-ylmethyl]-phenyl}-quinoline trans-1-Benzyl-4-(4-quinolin-3-yl-benzyl)-piperidin-3-ol (153 mg, 0.374 mmol), 1H-Imidazole (0.0765 g, 1.12 mmol) and tert-butyldimethylsilyl chloride (0.0847 g, 0.562 mmol) were combined in DMF (4.00 mL) and stirred at room temperature over a weekend. The mixture was then diluted with ethyl acetate (70 mL) and washed with water (2×20 mL). The organics were diluted with hexane (10 mL), washed with brine (50 mL), dried over sodium sulfate, filtered and concentrated in vacuo to afford 3-{4-[trans-1-benzyl-3-(tert-butyl-dimethyl-silanyloxy)-piperidin-4-ylmethyl]-phenyl}-quinoline (0.186 g, 95%). $^1$H NMR (400 MHz, DMSO-d6) δ 9.16 (1H, d, J=2.3 Hz), 8.54 (1H, d, J=2.3 Hz), 7.97 (2H, d, J=9.5 Hz), 7.74 (2H, d, J=8.3 Hz), 7.66-7.71 (1H, m), 7.53-7.60 (1H, m), 7.18-7.28 (7H, m), 3.31-3.51 (4H, m), 3.09-3.17 (1H, m), 2.82-2.88 (1H, m), 2.61-2.66 (1H, m), 2.12-2.23 (1H, m), 1.65-1.79 (2H, m), 1.33-1.43 (2H, m), 1.09-1.20 (1H, m), 0.80 (9H, s), −0.14-−0.07 (6H, m).

Step 6. trans-3-(tert-Butyl-dimethyl-silanyloxy)-4-(4-quinolin-3-yl-benzyl)-piperidine-1-carboxylic acid benzyl ester 3-{4-[trans-1-Benzyl-3-(t-butyl-dimethyl-silanyloxy)-piperidin-4-ylmethyl]-phenyl}-quinoline (0.95 g, 1.81 mmol) was dissolved in 1,2-dichloroethane (18.0 mL) then treated with benzyl chloroformate (0.800 mL, 5.60 mmol). After stirring overnight, a second aliquot of benzyl chloroformate (0.8 mL) was added and stirring was continued. After stirring overnight, the mixture was heated at 60° C. for 4h, which resulted in full debenzylation and formation of a quaternary quinolinium-benzyl carbamate. Addition of 5.00 M of NaOH in water (20.0 mL) and ethanol (20.0 mL) and subsequent heating for 3 h resulted in removal of the quaternary carbamate. The mixture was cooled, diluted with EtOAc (100 mL) and brine (50 mL) and the layers were separated. The organic phase was washed with brine (50 mL), dried over sodium sulfate and filtered. The filtrate was concentrated in vacuo onto silica gel (7 g) and purified on silica gel (80 g, 0-30% ethyl acetate:hexane) to afford trans-3-(t-Butyl-dimethyl-silanyloxy)-4-(4-quinolin-3-yl-benzyl)-piperidine-1-carboxylic acid benzyl ester (0.65 g, 63%) as a clear, colorless oil. rotameric mixture by $^1$H NMR (400 MHz, DCCl$_3$) δ ppm 9.18 (d, J=2.3 Hz, 1H) 8.24-8.34 (m, 1H) 8.13 (d, J=8.3 Hz, 1H) 7.88 (d, J=8.0 Hz, 1H) 7.68-7.77 (m, 1H) 7.61-7.67 (m, 2H) 7.54-7.61 (m, 1H) 7.27-7.39 (m, 7H) 5.00-5.26 (m, 2H) 4.15-4.43 (m, 1H) 3.21-3.45 (m, 2H) 2.54-3.08 (m, 2H) 2.08-2.24 (m, 1H) 1.63-1.94 (m, 2H) 1.10-1.24 (m, 1H) 0.83-1.03 (m, 10H) 0.03-0.24 (m, 6H); LCMS (ESI): 567 (M+H).

Step 8. 3-{4-[(3S,4R)-3-(tert-Butyldimethyl-silanyloxy)-piperidin-4-ylmethyl]-phenyl}-quinoline trans-3-(tert-Butyl-dimethyl-silanyloxy)-4-(4-quinolin-3-yl-benzyl)-piperidine-1-carboxylic acid benzyl ester (0.65 g, 1.1 mmol) was dissolved in 1,2-dichloroethane (20.0 mL, 254 mmol) and dimethyl sulfide (5.00 mL, 68.2 mmol) then boron trifluoride etherate (0.50 mL, 3.9 mmol) was added to the mixture which was stirred at room temperature for 24h. The mixture was quenched by the addition of satd. sodium bicarbonate (20 mL) and the mixture was extracted with DCM (3×10 mL). The organic extracts were washed with saturated sodium thiosulfate (50 mL) and brine (20 mL), dried over sodium sulfate, filtered and concentrated in vacuo. LCMS confirmed the formation 3-{4-[(3 S,4R)-3-(tert-Butyl-dimethyl-silanyloxy)-piperidin-4-ylmethyl]-phenyl}-quinoline with additional byproduct, the N-benzyl derivative.

Step 9. trans-3-(tert-Butyldimethylsilanyloxy)-4-(4-quinolin-3-yl-benzyl)-piperidin-1-yl]-(R)-tetrahydro-furan-2-yl-methanone (R)-Tetrahydrofuran-2-carboxylic acid (0.250 mL, 2.61 mmol), N,N-DIPEA (2.00 mL, 11.5 mmol) and HATU (0.872 g, 2.29 mmol) were combined in THF (6.0 mL) and stirred for 20 min, then the crude secondary amine mixture from Step g was added as a solution in THF (9.0 mL). After 3h, the mixture was diluted with ethyl acetate (50 mL), washed with water (20 mL) and brine (20 mL), dried over sodium sulfate, filtered and concentrated in vacuo. The residue was dissolved in DCM, applied to a silica gel loading cartridge (12 g) and purified on silica gel (24 g, 0-50% ethyl acetate:hexane) to afford trans-3-(tert-Butyl-dimethyl-silanyloxy)-4-(4-quinolin-3-yl-benzyl)-piperidin-1-yl]-(R)-tetrahydro-furan-2-yl-methanone (0.301 g, 49%, two steps). 1H NMR (400 MHz, DMSO-d6) δ 9.20-9.29 (m, 1H) 8.59-8.67 (m, 1H) 8.01-8.13 (m, 2H) 7.81-7.88 (m, 2H) 7.73-7.80 (m, 1H) 7.60-7.69 (m, 1H) 7.29-7.37 (m, 2H) 4.55-4.67 (m, 1H) 3.68-4.52 (m, 4H) 3.37-3.50 (m, 1H) 3.14-3.25 (m, 1H) 2.83-2.96 (m, 1H) 1.69-2.30 (m, 6H) 1.44-1.57 (m, 1H) 0.98-1.27 (m, 2H) 0.94 (s, 9H) 0.10-0.18 (m, 6H).

Step 10. [trans-3-Hydroxy-4-(4-quinolin-3-yl-benzyl)-piperidin-1-yl]-(R)-tetrahydro-furan-2-yl-methanone trans-3-(tert-Butyldimethyl-silanyloxy)-4-(4-quinolin-3-yl-benzyl)-piperidin-1-yl]-(R)-tetrahydrofuran-2-yl-methanone (0.299 g, 0.563 mmol) in THF (6.0 mL) was treated with triethylamine trishydrofluoride (0.200 mL, 1.23 mmol) at room temperature. After 4 h, no conversion to product was observed. 1.00 M of tetra-n-butylammonium fluoride in THF (1.0 mL, 1.0 mmol) was added and the mixture was stirred at room temperature. After 3 d, conversion was not complete. Additional 1.00 M of tetra-n-butylammonium fluoride in THF (1.0 mL, 1.0 mmol) was added and the mixture was heated at 50° C. under an atmosphere of nitrogen for 6 h, then was stirred over the weekend at room temperature. The mixture was partitioned between EtOAc (20 mL) and satd. aq. NaHCO₃ (10 mL). The layers were separated, the aq. extracted with ethyl acetate (10 mL) and the combined organic extracts were dried over Na₂SO₄, filtered and concentrated in vacuo. The residue was dissolved in a DCM, applied to a silica gel loading cartridge (5 g) and purified on silica gel (12 g, 40-100% EtOAc:hexane) to afford [trans-3-Hydroxy-4-(4-quinolin-3-yl-benzyl)-piperidin-1-yl]-(R)-tetrahydro-furan-2-yl-methanone (0.198 g, 84%). LCMS (ESI): 417 (M+H); ¹H NMR (400 MHz, DMSO-d6) δ 9.16-9.25 (m, 1H) 8.47-8.58 (m, 1H) 7.95-8.08 (m, 2H) 7.70-7.81 (m, 3H) 7.56-7.65 (m, 1H) 7.30-7.40 (m, 2H) 4.66-4.89 (m, 1H) 4.4-4.62 (m, 1H) 4.14-4.38 (m, 1H) 3.96-4.13 (m, 1H) 3.67-3.83 (m, 2H) 3.06-3.28 (m, 2H) 2.67-2.79 (m, 1H) 2.37-2.45 (m, 1H) 2.00-2.12 (m, 1H) 1.90-1.96 (m, 1H) 1.75-1.87 (m, 2H) 1.65-1.73 (m, 1H) 1.52-1.62 (m, 1H) 1.01-1.15 (m, 1H).

Example 225

1-(4-Fluoro-4-{Methoxy-[4-(8-methyl-quinolin-7-yl)-phenyl]-methyl}-piperidin-1-yl)-propan-1-one, HCl

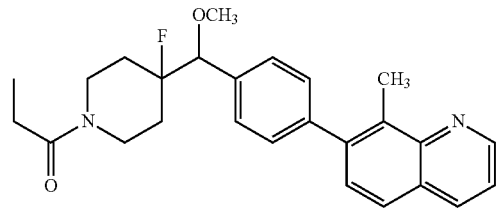 [SMILES: CCC(=O)N1CCC(F)(C(OC)c2ccc(-c3ccc4cccnc4c3C)cc2)CC1]

1-(4-Fluoro-4-{hydroxy-[4-(8-methyl-quinolin-7-yl)-phenyl]-methyl}-piperidin-1-yl)-propan-1-one (79 mg, 0.19 mmol; Example 189), methyl iodide (15.1 uL, 0.243 mmol) and sodium hydride, 60% disp. in mineral oil (77.7 mg, 1.94 mmol) were combined in DMF (2.00 mL) and the mixture was stirred at room temperature for 2 h. The mixture was quenched with water (10 mL) and ethyl acetate (10 mL) was added. The layers were separated, the aq. extracted with additional ethyl acetate (2×10 mL) and the combined organics were diluted with hexane (5 mL) and washed with water (10 mL) and brine (10 mL), then dried over sodium sulfate, filtered and concentrated in vacuo. The residue was dissolved in a DCM, applied to a silica gel loading cartridge (5 g) and purified on silica gel (12 g, 10-90% ethyl acetate:hexane) to afford purified free base, which was dissolved in ethyl acetate and treated with 2M HCl in ether (1 mL). Concentration in vacuo afforded 1-(4-Fluoro-4-{Methoxy-[4-(8-methyl-quinolin-7-yl)-phenyl]-methyl}-piperidin-1-yl)-propan-1-one hydrochloride (61 mg, 69%). ¹H NMR (400 MHz, DMSO-d6) δ 9.17 (dd, J=4.8, 1.5 Hz, 1H) 8.91 (d, J=7.8 Hz, 1H) 8.13 (d, J=8.5 Hz, 1H) 7.92 (dd, J=8.0, 4.8 Hz, 1H) 7.75 (d, J=8.3 Hz, 1H) 7.40-7.58 (m, 4H) 4.37 (d, J=17.1 Hz, 1H) 4.27-4.35 (m, 1H) 3.75-3.86 (m, 1H) 3.25 (s, 3H) 3.07-3.20 (m, 1H) 2.74 (s, 3H) 2.62-2.70 (m, 1H) 2.32 (q, J=7.3 Hz, 2H) 1.41-2.05 (m, 4H) 0.98 (t, J=7.4 Hz, 3H); ¹⁹F NMR (377 MHz, DMSO-d6) δ−171.14 (d, J=25.9 Hz, 1F); LCMS (ESI): 421 (M+H).

Example 226

1-(4-Fluoro-4-{(2-methoxy-ethoxy)-[4-(8-methyl-quinolin-7-yl)-phenyl]-methyl}-piperidin-1-yl)-propan-1-one, TFA Salt

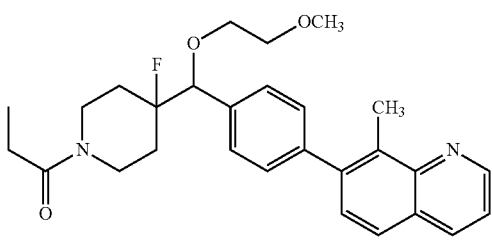 [SMILES: CCC(=O)N1CCC(F)(C(OCCOC)c2ccc(-c3ccc4cccnc4c3C)cc2)CC1]

1-(4-Fluoro-4-{hydroxy-[4-(8-methyl-quinolin-7-yl)-phenyl]-methyl}-piperidin-1-yl)-propan-1-one (83 mg, 0.20 mmol; Example 189), 1-chloro-2-methoxyethane (23.0 mg, 0.243 mmol), potassium iodide (22 mg, 0.13 mmol) and sodium hydride, 60% disp. in mineral oil (77.7 mg, 1.94 mmol) were combined in DMF ormamide (2.00 mL) and the mixture was stirred at room temperature for 2 h then at 50° C. for 20 h. The mixture was quenched with water (10 mL) and EtOAc (10 mL) was added. The layers were separated, the aq. extracted with additional EtOAc (2×10 mL) and the combined organics were diluted with hexane (5 mL) and washed with 2M NaOH (3×10 mL) and brine (10 mL), then dried over sodium sulfate and filtered. The residue was dissolved in DMSO and purified by preparative HPLC (5-50% acetonitrile:water, both containing 0.1% TFA) to afford 1-(4-Fluoro-4-{(2-methoxy ethoxy)-[4-(8-methyl-quinolin-7-yl)-phenyl]-methyl}-piperidin-1-yl)-propan-1-one TFA salt (26 mg, 22%) after lyophilization of product containing fractions. $^1$H NMR (400 MHz, DMSO-d6) δ 9.01 (dd, J=4.3, 1.8 Hz, 1H) 8.47 (d, J=7.8 Hz, 1H) 7.92 (d, J=8.5 Hz, 1H) 7.63 (dd, J=8.3, 4.3 Hz, 1H) 7.55 (d, J=8.3 Hz, 1H) 7.43-7.50 (m, 4H) 4.49 (d, J=17.3 Hz, 1H) 4.27-4.39 (m, 1H) 3.74-3.88 (m, 1H) 3.41-3.56 (m, 4H) 3.26 (s, 3H) 3.08-3.19 (m, 1H) 2.63-2.77 (m, 4H) 2.26-2.38 (m, 2H) 1.88-2.00 (m, 1H) 1.54-1.82 (m, 2H) 0.98 (t, J=7.4 Hz, 3H); $^{19}$F NMR (377 MHz, DMSO-d6) δ −74.67 (s, 3F) -171.33 (d, J=62.7 Hz, 1F); LCMS (ESI): 465 (M+H).

Example 227

1-{4-Fluoro-4-[[4-(8-methyl-quinolin-7-yl)-phenyl]-(2-morpholin-4-yl-ethoxy)-methyl]-piperidin-1-yl}-propan-1-one, TFA Salt

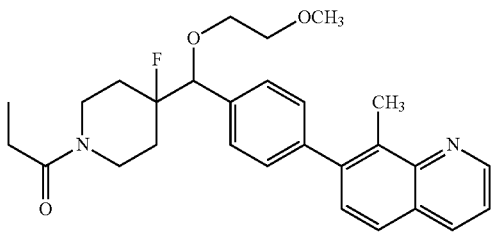 [SMILES: CCC(=O)N1CCC(F)(C(OCCOC)c2ccc(-c3ccc4cccnc4c3C)cc2)CC1]

1-(4-Fluoro-4-{hydroxy-[4-(8-methyl-quinolin-7-yl)-phenyl]-methyl}-piperidin-1-yl)-propan-1-one (79 mg, 0.19 mmol; Example 189), 4-(2-chloroethyl)-morpholine HCl (45.2 mg, 0.243 mmol), potassium iodide (26 mg, 0.16 mmol) and NaH, 60% disp. in mineral oil (77.7 mg, 1.94 mmol) were combined in DMF (2.00 mL) and the mixture was stirred at RT for 2 h then at 50° C. for 20 h. The mixture was quenched with water (10 mL) and EtOAc (10 mL) was added. The layers were separated, the aq. extracted with additional EtOAc (2×10 mL) and the combined organics were diluted with hexane (5 mL) and washed with 2M NaOH (3×10 mL) and brine (10 mL), then dried over Na$_2$SO$_4$ and filtered. The residue was dissolved in DMSO and purified by preparative HPLC (5-50% acetonitrile:water, both containing 0.1% trifluoroacetic acid) to afford 1-{4-fluoro-4-[[4-(8-methyl-quinolin-7-yl)-phenyl]-(2-morpholin-4-yl-ethoxy)-methyl]-piperidin-1-yl}-propan-1-one trifluoroacetic acid salt (23 mg, 19%) after lyophilization of product containing fractions. $^1$H NMR (400 MHz, DMSO-d6) δ 9.66-9.95 (m, 1H) 9.00 (dd, J=4.3, 1.8 Hz, 1H) 8.42 (dd, J=8.3, 1.8 Hz, 1H) 7.91 (d, J=8.3 Hz, 1H) 7.56-7.64 (m, 1H) 7.45-7.55 (m, 5H) 4.51-4.62 (m, 2H) 4.31-4.37 (m, 1H) 3.96-4.07 (m, 2H) 3.61-3.87 (m, 5H) 3.34-3.51 (m, 4H) 3.08-3.24 (m, 3H) 2.63-2.80 (m, 4H) 2.28-2.39 (m, 2H) 2.01-2.16 (m, 1H) 1.49-1.70 (m, 2H) 0.98 (t, J=7.4 Hz, 3H); $^{19}$F NMR (377 MHz, DMSO-d6) δ−74.39 (s, 3F) -172.13 (d, J=316.1 Hz, 1F); LCMS (ESI): 520 (M+H).

Example 228

N-ethyl-4-fluoro-[[4-(8-methyl-7-quinolyl)phenyl]methyl]piperidine-1-carboxamide, TFA Salt

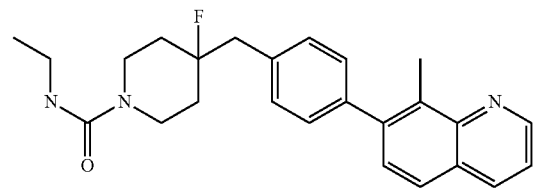 [SMILES: CCNC(=O)N1CCC(F)(Cc2ccc(-c3ccc4cccnc4c3C)cc2)CC1]

1-[4-fluoro-4-[[4-(8-methyl-7-quinolyl)phenyl]methyl]-1-piperidyl]propan-1-one HCl (0.235 g, 0.5504 mmol, Example 150) was combined with ethanol (3.0 mL) and KOH (1M in water) (2.5 mL, 2.5 mmol) and the mixture was heated in a CEM microwave (120° C., 2 h). The mixture was diluted with water (3 mL) then extracted with EtOAc (2×10 mL) and the combined organic extract was washed with brine (2 mL), dried over Na$_2$SO$_4$, filtered and concentrated in vacuo. The residue was dissolved in a mixture of THF (3.0 mL) and Et$_3$N (0.73 g, 1.0 mL, 7.2 mmol) then treated with ethyl isocyanate (0.100 mL, 1.24 mmol). After 2h, the mixture was concentrated in vacuo. The residue was dissolved in DMSO and purified by preparative HPLC (5-55% acetonitrile:water, both containing 0.1% TFA) to afford N-ethyl-4-fluoro-4-[[4-(8-methyl-7-quinolyl)phenyl]methyl]piperidine-1-carboxamide TFA salt (0.151 g, 0.291 mmol, 52.8% Yield) after lyophilization of product containing fractions. LCMS (ESI): 406 (M+1); $^1$H NMR (400 MHz, DMSO-d$_6$) δ 9.02 (dd, J=4.3, 1.8 Hz, 1H), 8.51 (d, J=7.5 Hz, 1H), 7.93 (d, J=8.3 Hz, 1H), 7.65 (dd, J=8.2, 4.4 Hz, 1H), 7.55 (d, J=8.3 Hz, 1H), 7.43-7.33 (m, 4H), 6.48 (br. s., 1H), 3.86-3.72 (m, 2H), 3.08-2.98 (m, 4H), 2.96-2.87 (m, 2H), 2.67 (s, 3H), 1.72-1.52 (m, 4H), 1.00 (t, J=7.2 Hz, 3H); $^{19}$F NMR (377 MHz, DMSO-d$_6$) δ−74.76 (s, 3F), −157.74 (s, 1F).

Example 229

N-ethyl-4-[[4-(8-methyl-7-quinolyl)phenyl]methyl]piperidine-1-carboxamide, HCl

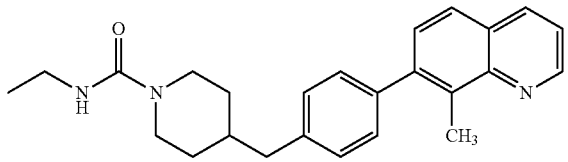 [SMILES: CCNC(=O)N1CCC(Cc2ccc(-c3ccc4cccnc4c3C)cc2)CC1]

To a solution of 8-methyl-7-[4-(4-piperidylmethyl)phenyl]quinoline 2HCl (0.1 g, 0.26 mmol) and DIPEA (452 µL, 2.57 mmol) in DCM (8 mL) at 0° C. was added isocyanatoethane (24 µL, 0.31 mmol) and stirred 1 h at 0° C. The reaction mixture was concentrated and the residue was purified by prep-HPLC. The product fractions were combined and neutralized with sat. NaHCO$_3$ solution (25 mL), extracted with DCM (3×25 mL), dried (Na$_2$SO$_4$), and concentrated. The product was dissolved in DCM (~5 mL) and mixed with 1.2 eq. of 2 M HCl in Et$_2$O and concentrated. The residue was dissolved in a small amount of DCM and concentrated—repeated this procedure several times, dried to give 89 mg (81%) as white solid. LCMS m/z=388 (M+1); $^1$H NMR (DMSO-d$_6$) δ: 9.11 (1H, d, J=3.5 Hz), 8.75 (1H, d, J=6.5 Hz), 8.04 (1H, d, J=8.3 Hz), 7.80 (1H, dd, J=7.7, 4.4 Hz), 7.65 (1H, d, J=8.5 Hz), 7.31-7.41 (4H, m), 6.23-6.53 (1H, m), 3.94 (2H, d, J=13.1 Hz), 3.03 (2H, q, J=7.3 Hz), 2.70 (3H, s), 2.55-2.65 (4H, m), 1.73 (1H, td, J=7.3, 3.8 Hz), 1.57 (2H, d, J=11.5 Hz), 1.03-1.13 (2H, m), 1.00 (3H, t, J=7.0 Hz).

The following compounds were synthesized using the procedure for Example 229.

Example 230

N-ethyl-4-[[4-(8-methoxy-7-quinolyl)phenyl]methyl]piperidine-1-carboxamide, HCl

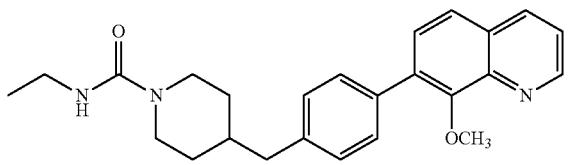 [SMILES: CCNC(=O)N1CCC(Cc2ccc(-c3ccc4cccnc4c3OC)cc2)CC1]

Analysis: Yellow solid. LCMS m/z=404 (M+1); $^1$H NMR (400 MHz, DMSO-d$_6$) δ: 9.12 (1H, dd, J=4.8, 1.5 Hz), 8.87 (1H, d, J=7.3 Hz), 8.02 (1H, d, J=8.5 Hz), 7.81-7.91 (2H, m), 7.64 (2H, d, J=8.0 Hz), 7.36 (2H, d, J=8.0 Hz), 6.25-6.51 (1H, m), 3.89-3.98 (2H, m), 3.76 (4H, s), 3.03 (3H, q, J=7.2 Hz), 2.54-2.65 (4H, m), 1.68-1.80 (1H, m), 1.53-1.61 (2H, m), 1.03-1.14 (2H, m), 0.99 (3H, t, J=7.2 Hz).

Example 231

N-methoxy-4-[[4-(8-methyl-7-quinolyl)phenyl]methyl]piperidine-1-carboxamide, HCl

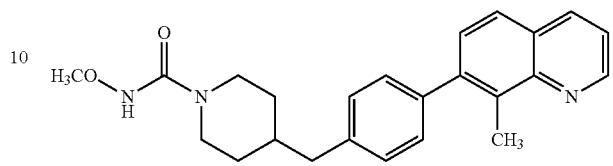

To a mixture of 8-methyl-7-[4-(4-piperidylmethyl)phenyl]quinoline 2HCl (100 mg, 0.26 mmol) and bis(trichloromethyl) carbonate (57 mg, 0.19 mmol) in DCM (15 mL) at 0° C. was added DIPEA (452 µL, 2.57 mmol). After stirred 1 h at rt, the reaction was added O-methylhydroxylamine HCl (85.7 mg, 1.03 mmol), DIPEA (452 µL, 2.57 mmol), and potassium carbonate (179 mg, 1.28 mmol). The reaction was heated at 48° C. for 18 h. After cooled room temp, the reaction was added DCM (50 mL), washed with water (30 mL), brine, dried (MgSO$_4$), and concentrated. The residue was purified by pre-HPLC and the product fractions were combined and neutralized with sat. NaHCO$_3$ solution (25 mL), extracted with DCM (3×25 mL), dried (Na$_2$SO$_4$), and concentrated. The product was dissolved in DCM (~5 mL) and mixed with 1.2 eq. of 2 M HCl in Et$_2$O and concentrated. The residue was dissolved in a small amount of DCM and concentrated-repeated this procedure several times, dried to give 67 mg (61%) as off-white solid. LCMS m/z=390 (M+1); $^1$H NMR (400 MHz, DMSO-d$_6$) δ: 9.49-9.88 (1H, m), 9.15 (1H, dd, J=4.8, 1.5 Hz), 8.87 (1H, d, J=7.3 Hz), 8.11 (1H, d, J=8.5 Hz), 7.86-7.93 (1H, m), 7.71 (1H, d, J=8.5 Hz), 7.32-7.43 (4H, m), 3.80-3.90 (2H, m), 3.52 (3H, s), 2.72 (3H, s), 2.57-2.69 (4H, m), 1.70-1.82 (1H, m), 1.54-1.63 (2H, m), 1.02-1.16 (2H, m).

The following compounds were synthesized using the procedure for Example 231.

Example 232

N-ethoxy-4-[[4-(8-methyl-7-quinolyl)phenyl]methyl]piperidine-1-carboxamide, HCl

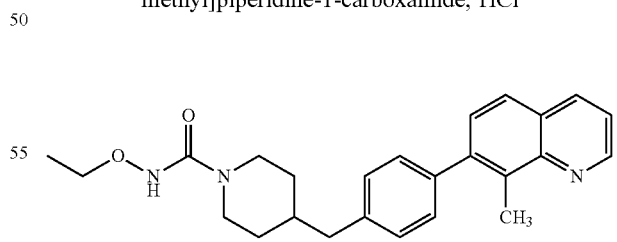

Analysis: Light-brown solid. LCMS m/z=404 (M+1); $^1$H NMR (400 MHz, DMSO-d$_6$) δ: 9.46-9.64 (1H, m), 9.09-9.15 (1H, m), 8.74-8.82 (1H, m), 8.06 (1H, d, J=8.5 Hz), 7.82 (1H, dd, J=8.0, 4.5 Hz), 7.66 (1H, d, J=8.3 Hz), 7.31-7.41 (4H, m), 3.81-3.90 (2H, m), 3.73 (2H, q, J=7.0 Hz), 2.71 (3H, s), 2.57-2.68 (4H, m), 1.69-1.82 (1H, m), 1.53-1.64 (2H, m), 1.11 (5H, t, J=7.0 Hz).

Example 233

N,N-dimethyl-4-[[4-(8-methyl-7-quinolyl)phenyl]methyl]piperidine-1-carboxamide, HCl

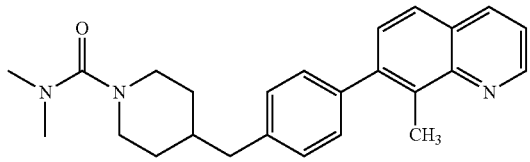 [SMILES: Cc1c(-c2ccc(CC3CCN(C(=O)N(C)C)CC3)cc2)ccc2cccnc12]

Analysis: Off-white solid. LCMS m/z=388 (M+1); $^1$H NMR (400 MHz, DMSO-d$_6$) δ: 9.11-9.16 (1H, m), 8.79-8.89 (1H, m), 8.05-8.13 (1H, m), 7.83-7.91 (1H, m), 7.65-7.74 (1H, m), 7.38-7.43 (2H, m), 7.32-7.36 (2H, m), 3.49-3.59 (2H, m), 2.69-2.76 (9H, m), 2.58-2.68 (4H, m), 1.67-1.80 (1H, m), 1.57-1.66 (2H, m), 1.11-1.26 (2H, m).

Example 234

[4-[[4-(8-methyl-7-quinolyl)phenyl]methyl]-1-piperidyl]-pyrrolidin-1-yl-methanone, HCl

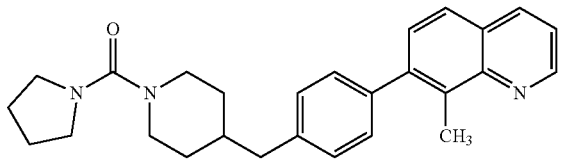 [SMILES: Cc1c(-c2ccc(CC3CCN(C(=O)N4CCCC4)CC3)cc2)ccc2cccnc12]

To a solution of 8-methyl-7-[4-(4-piperidylmethyl)phenyl]quinoline 2HCl (100 mg, 0.26 mmol) and DIPEA (452 µL, 2.57 mmol) in THF (8 mL) was added pyrrolidine-1-carbonyl chloride (34 µL, 0.31 mmol) and stirred for 4 h. The reaction mixture was concentrated and the residue was purified by Pre-HPLC. The product fractions were combined and neutralized with sat. NaHCO$_3$ solution (25 mL), extracted with DCM (3×25 mL), dried (Na$_2$SO$_4$), and concentrated. The product was dissolved in DCM (~5 mL) and mixed with 1.2 eq. of 2 M HCl in Et$_2$O and concentrated. The residue was dissolved in a small amount of DCM and concentrated—repeated this procedure several times, dried to give 94 mg (82%) as off-white solid. LCMS m/z=414 (M+1); $^1$H NMR (400 MHz, DMSO-d$_6$) δ: 9.11-9.17 (1H, m), 8.77-8.87 (1H, m), 8.05-8.11 (1H, m), 7.81-7.90 (1H, m), 7.65-7.72 (1H, m), 7.38-7.43 (2H, m), 7.31-7.37 (2H, m), 3.61-3.70 (2H, m), 3.20-3.28 (4H, m), 2.71 (3H, s), 2.57-2.68 (4H, m), 1.69-1.78 (5H, m), 1.57-1.66 (2H, m), 1.10-1.26 (2H, m).

A number of embodiments of the invention have been described herein. Nevertheless, As those skilled in the art will appreciate, numerous modifications and variations of the present invention are possible in light of the above teachings; without departing from the scope of the invention that is disclosed herein. It is therefore understood that within the scope of the appended claims, the invention may be practiced otherwise than as specifically described herein, and the scope of the invention is intended to encompass all such variations.

What is claimed is:
1. A compound according to Formula I:

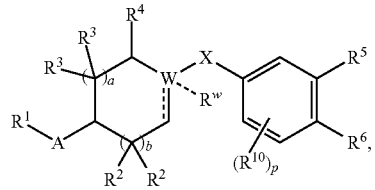

or a pharmaceutically acceptable salt thereof, wherein:

A is —C(=O)— or —SO$_2$—;

R$^1$ is selected from —H, —(C$_1$-C$_{10}$)hydrocarbyl, substituted —(C$_1$-C$_{10}$)hydrocarbyl, 3-7 membered heterocyclyl, substituted 3-7 membered heterocyclyl, —(C$_6$-C$_{10}$)aryl, substituted —(C$_6$-C$_{10}$)aryl, 5-6 membered heteroaryl, substituted 5-6 membered heteroaryl, —NR$^7$R$^8$, —N(OR$^8$)R$^7$, —SR$^7$, —N(SR$^8$)R$^7$, —C(=O)—(C$_1$-C$_6$) alkyl and —(C$_1$-C$_6$) heteroalkyl;

a and b are 1;

each R$^2$ and each R$^3$ is independently selected from —H and —(C$_1$-C$_4$) alkyl;

R$^4$ is —H, —C$_1$-C$_6$ alkyl, —OH, =O, —O(C$_1$-C$_6$) alkyl, halogen or —CN;

wherein one of the R$^3$ groups can be structurally connected to one of the R$^2$ groups to form an alkylene bridge to produce a bicyclic ring; or one of the R$^3$ groups can be structurally connected to the R$^1$ group to form a 5 to 7 membered heterocyclyl ring fused to the 1-2 face of the piperidine ring;

R$^5$ is selected from —H, —C$_1$-C$_7$ hydrocarbyl, —C$_3$-C$_6$ heterocyclyl; halogen, —(C$_1$-C$_3$) haloalkyl, —CN, —NR$^{7a}$R$^{8a}$, —O(CH$_2$)$_n$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O)NR$^{7a}$R$^{8a}$, —C(=O)OR$^{7a}$, 5-6 membered heteroaryl, and substituted 5-6 membered heteroaryl; wherein n is an integer selected from 1, 2, 3, and 4;

W is an sp3 hybridized carbon atom bonded to a R$^w$ substituent, or is an sp2 hybridized carbon atom, and no R$^w$ substituent is present;

═══ signifies that the designated bond is a carbon-carbon single bond or a carbon-carbon double bond;

------- signifies that the designated bond is a C—R$^w$ single bond when ═══ is a carbon-carbon single bond, i.e., W is an sp$^3$ hybridized carbon atom, and a R$^w$ substituent is present, and that the ------- bond is not present bond when ═══ is a carbon-carbon double bond, i.e., W is an sp$^2$ hybridized carbon atom, and there is no 1r substituent;

R$^6$ is selected from 9-10 membered bicyclic heteroaryl, and substituted 9-10 membered bicyclic heteroaryl; provided that, when R$^6$ is a 9-membered bicyclic heteroaryl or a substituted 9-membered bicyclic heteroaryl, the point of attachment of R$^6$ is on a 6-membered ring portion of the 9-membered bicyclic heteroaryl or substituted 9-membered bicyclic heteroaryl;

R$^7$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl;

R$^8$ is selected from —H, and —(C$_1$-C$_6$) alkyl, wherein R$^7$ can be structurally connected to R$^8$ to form a 5 to 7 membered heterocyclyl ring;

R$^{7a}$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl;

$R^{8a}$ is selected from —H, and —($C_1$-$C_6$) alkyl, wherein $R^{7a}$ can be structurally connected to $R^{8a}$ to form a 5 to 7 membered heterocyclyl ring;

X is selected from $CH_2$, $CHR^9$, $C(R^9)_2$, $C=C(R^{11})_2$, C(=O), C(=NO—($C_1$-$C_7$) hydrocarbyl), and C(=NO—C(=O)—($C_1$-$C_7$) hydrocarbyl);

each $R^9$ is independently selected from halogen, —($C_1$-$C_7$) hydrocarbyl, —O—($C_1$-$C_7$) hydrocarbyl, —NH—$R^{11}$, —O—$(CH_2)_m$-(5-6 membered heterocyclyl), and —($C_1$-$C_6$) heteroalkyl; or the two $R^9$ groups can together form a spirofused heterocyclic ring or carbocyclic ring; wherein m is an integer selected from 1, 2, 3 and 4;

$R^w$ is selected from —H, halogen, —CN, —OH, —($C_1$-$C_7$) hydrocarbyl, and substituted —($C_1$-$C_7$) hydrocarbyl;

each $R^{10}$ is independently selected from halogen, —CN, —OH, —($C_1$-$C_7$) hydrocarbyl, and substituted —($C_1$-$C_7$) hydrocarbyl; p is an integer selected from 0, 1 and 2; and $R^{11}$ is selected from —H and —($C_1$-$C_7$) hydrocarbyl.

2. The compound according to claim 1 or a pharmaceutically acceptable salt thereof wherein $R^6$ is selected from:

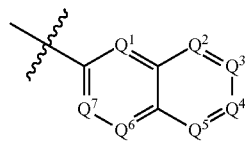
(i)

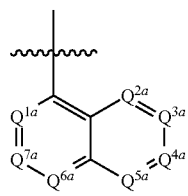
(ii)

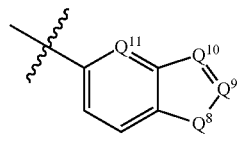
(iii)

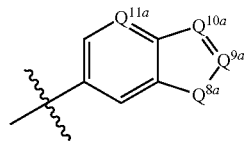
(iv)

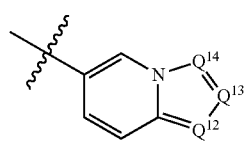
(v)

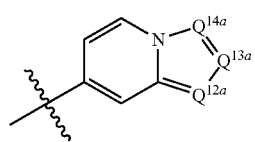
(vi)

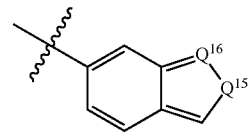
(vii)

wherein, when $R^6$ is (i), $Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;

when $R^6$ is $Q^{1a}$, $Q^{2a}$, $Q^{3a}$, $Q^{4a}$, $Q^{5a}$, $Q^{6a}$ and $Q^{7a}$ are independently selected from N and C—$R^{12}$, provided that 1, 2 or 3 of $Q^{1a}$, $Q^{2a}$, $Q^{3a}$, $Q^{4a}$, $Q^{5a}$, $Q^{6a}$ and $Q^{7a}$ are N, and the remainder of $Q^{1a}$, $Q^{2a}$, $Q^{3a}$, $Q^{4a}$, $Q^{5a}$, $Q^{6a}$ and $Q^{7a}$ are C—$R^{12}$;

when $R^6$ is (iii), $Q^8$ is selected from O, S, and N—$R^{12n}$, $Q^9$, $Q^{10}$ and $Q^{11}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (iv), $Q^{8a}$ is selected from O, S, and N—$R^{12n}$, $Q^{9a}$, $Q^{10a}$ and $Q^{11a}$ are independently selected from N and C—$R^{12}$, provided that 1 or 2 of $Q^{9a}$, $Q^{10a}$ and $Q^{11a}$ are N, and the remainder of $Q^{9a}$, $Q^{10a}$ and $Q^{11a}$ are C—$R^{12}$, when $R^6$ is (v), $Q^{12}$, $Q^{13}$ and $Q^{14}$ are independently selected from N and C—$R^{12}$; and when $R^6$ is (vi), $Q^{12a}$, $Q^{13a}$ and $Q^{14a}$ are independently selected from N and C—$R^{12}$, when $R^6$ is (vii), $Q^{15}$ is selected from N—$R^{12n}$ and C—$R^{12}$ and $Q^{16}$ is selected from N and C—$R^{12}$; provided that $Q^{15}$ and $Q^{16}$ are not both C—$R^{12}$;

wherein the non-bridgehead ring carbon ring atoms in (i), (ii), (iii), (iv), (v), (vi) and (vii) that are not designated as $Q^1$, $Q^2$, $Q^3$, $Q^4$, $Q^5$, $Q^6$, $Q^7$, $Q^8$, $Q^9$, $Q^{10}$, $Q^{11}$, $Q^{12}$, $Q^{13}$, $Q^{14}$, $Q^{15}$, $Q^{16}$, $Q^{1a}$, $Q^{2a}$, $Q^{3a}$, $Q^{4a}$, $Q^{5a}$, $Q^{6a}$, $Q^{7a}$, $Q^{8a}$, $Q^{9a}$, $Q^{10a}$, $Q^{11a}$, $Q^{12a}$, $Q^{13a}$ or $Q^{14a}$ are substituted or unsubstituted;

$R^{11}$ is selected from —H and —($C_1$-$C_7$) hydrocarbyl;

each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O$(CH_2)_r$-(5-6 membered heterocyclyl), —O$(CH_2)_r$—O($C_1$-$C_6$) alkyl, —$NH_2$, —CN, —NH($C_1$-$C_6$) alkyl, —N($C_1$-$C_6$ alkyl)$_2$, —NH$(CH_2)_r$—O($C_1$-$C_6$) alkyl, —NH$(CH_2)_r$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$; wherein r is an integer selected independently from 1, 2, 3, and 4; and each $R^{12n}$ is independently selected from —H, —($C_1$-$C_7$) hydrocarbyl and substituted —($C_1$-$C_7$) hydrocarbyl.

3. A compound according to Formula I:

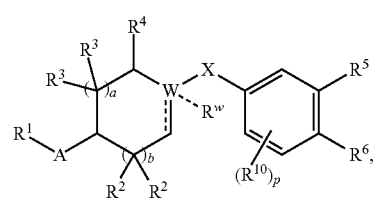

I or a pharmaceutically acceptable salt thereof, wherein:

A is —C(=O)— or —SO$_2$—;

R$^1$ is selected from —H, —(C$_1$-C$_{10}$)hydrocarbyl, substituted —(C$_1$-C$_{10}$)hydrocarbyl, 3-7 membered heterocyclyl, substituted 3-7 membered heterocyclyl, —(C$_6$-C$_{10}$)aryl, substituted —(C$_6$-C$_{10}$)aryl, 5-6 membered heteroaryl, substituted 5-6 membered heteroaryl, —NR$^7$R$^8$, —N(OR$^8$)R$^7$, —SR$^7$, —N(SR$^8$)R$^7$, —C(=O)—(C$_1$-C$_6$) alkyl and —(C$_1$-C$_6$) heteroalkyl;

a and b are independently selected from 0 and 1;

each R$^2$ and each R$^3$ is independently selected from —H and —(C$_1$-C$_4$) alkyl;

R$^4$ is —H, —C$_1$-C$_6$ alkyl, —OH, =O, —O(C$_1$-C$_6$) alkyl, halogen or —CN;

wherein one of the R$^3$ groups can be structurally connected to one of the R$^2$ groups to form an alkylene bridge to produce a bicyclic ring; or one of the R$^3$ groups can be structurally connected to the R$^1$ group to form a 5 to 7 membered heterocyclyl ring fused to the 1-2 face of the piperidine ring; or one of the R$^3$ groups can be structurally connected to the R$^4$ group to form a 5-7 membered carbocyclic or heterocyclic ring fused to the 2-3 face of the piperidine ring;

R$^5$ is selected from —H, —C$_1$-C$_7$ hydrocarbyl, heterocyclyl; halogen, —(C$_1$-C$_3$) haloalkyl, —OR$^{7a}$, —CN, —NR$^{7a}$R$^{8a}$, —O(CH$_2$)$_n$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O)NR$^{7a}$R$^{8a}$, —C(=O)OR$^{7a}$, 5-6 membered heteroaryl, and substituted 5-6 membered heteroaryl; wherein n is an integer selected from 1, 2, 3, and 4;

W is an sp3 hybridized carbon atom bonded to a R$^w$ substituent, or is an sp2 hybridized carbon atom, and no R$^w$ substituent is present;

═══ signifies that the designated bond is a carbon-carbon single bond or a carbon-carbon double bond;

------ signifies that the designated bond is a C—R$^w$ single bond when ═══ is a carbon-carbon single bond, i.e., W is an sp$^3$ hybridized carbon atom, and a R$^w$ substituent is present, and that the ------ bond is not present bond when ═══ is a carbon-carbon double bond, i.e., W is an sp$^2$ hybridized carbon atom, and there is no R$^w$ substituent;

wherein R$^6$ is:

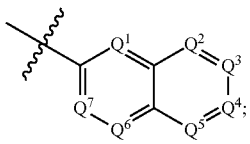

(i)

wherein 1 or 2 of Q$^1$, Q$^2$, Q$^3$, Q$^4$, Q$^5$, Q$^6$ and Q$^7$ are N, and the remainder of Q$^1$, Q$^2$, Q$^3$, Q$^4$, Q$^5$, Q$^6$ and Q$^7$ are C—R$^{12}$;

R$^7$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl;

R$^8$ is selected from —H, and —(C$_1$-C$_6$) alkyl, wherein R$^7$ can be structurally connected to R$^8$ to form a 5 to 7 membered heterocyclyl ring;

R$^{7a}$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl;

R$^{8a}$ is selected from —H, and —(C$_1$-C$_6$) alkyl, wherein R$^{7a}$ can be structurally connected to R$^{8a}$ to form a 5 to 7 membered heterocyclyl ring;

X is selected from CH$_2$, CHR$^9$, C(R$^9$)$_2$, C=C(R$^{11}$)$_2$, C(=O), C(=NO—(C$_1$-C$_7$) hydrocarbyl), and C(=NO—C(=O)—(C$_1$-C$_7$) hydrocarbyl);

each R$^9$ is independently selected from halogen, —(C$_1$-C$_7$) hydrocarbyl, —O—R$^{11}$, —NH—R$^{11}$, —O—(CH$_2$)$_m$-(5-6 membered heterocyclyl), and —(C$_1$-C$_6$) heteroalkyl; or the two R$^9$ groups can together form a spirofused heterocyclic ring or carbocyclic ring; wherein m is an integer selected from 1, 2, 3 and 4;

R$^w$ is selected from —H, halogen, —CN, —OH, —(C$_1$-C$_7$) hydrocarbyl, and substituted —(C$_1$-C$_7$) hydrocarbyl;

each R$^{10}$ is independently selected from halogen, —CN, —OH, —(C$_1$-C$_7$) hydrocarbyl, and substituted —(C$_1$-C$_7$) hydrocarbyl; p is an integer selected from 0, 1 and 2;

R$^{11}$ is selected from —H and —(C$_1$-C$_7$) hydrocarbyl; and each R$^{12}$ is independently selected from —H, halogen, —(C$_1$-C$_6$) alkyl, —(C$_3$-C$_6$) cycloalkyl, 5-6 membered heterocyclyl, —OH, —O(C$_1$-C$_6$) alkyl, —O(CH$_2$)$_r$-(5-6 membered heterocyclyl), —O(CH$_2$)$_r$—O(C$_1$-C$_6$) alkyl, —NH, —CN, —NH(C$_1$-C$_6$) alkyl, —N(C$_1$-C$_6$ alkyl)$_2$, —NH(CH$_2$)$_r$—O(C$_1$-C$_6$) alkyl, —NH(CH$_2$)$_r$—N(C$_1$-C$_6$ alkyl)$_2$, —C(=O)NH$_2$, —C(=O)NH(C$_1$-C$_6$) alkyl, and —C(=O)N(C$_1$-C$_6$ alkyl)$_2$; wherein r is an integer selected independently from 1, 2, 3, and 4.

4. The compound according to claim 3 or a pharmaceutically acceptable salt thereof, wherein R$^6$ is:

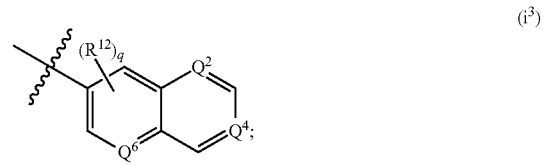

(i$^3$)

wherein one or two of Q$^2$, Q$^4$ and Q$^6$ is N, and the remainder of Q$^2$, Q$^4$ and Q$^6$ are C—R$^{12}$, and q is an integer selected from 0, 1, 2 and 3.

5. The compound according to claim 3 or a pharmaceutically acceptable salt thereof, wherein p is 0.

6. The compound according to claim 3 or a pharmaceutically acceptable salt thereof, wherein R$^1$ is selected from —(C$_1$-C$_{10}$) hydrocarbyl, —NR$^7$R$^8$, and —N(OR$^8$)R$^7$.

7. The compound according to claim 3 or a pharmaceutically acceptable salt thereof, wherein X is selected from —CH$_2$—, —CHF— and —CF$_2$—.

8. The compound according to claim 3 or a pharmaceutically acceptable salt thereof, wherein R$^4$ is —H or halogen.

9. The compound according to claim 1:

or a pharmaceutically acceptable salt thereof, wherein:

A is —C(=O)—;

R$^1$ is selected from —(C$_1$-C$_{10}$) hydrocarbyl, substituted —(C$_1$-C$_{10}$) hydrocarbyl, 3-7 membered heterocyclyl, substituted 3-7 membered heterocyclyl, —NR$^7$R$^8$, and —N(OR$^8$)R$^7$, —SR$^7$ and —N(SR$^8$)R$^7$;

a is 1; b is 1;

each R$^2$ is each R$^3$ is H;

R$^5$ is H;

W is an sp3 hybridized carbon atom bonded to a R$^w$ substituent;

═══ is a carbon-carbon single bond;

X is selected from —CH$_2$—, —CHR$^9$—, and —C(R$^9$)$_2$;

R$^9$ is independently selected from —(C$_1$-C$_7$) hydrocarbyl;

R$^w$ is selected from —H and halogen;

R⁶ is:

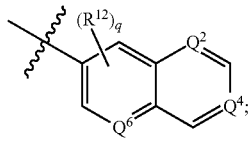

wherein at least one of Q², Q⁴ and Q⁶ is N, and the remainder of Q², Q⁴ and Q⁶ are C—R¹²;

each R¹² is independently selected from —H, halogen, —(C₁-C₆) alkyl, —(C₃-C₆) cycloalkyl, 5-6 membered heterocyclyl, —OH, —O(C₁-C₆) alkyl, —O(CH₂)ᵣ-(5-6 membered heterocyclyl), —O(CH₂)ᵣ—O(C₁-C₆) alkyl, —NH₂, —CN, —NH(C₁-C₆) alkyl, —N(C₁-C₆ alkyl)₂, —NH(CH₂)ᵣ—O(C₁-C₆) alkyl, —NH(CH₂)ᵣ—N(C₁-C₆ alkyl)₂, —C(═O)NH₂, —C(═O)NH(C₁-C₆) alkyl, and —C(═O)N(C₁-C₆ alkyl)₂; wherein q is an integer selected from 0, 1, and 2; and r is an integer selected from 1, 2, 3 or 4; or a salt thereof.

10. The compound according to claim 9 or a pharmaceutically acceptable salt thereof, wherein p is 0 or 1.

11. The compound according to claim 9 or a pharmaceutically acceptable salt thereof, wherein each R¹² is independently selected from —H, halogen, —(C₁-C₆) alkyl, —OH and —O(C₁-C₆) alkyl.

12. The compound according to claim 9 or a pharmaceutically acceptable salt thereof, wherein R¹ is selected from —(C₁-C₁₀) hydrocarbyl, —NR⁷R⁸, and —N(OR⁸)R⁷.

13. The compound according to claim 9 or a pharmaceutically acceptable salt thereof, wherein X is selected from —CH₂—, —CHF— and —CF₂—.

14. The compound according to claim 9 or a pharmaceutically acceptable salt thereof, wherein R⁴ is —H or halogen.

15. The compound according to claim 9 or a pharmaceutically acceptable salt thereof, wherein Q² is N; and Q⁴ and Q⁶ are C—R¹².

16. The compound according to claim 9 or a pharmaceutically acceptable salt thereof, wherein Q⁴ is N; and Q² and Q⁶ are C—R¹².

17. The compound according to claim 9 or a pharmaceutically acceptable salt thereof, wherein Q⁶ is N; and Q² and Q⁴ are C—R¹².

18. The compound according to claim 9 or a pharmaceutically acceptable salt thereof, wherein Rʷ is —H.

19. The compound according to claim 9, selected from:
1-[4-(4-quinolin-3-yl-benzyl)-piperidin-1-yl]-propan-1-one;
2-methyl-1-[4-(4-quinolin-3-yl-benzyl)-piperidin-1-yl]-propan-1-one;
cyclopropyl-[4-(4-quinolin-3-yl-benzyl)-piperidin-1-yl]-methanone;
4-(4-quinolin-3-yl-benzyl)-piperidin-1-yl]-(R)-tetrahydrofuran-2-yl-methanone;
4-(4-quinolin-3-yl-benzyl)-piperidin-1-yl]-(S)-tetrahydrofuran-2-yl-methanone;
1-{4-[4-(4-methylquinolin-3-yl)-benzyl]-piperidin-1-yl}-propan-1-one;
cyclopropyl-{4-[4-(4-methylquinolin-3-yl)-benzyl]-piperidin-1-yl}-methanone;
(3,3-difluorocyclobutyl)-{4-[4-(4-methylquinolin-3-yl)-benzyl]-piperidin-1-yl}-methanone;
{4-[4-(4-methylquinolin-3-yl)-benzyl]-piperidin-1-yl}-(R)-tetrahydrofuran-2-yl-methanone;
1-{4-[4-(4-chloroquinolin-3-yl)-benzyl]-piperidin-1-yl}-propan-1-one;
{4-[4-(4-chloroquinolin-3-yl)-benzyl]-piperidin-1-yl}-cyclopropylmethanone;
{4-[4-(4-chloroquinolin-3-yl)-benzyl]-piperidin-1-yl}-(3,3-difluorocyclobutyl)-methanone;
{4-[4-(4-chloroquinolin-3-yl)-benzyl]-piperidin-1-yl}-(R)-tetrahydrofuran-2-yl-methanone;
1-{4-[4-(8-methylquinolin-7-yl)-benzyl]-piperidin-1-yl}-propan-1-one;
cyclopropyl-{4-[4-(8-methylquinolin-7-yl)-benzyl]-piperidin-1-yl}-methanone;
{4-[4-(8-methylquinolin-7-yl)-benzyl]-piperidin-1-yl}-(R)-tetrahydrofuran-2-yl-methanone;
1-{4-[4-(8-chloroquinolin-7-yl)-benzyl]-piperidin-1-yl}-propan-1-one;
{4-[4-(8-chloroquinolin-7-yl)-benzyl]-piperidin-1-yl}-cyclopropylmethanone;
{4-[4-(8-chloroquinolin-7-yl)-benzyl]-piperidin-1-yl}-(R)-tetrahydrofuran-2-yl-methanone;
1-{4-[4-(8-methoxyquinolin-7-yl)-benzyl]-piperidin-1-yl}-propan-1-one;
cyclopropyl-{4-[4-(8-methoxyquinolin-7-yl)-benzyl]-piperidin-1-yl}-methanone;
{4-[4-(8-methoxyquinolin-7-yl)-benzyl]-piperidin-1-yl}-(R)-tetrahydrofuran-2-yl-methanone;
1-{4-[4-(1-methylisoquinolin-6-yl)-benzyl]-piperidin-1-yl}-propan-1-one;
cyclopropyl-{4-[4-(1-methylisoquinolin-6-yl)-benzyl]-piperidin-1-yl}-methanone;
{4-[4-(1-methylisoquinolin-6-yl)-benzyl]-piperidin-1-yl}-(R)-tetrahydrofuran-2-yl-methanone;
1-(4-(1-(4-(quinolin-3-yl)phenyl)ethyl)piperidin-1-yl)propan-1-one;
1-{4-[1-(4-quinolin-3-yl-phenyl)-cyclopropyl]-piperidin-1-yl}-propan-1-one;
1-{4-[1-(4-quinolin-7-yl-phenyl)-ethyl]-piperidin-1-yl}-propan-1-one;
cyclopropyl-{4-[1-(4-quinolin-3-yl-phenyl)-cyclopropyl]-piperidin-1-yl}-methanone;
cyclopropyl-{4-[1-(4-quinolin-7-yl-phenyl)-cyclopropyl]-piperidin-1-yl}-methanone
1-{4-[1-(4-quinolin-3-yl-phenyl)-propyl]-piperidin-1-yl}-propan-1-one;
1-{4-[cyclopropyl-(4-quinolin-3-yl-phenyl)-methyl]-piperidin-1-yl}-propan-1-one;
{4-[1-(4-quinolin-7-yl-phenyl)-ethyl]-piperidin-1-yl}-(R)-tetrahydrofuran-2-yl-methanone;
{4-[1-(4-quinolin-3-yl-phenyl)-ethyl]-piperidin-1-yl}-(R)-tetrahydrofuran-2-yl-methanone;
1-{4-[1-(4-quinolin-3-yl-phenyl)-butyl]-piperidin-1-yl}-propan-1-one;
cyclopropyl-{4-[1-(4-quinolin-3-yl-phenyl)-ethyl]-piperidin-1-yl}-methanone;
1-{4-[2-methyl-1-(4-quinolin-3-yl-phenyl)-propyl]-piperidin-1-yl}-propan-1-one;
1-(4-{1-[4-(8-methylquinolin-7-yl)-phenyl]-ethyl}-piperidin-1-yl)-propan-1-one;
cyclopropyl-(4-{1-[4-(8-methylquinolin-7-yl)-phenyl]-ethyl}-piperidin-1-yl)-methanone;
1-(4-{1-[4-(8-methoxyquinolin-7-yl)-phenyl]-ethyl}-piperidin-1-yl)-propan-1-one;
1-(4-{1-[4-(4-methylquinolin-3-yl)-phenyl]-ethyl}-piperidin-1-yl)-propan-1-one;
cyclopropyl-(4-{1-[4-(8-methoxyquinolin-7-yl)-phenyl]-ethyl}-piperidin-1-yl)-methanone;

1-{4-[1-(4-quinolin-3-yl-phenyl)-ethyl]-piperidin-1-yl}-propan-1-one;
(4-{1-[4-(8-methoxyquinolin-7-yl)-phenyl]-ethyl}-piperidin-1-yl)-(R)-tetrahydrofuran-2-yl-methanone; mixture of diastereomers;
(4-{1-[4-(8-methylquinolin-7-yl)-phenyl]-ethyl}-piperidin-1-yl)-(R)-tetrahydrofuran-2-yl-methanone; mixture of diastereomers;
(4-{1-[4-(4-methylquinolin-3-yl)-phenyl]-ethyl}-piperidin-1-yl)-(R)-tetrahydrofuran-2-yl-methanone; mixture of diastereomers;
1-(4-{1-[4-(8-chloroquinolin-7-yl)-phenyl]-ethyl}-piperidin-1-yl)-propan-1-one;
(4-{1-[4-(8-chloroquinolin-7-yl)-phenyl]-ethyl}-piperidin-1-yl)-cyclopropylmethanone;
(4-{1-[4-(8-chloroquinolin-7-yl)-phenyl]-ethyl}-piperidin-1-yl)-(R)-tetrahydrofuran-2-yl-methanone; mixture of diastereomers;
1-(4-{1-[4-(4-chloroquinolin-3-yl)-phenyl]-ethyl}-piperidin-1-yl)-propan-1-one;
(4-{1-[4-(4-chloroquinolin-3-yl)-phenyl]-ethyl}-piperidin-1-yl)-cyclopropylmethanone;
(4-{1-[4-(4-chloroquinolin-3-yl)-phenyl]-ethyl}-piperidin-1-yl)-(R)-tetrahydrofuran-2-yl-methanone; mixture of diastereomers;
(4-{1-[4-(1-methylisoquinolin-6-yl)-phenyl]-cyclopropyl}-piperidin-1-yl)-(R)-tetrahydrofuran-2-yl-methanone;
(4-{1-[4-(8-methylquinolin-7-yl)-phenyl]-cyclopropyl}-piperidin-1-yl)-(R)-tetrahydrofuran-2-yl-methanone;
1-(4-fluoro-4-(4-(quinolin-3-yl)benzyl)piperidin-1-yl)propan-1-one;
1-(4-fluoro-4-(4-(quinolin-7-yl)benzyl)piperidin-1-yl)propan-1-one;
1-(4-fluoro-4-(4-(isoquinolin-6-yl)benzyl)piperidin-1-yl)propan-1-one;
cyclopropyl(4-fluoro-4-(4-(quinolin-3-yl)benzyl)piperidin-1-yl)methanone;
cyclopropyl(4-fluoro-4-(4-(quinolin-7-yl)benzyl)piperidin-1-yl)methanone;
cyclopropyl(4-fluoro-4-(4-(isoquinolin-6-yl)benzyl)piperidin-1-yl)methanone;
(R)-(4-fluoro-4-(4-(4-methylquinolin-3-yl)benzyl)piperidin-1-yl)(tetrahydrofuran-2-yl)methanone;
cyclopropyl(4-fluoro-4-(4-(8-methylquinolin-7-yl)benzyl)piperidin-1-yl)methanone;
1-(4-fluoro-4-(4-(8-methylquinolin-7-yl)benzyl)piperidin-1-yl)propan-1-one;
(R)-(4-fluoro-4-(4-(quinolin-7-yl)benzyl)piperidin-1-yl)(tetrahydrofuran-2-yl)methanone;
(R)-(4-fluoro-4-(4-(quinolin-3-yl)benzyl)piperidin-1-yl)(tetrahydrofuran-2-yl)methanone;
cyclopropyl(4-fluoro-4-(4-(4-methylquinolin-3-yl)benzyl)piperidin-1-yl)methanone;
1-(4-(4-(4-chloroquinolin-3-yl)benzyl)-4-fluoropiperidin-1-yl)propan-1-one;
1-(4-fluoro-4-(4-(4-methylquinolin-3-yl)benzyl)piperidin-1-yl)propan-1-one;
(4-(4-(4-chloroquinolin-3-yl)benzyl)-4-fluoropiperidin-1-yl)(cyclopropyl)methanone;
(R)-(4-fluoro-4-(4-(8-methylquinolin-7-yl)benzyl)piperidin-1-yl)(tetrahydrofuran-2-yl)methanone;
(R)-(4-(4-(4-chloroquinolin-3-yl)benzyl)-4-fluoropiperidin-1-yl)(tetrahydrofuran-2-yl)-methanone;
cyclopropyl(4-(2-(4-(quinolin-3-yl)phenyl)propan-2-yl)piperidin-1-yl)methanone;
1-(4-(2-(4-(quinolin-3-yl)phenyl)propan-2-yl)piperidin-1-yl)propan-1-one;
1-[trans-3-hydroxy-4-(4-quinolin-3-yl-benzyl)-piperidin-1-yl]-propan-1-one;
1-[(trans)-3-methoxy-4-(4-quinolin-3-yl-benzyl)-piperidin-1-yl]-propan-1-one;
1-propionyl-4-(4-quinolin-3-yl-benzyl)-piperidin-3-one;
1-[cis-3-fluoro-4-(4-quinolin-3-yl-benzyl)-piperidin-1-yl]-propan-1-one;
[trans-3-hydroxy-4-(4-quinolin-3-yl-benzyl)-piperidin-1-yl]-(R)-tetrahydrofuran-2-yl-methanone;
N-ethyl-4-fluoro-4-[[4-(8-methyl-7-quinolyl)phenyl]methyl]piperidine-1-carboxamide;
N-ethyl-4-[[4-(8-methyl-7-quinolyl)phenyl]methyl]piperidine-1-carboxamide;
N-ethyl-4-[[4-(8-methoxy-7-quinolyl)phenyl]methyl]piperidine-1-carboxamide;
N-methoxy-4-[[4-(8-methyl-7-quinolyl)phenyl]methyl]piperidine-1-carboxamide;
N-ethoxy-4-[[4-(8-methyl-7-quinolyl)phenyl]methyl]piperidine-1-carboxamide;
N,N-dimethyl-4-[[4-(8-methyl-7-quinolyl)phenyl]methyl]piperidine-1-carboxamide;
[4-[[4-(8-methyl-7-quinolyl)phenyl]methyl]-1-piperidyl]-pyrrolidin-1-yl-methanone; and
pharmaceutically acceptable salts of such compounds.

20. A pharmaceutical composition comprising at least one compound according to claim 3 or a pharmaceutically acceptable salt thereof, and at least one pharmaceutically acceptable excipient.

21. A method of treatment of a subject suffering from a disorder mediated by fatty acid synthase, comprising administering to the subject a therapeutically effective amount of a compound according to claim 3 or a pharmaceutically acceptable salt thereof.

22. A method of treatment of a subject suffering from a disorder mediated by fatty acid synthase, comprising administering to the subject a therapeutically effective amount of a pharmaceutical composition according to claim 20.

23. A method of treating a subject who is suffering from weight gain associated with drug therapy with an antipsychotic agent, said method comprising administering a compound according to claim 3 or a pharmaceutically acceptable salt thereof.

24. The method of claim 23, wherein the antipsychotic agent is selected from clozapine, risperidone, aripiprazole, olanzapine, quetiapine and ziprasidone and combinations thereof.

25. The compound according to claim 1, selected from the group consisting of:
1-[4-(4-quinolin-3-yl-benzyl)-piperidin-1-yl]-propan-1-one;
2-methyl-1-[4-(4-quinolin-3-yl-benzyl)-piperidin-1-yl]-propan-1-one;
cyclopropyl-[4-(4-quinolin-3-yl-benzyl)-piperidin-1-yl]-methanone;
4-(4-quinolin-3-yl-benzyl)-piperidin-1-yl]-(R)-tetrahydro-furan-2-yl-methanone;
4-(4-quinolin-3-yl-benzyl)-piperidin-1-yl]-(S)-tetrahydro-furan-2-yl-methanone;
1-{4-[fluoro-(4-quinolin-3-yl-phenyl)-methyl]-piperidin-1-yl}-propan-1-one;
cyclopropyl-{4-[fluoro-(4-quinolin-3-yl-phenyl)-methyl]-piperidin-1-yl}-methanone;
{4-[fluoro-(4-quinolin-3-yl-phenyl)-methyl]-piperidin-1-yl}-(R)-tetrahydrofuran-2-yl-methanone;

1-(4-{difluoro-[4-(4-methyl-quinolin-3-yl)-phenyl]-methyl}-piperidin-1-yl)-propan-1-one;
cyclopropyl-(4-{difluoro-[4-(4-methyl-quinolin-3-yl)-phenyl]-methyl}-piperidin-1-yl)-methanone;
(4-{difluoro-[4-(4-methyl-quinolin-3-yl)-phenyl]-methyl}-piperidin-1-yl)-(R)-tetrahydrofuran-2-yl-methanone;
1-{4-[4-(4-methyl-quinolin-3-yl)-benzyl]-piperidin-1-yl}-propan-1-one;
cyclopropyl-{4-[4-(4-methyl-quinolin-3-yl)-benzyl]-piperidin-1-yl}-methanone;
(3,3-difluoro-cyclobutyl)-{4-[4-(4-methyl-quinolin-3-yl)-benzyl]-piperidin-1-yl}-methanone;
{4-[4-(4-methyl-quinolin-3-yl)-benzyl]-piperidin-1-yl}-(R)-tetrahydro-furan-2-yl-methanone;
1-{4-[difluoro-(4-quinolin-3-yl-phenyl)-methyl]-piperidin-1-yl}-propan-1-one;
cyclopropyl-{4-[difluoro-(4-quinolin-3-yl-phenyl)-methyl]-piperidin-1-yl}-methanone;
{4-[difluoro-(4-quinolin-3-yl-phenyl)-methyl]-piperidin-1-yl}-(R)-tetrahydrofuran-2-yl-methanone;
1-{4-[4-(4-chloro-quinolin-3-yl)-benzyl]-piperidin-1-yl}-propan-1-one;
{4-[4-(4-chloro-quinolin-3-yl)-benzyl]-piperidin-1-yl}-cyclopropylmethanone;
{4-[4-(4-chloro-quinolin-3-yl)-benzyl]-piperidin-1-yl}-(3,3-difluoro-cyclobutyl)-methanone;
{4-[4-(4-chloro-quinolin-3-yl)-benzyl]-piperidin-1-yl}-(R)-tetrahydrofuran-2-yl-methanone;
1-{4-[4-(8-methyl-quinolin-7-yl)-benzyl]-piperidin-1-yl}-propan-1-one;
cyclopropyl-{4-[4-(8-methyl-quinolin-7-yl)-benzyl]-piperidin-1-yl}-methanone;
{4-[4-(8-methyl-quinolin-7-yl)-benzyl]-piperidin-1-yl}-(R)-tetrahydro-furan-2-yl-methanone;
1-[4-(4-isoquinolin-3-yl-benzyl)-piperidin-1-yl]-propan-1-one;
cyclopropyl-[4-(4-isoquinolin-3-yl-benzyl)-piperidin-1-yl]-methanone;
[4-(4-isoquinolin-3-yl-benzyl)-piperidin-1-yl]-(R)-tetrahydro-furan-2-yl-methanone;
1-{4-[4-(8-chloro-quinolin-7-yl)-benzyl]-piperidin-1-yl}-propan-1-one;
{4-[4-(8-chloro-quinolin-7-yl)-benzyl]-piperidin-1-yl}-cyclopropylmethanone;
{4-[4-(8-chloro-quinolin-7-yl)-benzyl]-piperidin-1-yl}-(R)-tetrahydrofuran-2-yl-methanone;
1-{4-[4-(8-methoxy-quinolin-7-yl)-benzyl]-piperidin-1-yl}-propan-1-one;
cyclopropyl-{4-[4-(8-methoxy-quinolin-7-yl)-benzyl]-piperidin-1-yl}-methanone;
{4-[4-(8-methoxy-quinolin-7-yl)-benzyl]-piperidin-1-yl}-(R)-tetrahydrofuran-2-yl-methanone;
1-{4-[4(1-methyl-isoquinolin-6-yl)-benzyl]-piperidin-1-yl}-propan-1-one;
cyclopropyl-{4-[4-(1-methyl-isoquinolin-6-yl)-benzyl]-piperidin-1-yl}-methanone;
{4-[4-(1-methyl-isoquinolin-6-yl)-benzyl]-piperidin-1-yl}-(R)-tetrahydrofuran-2-yl-methanone;
1-(4-(1-(4-(quinolin-3-yl)phenyl)ethyl)piperidin-1-yl)propan-1-one;
1-{4-[1-(4-quinolin-3-yl-phenyl)-cyclopropyl]-piperidin-1-yl}-propan-1-one;
cyclopropyl-{4-[1-(4-quinolin-3-yl-phenyl)-vinyl]-piperidin-1-yl}-methanone;
1-{4-[1-(4-quinolin-7-yl-phenyl)-ethyl]-piperidin-1-yl}-propan-1-one;
1-{4-[amino-(4-quinolin-3-yl-phenyl)-methyl]-piperidin-1-yl}-propan-1-one;
cyclopropyl-{4-[1-(4-quinolin-3-yl-phenyl)-cyclopropyl]-piperidin-1-yl}-methanone;
cyclopropyl-{4-[1-(4-quinolin-7-yl-phenyl)-cyclopropyl]-piperidin-1-yl}-methanone;
1-{4-[[(E:Z)-methoxyimino]-(4-quinolin-3-yl-phenyl)-methyl]-piperidin-1-yl}-propan-1-one;
1-{4-[1-(4-quinolin-3-yl-phenyl)-propyl]-piperidin-1-yl}-propan-1-one;
1-{4-[cyclopropyl-(4-quinolin-3-yl-phenyl)-methyl]-piperidin-1-yl}-propan-1-one;
[4-(4-quinolin-3-yl-benzoyl)-piperidin-1-yl]-(R)-tetrahydro-furan-2-yl-methanone;
1-{4-[[methoxyimino]-(4-quinolin-7-yl-phenyl)-methyl]-piperidin-1-yl}-propan-1-one;
{4-[1-(4-quinolin-7-yl-phenyl)-ethyl]-piperidin-1-yl}-(R)-tetrahydrofuran-2-yl-methanone;
{4-[1-(4-quinolin-3-yl-phenyl)-ethyl]-piperidin-1-yl}-(R)-tetrahydrofuran-2-yl-methanone;
1-{4-[1-(4-quinolin-3-yl-phenyl)-butyl]-piperidin-1-yl}-propan-1-one;
1-[4-methyl-4-(4-quinolin-3-yl-benzoyl)-piperidin-1-yl]-propan-1-one;
cyclopropyl-{4-[1-(4-quinolin-3-yl-phenyl)-ethyl]-piperidin-1-yl}-methanone;
1-[4-methyl-4-(4-quinolin-3-yl-benzyl)-piperidin-1-yl]-propan-1-one;
4-[1-(4-quinolin-3-yl-phenyl)-ethyl]-piperidine-1-carbaldehyde;
1-{4-[2-methyl-1-(4-quinolin-3-yl-phenyl)-propyl]-piperidin-1-yl}-propan-1-one;
1-(4-{1-[4-(8-methyl-quinolin-7-yl)-phenyl]-ethyl}-piperidin-1-yl)-propan-1-one;
cyclopropyl-(4-{1-[4-(8-methyl-quinolin-7-yl)-phenyl]-ethyl}-piperidin-1-yl)-methanone;
1-(4-{1-[4-(8-methoxy-quinolin-7-yl)-phenyl]-ethyl}-piperidin-1-yl)-propan-1-one;
1-(4-{1-[4-(4-methyl-quinolin-3-yl)-phenyl]-ethyl}-piperidin-1-yl)-propan-1-one;
cyclopropyl-(4-{1-[4-(8-methoxy-quinolin-7-yl)-phenyl]-ethyl}-piperidin-1-yl)-methanone;
1-{4-[1-(4-quinolin-3-yl-phenyl)-ethyl]-piperidin-1-yl}-propan-1-one;
1-{4-[1-(4-quinolin-3-yl-phenyl)-ethyl]-piperidin-1-yl}-propan-1-one;
(4-{1-[4-(8-methoxy-quinolin-7-yl)-phenyl]-ethyl}-piperidin-1-yl)-(R)-tetrahydrofuran-2-yl-methanone; mixture of diastereomers;
(4-{1-[4-(8-methyl-quinolin-7-yl)-phenyl]-ethyl}-piperidin-1-yl)-(R)-tetrahydrofuran-2-yl-methanone; mixture of diastereomers;
(4-{1-[4-(4-methyl-quinolin-3-yl)-phenyl]-ethyl}-piperidin-1-yl)-(R)-tetrahydrofuran-2-yl-methanone; mixture of diastereomers;
1-(4-{1-[4-(8-chloro-quinolin-7-yl)-phenyl]-ethyl}-piperidin-1-yl)-propan-1-one;
(4-{1-[4-(8-chloro-quinolin-7-yl)-phenyl]-ethyl}-piperidin-1-yl)-cyclopropylmethanone;
(4-{1-[4-(8-chloro-quinolin-7-yl)-phenyl]-ethyl}-piperidin-1-yl)-(R)-tetrahydrofuran-2-yl-methanone; mixture of diastereomers;
1-(4-{1-[4-(4-chloro-quinolin-3-yl)-phenyl]-ethyl}-piperidin-1-yl)-propan-1-one;
(4-{1-[4-(4-chloro-quinolin-3-yl)-phenyl]-ethyl}-piperidin-1-yl)-cyclopropylmethanone;

(4-{1-[4-(4-chloro-quinolin-3-yl)-phenyl]-ethyl}-piperidin-1-yl)-(R)-tetrahydrofuran-2-yl-methanone; mixture of diastereomers;
(4-{1-[4-(1-methyl-isoquinolin-6-yl)-phenyl]-cyclopropyl}-piperidin-1-yl)-(R)-tetrahydrofuran-2-yl-methanone;
(4-{1-[4-(8-methyl-quinolin-7-yl)-phenyl]-cyclopropyl}-piperidin-1-yl)-(R)-tetrahydrofuran-2-yl-methanone;
(4-{(2-methoxy-ethoxy)-[4-(8-methyl-quinolin-7-yl)-phenyl]-methyl}-piperidin-1-yl)-(R)-tetrahydrofuran-2-yl-methanone;
1-(4-{(2-methoxy-ethoxy)-[4-(8-methyl-quinolin-7-yl)-phenyl]-methyl}-piperidin-1-yl)-propan-1-one;
(4-{(2-methoxy-ethoxy)-[4-(1-methyl-isoquinolin-6-yl)-phenyl]-methyl}-piperidin-1-yl)-(R)-tetrahydrofuran-2-yl-methanone; mixture of diastereomers;
(4-{(2-methoxy-ethoxy)-[4-(4-methyl-quinolin-3-yl)-phenyl]-methyl}-piperidin-1-yl)-(R)-tetrahydrofuran-2-yl-methanone;
{4-[[4-(8-methyl-quinolin-7-yl)-phenyl]-(3-morpholin-4-yl-propoxy)-methyl]-piperidin-1-yl}-(R)-tetrahydrofuran-2-yl-methanone;
1-{4-[[4-(8-methyl-quinolin-7-yl)-phenyl]-(3-morpholin-4-yl-propoxy)-methyl]-piperidin-1-yl}-propan-1-one;
{4-[[4-(1-methyl-isoquinolin-6-yl)-phenyl]-(3-morpholin-4-yl-propoxy)-methyl]-piperidin-1-yl}-(R)-tetrahydrofuran-2-yl-methanone;
{4-[[4-(4-methyl-quinolin-3-yl)-phenyl]-(3-morpholin-4-yl-propoxy)-methyl]-piperidin-1-yl}-(R)-tetrahydrofuran-2-yl-methanone;
{4-[(2-pyrrolidin-1-yl-ethoxy)-(4-quinolin-3-yl-phenyl)-methyl]-piperidin-1-yl}-(R)-tetrahydrofuran-2-yl-methanone;
{4-[[4-(8-methyl-quinolin-7-yl)-phenyl]-(2-pyrrolidin-1-yl-ethoxy)-methyl]-piperidin-1-yl}-(R)-tetrahydrofuran-2-yl-methanone;
{4-[[4-(1-methyl-isoquinolin-6-yl)-phenyl]-(2-pyrrolidin-1-yl-ethoxy)-methyl]-piperidin-1-yl}-(R)-tetrahydrofuran-2-yl-methanone;
4-[4-(8-methoxy-quinolin-7-yl)-benzyl]-1-((R)-tetrahydro-furan-2-carbonyl)-piperidine-4-carbonitrile;
4-[4-(8-methoxy-quinolin-7-yl)-benzyl]-1-propionyl-piperidine-4-carbonitrile;
{4-[4-(5-methyl-imidazo[1,2-a]pyridin-6-yl)-benzyl]-piperidin-1-yl}-(R)-tetrahydrofuran-2-yl-methanone;
1-{4-[4-(5-methyl-imidazo[1,2-a]pyridin-6-yl)-benzyl]-piperidin-1-yl}-propan-1-one;
cyclopropyl-{4-[4-(5-methyl-imidazo[1,2-a]pyridin-6-yl)-benzyl]-piperidin-1-yl}-methanone;
(1-hydroxy-cyclopropyl)-{4-[4-(5-methyl-imidazo[1,2-a]pyridin-6-yl)-benzyl]-piperidin-1-yl}-methanone;
(R)-(4-fluoro-4-(4-(5-methylimidazo[1,2-a]pyridin-6-yl)benzyl)piperidin-1-yl)(tetrahydrofuran-2-yl)methanone;
2,2,2-trifluoro-1-{4-[2-(4-quinolin-6-yl-phenyl)-1,3-dioxolan-2-yl]-piperidin-1-yl}-ethanone;
cyclopropyl-{4-[2-(4-quinolin-6-yl-phenyl)-1,3-dioxolan-2-yl]-piperidin-1-yl}-methanone;
4-[2-(4-quinolin-6-yl-phenyl)-1,3-dioxolan-2-yl]-piperidine-1-sulfonic acid dimethylamide;
2-methyl-1-{4-[2-(4-quinolin-6-yl-phenyl)-1,3-dioxolan-2-yl]-piperidin-1-yl}-propan-1-one;
4-[2-(4-quinolin-6-yl-phenyl)-1,3-dioxolan-2-yl]-piperidine-1-carboxylic acid dimethylamide;
1-{4-[2-(4-quinolin-6-yl-phenyl)-1,3-dioxolan-2-yl]-piperidin-1-yl}-propan-1-one;
1-{4-[2-(4-quinolin-6-yl-phenyl)-1,3-dioxolan-2-yl]-piperidin-1-yl}-butan-1-one;
1-{4-[2-(4-quinolin-6-yl-phenyl)-1,3-dioxolan-2-yl]-piperidin-1-yl}-ethanone;
4-[2-(4-quinolin-6-yl-phenyl)-1,3-dioxolan-2-yl]-piperidine-1-carboxylic acid cyclopentylamide;
6-(4-{2-[1-(tetrahydropyran-4-yl)-piperidin-4-yl]-1,3-dioxolan-2-yl}-phenyl)-quinoline;
2-methyl-1-[4-(4-quinolin-6-yl-benzoyl)-piperidin-1-yl]-propan-1-one;
2-methyl-1-{4-[2-(4-quinolin-7-yl-phenyl)-1,3-dioxolan-2-yl]-piperidin-1-yl}-propan-1-one;
cyclopropyl-{4-[2-(4-quinolin-7-yl-phenyl)-1,3-dioxolan-2-yl]-piperidin-1-yl}-methanone;
1-{4-[2-(4-quinolin-7-yl-phenyl)-1,3-dioxolan-2-yl]-piperidin-1-yl}-butan-1-one;
1-{4-[2-(4-quinolin-7-yl-phenyl)-1,3-dioxolan-2-yl]-piperidin-1-yl}-propan-1-one;
1-{4-[2-(4-isoquinolin-7-yl-phenyl)-1,3-dioxolan-2-yl]-piperidin-1-yl}-ethanone;
1-{4-[2-(4-isoquinolin-7-yl-phenyl)-1,3-dioxolan-2-yl]-piperidin-1-yl}-propan-1-one;
1-{4-[2-(4-isoquinolin-7-yl-phenyl)-1,3-dioxolan-2-yl]-piperidin-1-yl}-2-methyl-propan-1-one;
1-{4-[2-(4-isoquinolin-6-yl-phenyl)-1,3-dioxolan-2-yl]-piperidin-1-yl}-propan-1-one;
1-{4-[2-(4-isoquinolin-6-yl-phenyl)-1,3-dioxolan-2-yl]-piperidin-1-yl}-2-methyl-propan-1-one;
1-{4-[2-(4-isoquinolin-6-yl-phenyl)-1,3-dioxolan-2-yl]-piperidin-1-yl}-ethanone;
2-methyl-1-{4-[2-(4-quinolin-7-yl-phenyl)-1,3-dioxinan-2-yl]-piperidin-1-yl}-propan-1-one;
cyclopropyl-{4-[2-(4-quinolin-7-yl-phenyl)-1,3-dioxinan-2-yl]-piperidin-1-yl}-methanone;
1-{4-[2-(4-quinolin-7-yl-phenyl)-1,3-dioxinan-2-yl]-piperidin-1-yl}-propan-1-one;
1-[4-(4-quinolin-7-yl-benzoyl)-piperidin-1-yl]-propan-1-one;
1-[4-(2-fluoro-4-isoquinolin-6-yl-benzoyl)-piperidin-1-yl]-propan-1-one;
1-[4-(4-isoquinolin-6-yl-benzoyl)-piperidin-1-yl]-propan-1-one;
1-[4-(2,6-difluoro-4-isoquinolin-6-yl-benzoyl)-piperidin-1-yl]-propan-1-one;
1-{4-[2-(4-quinolin-3-yl-phenyl)-1,3-dioxolan-2-yl]-piperidin-1-yl}-propan-1-one;
2-methyl-1-{4-[2-(4-quinolin-3-yl-phenyl)-1,3-dioxolan-2-yl]-piperidin-1-yl}-propan-1-one;
cyclopropyl-{4-[2-(4-quinolin-3-yl-phenyl)-1,3-dioxolan-2-yl]-piperidin-1-yl}-methanone;
1-[4-(2-fluoro-4-quinolin-7-yl-benzoyl)-piperidin-1-yl]-propan-1-one;
1-[4-(2-fluoro-4-quinolin-3-yl-benzoyl)piperidin-1-yl]propan-1-one;
(4-hydroxy-4-(isoquinolin-3-yl)benzyl)piperidin-1-yl)(isoxazolidin-2-yl)methanone;
[4-hydroxy-4-(4-isoquinolin-3-yl-benzyl)-piperidin-1-yl]-(R)-tetrahydrofuran-2-yl-methanone;
1-[4-hydroxy-4-(4-isoquinolin-6-yl-benzyl)-piperidin-1-yl]-2-methyl-propan-1-one;
1-(4-hydroxy-4-(4-(quinolin-3-yl)benzyl)piperidin-1-yl)propan-1-one;
1-(4-hydroxy-4-(4-(quinolin-3-yl)benzyl)piperidin-1-yl)-2-methylpropan-1-one;
1-(4-hydroxy-4-(4-(quinolin-7-yl)benzyl)piperidin-1-yl)propan-1-one;

1-(4-hydroxy-4-(4-(quinolin-7-yl)benzyl)piperidin-1-yl)-2-methylpropan-1-one;
1-(4-(4-(benzofuran-5-yl)benzyl)-4-hydroxypiperidin-1-yl)propan-1-one;
1-(4-(4-(benzofuran-5-yl)benzyl)-4-hydroxypiperidin-1-yl)-2-methylpropan-1-one;
1-(4-(4-(1H-indol-5-yl)benzyl)-4-hydroxypiperidin-1-yl)propan-1-one;
1-(4-(4-(1H-indol-5-yl)benzyl)-4-hydroxypiperidin-1-yl)-2-methylpropan-1-one;
1-(4-hydroxy-4-(4-(isoquinolin-4-yl)benzyl)piperidin-1-yl)propan-1-one;
1-(4-hydroxy-4-(4-(isoquinolin-4-yl)benzyl)piperidin-1-yl)-2-methylpropan-1-one;
1-(4-hydroxy-4-(4-(isoquinolin-6-yl)benzyl)piperidin-1-yl)propan-1-one;
1-(4-fluoro-4-(4-(quinolin-3-yl)benzyl)piperidin-1-yl)propan-1-one;
1-(4-(4-(quinolin-3-yl)benzyl)-5,6-dihydropyridin-1(2H)-yl)propan-1-one;
1-(4-fluoro-4-(4-(quinolin-7-yl)benzyl)piperidin-1-yl)propan-1-one;
1-(4-(4-(quinolin-7-yl)benzyl)-5,6-dihydropyridin-1(2H)-yl)propan-1-one;
1-(4-fluoro-4-(4-(isoquinolin-6-yl)benzyl)piperidin-1-yl)propan-1-one;
1-(4-(4-(isoquinolin-6-yl)benzyl)-5,6-dihydropyridin-1(2H)-yl)propan-1-one;
1-(4-fluoro-4-(4-(isoquinolin-4-yl)benzyl)piperidin-1-yl)propan-1-one;
1-(4-(4-(isoquinolin-4-yl)benzyl)-5,6-dihydropyridin-1(2H)-yl)propan-1-one;
1-(4-(4-(benzofuran-5-yl)benzyl)-4-fluoropiperidin-1-yl)propan-1-one;
1-(4-(4-(benzofuran-5-yl)benzyl)-5,6-dihydropyridin-1(2H)-yl)propan-1-one;
cyclopropyl(4-fluoro-4-(4-(quinolin-3-yl)benzyl)piperidin-1-yl)methanone;
cyclopropyl(4-(4-(quinolin-3-yl)benzyl)-5,6-dihydropyridin-1(2H)-yl)methanone;
cyclopropyl(4-fluoro-4-(4-(quinolin-7-yl)benzyl)piperidin-1-yl)methanone;
cyclopropyl(4-(4-(quinolin-7-yl)benzyl)-5,6-dihydropyridin-1(2H)-yl)methanone;
cyclopropyl(4-fluoro-4-(4-(isoquinolin-6-yl)benzyl)piperidin-1-yl)methanone;
cyclopropyl(4-(4-(isoquinolin-6-yl)benzyl)-5,6-dihydropyridin-1(2H)-yl)methanone;
cyclopropyl(4-fluoro-4-(4-(isoquinolin-4-yl)benzyl)piperidin-1-yl)methanone;
cyclopropyl(4-(4-(isoquinolin-4-yl)benzyl)-5,6-dihydropyridin-1(2H)-yl)methanone;
(4-(4-(benzofuran-5-yl)benzyl)-4-fluoropiperidin-1-yl)(cyclopropyl)methanone;
(4-(4-(benzofuran-5-yl)benzyl)-5,6-dihydropyridin-1(2H)-yl)(cyclopropyl)methanone;
(R)-(4-fluoro-4-(4-(4-methylquinolin-3-yl)benzyl)piperidin-1-yl)(tetrahydrofuran-2-yl)methanone;
(R)-(4-(4-(4-methylquinolin-3-yl)benzyl)-5,6-dihydropyridin-1(2H)-yl)(tetrahydrofuran-2-yl)methanone;
cyclopropyl(4-fluoro-4-(4-(8-methylquinolin-7-yl)benzyl)piperidin-1-yl)methanone;
cyclopropyl(4-(4-(8-methylquinolin-7-yl)benzyl)-3,6-dihydropyridin-1(2H)-yl)methanone;
1-(4-fluoro-4-(4-(8-methylquinolin-7-yl)benzyl)piperidin-1-yl)propan-1-one;
1-(4-(4-(8-methylquinolin-7-yl)benzyl)-3,6-dihydropyridin-1(2H)-yl)propan-1-one;
(R)-(4-fluoro-4-(4-(quinolin-7-yl)benzyl)piperidin-1-yl)(tetrahydrofuran-2-yl)methanone;
(R)-(4-(4-(quinolin-7-yl)benzyl)-5,6-dihydropyridin-1(2H)-yl)(tetrahydrofuran-2-yl)methanone;
(R)-(4-fluoro-4-(4-(quinolin-3-yl)benzyl)piperidin-1-yl)(tetrahydrofuran-2-yl)methanone;
(R)-(4-(4-(quinolin-3-yl)benzyl)-5,6-dihydropyridin-1(2H)-yl)(tetrahydrofuran-2-yl)methanone;
cyclopropyl(4-fluoro-4-(4-(4-methylquinolin-3-yl)benzyl)piperidin-1-yl)methanone;
cyclopropyl(4-(4-(4-methylquinolin-3-yl)benzyl)-5,6-dihydropyridin-1(2H)-yl)methanone;
1-(4-(4-(4-chloroquinolin-3-yl)benzyl)-4-fluoropiperidin-1-yl)propan-1-one;
1-(4-(4-(4-chloroquinolin-3-yl)benzyl)-3,6-dihydropyridin-1(2H)-yl)propan-1-one;
1-(4-fluoro-4-(4-(4-methylquinolin-3-yl)benzyl)piperidin-1-yl)propan-1-one;
1-(4-(4-(4-Methylquinolin-3-yl)benzyl)-5,6-dihydropyridin-1(2H)-yl)propan-1-one;
(4-(4-(4-chloroquinolin-3-yl)benzyl)-4-fluoropiperidin-1-yl)(cyclopropyl)methanone;
(4-(4-(4-chloroquinolin-3-yl)benzyl)-3,6-dihydropyridin-1(2H)-yl)(cyclopropyl)methanone;
(R)-(4-fluoro-4-(4-(8-methylquinolin-7-yl)benzyl)piperidin-1-yl)(tetrahydrofuran-2-yl)methanone;
(R)-(4-(4-(8-methylquinolin-7-yl)benzyl)-3,6-dihydropyridin-1(2H)-yl)(tetrahydrofuran-2-yl)methanone;
(R)-(4-(4-(4-chloroquinolin-3-yl)benzyl)-4-fluoropiperidin-1-yl)(tetrahydrofuran-2-yl)methanone;
(R)-(4-(4-(4-chloroquinolin-3-yl)benzyl)-3,6-dihydropyridin-1(2H)-yl)(tetrahydrofuran-2-yl)methanone;
cyclopropyl(4-(2-(4-(quinolin-3-yl)phenyl)propan-2-yl)piperidin-1-yl)methanone;
1-(4-(2-(4-(quinolin-3-yl)phenyl)propan-2-yl)piperidin-1-yl)propan-1-one;
1-{4-[1-ethoxy-1-(4-quinolin-3-yl-phenyl)-ethyl]-piperidin-1-yl}-propan-1-one;
cyclopropyl-{4-[1-ethoxy-1-(4-quinolin-3-yl-phenyl)-ethyl]-piperidin-1-yl}-methanone;
1-{4-[1-methoxy-1-(4-quinolin-3-yl-phenyl)-ethyl]-piperidin-1-yl}-propan-1-one;
cyclopropyl-{4-[1-methoxy-1-(4-quinolin-3-yl-phenyl)-ethyl]-piperidin-1-yl}-methanone;
1-{4-[1-methoxy-1-(4-quinolin-3-yl-phenyl)-propyl]-piperidin-1-yl}-propan-1-one;
cyclopropyl-{4-[1-methoxy-1-(4-quinolin-3-yl-phenyl)-propyl]-piperidin-1-yl}-methanone;
1-{4-[1-methoxy-1-(4-quinolin-7-yl-phenyl)-ethyl]-piperidin-1-yl}-propan-1-one;
cyclopropyl-{4-[1-methoxy-1-(4-quinolin-7-yl-phenyl)-ethyl]-piperidin-1-yl}-methanone;
1-{4-[1-ethoxy-1-(4-quinolin-7-yl-phenyl)-ethyl]-piperidin-1-yl}-propan-1-one;
cyclopropyl-{4-[1-ethoxy-1-(4-quinolin-7-yl-phenyl)-ethyl]-piperidin-1-yl}-methanone;
1-{4-[1-methoxy-1-(4-quinolin-7-yl-phenyl)-propyl]-piperidin-1-yl}-propan-1-one;
cyclopropyl-{4-[1-methoxy-1-(4-quinolin-7-yl-phenyl)-propyl]-piperidin-1-yl}-methanone;
1-[trans-3-hydroxy-4-(4-quinolin-3-yl-benzyl)-piperidin-1-yl]-propan-1-one;
1-[(trans)-3-methoxy-4-(4-quinolin-3-yl-benzyl)-piperidin-1-yl]-propan-1-one;
1-propionyl-4-(4-quinolin-3-yl-benzyl)-piperidin-3-one;

1-[cis-3-fluoro-4-(4-quinolin-3-yl-benzyl)-piperidin-1-yl]-propan-1-one;
1-{4-fluoro-4-[4-(8-methyl-quinolin-7-yl)-benzoyl]-piperidin-1-yl}-propan-1-one;
[trans-3-hydroxy-4-(4-quinolin-3-yl-benzyl)-piperidin-1-yl]-(R)-tetrahydrofuran-2-yl-methanone;
1-(4-fluoro-4-{methoxy-[4-(8-methyl-quinolin-7-yl)-phenyl]-methyl}-piperidin-1-yl)-propan-1-one;
1-(4-fluoro-4-{(2-methoxy-ethoxy)-[4-(8-methyl-quinolin-7-yl)-phenyl]-methyl}-piperidin-1-yl)-propan-1-one;
1-{4-fluoro-4-[[4-(8-methyl-quinolin-7-yl)-phenyl]-(2-morpholin-4-yl-ethoxy)-methyl]-piperidin-1-yl}-propan-1-one;
N-ethyl-4-fluoro-4-[[4-(8-methyl-7-quinolyl)phenyl]methyl]piperidine-1-carboxamide;
N-ethyl-4-[[4-(8-methyl-7-quinolyl)phenyl]methyl]piperidine-1-carboxamide;
N-ethyl-4-[[4-(8-methoxy-7-quinolyl)phenyl]methyl]piperidine-1-carboxamide;
N-methoxy-4-[[4-(8-methyl-7-quinolyl)phenyl]methyl]piperidine-1-carboxamide;
N-ethoxy-4-[[4-(8-methyl-7-quinolyl)phenyl]methyl]piperidine-1-carboxamide;
N,N-dimethyl-4-[[4-(8-methyl-7-quinolyl)phenyl]methyl]piperidine-1-carboxamide;
[4-[[4-(8-methyl-7-quinolyl)phenyl]methyl]-1-piperidyl]-pyrrolidin-1-yl-methanone;
and pharmaceutically acceptable salts thereof.

26. A compound selected from the group consisting of:
1-(4-(1-(4-(1,2,3,4-tetrahydroquinolin-7-yl)phenyl)ethyl)piperidin-1-yl)propan-1-one;
1-{4-[hydroxy-(4-quinolin-6-yl-phenyl)-methyl]-piperidin-1-yl}-2-methylpropan-1-one;
1-{4-[hydroxy-(4-quinolin-7-yl-phenyl)-methyl]-piperidin-1-yl}-propan-1-one;
1-{4-[1-hydroxy-1-(4-quinolin-7-yl-phenyl)-ethyl]-piperidin-1-yl}-propan-1-one;
1-{4-[(2-fluoro-4-isoquinolin-6-yl-phenyl)-hydroxymethyl]-piperidin-1-yl}-propan-1-one;
1-{4-[hydroxy-(4-isoquinolin-6-yl-phenyl)-methyl]-piperidin-1-yl}-propan-1-one;
1-{4-[1-hydroxy-1-(4-isoquinolin-6-yl-phenyl)-ethyl]-piperidin-1-yl}-propan-1-one;
1-{4-[1-(2-fluoro-4-Isoquinolin-6-yl-phenyl)-1-hydroxy-ethyl]-piperidin-1-yl}-propan-1-one;
1-{3-[1-hydroxy-1-(4-isoquinolin-6-yl-phenyl)-ethyl]-pyrrolidin-1-yl}-propan-1-one;
1-{4-[2-(4'-dimethylaminomethyl-biphenyl-4-yl)-1,3-dioxolan-2-yl]piperidin-1-yl}-2-methyl-propan-1-one;
1-{4-[2-(4'-dimethylaminomethyl-biphenyl-4-yl)-1,3-dioxolan-2-yl]-piperidin-1-yl}-propan-1-one;
cyclopropyl-{4-[2-(4'-dimethylaminomethyl-biphenyl-4-yl)-1,3-dioxolan-2-yl]-piperidin-1-yl}-methanone;
1-(4-(4-(benzofuran-2-yl)benzyl)-4-hydroxypiperidin-1-yl)propan-1-one;
1-(4-(4-(benzofuran-2-yl)benzyl)-4-hydroxypiperidin-1-yl)-2-methylpropan-1-one;
1-{4-fluoro-4-[4-(8-methyl-quinolin-7-yl)-benzoyl]-piperidin-1-yl}-propan-1-one;
N-[(1-propionyl-piperidin-4-yl)-(4-quinolin-3-yl-phenyl)-methyl]-acetamide;
N-[(1-propionyl-piperidin-4-yl)-(4-quinolin-3-yl-phenyl)-methyl]-formamide;
4-[1-(4-quinolin-3-yl-phenyl)-ethyl]-piperidine-1-carboxylic acid tert-butyl ester;
4-[2-(4-quinolin-6-yl-phenyl)-1,3-dioxolan-2-yl]-piperidine-1-carboxylic acid ethyl ester;
4-(2-fluoro-4-quinolin-3-yl-benzoyl)piperidine-1-carboxylic acid methyl ester;
1-[3-(4-isoquinolin-6-yl-benzoyl)-pyrrolidin-1-yl]-propan-1-one;
and pharmaceutically acceptable salts thereof.

* * * * *